US012649788B2

(12) United States Patent
Foltz et al.

(10) Patent No.: US 12,649,788 B2
(45) Date of Patent: * Jun. 9, 2026

(54) TREM2 ANTIGEN BINDING PROTEINS AND USES THEREOF

(71) Applicant: AMGEN INC., Thousand Oaks, CA (US)

(72) Inventors: Ian N. Foltz, Thousand Oaks, CA (US); Shilpa Sambashivan, Thousand Oaks, CA (US); Irwin Chen, Thousand Oaks, CA (US); Susie Miki Harris, Thousand Oaks, CA (US); Dora Toledo Warshaviak, Thousand Oaks, CA (US); Ian Driver, Thousand Oaks, CA (US); Daniel Lu, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 1107 days.

This patent is subject to a terminal disclaimer.

(21) Appl. No.: 17/449,242

(22) Filed: Sep. 28, 2021

(65) Prior Publication Data

US 2022/0204611 A1     Jun. 30, 2022

Related U.S. Application Data

(63) Continuation of application No. 16/500,378, filed as application No. PCT/US2018/028691 on Apr. 20, 2018, now Pat. No. 11,186,636.

(60) Provisional application No. 62/580,400, filed on Nov. 1, 2017, provisional application No. 62/530,753, filed on Jul. 10, 2017, provisional application No. 62/488,691, filed on Apr. 21, 2017.

(51) Int. Cl.
*C07K 16/28* (2006.01)
*A61P 25/28* (2006.01)

(52) U.S. Cl.
CPC .......... *C07K 16/2803* (2013.01); *A61P 25/28* (2018.01); *C07K 2317/21* (2013.01); *C07K 2317/565* (2013.01)

(58) Field of Classification Search
CPC combination set(s) only.
See application file for complete search history.

(56) References Cited

U.S. PATENT DOCUMENTS

| | | | |
|---|---|---|---|
| 5,591,828 | A | 1/1997 | Bosslet et al. |
| 6,878,687 | B1 | 4/2005 | Ruben et al. |
| 7,388,079 | B2 | 6/2008 | Pardridge et al. |
| 8,231,878 | B2 | 7/2012 | Colonna et al. |
| 8,663,598 | B2 | 3/2014 | Yang et al. |
| 8,981,061 | B2 | 3/2015 | Colonna et al. |
| 9,066,928 | B1 | 6/2015 | Estus et al. |
| 10,101,333 | B2 * | 10/2018 | Smider .................. A61P 31/12 |
| 10,597,462 | B1 | 3/2020 | Valance-Washington et al. |
| 11,186,636 | B2 | 11/2021 | Foltz et al. |
| 2002/0004587 | A1 | 1/2002 | Miller et al. |
| 2002/0128444 | A1 | 9/2002 | Gingras et al. |
| 2002/0177166 | A1 | 11/2002 | Guthridge et al. |
| 2003/0027132 | A1 | 2/2003 | Ruben et al. |
| 2003/0077282 | A1 | 4/2003 | Bigler et al. |
| 2003/0165875 | A1 | 9/2003 | Colonna et al. |
| 2005/0155089 | A1 | 7/2005 | Lal et al. |
| 2006/0014679 | A1 | 1/2006 | Tojo et al. |
| 2006/0263770 | A1 | 11/2006 | Colonna et al. |
| 2007/0041905 | A1 | 2/2007 | Hoffman et al. |
| 2007/0072177 | A1 | 3/2007 | Bakker et al. |
| 2007/0148167 | A1 | 6/2007 | Strohl |
| 2007/0281319 | A1 | 12/2007 | Kolopp-Sarda et al. |
| 2008/0045443 | A1 | 2/2008 | Kikutani et al. |
| 2008/0131423 | A1 | 6/2008 | Mori et al. |
| 2008/0247955 | A1 | 10/2008 | Kuai et al. |
| 2009/0175867 | A1 | 7/2009 | Thompson et al. |
| 2010/0299767 | A1 | 11/2010 | Kang et al. |
| 2011/0250300 | A1 | 10/2011 | Biswal et al. |
| 2011/0256213 | A1 | 10/2011 | Onyuksel et al. |

(Continued)

FOREIGN PATENT DOCUMENTS

| | | |
|---|---|---|
| CA | 2551163 A1 | 1/2008 |
| CN | 102038698 A | 5/2011 |

(Continued)

OTHER PUBLICATIONS

Wang H, Li X, Wang Q, Ma J, Gao X, Wang M. TREM2, microglial and ischemic stroke. J Neuroimmunol. Aug. 15, 2023;381:578108. doi: 10.1016/j.jneuroim.2023.578108. Epub May 16, 20236 PMID: 37302170. (Year: 2023).*

Dobson R, Tanasescu R, Gran B. Editorial: Preventing multiple sclerosis. Front Neurol. Jul. 20, 2022;13:982411. doi: 10.3389/fneur.2022.982411. PMID: 35937063; PMCID: PMC9350543. (Year: 2022).*

Bang J, Spina S, Miller BL. Frontotemporal dementia. Lancet. Oct. 24, 2015;386(10004):1672-82. doi: 10.1016/S0140-6736(15)00461-4. PMID: 26595641; PMCID: PMC5970949. (Year: 2015).*

Colonna M. The biology of TREM receptors. Nat Rev Immunol. Sep. 2023;23(9):580-594. doi: 10.1038/s41577-023-00837-1. Epub Feb. 7, 2023. PMID: 36750615; PMCID: PMC9904274. (Year: 2023).*

(Continued)

*Primary Examiner* — Jeffrey Stucker
*Assistant Examiner* — Laura Ann Essex
(74) *Attorney, Agent, or Firm* — Sterne, Kessler, Goldstein & Fox P.L.L.C.

(57) ABSTRACT

The present invention relates to antigen binding proteins, such as monoclonal antibodies, that specifically bind to and activate human triggering receptor expressed on myeloid cells-2 (TREM2) and pharmaceutical compositions comprising such antigen binding proteins. The agonist antigen binding proteins (e.g. antibodies) of the invention are capable of activating TREM2/DAP12 signaling in myeloid cells in the absence of Fc-mediated cross-linking of the antigen binding proteins. Methods of treating or preventing conditions associated with TREM2 loss of function, such as Alzheimer's disease and multiple sclerosis, using the antigen binding proteins are also described.

18 Claims, 51 Drawing Sheets

Specification includes a Sequence Listing.

(56)

References Cited

U.S. PATENT DOCUMENTS

| | | |
|---|---|---|
| 2012/0107898 A1 | 5/2012 | Neumann et al. |
| 2012/0195900 A1 | 8/2012 | Ghayur et al. |
| 2012/0201746 A1 | 8/2012 | Liu et al. |
| 2012/0202733 A1 | 8/2012 | Sigalov |
| 2012/0213705 A1 | 8/2012 | Dimasi et al. |
| 2012/0295272 A1 | 11/2012 | Senn |
| 2013/0029921 A1 | 1/2013 | Gibot et al. |
| 2013/0058947 A1 | 3/2013 | Stull et al. |
| 2013/0130354 A1 | 5/2013 | Gidekel et al. |
| 2013/0195849 A1 | 8/2013 | Spreter Von Kreudenstein et al. |
| 2013/0267463 A1 | 10/2013 | Youn et al. |
| 2014/0079689 A1 | 3/2014 | Elliott et al. |
| 2014/0206849 A1 | 7/2014 | Rother et al. |
| 2014/0286898 A1 | 9/2014 | Gavin et al. |
| 2014/0302038 A1 | 10/2014 | Dimasi et al. |
| 2014/0336361 A1 | 11/2014 | Giese et al. |
| 2014/0342004 A1 | 11/2014 | Aprikyan et al. |
| 2015/0065567 A1 | 3/2015 | Imbimbo et al. |
| 2015/0110791 A1 | 4/2015 | Zhang et al. |
| 2015/0218274 A1 | 8/2015 | Sabatos-Peyton et al. |
| 2015/0232531 A1 | 8/2015 | Gibot et al. |
| 2015/0266960 A1 | 9/2015 | Georgiou et al. |
| 2015/0274835 A1 | 10/2015 | Marasco et al. |
| 2016/0008485 A1 | 1/2016 | Marquette et al. |
| 2016/0186137 A1 | 6/2016 | Thomson et al. |
| 2016/0327572 A1 | 11/2016 | Barnaby et al. |
| 2016/0347814 A1 | 12/2016 | Levine et al. |
| 2017/0002070 A1 | 1/2017 | Towne et al. |
| 2017/0218058 A1 | 8/2017 | Rosenthal |
| 2017/0218091 A1 | 8/2017 | Ambrosi |
| 2017/0240631 A1 | 8/2017 | Monroe et al. |
| 2017/0266219 A1 | 9/2017 | Kang et al. |
| 2017/0291946 A1 | 10/2017 | Krummel et al. |
| 2017/0298130 A1 | 10/2017 | Henriksen et al. |
| 2017/0334977 A1 | 11/2017 | Butovsky et al. |
| 2018/0141997 A1 | 5/2018 | Lazar et al. |
| 2018/0169255 A1 | 6/2018 | Gao et al. |
| 2018/0185372 A1 | 7/2018 | Schinazi et al. |
| 2018/0186878 A1 | 7/2018 | Rosenthal |
| 2018/0194861 A1 | 7/2018 | Dong et al. |
| 2018/0200259 A1 | 7/2018 | Davis |
| 2018/0208668 A1 | 7/2018 | Lazar et al. |
| 2018/0235195 A1 | 8/2018 | Dennis et al. |
| 2018/0244749 A1 | 8/2018 | Swanson et al. |
| 2018/0244770 A1 | 8/2018 | Monroe et al. |
| 2018/0318379 A1 | 11/2018 | Andreasson |
| 2018/0340945 A1 | 11/2018 | Mitsuhashi |
| 2018/0346605 A1 | 12/2018 | Chiu et al. |
| 2019/0002560 A1 | 1/2019 | Monroe et al. |
| 2019/0008812 A1 | 1/2019 | Colonna et al. |
| 2019/0040130 A1 | 2/2019 | Schwabe et al. |
| 2019/0040131 A1 | 2/2019 | Culp et al. |
| 2019/0046583 A1 | 2/2019 | Pan et al. |
| 2019/0048057 A1 | 2/2019 | Colonna et al. |
| 2019/0062427 A1 | 2/2019 | Rosenthal et al. |
| 2019/0085076 A1 | 3/2019 | Rosenthal et al. |
| 2019/0099499 A1 | 4/2019 | Katragadda et al. |
| 2019/0174730 A1 | 6/2019 | Tassi et al. |
| 2019/0185565 A1 | 6/2019 | Haass et al. |
| 2019/0241633 A1 | 8/2019 | Fotin-Mleczek et al. |
| 2019/0269758 A1 | 9/2019 | Kipnis et al. |
| 2019/0275150 A1 | 9/2019 | Pincetic et al. |
| 2019/0300608 A1 | 10/2019 | Pashine et al. |
| 2019/0309064 A1 | 10/2019 | Streuli et al. |
| 2019/0330335 A1 | 10/2019 | Schwabe et al. |
| 2019/0336615 A1 | 11/2019 | Thompson et al. |
| 2019/0343882 A1 | 11/2019 | Kurtzberg et al. |
| 2019/0359707 A1 | 11/2019 | Pincetic et al. |
| 2019/0365830 A1 | 12/2019 | Goodman et al. |
| 2019/0367623 A1 | 12/2019 | Schwartz-Eisenbach et al. |
| 2020/0022343 A1 | 1/2020 | Howell et al. |
| 2020/0038439 A1 | 2/2020 | Biffi et al. |
| 2020/0038456 A1 | 2/2020 | Kurtzberg et al. |
| 2020/0071680 A1 | 3/2020 | Abeliovich et al. |
| 2020/0095280 A1 | 3/2020 | Ko et al. |
| 2020/0131264 A1 | 4/2020 | Pincetic et al. |
| 2020/0140545 A1 | 5/2020 | Brand et al. |
| 2020/0157213 A1 | 5/2020 | Zhu et al. |
| 2020/0207830 A1 | 7/2020 | Feuerbach et al. |
| 2020/0239844 A1 | 7/2020 | Blurton-Jones et al. |
| 2020/0277373 A1 | 9/2020 | Chen et al. |

FOREIGN PATENT DOCUMENTS

| | | |
|---|---|---|
| CN | 102127168 A | 7/2011 |
| CN | 102517287 A | 6/2012 |
| CN | 103555829 A | 2/2014 |
| CN | 103866041 A | 6/2014 |
| CN | 105218669 A | 1/2016 |
| CN | 106244682 A | 12/2016 |
| CN | 106636330 A | 5/2017 |
| CN | 109112214 A | 1/2019 |
| CN | 109206503 A | 1/2019 |
| CN | 109646668 A | 4/2019 |
| CN | 109837330 A | 6/2019 |
| CN | 110241208 A | 9/2019 |
| CN | 110320368 A | 10/2019 |
| CN | 110511240 A | 11/2019 |
| CN | 110882262 A | 3/2020 |
| CN | 111135185 A | 5/2020 |
| CN | 111184742 A | 5/2020 |
| EP | 404097 A2 | 12/1990 |
| GR | 1007327 B | 6/2011 |
| KR | 20060135280 A | 12/2006 |
| KR | 20110086460 A | 7/2011 |
| KR | 20120112973 A | 10/2012 |
| KR | 20130101493 A | 9/2013 |
| KR | 20150010326 A | 1/2015 |
| KR | 20180112562 A | 10/2018 |
| KR | 102096282 B1 | 4/2020 |
| KR | 20200048069 A | 5/2020 |
| WO | 9311161 A1 | 6/1993 |
| WO | WO-2009038760 A2 | 3/2009 |
| WO | 2010132370 A2 | 11/2010 |
| WO | 2012016333 A1 | 2/2012 |
| WO | WO-2012125495 A2 | 9/2012 |
| WO | 2014074942 A1 | 5/2014 |
| WO | 2016023019 A2 | 2/2016 |
| WO | 2016064895 A1 | 4/2016 |
| WO | 2017019846 A1 | 2/2017 |
| WO | 2017058866 A1 | 4/2017 |
| WO | 2017062672 A2 | 4/2017 |
| WO | 2018015573 A2 | 1/2018 |
| WO | 2018134815 A2 | 7/2018 |
| WO | 2018157014 A1 | 8/2018 |
| WO | 2018195506 A1 | 10/2018 |
| WO | 2018213316 A1 | 11/2018 |
| WO | 2019016784 A1 | 1/2019 |
| WO | 2019028292 A1 | 2/2019 |
| WO | 2019032624 A1 | 2/2019 |
| WO | 2019055841 A1 | 3/2019 |
| WO | 2019068072 A1 | 4/2019 |
| WO | 2019079529 A1 | 4/2019 |
| WO | 2019095064 A1 | 5/2019 |
| WO | 2019118513 A1 | 6/2019 |
| WO | 2019152715 A1 | 8/2019 |
| WO | 2019161080 A1 | 8/2019 |
| WO | 2019168403 A2 | 9/2019 |
| WO | 2019180224 A1 | 9/2019 |
| WO | 2019199776 A1 | 10/2019 |
| WO | 2019236965 A1 | 12/2019 |
| WO | 2019237900 A1 | 12/2019 |
| WO | 2019246483 A1 | 12/2019 |
| WO | 2020006374 A2 | 1/2020 |
| WO | 2020014657 A1 | 1/2020 |
| WO | 2020018461 A1 | 1/2020 |
| WO | 2020023920 A1 | 1/2020 |
| WO | 2020047374 A1 | 3/2020 |
| WO | 2020051322 A1 | 3/2020 |
| WO | 2020055975 A1 | 3/2020 |
| WO | 2020056114 A1 | 3/2020 |
| WO | 2020065044 A1 | 4/2020 |
| WO | 2020079580 A1 | 4/2020 |
| WO | 2020097395 A1 | 5/2020 |

(56)                    References Cited

FOREIGN PATENT DOCUMENTS

| | | | |
|---|---|---|---|
| WO | 2020112889 A2 | 6/2020 | |
| WO | 2020121195 A1 | 6/2020 | |
| WO | 2020132230 A2 | 6/2020 | |
| WO | 2020142659 A2 | 7/2020 | |
| WO | 2020150214 A1 | 7/2020 | |
| WO | 2020152607 A1 | 7/2020 | |
| WO | 2020154348 A1 | 7/2020 | |
| WO | 2020160217 A1 | 8/2020 | |
| WO | 2020160441 A1 | 8/2020 | |
| WO | 2020160468 A1 | 8/2020 | |
| WO | 2020172450 A1 | 8/2020 | |
| WO | 2020194317 A1 | 10/2020 | |
| WO | 2021101823 A1 | 5/2021 | |
| WO | 2021113655 A1 | 6/2021 | |

OTHER PUBLICATIONS

Teipel S, Gustafson D, Ossenkoppele R, Hansson O, Babiloni C, Wagner M, Riedel-Heller SG, Kilimann I, Tang Y. Alzheimer Disease: Standard of Diagnosis, Treatment, Care, and Prevention. J Nucl Med. Jul. 2022;63(7):981-985. doi: 10.2967/jnumed.121. 262239. Epub Feb. 10, 2022. PMID: 35145015 (Year: 2022).*

Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol. Bioeng. 2004;87(5):614-22.

Yang et al., "CDR walking mutagenesis for the affinity maturation of a potent human anti-HIV-1 antibody into the picomolar range," J. Mol. Biol. 1995;254(3):392-403.

Yeh et al., "TREM2 Binds to Apolipoproteins, Including APOE and CLU/APOJ, and Thereby Facilitates Uptake of Amyloid-Beta by Microglia," Neuron. 2016;91(2):328-340.

Yelton et al., "Affinity maturation of the BR96 anti-carcinoma antibody by codon-based mutagenesis," J. Immunol. 1995;155(4):1994-2004.

Yuan et al., "TREM2 haplodeficiency in mice and humans impairs the microglia barrier function leading to decreased amyloid compaction and severe axonal dystrophy," Neuron. 2016;90(4):724-739.

Zapata et al., "Engineering linear F(ab')2 fragments for efficient production in *Escherichia coli* and enhanced antiproliferative activity," Protein Eng. 1995;8(10):1057-62.

Henikoff and Henikoff, "Amino acid substitution matrices from protein blocks," Proc. Natl. Acad. Sci. USA. 1992;89(22):10915-10919.

Holliger et al., ""Diabodies": small bivalent and bispecific antibody fragments," Proc. Natl. Acad. Sci. USA. 1993;90(14):6444-8.

Honegger and Pluckthun, "Yet another numbering scheme for immunoglobulin variable domains: an automatic modeling and analysis tool," J. Mol. Biol. 2001;309(3):657-70.

Hoogenboom, "Designing and optimizing library selection strategies for generating high-affinity antibodies," Trends Biotechnol. 1997;15(2):62-70.

Hsieh et al., "A Role of Trem2 ligands in phagocytosis of apoptotic neuronal cells by microglia," J Neurochem. 2009;109(4):1144-56.

Hu et al., "OSA: a fast and accurate alignment tool for RNA-Seq," Bioinformatics. 2012;28(14):1933-1934.

Hu et al., "Triggering Receptor Expressed on Myeloid Cells 2 (TREM2) Dependent Microglial Activation Promotes Cisplatin-Induced Peripheral Neuropathy in Mice," Brain Behav Immun. Feb. 2018;68:132-145.

Hugo et al., "VL position 34 is a key determinant for the engineering of stable antibodies with fast dissociation rates," Protein Eng. 2003;16(5):381-6.

Humphrey et al., "TREM2, a DAP12-Associated Receptor, Regulates Osteoclast Differentiation and Function", J Bone and Min Res 2006; 2(21):237-45.

Jackson et al., "In vitro antibody maturation. Improvement of a high affinity, neutralizing antibody against IL-1 beta," J. Immunol. 1995;154(7):3310-9.

Jakobovits et al., "Analysis of homozygous mutant chimeric mice: deletion of the immunoglobulin heavy-chain joining region blocks B-cell development and antibody production," Proc. Natl. Acad. Sci. USA. 1993;90(6):2551-2555.

Jakobovits et al., "Germ-line transmission and expression of a human-derived yeast artificial chromosome," Nature. 1993;362(6417):255-8.

Jalkanen et al., "Cell surface proteoglycan of mouse mammary epithelial cells is shed by cleavage of its matrix-binding ectodomain from its membrane-associated domain," J. Cell. Biol. 1987;105(6):3087-3096.

Jalkanen et al., "Heparan sulfate proteoglycans from mouse mammary epithelial cells: localization on the cell surface with a monoclonal antibody," J. Cell. Biol. 1985; 101(3):976-84.

Jay et al., "TREM2 deficiency eliminates TREM2+ inflammatory macrophages and ameliorates pathology in Alzheimer's disease mouse models," J. Exp. Med. 2015;212(3):287-95.

Jespers et al., "Guiding the Selection of Human Antibodies from Phage Display Repertoires to a Single Epitope of an Antigen," Biotechnology (N Y). 1994;12(9):899-903.

Jiang et al. "Upregulation of TREM2 Ameliorates Neuropathology and Rescues Spatial Cognitive Impairment in a Transgenic Mouse Model of Alzheimer's Disease," Neuropsychopharmacol. 2014; 39(13):2949-62.

Jones et al., "Replacing the complementarity-determining regions in a human antibody with those from a mouse," Nature. 1986;321(6069):522-5.

Jonsson et al., "Variant of TREM2 Associated with the Risk of Alzheimer's Disease," N. Engl. J. Med. 2013;368(2):107-116.

Kellermann and Green, "Antibody discovery: the use of transgenic mice to generate human monoclonal antibodies for therapeutics," Curr. Opin. Biotechnol. 2002;13(6):593-7.

Kelsey et al., "Species- and tissue-specific expression of human alpha 1-antitrypsin in transgenic mice," Genes Dev. 1987;1(2):161-71.

Kiialainen et al., "Dap12 and Trem2, molecules involved in innate immunity and neurodegeneration, are co-expressed in the CNS," Neurobiol. Dis. 2005;18(2):314-22.

Kirkland et al., "Analysis of the fine specificity and cross-reactivity of monoclonal anti-lipid A antibodies," J. Immunol. 1986;137(11):3614-9.

Kobayashi et al. "TREM2/DAP12 Signal Elicits Proinflammatory Response in Microglia and Exacerbates Neuropathic Pain," J Neurosci. 2016, 36(43):11138-11502.

Kollias et al., "Regulated expression of human A gamma-, beta-, and hybrid gamma beta-globin genes in transgenic mice: manipulation of the developmental expression patterns," Cell. 1986;46(1):89-94.

Kostelny et al., "Formation of a bispecific antibody by the use of leucine zippers," J. Immunol. 1992;148(5):1547-53.

Krieg et al., "Functional analysis of B and T lymphocyte attenuator engagement on CD4+ and CD8+ T cells.", J of Immunology, Baltimore, MD, 2005, 175(10):6420-6427.

Krumlauf et al., "Developmental regulation of alpha-fetoprotein genes in transgenic mice," Mol. Cell. Biol. 1985;5(7):1639-48.

Kumaraswamy and Tobias, "Label-free kinetic analysis of an antibody-antigen interaction using biolayer interferometry," Methods Mol. Biol. 2015;1278:165-82.

Leder et al., "Consequences of widespread deregulation of the c-myc gene in transgenic mice: Multiple neoplasms and normal development," Cell. 1986;45(4):485-95.

Lefranc et al., "IMGT unique numbering for immunoglobulin and T cell receptor constant domains and Ig superfamily C-like domains," Dev. Comp. Immunol. 2005;29(3):185-203.

Leyns et al. "TREM2 Deficiency Attenuates Neuroinflammation and Protects Against Neurodegeneration in a Mouse Model of Tauopathy," Proc Natl Acad Sci U S A. Oct. 24, 2017;114(43):11524-11529.

Li and Dewey, "RSEM: accurate transcript quantification from RNA-Seq data with or without a reference genome," BMC Bioinformatics. 2011;12:323.

Lindmark et al., "Binding of immunoglobulins to protein A and immunoglobulin levels in mammalian sera," J. Immunol. Methods. 1983;62(1):1-13.

(56)          References Cited

OTHER PUBLICATIONS

Liu et al., "Biological Characterization of a Stable Effector Functionless (SEFL) Monoclonal Antibody Scaffold in Vitro," J Biol Chem, 2016, 292(5):1876-83.
Lonberg and Huszar, "Human antibodies from transgenic mice," Int. Rev. Immunol. 1995;13(1):65-93.
Lonberg et al., "Antigen-specific human antibodies from mice comprising four distinct genetic modifications," Nature. 368(6474):856-9.
Love et al., "Moderated estimation of fold change and dispersion for RNA-seq data with DESeq2," Genome Biol. 2014;15(12):550.
Low et al., "Mimicking Somatic Hypermutation: Affinity Maturation of Antibodies Displayed on Bacteriophage Using a Bacterial Mutator Strain," J. Mol. Biol. 1996;260(3):359-68.
Macdonald, "Expression of the pancreatic elastase I gene in transgenic mice," Hepatology. 1987;7(1 Suppl):42S-51S.
Magram et al., "Developmental regulation of a cloned adult ?-globin gene in transgenic mice," Nature. 1985;315(6017):338-40.
Marks et al., "By-passing immunization: building high affinity human antibodies by chain shuffling," Biotechnology (NY). 1992;10(7):779-83.
Martinez et al., "Disulfide Connectivity of Human Immunoglobulin G2 Structural Isoforms," Biochemistry. 2008;47(28):7496-7508.
Mason et al., "The hypogonadal mouse: reproductive functions restored by gene therapy," Science. 1986;234(4782):1372-1378.
Mather et al., "Culture of testicular cells in hormone-supplemented serum-free medium," Ann. N.Y. Acad. Sci. 1982;383:44-68.
Mather, "Establishment and characterization of two distinct mouse testicular epithelial cell lines," Biol. Reprod. 1980;23(1):243-52.
Mazaheri et al., "TREM2 deficiency impairs chemotaxis and microglial responses to neuronal injury," EMBO Rep. 2017;18:1186-1198.
Mendez et al., "Functional transplant of megabase human immunoglobulin loci recapitulates human antibody response in mice," Nat. Genet. 1997;15(2):146-56.
Moldenhauer et al., "Identity of HML-1 antigen on intestinal intraepithelial T cells and of B-ly7 antigen on hairy cell leukaemia," Scand. J. Immunol. 1990;32(2):77-82.
Morel et al., "Monoclonal antibodies to bovine serum albumin: affinity and specificity determinations," Mol. Immunol. 1988;25(1):7-15.
Turk et al., "X-linked adrenoleukodystrophy: Pathology, pathophysiology, diagnostic testing, newborn screening and therapies", Int J Dev Neurosci. Feb. 2020;80(1):52-72. doi: 10.1002/jdn.10003.
Gong et al., "Microglial dysfunction as a key pathological change in adrenomyeloneuropathy", Ann Neurol. Nov. 2017;82(5):813-827. doi: 10.1002/ana.25085.
International Searching Authority, International Search Report and Written Opinion issued in corresponding PCT/US21/72749, Mailing date May 5, 2022, 14 total pages.
Morrison et al., "Chimeric human antibody molecules: mouse antigen-binding domains with human constant region domains," Proc. Natl. Acad. Sci. USA. 1984;81(21):6851-6855.
Muruganandam et al., "Selection of phage-displayed llama single-domain antibodies that transmigrate across human blood-brain barrier endothelium," Faseb J. 2002;16(2):240-2.
Natoni et al., "TRAIL signals to apoptosis in chronic lymphocytic leukaemia cells primarily through TRAIL-R1 whereas cross-linked agonistic TRAIL-R2 antibodies facilitate signalling via TRAIL-R2," Br. J. Haematol. 2007;139(4):568-77.
Needleman and Wunsch, "A general method applicable to the search for similarities in the amino acid sequence of two proteins," J. Mol. Biol. 1970;48(3):443-53.
Olafsen et al., "Covalent disulfide?linked anti?CEA diabody allows site?specific conjugation and radiolabeling for tumor targeting applications," Protein Eng. Des. Sel. 2004;17(1):21-27.
Ornitz et al., "Elastase I promoter directs expression of human growth hormone and SV40 T antigen genes to pancreatic acinar cells in transgenic mice," Cold Spring Harb. Symp. Quant. Biol. 1985;50:399-409.

Paloneva et al., "Mutations in Two Genes Encoding Different Subunits of a Receptor signaling Complex Results in an Identical Disease Phenotype," Am Hum Genet. 2002; 71(3):656-62.
Paradowska-Gorycka and Jurkowska, "Structure, expression pattern and biological activity of molecular complex TREM-2/DAP12," Hum. Immunol. 2013;74(6):730-7.
Parkhomchuk et al., "Transcriptome analysis by strand-specific sequencing of complementary DNA," Nucleic Acids Res. 2009;37(18):e123.
Patten et al., "Applications of DNA shuffling to pharmaceuticals and vaccines," Curr. Opin. Biotechnol. 1997;8(6):724-33.
PCT Search Report and Written Opinion for PCT/US2018/028691 mailed Sep. 27, 2018.
Perkins et al., "A strand-specific RNA-Seq analysis of the transcriptome of the typhoid bacillus Salmonella typhi," PLoS Genet. 2009;5(7):e1000569.
Piccio et al., "Identification of soluble TREM-2 in the cerebrospinal fluid and its association with multiple sclerosis and CNS inflammation," Brain. 2008;131(11):3081-3091.
Pinkert et al., "An albumin enhancer located 10 kb upstream functions along with its promoter to direct efficient, liver-specific expression in transgenic mice," Genes Dev. 1987;1(3):268-76.
Powers et al., "Expression of single-chain Fv-Fc fusions in Pichia pastoris," J. Immunol. Methods. 2001;251(1-2):123-35.
Rathanaswami et al., "High-affinity binding measurements of antibodies to cell-surface-expressed antigens," Anal. Biochem. 2008;373(1):52-60.
Readhead et al., "Expression of a myelin basic protein gene in transgenic shiverer mice: correction of the dysmyelinating phenotype," Cell. 1987;48(4):703-12.
Riechmann et al., "Reshaping human antibodies for therapy," Nature. 1988;332(6162):323-7.
Rothman et al., "Antibody-dependent cytotoxicity mediated by natural killer cells is enhanced by castanospermine-induced alterations of IgG glycosylation," Mol. Immunol. 1989;26(12):1113-23.
Schier et al., "Identification of functional and structural amino-acid residues by parsimonious mutagenesis," Gene. 1996;169(2):147-155.
Schlepckow et al. "Enhancing Protective Microglial Activities With a Dual Function TREM2 Antibody to the Stalk Region," EMBO Mol Med. Apr. 7, 2020; 12(4):e11227.
Schmid et al., "Heterogeneous expression of the triggering receptor expressed on myeloid cells-2 on adult murine microglia," J. Neurochem. 2002;83(6):1309-1320.
Sessa et al., "Distribution and Signaling of TREM2/DAP12, the Receptor System Mutatedin Human Polycystic Lipomembraneous Osteodysplasia With Sclerosing Leukoencephalopathy Dementia," Eur J Neurosci. 2004; 20(10):2617-28.
Shani, "Tissue-specific expression of rat myosin light-chain 2 gene in transgenic mice," Nature. 1985;314(6008):283-6.
Shields et al., "Lack of fucose on human IgG1 N-linked oligosaccharide improves binding to human Fcgamma RIII and antibody-dependent cellular toxicity," J. Biol. Chem. 2002;277(30):26733-40.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J. Biol. Chem. 2003;278(5):3466-73.
Songsivilai and Lachmann, "Bispecific antibody: a tool for diagnosis and treatment of disease," Clin. Exp. Immunol. 1990;79(3):315-321.
Spiess et al., "Alternative molecular formats and therapeutic applications for bispecific antibodies," Mol. Immunol. 2015;67(2 Pt A):95-106.
Stähli et al., "[20] Distinction of epitopes by monoclonal antibodies," Methods in Enzymology. 1983;92:242-253.
Sun et al. "TREM-2 Promotes Host Resistance Against Pseudomonas Aeruginosa Infection by Suppressing Corneal Inflammation via a PI3K/Akt Signaling Pathway," Invest Ophthalmol Vis Sci. May 17, 2013;54(5):3451-62.
Swift et al., "Tissue-specific expression of the rat pancreatic elastase I gene in transgenic mice," Cell. 1984;38(3):639-646.

(56)         References Cited

OTHER PUBLICATIONS

Taylor et al., "A transgenic mouse that expresses a diversity of human sequence heavy and light chain immunoglobulins," Nucleic Acids Res. 1992;20(23):6287-6295.

Taylor et al., "Human immunoglobulin transgenes undergo rearrangement, somatic mutation and class switching in mice that lack endogenous IgM," Int. Immunol. 1994;6(4):579-91.

Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol. 1996:256(1):77-88.

Thomsen et al., "Promoter-regulatory region of the major immediate early gene of human cytomegalovirus," Proc. Natl. Acad. Sci. USA. 1984;81(3):659-63.

Tuaillon et al., "Biased utilization of DHQ52 and JH4 gene segments in a human Ig transgenic minilocus is independent of antigenic selection," J. Immunol. 1994;152(6):2912-2920.

Ulrich and Holtzman, "TREM2 Function in Alzheimer's Disease and Neurodegeneration," ACS Chem. Neurosci. 2016;7(4):420-427.

Umaña et al., "Engineered glycoforms of an antineuroblastoma IgG1 with optimized antibody-dependent cellular cytotoxic activity," Nat. Biotechnol. 1999;17(2):176-80.

Urlaub and Chasin, "Isolation of Chinese hamster cell mutants deficient in dihydrofolate reductase activity," Proc. Natl. Acad. Sci. USA. 1980;77(7):4216-4220.

Vaughan et al., "Human antibodies by design," Nat. Biotechnol. 1998;16(6):535-9.

Verhoeyen et al., "Reshaping human antibodies: grafting an antilysozyme activity," Science. 1988;239(4847):1534-6.

Villa-Komaroff et al., "A bacterial clone synthesizing proinsulin," Proc. Natl. Acad. Sci. USA. 1978;75(8):3727-31.

Vonderheide and Glennie, "Agonistic CD40 antibodies and cancer therapy," Clin. Cancer. Res. 2013;19(5):1035-43.

Wagner et al., "Nucleotide sequence of the thymidine kinase gene of herpes simplex virus type 1," Proc. Natl. Acad. Sci. USA. 1981;78(3):1441-1445.

Wang et al. "TREM2-mediated Early Microglial Response Limits Diffusion and Toxicity of Amyloid Plaques," J Exp Med. May 2, 2016;213(5):667-75.

Wang et al., "TREM2 lipid sensing sustains the microglial response in an Alzheimer's disease model," Cell. 2015;160(6):1061-71.

White et al., "Conformation of the Human Immunoglobulin G2 Hinge Impacts Superagonistic Properties to Immunostimulatory Anticancer Antibodies," Cell. 2015;27:138-148.

Williams and Polli, "The Lyophilization of Pharmaceuticals: A Literature Review," PDA Journal of Pharmaceutical Science and Technology. 1984;38(2):48-60.

Wu et al., "TREM-2 promotes macrophage survival and lung disease after respiratory viral infection," J. Exp. Med. 2015;212(5):681-697.

Yamamoto et al., "Identification of a functional promoter in the long terminal repeat of Rous sarcoma virus," Cell. 1980;22(3):787-797.

Abulrob et al., "The blood-brain barrier transmigrating single domain antibody: mechanisms of transport and antigenic epitopes in human brain endothelial cells," J. Neurochem. 2005;95(4):1201-14.

Adams et al., "The c-myc oncogene driven by immunoglobulin enhancers induces lymphoid malignancy in transgenic mice," Nature. 1985;318:533-538.

Alexander et al., "Expression of the c-myc oncogene under control of an immunoglobulin enhancer in E mu-myc transgenic mice," Mol. Cell. Biol. 1987;7(4):1436-1444.

Arts et al., "TREM?1: intracellular signaling pathways and interaction with pattern recognition receptors," J. Leukoc. Biol. 2013;93(2):209-15.

Atagi et al. "Apolipoprotein E Is a Ligand for Triggering Receptor Expressed on Myeloid Cells 2 (TREM2)," J Biol Chem. 2015; 290(43):26043-50.

Babcook et al., "A novel strategy for generating monoclonal antibodies from single, isolated lymphocytes producing antibodies of defined specificities," Proc. Natl. Acad. Sci. USA. 1996;93(15):7843-7848.

Barbas et al., "In vitro evolution of a neutralizing human antibody to human immunodeficiency virus type 1 to enhance affinity and broaden strain cross-reactivity," Proc. Natl. Acad. Sci. USA. 1994;91(9):3809-3813.

Barnes and Sato, "Methods for growth of cultured cells in serum-free medium," Anal. Biochem. 1980;102(2):255-70.

Benoist and Chambon, "In vivo sequence requirements of the SV40 early promotor region," Nature. 1981;290(5804):304-10.

Bouchon et al., "A DAP12-mediated pathway regulates expression of CC chemokine receptor 7 and maturation of human dendritic cells," J. Exp. Med. 2001;194(8):1111-22.

Brinkmann and Kontermann, "The making of bispecific antibodies," MAbs. 2017;9(2):182-212.

Brinster et al., "Regulation of metallothionein—thymidine kinase fusion plasmids injected into mouse eggs," Nature. 1982;296(5852):39-42.

Brüggemann et al., "Designer mice: the production of human antibody repertoires in transgenic animals," Year Immunol. 1993;7:33-40.

Cady et al. "TREM2 Variant p.R47H as a Risk Factor for Sporadic Amyotrophic Lateral Sclerosis," JAMA Neurol. 2014;70(4):449-53.

Carpenter et al., "Interactions of stabilizing additives with proteins during freeze-thawing and freeze-drying," Dev. Biol. Stand. 1992;74:225-239.

Carrillo and Lipman, "The Multiple Sequence Alignment Problem in Biology," Siam J. Appl. Math. 1988;48(5):1073-1082.

Cash et al., "Chapter 17. Zymosan?Induced Peritonitis as a Simple Experimental System for the Study of Inflammation," Methods Enzymol. 2009;461:379-96.

Caton and Koprowski, "Influenza virus hemagglutinin-specific antibodies isolated from a combinatorial expression library are closely related to the immune response of the donor," Proc. Natl. Acad. Sci. USA. 1990;87(16):6450-6454.

Chanput et al., "THP-1 cell line: an in vitro cell model for immune modulation approach," Int. Immunopharmacol. 2014;23(1):37-45.

Chen et al., "Immunoglobulin gene rearrangement in B cell deficient mice generated by targeted deletion of the JH locus," Int Immunol. 1993;5(6):647-56.

Chen, "Formulation concerns of protein drugs," Drug Development and Industrial Pharmacy. 1992;18(11&12):1311-1354.

Cheng et al. "TREM2-activating antibodies abrogate the negative pleiotropic effects of the Alzheimer's disease variant TREM2R47H on murine myeloid cell function," J Biol Chem. Mar. 29, 2018, 293, 12620-12633.

Cheung et al., "Epitope-specific antibody response to the surface antigen of duck hepatitis B virus in infected ducks," Virology. 1990;176(2):546-552.

Chothia and Lesk, "Canonical structures for the hypervariable regions of immunoglobulins," J. Mol. Biol. 1987;196(4):901-17.

Chothia et al., "Conformations of immunoglobulin hypervariable regions," Nature. 1989;342(6252):877-83.

Choulier et al., "Covariance analysis of protein families: The case of the variable domains of antibodies," Proteins. 2000;41(4):475-484.

Colonna, "TREMs in the immune system and beyond," Nat. Rev. Immunol. 2003;3(6):445-53.

Cortez-Retamozo et al., "Efficient cancer therapy with a nanobody-based conjugate," Cancer Res. 2004;64(8):2853-7.

Cosman et al., "Cloning, sequence and expression of human interleukin-2 receptor," Nature. 1984;312(5996):768-71.

Crameri et al., "DNA shuffling of a family of genes from diverse species accelerates directed evolution," Nature. 1998;391(6664):288-91.

DeBoer et al., "The tac promoter: a functional hybrid derived from the trp and lac promoters," Proc. Natl. Acad. Sci. USA. 1983;80(1):21-25.

Demarest et al., "Optimization of the Antibody CH3 Domain by Residue Frequency Analysis of IgG Sequences," J. Mol. Biol. 2004;335(1):41-48.

(56)          References Cited

OTHER PUBLICATIONS

Dillon et al., "Structural and Functional Characterization of Disulfide Isoforms of the Human IgG2 Subclass," J. Biol. Chem. 2008;283(23):16206-16215.

Edelman et al., "The covalent structure of an entire gammaG immunoglobulin molecule," Proc. Natl. Acad. Sci. USA. 1969;63(1):78-85.

Feinstein et al., "Peroxisome proliferator-activated receptor-gamma agonists prevent experimental autoimmune encephalomyelitis," Ann. Neurol. 2002;51(6):694-702.

Fishwild et al., "High-avidity human IgG kappa monoclonal antibodies from a novel strain of minilocus transgenic mice," Nat. Biotechnol. 1996;14(7):845-51.

Fredericks et al., "Identification of potent human anti?IL?IR1 antagonist antibodies," Protein Eng. Des. Sel. 2004;17(1):95-106.

Graham et al., "Characteristics of a human cell line transformed by DNA from human adenovirus type 5," J. Gen. Virol. 1977;36(1):59-74.

Gratuze et al. "New Insights Into the Role of TREM2 in Alzheimer's Disease," Mol Neurodegener. Dec. 20, 2018;13(1):66.

Green and Jakobovits, "Regulation of B cell development by variable gene complexity in mice reconstituted with human immunoglobulin yeast artificial chromosomes," J. Exp. Med. 1988;188(3):483-95.

Green et al., "Antigen-specific human monoclonal antibodies from mice engineered with human Ig heavy and light chain YACs," Nat. Genet. 1994;7(1):13-21.

Green, "Antibody engineering via genetic engineering of the mouse: XenoMouse strains are a vehicle for the facile generation of therapeutic human monoclonal antibodies," J. Immunol. Methods. 1999;231(1-2):11-23.

Grosschedl et al., "Introduction of a m immunoglobulin gene into the mouse germ line: Specific expression in lymphoid cells and synthesis of functional antibody," Cell. 1984;38(3):647-658.

Guerreiro et al. "Using Exome Sequencing to Reveal Mutations in TREM2 Presenting as a Frontotemporal Dementia-Like Syndrome Without Bone Involvement," JAMA Neurol. 2013; 70(1):78-84.

Guerreiro et al., "TREM2 variants in Alzheimer's disease," N. Engl. J. Med. 2013;368(2):117-27.

Guss et al., "Structure of the IgG-binding regions of streptococcal protein G," EMBO J. 1986;5(7):1567-1575.

Ham and McKeehan, "Media and growth requirements," Methods Enzymol. 1979;58:44-93.

Hammer et al., "Diversity of alpha-fetoprotein gene expression in mice is generated by a combination of separate enhancer elements," Science. 1987;235(4784):53-8.

Hanahan, "Heritable formation of pancreatic beta-cell tumours in transgenic mice expressing recombinant insulin/simian virus 40 oncogenes," Nature. 1985;315(6015):115-22.

Hawkins et al., "Selection of phage antibodies by binding affinity. Mimicking affinity maturation," J. Mol. Biol. 1992;226(3):889-96.

Morris, G.E., "Epitope Mapping of Protein Antigens by Competition ELISA," The Protein Protocols Handbook, pp. 595-600, Humana Press, Totowa, United States (1996).

Jay, T.R., et al., "TREM2 in Neurodegenerative Diseases," Mol Neurodegener 12(1):56, pp. 1-33, BioMed Central, United Kingdom (Aug. 2017).

* cited by examiner

| Ab ID. | Germline | SEQ ID NO: | K_FR1 | K_CDR1 | K_FR2 | K_CDR2 |
|---|---|---|---|---|---|---|
|  | VK4\|B3/JK5 | 64 | DIVMTQSPDSLAVSLGERATINC | KSS---QSVLYSSNNKNYLA | WYQQKPGQPPKLLIY | W-------ASTRES |
| 24C12 | VK4\|B3/JK5 | 51 | G................. | ......R........... | .........V... | ........... |
|  | VK4\|B3/JK4 | 65 | DIVMTQSPDSLAVSLGERATINC | KSS---QSVLYSSNNKNYLA | WYQQKPGQPPKLLIY | W-------ASTRES |
| 24G6 | VK4\|B3/JK4 | 52 | .................. | ......HF.. | ........... | ........... |
|  | VK4\|B3/JK2 | 66 | DIVMTQSPDSLAVSLGERATINC | KSS---QSVLYSSNNKNYLA | WYQQKPGQPPKLLIY | W-------ASTRES |
| 24A10 | VK4\|B3/JK2 | 53 | .........T........ | ....HN.... | ........... | ........... |
|  | VK3\|L2/JK3 | 67 | EIVMTQSPATLSVSPGERATLSC | RAS--QSVS------SNLA | WYQQKPGQAPRLLIY | G-------ASTRAT |
| 10E3 | VK3\|L2/JK3 | 54 | .................. | .......... | ...F........ | ........... |
| 13E7 14C12 | VK3\|L2/JK3 | 55 | .................. | .......... | ...F........ | ........... |
|  | VK3\|L2/JK1 | 68 | EIVMTQSPATLSVSPGERATLSC | RAS--QSVS------SNLA | WYQQKPGQAPRLLIY | G-------ASTRAT |
| 25FL2 | VK3\|L2/JK1 | 56 | ...K.............. | ....N.....N... | ........... | ........... |
|  | VK3\|A27/JK5 | 69 | EIVLTQSPGTLSLSPGERATLSC | RAS--QSVSS-----SYLA | WYQQKPGQAPRLLIY | G-------ASSRAT |
| 32E3 | VK3\|A27/JK5 | 57 | .F................ | .....II........N... | ........... | S.......... |
|  | VK3\|A27/JK3 | 70 | EIVLTQSPGTLSLSPGERATLSC | RAS---QSVSS-----SYLA | WYQQKPGQAPRLLIY | G-------ASSRAT |
| 24F4 | VK3\|A27/JK3 | 58 | .................. | .......... | ........... | ........... |
|  | VK1\|L5/JK5 | 71 | DIQMTQSPSSVSASVGDRVTITC | RAS--QGIS------SWLA | WYQQKPGKAPKLLIY | A-------ASSLQS |
| 16B8 | VK1\|L5/JK5 | 59 | .........V.. | .......... | ........... | ...........T |
|  | VK1\|L5/JK2 | 72 | DIQMTQSPSSVSASVGDRVTITC | RAS--QGIS------SWLA | WYQQKPGKAPKLLIY | A-------ASSLQS |
| 4C5 | VK1\|L5/JK2 | 60 | .................. | ....D.N.... | ........... | .........V |
| 6E7 | VK1\|L5/JK2 | 61 | .................. | .......N... | ........... | ........N |
|  | VK1\|L1/JK3 | 73 | DIQMTQSPSSLSASVGDRVTITC | RAS--QGIS------NYLA | WFQQKPGKAPKSLIY | A-------ASSLQS |
| 5E3 | VK1\|L1/JK3 | 62 | .................. | .......... | ........... | ........... |
|  | VK1\|A30/JK1 | 74 | DIQMTQSPSSLSASVGDRVTITC | RAS--QGIR------NDLG | WYQQKPGKAPKRLLIY | A-------ASSLQS |
| 4G10 | VK1\|A30/JK1 | 63 | .................. | .......... | ....N...... | .........P. |

FIG. 2A

| Ab ID. | Germline | SEQ ID NO: | K_FR3 | K_CDR3 | K_FR4 |
|---|---|---|---|---|---|
| 24C12 | VK4\|B3/JK5 | 64 | GVPDRFSGSGSG---TDFTLTISSLQAEDVAVYYC | QQYYS---......TPIT | FGQGTRLEIK |
|  | VK4\|B3/JK5 | 51 | .................N. | .....I.............. | .......... |
| 24G6 | VK4\|B3/JK4 | 65 | GVPDRFSGSGSG---TDFTLTISSLQAEDVAVYYC | QQYYS---......TPLT | FGGGTKVEIK |
|  | VK4\|B3/JK4 | 52 | ..............F... | .................... | .......... |
|  | VK4\|B3/JK2 | 66 | GVPDRFSGSGSG---TDFTLTISSLQAEDVAVYYC | QQYYS---......TPYT | FGQGTKLEIK |
| 24A10 | VK4\|B3/JK2 | 53 | H............. | H...........CS | .......... |
| 10E3 | VK3\|L2/JK3 | 67 | GIPARFSGSGSG---TEFTLTITISSLQSEDFAVYYC | QQYNN---......WPFT | FGPGTKVDIK |
|  | VK3\|L2/JK3 | 54 | .........V..F... | L.D..........P. | .......... |
| 13E7 / 14C12 | VK3\|L2/JK3 | 55 | .........V........ | L.D...........P. | .......... |
| 25F12 | VK3\|L2/JK1 | 68 | GIPARFSGSGSG---TEFTLTITISSLQSEDFAVYYC | QQYNN---......WPWT | FGGGTKVEIK |
|  | VK3\|L2/JK1 | 56 | .................. | .............R. | .......... |
| 32E3 | VK3\|A27/JK5 | 69 | GIPDRFSGSGSG---TDFTLTISRLEPEDFAVYYC | QQYGS---......SPIT | FGQGTRLEIK |
|  | VK3\|A27/JK5 | 57 | .........FD.... | ..R.....D. | .......... |
| 24F4 | VK3\|A27/JK3 | 70 | GIPDRFSGSGSG---TDFTLTISRLEPEDFAVYYC | QQYGS---......SPFT | FGPGTKVDIK |
|  | VK3\|A27/JK3 | 58 | .........L........ | ...DT........ | .......... |
| 16B8 | VK1\|L5/JK5 | 71 | GVPSRFSGSGSG---TDFTLTISSLQPEDFATYYC | QQANS---......FPIT | FGQGTRLEIK |
|  | VK1\|L5/JK5 | 59 | ..........S........ | ....S........ | .......... |
| 4C5 | VK1\|L5/JK2 | 72 | GVPSRFSGSGSG---TDFTLTISSLQPEDFATYYC | QQANS---......FPYT | FGQGTKLEIK |
|  | VK1\|L5/JK2 | 60 | ...L.......... | ....D........RN | .......... |
| 6E7 | VK1\|L5/JK2 | 61 | ..............F... | ....D........R. | .......... |
| 5E3 | VK1\|L1/JK3 | 73 | GVPSRFSGSGSG---TDFTLTISSLQPEDFATYYC | QQYNS---......YPFT | FGPGTKVDIK |
|  | VK1\|L1/JK3 | 62 | ...K.......... | ...ST........ | .......... |
| 4G10 | VK1\|A30/JK1 | 74 | GVPSRFSGSGSG---TEFTLTISSLQPEDFATYYC | LQHNS---......YPWT | FGQGTKVEIK |
|  | VK1\|A30/JK1 | 63 | .........P.... | ..................... | ..........T |

FIG. 2B

| Ab ID. | Germline | SEQ ID NO: | L_FR1 | L_CDR1 | L_FR2 | L_CDR2 |
|---|---|---|---|---|---|---|
| 12G10 | VL5\|5c/JL2 | 75 | QAVLTQP--ASLSASPGASASLTC | TLRS-GINVGT-----YRIY | WYQQKPGSPPQYLLR | YKS-----DSDKQQGS |
|  | VL5\|5c/JL2 | 46 | ...P.....S........VL...... | .................. | ............... | ................ |
|  | VL3\|3r/JL2 | 76 | SYELTQP-PSVSVSPGQTASITC | SGD----KLGD-----KYAC | WYQQKPGQSPVLVIY | Q-------DSKRPS |
| 26A10 | VL3\|3r/JL2 | 47 | ................. | V. | ............... | ................ |
| 26C10 | VL3\|3r/JL2 | 48 | .F............... | V. | ........M..... | ....T.... |
| 26F2 | VL3\|3r/JL2 | 49 | ................. | V. | ...........F | ................ |
| 33B12 | VL3\|3r/JL2 | 50 | ................. | V. | ............... | ................ |

FIG. 3A

| Ab ID. | Germline | SEQ ID NO: | L_FR3 | L_CDR3 | | L_FR4 |
|---|---|---|---|---|---|---|
| 12G10 | VL5\|5c/JL2 | 75 | GVPSRFSGSKDASANAGILLISGLQSEDEADYYC | MIWHS------------SASVV | | FGGGTKLTVL |
| | VL5\|5c/JL2 | 46 | ................................ | ...Y.........-SA.. | | ......... |
| 26A10 | VL3\|3r/JL2 | 76 | GIPERFSGSNSG---NTATLTISGTQAMDEADYYC | QAWDS-------STAVV | | FGGGTKLTVL |
| | VL3\|3r/JL2 | 47 | .................................. | ........-NT.. | | ......... |
| 26C10 | VL3\|3r/JL2 | 48 | .................................. | .........-ST.. | | ......... |
| 26F2 | VL3\|3r/JL2 | 49 | .................................. | .........-ST.. | | ......... |
| 33B12 | VL3\|3r/JL2 | 50 | .................................. | .........-ST.. | | ......... |

FIG. 3B

| Ab ID. | Germline | SEQ ID NO: | H_FR1 | H_CDR1 | H_FR2 | H_CDR2 |
|---|---|---|---|---|---|---|
| 12G10 | VH3\|3-23/D3\|3-16\|RF2/JH4 | 127 | EVQLLES-GGGLVQPGGSLRLSCAASG-FTFS | S------YAMS | WVRQAPGKGLEWVS | AISGS---GGSTYYADSVKG |
|  | VH3\|3-23/D3\|3-16\|RF2/JH4 | 110 | ................................ | ........... | .............. | ..G.G....V..C....... |
| 24C12 | VH3\|3-23/D3\|3-16\|RF2/JH4 | 110 | ................................ | ........... | .............. | ..G.G....V..C....... |
| 26A10 | VH3\|3-48/D7\|7-27\|RF1/JH6 | 128 | EVQLVES-GGGLVQPGGSLRLSCAASG-FTFS | S------YSMN | WVRQAPGKGLEWVS | YISSS----SSTIYYADSVKG |
|  | VH3\|3-48/D7\|7-27\|RF1/JH6 | 111 | .........A..R................... | ......FG.S | .............. | ....F................ |
| 26C10 | VH3\|3-48/D7\|7-27\|RF1/JH6 | 112 | .........A...................... | ......FG.S | ........I..... | ....F................ |
| 26F2 | VH3\|3-48/D7\|7-27\|RF1/JH6 | 113 | .........A...................... | ......FG.S | .............. | ....F................ |
| 33B12 | VH3\|3-48/D7\|7-27\|RF1/JH6 | 114 | .........A...................... | ......FG.S | .............. | ..K..F............... |
| 24G6 | VH3\|3-23/D2\|2-21\|RF2/JH4 | 129 | EVQLLES-GGGLVQPGGSLRLSCAASG-FTFS | S------YAMS | WVRQAPGKGLEWVS | AISGS---GGSTYYADSVKG |
|  | VH3\|3-23/D2\|2-21\|RF2/JH4 | 115 | ................................ | ........... | .............. | .................... |
| 24A10 | VH3\|3-23/D1\|1-1\|RF1/JH1 | 130 | EVQLLES-GGGLVQPGGSLRLSCAASG-FTFS | S------YAMS | WVRQAPGKGLEWVS | AISGS---GGSTYYADSVKG |
|  | VH3\|3-23/D1\|1-1\|RF1/JH1 | 116 | ...V............................ | N.......... | .............. | .................... |
| 10E3 | VH5\|5-51/D1\|1-1\|RF1/JH4 | 131 | EVQLVQS-GAEVKKPGESLKISCKGSG-YSFT | S------YWIG | WVRQMPGKGLEWMG | IIYPG---DSDTRYSPSFQG |
|  | VH5\|5-51/D1\|1-1\|RF1/JH4 | 117 | .........M...................... | N.......... | .............. | .................... |
| 13E7 | VH5\|5-51/D1\|1-1\|RF1/JH4 | 118 | .........M...................... | N.......... | .............. | .................... |
| 14C12 |  |  |  |  |  |  |
| 25F12 | VH4\|4-34/D1\|1-1\|RF3/JH3 | 132 | QVQLQQW-GAGLLKPSETLSLTCAVYG-GSFS | G------YYWS | WIRQPPGKGLEWIG | EINH------SGSTNYNPSLKS |
|  | VH4\|4-34/D1\|1-1\|RF3/JH3 | 119 | ................................ | S.......... | .............. | N..................... |
| 32E3 | VH5\|5-51/D5\|5-12\|RF1/JH3 | 133 | EVQLVQS-GAEVKKPGESLKISCKGSG-YSFT | S------YWIG | WVRQMPGKGLEWMG | IIYPG---DSDTRYSPSFQG |
|  | VH5\|5-51/D5\|5-12\|RF1/JH3 | 120 | ................................ | ........... | .............. | .................... |
| 24F4 | VH5\|5-51/D5\|5-12\|RF1/JH5 | 134 | EVQLVQS-GAEVKKPGESLKISCKGSG-YSFT | S------YWIG | WVRQMPGKGLEWMG | IIYPG---DSDTRYSPSFQG |
|  | VH5\|5-51/D5\|5-12\|RF1/JH5 | 121 | ......T......................... | ........... | .............. | .................... |
| 16B8 | VH1\|1-18/D1\|1-26\|RF3/JH4 | 135 | QVQLVQS-GAEVKKPGASVKVSCKASG-YTFT | S------YGIS | WVRQAPGQGLEWMG | WISAY---NGNTNYAQKLQG |
|  | VH1\|1-18/D1\|1-26\|RF3/JH4 | 122 | ................................ | N.......... | .....L........ | ..Y................. |
| 4C5 | VH5\|5-51/D5\|5-12\|RF3/JH4 | 136 | EVQLVQS-GAEVKKPGESLKISCKGSG-YSFT | S------YWIG | WVRQMPGKGLEWMG | IIYPG---DSDTRYSPSFQG |
|  | VH5\|5-51/D5\|5-12\|RF3/JH4 | 123 | ......H......................... | N........A. | .............. | .................... |
| 6E7 | VH5\|5-51/D5\|5-12\|RF3/JH4 | 124 | ................................ | N........A. | .............. | .................... |
| 5E3 | VH1\|1-02/D4\|4-17\|RF2/JH6 | 137 | QVQLVQS-GAEVKKPGASVKVSCKASG-YTFT | G------YYMH | WVRQAPGQGLEWMG | WINPN---SGGTNYAQKFQG |
|  | VH1\|1-02/D4\|4-17\|RF2/JH6 | 125 | ......I......................... | ........... | .....L........ | ..Y....TS.......... |
| 4G10 | VH5\|5-51/D5\|5-12\|RF1/JH6 | 138 | EVQLVQS-GAEVKKPGESLKISCKGSG-YSFT | S------YWIG | WVRQMPGKGLEWMG | IIYPG---DSDTRYSPSFQG |
|  | VH5\|5-51/D5\|5-12\|RF1/JH6 | 126 | .........P...................... | ........A. | .............. | .................... |

FIG. 4A

| Ab ID. | Germline | SEQ ID NO: | H_FR3 | H_CDR3 | H_FR4 |
|---|---|---|---|---|---|
| 12G10 | VH3\|3-23/D3\|3-16\|RF2/JH4 | 127 | RFTISRDNSKNTLYLQMNSLRAEDTAVYYCAK | YYDYVWGS------YRYTYFDY | WGQGTLVTVSS |
| 24C12 | VH3\|3-23/D3\|3-16\|RF2/JH4 | 110 | ............ | F.IA.A-----GSH.... | ......... |
| | VH3\|3-23/D3\|3-16\|RF2/JH4 | 110 | ............ | F.IA.A-----GSH.... | ......... |
| 26A10 | VH3\|3-48/D7\|7-27\|RF1/JH6 | 128 | RFTISRDNAKNSLYLQMNSLRDEDTAVYYCAR | LTGYYY--------YYGMDV | WGQGTTVTVSS |
| 26C10 | VH3\|3-48/D7\|7-27\|RF1/JH6 | 111 | .........F.. | EG.LTMVRG.VSS..L... | ......... |
| 26F2 | VH3\|3-48/D7\|7-27\|RF1/JH6 | 112 | .........F.. | EG.ITMVRG.VSS...... | ......... |
| 33B12 | VH3\|3-48/D7\|7-27\|RF1/JH6 | 113 | .........F.. | EG.ITMVRG.VSS...... | ......... |
| | VH3\|3-48/D7\|7-27\|RF1/JH6 | 114 | .........F.. | EG.LTMVRG.VSS..L... | ......... |
| 24G6 | VH3\|3-23/D2\|2-21\|RF2/JH4 | 129 | RFTISRDNSKNTLYLQMNSLRAEDTAVYYCAK | AVCGGDC-----YSYFDY | WGQGTLVTVSS |
| | VH3\|3-23/D2\|2-21\|RF2/JH4 | 115 | ............ | .TPM----AF... | ......... |
| 24A10 | VH3\|3-23/D1\|1-1\|RF1/JH1 | 130 | RFTISRDNSKNTLYLQMNSLRAEDTAVYYCAR | GTTGTA-----EYFQH | WGQGTLVTVSS |
| | VH3\|3-23/D1\|1-1\|RF1/JH1 | 116 | ............ | .GWE-------LFY | ......... |
| 10E3 | VH5\|5-51/D1\|1-1\|RF1/JH4 | 131 | QVTISADKSISTAYLQWSSLKASDTAMYYCAR | GTTGT-------YFDY | WGQGTLVTVSS |
| 13E7 | VH5\|5-51/D1\|1-1\|RF1/JH4 | 117 | .............F | RRQ.IW....GDAL.I | ......... |
| 14C12 | VH5\|5-51/D1\|1-1\|RF1/JH4 | 118 | .............F | RRQ.IW....GDAL.F | ......... |
| 25F12 | VH4\|4-34/D1\|1-1\|RF3/JH3 | 132 | RVTISVDTSKNQFSLKLSSVTAADTAVYYCAR | YNWND------DAFDI | WGQGTMVTVSS |
| | VH4\|4-34/D1\|1-1\|RF3/JH3 | 119 | ............ | EGYY.I.T---.GYH......F. | .D.......F. |
| 32E3 | VH5\|5-51/D5\|5-12\|RF1/JH3 | 133 | QVTISADKSISTAYLQWSSLKASDTAMYYCAR | VDIVAT-----IDAFDI | WGQGTMVTVSS |
| | VH5\|5-51/D5\|5-12\|RF1/JH3 | 120 | ....T......I. | H..IPAA....PG.... | ......... |
| 24F4 | VH5\|5-51/D5\|5-12\|RF1/JH5 | 134 | QVTISADKSISTAYLQWSSLKASDTAMYYCAR | VDIVAT-----INWFDP | WGQGTLVTVSS |
| | VH5\|5-51/D5\|5-12\|RF1/JH5 | 121 | ...V..S....I..T | QA.AV.G.-----LGG.... | ......... |
| 16B8 | VH1\|1-18/D1\|1-26\|RF3/JH4 | 135 | RVTMTTDTSTSTAYMELRSLRSDDTAVYYCAR | YSGSY------YYFDY | WGQGTLVTVSS |
| | VH1\|1-18/D1\|1-26\|RF3/JH4 | 122 | ........V.... | RGY.......GS.... | ......... |
| 4C5 | VH5\|5-51/D5\|5-12\|RF3/JH4 | 136 | QVTISADKSISTAYLQWSSLKASDTAMYYCAR | YSGSY------YYFDY | WGQGTLVTVSS |
| | VH5\|5-51/D5\|5-12\|RF3/JH4 | 123 | ........V.F.. | QRTF.YD...SSG.... | ......... |
| 6E7 | VH5\|5-51/D5\|5-12\|RF3/JH4 | 124 | .............F | QRTF.YD...SSD.... | ......... |
| 5E3 | VH1\|1-02/D4\|4-17\|RF2/JH6 | 137 | RVTMTRDTSISTAYMELSRLRSDDTAVYYCAR | DYGDYYY----YYYGMDV | WGQGTLVTVSS |
| | VH1\|1-02/D4\|4-17\|RF2/JH6 | 125 | .........S.... | .G.YLA-----L.T... | ......... |
| 4G10 | VH5\|5-51/D5\|5-12\|RF1/JH6 | 138 | QVTISADKSISTAYLQWSSLKASDTAMYYCAR | VDIVATIY---YYYYGMDV | WGQGTTVTVSS |
| | VH5\|5-51/D5\|5-12\|RF1/JH6 | 126 | .......F.K.... | QG.EV.G----TG.L.. | ......... |

FIG. 4B

— TREM2$^{+/+}$ +control antibody

----- TREM2$^{+/+}$ +TREM2 antibody

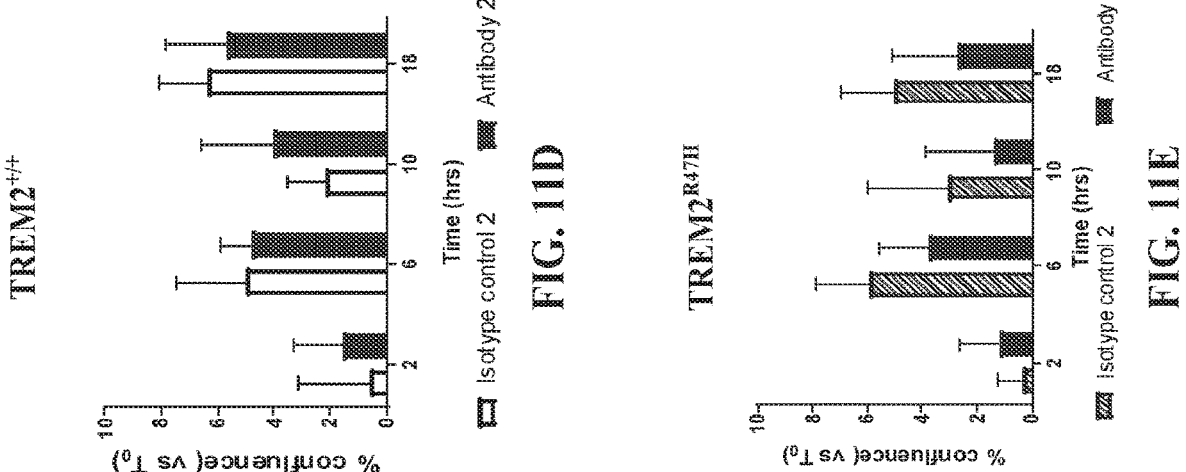

CDC20

PKB

NDC80

CCR2

FIG. 16C
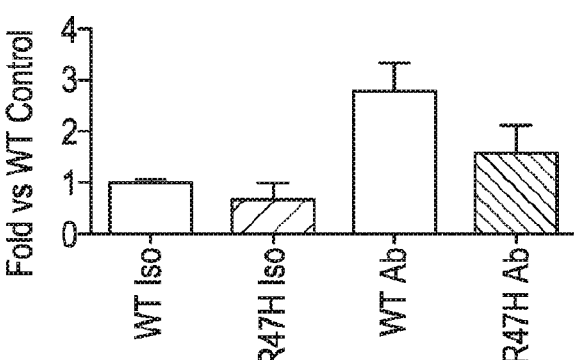
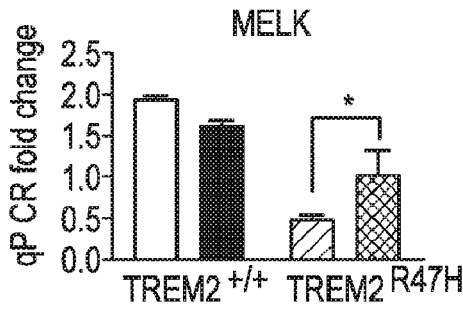
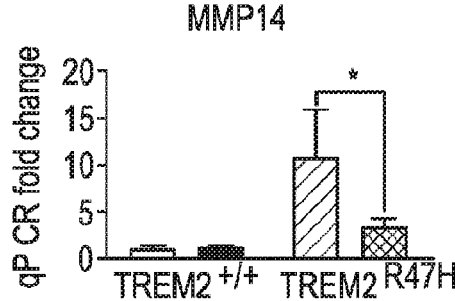

SEQUENCE LISTING

<160> NUMBER OF SEQ ID NOS: 372

<210> SEQ ID NO 1

-continued

```
<211> LENGTH: 230
<212> TYPE: PRT
<213> ORGANISM: Homo sapiens

<400> SEQUENCE: 1

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
            35                  40                  45

Ala Trp Cys Arg Gln Leu Gly Glu Lys Gly Pro Cys Gln Arg Val Val
        50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Phe Pro
        130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
                180                 185                 190

Leu Trp Ala Ala Ala Trp His Gly Gln Lys Pro Gly Thr His Pro Pro
            195                 200                 205

Ser Glu Leu Asp Cys Gly His Asp Pro Gly Tyr Gln Leu Gln Thr Leu
        210                 215                 220

Pro Gly Leu Arg Asp Thr
225                 230

<210> SEQ ID NO 2
<211> LENGTH: 174
<212> TYPE: PRT
<213> ORGANISM: Homo sapiens

<400> SEQUENCE: 2

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
            35                  40                  45

Ala Trp Cys Arg Gln Leu Gly Glu Lys Gly Pro Cys Gln Arg Val Val
        50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110
```

-continued

```
Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser
                165                 170

<210> SEQ ID NO 3
<211> LENGTH: 113
<212> TYPE: PRT
<213> ORGANISM: Homo sapiens

<400> SEQUENCE: 3

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
                20                  25                  30

Cys Ser Cys Ser Thr Val Ser Pro Gly Val Leu Ala Gly Ile Val Met
            35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
                100                 105                 110

Lys

<210> SEQ ID NO 4
<211> LENGTH: 234
<212> TYPE: PRT
<213> ORGANISM: Homo sapiens

<400> SEQUENCE: 4

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
                20                  25                  30

Glu Gly Gln Thr Leu Asp Val Lys Cys Asp Tyr Thr Leu Glu Lys Phe
            35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
                100                 105                 110

Cys Val Ile Tyr Gln Pro Pro Lys Glu Pro His Met Leu Phe Asp Arg
            115                 120                 125

Ile Arg Leu Val Val Thr Lys Gly Phe Ser Gly Thr Pro Gly Ser Asn
    130                 135                 140
```

-continued

```
Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
                180                 185                 190

Thr Asn Val Thr Asp Ile Ile Arg Val Pro Val Phe Asn Ile Val Ile
            195                 200                 205

Leu Leu Ala Gly Gly Phe Leu Ser Lys Ser Leu Val Phe Ser Val Leu
        210                 215                 220

Phe Ala Val Thr Leu Arg Ser Phe Val Pro
225                 230

<210> SEQ ID NO 5
<211> LENGTH: 14
<212> TYPE: PRT
<213> ORGANISM: Artificial Sequence
<220> FEATURE:
<223> OTHER INFORMATION: CRDL1 Antibody ID 12G10

<400> SEQUENCE: 5

Thr Leu Arg Ser Gly Ile Asn Val Gly Thr Tyr Arg Ile Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CDRL1 Antibody ID 26C10

<400> SEQUENCE: 6

Ser Gly Asp Lys Leu Gly Asp Lys Tyr Val Cys
1               5                   10

<210> SEQ ID NO 7
<211> LENGTH: 17
<212> TYPE: PRT
<213> ORGANISM: Artificial Sequence
<220> FEATURE:
<223> OTHER INFORMATION: CDRL1 Antibody ID 24C12

<400> SEQUENCE: 7

Lys Ser Ser Arg Ser Val Leu Tyr Ser Ser Asn Asn Lys Asn Tyr Leu
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: CDRL1 Antibody ID 24G6

<400> SEQUENCE: 8

Lys Ser Ser Gln Ser Val Leu Tyr Ser Ser Asn Asn Lys His Phe Leu
1               5                   10                  15

Ala

<210> SEQ ID NO 9
<211> LENGTH: 17
<212> TYPE: PRT
<213> ORGANISM: Artificial Sequence
```

-continued

```
<220> FEATURE:
<223> OTHER INFORMATION: CDRL1 Antibody ID 24A10

<400> SEQUENCE: 9

Lys Ser Ser His Asn Val Leu Tyr Ser Ser Asn Asn Lys Asn Tyr Leu
1               5                   10                  15

Ala

<210> SEQ ID NO 10
<211> LENGTH: 11
<212> TYPE: PRT
<213> ORGANISM: Artificial Sequence
<220> FEATURE:
<223> OTHER INFORMATION: CDRL1 Antibody ID 10E3

<400> SEQUENCE: 10

Arg Ala Ser Gln Ser Val Ser Ser Asn Leu Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: CDRL1 Antibody ID 25F12

<400> SEQUENCE: 11

Arg Ala Ser Gln Ser Val Asn Asn Asn Leu Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: CDRL1 Antibody ID 32E3

<400> SEQUENCE: 12

Arg Ala Ser Gln Ile Ile Ser Ser Asn Tyr Leu Ala
1               5                   10

<210> SEQ ID NO 13
<211> LENGTH: 12
<212> TYPE: PRT
<213> ORGANISM: Artificial Sequence
<220> FEATURE:
<223> OTHER INFORMATION: CDRL1 Antibody ID 24F4

<400> SEQUENCE: 13

Arg Ala Ser Gln Ser Val Ser Ser Ser Tyr Leu Ala
1               5                   10

<210> SEQ ID NO 14
<211> LENGTH: 11
<212> TYPE: PRT
<213> ORGANISM: Artificial Sequence
<220> FEATURE:
<223> OTHER INFORMATION: CDRL1 Antibody ID 16B8

<400> SEQUENCE: 14

Arg Ala Ser Gln Asp Ile Asn Ser Trp Leu Ala
1               5                   10

<210> SEQ ID NO 15
<211> LENGTH: 11
<212> TYPE: PRT
```

-continued

```
<213> ORGANISM: Artificial Sequence
<220> FEATURE:
<223> OTHER INFORMATION: CDRL1 Antibody ID 4C5

<400> SEQUENCE: 15

Arg Ala Ser Gln Gly Ile Ser Asn Trp Leu Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: CDRL1 Antibody ID 6E7

<400> SEQUENCE: 16

Arg Ala Ser Gln Gly Ile Ser Ser Trp Leu Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: CDRL1 Antibody ID 5E3

<400> SEQUENCE: 17

Arg Ala Ser Gln Gly Ile Ser Asn Tyr Leu Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: CDRL1 Antibody ID 4G10

<400> SEQUENCE: 18

Arg Ala Ser Gln Gly Ile Arg Asn Asp Leu Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: CDRL2 Antibody ID 12G10

<400> SEQUENCE: 19

Tyr Lys Ser Asp Ser Asp Lys Gln Gln Gly Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: CDRL2 Antibody ID 26C10

<400> SEQUENCE: 20

Gln Asp Ser Lys Arg Pro Ser
1               5

<210> SEQ ID NO 21
<211> LENGTH: 7
<212> TYPE: PRT
<213> ORGANISM: Artificial Sequence
```

-continued

```
<220> FEATURE:
<223> OTHER INFORMATION: CDRL2 Antibody ID 26C10

<400> SEQUENCE: 21

Gln Asp Thr Lys Arg Pro Ser
1               5

<210> SEQ ID NO 22
<211> LENGTH: 7
<212> TYPE: PRT
<213> ORGANISM: Artificial Sequence
<220> FEATURE:
<223> OTHER INFORMATION: CDRL2 Antibody ID 24C12

<400> SEQUENCE: 22

Trp Ala Ser Thr Arg Glu Ser
1               5

<210> SEQ ID NO 23
<211> LENGTH: 7
<212> TYPE: PRT
<213> ORGANISM: Artificial Sequence
<220> FEATURE:
<223> OTHER INFORMATION: CDRL2 Antibody ID 10E3

<400> SEQUENCE: 23

Gly Ala Ser Thr Arg Ala Thr
1               5

<210> SEQ ID NO 24
<211> LENGTH: 7
<212> TYPE: PRT
<213> ORGANISM: Artificial Sequence
<220> FEATURE:
<223> OTHER INFORMATION: CDRL2 Antibody ID 32E3

<400> SEQUENCE: 24

Ser Ala Ser Ser Arg Ala Thr
1               5

<210> SEQ ID NO 25
<211> LENGTH: 7
<212> TYPE: PRT
<213> ORGANISM: Artificial Sequence
<220> FEATURE:
<223> OTHER INFORMATION: CDRL2 Antibody ID 24F4

<400> SEQUENCE: 25

Gly Ala Ser Ser Arg Ala Thr
1               5

<210> SEQ ID NO 26
<211> LENGTH: 7
<212> TYPE: PRT
<213> ORGANISM: Artificial Sequence
<220> FEATURE:
<223> OTHER INFORMATION: CDRL2 Antibody ID 16B8

<400> SEQUENCE: 26

Ala Ala Ser Ser Leu Gln Thr
1               5

<210> SEQ ID NO 27
<211> LENGTH: 7
<212> TYPE: PRT
<213> ORGANISM: Artificial Sequence
<220> FEATURE:
```

<223> OTHER INFORMATION: CDRL2 Antibody ID 4C5

<400> SEQUENCE: 27

Ala Ala Ser Ser Leu Gln Val
1               5

<210> SEQ ID NO 28
<211> LENGTH: 7
<212> TYPE: PRT
<213> ORGANISM: Artificial Sequence
<220> FEATURE:
<223> OTHER INFORMATION: CDRL2 Antibody ID 6E7

<400> SEQUENCE: 28

Ala Ala Ser Ser Leu Gln Asn
1               5

<210> SEQ ID NO 29
<211> LENGTH: 7
<212> TYPE: PRT
<213> ORGANISM: Artificial Sequence
<220> FEATURE:
<223> OTHER INFORMATION: CDRL2 Antibody ID 5E3

<400> SEQUENCE: 29

Ala Ala Ser Ser Leu Gln Ser
1               5

<210> SEQ ID NO 30
<211> LENGTH: 7
<212> TYPE: PRT
<213> ORGANISM: Artificial Sequence
<220> FEATURE:
<223> OTHER INFORMATION: CDRL2 Antibody ID 4G10

<400> SEQUENCE: 30

Ala Ala Ser Ser Leu Pro Ser
1               5

<210> SEQ ID NO 31
<211> LENGTH: 9
<212> TYPE: PRT
<213> ORGANISM: Artificial Sequence
<220> FEATURE:
<223> OTHER INFORMATION: CDRL3 Antibody ID 12G10

<400> SEQUENCE: 31

Met Ile Trp Tyr Ser Ser Ala Val Val
1               5

<210> SEQ ID NO 32
<211> LENGTH: 9
<212> TYPE: PRT
<213> ORGANISM: Artificial Sequence
<220> FEATURE:
<223> OTHER INFORMATION: CDRL3 Antibody ID 26A10

<400> SEQUENCE: 32

Gln Ala Trp Asp Ser Asn Thr Val Val
1               5

<210> SEQ ID NO 33
<211> LENGTH: 9
<212> TYPE: PRT
<213> ORGANISM: Artificial Sequence
<220> FEATURE:
<223> OTHER INFORMATION: CDRL3 Antibody ID 26C10

<400> SEQUENCE: 33

Gln Ala Trp Asp Ser Ser Thr Val Val
1               5

<210> SEQ ID NO 34
<211> LENGTH: 9
<212> TYPE: PRT
<213> ORGANISM: Artificial Sequence
<220> FEATURE:
<223> OTHER INFORMATION: CDRL3 Antibody ID 24C12

<400> SEQUENCE: 34

Gln Gln Tyr Tyr Ile Thr Pro Ile Thr
1               5

<210> SEQ ID NO 35
<211> LENGTH: 9
<212> TYPE: PRT
<213> ORGANISM: Artificial Sequence
<220> FEATURE:
<223> OTHER INFORMATION: CDRL3 Antibody ID 24G6

<400> SEQUENCE: 35

Gln Gln Tyr Tyr Ser Thr Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: CDRL3 Antibody 24A10

<400> SEQUENCE: 36

His Gln Tyr Tyr Ser Thr Pro Cys Ser
1               5

<210> SEQ ID NO 37
<211> LENGTH: 9
<212> TYPE: PRT
<213> ORGANISM: Artificial Sequence
<220> FEATURE:
<223> OTHER INFORMATION: CDRL3 Antibody ID 10E3

<400> SEQUENCE: 37

Leu Gln Asp Asn Asn Trp Pro Pro Thr
1               5

<210> SEQ ID NO 38
<211> LENGTH: 9
<212> TYPE: PRT
<213> ORGANISM: Artificial Sequence
<220> FEATURE:
<223> OTHER INFORMATION: CDRL3 Antibody ID 25F12

<400> SEQUENCE: 38

Gln Gln Tyr Asn Asn Trp Pro Arg Thr
1               5

<210> SEQ ID NO 39
<211> LENGTH: 9
<212> TYPE: PRT
<213> ORGANISM: Artificial Sequence
<220> FEATURE:
<223> OTHER INFORMATION: CDRL3 Antibody ID 32E3

-continued

```
<400> SEQUENCE: 39

Gln Gln Phe Asp Ser Ser Pro Ile Thr
1               5

<210> SEQ ID NO 40
<211> LENGTH: 9
<212> TYPE: PRT
<213> ORGANISM: Artificial Sequence
<220> FEATURE:
<223> OTHER INFORMATION: CDRL3 Antibody ID 24F4

<400> SEQUENCE: 40

Gln Gln Tyr Asp Thr Ser Pro Phe Thr
1               5

<210> SEQ ID NO 41
<211> LENGTH: 9
<212> TYPE: PRT
<213> ORGANISM: Artificial Sequence
<220> FEATURE:
<223> OTHER INFORMATION: CDRL3 Antibody ID 16B8

<400> SEQUENCE: 41

Gln Gln Ser Asn Ser Phe Pro Ile Thr
1               5

<210> SEQ ID NO 42
<211> LENGTH: 9
<212> TYPE: PRT
<213> ORGANISM: Artificial Sequence
<220> FEATURE:
<223> OTHER INFORMATION: CDRL3 Antibody ID 4C5

<400> SEQUENCE: 42

Gln Gln Ala Asp Ser Phe Pro Arg Asn
1               5

<210> SEQ ID NO 43
<211> LENGTH: 9
<212> TYPE: PRT
<213> ORGANISM: Artificial Sequence
<220> FEATURE:
<223> OTHER INFORMATION: CDRL3 Antibody ID 6E7

<400> SEQUENCE: 43

Gln Gln Ala Asp Ser Phe Pro Arg Thr
1               5

<210> SEQ ID NO 44
<211> LENGTH: 9
<212> TYPE: PRT
<213> ORGANISM: Artificial Sequence
<220> FEATURE:
<223> OTHER INFORMATION: CDRL3 Antibody ID 5E3

<400> SEQUENCE: 44

Gln Gln Tyr Ser Thr Tyr Pro Phe Thr
1               5

<210> SEQ ID NO 45
<211> LENGTH: 9
<212> TYPE: PRT
<213> ORGANISM: Artificial Sequence
<220> FEATURE:
<223> OTHER INFORMATION: CDRL3 Antibody ID 4G10

<400> SEQUENCE: 45
```

-continued

Leu Gln His Asn Ser Tyr Pro Trp Thr
1               5

<210> SEQ ID NO 46
<211> LENGTH: 115
<212> TYPE: PRT
<213> ORGANISM: Artificial Sequence
<220> FEATURE:
<223> OTHER INFORMATION: VL Amino Acid Sequence Antibody ID 12G10

<400> SEQUENCE: 46

Gln Ala Val Pro Thr Gln Pro Ser Ser Leu Ser Ala Ser Pro Gly Val
1               5                   10                  15

Leu Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp Tyr Ser Ser Ala Val Val Phe Gly Gly Gly Thr Lys Leu
            100                 105                 110

Thr Val Leu
        115

<210> SEQ ID NO 47
<211> LENGTH: 106
<212> TYPE: PRT
<213> ORGANISM: Artificial Sequence
<220> FEATURE:
<223> OTHER INFORMATION: VL Amino Acid Sequence Antibody ID 26A10

<400> SEQUENCE: 47

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr Val Val
                85                  90                  95

Phe Gly Gly Gly Thr Lys Leu Thr Val Leu
            100                 105

<210> SEQ ID NO 48
<211> LENGTH: 106
<212> TYPE: PRT
<213> ORGANISM: Artificial Sequence
<220> FEATURE:
<223> OTHER INFORMATION: VL Amino Acid Sequence Antibody ID 26C10

<400> SEQUENCE: 48

```
Ser Phe Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Met Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

```
<210> SEQ ID NO 49
<211> LENGTH: 106
<212> TYPE: PRT
<213> ORGANISM: Artificial Sequence
<220> FEATURE:
<223> OTHER INFORMATION: VL Amino Acid Sequence Antibody ID 26F2

<400> SEQUENCE: 49
```

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Phe
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

```
<210> SEQ ID NO 50
<211> LENGTH: 106
<212> TYPE: PRT
<213> ORGANISM: Artificial Sequence
<220> FEATURE:
<223> OTHER INFORMATION: VL Amino Acid Sequence Antibody ID 33B12

<400> SEQUENCE: 50
```

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95
```

-continued

```
Phe Gly Gly Gly Thr Lys Leu Thr Val Leu
            100                 105

<210> SEQ ID NO 51
<211> LENGTH: 113
<212> TYPE: PRT
<213> ORGANISM: Artificial Sequence
<220> FEATURE:
<223> OTHER INFORMATION: VL Amino Acid Sequence Antobody ID 24C12

<400> SEQUENCE: 51

Gly Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Asn Cys Gln Gln
                85                  90                  95

Tyr Tyr Ile Thr Pro Ile Thr Phe Gly Gln Gly Thr Arg Leu Glu Ile
            100                 105                 110

Lys

<210> SEQ ID NO 52
<211> LENGTH: 113
<212> TYPE: PRT
<213> ORGANISM: Artificial Sequence
<220> FEATURE:
<223> OTHER INFORMATION: VL Amino Acid Sequence Antibody ID 24G6

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys His Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Phe Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 53
<211> LENGTH: 113
<212> TYPE: PRT
<213> ORGANISM: Artificial Sequence
<220> FEATURE:
<223> OTHER INFORMATION: VL Amino Acid Sequence Antibody ID 24A10

<400> SEQUENCE: 53
```

```
Asp Ile Val Met Thr Gln Ser Pro Asp Ser Leu Ala Val Ser Leu Gly
1               5                   10                  15

Glu Arg Ala Thr Ile Thr Cys Lys Ser Ser His Asn Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Thr Pro Cys Ser Phe Gly Gln Gly Thr Lys Leu Glu Ile
            100                 105                 110

Lys
```

```
<210> SEQ ID NO 54
<211> LENGTH: 107
<212> TYPE: PRT
<213> ORGANISM: Artificial Sequence
<220> FEATURE:
<223> OTHER INFORMATION: VL Amino Acid Sequence Antibody ID 10E3

<400> SEQUENCE: 54
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Phe Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Val
        50                  55                  60

Ser Gly Ser Gly Thr Glu Phe Thr Leu Thr Ile Ser Ser Leu Gln Ser
65                  70                  75                  80

Glu Asp Phe Ala Phe Tyr Tyr Cys Leu Gln Asp Asn Asn Trp Pro Pro
                85                  90                  95

Thr Phe Gly Pro Gly Thr Lys Val Asp Ile Lys
            100                 105
```

```
<210> SEQ ID NO 55
<211> LENGTH: 107
<212> TYPE: PRT
<213> ORGANISM: Artificial Sequence
<220> FEATURE:
<223> OTHER INFORMATION: VL Amino Acid Sequence Antibody ID 13E7 14C12

<400> SEQUENCE: 55
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Phe Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Val
        50                  55                  60

Ser Gly Ser Gly Thr Glu Phe Thr Leu Thr Ile Ser Ser Leu Gln Ser
65                  70                  75                  80
```

-continued

```
Glu Asp Phe Ala Val Tyr Tyr Cys Leu Gln Asp Asn Asn Trp Pro Pro
                85                  90                  95

Thr Phe Gly Pro Gly Thr Lys Val Asp Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: VL Amino Acid Sequence Antibody ID 25F12

<400> SEQUENCE: 56

Glu Lys Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Asn Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105

<210> SEQ ID NO 57
<211> LENGTH: 108
<212> TYPE: PRT
<213> ORGANISM: Artificial Sequence
<220> FEATURE:
<223> OTHER INFORMATION: VL Amino Acid Sequence Antibody ID 25F12

<400> SEQUENCE: 57

Glu Phe Val Leu Thr Gln Ser Pro Gly Thr Leu Ser Leu Ser Pro Gly
1               5                   10                  15

Glu Arg Ala Thr Leu Ser Cys Arg Ala Ser Gln Ile Ile Ser Ser Asn
                20                  25                  30

Tyr Leu Ala Trp Tyr Gln Gln Lys Pro Gly Gln Ala Pro Arg Leu Leu
            35                  40                  45

Ile Tyr Ser Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Ile Thr Phe Gly Arg Gly Thr Arg Leu Asp Ile Lys
            100                 105

<210> SEQ ID NO 58
<211> LENGTH: 108
<212> TYPE: PRT
<213> ORGANISM: Artificial Sequence
<220> FEATURE:
<223> OTHER INFORMATION: VL Amino Acid Sequence Antibody ID 24F4

<400> SEQUENCE: 58
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Tyr Asp Thr Ser Pro
                85                  90                  95

Phe Thr Phe Gly Pro Gly Thr Lys Val Asp Ile Lys
                100                 105
```

```
<210> SEQ ID NO 59
<211> LENGTH: 107
<212> TYPE: PRT
<213> ORGANISM: Artificial Sequence
<220> FEATURE:
<223> OTHER INFORMATION: VL Amino Acid Sequence Antibody ID 16B8

<400> SEQUENCE: 59
```

```
Asp Ile Gln Met Thr Gln Ser Pro Ser Ser Val Ser Ala Ser Val Gly
1               5                   10                  15

Asp Arg Val Thr Val Thr Cys Arg Ala Ser Gln Asp Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Ser Asn Ser Phe Pro Ile
                85                  90                  95

Thr Phe Gly Gln Gly Thr Arg Leu Glu Ile Lys
                100                 105
```

```
<210> SEQ ID NO 60
<211> LENGTH: 107
<212> TYPE: PRT
<213> ORGANISM: Artificial Sequence
<220> FEATURE:
<223> OTHER INFORMATION: VL Amino Acid Sequence Antibody ID 4C5

<400> SEQUENCE: 60
```

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Val Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Arg
                85                  90                  95
```

Asn Phe Gly Gln Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: VL Amino Acid Sequence Antibody ID 6E7

<400> SEQUENCE: 61

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
                85                  90                  95

Thr Phe Gly Gln Gly Thr Lys Leu Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: VL Amino Acid Sequence Antibody ID 5E3

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Phe
                85                  90                  95

Thr Phe Gly Pro Gly Thr Lys Val Asp Ile Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: Exemplary Anti-Human TREM2 Antibody Light Chain
        Variable Region Amino Acid Sequences - VL Amino Acid Sequence

<400> SEQUENCE: 63

Asp Ile Gln Met Thr Gln Ser Pro Ser Ser Leu Ser Ala Ser Val Gly
1               5                   10                  15

-continued

```
Asp Arg Val Thr Ile Thr Cys Arg Ala Ser Gln Gly Ile Arg Asn Asp
            20                  25                  30

Leu Gly Trp Tyr Gln Gln Lys Pro Gly Asn Ala Pro Lys Arg Leu Ile
            35                  40                  45

Tyr Ala Ala Ser Ser Leu Pro Ser Gly Val Pro Ser Arg Phe Ser Gly
    50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Thr
            100                 105
```

```
<210> SEQ ID NO 64
<211> LENGTH: 113
<212> TYPE: PRT
<213> ORGANISM: Homo sapiens

<400> SEQUENCE: 64
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gln Gly Thr Arg Leu Glu Ile
            100                 105                 110

Lys
```

```
<210> SEQ ID NO 65
<211> LENGTH: 113
<212> TYPE: PRT
<213> ORGANISM: Homo sapiens

<400> SEQUENCE: 65
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gln Gly Thr Arg Leu Glu Ile
            100                 105                 110
```

-continued

Lys

<210> SEQ ID NO 66
<211> LENGTH: 113
<212> TYPE: PRT
<213> ORGANISM: Homo sapiens

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 67
<211> LENGTH: 107
<212> TYPE: PRT
<213> ORGANISM: Homo sapiens

<400> SEQUENCE: 67

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 68
<211> LENGTH: 107
<212> TYPE: PRT
<213> ORGANISM: Homo sapiens

<400> SEQUENCE: 68

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

-continued

```
Tyr Gly Ala Ser Thr Arg Ala Thr Gly Ile Pro Ala Arg Phe Ser Gly
    50              55                  60

Ser Gly Ser Gly Thr Glu Phe Thr Leu Thr Ile Ser Ser Leu Gln Ser
65              70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 69
<211> LENGTH: 108
<212> TYPE: PRT
<213> ORGANISM: Homo sapiens

<400> SEQUENCE: 69

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50              55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 70
<211> LENGTH: 108
<212> TYPE: PRT
<213> ORGANISM: Homo sapiens

<400> SEQUENCE: 70

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50              55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 71
<211> LENGTH: 107
<212> TYPE: PRT
<213> ORGANISM: Homo sapiens

<400> SEQUENCE: 71

Asp Ile Gln Met Thr Gln Ser Pro Ser Ser Val Ser Ala Ser Val Gly
```

-continued

```
1               5               10              15

Asp Arg Val Thr Ile Thr Cys Arg Ala Ser Gln Gly Ile Ser Ser Trp
            20              25              30

Leu Ala Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ala Asn Ser Phe Pro Ile
            85              90              95

Thr Phe Gly Gln Gly Thr Arg Leu Glu Ile Lys
        100             105
```

<210> SEQ ID NO 72
<211> LENGTH: 107
<212> TYPE: PRT
<213> ORGANISM: Homo sapiens

<400> SEQUENCE: 72

```
Asp Ile Gln Met Thr Gln Ser Pro Ser Ser Val Ser Ala Ser Val Gly
1               5               10              15

Asp Arg Val Thr Ile Thr Cys Arg Ala Ser Gln Gly Ile Ser Ser Trp
            20              25              30

Leu Ala Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ala Asn Ser Phe Pro Tyr
            85              90              95

Thr Phe Gly Gln Gly Thr Lys Leu Glu Ile Lys
        100             105
```

<210> SEQ ID NO 73
<211> LENGTH: 107
<212> TYPE: PRT
<213> ORGANISM: Homo sapiens

<400> SEQUENCE: 73

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Asn Tyr
            20              25              30

Leu Ala Trp Phe Gln Gln Lys Pro Gly Lys Ala Pro Lys Ser Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Asn Ser Tyr Pro Phe
            85              90              95

Thr Phe Gly Pro Gly Thr Lys Val Asp Ile Lys
        100             105
```

<210> SEQ ID NO 74
<211> LENGTH: 107
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
            85                  90                  95

Thr Phe Gly Gln Gly Thr Lys Val Glu Ile Lys
            100                 105

<210> SEQ ID NO 75
<211> LENGTH: 116
<212> TYPE: PRT
<213> ORGANISM: Homo sapiens

<400> SEQUENCE: 75

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
            85                  90                  95

Met Ile Trp His Ser Ser Ala Ser Val Val Phe Gly Gly Gly Thr Lys
            100                 105                 110

Leu Thr Val Leu
        115

<210> SEQ ID NO 76
<211> LENGTH: 107
<212> TYPE: PRT
<213> ORGANISM: Homo sapiens

<400> SEQUENCE: 76

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu
            100                 105

<210> SEQ ID NO 77
<211> LENGTH: 5
<212> TYPE: PRT
<213> ORGANISM: Artificial Sequence
<220> FEATURE:
<223> OTHER INFORMATION: Exemplary Anti-Human TREM2 Antibody Heavy Chain
      Variable Region Amino Acid Sequences - CDRH1

<400> SEQUENCE: 77

Ser Tyr Ala Met Ser
1               5

<210> SEQ ID NO 78
<211> LENGTH: 5
<212> TYPE: PRT
<213> ORGANISM: Artificial Sequence
<220> FEATURE:
<223> OTHER INFORMATION: CDRH1 Antibody ID 26A10

<400> SEQUENCE: 78

Ser Phe Gly Met Ser
1               5

<210> SEQ ID NO 79
<211> LENGTH: 5
<212> TYPE: PRT
<213> ORGANISM: Artificial Sequence
<220> FEATURE:
<223> OTHER INFORMATION: CDRH1 Antibody ID 24A10

<400> SEQUENCE: 79

Asn Tyr Ala Met Ser
1               5

<210> SEQ ID NO 80
<211> LENGTH: 5
<212> TYPE: PRT
<213> ORGANISM: Artificial Sequence
<220> FEATURE:
<223> OTHER INFORMATION: CDRH1 Antibody ID 10E3

<400> SEQUENCE: 80

Asn Tyr Trp Ile Gly
1               5

<210> SEQ ID NO 81
<211> LENGTH: 5
<212> TYPE: PRT
<213> ORGANISM: Artificial Sequence
<220> FEATURE:
<223> OTHER INFORMATION: CDRH1 Antibody ID 13E7 14C12

<400> SEQUENCE: 81

Ser Tyr Trp Ile Gly
1               5

<210> SEQ ID NO 82
<211> LENGTH: 5

-continued

```
<212> TYPE: PRT
<213> ORGANISM: Artificial Sequence
<220> FEATURE:
<223> OTHER INFORMATION: CDRH1 Antibody ID 25F12

<400> SEQUENCE: 82

Ser Tyr Tyr Trp Ser
1               5

<210> SEQ ID NO 83
<211> LENGTH: 5
<212> TYPE: PRT
<213> ORGANISM: Artificial Sequence
<220> FEATURE:
<223> OTHER INFORMATION: CDRH1 Antibody 16B8

<400> SEQUENCE: 83

Asn Tyr Gly Ile Ser
1               5

<210> SEQ ID NO 84
<211> LENGTH: 5
<212> TYPE: PRT
<213> ORGANISM: Artificial Sequence
<220> FEATURE:
<223> OTHER INFORMATION: CDRH1 Antibody ID 4C5

<400> SEQUENCE: 84

Asn Tyr Trp Ile Ala
1               5

<210> SEQ ID NO 85
<211> LENGTH: 5
<212> TYPE: PRT
<213> ORGANISM: Artificial Sequence
<220> FEATURE:
<223> OTHER INFORMATION: CDRH1 Antibody ID 6E7

<400> SEQUENCE: 85

Ser Tyr Trp Ile Ala
1               5

<210> SEQ ID NO 86
<211> LENGTH: 5
<212> TYPE: PRT
<213> ORGANISM: Artificial Sequence
<220> FEATURE:
<223> OTHER INFORMATION: CDRH1 Antibody ID 5E3

<400> SEQUENCE: 86

Gly Tyr Tyr Ile His
1               5

<210> SEQ ID NO 87
<211> LENGTH: 17
<212> TYPE: PRT
<213> ORGANISM: Artificial Sequence
<220> FEATURE:
<223> OTHER INFORMATION: CDRH2 Antibody ID 12G10 24C12

<400> SEQUENCE: 87

Ala Ile Gly Gly Gly Gly Val Ser Thr Tyr Cys Ala Asp Ser Val Lys
1               5                   10                  15

Gly

<210> SEQ ID NO 88
```

<211> LENGTH: 17
<212> TYPE: PRT
<213> ORGANISM: Artificial Sequence
<220> FEATURE:
<223> OTHER INFORMATION: Exemplary Anti-Human TREM2 Antibody Heavy Chain
      Variable Region Amino Acid Sequences - CDRH2

<400> SEQUENCE: 88

Tyr Ile Ser Ser Ser Ser Phe Thr Ile Tyr Tyr Ala Asp Ser Val Lys
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: CDRH2 Antibidy 26A10

<400> SEQUENCE: 89

Tyr Ile Ser Lys Ser Ser Phe Thr Ile Tyr Tyr Ala Asp Ser Val Lys
1               5                   10                  15

Gly

<210> SEQ ID NO 90
<211> LENGTH: 17
<212> TYPE: PRT
<213> ORGANISM: Artificial Sequence
<220> FEATURE:
<223> OTHER INFORMATION: CDRH2 Antibody ID24G6

<400> SEQUENCE: 90

Ala Ile Ser Gly Ser Gly Gly Ser Thr Tyr Tyr Ala Asp Ser Val Lys
1               5                   10                  15

Gly

<210> SEQ ID NO 91
<211> LENGTH: 17
<212> TYPE: PRT
<213> ORGANISM: Artificial Sequence
<220> FEATURE:
<223> OTHER INFORMATION: CDRH2 Antibody ID 10E3

<400> SEQUENCE: 91

Ile Ile Tyr Pro Gly Asp Ser Asp Thr Arg Tyr Ser Pro Ser Phe Gln
1               5                   10                  15

Gly

<210> SEQ ID NO 92
<211> LENGTH: 16
<212> TYPE: PRT
<213> ORGANISM: Artificial Sequence
<220> FEATURE:
<223> OTHER INFORMATION: CDRH2 Antibody ID 25F12

<400> SEQUENCE: 92

Glu Ile Asn His Ser Gly Asn Thr Asn Tyr Asn Pro Ser Leu Lys Ser
1               5                   10                  15

<210> SEQ ID NO 93
<211> LENGTH: 17
<212> TYPE: PRT
<213> ORGANISM: Artificial Sequence
<220> FEATURE:
<223> OTHER INFORMATION: CDRH2 Antibody ID 16B8

<400> SEQUENCE: 93

Trp Ile Ser Ala Tyr Asn Gly Asn Thr Asn Tyr Ala Gln Lys Leu Gln
1               5                   10                  15

Gly

<210> SEQ ID NO 94
<211> LENGTH: 17
<212> TYPE: PRT
<213> ORGANISM: Artificial Sequence
<220> FEATURE:
<223> OTHER INFORMATION: CDRH2 Antibody 4C5

<400> SEQUENCE: 94

Trp Ile Asn Pro Tyr Ser Gly Gly Thr Thr Ser Ala Gln Lys Phe Gln
1               5                   10                  15

Gly

<210> SEQ ID NO 95
<211> LENGTH: 12
<212> TYPE: PRT
<213> ORGANISM: Artificial Sequence
<220> FEATURE:
<223> OTHER INFORMATION: CDRH3 Antibody 12G10 24C12

<400> SEQUENCE: 95

Phe Tyr Ile Ala Val Ala Gly Ser His Phe Asp Tyr
1               5                   10

<210> SEQ ID NO 96
<211> LENGTH: 17
<212> TYPE: PRT
<213> ORGANISM: Artificial Sequence
<220> FEATURE:
<223> OTHER INFORMATION: CDRH3 Antibody ID 26A10

<400> SEQUENCE: 96

Glu Gly Gly Leu Thr Met Val Arg Gly Val Ser Ser Tyr Gly Leu Asp
1               5                   10                  15

Val

<210> SEQ ID NO 97
<211> LENGTH: 17
<212> TYPE: PRT
<213> ORGANISM: Artificial Sequence
<220> FEATURE:
<223> OTHER INFORMATION: CDRH3 Antibody ID 26C10

<400> SEQUENCE: 97

Glu Gly Gly Ile Thr Met Val Arg Gly Val Ser Ser Tyr Gly Met Asp
1               5                   10                  15

Val

<210> SEQ ID NO 98
<211> LENGTH: 10
<212> TYPE: PRT
<213> ORGANISM: Artificial Sequence
<220> FEATURE:
<223> OTHER INFORMATION: CDRH3 Antibody ID 24G6

<400> SEQUENCE: 98

Ala Tyr Thr Pro Met Ala Phe Phe Asp Tyr
1               5                   10

-continued

<210> SEQ ID NO 99
<211> LENGTH: 7
<212> TYPE: PRT
<213> ORGANISM: Artificial Sequence
<220> FEATURE:
<223> OTHER INFORMATION: CDRH3 Antibody ID 24A10

<400> SEQUENCE: 99

Gly Gly Trp Glu Leu Phe Tyr
1               5

<210> SEQ ID NO 100
<211> LENGTH: 12
<212> TYPE: PRT
<213> ORGANISM: Artificial Sequence
<220> FEATURE:
<223> OTHER INFORMATION: CDRH3 Antibody ID 10E3

<400> SEQUENCE: 100

Arg Arg Gln Gly Ile Trp Gly Asp Ala Leu Asp Ile
1               5                   10

<210> SEQ ID NO 101
<211> LENGTH: 12
<212> TYPE: PRT
<213> ORGANISM: Artificial Sequence
<220> FEATURE:
<223> OTHER INFORMATION: CDRH3 Antibody ID 13E7 14C12

<400> SEQUENCE: 101

Arg Arg Gln Gly Ile Trp Gly Asp Ala Leu Asp Phe
1               5                   10

<210> SEQ ID NO 102
<211> LENGTH: 16
<212> TYPE: PRT
<213> ORGANISM: Artificial Sequence
<220> FEATURE:
<223> OTHER INFORMATION: CDRH3 Antibody ID 25F12

<400> SEQUENCE: 102

Glu Gly Tyr Tyr Asp Ile Leu Thr Gly Tyr His Asp Ala Phe Asp Ile
1               5                   10                  15

<210> SEQ ID NO 103
<211> LENGTH: 13
<212> TYPE: PRT
<213> ORGANISM: Artificial Sequence
<220> FEATURE:
<223> OTHER INFORMATION: CDRH3 Antibody ID 32E3

<400> SEQUENCE: 103

His Asp Ile Ile Pro Ala Ala Pro Gly Ala Phe Asp Ile
1               5                   10

<210> SEQ ID NO 104
<211> LENGTH: 13
<212> TYPE: PRT
<213> ORGANISM: Artificial Sequence
<220> FEATURE:
<223> OTHER INFORMATION: CDRH3 Antibody ID 24F4

<400> SEQUENCE: 104

Gln Ala Ile Ala Val Thr Gly Leu Gly Gly Phe Asp Pro
1               5                   10

<210> SEQ ID NO 105
<211> LENGTH: 10
<212> TYPE: PRT
<213> ORGANISM: Artificial Sequence
<220> FEATURE:
<223> OTHER INFORMATION: CDRH3 Antibody ID 16B8

<400> SEQUENCE: 105

Arg Gly Tyr Ser Tyr Gly Ser Phe Asp Tyr
1               5                   10

<210> SEQ ID NO 106
<211> LENGTH: 14
<212> TYPE: PRT
<213> ORGANISM: Artificial Sequence
<220> FEATURE:
<223> OTHER INFORMATION: CDRH3 Antibody ID 4C5

<400> SEQUENCE: 106

Gln Arg Thr Phe Tyr Tyr Asp Ser Ser Gly Tyr Phe Asp Tyr
1               5                   10

<210> SEQ ID NO 107
<211> LENGTH: 14
<212> TYPE: PRT
<213> ORGANISM: Artificial Sequence
<220> FEATURE:
<223> OTHER INFORMATION: CDRH3 Antibody ID 6E7

<400> SEQUENCE: 107

Gln Arg Thr Phe Tyr Tyr Asp Ser Ser Asp Tyr Phe Asp Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: CDRH3 Antibody ID 5E3

<400> SEQUENCE: 108

Asp Gly Gly Tyr Leu Ala Leu Tyr Gly Thr Asp Val
1               5                   10

<210> SEQ ID NO 109
<211> LENGTH: 13
<212> TYPE: PRT
<213> ORGANISM: Artificial Sequence
<220> FEATURE:
<223> OTHER INFORMATION: CDRH3 Antibody ID 4G10

<400> SEQUENCE: 109

Gln Gly Ile Glu Val Thr Gly Thr Gly Gly Leu Asp Val
1               5                   10

<210> SEQ ID NO 110
<211> LENGTH: 121
<212> TYPE: PRT
<213> ORGANISM: Artificial Sequence
<220> FEATURE:
<223> OTHER INFORMATION: VH Amino Acid Sequence Antibody ID 12G10 24C12

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

```
Ala Met Ser Trp Val Arg Gln Ala Pro Gly Lys Gly Leu Glu Trp Val
        35                  40                  45

Ser Ala Ile Gly Gly Gly Val Ser Thr Tyr Cys Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Tyr Ile Ala Val Ala Gly Ser His Phe Asp Tyr Trp Gly
            100                 105                 110

Gln Gly Thr Leu Val Thr Val Ser Ser
        115                 120
```

<210> SEQ ID NO 111
<211> LENGTH: 126
<212> TYPE: PRT
<213> ORGANISM: Artificial Sequence
<220> FEATURE:
<223> OTHER INFORMATION: VH Amino Acid Sequence Antibody ID 26A10

<400> SEQUENCE: 111

```
Glu Val Gln Leu Val Glu Ser Gly Gly Ala Leu Val Gln Arg Gly Gly
1               5                   10                  15

Ser Leu Arg Leu Ser Cys Ala Ala Ser Arg Phe Thr Phe Ser Ser Phe
            20                  25                  30

Gly Met Ser Trp Val Arg Gln Ala Pro Gly Lys Gly Leu Glu Trp Val
        35                  40                  45

Ser Tyr Ile Ser Ser Ser Ser Phe Thr Ile Tyr Tyr Ala Asp Ser Val
    50                  55                  60

Lys Gly Arg Phe Thr Ile Ser Arg Asp Asn Ala Lys Asn Ser Phe Tyr
65                  70                  75                  80

Leu Gln Met Asn Ser Leu Arg Asp Glu Asp Thr Ala Val Tyr Tyr Cys
                85                  90                  95

Ala Arg Glu Gly Gly Leu Thr Met Val Arg Gly Val Ser Ser Tyr Gly
            100                 105                 110

Leu Asp Val Trp Gly Gln Gly Thr Thr Val Thr Val Ser Ser
        115                 120                 125
```

<210> SEQ ID NO 112
<211> LENGTH: 126
<212> TYPE: PRT
<213> ORGANISM: Artificial Sequence
<220> FEATURE:
<223> OTHER INFORMATION: VH Amino Acid Sequence Antibody ID 26C10

<400> SEQUENCE: 112

```
Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Tyr Ile Ser Ser Ser Ser Phe Thr Ile Tyr Tyr Ala Asp Ser Val
    50                  55                  60

Lys Gly Arg Phe Thr Ile Ser Arg Asp Asn Ala Lys Asn Ser Phe Tyr
65                  70                  75                  80

Leu Gln Met Asn Ser Leu Arg Asp Glu Asp Thr Ala Val Tyr Phe Cys
```

-continued

```
                  85                  90                  95
Val Arg Glu Gly Gly Ile Thr Met Val Arg Gly Val Ser Ser Tyr Gly
            100                 105                 110

Met Asp Val Trp Gly Gln Gly Thr Thr Val Thr Val Ser Ser
        115                 120                 125

<210> SEQ ID NO 113
<211> LENGTH: 126
<212> TYPE: PRT
<213> ORGANISM: Artificial Sequence
<220> FEATURE:
<223> OTHER INFORMATION: VH Amino Acid Sequence Antibody ID 26F2

<400> SEQUENCE: 113

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Ile
        35                  40                  45

Ser Tyr Ile Ser Ser Ser Ser Phe Thr Ile Tyr Tyr Ala Asp Ser Val
    50                  55                  60

Lys Gly Arg Phe Thr Ile Ser Arg Asp Asn Ala Lys Asn Ser Phe Tyr
65                  70                  75                  80

Leu Gln Met Asn Ser Leu Arg Asp Glu Asp Thr Ala Val Tyr Phe Cys
                85                  90                  95

Ala Arg Glu Gly Gly Ile Thr Met Val Arg Gly Val Ser Ser Tyr Gly
            100                 105                 110

Met Asp Val Trp Gly Gln Gly Thr Thr Val Thr Val Ser Ser
        115                 120                 125

<210> SEQ ID NO 114
<211> LENGTH: 126
<212> TYPE: PRT
<213> ORGANISM: Artificial Sequence
<220> FEATURE:
<223> OTHER INFORMATION: VH Amino Acid Sequence Antibody ID 33B12

<400> SEQUENCE: 114

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Tyr Ile Ser Lys Ser Ser Phe Thr Ile Tyr Tyr Ala Asp Ser Val
    50                  55                  60

Lys Gly Arg Phe Thr Ile Ser Arg Asp Asn Ala Lys Asn Ser Phe Tyr
65                  70                  75                  80

Leu Gln Met Asn Ser Leu Arg Asp Glu Asp Thr Ala Val Tyr Tyr Cys
                85                  90                  95

Ala Arg Glu Gly Gly Leu Thr Met Val Arg Gly Val Ser Ser Tyr Gly
            100                 105                 110

Leu Asp Val Trp Gly Gln Gly Thr Thr Val Thr Val Ser Ser
        115                 120                 125

<210> SEQ ID NO 115
<211> LENGTH: 119
```

<212> TYPE: PRT
<213> ORGANISM: Artificial Sequence
<220> FEATURE:
<223> OTHER INFORMATION: VH Amino Acid Sequence Antibody ID 24G6

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Thr Pro Met Ala Phe Phe Asp Tyr Trp Gly Gln Gly
            100                 105                 110

Thr Leu Val Thr Val Ser Ser
        115

<210> SEQ ID NO 116
<211> LENGTH: 116
<212> TYPE: PRT
<213> ORGANISM: Artificial Sequence
<220> FEATURE:
<223> OTHER INFORMATION: VH Amino Acid Sequence Antibody ID 24A10

<400> SEQUENCE: 116

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Trp Glu Leu Phe Tyr Trp Gly Gln Gly Thr Leu Val
            100                 105                 110

Thr Val Ser Ser
        115

<210> SEQ ID NO 117
<211> LENGTH: 121
<212> TYPE: PRT
<213> ORGANISM: Artificial Sequence
<220> FEATURE:
<223> OTHER INFORMATION: VH Amino Acid Sequence Antibody ID 10E3

<400> SEQUENCE: 117

Glu Val Gln Leu Val Gln Ser Gly Ala Glu Val Lys Lys Pro Gly Glu
1               5                   10                  15

Ser Leu Met Ile Ser Cys Lys Gly Ser Gly Tyr Ser Phe Thr Asn Tyr

-continued

```
                20              25              30

Trp Ile Gly Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Phe Cys
            85              90              95

Ala Arg Arg Arg Gln Gly Ile Trp Gly Asp Ala Leu Asp Ile Trp Gly
            100             105             110

Gln Gly Thr Leu Val Thr Val Ser Ser
        115             120
```

<210> SEQ ID NO 118
<211> LENGTH: 121
<212> TYPE: PRT
<213> ORGANISM: Artificial Sequence
<220> FEATURE:
<223> OTHER INFORMATION: VH Amino Acid Sequence Antibody ID 13E7 14C12

<400> SEQUENCE: 118

```
Glu Val Gln Leu Val Gln Ser Gly Ala Glu Val Lys Lys Pro Gly Glu
1               5               10              15

Ser Leu Met Ile Ser Cys Lys Gly Ser Gly Tyr Ser Phe Thr Ser Tyr
                20              25              30

Trp Ile Gly Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Phe Cys
            85              90              95

Ala Arg Arg Arg Gln Gly Ile Trp Gly Asp Ala Leu Asp Phe Trp Gly
            100             105             110

Gln Gly Thr Leu Val Thr Val Ser Ser
        115             120
```

<210> SEQ ID NO 119
<211> LENGTH: 124
<212> TYPE: PRT
<213> ORGANISM: Artificial Sequence
<220> FEATURE:
<223> OTHER INFORMATION: VH Amino Acid Sequence Antibody ID 25F12

<400> SEQUENCE: 119

```
Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Ser Tyr
                20              25              30

Tyr Trp Ser Trp Ile Arg Gln Pro Pro Gly Lys Gly Leu Glu Trp Ile
        35              40              45

Gly Glu Ile Asn His Ser Gly Asn Thr Asn Tyr Asn Pro Ser Leu Lys
    50              55              60

Ser Arg Val Thr Ile Ser Val Asp Thr Ser Lys Asn Gln Phe Ser Leu
65              70              75              80
```

-continued

---

```
Lys Leu Ser Ser Val Thr Ala Ala Asp Thr Ala Val Tyr Tyr Cys Ala
            85                  90                  95

Arg Glu Gly Tyr Tyr Asp Ile Leu Thr Gly Tyr His Asp Ala Phe Asp
            100                 105                 110

Ile Trp Asp Gln Gly Thr Met Val Thr Val Phe Ser
        115                 120

<210> SEQ ID NO 120
<211> LENGTH: 122
<212> TYPE: PRT
<213> ORGANISM: Artificial Sequence
<220> FEATURE:
<223> OTHER INFORMATION: VH Amino Acid Sequence Antibody ID 32E3

<400> SEQUENCE: 120

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Thr Leu Lys Ala Ser Asp Thr Ala Ile Tyr Tyr Cys
            85                  90                  95

Ala Arg His Asp Ile Ile Pro Ala Ala Pro Gly Ala Phe Asp Ile Trp
            100                 105                 110

Gly Gln Gly Thr Met Val Thr Val Ser Ser
        115                 120

<210> SEQ ID NO 121
<211> LENGTH: 122
<212> TYPE: PRT
<213> ORGANISM: Artificial Sequence
<220> FEATURE:
<223> OTHER INFORMATION: VH Amino Acid Sequence Antibody ID 24F4

<400> SEQUENCE: 121

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
        50                  55                  60

Gln Gly Gln Val Thr Ile Ser Val Asp Lys Ser Ser Ser Thr Ala Tyr
65                  70                  75                  80

Leu Gln Trp Ser Ser Leu Lys Ala Ser Asp Thr Ala Ile Tyr Tyr Cys
            85                  90                  95

Thr Arg Gln Ala Ile Ala Val Thr Gly Leu Gly Gly Phe Asp Pro Trp
            100                 105                 110

Gly Gln Gly Thr Leu Val Thr Val Ser Ser
        115                 120

<210> SEQ ID NO 122
```

```
<211> LENGTH: 119
<212> TYPE: PRT
<213> ORGANISM: Artificial Sequence
<220> FEATURE:
<223> OTHER INFORMATION: VH Amino Acid Sequence Antibody ID 16B8

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Arg Gly Tyr Ser Tyr Gly Ser Phe Asp Tyr Trp Gly Gln Gly
            100                 105                 110

Thr Leu Val Thr Val Ser Ser
        115

<210> SEQ ID NO 123
<211> LENGTH: 123
<212> TYPE: PRT
<213> ORGANISM: Artificial Sequence
<220> FEATURE:
<223> OTHER INFORMATION: VH Amino Acid Sequence Antibody ID 4C5

<400> SEQUENCE: 123

Glu Val Gln Leu Val Gln Ser Gly Ala Glu Val Lys Lys Pro Gly Glu
1               5                   10                  15

Ser Leu Lys Ile Ser Cys Lys Gly Ser Gly His Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Phe Cys
                85                  90                  95

Ala Arg Gln Arg Thr Phe Tyr Tyr Asp Ser Ser Gly Tyr Phe Asp Tyr
            100                 105                 110

Trp Gly Gln Gly Thr Leu Val Thr Val Ser Ser
        115                 120

<210> SEQ ID NO 124
<211> LENGTH: 123
<212> TYPE: PRT
<213> ORGANISM: Artificial Sequence
<220> FEATURE:
<223> OTHER INFORMATION: VH Amino Acid Sequence Antibody ID 6E7

<400> SEQUENCE: 124

Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
        20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Phe Asp Tyr
            100                 105                 110

Trp Gly Gln Gly Thr Leu Val Thr Val Ser Ser
        115                 120

<210> SEQ ID NO 125
<211> LENGTH: 121
<212> TYPE: PRT
<213> ORGANISM: Artificial Sequence
<220> FEATURE:
<223> OTHER INFORMATION: VH Amino Acid Sequence Antibody ID 5E3

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
        20                  25                  30

Tyr Ile His Trp Val Arg Gln Ala Pro Gly Leu Gly Leu Glu Trp Met
        35                  40                  45

Gly Trp Ile Asn Pro Tyr Ser Gly Gly Thr Thr Ser Ala Gln Lys Phe
    50                  55                  60

Gln Gly Arg Val Thr Met Thr Arg Asp Thr Ser Ile Ser Ser Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Tyr Leu Ala Leu Tyr Gly Thr Asp Val Trp Gly
            100                 105                 110

Gln Gly Thr Thr Val Thr Val Ser Ser
        115                 120

<210> SEQ ID NO 126
<211> LENGTH: 122
<212> TYPE: PRT
<213> ORGANISM: Artificial Sequence
<220> FEATURE:
<223> OTHER INFORMATION: VH Amino Acid Sequence Antibody ID 4G10

<400> SEQUENCE: 126

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Pro Ser Tyr
        20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Phe
65                  70                  75                  80
```

```
Leu Lys Trp Ser Ser Leu Lys Ala Ser Asp Thr Ala Met Tyr Phe Cys
                85                  90                  95

Ala Arg Gln Gly Ile Glu Val Thr Gly Thr Gly Gly Leu Asp Val Trp
            100                 105                 110

Gly Gln Gly Thr Thr Val Thr Val Ser Ser
        115                 120

<210> SEQ ID NO 127
<211> LENGTH: 125
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Tyr Asp Tyr Val Trp Gly Ser Tyr Arg Tyr Thr Tyr Phe
            100                 105                 110

Asp Tyr Trp Gly Gln Gly Thr Leu Val Thr Val Ser Ser
        115                 120                 125

<210> SEQ ID NO 128
<211> LENGTH: 121
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Leu Thr Gly Tyr Tyr Tyr Tyr Tyr Gly Met Asp Val Trp Gly
            100                 105                 110

Gln Gly Thr Thr Val Thr Val Ser Ser
        115                 120

<210> SEQ ID NO 129
<211> LENGTH: 122
<212> TYPE: PRT
<213> ORGANISM: Homo sapiens
```

-continued

```
<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Cys Gly Gly Asp Cys Tyr Ser Tyr Phe Asp Tyr Trp
            100                 105                 110

Gly Gln Gly Thr Leu Val Thr Val Ser Ser
        115                 120

<210> SEQ ID NO 130
<211> LENGTH: 120
<212> TYPE: PRT
<213> ORGANISM: Homo sapiens

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Gly Thr Ala Glu Tyr Phe Gln His Trp Gly Gln
            100                 105                 110

Gly Thr Leu Val Thr Val Ser Ser
        115                 120

<210> SEQ ID NO 131
<211> LENGTH: 118
<212> TYPE: PRT
<213> ORGANISM: Homo sapiens

<400> SEQUENCE: 131

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

-continued

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Thr Thr Gly Thr Tyr Phe Asp Tyr Trp Gly Gln Gly Thr
            100                 105                 110

Leu Val Thr Val Ser Ser
        115

<210> SEQ ID NO 132
<211> LENGTH: 118
<212> TYPE: PRT
<213> ORGANISM: Homo sapiens

<400> SEQUENCE: 132

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Asn Trp Asn Asp Asp Ala Phe Asp Ile Trp Gly Gln Gly Thr
            100                 105                 110

Met Val Thr Val Ser Ser
        115

<210> SEQ ID NO 133
<211> LENGTH: 121
<212> TYPE: PRT
<213> ORGANISM: Homo sapiens

<400> SEQUENCE: 133

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Asp Ile Val Ala Thr Ile Asp Ala Phe Asp Ile Trp Gly
            100                 105                 110

Gln Gly Thr Met Val Thr Val Ser Ser
        115                 120

<210> SEQ ID NO 134
<211> LENGTH: 121
```

<212> TYPE: PRT
<213> ORGANISM: Homo sapiens

<400> SEQUENCE: 134

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Asp Ile Val Ala Thr Ile Asn Trp Phe Asp Pro Trp Gly
            100                 105                 110

Gln Gly Thr Leu Val Thr Val Ser Ser
        115                 120
```

<210> SEQ ID NO 135
<211> LENGTH: 119
<212> TYPE: PRT
<213> ORGANISM: Homo sapiens

<400> SEQUENCE: 135

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Gly Ser Tyr Tyr Tyr Phe Asp Tyr Trp Gly Gln Gly
            100                 105                 110

Thr Leu Val Thr Val Ser Ser
        115
```

<210> SEQ ID NO 136
<211> LENGTH: 119
<212> TYPE: PRT
<213> ORGANISM: Homo sapiens

<400> SEQUENCE: 136

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
```

-continued

```
          50                    55                    60

Gln Gly Gln Val Thr Ile Ser Ala Asp Lys Ser Ile Ser Thr Ala Tyr
65                    70                    75                    80

Leu Gln Trp Ser Ser Leu Lys Ala Ser Asp Thr Ala Met Tyr Tyr Cys
                  85                    90                    95

Ala Arg Tyr Ser Gly Ser Tyr Tyr Tyr Phe Asp Tyr Trp Gly Gln Gly
              100                   105                   110

Thr Leu Val Thr Val Ser Ser
          115

<210> SEQ ID NO 137
<211> LENGTH: 123
<212> TYPE: PRT
<213> ORGANISM: Homo sapiens

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
              20                  25                  30

Tyr Met His Trp Val Arg Gln Ala Pro Gly Gln Gly Leu Glu Trp Met
          35                  40                  45

Gly Trp Ile Asn Pro Asn Ser Gly Gly Thr Asn Tyr Ala Gln Lys Phe
      50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                  85                  90                  95

Ala Arg Asp Tyr Gly Asp Tyr Tyr Tyr Tyr Tyr Gly Met Asp Val
              100                 105                 110

Trp Gly Gln Gly Thr Thr Val Thr Val Ser Ser
          115                 120

<210> SEQ ID NO 138
<211> LENGTH: 125
<212> TYPE: PRT
<213> ORGANISM: Homo sapiens

<400> SEQUENCE: 138

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
              20                  25                  30

Trp Ile Gly Trp Val Arg Gln Met Pro Gly Lys Gly Leu Glu Trp Met
          35                  40                  45

Gly Ile Ile Tyr Pro Gly Asp Ser Asp Thr Arg Tyr Ser Pro Ser Phe
      50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                  85                  90                  95

Ala Arg Val Asp Ile Val Ala Thr Ile Tyr Tyr Tyr Tyr Gly Met
              100                 105                 110

Asp Val Trp Gly Gln Gly Thr Thr Val Thr Val Ser Ser
          115                 120                 125
```

```
<210> SEQ ID NO 139
<211> LENGTH: 7
<212> TYPE: PRT
<213> ORGANISM: Artificial Sequence
<220> FEATURE:
<223> OTHER INFORMATION: CDRL2 Consensus for 6E7 improved Affinity
      variants
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (5)..(5)
<223> OTHER INFORMATION: X is L or R
<220> FEATURE:
<221> NAME/KEY: MISC_FEATURE
<222> LOCATION: (7)..(7)
<223> OTHER INFORMATION: X is N, K, R, L, or T

<400> SEQUENCE: 139

Xaa Ala Ser Ser Xaa Gln Xaa
1               5

<210> SEQ ID NO 140
<211> LENGTH: 9
<212> TYPE: PRT
<213> ORGANISM: Artificial Sequence
<220> FEATURE:
<223> OTHER INFORMATION: CDRL3 Consensus for 6E7 improved Affinity
      variants
<220> FEATURE:
<221> NAME/KEY: MISC_FEATURE
<222> LOCATION: (1)..(1)
<223> OTHER INFORMATION: X is Q or G
<220> FEATURE:
<221> NAME/KEY: MISC_FEATURE
<222> LOCATION: (5)..(5)
<223> OTHER INFORMATION: X is S or R
<220> FEATURE:
<221> NAME/KEY: MISC_FEATURE
<222> LOCATION: (6)..(6)
<223> OTHER INFORMATION: X is F, L or Y
<220> FEATURE:
<221> NAME/KEY: MISC_FEATURE
<222> LOCATION: (8)..(8)
<223> OTHER INFORMATION: X is R or H

<400> SEQUENCE: 140

Xaa Gln Ala Asp Xaa Xaa Pro Xaa Thr
1               5

<210> SEQ ID NO 141
<211> LENGTH: 17
<212> TYPE: PRT
<213> ORGANISM: Artificial Sequence
<220> FEATURE:
<223> OTHER INFORMATION: CDRH2 Consensus for 6E7 improved Affinity
      variants
<220> FEATURE:
<221> NAME/KEY: MISC_FEATURE
<222> LOCATION: (1)..(1)
<223> OTHER INFORMATION: X is I or T
<220> FEATURE:
<221> NAME/KEY: MISC_FEATURE
<222> LOCATION: (9)..(9)
<223> OTHER INFORMATION: X is T or V
<220> FEATURE:
<221> NAME/KEY: MISC_FEATURE
<222> LOCATION: (11)..(11)
<223> OTHER INFORMATION: X is Y or L
<220> FEATURE:
<221> NAME/KEY: MISC_FEATURE
<222> LOCATION: (12)..(12)
<223> OTHER INFORMATION: X is S or A
```

-continued

```
<220> FEATURE:
<221> NAME/KEY: MISC_FEATURE
<222> LOCATION: (14)..(14)
<223> OTHER INFORMATION: X is S, G, or E
<220> FEATURE:
<221> NAME/KEY: MISC_FEATURE
<222> LOCATION: (17)..(17)
<223> OTHER INFORMATION: X is G or D

<400> SEQUENCE: 141

Xaa Ile Tyr Pro Gly Asp Ser Asp Xaa Arg Xaa Xaa Pro Xaa Phe Gln
1               5                   10                  15

Xaa

<210> SEQ ID NO 142
<211> LENGTH: 14
<212> TYPE: PRT
<213> ORGANISM: Artificial Sequence
<220> FEATURE:
<223> OTHER INFORMATION: CDRH3 Consensus for 6E7 improved Affinity
      variants
<220> FEATURE:
<221> NAME/KEY: MISC_FEATURE
<222> LOCATION: (1)..(1)
<223> OTHER INFORMATION: X is Q, G, S, or M
<220> FEATURE:
<221> NAME/KEY: MISC_FEATURE
<222> LOCATION: (12)..(12)
<223> OTHER INFORMATION: X is F or S

<400> SEQUENCE: 142

Xaa Arg Thr Phe Tyr Tyr Asp Ser Ser Asp Tyr Xaa Asp Tyr
1               5                   10

<210> SEQ ID NO 143
<211> LENGTH: 7
<212> TYPE: PRT
<213> ORGANISM: Artificial Sequence
<220> FEATURE:
<223> OTHER INFORMATION: CDRL2 Antibody ID V3

<400> SEQUENCE: 143

Ala Ala Ser Ser Arg Gln Asn
1               5

<210> SEQ ID NO 144
<211> LENGTH: 7
<212> TYPE: PRT
<213> ORGANISM: Artificial Sequence
<220> FEATURE:
<223> OTHER INFORMATION: CDRL2 Antibody ID V24 C01

<400> SEQUENCE: 144

Ala Ala Ser Ser Leu Gln Lys
1               5

<210> SEQ ID NO 145
<211> LENGTH: 7
<212> TYPE: PRT
<213> ORGANISM: Artificial Sequence
<220> FEATURE:
<223> OTHER INFORMATION: CDRL2 Antibody ID V27 C04

<400> SEQUENCE: 145

Ala Ala Ser Ser Leu Gln Arg
1               5

<210> SEQ ID NO 146
```

```
<211> LENGTH: 7
<212> TYPE: PRT
<213> ORGANISM: Artificial Sequence
<220> FEATURE:
<223> OTHER INFORMATION: CDRL2 Anitbody ID V40 D05

<400> SEQUENCE: 146

Ala Ala Ser Ser Leu Gln Leu
1               5

<210> SEQ ID NO 147
<211> LENGTH: 7
<212> TYPE: PRT
<213> ORGANISM: Artificial Sequence
<220> FEATURE:
<223> OTHER INFORMATION: CDRL2 Antibody ID V84 H01

<400> SEQUENCE: 147

Gly Ala Ser Ser Leu Gln Asn
1               5

<210> SEQ ID NO 148
<211> LENGTH: 9
<212> TYPE: PRT
<213> ORGANISM: Artificial Sequence
<220> FEATURE:
<223> OTHER INFORMATION: CDRL3 Antibody ID V40 D05

<400> SEQUENCE: 148

Gln Gln Ala Asp Arg Phe Pro Arg Thr
1               5

<210> SEQ ID NO 149
<211> LENGTH: 9
<212> TYPE: PRT
<213> ORGANISM: Artificial Sequence
<220> FEATURE:
<223> OTHER INFORMATION: CDRL3 Antibody ID V24 C01

<400> SEQUENCE: 149

Gln Gln Ala Asp Ser Phe Pro His Thr
1               5

<210> SEQ ID NO 150
<211> LENGTH: 9
<212> TYPE: PRT
<213> ORGANISM: Artificial Sequence
<220> FEATURE:
<223> OTHER INFORMATION: CDRL3 Antibody ID V48 E01

<400> SEQUENCE: 150

Gln Gln Ala Asp Ser Leu Pro Arg Thr
1               5

<210> SEQ ID NO 151
<211> LENGTH: 9
<212> TYPE: PRT
<213> ORGANISM: Artificial Sequence
<220> FEATURE:
<223> OTHER INFORMATION: CDRL3 Antibody ID V49 E02 V73 G02

<400> SEQUENCE: 151

Gln Gln Ala Asp Ser Tyr Pro Arg Thr
1               5

<210> SEQ ID NO 152
<211> LENGTH: 9
```

-continued

```
<212> TYPE: PRT
<213> ORGANISM: Artificial Sequence
<220> FEATURE:
<223> OTHER INFORMATION: CDRL3 Antibody ID V60 F01

<400> SEQUENCE: 152

Gly Gln Ala Asp Ser Phe Pro Arg Thr
1               5

<210> SEQ ID NO 153
<211> LENGTH: 107
<212> TYPE: PRT
<213> ORGANISM: Artificial Sequence
<220> FEATURE:
<223> OTHER INFORMATION: VL Amino Acid Sequence Antibody ID V3

<400> SEQUENCE: 153

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Arg Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Arg Phe Pro Arg
                85                  90                  95

Thr Phe Gly Gln Gly Thr Lys Leu Glu Ile Lys
            100                 105

<210> SEQ ID NO 154
<211> LENGTH: 107
<212> TYPE: PRT
<213> ORGANISM: Artificial Sequence
<220> FEATURE:
<223> OTHER INFORMATION: VL Amino Acid Sequence Antibody ID V24 C01

<400> SEQUENCE: 154

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro His
                85                  90                  95

Thr Phe Gly Gln Gly Thr Lys Leu Glu Ile Lys
            100                 105

<210> SEQ ID NO 155
<211> LENGTH: 107
<212> TYPE: PRT
<213> ORGANISM: Artificial Sequence
<220> FEATURE:
<223> OTHER INFORMATION: VL Amino Acid Sequence Antibody ID V27 C04
```

-continued

```
<400> SEQUENCE: 155

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
                85                  90                  95

Thr Phe Gly Gln Gly Thr Lys Leu Glu Ile Lys
            100                 105

<210> SEQ ID NO 156
<211> LENGTH: 107
<212> TYPE: PRT
<213> ORGANISM: Artificial Sequence
<220> FEATURE:
<223> OTHER INFORMATION: VL Amino Acid Sequence Antibody ID V40 D05

<400> SEQUENCE: 156

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Leu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Arg Phe Pro Arg
                85                  90                  95

Thr Phe Gly Gln Gly Thr Lys Leu Glu Ile Lys
            100                 105

<210> SEQ ID NO 157
<211> LENGTH: 107
<212> TYPE: PRT
<213> ORGANISM: Artificial Sequence
<220> FEATURE:
<223> OTHER INFORMATION: VL Amino Acid Sequence Antibody ID V48 E01

<400> SEQUENCE: 157

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Phe Cys Gln Gln Ala Asp Ser Leu Pro Arg
                85                  90                  95

Thr Phe Gly Gln Gly Thr Lys Leu Glu Ile Lys
            100                 105

<210> SEQ ID NO 158
<211> LENGTH: 107
<212> TYPE: PRT
<213> ORGANISM: Artificial Sequence
<220> FEATURE:
<223> OTHER INFORMATION: VL Amino Acid Sequence Antibody ID V49 E02 V73
      G02

<400> SEQUENCE: 158

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Arg Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Tyr Pro Arg
                85                  90                  95

Thr Phe Gly Gln Gly Thr Lys Leu Glu Ile Lys
            100                 105

<210> SEQ ID NO 159
<211> LENGTH: 107
<212> TYPE: PRT
<213> ORGANISM: Artificial Sequence
<220> FEATURE:
<223> OTHER INFORMATION: VL Amino Acid Sequence Antibody ID V52 E05

<400> SEQUENCE: 159

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Arg Phe Pro Arg
                85                  90                  95

Thr Phe Gly Gln Gly Thr Lys Leu Glu Ile Lys
            100                 105

<210> SEQ ID NO 160
<211> LENGTH: 107
<212> TYPE: PRT
<213> ORGANISM: Artificial Sequence
<220> FEATURE:
<223> OTHER INFORMATION: VL Amino Acid Sequence Antibody ID V60 F01

<400> SEQUENCE: 160
```

-continued

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gly Gln Ala Asp Ser Phe Pro Arg
                85                  90                  95

Thr Phe Gly Gln Gly Thr Lys Leu Glu Ile Lys
            100                 105
```

<210> SEQ ID NO 161
<211> LENGTH: 107
<212> TYPE: PRT
<213> ORGANISM: Artificial Sequence
<220> FEATURE:
<223> OTHER INFORMATION: VL Amino Acid Sequence Antibody ID V76 G05

<400> SEQUENCE: 161

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Lys Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
                85                  90                  95

Thr Phe Gly Gln Gly Thr Lys Leu Glu Ile Lys
            100                 105
```

<210> SEQ ID NO 162
<211> LENGTH: 107
<212> TYPE: PRT
<213> ORGANISM: Artificial Sequence
<220> FEATURE:
<223> OTHER INFORMATION: VL Amino Acid Sequence Antibody ID V84 H01

<400> SEQUENCE: 162

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
```

-continued

```
                   85              90              95

Thr Phe Gly Gln Gly Thr Lys Leu Glu Ile Lys
            100             105

<210> SEQ ID NO 163
<211> LENGTH: 4
<212> TYPE: PRT
<213> ORGANISM: Artificial Sequence
<220> FEATURE:
<223> OTHER INFORMATION: FR1/CDRH1 border
      Antibody ID 6E7

<400> SEQUENCE: 163

Tyr Ser Phe Thr
1

<210> SEQ ID NO 164
<211> LENGTH: 4
<212> TYPE: PRT
<213> ORGANISM: Artificial Sequence
<220> FEATURE:
<223> OTHER INFORMATION: Heavy Chain Variable Region Amino Acid
      Sequences for Reduced Affinity TREM2 Antibodies - FR1/CDRH1 border

<400> SEQUENCE: 164

Tyr Ser Phe Ala
1

<210> SEQ ID NO 165
<211> LENGTH: 4
<212> TYPE: PRT
<213> ORGANISM: Artificial Sequence
<220> FEATURE:
<223> OTHER INFORMATION: FR1/CDRH1 border
      Antibody ID V3 A04

<400> SEQUENCE: 165

Tyr Ser Phe Gly
1

<210> SEQ ID NO 166
<211> LENGTH: 4
<212> TYPE: PRT
<213> ORGANISM: Artificial Sequence
<220> FEATURE:
<223> OTHER INFORMATION: FR1/CDRH1 border
      Antibody ID V49 E02

<400> SEQUENCE: 166

Tyr Ser Phe Asn
1

<210> SEQ ID NO 167
<211> LENGTH: 4
<212> TYPE: PRT
<213> ORGANISM: Artificial Sequence
<220> FEATURE:
<223> OTHER INFORMATION: FR1/CDRH1 border
      Antibody ID V52 E05

<400> SEQUENCE: 167

Tyr Ser Phe Glu
1

<210> SEQ ID NO 168
<211> LENGTH: 4
<212> TYPE: PRT
```

-continued

```
<213> ORGANISM: Artificial Sequence
<220> FEATURE:
<223> OTHER INFORMATION: FR1/CDRH1 border
      Antibody ID V60 F01

<400> SEQUENCE: 168

Tyr His Phe Thr
1

<210> SEQ ID NO 169
<211> LENGTH: 4
<212> TYPE: PRT
<213> ORGANISM: Artificial Sequence
<220> FEATURE:
<223> OTHER INFORMATION: FR1/CDRH1 border
      Antibody ID V76 G05 V84 H01

<400> SEQUENCE: 169

Tyr Gly Phe Thr
1

<210> SEQ ID NO 170
<211> LENGTH: 17
<212> TYPE: PRT
<213> ORGANISM: Artificial Sequence
<220> FEATURE:
<223> OTHER INFORMATION: CDRH2 Antibody ID 6E7 V3 A04

<400> SEQUENCE: 170

Ile Ile Tyr Pro Gly Asp Ser Asp Thr Arg Tyr Ser Pro Ser Phe Gln
1               5                   10                  15

Asp

<210> SEQ ID NO 171
<211> LENGTH: 17
<212> TYPE: PRT
<213> ORGANISM: Artificial Sequence
<220> FEATURE:
<223> OTHER INFORMATION: CDRH2 Antibody ID V24 C01

<400> SEQUENCE: 171

Ile Ile Tyr Pro Gly Asp Ser Asp Val Arg Tyr Ser Pro Ser Phe Gln
1               5                   10                  15

Gly

<210> SEQ ID NO 172
<211> LENGTH: 17
<212> TYPE: PRT
<213> ORGANISM: Artificial Sequence
<220> FEATURE:
<223> OTHER INFORMATION: CDRH2 Antibody ID V27 C04

<400> SEQUENCE: 172

Ile Ile Tyr Pro Gly Asp Ser Asp Thr Arg Tyr Ala Pro Ser Phe Gln
1               5                   10                  15

Gly

<210> SEQ ID NO 173
<211> LENGTH: 17
<212> TYPE: PRT
<213> ORGANISM: Artificial Sequence
<220> FEATURE:
<223> OTHER INFORMATION: CDRH2 Antibody ID V49 E02

<400> SEQUENCE: 173
```

-continued

```
Thr Ile Tyr Pro Gly Asp Ser Asp Thr Arg Leu Ser Pro Ser Phe Gln
1               5                   10                  15

Gly

<210> SEQ ID NO 174
<211> LENGTH: 17
<212> TYPE: PRT
<213> ORGANISM: Artificial Sequence
<220> FEATURE:
<223> OTHER INFORMATION: CDRH2 Antibody ID V73 G02

<400> SEQUENCE: 174

Ile Ile Tyr Pro Gly Asp Ser Asp Thr Arg Tyr Ser Pro Gly Phe Gln
1               5                   10                  15

Gly

<210> SEQ ID NO 175
<211> LENGTH: 17
<212> TYPE: PRT
<213> ORGANISM: Artificial Sequence
<220> FEATURE:
<223> OTHER INFORMATION: CDRH2 Antibody ID V76 G05

<400> SEQUENCE: 175

Ile Ile Tyr Pro Gly Asp Ser Asp Thr Arg Tyr Ser Pro Glu Phe Gln
1               5                   10                  15

Gly

<210> SEQ ID NO 176
<211> LENGTH: 14
<212> TYPE: PRT
<213> ORGANISM: Artificial Sequence
<220> FEATURE:
<223> OTHER INFORMATION: CDRH3 Antibody ID V3 A04

<400> SEQUENCE: 176

Gly Arg Thr Phe Tyr Tyr Asp Ser Ser Asp Tyr Phe Asp Tyr
1               5                   10

<210> SEQ ID NO 177
<211> LENGTH: 14
<212> TYPE: PRT
<213> ORGANISM: Artificial Sequence
<220> FEATURE:
<223> OTHER INFORMATION: CDRH3 Antibody ID V24 C01

<400> SEQUENCE: 177

Ser Arg Thr Phe Tyr Tyr Asp Ser Ser Asp Tyr Phe Asp Tyr
1               5                   10

<210> SEQ ID NO 178
<211> LENGTH: 14
<212> TYPE: PRT
<213> ORGANISM: Artificial Sequence
<220> FEATURE:
<223> OTHER INFORMATION: CDRH3 Antibody ID V60 F01

<400> SEQUENCE: 178

Gln Arg Thr Phe Tyr Tyr Asp Ser Ser Asp Tyr Ser Asp Tyr
1               5                   10

<210> SEQ ID NO 179
<211> LENGTH: 14
<212> TYPE: PRT
<213> ORGANISM: Artificial Sequence
```

-continued

```
<220> FEATURE:
<223> OTHER INFORMATION: CDRH3 Antibody ID V48 E01

<400> SEQUENCE: 179

Met Arg Thr Phe Tyr Tyr Asp Ser Ser Asp Tyr Phe Asp Tyr
1               5                   10

<210> SEQ ID NO 180
<211> LENGTH: 123
<212> TYPE: PRT
<213> ORGANISM: Artificial Sequence
<220> FEATURE:
<223> OTHER INFORMATION: VH Amino Acid Sequence Antibody ID V3 A04

<400> SEQUENCE: 180

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ala Ser Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Arg Thr Phe Tyr Tyr Asp Ser Ser Asp Tyr Phe Asp Tyr
            100                 105                 110

Trp Gly Gln Gly Thr Leu Val Thr Val Ser Ser
        115                 120

<210> SEQ ID NO 181
<211> LENGTH: 123
<212> TYPE: PRT
<213> ORGANISM: Artificial Sequence
<220> FEATURE:
<223> OTHER INFORMATION: VH Amino Acid Sequence Antibody ID V24 C01

<400> SEQUENCE: 181

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Val Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Ser Arg Thr Phe Tyr Tyr Asp Ser Ser Asp Tyr Phe Asp Tyr
            100                 105                 110

Trp Gly Gln Gly Thr Leu Val Thr Val Ser Ser
        115                 120

<210> SEQ ID NO 182
<211> LENGTH: 123
```

<212> TYPE: PRT
<213> ORGANISM: Artificial Sequence
<220> FEATURE:
<223> OTHER INFORMATION: VH Amino Acid Sequence Antibody ID V27 C04

<400> SEQUENCE: 182

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ala Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
            85                  90                  95

Val Arg Ser Arg Thr Phe Tyr Tyr Asp Ser Ser Asp Tyr Phe Asp Tyr
            100                 105                 110

Trp Gly Gln Gly Thr Leu Val Thr Val Ser Ser
        115                 120
```

<210> SEQ ID NO 183
<211> LENGTH: 123
<212> TYPE: PRT
<213> ORGANISM: Artificial Sequence
<220> FEATURE:
<223> OTHER INFORMATION: VH Amino Acid Sequence Antibody ID V40 D05

<400> SEQUENCE: 183

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Gly Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Val Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
            85                  90                  95

Ala Arg Gln Arg Thr Phe Tyr Tyr Asp Ser Ser Asp Tyr Ser Asp Tyr
            100                 105                 110

Trp Gly Gln Gly Thr Leu Val Thr Val Ser Ser
        115                 120
```

<210> SEQ ID NO 184
<211> LENGTH: 123
<212> TYPE: PRT
<213> ORGANISM: Artificial Sequence
<220> FEATURE:
<223> OTHER INFORMATION: VH Amino Acid Sequence Antibody ID V48 E01

<400> SEQUENCE: 184

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Gly Ser Tyr
```

```
               20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Val Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Met Arg Thr Phe Tyr Tyr Asp Ser Ser Asp Tyr Phe Asp Tyr
                100                 105                 110

Trp Gly Gln Gly Thr Leu Val Thr Val Ser Ser
        115                 120
```

```
<210> SEQ ID NO 185
<211> LENGTH: 123
<212> TYPE: PRT
<213> ORGANISM: Artificial Sequence
<220> FEATURE:
<223> OTHER INFORMATION: Heavy Chain Variable Region Amino Acid
      Sequences for Improved Affinity TREM2 Antibodies - VH Amino Acid
      Sequence

<400> SEQUENCE: 185

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
                20                  25                  30

Trp Ile Ala Trp Val Arg Gln Met Pro Gly Lys Gly Leu Glu Trp Met
        35                  40                  45

Gly Thr Ile Tyr Pro Gly Asp Ser Asp Thr Arg Leu Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Ser Arg Thr Phe Tyr Tyr Asp Ser Ser Asp Tyr Phe Asp Tyr
                100                 105                 110

Trp Gly Gln Gly Thr Leu Val Thr Val Ser Ser
        115                 120
```

```
<210> SEQ ID NO 186
<211> LENGTH: 123
<212> TYPE: PRT
<213> ORGANISM: Artificial Sequence
<220> FEATURE:
<223> OTHER INFORMATION: VH Amino Acid Sequence Antibody ID V49 E02

<400> SEQUENCE: 186

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Glu Ser Tyr
                20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
```

-continued

```
65                  70                  75                  80

Leu Gln Trp Ser Ser Leu Lys Ala Ser Asp Thr Ala Met Tyr Phe Cys
                85                  90                  95

Ala Arg Gly Arg Thr Phe Tyr Tyr Asp Ser Ser Asp Tyr Phe Asp Tyr
                100                 105                 110

Trp Gly Gln Gly Thr Leu Val Thr Val Ser Ser
        115                 120

<210> SEQ ID NO 187
<211> LENGTH: 123
<212> TYPE: PRT
<213> ORGANISM: Artificial Sequence
<220> FEATURE:
<223> OTHER INFORMATION: VH Amino Acid Sequence Antibody ID V60 F01

<400> SEQUENCE: 187

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr His Phe Thr Ser Tyr
                20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Val Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Ser Asp Tyr
                100                 105                 110

Trp Gly Gln Gly Thr Leu Val Thr Val Ser Ser
        115                 120

<210> SEQ ID NO 188
<211> LENGTH: 123
<212> TYPE: PRT
<213> ORGANISM: Artificial Sequence
<220> FEATURE:
<223> OTHER INFORMATION: VH Amino Acid Sequence Antibody ID V73 G02

<400> SEQUENCE: 188

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Gly Ser Tyr
                20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Gly Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Arg Thr Phe Tyr Tyr Asp Ser Ser Asp Tyr Phe Asp Tyr
                100                 105                 110

Trp Gly Gln Gly Thr Leu Val Thr Val Ser Ser
        115                 120
```

-continued

```
<210> SEQ ID NO 189
<211> LENGTH: 123
<212> TYPE: PRT
<213> ORGANISM: Artificial Sequence
<220> FEATURE:
<223> OTHER INFORMATION: VH Amino Acid Sequence Antibody ID V76 G05

<400> SEQUENCE: 189

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Gly Ser Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Glu Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Ser Asp Tyr
                100                 105                 110

Trp Gly Gln Gly Thr Leu Val Thr Val Ser Ser
            115                 120

<210> SEQ ID NO 190
<211> LENGTH: 123
<212> TYPE: PRT
<213> ORGANISM: Artificial Sequence
<220> FEATURE:
<223> OTHER INFORMATION: VH Amino Acid Sequence Antibody ID V84 H01

<400> SEQUENCE: 190

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Gly Phe Thr Ser Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Ser Asp Tyr
                100                 105                 110

Trp Gly Gln Gly Thr Leu Val Thr Val Ser Ser
            115                 120

<210> SEQ ID NO 191
<211> LENGTH: 106
<212> TYPE: PRT
<213> ORGANISM: Homo sapiens

<400> SEQUENCE: 191

Gly Gln Pro Lys Ala Asn Pro Thr Val Thr Leu Phe Pro Pro Ser Ser
1               5                   10                  15
```

```
Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 192
<211> LENGTH: 106
<212> TYPE: PRT
<213> ORGANISM: Homo sapiens

<400> SEQUENCE: 192
```

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 193
<211> LENGTH: 105
<212> TYPE: PRT
<213> ORGANISM: Homo sapiens

<400> SEQUENCE: 193
```

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

```
<210> SEQ ID NO 194
<211> LENGTH: 106
```

<212> TYPE: PRT
<213> ORGANISM: Homo sapiens

<400> SEQUENCE: 194

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 195
<211> LENGTH: 106
<212> TYPE: PRT
<213> ORGANISM: Homo sapiens

<400> SEQUENCE: 195

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

<210> SEQ ID NO 196
<211> LENGTH: 106
<212> TYPE: PRT
<213> ORGANISM: Homo sapiens

<400> SEQUENCE: 196

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
```

```
                    85              90              95

Val Thr Lys Ser Phe Asn Arg Gly Glu Cys
            100             105
```

<210> SEQ ID NO 197
<211> LENGTH: 107
<212> TYPE: PRT
<213> ORGANISM: Homo sapiens

<400> SEQUENCE: 197

```
Arg Thr Val Ala Ala Pro Ser Val Phe Ile Phe Pro Pro Ser Asp Glu
1               5               10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
        35              40              45

Ser Gly Asn Ser Gln Glu Ser Val Thr Glu Gln Asp Ser Lys Asp Ser
    50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
            85              90              95

Pro Val Thr Lys Ser Phe Asn Arg Gly Glu Cys
            100             105
```

<210> SEQ ID NO 198
<211> LENGTH: 330
<212> TYPE: PRT
<213> ORGANISM: Homo sapiens

<400> SEQUENCE: 198

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
```

```
                195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 199
<211> LENGTH: 330
<212> TYPE: PRT
<213> ORGANISM: Homo sapiens

<400> SEQUENCE: 199

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

-continued

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 200
<211> LENGTH: 330
<212> TYPE: PRT
<213> ORGANISM: Homo sapiens

<400> SEQUENCE: 200

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

-continued

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 201
<211> LENGTH: 330
<212> TYPE: PRT
<213> ORGANISM: Homo sapiens

<400> SEQUENCE: 201

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

-continued

```
                325                 330

<210> SEQ ID NO 202
<211> LENGTH: 330
<212> TYPE: PRT
<213> ORGANISM: Homo sapiens

<400> SEQUENCE: 202

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 203
<211> LENGTH: 330
<212> TYPE: PRT
<213> ORGANISM: Homo sapiens
```

<400> SEQUENCE: 203

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
                165                 170                 175

Glu Gln Tyr Gly Ser Thr Tyr Arg Cys Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 204
<211> LENGTH: 326
<212> TYPE: PRT
<213> ORGANISM: Homo sapiens

<400> SEQUENCE: 204

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

Phe Pro Glu Pro Val Thr Val Ser Trp Asn Ser Gly Ala Leu Thr Ser
        35                      40                  45

Gly Val His Thr Phe Pro Ala Val Leu Gln Ser Ser Gly Leu Tyr Ser
        50                      55                  60

Leu Ser Ser Val Val Thr Val Pro Ser Ser Asn Phe Gly Thr Gln Thr
65                      70                  75                  80

Tyr Thr Cys Asn Val Asp His Lys Pro Ser Asn Thr Lys Val Asp Lys
                85                      90                  95

Thr Val Glu Arg Lys Cys Cys Val Glu Cys Pro Pro Cys Pro Ala Pro
            100                     105                 110

Pro Val Ala Gly Pro Ser Val Phe Leu Phe Pro Pro Lys Pro Lys Asp
            115                     120                 125

Thr Leu Met Ile Ser Arg Thr Pro Glu Val Thr Cys Val Val Val Asp
    130                     135                 140

Val Ser His Glu Asp Pro Glu Val Gln Phe Asn Trp Tyr Val Asp Gly
145                     150                 155                 160

Val Glu Val His Asn Ala Lys Thr Lys Pro Arg Glu Glu Gln Phe Asn
                165                     170                 175

Ser Thr Phe Arg Val Val Ser Val Leu Thr Val Val His Gln Asp Trp
            180                     185                 190

Leu Asn Gly Lys Glu Tyr Lys Cys Lys Val Ser Asn Lys Gly Leu Pro
            195                     200                 205

Ala Pro Ile Glu Lys Thr Ile Ser Lys Thr Lys Gly Gln Pro Arg Glu
        210                     215                 220

Pro Gln Val Tyr Thr Leu Pro Pro Ser Arg Glu Glu Met Thr Lys Asn
225                     230                 235                 240

Gln Val Ser Leu Thr Cys Leu Val Lys Gly Phe Tyr Pro Ser Asp Ile
                245                     250                 255

Ala Val Glu Trp Glu Ser Asn Gly Gln Pro Glu Asn Asn Tyr Lys Thr
            260                     265                 270

Thr Pro Pro Met Leu Asp Ser Asp Gly Ser Phe Phe Leu Tyr Ser Lys
            275                     280                 285

Leu Thr Val Asp Lys Ser Arg Trp Gln Gln Gly Asn Val Phe Ser Cys
        290                     295                 300

Ser Val Met His Glu Ala Leu His Asn His Tyr Thr Gln Lys Ser Leu
305                     310                 315                 320

Ser Leu Ser Pro Gly Lys
                325

<210> SEQ ID NO 205
<211> LENGTH: 330
<212> TYPE: PRT
<213> ORGANISM: Homo sapiens

<400> SEQUENCE: 205

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                      25                  30

Phe Pro Glu Pro Val Thr Val Ser Trp Asn Ser Gly Ala Leu Thr Ser
        35                      40                  45

Gly Val His Thr Phe Pro Ala Val Leu Gln Ser Ser Gly Leu Tyr Ser
        50                      55                  60

Leu Ser Ser Val Val Thr Val Pro Ser Ser Ser Leu Gly Thr Gln Thr
65                      70                  75                  80

-continued

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
               100                 105                 110

Pro Ala Pro Glu Leu Leu Gly Gly Pro Ser Val Phe Leu Phe Pro Pro
               115                 120                 125

Lys Pro Lys Asp Thr Leu Met Ile Ser Arg Thr Pro Glu Val Thr Cys
       130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
               165                 170                 175

Glu Gln Tyr Gly Ser Thr Tyr Arg Cys Val Ser Val Leu Thr Val Leu
               180                 185                 190

His Gln Asp Trp Leu Asn Gly Lys Glu Tyr Lys Cys Lys Val Ser Asn
       195                 200                 205

Lys Ala Leu Pro Ala Pro Ile Glu Lys Thr Ile Ser Lys Ala Lys Gly
       210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
               245                 250                 255

Pro Ser Asp Ile Ala Val Glu Trp Glu Ser Asn Gly Gln Pro Glu Asn
               260                 265                 270

Asn Tyr Lys Thr Thr Pro Pro Val Leu Asp Ser Asp Gly Ser Phe Phe
       275                 280                 285

Leu Tyr Ser Lys Leu Thr Val Asp Lys Ser Arg Trp Gln Gln Gly Asn
       290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
               325                 330
```

```
<210> SEQ ID NO 206
<211> LENGTH: 12
<212> TYPE: PRT
<213> ORGANISM: Homo sapiens

<400> SEQUENCE: 206

Glu Arg Lys Cys Cys Val Glu Cys Pro Pro Cys Pro
1               5                   10
```

```
<210> SEQ ID NO 207
<211> LENGTH: 110
<212> TYPE: PRT
<213> ORGANISM: Homo sapiens

<400> SEQUENCE: 207

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
               20                  25                  30

Phe Pro Glu Pro Val Thr Val Ser Trp Asn Ser Gly Ala Leu Thr Ser
           35                  40                  45

Gly Val His Thr Phe Pro Ala Val Leu Gln Ser Ser Gly Leu Tyr Ser
       50                  55                  60
```

-continued

```
Leu Ser Ser Val Val Thr Val Pro Ser Ser Asn Phe Gly Thr Gln Thr
65                  70              75                  80

Tyr Thr Cys Asn Val Asp His Lys Pro Ser Asn Thr Lys Val Asp Lys
                    85              90                  95

Thr Val Glu Arg Lys Cys Cys Val Glu Cys Pro Pro Cys Pro
                100             105             110
```

```
<210> SEQ ID NO 208
<211> LENGTH: 345
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 12G10

<400> SEQUENCE: 208
caggctgtgc cgactcagcc gtcttccctc tctgcatctc ctggagtatt agccagtctc      60
acctgcacct tacgcagtgg catcaatgtt ggtacctaca ggatatactg gtaccagcag     120
aagccaggga gtcctcccca gtatctcctg aggtacaaat cagactcaga taagcagcag     180
ggctctggag tccccagccg cttctctgga tccaaggatg cttcggccaa tgcagggatt     240
ttactcatct ctgggctcca gtctgaggat gaggctgact attactgtat gatttggtac     300
agcagtgctg tggtattcgg cggagggacc aaactgaccg tccta                     345
```

```
<210> SEQ ID NO 209
<211> LENGTH: 318
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 26A10

<400> SEQUENCE: 209
tcctatgagc tgactcagcc accctcagtg tccgtgtccc aggacagac agccagcatc       60 acctgctctg agataaaatt gggagataag tatgtttgct ggtatcagca gaagccaggc     120
cagtcccctg tgctggtcat ctatcaagat agcaagcggc cctcaggat ccctgagcga      180 ttctctggct ccaactctgg gaacacagcc actctgacca tcagcgggac ccaggctatg     240
gatgaggctg actattactg tcaggcgtgg gacagtaaca ctgtggtatt cggcggaggg     300
accaagctga ccgtccta                                                    318
```

```
<210> SEQ ID NO 210
<211> LENGTH: 318
<212> TYPE: DNA
<213> ORGANISM: Artificial Sequence
<220> FEATURE:
<223> OTHER INFORMATION: Anti-TREM2 Antibody Variable Region Nucleic
      Acid - LV  Antibody ID 26C10

<400> SEQUENCE: 210
tcctttgagc tgactcagcc accctcagtg tccgtgtccc aggacagac agccagcatc       60 acctgctctg agataaaatt gggggataag tatgtttgct ggtatcagca gaagccaggc     120
cagtccccta tgttggtcat ctatcaagat accaagcggc cctcaggat ccctgaacga      180 ttctctggct ccaactctgg gaacacagcc actctgacca tcagcgggac ccaggctatg     240
gatgaggctg actattactg tcaggcgtgg gacagcagca ctgtggtctt cggcggaggg     300
accaagctga ccgtccta                                                    318
```

-continued

```
<210> SEQ ID NO 211
<211> LENGTH: 318
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 26F2

<400> SEQUENCE: 211
tcctatgagc tgactcagcc accctcagtg tccgtgtccc caggacagac agccagcatc      60
acctgctctg gagataaatt gggggataag tatgtttgct ggtatcagca gaagccaggc     120
cagtcccctg tgttggtcat ctttcaagat agcaagcggc cctcagggat ccctgagcga     180
ttctctggct ccaactctgg gaacacagcc actctgacca tcagcgggac ccaggctatg     240
gatgaggctg actattactg tcaggcgtgg gacagcagca ctgtggtatt cggcggaggg     300
accaagctga ccgtccta                                                     318

<210> SEQ ID NO 212
<211> LENGTH: 318
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 33B12

<400> SEQUENCE: 212
tcctatgagc tgactcagcc accctcagtg tccgtgtccc caggacagac agccagcatc      60
acctgctctg gagataaatt gggggataag tatgtttgct ggtatcagca gaagccaggc     120
cagtcccctg tgttggtcat ctatcaagat agcaagcggc cctcagggat ccctgagcga     180
ttctctggct ccaactctgg gaacacagcc actctgacca tcagcgggac ccaggctatg     240
gatgaggctg actattactg tcaggcgtgg gacagtagca ctgtggtatt cggcggaggg     300
accaagctga ccgtccta                                                     318

<210> SEQ ID NO 213
<211> LENGTH: 339
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 24C12

<400> SEQUENCE: 213
ggcatcgtga tgacccagtc tccagactcc ctggctgtgt ctctgggcga gagggccacc      60
atcaactgca agtccagccg gagtgttttg tacagctcca acaataagaa ctacttagct     120
tggtaccagc agaaaccagg acagcctcct aaggtgctca tttactgggc atctacccgg     180
gaatccgggg tccctgaccg attcagtggc agcgggtctg ggacagattt cactctcacc     240
atcagcagcc tgcaggctga agatgtggca gtttataact gtcagcaata ttatattact     300
ccgatcacct tcggccaagg gacacgactg gagattaaa                             339

<210> SEQ ID NO 214
<211> LENGTH: 339
<212> TYPE: PRT
<213> ORGANISM: Artificial Sequence
<220> FEATURE:
<223> OTHER INFORMATION: Anti-TREM2 Antibody Variable Region Nucleic
      Acid - LV Antibody ID 24G6

<400> SEQUENCE: 214
```

-continued

```
Gly Ala Cys Ala Thr Cys Gly Thr Gly Ala Thr Gly Ala Cys Cys Cys
1               5                   10                  15

Ala Gly Thr Cys Thr Cys Cys Ala Gly Ala Cys Thr Cys Cys Cys Thr
                20                  25                  30

Gly Gly Cys Thr Gly Thr Gly Thr Cys Thr Cys Thr Gly Gly Gly Cys
        35                  40                  45

Gly Ala Gly Ala Gly Gly Gly Cys Cys Ala Cys Cys Ala Thr Cys Ala
    50                  55                  60

Ala Cys Thr Gly Cys Ala Ala Gly Thr Cys Cys Ala Gly Cys Cys Ala
65                  70                  75                  80

Gly Ala Gly Thr Gly Thr Thr Thr Ala Thr Ala Cys Ala Gly Cys
                85                  90                  95

Thr Cys Cys Ala Ala Cys Ala Ala Thr Ala Ala Gly Cys Ala Cys Thr
            100                 105                 110

Thr Cys Thr Thr Ala Gly Cys Thr Thr Gly Gly Thr Ala Cys Cys Ala
        115                 120                 125

Gly Cys Ala Gly Ala Ala Ala Cys Cys Ala Gly Gly Ala Cys Ala Gly
    130                 135                 140

Cys Cys Thr Cys Cys Thr Ala Ala Gly Cys Thr Gly Cys Thr Cys Ala
145                 150                 155                 160

Thr Thr Thr Ala Cys Thr Gly Gly Gly Cys Ala Thr Cys Thr Ala Cys
            165                 170                 175

Cys Cys Gly Gly Gly Ala Gly Thr Cys Cys Gly Gly Gly Gly Thr Cys
            180                 185                 190

Cys Cys Thr Gly Ala Cys Cys Gly Ala Thr Thr Cys Ala Gly Thr Gly
        195                 200                 205

Gly Cys Ala Gly Cys Gly Gly Gly Thr Cys Thr Gly Gly Gly Ala Cys
    210                 215                 220

Ala Gly Ala Thr Thr Thr Cys Ala Cys Thr Cys Thr Cys Ala Cys Cys
225                 230                 235                 240

Ala Thr Cys Ala Gly Cys Ala Gly Cys Cys Thr Gly Cys Ala Gly Gly
            245                 250                 255

Cys Thr Gly Ala Ala Gly Ala Thr Gly Thr Gly Gly Cys Ala Thr Thr
            260                 265                 270

Thr Thr Ala Thr Thr Ala Cys Thr Gly Thr Cys Ala Gly Cys Ala Ala
        275                 280                 285

Thr Ala Thr Thr Ala Thr Ala Gly Thr Ala Cys Thr Cys Cys Gly Cys
    290                 295                 300

Thr Cys Ala Cys Thr Thr Thr Cys Gly Gly Cys Gly Gly Ala Gly Gly
305                 310                 315                 320

Gly Ala Cys Cys Ala Ala Gly Gly Thr Gly Gly Ala Gly Ala Thr Cys
        325                 330                 335

Ala Ala Ala
```

<210> SEQ ID NO 215
<211> LENGTH: 339
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody 24A10

<400> SEQUENCE: 215
gacatcgtga tgacccagtc tccagactcc ctggctgtgt ctctgggcga gagggccacc        60

-continued

```
atcacctgca agtccagcca caatgtttta tacagctcca acaataagaa ctacttagct      120
tggtatcagc agaaaccagg acagcctcct aaactgctca tttactgggc atctacccgg      180
gaatccgggg tccctgaccg attcagtggc agcgggtctg ggacagattt cactctcacc      240
atcagcagcc tgcaggctga agatgtggca gtttattact gtcaccaata ttatagtact      300
ccgtgcagtt ttggccaggg gaccaagctg gagatcaaa                           339
```

```
<210> SEQ ID NO 216
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 10E3

<400> SEQUENCE: 216
gaaatagtga tgacgcagtc tccagccacc ctgtctgtgt ctccagggga aagagccacc      60
ctctcctgca gggccagtca gagtgttagc agcaacttag cctggttcca gcagaaacct      120
ggccaggctc ccaggctcct catctatggt gcttccacca gggccactgg tattccagcc      180
aggttcagtg tcagtgggtc tgggacagag ttcactctca ccatcagcag cctgcagtct      240
gaagattttg catttttatta ctgtctgcag gataataatt ggcctcccac tttcggccct      300
gggaccaaag tggatatcaa a                                              321
```

```
<210> SEQ ID NO 217
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 13E7

<400> SEQUENCE: 217
gaaatagtga tgacgcagtc tccagccacc ctgtctgtgt ctccagggga aagagccacc      60
ctctcctgca gggccagtca gagtgttagc agcaacttag cctggttcca gcagaaacct      120
ggccaggctc ccaggctcct catctatggt gcttccacca gggccactgg tattccagcc      180
aggttcagtg tcagtgggtc tgggacagag ttcactctca ccatcagcag cctgcagtct      240
gaagattttg cagtttatta ctgtctgcag gataataatt ggcctcccac tttcggccct      300
gggaccaaag tggatatcaa a                                              321
```

```
<210> SEQ ID NO 218
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 25F12

<400> SEQUENCE: 218
gaaaaagtga tgacgcagtc tccagccacc ctgtctgtgt ctccagggga aagagccacc      60
ctctcctgca gggccagtca gagtgttaac aacaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcag tataataact ggcctcggac gttcggccaa      300
gggaccaagg tggaaatcaa a                                              321
```

-continued

```
<210> SEQ ID NO 219
<211> LENGTH: 324
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 32E3

<400> SEQUENCE: 219
gaatttgtgt tgacgcagtc tccaggcacc ctgtctttgt ctccggggga aagagccacc      60
ctctcctgca gggccagtca gattattagc agcaactact tagcctggta ccagcagaaa     120
cctggccagg ctcccaggct cctcatctat agtgcatcca gcagggccac tggcatccca     180
gacaggttca gtggcagtgg gtctgggaca gacttcactc tcaccatcag cagactggag     240
cctgaagatt ttgcagtgta ttactgtcag cagtttgata gctcaccgat caccttcggc     300
cgagggacac gactggacat taaa                                           324

<210> SEQ ID NO 220
<211> LENGTH: 324
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 24F4

<400> SEQUENCE: 220
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcactgta ttactgtcag cagtatgata cctcaccatt cactttcggc     300
cctgggacca aagtggatat caaa                                           324

<210> SEQ ID NO 221
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 16B8

<400> SEQUENCE: 221
gacatccaga tgacccagtc tccatcttcc gtgtctgcat ctgtaggaga cagagtcacc      60
gtcacttgtc gggcgagtca ggatattaac agctggttag cctggtatca gcagaaacca     120
gggaaagccc ctaagctcct gatctatgct gcatcctctt tgcaaactgg ggtcccttca     180
aggttcagcg gcagtggatc tgggacagat ttcactctca ccatcagcag cctgcagcct     240
gaagattttg caacttactc ttgtcaacag tctaacagtt ccccgatcac cttcggccaa     300
gggacacgac tggagattaa a                                              321

<210> SEQ ID NO 222
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 4C5

<400> SEQUENCE: 222
```

-continued

```
gacatccaga tgacccagtc tccatcttcc gtgtctgcat ctgtaggaga cagagtcacc      60
atcacttgtc gggcgagtca gggtattagc aactggttag cctggtatca gcagaaacca     120
gggaaagccc ctaagctcct gatctatgct gcatccagtt tgcaagttgg ggtcccatta     180
aggttcagcg gcagtggatc tgggacagat ttcactctca ccatcagcag cctgcagcct     240
gaagattttg caacttacta ttgtcaacag gctgacagtt ccctcgcaa ttttggccag      300 gggaccaagc tggagatcaa a                                               321
```

<210> SEQ ID NO 223
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 6E7 V9 A10 V30 C07 V33 C10 V44 D09 V68 F09

<400> SEQUENCE: 223

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt ccctcgcac ttttggccag       300 gggaccaagc tggagatcaa a                                               321
```

<210> SEQ ID NO 224
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV - Antibody ID 5E3

<400> SEQUENCE: 224

```
gacatccaga tgacccagtc tccatcctca ctgtctgcat ctgtaggaga cagagtcacc      60
atcacttgtc gggcgagtca gggcattagc aattatttag cctggtttca gcagaaacca     120
gggaaagccc ctaaatccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacag tatagtactt acccattcac tttcggccct     300
gggaccaaag tggatatcaa a                                               321
```

<210> SEQ ID NO 225
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID 4G10

<400> SEQUENCE: 225

```
gacatccaga tgacccagtc tccatcctcc ctgtctgcat ctgtaggaga cagagtcacc      60
atcacttgcc gggcaagtca gggcataaga aatgatttag gctggtatca gcagaaacca     120
gggaatgccc ctaagcgcct gatctatgct gcatccagtt tgccaagtgg ggtcccatca     180
aggttcagcg gcagtggatc tgggccagaa ttcactctca caatcagcag tctgcagcct     240
gaagattttg caacttatta ctgtctacag cataatagtt acccgtggac gttcggccaa     300
```
gggaccaagg tggaaatcac a                                                321

<210> SEQ ID NO 226
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V3 A04

<400> SEQUENCE: 226
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagta ggcaaaatgg ggtcccatca     180
aggttcagcg gcagtggatc tgggacagat ttcactctca ccatcagcag cctgcagcct     240
gaagattttg caacttactt ttgtcaacag gctgacaggt ccctcgcac ttttggccag      300 gggaccaagc tggagatcaa a                                                321

<210> SEQ ID NO 227
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V24 C01

<400> SEQUENCE: 227
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaaaggg ggtcccatca     180
aggttcagcg gcagtggatc tgggacagat ttcactctca ccatcagcag cctgcagcct     240
gaagattttg caacttactt ttgtcaacag gctgacagtt ccctcatac ttttggccag      300 gggaccaagc tggagatcaa a                                                321

<210> SEQ ID NO 228
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V27

<400> SEQUENCE: 228
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaacgtgg ggtcccatca     180
aggttcagcg gcagtggatc tgggacagat ttcactctca ccatcagcag cctgcagcct     240
gaagattttg caacttactt ttgtcaacag gctgacagtt ccctcgcac ttttggccag      300 gggaccaagc tggagatcaa a                                                321

<210> SEQ ID NO 229
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic -continued Acid - LV Antibody ID V40 D05

<400> SEQUENCE: 229
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaacttgg ggtcccatca     180
aggttcagcg gcagtggatc tgggacagat ttcactctca ccatcagcag cctgcagcct     240
gaagattttg caacttactt ttgtcaacag gctgaccgtt ccctcgcac ttttggccag      300 gggaccaagc tggagatcaa a                                              321

<210> SEQ ID NO 230
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V48 E01

<400> SEQUENCE: 230
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaacggg ggtcccatca     180
aggttcagcg gcagtggatc tgggacagat ttcactctca ccatcagcag cctgcagcct     240
gaagattttg caacttactt ttgtcaacag gctgacagtt tgcctcgcac ttttggccag      300
gggaccaagc tggagatcaa a                                              321

<210> SEQ ID NO 231
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V49 E02

<400> SEQUENCE: 231
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtc ggcaaaatgg ggtcccatca     180
aggttcagcg gcagtggatc tgggacagat ttcactctca ccatcagcag cctgcagcct     240
gaagattttg caacttactt ttgtcaacag gctgacagtt atcctcgcac ttttggccag      300
gggaccaagc tggagatcaa a                                              321

<210> SEQ ID NO 232
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V52 E05

<400> SEQUENCE: 232
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagggg ggtcccatca     180

```
aggttcagcg gcagtggatc tgggacagat ttcactctca ccatcagcag cctgcagcct    240
gaagattttg caacttactt ttgtcaacag gctgaccgtt ccctcgcac tttttggccag    300 gggaccaagc tggagatcaa a                                              321
```

```
<210> SEQ ID NO 233
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V60 F01

<400> SEQUENCE: 233
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaagggg ggtcccatca    180
aggttcagcg gcagtggatc tgggacagat ttcactctca ccatcagcag cctgcagcct    240
gaagattttg caacttactt ttgtgggcag gctgacagtt ccctcgcac tttttggccag    300 gggaccaagc tggagatcaa a                                              321
```

```
<210> SEQ ID NO 234
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V73 G02

<400> SEQUENCE: 234
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtc gtcaaaatgg ggtcccatca    180
aggttcagcg gcagtggatc tgggacagat ttcactctca ccatcagcag cctgcagcct    240
gaagattttg caacttactt ttgtcaacag gctgacagtt atcctcgcac tttttggccag    300 gggaccaagc tggagatcaa a                                              321
```

```
<210> SEQ ID NO 235
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V76 G05

<400> SEQUENCE: 235
gacatccaga tgacccagtc tccatcttcc gtgtctgcat ctgtaggaga cagagtcacc     60
atcacttgtc gggcgagtca gggtattagc agctggttag cctggtatca gcagaaacca    120
gggaaagccc ctaagctcct gatctatgct gcatccagtt tgcaaaaggg ggtcccatca    180
aggttcagcg gcagtggatc tgggagagat ttcactctca ccatcagcag cctgcagcct    240
gaagattttg caacttactt ttgtcaacag gctgacagtt ccctcgcac tttttggccag    300 gggaccaagc tggagatcaa a                                              321
```

```
<210> SEQ ID NO 236
<211> LENGTH: 321
<212> TYPE: DNA
```

-continued

```
<213> ORGANISM: Artificial Sequence
<220> FEATURE:
<223> OTHER INFORMATION: Anti-TREM2 Antibody Variable Region Nucleic
      Acid - LV Antibody ID V84 H01

<400> SEQUENCE: 236
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatggt gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt cccgcgcac  ttttggccag      300 gggaccaagc tggagatcaa a                                               321

<210> SEQ ID NO 237
<211> LENGTH: 363
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 12G10 24C12

<400> SEQUENCE: 237
gaggtgcagc tgttggagtc tggggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attggtggtg gtggtgttag cacatactgc     180
gcagactccg tgaagggccg gttcaccatc tccagagaca attccaagaa tacgctgtat     240
ctgcaaatga acagcctgag agccgaggac acggccgtat attactgtgc gaaattttat     300
atagcagtgg ctggttctca ctttgactac tggggccagg gaaccctggt caccgtctcc     360
tca                                                                   363

<210> SEQ ID NO 238
<211> LENGTH: 378
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 26A10

<400> SEQUENCE: 238
gaggtgcaac tggtggagtc tggggggagcc ttggtacagc ggggggggtc cctgagactc      60
tcctgtgcag cctctagatt cacctttcagt agctttggca tgagctgggt ccgccaggct     120
ccagggaagg ggctggagtg ggtttcatac attagtagta gtagtttttac catatattac      180 gcagactctg tgaagggccg attcaccatc tccagagaca atgccaagaa ttcattctat     240
ctgcaaatga acagcctgag agacgaggac acggctgtgt attactgtgc gagagagggg     300
ggtcttacta tggttcgggg agtctcttcc tacggtttgg acgtctgggg ccaagggacc     360
acggtcaccg tctcctca                                                   378

<210> SEQ ID NO 239
<211> LENGTH: 378
<212> TYPE: DNA
<213> ORGANISM: Artificial Sequence
<220> FEATURE:
<223> OTHER INFORMATION: Anti-TREM2 Antibody Variable Region Nucleic
      Acid - HV 26C10

<400> SEQUENCE: 239
```

-continued

```
gaggtgcaac tggtggagtc tggggggagcc ttggtacagc ctgggggggtc cctgagactc        60 tcctgtgcag cctctggatt caccttcagt agctttggca tgagctgggt ccgccaggct       120
ccagggaagg ggctggagtg ggtttcatac attagtagta gtagttttac catatactac       180
gcagactctg tgaagggccg attcaccatc tccagagaca atgccaagaa ttcgttctat       240
ctgcaaatga acagcctgag agacgaggac acggctgtgt atttctgtgt gagagagggg       300
ggtataacta tggttcgggg agtctcttcc tacggtatgg acgtctgggg ccaagggacc       360
acggtcaccg tctcctca                                                     378
```

<210> SEQ ID NO 240
<211> LENGTH: 378
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 26F2

<400> SEQUENCE: 240

```
gaggtgcaac tggtggagtc tggggggagcc ttggtacagc ctgggggggtc cctgagactc        60 tcctgtgcag cctctggatt caccttcagt agctttggca tgagctgggt ccgccaggct       120
ccagggaagg ggctggagtg gatttcatac attagtagta gtagttttac catatactac       180
gcagactctg tgaagggccg attcaccatc tccagagaca atgccaagaa ttcattctat       240
ctgcaaatga acagcctgag agacgaggac acggctgtgt atttctgtgc gagagagggg       300
ggtattacta tggttcgggg agtctcttcc tacggtatgg acgtctgggg ccaagggacc       360
acggtcaccg tctcctca                                                     378
```

<210> SEQ ID NO 241
<211> LENGTH: 378
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 33B12

<400> SEQUENCE: 241

```
gaggtgcaac tggtggagtc tggggggagcc ttggtacagc ctgggggggtc cctgagactc        60 tcctgtgcag cctctggatt caccttcagt agctttggca tgagctgggt ccgccaggct       120
ccagggaagg gcctggagtg ggtttcatac attagtaaaa gtagttttac catatactac       180
gcagactctg tgaagggccg attcaccatc tccagagaca atgccaagaa ttcattctat       240
ctgcaaatga acagcctgag agacgaggac acggctgtgt attactgtgc gagagagggg       300
ggtcttacta tggttcgggg agtctcttcc tacggtttgg acgtctgggg ccaagggacc       360
acggtcaccg tctcctca                                                     378
```

<210> SEQ ID NO 242
<211> LENGTH: 357
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 24G6

<400> SEQUENCE: 242

```
gaggtgcagc tgttggagtc tggggggaggc ttggtacagc ctggggggtc cctgagactc        60
tcctgtgcag cctctggatt cacctttagc agctatgcca tgagctgggt ccgccaggct       120
```

-continued

```
ccagggaagg gactggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaggcgtat      300
acacctatgg cattctttga ctactggggc cagggaaccc tggtcaccgt ctcctca        357
```

```
<210> SEQ ID NO 243
<211> LENGTH: 348
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 24A10

<400> SEQUENCE: 243
gaggtgcagg tgttggagtc tgggggaggc ttggtacagc ctggggggtc cctgagactc       60
tcctgtgcag cctctggatt cacctttagc aactatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaaggaggg      300
tgggagctat tttactgggg ccagggaacc ctggtcaccg tctcctca                  348
```

```
<210> SEQ ID NO 244
<211> LENGTH: 363
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 10E3

<400> SEQUENCE: 244
gaggtgcagc tggtgcagtc tggagcagag gtgaaaaagc ccggggagtc tctgatgatc       60
tcctgtaagg gttctggata cagctttacc aactactgga tcggctgggt gcgccagatg      120
cccgggaaag gcctggagtg gatggggatc atctatcctg agactctga taccagatac      180 agcccgtcct ccaaggcca ggtcaccatc tcagccgaca agtccatcag caccgcctac      240
ctgcagtgga gcagcctgaa ggcctcggac accgccatgt atttctgtgc gagacggaga      300
caggggatct ggggtgatgc tcttgatatc tggggccaag ggacattggt caccgtctct      360
tca                                                                    363
```

```
<210> SEQ ID NO 245
<211> LENGTH: 363
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 13E7

<400> SEQUENCE: 245
gaggtgcagc tggtgcagtc tggagcagag gtgaaaaagc ccggggagtc tctgatgatc       60
tcctgtaagg gttctggata cagctttacc agctactgga tcggctgggt gcgccagatg      120
cccgggaaag gcctggagtg gatggggatc atctatcctg agactctga taccagatac      180 agcccgtcct ccaaggcca ggtcaccatc tcagccgaca agtccatcag caccgcctac      240
ctgcagtgga gcagcctgaa ggcctcggac accgccatgt atttctgtgc gagacggaga      300
caggggatct ggggtgatgc tcttgatttc tggggccaag ggacattggt caccgtctct      360
```

-continued

```
tca                                                              363
```

```
<210> SEQ ID NO 246
<211> LENGTH: 372
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 25F12
<220> FEATURE:
<221> NAME/KEY: misc_feature
<222> LOCATION: (366)..(366)
<223> OTHER INFORMATION: n is a, c, g, or t

<400> SEQUENCE: 246
caggtgcagc tacagcagtg gggcgcagga ctgttgaagc cttcggagac cctgtccctc    60
acctgcgctg tctatggtgg gtccttcagt agttactact ggagctggat ccgccagccc   120
ccagggaagg ggctggagtg gattggggaa atcaatcata gtggaaacac caactacaac   180
ccgtccctca agagtcgagt caccatatca gtagacacgt ccaagaacca gttctccctg   240
aagctgagct ctgtgaccgc cgcggacacg gctgtgtatt actgtgcgag agaggggtat   300
tacgatatct tgactggtta tcatgatgct tttgatattt gggaccaagg gacaatggtc   360
accgtntttt ca                                                      372
```

```
<210> SEQ ID NO 247
<211> LENGTH: 366
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 32E3

<400> SEQUENCE: 247
gaggtgcagc tggtgcagtc tggagcagag gtgaaaaagc ccggggagtc tctgaagatc    60
tcctgtaagg gttctggata cagctttacc agctactgga tcggctgggt cgcgccagatg   120 cccgggaaag gcctggagtg gatggggatc atctatcctg gtgactctga taccagatac   180
agcccgtcct tccaaggcca ggtcaccatc tcagccgaca gtccatcag caccgcctac   240 ctgcagtgga gcaccctgaa ggcctcggac accgccatat attactgtgc gcgacatgac   300
attataccag cagcccctgg tgcttttgat atctggggcc aagggacaat ggtcaccgtc   360
tcttca                                                              366
```

```
<210> SEQ ID NO 248
<211> LENGTH: 366
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 24F4

<400> SEQUENCE: 248
gaggtgcagc tggtgcagtc tggagcagag gtgaaaaagc ccggggagtc tctgaagatc    60
tcctgtaagg gttctggata cacctttacc agctactgga tcggctgggt cgcgccagatg   120 cccgggaaag gcctggagtg gatggggatc atctatcctg gtgactctga taccagatac   180
agcccgtcct tccaaggcca ggtcaccatc tcagtcgaca gtccagcag caccgcctac   240 ctgcagtgga gcagcctgaa ggcctcggac accgccatat attactgtac gagacaggcc   300
atagcagtga ctggtttggg gggtttcgac ccctggggcc agggaaccct ggtcaccgtc   360
``` tcctca                                                                         366

```
<210> SEQ ID NO 249
<211> LENGTH: 357
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 16B8

<400> SEQUENCE: 249
caggttcagc tggtgcagtc tggagctgag gtgaagaagc ctgggggcctc agtgaaggtc    60 tcctgcaagg cttctggtta cacctttacc aactatggta tcagctgggt gcgacaggcc   120
cctggacaag ggcttgagtg gatgggatgg atcagcgctt acaatggtaa cacaaactat   180
gcacagaagc tccagggcag agtcaccatg accacagaca tccacgag tacagtctac    240 atggagctga ggagcctgag atctgacgac acggccgtgt attactgtgc gagacgggga   300
tacagctatg gttcctttga ctactggggc cagggaaccc tggtcaccgt ctcctca      357

<210> SEQ ID NO 250
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 4C5

<400> SEQUENCE: 250
gaggtgcagc tggtgcagtc tggagcagaa gtgaaaaagc ccggggagtc tctgaagatc    60
tcctgtaagg gttctggaca cagtttttacc aactactgga tcgcctgggt gcgccagatg  120
cccgggaaag gcctggagtg gatggggatc atctatcctg gtgactctga taccagatac   180
agcccgtcct tccaaggcca ggtcaccatc tcagccgaca gtccatcag caccgcctac    240 ctgcagtgga gcagcctgaa ggcctcggac accgccgtgt atttctgtgc gagacaaagg   300
acgttttact atgatagtag tggttatttt gactactggg ccagggaac cctggtcacc    360 gtctcctca                                                            369

<210> SEQ ID NO 251
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID 6E7

<400> SEQUENCE: 251
gaggtgcagc tggtgcagtc tggagcagag gtgaaaaagc ccggggagtc tctgaagatc    60
tcctgtaagg gttctggata cagtttttacc agctactgga tcgcctgggt gcgccagatg  120
cccgggaaag gcctggagtg gatggggatc atctatcctg gtgactctga taccagatac   180
agcccgtcct tccaaggcca ggtcaccatc tcagccgaca gtccatcag caccgcctac    240 ctacagtgga gcagcctgaa ggcctcggac accgccatgt atttctgtgc gagacaaagg   300 acgtttatt atgatagtag tgattattttt gactactggg ccagggaac cctggtcacc    360 gtctcctca                                                            369

<210> SEQ ID NO 252
<211> LENGTH: 363
```

<212> TYPE: DNA
<213> ORGANISM: Artificial Sequence
<220> FEATURE:
<223> OTHER INFORMATION: Anti-TREM2 Antibody Variable Region Nucleic
     Acid - HV Antibody ID 5E3

<400> SEQUENCE: 252
caggtgcagc tggtgcagtc tggggctgag gtgaagaagc ctggggcctc agtgaaggtc        60
tcctgcaagg cttctggata caccttcacc ggctactata tacactgggt gcgacaggcc       120
cctggactag ggcttgagtg gatgggatgg atcaaccc005 acagtggtgg cacaacctct       180
gcacagaagt ttcagggcag ggtcaccatg accaggga ca cgtccatcag ctcagcctac       240
atggaactga gcaggctgag atctgacgac acggccgtgt attactgtgc gagagatgga       300
ggctacctgg ccctctacgg tacggacgtc tggggccaag gaccacggt caccgtctcc       360 tca                                                                       363

<210> SEQ ID NO 253
<211> LENGTH: 366
<212> TYPE: DNA
<213> ORGANISM: Artificial Sequence
<220> FEATURE:
<223> OTHER INFORMATION: Anti-TREM2 Antibody Variable Region Nucleic
     Acid - HV Antibody ID 4G10

<400> SEQUENCE: 253
gaggtgcagc tggtgcagtc tggagcagag gtgaaaaagc ccggggagtc tctgaagatc        60
tcctgtaagg gttctggata cagctttccc agctactgga tcgcctgggt gcgccagatg       120
cccgggaaag gcctggagtg gatggggatc atctatcctg gtgactctga taccagatac       180
agcccgtcct tccaaggcca ggtcaccatc tcagccgaca gtccatcag caccgcc ttt       240 ttgaagtgga gtagcctgaa ggcctcggac accgccatgt atttctgtgc gcgacagggt       300
atagaagtga ctggtacggg aggtttggac gtctggggcc aagggaccac ggtcaccgtc       360
tcctca                                                                    366

<210> SEQ ID NO 254
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
     Acid - HV Antibody ID V3 A04

<400> SEQUENCE: 254
gaggtgcagc tggtgcagtc tggagcagag gtgaaaaagc ccggggagtc tctgaagatc        60
tcctgtaagg gttctggata cagttttgcg agctactgga tcgcctgggt gcgccagatg       120
cccgggaaag gcctggagtg gatggggatc atctatcctg gtgactctga taccagatac       180
agcccgtcct tccaagatca ggtcaccatc tcagccgaca gtccatcag caccgcctac       240 ctacagtgga gcagcctgaa ggcctcggac accgccatgt atttctgtgc gagagggagg       300 acgtttt att atgatagtag tgattatttt gactactggg gccagggaac cctggtcacc       360
gtgtcctca                                                                 369

<210> SEQ ID NO 255
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic

```
                 Acid - HV Antibody ID V24 C01

<400> SEQUENCE: 255
gaggtgcagc tggtgcagtc tggagcagag gtgaaaaagc ccggggagtc tctgaagatc      60
tcctgtaagg gttctggata cagttttacc agctactgga ttgcctgggt cgcccagatg     120
cccgggaaag gcctggagtg gatggggatc atctatcctg gtgactctga tgtgagatac     180
agcccgtcct ccaaggcca ggtcaccatc tcagccgaca gtccatcag caccgcctac      240 ctacagtgga gcagcctgaa ggcctcggac accgccatgt atttctgtgc gagatctagg     300
acgtttattt atgatagtag tgattatttt gactactggg gccagggaac cctggtcacc     360
gtgtcctca                                                            369

<210> SEQ ID NO 256
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V27 C04

<400> SEQUENCE: 256
gaggtgcagc tggtgcagtc tggagcagag gtgaaaaagc ccggggagtc tctgaagatc      60
tcctgtaagg gttctggata cagttttacc agctactgga tcgcctgggt cgcccagatg     120
cccgggaaag gcctggagtg gatggggatc atctatcctg gtgactctga taccagatac     180
gctccgtcct ccaaggcca ggtcaccatc tcagccgaca gtccatcag caccgcctac      240 ctacagtgga gcagcctgaa ggcctcggac accgccatgt atttctgtgt gagaagtagg     300
acgtttattt atgatagtag tgattatttt gactactggg gccagggaac cctggtcacc     360
gtgtcctca                                                            369

<210> SEQ ID NO 257
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V40 D05

<400> SEQUENCE: 257
gaggtgcagc tggtgcagtc tggagcagag gtgaaaaagc ccggggagtc tctgaagatc      60
tcctgtaagg gttctggata cagttttggg agctactgga tcgcctgggt cgcccagatg     120
cccgggaaag gcctggagtg gatggggatc atctatcctg gtgactctga tgttagatac     180
agcccgtcct ccaaggcca ggtcaccatc tcagccgaca gtccatcag caccgcctac      240 ctacagtgga gcagcctgaa ggcctcggac accgccatgt atttctgtgc gagacaaagg     300
acgtttattt atgatagtag tgattattcg gactactggg gccagggaac cctggtcacc     360
gtgtcctca                                                            369

<210> SEQ ID NO 258
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V48 E01

<400> SEQUENCE: 258
```

-continued

```
gaggtgcagc tggtgcagtc tggagcagag gtgaaaaagc ccggggagtc tctgaagatc      60
tcctgtaagg gttctggata cagttttggt agctactgga tcgcctgggt gcgccagatg     120
cccgggaaag gcctggagtg gatggggatc atctatcctg gtgactctga tgtgagatac     180
agcccgtcct ccaaggcca ggtcaccatc tcagccgaca agtccatcag caccgcctac     240
ctacagtgga gcagcctgaa ggcctcggac accgccatgt atttctgtgc gagaatgagg     300 acgtttatt atgatagtag tgattatttt gactactggg gccagggaac cctggtcacc     360
gtgtcctca                                                            369
```

```
<210> SEQ ID NO 259
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V49 E02

<400> SEQUENCE: 259
gaggtgcagc tggtgcagtc tggagcagag gtgaaaaagc ccggggagtc tctgaagatc      60
tcctgtaagg gttctggata cagttttaat agctactgga tcgcctgggt gcgccagatg     120
cccgggaaag gcctggagtg gatggggacg atctatcctg gtgactctga taccagactg     180
agcccgtcct ccaaggcca ggtcaccatc tcagccgaca agtccatcag caccgcctac     240
ctacagtgga gcagcctgaa ggcctcggac accgccatgt atttctgtgc gagaagtagg     300 acgtttatt atgatagtag tgattatttt gactactggg gccagggaac cctggtcacc     360
gtgtcctca                                                            369
```

```
<210> SEQ ID NO 260
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V52 E05

<400> SEQUENCE: 260
gaggtgcagc tggtgcagtc tggagcagag gtgaaaaagc ccggggagtc tctgaagatc      60
tcctgtaagg gttctggata cagttttgag agctactgga tcgcctgggt gcgccagatg     120
cccgggaaag gcctggagtg gatggggatc atctatcctg gtgactctga taccagatac     180
agcccgtcct ccaaggcca ggtcaccatc tcagccgaca agtccatcag caccgcctac     240
ctacagtgga gcagcctgaa ggcctcggac accgccatgt atttctgtgc gagagggagg     300 acgtttatt atgatagtag tgattatttt gactactggg gccagggaac cctggtcacc     360
gtgtcctca                                                            369
```

```
<210> SEQ ID NO 261
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V60 F01

<400> SEQUENCE: 261
gaggtgcagc tggtgcagtc tggagcagag gtgaaaaagc ccggggagtc tctgaagatc      60
tcctgtaagg gttctggata ccattttacc agctactgga tcgcctgggt gcgccagatg     120
```

```
cccgggaaag gcctggagtg gatggggatc atctatcctg gtgactctga tgtgagatac        180
agcccgtcct tccaaggcca ggtcaccatc tcagccgaca agtccatcag caccgcctac        240
ctacagtgga gcagcctgaa ggcctcggac accgccatgt atttctgtgc gagacaaagg        300 acgtttatt atgatagtag tgattatagt gactactggg gccagggaac cctggtcacc         360
gtgtcctca                                                                369
```

```
<210> SEQ ID NO 262
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V73 G02

<400> SEQUENCE: 262
gaggtgcagc tggtgcagtc tggagcagag gtgaaaaagc ccggggagtc tctgaagatc        60
tcctgtaagg gttctggata cagttttggt agctactgga tcgcctgggt gcgccagatg        120
cccgggaaag gcctggagtg gatggggatc atctatcctg gtgactctga taccagatac        180
agcccggggt tccaaggcca ggtcaccatc tcagccgaca agtccatcag caccgcctac        240
ctacagtgga gcagcctgaa ggcctcggac accgccatgt atttctgtgc gagagggagg        300 acgtttatt atgatagtag tgattatttt gactactggg gccagggaac cctggtcacc         360
gtgtcctca                                                                369
```

```
<210> SEQ ID NO 263
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V76 G05

<400> SEQUENCE: 263
gaggtgcagc tggtgcagtc tggagcagag gtgaaaaagc ccggggagtc tctgaagatc        60
tcctgtaagg gttctggata cagttttggg agctactgga tcgcctgggt gcgccagatg        120
cccgggaaag gcctggagtg gatggggatc atctatcctg gtgactctga taccagatac        180
agcccggagt tccaaggcca ggtcaccatc tcagccgaca agtccatcag caccgcctac        240
ctacagtgga gcagcctgaa ggcctcggac accgccatgt atttctgtgc gagacaaagg        300 acgtttatt atgatagtag tgattatagt gactactggg gccagggaac cctggtcacc         360
gtgtcctca                                                                369
```

```
<210> SEQ ID NO 264
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V84 H01

<400> SEQUENCE: 264
gaggtgcagc tggtgcagtc tggagcagag gtgaaaaagc ccggggagtc tctgaagatc        60
tcctgtaagg gttctggata cgggtttacc agctactgga tcgcctgggt gcgccagatg        120
cccgggaaag gcctggagtg gatggggatc atctatcctg gtgacagtga taccagatac        180
agcccgtcct tccaaggcca ggtcaccatc tcagccgaca agtccatcag caccgcctac        240
```
ctacagtgga gcagcctgaa ggcctcggac accgccatgt atttctgtgc gagacaaagg     300 acgtttatt atgatagtag tgattattcg gactactggg gccagggaac cctggtcacc       360
gtgtcctca                                                              369

<210> SEQ ID NO 265
<211> LENGTH: 22
<212> TYPE: PRT
<213> ORGANISM: Artificial Sequence
<220> FEATURE:
<223> OTHER INFORMATION: Secretory peptide #1

<400> SEQUENCE: 265

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 266
<211> LENGTH: 19
<212> TYPE: PRT
<213> ORGANISM: Artificial Sequence
<220> FEATURE:
<223> OTHER INFORMATION: Secretory peptide #2

<400> SEQUENCE: 266

Met Ala Trp Ala Leu Leu Leu Leu Thr Leu Leu Thr Gln Gly Thr Gly
1               5                   10                  15

Ser Trp Ala

<210> SEQ ID NO 267

<400> SEQUENCE: 267

000

<210> SEQ ID NO 268
<211> LENGTH: 20
<212> TYPE: PRT
<213> ORGANISM: Artificial Sequence
<220> FEATURE:
<223> OTHER INFORMATION: Secretory peptide #4

<400> SEQUENCE: 268

Met Glu Ala Pro Ala Gln Leu Leu Phe Leu Leu Leu Leu Trp Leu Pro
1               5                   10                  15

Asp Thr Thr Gly
            20

<210> SEQ ID NO 269
<211> LENGTH: 19
<212> TYPE: PRT
<213> ORGANISM: Artificial Sequence
<220> FEATURE:
<223> OTHER INFORMATION: Secretory peptide #5

<400> SEQUENCE: 269

Met Glu Trp Thr Trp Arg Val Leu Phe Leu Val Ala Ala Ala Thr Gly
1               5                   10                  15

Ala His Ser

<210> SEQ ID NO 270
<211> LENGTH: 20
<212> TYPE: PRT

-continued

```
<213> ORGANISM: Artificial Sequence
<220> FEATURE:
<223> OTHER INFORMATION: Secretory peptide #6

<400> SEQUENCE: 270

Met Glu Thr Pro Ala Gln Leu Leu Phe Leu Leu Leu Leu Trp Leu Pro
1               5                   10                  15

Asp Thr Thr Gly
            20

<210> SEQ ID NO 271
<211> LENGTH: 9
<212> TYPE: PRT
<213> ORGANISM: Artificial Sequence
<220> FEATURE:
<223> OTHER INFORMATION: CDRL3 Antibody ID V83

<400> SEQUENCE: 271

Gln Gln Ala Val Ser Phe Pro Arg Thr
1               5

<210> SEQ ID NO 272
<211> LENGTH: 19
<212> TYPE: PRT
<213> ORGANISM: Artificial Sequence
<220> FEATURE:
<223> OTHER INFORMATION: Secretory peptide #8

<400> SEQUENCE: 272

Met Lys His Leu Trp Phe Phe Leu Leu Leu Val Ala Ala Pro Arg Trp
1               5                   10                  15

Val Leu Ser

<210> SEQ ID NO 273
<211> LENGTH: 19
<212> TYPE: PRT
<213> ORGANISM: Artificial Sequence
<220> FEATURE:
<223> OTHER INFORMATION: Secretory peptide #9

<400> SEQUENCE: 273

Met Glu Trp Ser Trp Val Phe Leu Phe Phe Leu Ser Val Thr Thr Gly
1               5                   10                  15

Val His Ser

<210> SEQ ID NO 274
<211> LENGTH: 22
<212> TYPE: PRT
<213> ORGANISM: Artificial Sequence
<220> FEATURE:
<223> OTHER INFORMATION: Secretory peptide #10

<400> SEQUENCE: 274

Met Asp Ile Arg Ala Pro Thr Gln Leu Leu Gly Leu Leu Leu Leu Trp
1               5                   10                  15

Leu Pro Gly Ala Lys Cys
            20

<210> SEQ ID NO 275
<211> LENGTH: 22
<212> TYPE: PRT
<213> ORGANISM: Artificial Sequence
<220> FEATURE:
<223> OTHER INFORMATION: Secretory peptide #11
```

-continued

<400> SEQUENCE: 275

Met Asp Ile Arg Ala Pro Thr Gln Leu Leu Gly Leu Leu Leu Trp
1               5                   10                  15

Leu Pro Gly Ala Arg Cys
            20

<210> SEQ ID NO 276
<211> LENGTH: 22
<212> TYPE: PRT
<213> ORGANISM: Artificial Sequence
<220> FEATURE:
<223> OTHER INFORMATION: Secretory peptide #12

<400> SEQUENCE: 276

Met Asp Thr Arg Ala Pro Thr Gln Leu Leu Gly Leu Leu Leu Trp
1               5                   10                  15

Leu Pro Gly Ala Thr Phe
            20

<210> SEQ ID NO 277
<211> LENGTH: 22
<212> TYPE: PRT
<213> ORGANISM: Artificial Sequence
<220> FEATURE:
<223> OTHER INFORMATION: Secretory peptide #13

<400> SEQUENCE: 277

Met Asp Thr Arg Ala Pro Thr Gln Leu Leu Gly Leu Leu Leu Trp
1               5                   10                  15

Leu Pro Gly Ala Arg Cys
            20

<210> SEQ ID NO 278
<211> LENGTH: 19
<212> TYPE: PRT
<213> ORGANISM: Artificial Sequence
<220> FEATURE:
<223> OTHER INFORMATION: Secretory peptide #14

<400> SEQUENCE: 278

Met Glu Thr Gly Leu Arg Trp Leu Leu Leu Val Ala Val Leu Lys Gly
1               5                   10                  15

Val Gln Cys

<210> SEQ ID NO 279
<211> LENGTH: 21
<212> TYPE: PRT
<213> ORGANISM: Artificial Sequence
<220> FEATURE:
<223> OTHER INFORMATION: Secretory peptide #15

<400> SEQUENCE: 279

Met Glu Thr Gly Leu Arg Trp Leu Leu Leu Val Ala Val Leu Lys Gly
1               5                   10                  15

Val Gln Cys Gln Glu
            20

<210> SEQ ID NO 280
<211> LENGTH: 22
<212> TYPE: PRT
<213> ORGANISM: Artificial Sequence
<220> FEATURE:
<223> OTHER INFORMATION: Secretory peptide #16

-continued

<400> SEQUENCE: 280

Met Asp Met Arg Ala Pro Thr Gln Leu Leu Gly Leu Leu Leu Trp
1               5                   10                  15

Leu Pro Gly Ala Arg Cys
            20

<210> SEQ ID NO 281
<211> LENGTH: 217
<212> TYPE: PRT
<213> ORGANISM: Homo sapiens

<400> SEQUENCE: 281

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Gly Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 282
<211> LENGTH: 217
<212> TYPE: PRT
<213> ORGANISM: Homo sapiens

<400> SEQUENCE: 282

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Cys Glu Glu
    50                  55                  60

Gln Tyr Gly Ser Thr Tyr Arg Cys Val Ser Val Leu Thr Val Leu His

-continued

```
65                 70                 75                 80

Gln Asp Trp Leu Asn Gly Lys Glu Tyr Lys Cys Lys Val Ser Asn Lys
                85                 90                 95

Ala Leu Pro Ala Pro Ile Glu Lys Thr Ile Ser Lys Ala Lys Gly Gln
                100                105                110

Pro Arg Glu Pro Gln Val Tyr Thr Leu Pro Pro Ser Arg Glu Glu Met
        115                120                125

Thr Lys Asn Gln Val Ser Leu Thr Cys Leu Val Lys Gly Phe Tyr Pro
        130                135                140

Ser Asp Ile Ala Val Glu Trp Glu Ser Asn Gly Gln Pro Glu Asn Asn
145                150                155                160

Tyr Lys Thr Thr Pro Pro Val Leu Asp Ser Asp Gly Ser Phe Phe Leu
                165                170                175

Tyr Ser Lys Leu Thr Val Asp Lys Ser Arg Trp Gln Gln Gly Asn Val
                180                185                190

Phe Ser Cys Ser Val Met His Glu Ala Leu His Asn His Tyr Thr Gln
                195                200                205

Lys Ser Leu Ser Leu Ser Pro Gly Lys
        210                215
```

```
<210> SEQ ID NO 283
<211> LENGTH: 21
<212> TYPE: PRT
<213> ORGANISM: Artificial Sequence
<220> FEATURE:
<223> OTHER INFORMATION: MOG peptide 35-55

<400> SEQUENCE: 283

Met Glu Val Gly Trp Tyr Arg Ser Pro Phe Ser Arg Val Val His Leu
1               5                  10                 15

Tyr Arg Asn Gly Lys
            20
```

```
<210> SEQ ID NO 284
<211> LENGTH: 11
<212> TYPE: PRT
<213> ORGANISM: Artificial Sequence
<220> FEATURE:
<223> OTHER INFORMATION: CDRL1 Consensus for 6E7 reduced Affinity
      variants
<220> FEATURE:
<221> NAME/KEY: MISC_FEATURE
<222> LOCATION: (1)..(1)
<223> OTHER INFORMATION: X is R OR A
<220> FEATURE:
<221> NAME/KEY: MISC_FEATURE
<222> LOCATION: (8)..(8)
<223> OTHER INFORMATION: X IS S OR R

<400> SEQUENCE: 284

Xaa Ala Ser Gln Gly Ile Ser Xaa Trp Leu Ala
1               5                  10
```

```
<210> SEQ ID NO 285
<211> LENGTH: 7
<212> TYPE: PRT
<213> ORGANISM: Artificial Sequence
<220> FEATURE:
<223> OTHER INFORMATION: CDRL2 Consensus for 6E7 reduced Affinity
      variants
<220> FEATURE:
<221> NAME/KEY: MISC_FEATURE
<222> LOCATION: (1)..(1)
<223> OTHER INFORMATION: X is A or S
```

```
<220> FEATURE:
<221> NAME/KEY: MISC_FEATURE
<222> LOCATION: (3)..(3)
<223> OTHER INFORMATION: X is S or G

<400> SEQUENCE: 285

Xaa Ala Xaa Ser Leu Gln Asn
1               5

<210> SEQ ID NO 286
<211> LENGTH: 9
<212> TYPE: PRT
<213> ORGANISM: Artificial Sequence
<220> FEATURE:
<223> OTHER INFORMATION: CDRL3 Consensus for 6E7 reduced Affinity
      variants
<220> FEATURE:
<221> NAME/KEY: MISC_FEATURE
<222> LOCATION: (4)..(4)
<223> OTHER INFORMATION: X is D or V
<220> FEATURE:
<221> NAME/KEY: MISC_FEATURE
<222> LOCATION: (8)..(8)
<223> OTHER INFORMATION: X is R or L

<400> SEQUENCE: 286

Gln Gln Ala Xaa Ser Phe Pro Xaa Thr
1               5

<210> SEQ ID NO 287
<211> LENGTH: 5
<212> TYPE: PRT
<213> ORGANISM: Artificial Sequence
<220> FEATURE:
<223> OTHER INFORMATION: CDRH1 Consensus for 6E7 reduced Affinity
      variants
<220> FEATURE:
<221> NAME/KEY: MISC_FEATURE
<222> LOCATION: (2)..(2)
<223> OTHER INFORMATION: X is Y or E

<400> SEQUENCE: 287

Ser Xaa Trp Ile Ala
1               5

<210> SEQ ID NO 288
<211> LENGTH: 17
<212> TYPE: PRT
<213> ORGANISM: Artificial Sequence
<220> FEATURE:
<223> OTHER INFORMATION: CDRH2 Consensus for 6E7 reduced Affinity
      variants
<220> FEATURE:
<221> NAME/KEY: MISC_FEATURE
<222> LOCATION: (5)..(5)
<223> OTHER INFORMATION: X is G or S

<400> SEQUENCE: 288

Ile Ile Tyr Pro Xaa Asp Ser Asp Thr Arg Tyr Ser Pro Ser Phe Gln
1               5                   10                  15

Gly

<210> SEQ ID NO 289
<211> LENGTH: 14
<212> TYPE: PRT
<213> ORGANISM: Artificial Sequence
<220> FEATURE:
<223> OTHER INFORMATION: CDRH3 Consensus for 6E7 reduced Affinity
      variants
<220> FEATURE:
```

```
<221> NAME/KEY: MISC_FEATURE
<222> LOCATION: (3)..(3)
<223> OTHER INFORMATION: X is T or G
<220> FEATURE:
<221> NAME/KEY: MISC_FEATURE
<222> LOCATION: (5)..(5)
<223> OTHER INFORMATION: X is Y or R
<220> FEATURE:
<221> NAME/KEY: MISC_FEATURE
<222> LOCATION: (6)..(6)
<223> OTHER INFORMATION: X is Y or G

<400> SEQUENCE: 289

Gln Arg Xaa Phe Xaa Xaa Asp Ser Ser Asp Tyr Phe Asp Tyr
1               5                   10

<210> SEQ ID NO 290
<211> LENGTH: 11
<212> TYPE: PRT
<213> ORGANISM: Artificial Sequence
<220> FEATURE:
<223> OTHER INFORMATION: CDRL1 Antibody ID V57 E10

<400> SEQUENCE: 290

Ala Ala Ser Gln Gly Ile Ser Ser Trp Leu Ala
1               5                   10

<210> SEQ ID NO 291
<211> LENGTH: 11
<212> TYPE: PRT
<213> ORGANISM: Artificial Sequence
<220> FEATURE:
<223> OTHER INFORMATION: CDRL1 Antibody ID V90 H07

<400> SEQUENCE: 291

Arg Ala Ser Gln Gly Ile Ser Arg Trp Leu Ala
1               5                   10

<210> SEQ ID NO 292
<211> LENGTH: 7
<212> TYPE: PRT
<213> ORGANISM: Artificial Sequence
<220> FEATURE:
<223> OTHER INFORMATION: CDRL2 Antibody ID V10 A11

<400> SEQUENCE: 292

Ser Ala Ser Ser Leu Gln Asn
1               5

<210> SEQ ID NO 293
<211> LENGTH: 7
<212> TYPE: PRT
<213> ORGANISM: Artificial Sequence
<220> FEATURE:
<223> OTHER INFORMATION: CDRL2 Antibody ID V70 F11

<400> SEQUENCE: 293

Ala Ala Gly Ser Leu Gln Asn
1               5

<210> SEQ ID NO 294
<211> LENGTH: 9
<212> TYPE: PRT
<213> ORGANISM: Artificial Sequence
<220> FEATURE:
<223> OTHER INFORMATION: CDRL2 Antibody ID V23 B12

<400> SEQUENCE: 294
```

-continued

```
Gln Gln Ala Asp Ser Phe Pro Leu Thr
1               5

<210> SEQ ID NO 295
<211> LENGTH: 107
<212> TYPE: PRT
<213> ORGANISM: Artificial Sequence
<220> FEATURE:
<223> OTHER INFORMATION: VL Amino Acid Sequence Antibody ID V10 A11

<400> SEQUENCE: 295

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ser Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
                85                  90                  95

Thr Phe Gly Gln Gly Thr Lys Leu Glu Ile Lys
            100                 105

<210> SEQ ID NO 296
<211> LENGTH: 107
<212> TYPE: PRT
<213> ORGANISM: Artificial Sequence
<220> FEATURE:
<223> OTHER INFORMATION: VL Amino Acid Sequence Antibody ID V23 B12

<400> SEQUENCE: 296

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Leu
                85                  90                  95

Thr Phe Gly Gln Gly Thr Lys Leu Glu Ile Lys
            100                 105

<210> SEQ ID NO 297
<211> LENGTH: 107
<212> TYPE: PRT
<213> ORGANISM: Artificial Sequence
<220> FEATURE:
<223> OTHER INFORMATION: VL Amino Acid Sequence Antibody ID V57 E10

<400> SEQUENCE: 297

Asp Ile Gln Met Thr Gln Ser Pro Ser Ser Val Ser Ala Ser Val Gly
1               5                   10                  15

Asp Arg Val Thr Ile Thr Cys Ala Ala Ser Gln Gly Ile Ser Ser Trp
```

-continued

```
              20                 25                 30

Leu Ala Trp Tyr Gln Gln Lys Pro Gly Lys Ala Pro Lys Leu Leu Ile
        35                 40                 45

Tyr Ala Ala Ser Ser Leu Gln Asn Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Phe Cys Gln Gln Ala Asp Ser Phe Pro Arg
                85                 90                 95

Thr Phe Gly Gln Gly Thr Lys Leu Glu Ile Lys
            100                105

<210> SEQ ID NO 298
<211> LENGTH: 107
<212> TYPE: PRT
<213> ORGANISM: Artificial Sequence
<220> FEATURE:
<223> OTHER INFORMATION: VL Amino Acid Sequence Antibody ID V70 F11

<400> SEQUENCE: 298

Asp Ile Gln Met Thr Gln Ser Pro Ser Ser Val Ser Ala Ser Val Gly
1               5                 10                 15

Asp Arg Val Thr Ile Thr Cys Arg Ala Ser Gln Gly Ile Ser Ser Trp
            20                 25                 30

Leu Ala Trp Tyr Gln Gln Lys Pro Gly Lys Ala Pro Lys Leu Leu Ile
        35                 40                 45

Tyr Ala Ala Gly Ser Leu Gln Asn Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Phe Cys Gln Gln Ala Asp Ser Phe Pro Arg
                85                 90                 95

Thr Phe Gly Gln Gly Thr Lys Leu Glu Ile Lys
            100                105

<210> SEQ ID NO 299
<211> LENGTH: 107
<212> TYPE: PRT
<213> ORGANISM: Artificial Sequence
<220> FEATURE:
<223> OTHER INFORMATION: VL Amino Acid Sequence Antibody ID V83 G12

<400> SEQUENCE: 299

Asp Ile Gln Met Thr Gln Ser Pro Ser Ser Val Ser Ala Ser Val Gly
1               5                 10                 15

Asp Arg Val Thr Ile Thr Cys Arg Ala Ser Gln Gly Ile Ser Ser Trp
            20                 25                 30

Leu Ala Trp Tyr Gln Gln Lys Pro Gly Lys Ala Pro Lys Leu Leu Ile
        35                 40                 45

Tyr Ala Ala Ser Ser Leu Gln Asn Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Phe Cys Gln Gln Ala Val Ser Phe Pro Arg
                85                 90                 95

Thr Phe Gly Gln Gly Thr Lys Leu Glu Ile Lys
            100                105
```

```
<210> SEQ ID NO 300
<211> LENGTH: 107
<212> TYPE: PRT
<213> ORGANISM: Artificial Sequence
<220> FEATURE:
<223> OTHER INFORMATION: VL Amino Acid Sequence Antibody ID V90 H07

<400> SEQUENCE: 300

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Arg
                85                  90                  95

Thr Phe Gly Gln Gly Thr Lys Leu Glu Ile Lys
            100                 105

<210> SEQ ID NO 301
<211> LENGTH: 4
<212> TYPE: PRT
<213> ORGANISM: Artificial Sequence
<220> FEATURE:
<223> OTHER INFORMATION: FR1/
     CDRH1 border
     Antibody ID V30 C07

<400> SEQUENCE: 301

Ser Ser Phe Thr
1

<210> SEQ ID NO 302
<211> LENGTH: 5
<212> TYPE: PRT
<213> ORGANISM: Artificial Sequence
<220> FEATURE:
<223> OTHER INFORMATION: CDRH1 Antibody ID V90 H07

<400> SEQUENCE: 302

Ser Glu Trp Ile Ala
1               5

<210> SEQ ID NO 303
<211> LENGTH: 17
<212> TYPE: PRT
<213> ORGANISM: Artificial Sequence
<220> FEATURE:
<223> OTHER INFORMATION: CDRH2 Antibody ID V44 D09

<400> SEQUENCE: 303

Ile Ile Tyr Pro Ser Asp Ser Asp Thr Arg Tyr Ser Pro Ser Phe Gln
1               5                   10                  15

Gly

<210> SEQ ID NO 304
<211> LENGTH: 14
<212> TYPE: PRT
<213> ORGANISM: Artificial Sequence
```

-continued

```
<220> FEATURE:
<223> OTHER INFORMATION: CDRH3 Antibody ID V9 A10

<400> SEQUENCE: 304

Gln Arg Gly Phe Tyr Tyr Asp Ser Ser Asp Tyr Phe Asp Tyr
1               5               10

<210> SEQ ID NO 305
<211> LENGTH: 14
<212> TYPE: PRT
<213> ORGANISM: Artificial Sequence
<220> FEATURE:
<223> OTHER INFORMATION: CDRH3 Antibody ID V33 C10

<400> SEQUENCE: 305

Gln Arg Thr Phe Tyr Gly Asp Ser Ser Asp Tyr Phe Asp Tyr
1               5               10

<210> SEQ ID NO 306
<211> LENGTH: 14
<212> TYPE: PRT
<213> ORGANISM: Artificial Sequence
<220> FEATURE:
<223> OTHER INFORMATION: CDRH3 Antibody ID V68 F09

<400> SEQUENCE: 306

Gln Arg Thr Phe Arg Tyr Asp Ser Ser Asp Tyr Phe Asp Tyr
1               5               10

<210> SEQ ID NO 307
<211> LENGTH: 123
<212> TYPE: PRT
<213> ORGANISM: Artificial Sequence
<220> FEATURE:
<223> OTHER INFORMATION: VH Amino Acid Sequence Antibody ID V9 A10

<400> SEQUENCE: 307

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
                20              25              30

Trp Ile Ala Trp Val Arg Gln Met Pro Gly Lys Gly Leu Glu Trp Met
            35              40              45

Gly Ile Ile Tyr Pro Gly Asp Ser Asp Thr Arg Tyr Ser Pro Ser Phe
        50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Phe Cys
                85              90              95

Ala Arg Gln Arg Gly Phe Tyr Tyr Asp Ser Ser Asp Tyr Phe Asp Tyr
            100             105             110

Trp Gly Gln Gly Thr Leu Val Thr Val Ser Ser
        115             120

<210> SEQ ID NO 308
<211> LENGTH: 123
<212> TYPE: PRT
<213> ORGANISM: Artificial Sequence
<220> FEATURE:
<223> OTHER INFORMATION: VH Amino Acid Sequence Antibody ID V30 C07

<400> SEQUENCE: 308

Glu Val Gln Leu Val Gln Ser Gly Ala Glu Val Lys Lys Pro Gly Glu
```

-continued

```
1               5               10              15

Ser Leu Lys Ile Ser Cys Lys Gly Ser Gly Ser Ser Phe Thr Ser Tyr
            20              25              30

Trp Ile Ala Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Phe Cys
            85              90              95

Ala Arg Gln Arg Thr Phe Tyr Tyr Asp Ser Ser Asp Tyr Phe Asp Tyr
            100             105             110

Trp Gly Gln Gly Thr Leu Val Thr Val Ser Ser
        115             120
```

<210> SEQ ID NO 309
<211> LENGTH: 123
<212> TYPE: PRT
<213> ORGANISM: Artificial Sequence
<220> FEATURE:
<223> OTHER INFORMATION: VH Amino Acid Sequence Antibody ID V33 C10

<400> SEQUENCE: 309

```
Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
            20              25              30

Trp Ile Ala Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Phe Cys
            85              90              95

Ala Arg Gln Arg Thr Phe Tyr Gly Asp Ser Ser Asp Tyr Phe Asp Tyr
            100             105             110

Trp Gly Gln Gly Thr Leu Val Thr Val Ser Ser
        115             120
```

<210> SEQ ID NO 310
<211> LENGTH: 123
<212> TYPE: PRT
<213> ORGANISM: Artificial Sequence
<220> FEATURE:
<223> OTHER INFORMATION: VH Amino Acid Sequence Antibody ID V44 D09

<400> SEQUENCE: 310

```
Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
            20              25              30

Trp Ile Ala Trp Val Arg Gln Met Pro Gly Lys Gly Leu Glu Trp Met
        35              40              45

Gly Ile Ile Tyr Pro Ser Asp Ser Asp Thr Arg Tyr Ser Pro Ser Phe
    50              55              60
```

-continued

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Phe Asp Tyr
            100                 105                 110

Trp Gly Gln Gly Thr Leu Val Thr Val Ser Ser
            115                 120
```

```
<210> SEQ ID NO 311
<211> LENGTH: 123
<212> TYPE: PRT
<213> ORGANISM: Artificial Sequence
<220> FEATURE:
<223> OTHER INFORMATION: VH Amino Acid Sequence Antibody ID V68 F09

<400> SEQUENCE: 311

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Arg Tyr Asp Ser Ser Asp Tyr Phe Asp Tyr
            100                 105                 110

Trp Gly Gln Gly Thr Leu Val Thr Val Ser Ser
            115                 120
```

```
<210> SEQ ID NO 312
<211> LENGTH: 123
<212> TYPE: PRT
<213> ORGANISM: Artificial Sequence
<220> FEATURE:
<223> OTHER INFORMATION: VH Amino Acid Sequence Antibody ID V90 H07

<400> SEQUENCE: 312

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Glu
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gln Arg Thr Phe Tyr Tyr Asp Ser Ser Asp Tyr Phe Asp Tyr
            100                 105                 110

Trp Gly Gln Gly Thr Leu Val Thr Val Ser Ser
            115                 120
```

<210> SEQ ID NO 313
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V10 A11

<400> SEQUENCE: 313
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctattct gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt ccctcgcac tttggccag     300 gggaccaagc tggagatcaa a                                              321

<210> SEQ ID NO 314
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V23 B12

<400> SEQUENCE: 314
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt ccctcttac tttggccag     300 gggaccaagc tggagatcaa a                                              321

<210> SEQ ID NO 315
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V57 E10

<400> SEQUENCE: 315
gacatccaga tgacccagtc tccatcttcc gtgtctgcat ctgtaggaga cagagtcacc      60
atcacttgtg cggcgagtca gggtattagc agctggttag cctggtatca gcagaaacca     120
gggaaagccc ctaagctcct gatctatgct gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt ccctcgcac tttggccag     300 gggaccaagc tggagatcaa a                                              321

<210> SEQ ID NO 316
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V70 F11

```
<400> SEQUENCE: 316
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcagggagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt ccctcgcac ttttggccag      300 gggaccaagc tggagatcaa a                                               321

<210> SEQ ID NO 317
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V83

<400> SEQUENCE: 317
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgtgagtt ccctcgcac ttttggccag      300 gggaccaagc tggagatcaa a                                               321

<210> SEQ ID NO 318
<211> LENGTH: 321
<212> TYPE: DNA
<213> ORGANISM: Artificial Sequence
<220> FEATURE:
<223> OTHER INFORMATION: Anti-TREM2 Antibody Variable Region Nucleic
      Acid - LV Antibody ID V90 H07

<400> SEQUENCE: 318
gacatccaga tgacccagtc tccatcttcc gtgtctgcat ctgtaggaga cagagtcacc      60
atcacttgtc gggcgagtca gggtattagc agatggttag cctggtatca gcagaaacca     120
gggaaagccc ctaagctcct gatctatgct gcatccagtt tgcaaaatgg ggtcccatca     180
aggttcagcg gcagtggatc tgggacagat ttcactctca ccatcagcag cctgcagcct     240
gaagattttg caacttactt ttgtcaacag gctgacagtt ccctcgcac ttttggccag      300 gggaccaagc tggagatcaa a                                               321

<210> SEQ ID NO 319
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V9 A10

<400> SEQUENCE: 319
gaggtgcagc tggtgcagtc tggagcagag gtgaaaaagc ccgggggagtc tctgaagatc      60 tcctgtaagg gttctggata cagttttacc agctactgga tcgcctgggt gcgccagatg     120
cccgggaaag cctggagtg gatgggggatc atctatcctg gtgactctga taccagatac     180
agcccgtcct ccaaggcca ggtcaccatc tcagccgaca agtccatcag caccgcctac     240
```

-continued

```
ctacagtgga gcagcctgaa ggcctcggac accgccatgt atttctgtgc gagacaaagg      300 gggtttttatt atgatagtag tgattatttt gactactggg gccagggaac cctggtcacc      360
gtgtcctca                                                              369
```

<210> SEQ ID NO 320
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V10 A11 V23 B12 V57 E10 V70 F11 V83 G12

<400> SEQUENCE: 320

```
gaggtgcagc tggtgcagtc tggagcagag gtgaaaaagc ccggggagtc tctgaagatc       60
tcctgtaagg gttctggata cagttttacc agctactgga tcgcctgggt cgcccagatg      120
cccgggaaag gcctggagtg gatggggatc atctatcctg gtgactctga taccagatac      180
agcccgtcct tccaaggcca ggtcaccatc tcagccgaca gtccatcag caccgcctac      240 ctacagtgga gcagcctgaa ggcctcggac accgccatgt atttctgtgc gagacaaagg      300 acgtttttatt atgatagtag tgattatttt gactactggg gccagggaac cctggtcacc      360
gtgtcctca                                                              369
```

<210> SEQ ID NO 321
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V30 C07

<400> SEQUENCE: 321

```
gaggtgcagc tggtgcagtc tggagcagag gtgaaaaagc ccggggagtc tctgaagatc       60
tcctgtaagg gttctggatc gagttttacc agctactgga tcgcctgggt cgcccagatg      120
cccgggaaag gcctggagtg gatggggatc atctatcctg gtgactctga taccagatac      180
agcccgtcct tccaaggcca ggtcaccatc tcagccgaca gtccatcag caccgcctac      240 ctacagtgga gcagcctgaa ggcctcggac accgccatgt atttctgtgc gagacaaagg      300 acgtttttatt atgatagtag tgattatttt gactactggg gccagggaac cctggtcacc      360
gtgtcctca                                                              369
```

<210> SEQ ID NO 322
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V33 C10

<400> SEQUENCE: 322

```
gaggtgcagc tggtgcagtc tggagcagag gtgaaaaagc ccggggagtc tctgaagatc       60
tcctgtaagg gttctggata cagttttacc agctactgga tcgcctgggt cgcccagatg      120
cccgggaaag gcctggagtg gatggggatc atctatcctg gtgactctga taccagatac      180
agcccgtcct tccaaggcca ggtcaccatc tcagccgaca gtccatcag caccgcctac      240 ctacagtgga gcagcctgaa ggcctcggac accgccatgt atttctgtgc gagacaaagg      300
acgttttatg gggatagtag tgattatttt gactactggg gccagggaac cctggtcacc      360
```

-continued

```
gtgtcctca                                                         369
```

```
<210> SEQ ID NO 323
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V44 D09

<400> SEQUENCE: 323
gaggtgcagc tggtgcagtc tggagcagag gtgaaaaagc ccgggggagtc tctgaagatc     60 tcctgtaagg gttctggata cagttttacc agctactgga tcgcctgggt gcgccagatg    120
cccgggaaag gcctggagtg gatggggatc atctatccta gtgactctga taccagatac    180
agcccgtcct ccaaggcca ggtcaccatc tcagccgaca agtccatcag caccgcctac      240
ctacagtgga gcagcctgaa ggcctcggac accgccatgt atttctgtgc gagacaaagg     300 acgtttttatt atgatagtag tgattatttt gactactggg gccagggaac cctggtcacc     360
gtgtcctca                                                         369
```

```
<210> SEQ ID NO 324
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V68 F09

<400> SEQUENCE: 324
gaggtgcagc tggtgcagtc tggagcagag gtgaaaaagc ccgggggagtc tctgaagatc     60 tcctgtaagg gttctggata cagttttacc agctactgga tcgcctgggt gcgccagatg    120
cccgggaaag gcctggagtg gatggggatc atctatcctg gtgactctga taccagatac    180
agcccgtcct ccaaggcca ggtcaccatc tcagccgaca agtccatcag caccgcctac      240
ctacagtgga gcagcctgaa ggcctcggac accgccatgt atttctgtgc gagacaaagg     300
acgtttaggt atgatagtag tgattatttt gactactggg gccagggaac cctggtcacc     360
gtgtcctca                                                         369
```

```
<210> SEQ ID NO 325
<211> LENGTH: 369
<212> TYPE: DNA
<213> ORGANISM: Artificial Sequence
<220> FEATURE:
<223> OTHER INFORMATION: Anti-TREM2 Antibody Variable Region Nucleic
      Acid - HV Antibody ID V90 H07

<400> SEQUENCE: 325
gaggtgcagc tggtgcagtc tggagcagag gtgaaaaagc ccgggggagtc tctgaagatc     60 tcctgtaagg gttctggata cagttttacc agcgagtgga tcgcctgggt gcgccagatg    120
cccgggaaag gcctggagtg gatggggatc atctatcctg gtgactctga taccagatac    180
agcccgtcct ccaaggcca ggtcaccatc tcagccgaca agtccatcag caccgcctac      240
ctacagtgga gcagcctgaa ggcctcggac accgccatgt atttctgtgc gagacaaagg     300 acgtttttatt atgatagtag tgattatttt gactactggg gccagggaac cctggtcacc     360
gtgtcctca                                                         369
```

```
<210> SEQ ID NO 326
```

-continued

```
<211> LENGTH: 113
<212> TYPE: PRT
<213> ORGANISM: Artificial Sequence
<220> FEATURE:
<223> OTHER INFORMATION: LC variable region sequence 24G6

<400> SEQUENCE: 326

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys His Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 327
<211> LENGTH: 119
<212> TYPE: PRT
<213> ORGANISM: Artificial Sequence
<220> FEATURE:
<223> OTHER INFORMATION: HC variable region sequence 24G6

<400> SEQUENCE: 327

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Thr Pro Met Ala Phe Phe Asp Tyr Trp Gly Gln Gly
            100                 105                 110

Thr Leu Val Thr Val Ser Ser
        115

<210> SEQ ID NO 328
<211> LENGTH: 107
<212> TYPE: PRT
<213> ORGANISM: Artificial Sequence
<220> FEATURE:
<223> OTHER INFORMATION: LC variable region sequence 6E7

<400> SEQUENCE: 328

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
```

-continued

```
                  20                25                30

Leu Ala Trp Tyr Gln Gln Lys Pro Gly Lys Ala Pro Lys Leu Leu Ile
          35                40                45

Tyr Ala Ala Ser Ser Leu Gln Ser Gly Val Pro Ser Arg Phe Ser Gly
      50                55                60

Ser Gly Ser Gly Thr Asp Phe Thr Leu Thr Ile Ser Ser Leu Gln Pro
65                70                75                80

Glu Asp Phe Ala Thr Tyr Phe Cys Gln Gln Ala Asp Ala Phe Pro Arg
                  85                90                95

Thr Phe Gly Gln Gly Thr Lys Leu Glu Ile Lys
              100               105

<210> SEQ ID NO 329
<211> LENGTH: 123
<212> TYPE: PRT
<213> ORGANISM: Artificial Sequence
<220> FEATURE:
<223> OTHER INFORMATION: HC variable region sequence 6E7

<400> SEQUENCE: 329

Glu Val Gln Leu Val Gln Ser Gly Ala Glu Val Lys Lys Pro Gly Glu
1                 5                 10                15

Ser Leu Lys Ile Ser Cys Lys Gly Ser Gly Tyr Ser Phe Thr Ser Tyr
              20                25                30

Trp Ile Ala Trp Val Arg Gln Met Pro Gly Lys Gly Leu Glu Trp Met
          35                40                45

Gly Ile Ile Tyr Pro Gly Asp Ala Asp Ala Arg Tyr Ser Pro Ser Phe
      50                55                60

Gln Gly Gln Val Thr Ile Ser Ala Asp Lys Ser Ile Ser Thr Ala Tyr
65                70                75                80

Leu Gln Trp Ser Ser Leu Lys Ala Ser Asp Thr Ala Met Tyr Phe Cys
                  85                90                95

Ala Arg Gln Arg Thr Phe Tyr Tyr Asp Ser Ser Asp Tyr Phe Asp Tyr
              100               105               110

Trp Gly Gln Gly Thr Leu Val Thr Val Ser Ser
          115               120

<210> SEQ ID NO 330
<211> LENGTH: 107
<212> TYPE: PRT
<213> ORGANISM: Artificial Sequence
<220> FEATURE:
<223> OTHER INFORMATION: LC variable region sequence 13E7

<400> SEQUENCE: 330

Glu Ile Val Met Thr Gln Ser Pro Ala Thr Leu Ser Val Ser Pro Gly
1                 5                 10                15

Glu Arg Ala Thr Leu Ser Cys Arg Ala Ser Gln Ser Val Ser Ser Asn
              20                25                30

Leu Ala Trp Phe Gln Gln Lys Pro Gly Gln Ala Pro Arg Leu Leu Ile
          35                40                45

Tyr Gly Ala Ser Thr Arg Ala Thr Gly Ile Pro Ala Arg Phe Ser Gly
      50                55                60

Ser Gly Ser Gly Thr Glu Phe Thr Leu Thr Ile Ser Ser Leu Gln Pro
65                70                75                80

Glu Asp Phe Ala Val Tyr Tyr Cys Leu Gln Asp Asn Asn Phe Pro Pro
                  85                90                95
```

-continued

```
Thr Phe Gly Gln Gly Thr Lys Val Asp Ile Lys
            100                 105

<210> SEQ ID NO 331
<211> LENGTH: 121
<212> TYPE: PRT
<213> ORGANISM: Artificial Sequence
<220> FEATURE:
<223> OTHER INFORMATION: HC variable region sequence 13E7

<400> SEQUENCE: 331

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ala Asp Ala Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
            85                  90                  95

Ala Arg Arg Arg Gln Gly Ile Phe Gly Asp Ala Leu Asp Phe Trp Gly
            100                 105                 110

Gln Gly Thr Leu Val Thr Val Ser Ser
        115                 120

<210> SEQ ID NO 332
<211> LENGTH: 107
<212> TYPE: PRT
<213> ORGANISM: Artificial Sequence
<220> FEATURE:
<223> OTHER INFORMATION: LC variable region sequence 5E3

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Phe
            85                  90                  95

Thr Phe Gly Gln Gly Thr Lys Val Asp Ile Lys
            100                 105

<210> SEQ ID NO 333
<211> LENGTH: 121
<212> TYPE: PRT
<213> ORGANISM: Artificial Sequence
<220> FEATURE:
<223> OTHER INFORMATION: HC variable region sequence 5E3

<400> SEQUENCE: 333

Gln Val Gln Leu Val Gln Ser Gly Ala Glu Val Lys Lys Pro Gly Ala
```

-continued

```
1              5               10              15

Ser Val Lys Val Ser Cys Lys Ala Ser Gly Tyr Thr Phe Thr Gly Tyr
            20              25              30

Tyr Ile His Trp Val Arg Gln Ala Pro Gly Gln Gly Leu Glu Trp Met
        35              40              45

Gly Trp Ile Asn Pro Tyr Ser Gly Gly Thr Thr Ser Ala Gln Lys Phe
    50              55              60

Gln Gly Arg Val Thr Met Thr Arg Asp Thr Ser Thr Ser Ser Ala Tyr
65              70              75              80

Met Glu Leu Ser Arg Leu Arg Ser Asp Asp Thr Ala Val Tyr Tyr Cys
            85              90              95

Ala Arg Asp Ala Gly Tyr Leu Ala Leu Tyr Gly Thr Asp Val Trp Gly
            100             105             110

Gln Gly Thr Leu Val Thr Val Ser Ser
        115             120
```

```
<210> SEQ ID NO 334
<211> LENGTH: 242
<212> TYPE: PRT
<213> ORGANISM: Artificial Sequence
<220> FEATURE:
<223> OTHER INFORMATION: AA sequence LC SST28347

<400> SEQUENCE: 334

Met Asp Met Arg Val Pro Ala Gln Leu Leu Gly Leu Leu Leu Leu Trp
1              5               10              15

Leu Arg Gly Ala Arg Cys Asp Ile Val Met Thr Gln Ser Pro Asp Ser
            20              25              30

Leu Ala Val Ser Leu Gly Glu Arg Ala Thr Ile Asn Cys Lys Ser Ser
        35              40              45

Gln Ser Val Leu Tyr Ser Ser Asn Asn Lys His Phe Leu Ala Trp Tyr
    50              55              60

Gln Gln Lys Pro Gly Gln Pro Pro Lys Leu Leu Ile Tyr Trp Ala Ser
65              70              75              80

Thr Arg Glu Ser Gly Val Pro Asp Arg Phe Ser Gly Ser Gly Ser Gly
            85              90              95

Thr Asp Phe Thr Leu Thr Ile Ser Ser Leu Gln Ala Glu Asp Val Ala
            100             105             110

Val Tyr Tyr Cys Gln Gln Tyr Tyr Ser Thr Pro Leu Thr Phe Gly Gly
            115             120             125

Gly Thr Lys Val Glu Ile Lys Arg Thr Val Ala Ala Pro Ser Val Phe
        130             135             140

Ile Phe Pro Pro Ser Asp Glu Gln Leu Lys Ser Gly Thr Ala Ser Val
145             150             155             160

Val Cys Leu Leu Asn Asn Phe Tyr Pro Arg Glu Ala Lys Val Gln Trp
            165             170             175

Lys Val Asp Asn Ala Leu Gln Ser Gly Asn Ser Gln Glu Ser Val Thr
            180             185             190

Glu Gln Asp Ser Lys Asp Ser Thr Tyr Ser Leu Ser Ser Thr Leu Thr
            195             200             205

Leu Ser Lys Ala Asp Tyr Glu Lys His Lys Val Tyr Ala Cys Glu Val
        210             215             220

Thr His Gln Gly Leu Ser Ser Pro Val Thr Lys Ser Phe Asn Arg Gly
225             230             235             240

Glu Cys
```

```
<210> SEQ ID NO 335
<211> LENGTH: 471
<212> TYPE: PRT
<213> ORGANISM: Artificial Sequence
<220> FEATURE:
<223> OTHER INFORMATION: AA sequence HC SST28347

<400> SEQUENCE: 335

Met Asp Met Arg Val Pro Ala Gln Leu Leu Gly Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Glu Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ala Tyr Thr Pro Met Ala Phe Phe
            115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Cys Glu Glu Gln Tyr
305                 310                 315                 320

Gly Ser Thr Tyr Arg Cys Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365
```

```
Glu Pro Gln Val Tyr Thr Leu Pro Pro Ser Arg Glu Glu Met Thr Lys
    370                 375             380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405             410                 415

Thr Thr Pro Pro Val Leu Asp Ser Asp Gly Ser Phe Phe Leu Tyr Ser
            420             425                 430

Lys Leu Thr Val Asp Lys Ser Arg Trp Gln Gln Gly Asn Val Phe Ser
        435             440             445

Cys Ser Val Met His Glu Ala Leu His Asn His Tyr Thr Gln Lys Ser
    450             455             460

Leu Ser Leu Ser Pro Gly Lys
465             470

<210> SEQ ID NO 336
<211> LENGTH: 468
<212> TYPE: PRT
<213> ORGANISM: Artificial Sequence
<220> FEATURE:
<223> OTHER INFORMATION: AA sequence HC SST204812

<400> SEQUENCE: 336

Met Asp Met Arg Val Pro Ala Gln Leu Leu Gly Leu Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Glu Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ala Tyr Thr Pro Met Ala Phe Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Glu Leu Leu
                245                 250                 255
```

-continued

```
Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Cys Glu Glu Gln Tyr Gly Ser Thr
305                 310                 315                 320

Tyr Arg Cys Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465
```

```
<210> SEQ ID NO 337
<211> LENGTH: 236
<212> TYPE: PRT
<213> ORGANISM: Artificial Sequence
<220> FEATURE:
<223> OTHER INFORMATION: AA sequence SST29857

<400> SEQUENCE: 337
```

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
            35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Phe Cys Gln Gln
            100                 105                 110

Ala Asp Ala Phe Pro Arg Thr Phe Gly Gln Gly Thr Lys Leu Glu Ile
    115                 120                 125

Lys Arg Thr Val Ala Ala Pro Ser Val Phe Ile Phe Pro Pro Ser Asp
    130                 135                 140
```

-continued

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 338
<211> LENGTH: 236
<212> TYPE: PRT
<213> ORGANISM: Artificial Sequence
<220> FEATURE:
<223> OTHER INFORMATION: AA sequence LC SST29857

<400> SEQUENCE: 338

Met Asp Met Arg Val Pro Ala Gln Leu Leu Gly Leu Leu Leu Leu Trp
1               5                   10                  15

Leu Arg Gly Ala Arg Cys Glu Ile Val Met Thr Gln Ser Pro Ala Thr
            20                  25                  30

Leu Ser Val Ser Pro Gly Glu Arg Ala Thr Leu Ser Cys Arg Ala Ser
        35                  40                  45

Gln Ser Val Ser Ser Asn Leu Ala Trp Phe Gln Gln Lys Pro Gly Gln
    50                  55                  60

Ala Pro Arg Leu Leu Ile Tyr Gly Ala Ser Thr Arg Ala Thr Gly Ile
65                  70                  75                  80

Pro Ala Arg Phe Ser Gly Ser Gly Ser Gly Thr Glu Phe Thr Leu Thr
                85                  90                  95

Ile Ser Ser Leu Gln Pro Glu Asp Phe Ala Val Tyr Tyr Cys Leu Gln
            100                 105                 110

Asp Asn Asn Phe Pro Pro Thr Phe Gly Gln Gly Thr Lys Val Asp Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 339
<211> LENGTH: 236
<212> TYPE: PRT
<213> ORGANISM: Artificial Sequence
```

```
<220> FEATURE:
<223> OTHER INFORMATION: AA sequence LC SST202443

<400> SEQUENCE: 339

Met Asp Met Arg Val Pro Ala Gln Leu Leu Gly Leu Leu Leu Leu Trp
1               5                   10                  15

Leu Arg Gly Ala Arg Cys Glu Ile Val Met Thr Gln Ser Pro Ala Thr
            20                  25                  30

Leu Ser Val Ser Pro Gly Glu Arg Ala Thr Leu Ser Cys Arg Ala Ser
        35                  40                  45

Gln Ser Val Ser Asn Leu Ala Trp Phe Gln Gln Lys Pro Gly Gln
    50                  55                  60

Ala Pro Arg Leu Leu Ile Tyr Gly Ala Ser Thr Arg Ala Thr Gly Ile
65                  70                  75                  80

Pro Ala Arg Phe Ser Gly Ser Gly Ser Gly Thr Glu Phe Thr Leu Thr
                85                  90                  95

Ile Ser Ser Leu Gln Pro Glu Asp Phe Ala Val Tyr Tyr Cys Leu Gln
            100                 105                 110

Asp Asn Asn Phe Pro Pro Thr Phe Gly Gln Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 340
<211> LENGTH: 473
<212> TYPE: PRT
<213> ORGANISM: Artificial Sequence
<220> FEATURE:
<223> OTHER INFORMATION: AA sequence HC SST202443

<400> SEQUENCE: 340

Met Asp Met Arg Val Pro Ala Gln Leu Leu Gly Leu Leu Leu Leu Trp
1               5                   10                  15

Leu Arg Gly Ala Arg Cys Glu Val Gln Leu Val Gln Ser Gly Ala Glu
            20                  25                  30

Val Lys Lys Pro Gly Glu Ser Leu Lys Ile Ser Cys Lys Gly Ser Gly
        35                  40                  45

Tyr Ser Phe Thr Ser Tyr Trp Ile Gly Trp Val Arg Gln Met Pro Gly
    50                  55                  60

Lys Gly Leu Glu Trp Met Gly Ile Ile Tyr Pro Gly Asp Ala Asp Ala
65                  70                  75                  80

Arg Tyr Ser Pro Ser Phe Gln Gly Gln Val Thr Ile Ser Ala Asp Lys
                85                  90                  95

Ser Ile Ser Thr Ala Tyr Leu Gln Trp Ser Ser Leu Lys Ala Ser Asp
```

-continued

```
                 100              105              110

Thr Ala Met Tyr Phe Cys Ala Arg Arg Arg Gln Gly Ile Phe Gly Asp
        115              120              125

Ala Leu Asp Phe Trp Gly Gln Gly Thr Leu Val Thr Val Ser Ser Ala
    130              135              140

Ser Thr Lys Gly Pro Ser Val Phe Pro Leu Ala Pro Ser Ser Lys Ser
145              150              155              160

Thr Ser Gly Gly Thr Ala Ala Leu Gly Cys Leu Val Lys Asp Tyr Phe
            165              170              175

Pro Glu Pro Val Thr Val Ser Trp Asn Ser Gly Ala Leu Thr Ser Gly
            180              185              190

Val His Thr Phe Pro Ala Val Leu Gln Ser Ser Gly Leu Tyr Ser Leu
        195              200              205

Ser Ser Val Val Thr Val Pro Ser Ser Ser Leu Gly Thr Gln Thr Tyr
    210              215              220

Ile Cys Asn Val Asn His Lys Pro Ser Asn Thr Lys Val Asp Lys Lys
225              230              235              240

Val Glu Pro Lys Ser Cys Asp Lys Thr His Thr Cys Pro Pro Cys Pro
            245              250              255

Ala Pro Glu Leu Leu Gly Gly Pro Ser Val Phe Leu Phe Pro Pro Lys
            260              265              270

Pro Lys Asp Thr Leu Met Ile Ser Arg Thr Pro Glu Val Thr Cys Val
            275              280              285

Val Val Asp Val Ser His Glu Asp Pro Glu Val Lys Phe Asn Trp Tyr
        290              295              300

Val Asp Gly Val Glu Val His Asn Ala Lys Thr Lys Pro Cys Glu Glu
305              310              315              320

Gln Tyr Gly Ser Thr Tyr Arg Cys Val Ser Val Leu Thr Val Leu His
            325              330              335

Gln Asp Trp Leu Asn Gly Lys Glu Tyr Lys Cys Lys Val Ser Asn Lys
            340              345              350

Ala Leu Pro Ala Pro Ile Glu Lys Thr Ile Ser Lys Ala Lys Gly Gln
        355              360              365

Pro Arg Glu Pro Gln Val Tyr Thr Leu Pro Pro Ser Arg Glu Glu Met
    370              375              380

Thr Lys Asn Gln Val Ser Leu Thr Cys Leu Val Lys Gly Phe Tyr Pro
385              390              395              400

Ser Asp Ile Ala Val Glu Trp Glu Ser Asn Gly Gln Pro Glu Asn Asn
            405              410              415

Tyr Lys Thr Thr Pro Pro Val Leu Asp Ser Asp Gly Ser Phe Phe Leu
            420              425              430

Tyr Ser Lys Leu Thr Val Asp Lys Ser Arg Trp Gln Gln Gly Asn Val
        435              440              445

Phe Ser Cys Ser Val Met His Glu Ala Leu His Asn His Tyr Thr Gln
    450              455              460

Lys Ser Leu Ser Leu Ser Pro Gly Lys
465              470
```

<210> SEQ ID NO 341
<211> LENGTH: 236
<212> TYPE: PRT
<213> ORGANISM: Artificial Sequence
<220> FEATURE:
<223> OTHER INFORMATION: AA sequence LC SST29825

<400> SEQUENCE: 341

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Asn Tyr Leu Ala Trp Tyr Gln Gln Lys Pro Gly Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Tyr Pro Phe Thr Phe Gly Gln Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 342
<211> LENGTH: 470
<212> TYPE: PRT
<213> ORGANISM: Artificial Sequence
<220> FEATURE:
<223> OTHER INFORMATION: AA sequence HC SST29825

<400> SEQUENCE: 342

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr Tyr Ile His Trp Val Arg Gln Ala Pro Gly
    50                  55                  60

Gln Gly Leu Glu Trp Met Gly Trp Ile Asn Pro Tyr Ser Gly Gly Thr
65                  70                  75                  80

Thr Ser Ala Gln Lys Phe Gln Gly Arg Val Thr Met Thr Arg Asp Thr
                85                  90                  95

Ser Thr Ser Ser Ala Tyr Met Glu Leu Ser Arg Leu Arg Ser Asp Asp
            100                 105                 110

Thr Ala Val Tyr Tyr Cys Ala Arg Asp Ala Gly Tyr Leu Ala Leu Tyr

-continued

```
            115                 120                 125

Gly Thr Asp Val Trp Gly Gln Gly Thr Leu Val Thr Val Ser Ser Ala
    130                 135                 140

Ser Thr Lys Gly Pro Ser Val Phe Pro Leu Ala Pro Ser Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
    290                 295                 300

Val Glu Val His Asn Ala Lys Thr Lys Pro Cys Glu Glu Gln Tyr Gly
305                 310                 315                 320

Ser Thr Tyr Arg Cys Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 343
<211> LENGTH: 339
<212> TYPE: DNA
<213> ORGANISM: Artificial Sequence
<220> FEATURE:
<223> OTHER INFORMATION: LC variable region sequence SST28347 and
      SST204812

<400> SEQUENCE: 343

-continued

```
gacatcgtga tgacccagtc tccagactcc ctggctgtgt ctctgggcga gagggccacc      60
atcaactgca agtccagcca gagtgtttta tacagctcca acaataagca cttcttagct     120
tggtaccagc agaaaccagg acagcctcct aagctgctca tttactgggc atctacccgg     180
gagtccgggg tccctgaccg attcagtggc agcgggtctg ggacagattt cactctcacc     240
atcagcagcc tgcaggctga agatgtggca gtttattact gtcagcaata ttatagtact     300
ccgctcactt tcggcggagg gaccaaggtg gagatcaaa                           339

<210> SEQ ID NO 344
<211> LENGTH: 357
<212> TYPE: DNA
<213> ORGANISM: Artificial Sequence
<220> FEATURE:
<223> OTHER INFORMATION: HC variable region sequence SST28347 and
      SST204812

<400> SEQUENCE: 344
gaggtgcagc tgttggagtc tgggggaggc ttggtacagc ctggggggtc cctgagactc      60
tcctgtgcag cctctggatt caccttagc agctatgcca tgagctgggt ccgccaggct     120
ccagggaagg gactggagtg ggtctcagct attagtggta gtggtggtag cacatactac     180
gcagaatccg tgaagggccg gttcaccatc tccagagaca attccaagaa cacgctgtat     240
ctgcaaatga acagcctgag agccgaggac acggccgtat attactgtgc gaaggcgtat     300
acacctatgg cattctttga ctactggggc cagggaaccc tggtcaccgt ctcctca       357

<210> SEQ ID NO 345
<211> LENGTH: 321
<212> TYPE: DNA
<213> ORGANISM: Artificial Sequence
<220> FEATURE:
<223> OTHER INFORMATION: LC variable region sequence SST29857

<400> SEQUENCE: 345
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttactt ttgtcaacag gctacgctt cccctcgcac ttttggccag     300
gggaccaagc tggagatcaa a                                              321

<210> SEQ ID NO 346
<211> LENGTH: 369
<212> TYPE: DNA
<213> ORGANISM: Artificial Sequence
<220> FEATURE:
<223> OTHER INFORMATION: HC variable region sequence SST29857

<400> SEQUENCE: 346
gaggtgcagc tggtgcagtc tggagcagag gtgaaaaagc ccggggagtc tctgaagatc      60
tcctgtaagg gttctggata cagttttacc agctactgga tcgcctgggt gcgccagatg     120
cccgggaaag cctggagtg gatggggatc atctatcctg gtgacgctga tgccagatac     180
agcccgtcct tccaaggcca ggtcaccatc tcagccgaca gtccatcag caccgcctac     240 ctacagtgga gcagcctgaa ggcctcggac accgccatgt atttctgtgc gagacaaagg     300
acgtttattt atgatagtag tgattatttt gactactggg gccagggaac cctggtcacc     360
```

-continued gtgtcctca                                                        369

<210> SEQ ID NO 347
<211> LENGTH: 321
<212> TYPE: DNA
<213> ORGANISM: Artificial Sequence
<220> FEATURE:
<223> OTHER INFORMATION: LC variable region sequence SST202443

<400> SEQUENCE: 347
gaaatagtga tgacgcagtc tccagccacc ctgtctgtgt ctccagggga aagagccacc      60
ctctcctgca gggccagtca gagtgttagc agcaacttag cctggttcca gcagaaacct     120
ggccaggctc ccaggctcct catctatggt gcttccacca gggccactgg tattccagcc     180
aggttcagtg gcagtgggtc tgggacagag ttcactctca ccatcagcag cctgcagcct     240
gaagattttg cagtttatta ctgtctgcag gataataatt ccctcccac tttcggccaa      300 gggaccaaag tggatatcaa a                                               321

<210> SEQ ID NO 348
<211> LENGTH: 363
<212> TYPE: DNA
<213> ORGANISM: Artificial Sequence
<220> FEATURE:
<223> OTHER INFORMATION: HC variable region sequence SST202443

<400> SEQUENCE: 348
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatgggggatc atctatcctg agatgctga tgccagatac      180 agcccgtcct ccaaggcca ggtcaccatc tcagccgaca gtccatcag caccgcctac      240 ctgcagtgga gcagcctgaa ggcctcggac accgccatgt atttctgtgc gaggcggaga     300 cagggggatct tcggtgatgc tcttgatttc tggggccaag ggacattggt caccgtgtct     360
tca                                                                   363

<210> SEQ ID NO 349
<211> LENGTH: 321
<212> TYPE: DNA
<213> ORGANISM: Artificial Sequence
<220> FEATURE:
<223> OTHER INFORMATION: LC variable region sequence SST29825

<400> SEQUENCE: 349
gacatccaga tgacccagtc tccatcctca ctgtctgcat ctgtaggaga cagagtcacc      60
atcacttgtc gggcgagtca gggcattagc aattatttag cctggtatca gcagaaacca     120
gggaaagccc ctaaatccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tatagtactt acccattcac tttcggccaa      300
gggaccaaag tggatatcaa a                                               321

<210> SEQ ID NO 350
<211> LENGTH: 363
<212> TYPE: DNA
<213> ORGANISM: Artificial Sequence
<220> FEATURE:
<223> OTHER INFORMATION: HC variable region sequence SST29825

<400> SEQUENCE: 350

-continued

```
caggtgcagc tggtgcagtc tggggctgag gtgaagaagc ctggggcctc agtgaaggtg      60
tcctgcaagg cttctggata caccttcacc ggctactata tccactgggt gcgacaggcc     120
cctggacaag ggcttgagtg gatgggatgg atcaacccct acagtggtgg cacaacctct     180
gcacagaagt tcagggcag ggtcaccatg accagggaca cgtccaccag ctcagcctac      240
atggaactga gcaggctgag atctgacgac acggccgtgt attactgtgc gagagatgca     300
ggctacctgg ccctctacgg tacggacgtc tggggccaag ggaccttggt caccgtgtcc     360
tca                                                                   363

<210> SEQ ID NO 351
<211> LENGTH: 726
<212> TYPE: DNA
<213> ORGANISM: Artificial Sequence
<220> FEATURE:
<223> OTHER INFORMATION: NA sequence LC SST28347

<400> SEQUENCE: 351
atggacatga gggtgcccgc tcagctcctg gggctcctgc tgctgtggct gagaggtgcg      60
cgctgtgaca tcgtgatgac ccagtctcca gactccctgg ctgtgtctct gggcgagagg     120
gccaccatca actgcaagtc cagccagagt gttttataca gctccaacaa taagcacttc     180
ttagcttggt accagcagaa accaggacag cctcctaagc tgctcattta ctgggcatct     240
acccgggagt ccggggtccc tgaccgattc agtggcagcg ggtctgggac agatttcact     300
ctcaccatca gcagcctgca ggctgaagat gtggcagttt attactgtca gcaatattat     360
agtactccgc tcactttcgg cggagggacc aaggtggaga tcaaacgaac ggtggctgca     420
ccatctgtct tcatcttccc gccatctgat gagcagttga aatctggaac tgcctctgtt     480
gtgtgcctgc tgaataactt ctatcccaga gaggccaaag tacagtggaa ggtggataac     540
gccctccaat cgggtaactc ccaggagagt gtcacagagc aggacagcaa ggacagcacc     600
tacagcctca gcagcaccct gacgctgagc aaagcagact acgagaaaca caaagtctac     660
gcctgcgaag tcacccatca gggcctgagc tcgcccgtca caaagagctt caacagggga     720
gagtgt                                                                726

<210> SEQ ID NO 352
<211> LENGTH: 1413
<212> TYPE: DNA
<213> ORGANISM: Artificial Sequence
<220> FEATURE:
<223> OTHER INFORMATION: NA sequence HC SST28347

<400> SEQUENCE: 352
atggacatga gggtgcccgc tcagctcctg gggctcctgc tgctgtggct gagaggtgcg      60
cgctgtgagg tgcagctgtt ggagtctggg ggaggcttgg tacagcctgg ggggtccctg     120
agactctcct gtgcagcctc tggattcacc tttagcagct atgccatgag ctgggtccgc     180
caggctccag ggaagggact ggagtgggtc tcagctatta gtggtagtgg tggtagcaca     240
tactacgcag aatccgtgaa gggccggttc accatctcca gagacaattc caagaacacg     300
ctgtatctgc aaatgaacag cctgagagcc gaggacacgg ccgtatatta ctgtgcgaag     360
gcgtatacac ctatggcatt ctttgactac tggggccagg gaaccctggt caccgtctcc     420
tcagcctcca ccaagggccc atcggtcttc cccctggcac cctcctccaa gagcacctct     480
gggggcacag cggccctggg ctgcctggtc aaggactact ccccgaacc ggtgacggtg      540
```

-continued

```
tcgtggaact caggcgccct gaccagcggc gtgcacacct tcccggctgt cctacagtcc      600
tcaggactct actccctcag cagcgtggtg accgtgccct ccagcagctt gggcacccag      660
acctacatct gcaacgtgaa tcacaagccc agcaacacca aggtggacaa gaaagttgag      720
cccaaatctt gtgacaaaac tcacacatgc ccaccgtgcc cagcacctga actcctgggg      780
ggaccgtcag tcttcctctt ccccccaaaa cccaaggaca ccctcatgat ctcccggacc      840
cctgaggtca catgcgtggt ggtggacgtg agccacgaag accctgaggt caagttcaac      900
tggtacgtgg acggcgtgga ggtgcataat gccaagacaa agccgcgcga ggagcagtac      960
ggcagcacgt accgttgcgt cagcgtcctc accgtcctgc accaggactg gctgaatggc     1020
aaggagtaca agtgcaaggt gtccaacaaa gccctcccag cccccatcga gaaaaccatc     1080
tccaaagcca aagggcagcc ccgagaacca caggtgtaca ccctgccccc atcccgggag     1140
gagatgacca agaaccaggt cagcctgacc tgcctggtca aaggcttcta tcccagcgac     1200
atcgccgtgg agtgggagag caatgggcag ccggagaaca actacaagac cacgcctccc     1260
gtgctggact ccgacggctc cttcttcctc tatagcaagc tcaccgtgga caagagcagg     1320
tggcagcagg ggaacgtctt ctcatgctcc gtgatgcatg aggctctgca caaccactac     1380
acgcagaaga gcctctccct gtctccgggc aaa                                   1413
```

<210> SEQ ID NO 353
<211> LENGTH: 1404
<212> TYPE: DNA
<213> ORGANISM: Artificial Sequence
<220> FEATURE:
<223> OTHER INFORMATION: NA sequence HC SST204812

<400> SEQUENCE: 353

```
atggacatga gggtgcccgc tcagctcctg gggctcctgc tgctgtggct gagaggtgcg       60
cgctgtgagg tgcagctgtt ggagtctggg ggaggcttgg tacagcctgg ggggtccctg      120
agactctcct gtgcagcctc tggattcacc tttagcagct atgccatgag ctgggtccgc      180
caggctccag ggaagggact ggagtgggtg tcagctatta gtggtagtgg tggtagcaca      240
tactacgcag aatccgtgaa gggccggttc accatctcca gagacaattc caagaacacg      300
ctgtatctgc aaatgaacag cctgagagcc gaggacacgg ccgtatatta ctgtgcgaag      360
gcgtatacac ctatggcatt ctttgactac tggggccagg gaaccctggt caccgtgtcc      420
tcagcctcca ccaagggccc atcggtcttc cccctggcgc ccagctccag gagcacctcc      480
gagagcacag cggccctggg ctgcctggtc aaggactact tccccgaacc ggtgacggtg      540
tcgtggaact caggcgctct gaccagcggc gtgcacacct tcccagctgt cctacagtcc      600
tcaggactct actccctcag cagcgtggtg accgtgccct ccagcaactt cggcacccag      660
acctacacct gcaacgtaga tcacaagccc agcaacacca aggtggacaa gacagttgag      720
cgcaaatgtt gtgtcgagtg cccaccgtgc ccagcacctg aactcctggg gggaccgtca      780
gtcttcctct tccccccaaa acccaaggac accctcatga tctcccggac ccctgaggtc      840
acatgcgtgg tggtggacgt gagccacgaa gaccctgagg tcaagttcaa ctggtacgtg      900
gacggcgtgg aggtgcataa tgccaagaca aagccgtgcg aggagcagta cggcagcacg      960
taccgttgcg tcagcgtcct caccgtcctg caccaggact ggctgaatgg caaggagtac     1020
aagtgcaagg tgtccaacaa agccctccca gcccccatcg agaaaaccat ctccaaagcc     1080
aaagggcagc cccgagaacc acaggtgtac accctgcccc catcccggga ggagatgacc     1140
aagaaccagg tcagcctgac ctgcctggtc aaaggcttct atcccagcga catcgccgtg     1200
```

-continued

```
gagtgggaga gcaatgggca gccggagaac aactacaaga ccacgcctcc cgtgctggac      1260
tccgacggct ccttcttcct ctatagcaag ctcaccgtgg acaagagcag gtggcagcag      1320
gggaacgtct tctcatgctc cgtgatgcat gaggctctgc acaaccacta cacgcagaag      1380
agcctctccc tgtctccggg caaa                                            1404

<210> SEQ ID NO 354
<211> LENGTH: 708
<212> TYPE: DNA
<213> ORGANISM: Artificial Sequence
<220> FEATURE:
<223> OTHER INFORMATION: NA sequence LC SST29857

<400> SEQUENCE: 354
atggacatga gggtgcccgc tcagctcctg gggctcctgc tgctgtggct gagaggtgcg        60
cgctgtgaca tccagatgac ccagtctcca tcttccgtgt ctgcatctgt aggagacaga       120
gtcaccatca cttgtcgggc gagtcagggt attagcagct ggttagcctg gtatcagcag       180
aaaccaggga agcccctaa gctcctgatc tatgctgcat ccagtttgca aagtggggtc        240
ccatcaaggt tcagcggcag tggatctggg acagatttca ctctcaccat cagcagcctg       300
cagcctgaag attttgcaac ttacttttgt caacaggctg acgctttccc tcgcactttt       360
ggccagggga ccaagctgga gatcaaacga acggtggctg caccatctgt cttcatcttc       420
ccgccatctg atgagcagtt gaaatctgga actgcctctg ttgtgtgcct gctgaataac       480
ttctatccca gagaggccaa agtacagtgg aaggtggata acgccctcca atcgggtaac       540
tcccaggaga gtgtcacaga gcaggacagc aaggacagca cctacagcct cagcagcacc       600
ctgacgctga gcaaagcaga ctacgagaaa cacaaagtct acgcctgcga agtcacccat       660
cagggcctga gctcgcccgt cacaaagagc ttcaacaggg gagagtgt                  708

<210> SEQ ID NO 355
<211> LENGTH: 1416
<212> TYPE: DNA
<213> ORGANISM: Artificial Sequence
<220> FEATURE:
<223> OTHER INFORMATION: NA sequence HC SST29857

<400> SEQUENCE: 355
atggacatga gggtgcccgc tcagctcctg gggctcctgc tgctgtggct gagaggtgcg        60
cgctgtgagg tgcagctggt gcagtctgga gcagaggtga aaaagcccgg ggagtctctg       120
aagatctcct gtaagggttc tggatacagt tttaccagct actggatcgc ctgggtgcgc       180
cagatgcccg ggaaaggcct ggagtggatg gggatcatct atcctggtga cgctgatgcc       240
agatacagcc cgtccttcca aggccaggtc accatctcag ccgacaagtc catcagcacc       300
gcctacctac agtggagcag cctgaaggcc tcggacaccg ccatgtattt ctgtgcgaga       360
caaaggacgt tttattatga tagtagtgat tattttgact actggggcca gggaaccctg       420
gtcaccgtgt cctcagcctc caccaagggc ccatcggtct tccccctggc gccagctcc       480 aggagcacct ccgagagcac agcggccctg ggctgcctgg tcaaggacta cttccccgaa       540
ccggtgacgg tgtcgtggaa ctcaggcgct ctgaccagcg gcgtgcacac cttcccagct       600
gtcctacagt cctcaggact ctactccctc agcagcgtgg tgaccgtgcc ctccagcaac       660
ttcggcaccc agacctacac ctgcaacgta gatcacaagc ccagcaacac caaggtggac       720
aagacagttg agcgcaaatg ttgtgtcgag tgcccaccgt gcccagcacc tgaactcctg       780
```

-continued

```
gggggaccgt cagtcttcct cttcccccca aaacccaagg acaccctcat gatctcccgg      840
acccctgagg tcacatgcgt ggtggtggac gtgagccacg aagaccctga ggtcaagttc      900
aactggtacg tggacggcgt ggaggtgcat aatgccaaga caaagccgtg cgaggagcag      960
tacggcagca cgtaccgttg cgtcagcgtc ctcaccgtcc tgcaccagga ctggctgaat     1020
ggcaaggagt acaagtgcaa ggtgtccaac aaagccctcc cagcccccat cgagaaaacc     1080
atctccaaag ccaaagggca gccccgagaa ccacaggtgt acaccctgcc cccatcccgg     1140
gaggagatga ccaagaacca ggtcagcctg acctgcctgg tcaaaggctt ctatcccagc     1200
gacatcgccg tggagtggga gagcaatggg cagccggaga acaactacaa gaccacgcct     1260
cccgtgctgg actccgacgg ctccttcttc ctctatagca agctcaccgt ggacaagagc     1320
aggtggcagc aggggaacgt cttctcatgc tccgtgatgc atgaggctct gcacaaccac     1380
tacacgcaga gagcctctc cctgtctccg ggcaaa                                1416
```

```
<210> SEQ ID NO 356
<211> LENGTH: 708
<212> TYPE: DNA
<213> ORGANISM: Artificial Sequence
<220> FEATURE:
<223> OTHER INFORMATION: NA sequence LC SST202443

<400> SEQUENCE: 356
atggacatga gggtgcccgc tcagctcctg gggctcctgc tgctgtggct gagaggtgcg       60
cgctgtgaaa tagtgatgac gcagtctcca gccaccctgt ctgtgtctcc aggggaaaga      120
gccaccctct cctgcagggc cagtcagagt gttagcagca acttagcctg gttccagcag      180
aaacctggcc aggctcccag gctcctcatc tatggtgctt ccaccagggc cactggtatt      240
ccagccaggt tcagtggcag tgggtctggg acagagttca ctctcaccat cagcagcctg      300
cagcctgaag attttgcagt ttattactgt ctgcaggata ataatttccc tcccactttc      360
ggccaaggga ccaaagtgga tatcaaacga acggtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                   708
```

```
<210> SEQ ID NO 357
<211> LENGTH: 1419
<212> TYPE: DNA
<213> ORGANISM: Artificial Sequence
<220> FEATURE:
<223> OTHER INFORMATION: NA sequence HC SST202443

<400> SEQUENCE: 357
atggacatga gggtgcccgc tcagctcctg gggctcctgc tgctgtggct gagaggtgcg       60
cgctgtgagg tgcagctggt gcagtctgga gcagaggtga aaaagcccgg ggagtctctg      120
aagatctcct gtaagggttc tggatacagc tttaccagct actggatcgg ctgggtgcgc      180
cagatgcccg ggaaaggcct ggagtggatg gggatcatct atcctggaga tgctgatgcc      240
agatacagcc cgtccttcca aggccaggtc accatctcag ccgacaagtc catcagcacc      300
gcctacctgc agtggagcag cctgaaggcc tcggacaccg ccatgtattt ctgtgcgagg      360
cggagacagg ggatcttcgg tgatgctctt gatttctggg gccaagggac attggtcacc      420
```

-continued

```
gtgtcttcag cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca acaccaaggt ggacaagaaa     720
gttgagccca atcttgtga caaaactcac acatgcccac cgtgcccagc acctgaactc     780
ctggggggac cgtcagtctt cctcttcccc ccaaaaccca aggacaccct catgatctcc     840
cggacccctg aggtcacatg cgtggtggtg gacgtgagcc acgaagaccc tgaggtcaag     900
ttcaactggt acgtggacgg cgtggaggtg cataatgcca agacaaagcc gtgcgaggag     960
cagtacggca gcacgtaccg ttgcgtcagc gtcctcaccg tcctgcacca ggactggctg     1020
aatggcaagg agtacaagtg caaggtgtcc aacaaagccc tcccagcccc catcgagaaa     1080
accatctcca aagccaaagg gcagccccga gaaccacagg tgtacaccct gcccccatcc     1140
cgggaggaga tgaccaagaa ccaggtcagc ctgacctgcc tggtcaaagg cttctatccc     1200
agcgacatcg ccgtggagtg ggagagcaat gggcagccgg agaacaacta caagaccacg     1260
cctcccgtgc tggactccga cggctccttc ttcctctata gcaagctcac cgtggacaag     1320
agcaggtggc agcaggggaa cgtcttctca tgctccgtga tgcatgaggc tctgcacaac     1380
cactacacgc agaagagcct ctccctgtct ccgggcaaa     1419
```

```
<210> SEQ ID NO 358
<211> LENGTH: 708
<212> TYPE: DNA
<213> ORGANISM: Artificial Sequence
<220> FEATURE:
<223> OTHER INFORMATION: NA sequence LC SST29825

<400> SEQUENCE: 358
```

```
atggacatga gggtgcccgc tcagctcctg gggctcctgc tgctgtggct gagaggtgcg     60
cgctgtgaca tccagatgac ccagtctcca tcctcactgt ctgcatctgt aggagacaga     120
gtcaccatca cttgtcgggc gagtcagggc attagcaatt atttagcctg gtatcagcag     180
aaaccaggga aagcccctaa atccctgatc tatgctgcat ccagtttgca aagtggggtc     240
ccatcaaggt tcagcggcag tggatctggg acagatttca ctctcaccat cagcagcctg     300
cagcctgaag attttgcaac ttattactgc caacagtata gtacttaccc attcactttc     360
ggccaaggga ccaaagtgga tatcaaacga acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt     708
```

```
<210> SEQ ID NO 359
<211> LENGTH: 1410
<212> TYPE: DNA
<213> ORGANISM: Artificial Sequence
<220> FEATURE:
<223> OTHER INFORMATION: NA sequence HC SST29825

<400> SEQUENCE: 359
```

-continued

```
atggacatga gggtgcccgc tcagctcctg gggctcctgc tgctgtggct gagaggtgcg      60
cgctgtcagg tgcagctggt gcagtctggg gctgaggtga agaagcctgg ggcctcagtg     120
aaggtgtcct gcaaggcttc tggatacacc ttcaccggct actatatcca ctgggtgcga     180
caggcccctg gacaagggct tgagtggatg ggatggatca acccttacag tggtggcaca     240
acctctgcac agaagtttca gggcagggtc accatgacca gggacacgtc caccagctca     300
gcctacatgg aactgagcag gctgagatct gacgacacgg ccgtgtatta ctgtgcgaga     360
gatgcaggct acctggccct ctacggtacg gacgtctggg gccaagggac cttggtcacc     420
gtgtcctcag cctccaccaa gggcccatcg gtcttccccc tggcgcccag ctccaggagc     480
acctccgaga gcacagcggc cctgggctgc ctggtcaagg actacttccc cgaaccggtg     540
acggtgtcgt ggaactcagg cgctctgacc agcggcgtgc acaccttccc agctgtccta     600
cagtcctcag gactctactc cctcagcagc gtggtgaccg tgccctccag caacttcggc     660
acccagacct acacctgcaa cgtagatcac aagcccagca acaccaaggt ggacaagaca     720
gttgagcgca aatgttgtgt cgagtgccca ccgtgcccag cacctgaact cctgggggga     780
ccgtcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cgtgcgagga gcagtacggc     960
agcacgtacc gttgcgtcag cgtcctcacc gtcctgcacc aggactggct gaatggcaag    1020
gagtacaagt gcaaggtgtc caacaaagcc ctcccagccc ccatcgagaa aaccatctcc    1080
aaagccaaag ggcagccccg agaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctat agcaagctca ccgtggacaa gagcaggtgg    1320
cagcagggga acgtcttctc atgctccgtg atgcatgagg ctctgcacaa ccactacacg    1380
cagaagagcc tctccctgtc tccgggcaaa                                      1410
```

```
<210> SEQ ID NO 360
<211> LENGTH: 10
<212> TYPE: PRT
<213> ORGANISM: Artificial Sequence
<220> FEATURE:
<223> OTHER INFORMATION: Peptides from epitope mapping experiments

<400> SEQUENCE: 360

His Arg Asp Ala Gly Asp Leu Trp Phe Pro
1               5                   10

<210> SEQ ID NO 361
<211> LENGTH: 9
<212> TYPE: PRT
<213> ORGANISM: Artificial Sequence
<220> FEATURE:
<223> OTHER INFORMATION: Peptides from epitope mapping experiments

<400> SEQUENCE: 361

Ala Gly Asp Leu Trp Phe Pro Gly Glu
1               5

<210> SEQ ID NO 362
<211> LENGTH: 10
<212> TYPE: PRT
<213> ORGANISM: Artificial Sequence
```

-continued

```
<220> FEATURE:
<223> OTHER INFORMATION: Peptides from epitope mapping experiments

<400> SEQUENCE: 362

Gly Asp Leu Trp Phe Pro Gly Glu Ser Glu
1               5                   10

<210> SEQ ID NO 363
<211> LENGTH: 14
<212> TYPE: PRT
<213> ORGANISM: Artificial Sequence
<220> FEATURE:
<223> OTHER INFORMATION: Peptides from epitope mapping experiments

<400> SEQUENCE: 363

His Arg Asp Ala Gly Asp Leu Trp Phe Pro Gly Glu Ser Glu
1               5                   10

<210> SEQ ID NO 364
<211> LENGTH: 17
<212> TYPE: PRT
<213> ORGANISM: Artificial Sequence
<220> FEATURE:
<223> OTHER INFORMATION: Peptides from epitope mapping experiments

<400> SEQUENCE: 364

Pro Leu Asp His Arg Asp Ala Gly Asp Leu Trp Phe Pro Gly Glu Ser
1               5                   10                  15

Glu

<210> SEQ ID NO 365
<211> LENGTH: 17
<212> TYPE: PRT
<213> ORGANISM: Artificial Sequence
<220> FEATURE:
<223> OTHER INFORMATION: Peptides from epitope mapping experiments

<400> SEQUENCE: 365

Pro Leu Asp His Arg Asp Ala Gly Asp Ala Trp Phe Pro Gly Glu Ser
1               5                   10                  15

Glu

<210> SEQ ID NO 366
<211> LENGTH: 17
<212> TYPE: PRT
<213> ORGANISM: Artificial Sequence
<220> FEATURE:
<223> OTHER INFORMATION: Peptides from epitope mapping experiments

<400> SEQUENCE: 366

Pro Leu Asp His Arg Asp Ala Gly Asp Leu Trp Ala Pro Gly Glu Ser
1               5                   10                  15

Glu

<210> SEQ ID NO 367
<211> LENGTH: 6
<212> TYPE: PRT
<213> ORGANISM: Artificial Sequence
<220> FEATURE:
<223> OTHER INFORMATION: Peptides from epitope mapping experiments

<400> SEQUENCE: 367

Gly Asp Leu Trp Phe Pro
1               5
```

```
<210> SEQ ID NO 368
<211> LENGTH: 9
<212> TYPE: PRT
<213> ORGANISM: Artificial Sequence
<220> FEATURE:
<223> OTHER INFORMATION: CDRL3 of Engineered Variant of 13E7 Antibody

<400> SEQUENCE: 368

Leu Gln Asp Asn Asn Phe Pro Pro Thr
1               5

<210> SEQ ID NO 369
<211> LENGTH: 17
<212> TYPE: PRT
<213> ORGANISM: Artificial Sequence
<220> FEATURE:
<223> OTHER INFORMATION: CDRH2 of Engineered Variant of 13E7 Antibody

<400> SEQUENCE: 369

Ile Ile Tyr Pro Gly Asp Ala Asp Ala Arg Tyr Ser Pro Ser Phe Gln
1               5                   10                  15

Gly

<210> SEQ ID NO 370
<211> LENGTH: 12
<212> TYPE: PRT
<213> ORGANISM: Artificial Sequence
<220> FEATURE:
<223> OTHER INFORMATION: CDRH3 of Engineered Variant of 13E7 Antibody

<400> SEQUENCE: 370

Arg Arg Gln Gly Ile Phe Gly Asp Ala Leu Asp Phe
1               5                   10

<210> SEQ ID NO 371
<211> LENGTH: 214
<212> TYPE: PRT
<213> ORGANISM: Artificial Sequence
<220> FEATURE:
<223> OTHER INFORMATION: LC Antibody ID 13E7 SST202443

<400> SEQUENCE: 371

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Val Tyr Tyr Cys Leu Gln Asp Asn Asn Phe Pro Pro
                85                  90                  95

Thr Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

-continued

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 372
<211> LENGTH: 451
<212> TYPE: PRT
<213> ORGANISM: Artificial Sequence
<220> FEATURE:
<223> OTHER INFORMATION: HC Antibody ID 13E7 SST202443

<400> SEQUENCE: 372

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
                35                  40                  45

Gly Ile Ile Tyr Pro Gly Asp Ala Asp Ala Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Arg Arg Gln Gly Ile Phe Gly Asp Ala Leu Asp Phe Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Cys Glu Glu Gln Tyr Gly Ser Thr Tyr
```

-continued

```
     290              295              300

Arg Cys Val Ser Val Leu Thr Val Leu His Gln Asp Trp Leu Asn Gly
305              310              315              320

Lys Glu Tyr Lys Cys Lys Val Ser Asn Lys Ala Leu Pro Ala Pro Ile
             325              330              335

Glu Lys Thr Ile Ser Lys Ala Lys Gly Gln Pro Arg Glu Pro Gln Val
             340              345              350

Tyr Thr Leu Pro Pro Ser Arg Glu Glu Met Thr Lys Asn Gln Val Ser
         355              360              365

Leu Thr Cys Leu Val Lys Gly Phe Tyr Pro Ser Asp Ile Ala Val Glu
     370              375              380

Trp Glu Ser Asn Gly Gln Pro Glu Asn Asn Tyr Lys Thr Thr Pro Pro
385              390              395              400

Val Leu Asp Ser Asp Gly Ser Phe Phe Leu Tyr Ser Lys Leu Thr Val
             405              410              415

Asp Lys Ser Arg Trp Gln Gln Gly Asn Val Phe Ser Cys Ser Val Met
             420              425              430

His Glu Ala Leu His Asn His Tyr Thr Gln Lys Ser Leu Ser Leu Ser
         435              440              445

Pro Gly Lys
    450
```

TREM2 ANTIGEN BINDING PROTEINS AND USES THEREOF

CROSS-REFERENCE TO RELATED APPLICATIONS

This Application is a Continuation of Application of U.S. patent application Ser. No. 16/500,378 filed on Oct. 2, 2019, which is a national stage filing under § 371 of PCT International Application No. PCT/US2018/028691, filed Apr. 20, 2018, which claims the benefit under 35 U.S.C. § 119(e) to U.S. Provisional Application No. 62/580,400, filed on Nov. 1, 2017, U.S. Provisional Application No. 62/530,753, filed on Jul. 10, 2017, and U.S. Provisional Application No. 62/488,691, filed on Apr. 21, 2017, each of which is hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 403433_001USC1_SL.txt, date created: Sep. 28, 2021, size: 291,767 bytes).

FIELD OF THE INVENTION

The present invention relates to the field of biopharmaceuticals. In particular, the invention relates to antigen binding proteins, such as antibodies, that specifically bind to and activate human triggering receptor expressed on myeloid cells-2 (TREM2), pharmaceutical compositions comprising the antigen binding proteins, and methods of producing and using such antigen binding proteins.

BACKGROUND OF THE INVENTION

TREM2 is a member of the Ig superfamily of receptors that is expressed on cells of myeloid lineage, including macrophages, dendritic cells, and microglia (Schmid et al., Journal of Neurochemistry, Vol. 83: 1309-1320, 2002; Colonna, Nature Reviews Immunology, Vol. 3: 445-453, 2003; Kiialainen et al., Neurobiology of Disease, Vol. 18: 314-322, 2005). TREM2 is an orphan immune receptor with a short intracellular domain and functions by signaling through the adaptor protein DAP12, the cytoplasmic domain of which comprises an ITAM motif (Bouchon et al., The Journal of Experimental Medicine, Vol. 194: 1111-1122, 2001). Upon activation of TREM2, tyrosine residues within the ITAM motif in DAP12 are phosphorylated by the Src family of kinases, providing docking sites for the tyrosine kinase ζ-chain-associated protein 70 (ZAP70) and spleen tyrosine kinase (Syk) via their SH2 domains (Colonna, Nature Reviews Immunology, Vol. 3: 445-453, 2003; Ulrich and Holtzman, ACS Chem. Neurosci., Vol. 7: 420-427, 2016). The ZAP70 and Syk kinases induce activation of several downstream signaling cascades, including phosphatidylinositol 3-kinase (PI3K), protein kinase C (PKC), extracellular regulated kinase (ERK), and elevation of intracellular calcium (Colonna, Nature Reviews Immunology, Vol. 3: 445-453, 2003; Ulrich and Holtzman, ACS Chem. Neurosci., Vol. 7: 420-427, 2016).

TREM2 has been implicated in several myeloid cell processes, including phagocytosis, proliferation, survival, and regulation of inflammatory cytokine production (Ulrich and Holtzman, ACS Chem. Neurosci., Vol. 7: 420-427, 2016). In the last few years, TREM2 has been linked to several diseases. For instance, mutations in both TREM2 and DAP12 have been linked to the autosomal recessive disorder Nasu-Hakola Disease, which is characterized by bone cysts, muscle wasting and demyelination phenotypes (Guerreiro et al., New England Journal of Medicine, Vol. 368: 117-127, 2013). More recently, variants in the TREM2 gene have been linked to increased risk for Alzheimer's disease (AD) and other forms of dementia including frontotemporal dementia (Jonsson et al., New England Journal of Medicine, Vol. 368: 107-116, 2013; Guerreiro et al., JAMA Neurology, Vol. 70:78-84, 2013; Jay et al., Journal of Experimental Medicine, Vol. 212: 287-295, 2015). In particular, the R47H variant has been identified in genome-wide studies as being associated with increased risk for late-onset AD with an overall adjusted odds ratio (for populations of all ages) of 2.3, second only to the strong genetic association of ApoE to Alzheimer's. The R47H mutation resides on the extracellular Ig V-set domain of the TREM2 protein and has been shown to impact lipid binding and uptake of apoptotic cells and Abeta (Wang et al., Cell, Vol. 160: 1061-1071, 2015; Yeh et al., Neuron, Vol. 91: 328-340, 2016), suggestive of a loss-of-function linked to disease. Further, postmortem comparison of AD patients' brains with and without the R47H mutation are supportive of a novel loss-of-microglial barrier function for the carriers of the mutation, with the R47H carrier microglia putatively demonstrating a reduced ability to compact plaques and limit their spread (Yuan et al., Neuron, Vol. 90: 724-739, 2016). Impairment in microgliosis has been reported in animal models of prion disease, multiple sclerosis, and stroke, suggesting that TREM2 may play an important role in supporting microgliosis in response to pathology or damage in the central nervous system (Ulrich and Holtzman, ACS Chem. Neurosci., Vol. 7: 420-427, 2016).

In view of the data indicating that deficits in TREM2 activity affect macrophage and microglia function and correlate with certain neurodegenerative disorders, there is a need in the art for therapeutic molecules that can induce or enhance TREM2-mediated functions.

SUMMARY OF THE INVENTION

The present invention is based, in part, on the design and generation of antigen binding proteins (e.g. antibodies) that specifically bind to and activate human TREM2 without the need for additional cross-linking. The agonist antigen binding proteins of the invention are capable of activating TREM2/DAP12 signaling in myeloid cells in the absence of aggregation, clustering, and/or Fc-mediated cross-linking of the antigen binding proteins. Accordingly, in certain embodiments, the present invention provides isolated agonist antigen binding proteins that specifically bind to human TREM2 and induce or activate one or more TREM2-mediated functions.

In some embodiments, the TREM2 agonist antigen binding proteins increase phosphorylated Syk (pSyk) levels in the absence of a cross-linking agent in cells expressing TREM2. The cells may be cells of the myeloid lineage, including monocytes, dendritic cells, microglial cells, and macrophages. In certain embodiments, the TREM2 agonist antigen bindings increase pSyk levels in TREM2-expressing cells with an EC50 less than 500 pM in the absence of a cross-linking agent as measured by a cell-based pSyk assay. In other embodiments, the TREM2 agonist antigen bindings increase pSyk levels in TREM2-expressing cells with an EC50 less than 300 pM in the absence of a cross-linking agent as measured by a cell-based pSyk assay. In yet other embodiments, the TREM2 agonist antigen bindings increase pSyk levels in TREM2-expressing cells with an EC50 from about 150 pM to about 500 pM in the absence of a cross-linking agent as measured by a cell-based pSyk assay.

The TREM2 agonist antigen binding proteins specifically bind to human TREM2 (SEQ ID NO: 1) or an extracellular domain (ECD) of human TREM2 (e.g. ECD set forth in SEQ ID NO: 2), for example with an equilibrium dissociation constant ($K_D$) less than 50 nM, less than 25 nM, less than 10 nM, or less than 5 nM. In certain embodiments, the TREM2 agonist antigen binding proteins do not cross-react with other TREM proteins, such as human TREM1. Thus, in one embodiment, the TREM2 agonist antigen binding proteins do not specifically bind to human TREM1 (SEQ ID NO: 4).

The TREM2 agonist antigen binding proteins of the invention can compete with any of the anti-TREM2 antibodies described herein (e.g. antibodies listed in Tables 1A, 1B, 2A, 2B, 3A and 3B) for binding to human TREM2. In one embodiment, the TREM2 agonist antigen binding protein competes with a reference antibody for binding to human TREM2, wherein the reference antibody comprises a light chain variable region comprising the sequence of SEQ ID NO: 61 and a heavy chain variable region comprising the sequence of SEQ ID NO: 124. In another embodiment, the TREM2 agonist antigen binding protein competes with a reference antibody for binding to human TREM2, wherein the reference antibody comprises a light chain variable region comprising the sequence of SEQ ID NO: 62 and a heavy chain variable region comprising the sequence of SEQ ID NO: 125. In yet another embodiment, the TREM2 agonist antigen binding protein competes with a reference antibody for binding to human TREM2, wherein the reference antibody comprises a light chain variable region comprising the sequence of SEQ ID NO: 52 and a heavy chain variable region comprising the sequence of SEQ ID NO: 115. In still another embodiment, the TREM2 agonist antigen binding protein competes with a reference antibody for binding to human TREM2, wherein the reference antibody comprises a light chain variable region comprising the sequence of SEQ ID NO: 56 and a heavy chain variable region comprising the sequence of SEQ ID NO: 119.

In certain embodiments, the TREM2 agonist antigen binding proteins of the invention comprise a light chain variable region comprising complementarity determining regions CDRL1, CDRL2, and CDRL3 and a heavy chain variable region comprising complementarity determining regions CDRH1, CDRH2, and CDRH3. The light chain and heavy chain variable regions or CDRs may be from any of the anti-TREM2 antibodies described herein or a variant thereof. For instance, in some embodiments, the TREM2 agonist antigen binding proteins comprise a CDRL1 comprising a sequence selected from SEQ ID NOs: 5-18 or a variant thereof having one, two, three or four amino acid substitutions; a CDRL2 comprising a sequence selected from SEQ ID NOs: 19-30 or a variant thereof having one, two, three or four amino acid substitutions; a CDRL3 comprising a sequence selected from SEQ ID NOs: 31-45 or a variant thereof having one, two, three or four amino acid substitutions; a CDRH1 comprising a sequence selected from SEQ ID NOs: 77-86 or a variant thereof having one, two, three or four amino acid substitutions; a CDRH2 comprising a sequence selected from SEQ ID NOs: 87-94 or a variant thereof having one, two, three or four amino acid substitutions; and a CDRH3 comprising a sequence selected from SEQ ID NOs: 95-109 or a variant thereof having one, two, three or four amino acid substitutions.

In some embodiments, the TREM2 agonist antigen binding proteins comprise a light chain variable region comprising a sequence selected from SEQ ID NOs: 46-63 and a heavy chain variable region comprising a sequence selected from SEQ ID NOs: 110-126. In one embodiment, the TREM2 agonist antigen binding protein comprises a light chain variable region comprising the sequence of SEQ ID NO: 54 and a heavy chain variable region comprising the sequence of SEQ ID NO: 117. In another embodiment, the TREM2 agonist antigen binding protein comprises a light chain variable region comprising the sequence of SEQ ID NO: 55 and a heavy chain variable region comprising the sequence of SEQ ID NO: 118. In another embodiment, the TREM2 agonist antigen binding protein comprises a light chain variable region comprising the sequence of SEQ ID NO: 60 and a heavy chain variable region comprising the sequence of SEQ ID NO: 123. In still another embodiment, the TREM2 agonist antigen binding protein comprises a light chain variable region comprising the sequence of SEQ ID NO: 61 and a heavy chain variable region comprising the sequence of SEQ ID NO: 124. In another embodiment, the TREM2 agonist antigen binding protein comprises a light chain variable region comprising the sequence of SEQ ID NO: 62 and a heavy chain variable region comprising the sequence of SEQ ID NO: 125. In yet another embodiment, the TREM2 agonist antigen binding protein comprises a light chain variable region comprising the sequence of SEQ ID NO: 52 and a heavy chain variable region comprising the sequence of SEQ ID NO: 115.

In some embodiments, the TREM2 agonist antigen binding proteins comprise a light chain variable region that is derived from a light chain variable region from any of the anti-TREM2 antibodies described herein. Thus, in some embodiments, the light chain variable region of the TREM2 agonist antigen binding proteins comprises a sequence that is at least 90% identical, at least 91% identical, at least 92% identical, at least 93% identical, at least 94% identical, or at least 95% identical to a sequence selected from SEQ ID NOs: 46-63. For instance, the TREM2 agonist antigen binding proteins can comprise a light chain variable region from any of the engineered anti-TREM2 antibody variants set forth in Tables 13-18. In one embodiment, the TREM2 agonist antigen binding protein comprises a light chain variable region comprising the sequence of SEQ ID NO: 54 with a mutation at one or more amino acid positions 64, 79, 80, 85, 94, and/or 100. In some such embodiments, the mutation is V64G, V64A, Q79E, Q79D, S80P, S80A, F85V, F85L, F85A, F85D, F85I, F85L, F85M, F85T, W94F, W94Y, W94S, W94T, W94A, W94H, W94I, W94Q, P100R, P100Q, P100G, or combinations thereof. In another embodiment, the TREM2 agonist antigen binding protein comprises a light chain variable region comprising the sequence of SEQ ID NO: 55 with a mutation at one or more amino acid positions 64, 79, 80, 94, and/or 100. Such mutations can include V64G, V64A, Q79E, Q79D, S80P, S80A, W94F, W94Y, W94S, W94T, W94A, W94H, W94I, W94Q, P100R, P100Q, P100G, or combinations thereof. In certain embodiments, the mutation is V64G, V64A, Q79E, S80P, S80A, W94Y, W94S, P100R, P100Q, or combinations thereof. In another embodiment, the TREM2 agonist antigen binding protein comprises a light chain variable region comprising the sequence of SEQ ID NO: 60 with a mutation at one or more amino acid positions 60, 92, and/or 93. The mutation in such embodiments can be selected from L60S, L60P, L60D, L60A, D92E, D92Q, D92T, D92N, S93A, S93N, S93Q, S93V, or combinations thereof. In yet another embodiment, the TREM2 agonist antigen binding protein comprises a light chain variable region comprising the sequence of SEQ ID NO: 61 with a mutation at one or more amino acid positions 56, 57, 92, and/or 93. In such embodiments, the mutation can be N56S, N56T, N56Q, N56E, G57A, G57V, D92E, D92Q, D92T, D92N, S93A, S93N, S93Q, S93V, or combinations thereof. In certain embodiments, the mutation is N56S, N56Q, G57A, D92E, D92Q, S93A, or combinations thereof. In still another embodiment, the TREM2 agonist antigen binding protein comprises a light chain variable region comprising the sequence of SEQ ID NO: 62 with a mutation at amino acid position 36, 46, 61 and/or 100. Such mutations can include F36Y, S46L, S46R, S46V, S46F, K61R, P100Q, P100G, P100R or combinations thereof. In particular embodiments, the mutation is F36Y, K61R, P100Q, or combinations thereof. In another embodiment, the TREM2 agonist antigen binding protein comprises a light chain variable region comprising the sequence of SEQ ID NO: 52 with a mutation at amino acid position 91, which can be selected from F91V, F91I, F91T, F91L, or F91D. In one embodiment, the mutation is F91V.

In certain embodiments, the TREM2 agonist antigen binding proteins comprise a heavy chain variable region that is derived from a heavy chain variable region from any of the anti-TREM2 antibodies described herein. Thus, in some embodiments, the heavy chain variable region of the TREM2 agonist antigen binding proteins comprises a sequence that is at least 90% identical, at least 91% identical, at least 92% identical, at least 93% identical, at least 94% identical, or at least 95% identical to a sequence selected from SEQ ID NOs: 110-126. For instance, the TREM2 agonist antigen binding proteins can comprise a heavy chain variable region from any of the engineered anti-TREM2 antibody variants set forth in Tables 13-18. In one embodiment, the TREM2 agonist antigen binding protein comprises a heavy chain variable region comprising the sequence of SEQ ID NO: 117 with a mutation at one or more amino acid positions 19, 55, 56, 57, 58, and/or 104. In some such embodiments, the mutation is M19K, M19R, M19T, M19E, M19N, M19Q, D55E, D55Q, D55N, D55T, S56A, S56Q, S56V, D57S, D57E, D57Q, T58A, T58V, W104F, W104Y, W104T, W104S, W104A, W104H, W104I, W104Q, or combinations thereof. In another embodiment, the TREM2 agonist antigen binding protein comprises a heavy chain variable region comprising the sequence of SEQ ID NO: 118 with a mutation at one or more amino acid positions 19, 55, 56, 57, 58, and/or 104. Such mutations can include M19K, M19R, M19T, M19E, M19N, M19Q, D55E, D55Q, D55N, D55T, S56A, S56Q, S56V, D57S, D57E, D57Q, T58A, T58V, W104F, W104Y, W104T, W104S, W104A, W104H, W104I, W104Q, or combinations thereof. In certain embodiments, the mutation is M19K, D55E, S56A, D57E, T58A, W104Y, W104T, or combinations thereof. In another embodiment, the TREM2 agonist antigen binding protein comprises a heavy chain variable region comprising the sequence of SEQ ID NO: 123 with a mutation at one or more amino acid positions 27, 55, 56, 57, 58, 105, and/or 106. In some embodiments, the mutation is selected from H27Y, H27D, H27F, H27N, D55E, D55Q, D55N, D55T, S56A, S56Q, S56V, D57S, D57E, D57Q, T58A, T58V, D105E, D105Q, D105T, D105N, D105G, S106A, S106Q, S106V, S106T, or combinations thereof. In yet another embodiment, the TREM2 agonist antigen binding protein comprises a heavy chain variable region comprising the sequence of SEQ ID NO: 124 with a mutation at one or more amino acid positions 55, 56, 57, 58, 105, and/or 106. The mutation in such embodiments can be selected from D55E, D55Q, D55N, D55T, S56A, S56Q, S56V, D57S, D57E, D57Q, T58A, T58V, D105E, D105Q, D105T, D105N, D105G, S106A, S106Q, S106V, S106T, or combinations thereof. In certain embodiments, the mutation is D55E, D55Q, S56A, D57E, T58A, D105E, D105N, S106A, or combinations thereof. In still another embodiment, the TREM2 agonist antigen binding protein comprises a heavy chain variable region comprising the sequence of SEQ ID NO: 125 with a mutation at one or more amino acid positions 43, 76, 85, 99, 100, and/or 116. Such mutations can include L43Q, L43K, L43H, I76T, R85S, R85G, R85N, R85D, D99E, D99Q, D99S, D99T, G100A, G100Y, G100V, T116L, T116M, T116P, T116R, or combinations thereof. In certain embodiments, the mutation is L43Q, R85S, D99E, G100A, G100Y, T116L, or combinations thereof. In another embodiment, the TREM2 agonist antigen binding protein comprises a heavy chain variable region comprising the sequence of SEQ ID NO: 115 with a mutation at amino acid position 62 and/or 63. In such embodiments, the mutation can be selected from D62E, D62Q, D62T, D62N, S63A, S63Q, S63V, or combinations thereof. In some embodiments, the mutation is D62E, D62Q, S63A, or combinations thereof.

In some embodiments, the TREM2 agonist antigen binding proteins comprise one or more CDRs of a variant of the anti-TREM2 antibodies described herein. For instance, the TREM2 agonist antigen binding proteins may comprise one or more CDRs of the anti-TREM2 antibody variants set forth in Tables 2A, 2B, 3A, 3B, and 19. In certain embodiments, the TREM2 agonist antigen binding proteins comprise one or more CDRs of anti-TREM2 antibody variants with improved binding affinity. In these and other embodiments, the TREM2 agonist antigen binding proteins comprise a CDRL1 comprising the sequence of SEQ ID NO: 16; a CDRL2 comprising a CDRL2 consensus sequence; a CDRL3 comprising a CDRL3 consensus sequence; a CDRH1 comprising the sequence of SEQ ID NO: 85, a CDRH2 comprising a CDRH2 consensus sequence; and a CDRH3 comprising a CDRH3 consensus sequence. In one embodiment, the CDRL2 consensus sequence is $X_1ASSX_2QX_3$ (SEQ ID NO: 139), where $X_1$ is A or G; $X_2$ is L or R; and $X_3$ is N, K, R, L, or T. In related embodiments, the CDRL3 consensus sequence is $X_1QADX_2X_3PX_4T$ (SEQ ID NO: 140), where $X_1$ is Q or G; $X_2$ is S or R; $X_3$ is F, L, or Y; and $X_4$ is R or H. In these and other embodiments, the CDRH2 consensus sequence is $X_1IYPGDSDX_2RX_3X_4PX_5FQX_6$ (SEQ ID NO: 141), where $X_1$ is I or T; $X_2$ is T or V; $X_3$ is Y or L; $X_4$ is S or A; $X_5$ is S, G, or E; and $X_6$ is G or D. The CDRH3 consensus may be $X_1RTFYYDSSDYX_2DY$ (SEQ ID NO: 142), where $X_1$ is Q, G, S, or M; and $X_2$ is F or S. In further embodiments, the CDRL2 of the TREM2 agonist antigen binding proteins of the invention may comprise a sequence selected from SEQ ID NOs: 26 and 143-147. In still further embodiments, the CDRL3 of the TREM2 agonist antigen binding proteins of the invention may comprise a sequence selected from SEQ ID NOs: 43 and 148-152. In some embodiments, the CDRH2 of the TREM2 agonist antigen binding proteins of the invention may comprise a sequence selected from SEQ ID NOs: 91 and 170-175. In other embodiments, the CDRH3 of the TREM2 agonist antigen binding proteins of the invention may comprise a sequence selected from SEQ ID NOs: 176-179.

In other embodiments, the TREM2 agonist antigen binding proteins comprise one or more CDRs of anti-TREM2 antibody variants with reduced binding affinity. In these and other embodiments, the TREM2 agonist antigen binding proteins comprise a CDRL1 comprising a CDRL1 consensus sequence; a CDRL2 comprising a CDRL2 consensus sequence; a CDRL3 comprising a CDRL3 consensus sequence; a CDRH1 comprising a CDRH1 consensus sequence, a CDRH2 comprising a CDRH2 consensus sequence; and a CDRH3 comprising a CDRH3 consensus sequence. In one embodiment, the CDRL1 consensus sequence is $X_1ASQGISX_2WLA$ (SEQ ID NO: 284), where $X_1$ is R or A; and $X_2$ is S or R. In related embodiments, the CDRL2 consensus sequence is $X_1AX_2SLQN$ (SEQ ID NO: 285), where $X_1$ is A or S; and $X_2$ is S or G. In other related embodiments, the CDRL3 consensus sequence is $QQAX_1SFPX_2T$ (SEQ ID NO: 286), where $X_1$ is D or V; and $X_2$ is R or L. In these and other embodiments, the CDRH1 consensus sequence is $SX_1WIA$ (SEQ ID NO: 287), where $X_1$ is Y or E. In related embodiments, the CDRH2 consensus sequence is $IIYPX_1DSDTRYSPSFQG$ (SEQ ID NO: 288), where $X_1$ is G or S. The CDRH3 consensus may be $QRX_1FX_2X_3DSSDYFDY$ (SEQ ID NO: 289), where $X_1$ is T or G; $X_2$ is Y or R; and $X_3$ is Y or G. In some embodiments, the CDRL1 of the TREM2 agonist antigen binding proteins of the invention may comprise a sequence selected from SEQ ID NOs: 16, 290, and 291. In further embodiments, the CDRL2 of the TREM2 agonist antigen binding proteins of the invention may comprise a sequence selected from SEQ ID NOs: 28, 292, and 293. In still further embodiments, the CDRL3 of the TREM2 agonist antigen binding proteins of the invention may comprise a sequence selected from SEQ ID NOs: 43, 294, and 271. In some embodiments, the CDRH1 of the TREM2 agonist antigen binding proteins of the invention may comprise the sequence of SEQ ID NO: 85 or SEQ ID NO: 302. In other embodiments, the CDRH2 of the TREM2 agonist antigen binding proteins of the invention may comprise the sequence of SEQ ID NO: 91 or SEQ ID NO: 303. In still other embodiments, the CDRH3 of the TREM2 agonist antigen binding proteins of the invention may comprise a sequence selected from SEQ ID NOs: 107 and 304-306.

In certain embodiments, the TREM2 agonist antigen binding proteins comprise a light chain variable region and/or heavy chain variable region from any of the anti-TREM2 variant antibodies set forth in Tables 2A, 2B, 3A, 3B, and 19. Accordingly, in some embodiments, the light chain variable region of the TREM2 agonist antigen binding proteins comprises a sequence that is at least 90% identical, at least 91% identical, at least 92% identical, at least 93% identical, at least 94% identical, or at least 95% identical to a sequence selected from SEQ ID NOs: 61, 153-162, and 295-300. In these and other embodiments, the heavy chain variable region of the TREM2 agonist antigen binding proteins comprises a sequence that is at least 90% identical, at least 91% identical, at least 92% identical, at least 93% identical, at least 94% identical, or at least 95% identical to a sequence selected from SEQ ID NOs: 124, 180-190, and 307-312.

In any of the embodiments described herein, including the embodiments described above, the TREM2 agonist antigen binding protein is an antibody or binding fragment thereof, preferably a monoclonal antibody or binding fragment thereof. In some embodiments, the monoclonal antibody or binding fragment thereof is a chimeric antibody or binding fragment thereof. In other embodiments, the monoclonal antibody or binding fragment thereof is a humanized antibody or binding fragment thereof. In yet other embodiments, the monoclonal antibody or binding fragment thereof is a fully human antibody or binding fragment thereof. The monoclonal antibody can be of any isotype, such as a human IgG1, IgG2, IgG3, or IgG4. In one particular embodiment, the monoclonal antibody is a human IgG1 antibody. In another particular embodiment, the monoclonal antibody is a human IgG2 antibody.

In certain embodiments in which the TREM2 agonist antigen binding protein is an antibody (e.g. monoclonal antibody), the antibody may contain one or more modifications that affect the glycosylation of the antibody. In some embodiments, the antibody comprises one or more mutations to reduce or eliminate glycosylation. In such embodiments, the aglycosylated antibody may comprise a mutation at amino acid position N297 (according to the EU numbering scheme), such as a N297G mutation, in its heavy chain. The aglycosylated antibody may comprise further mutations to stabilize the antibody structure. Such mutations can include pairs of cysteine substitutions, such as A287C and L306C, V259C and L306C, R292C and V302C, and V323C and I332C (amino acid positions according to the EU numbering scheme). In one embodiment, the aglycosylated antibody comprises R292C and V302C mutations (according to the EU numbering scheme) in its heavy chain. In certain embodiments, the aglycosylated anti-TREM2 agonist antibody comprises a heavy chain constant region comprising the amino acid sequence of SEQ ID NO: 202 or SEQ ID NO: 203.

In further embodiments in which the TREM2 agonist antigen binding protein is a human IgG2 antibody (e.g. monoclonal antibody) or comprises a CH1 region and hinge region from a human IgG2 antibody, the antibody may contain one or more modifications that affect the hinge structure of the antibody. In one such embodiment, the anti-TREM2 agonist antibody comprises a C131S mutation (according to the EU numbering scheme) in its heavy chain. In another embodiment, the anti-TREM2 agonist antibody comprises a C214S mutation (according to the EU numbering scheme) in its light chain and a C219S mutation (according to the EU numbering scheme) in its heavy chain. In another embodiment, the anti-TREM2 agonist antibody comprises a C214S mutation (according to the EU numbering scheme) in its light chain and a C220S mutation (according to the EU numbering scheme) in its heavy chain.

In certain embodiments, the TREM2 agonist antigen binding proteins of the invention may comprise a CH1 region and hinge region from a human IgG2 antibody (e.g. the amino acid of SEQ ID NO: 207), and an Fc region from a human IgG1 antibody. In one embodiment, the TREM2 agonist antigen binding protein comprises a CH1 region and hinge region from a human IgG2 antibody (e.g. the amino acid sequence of SEQ ID NO: 207) and an Fc region from a human IgG1 antibody, wherein the Fc region comprises the amino acid sequence of SEQ ID NO: 281.

In certain embodiments, the TREM2 agonist antigen binding proteins of the invention comprise a light chain comprising a light chain variable region and a heavy chain comprising a heavy chain variable region, wherein: (a) the light chain variable region having the amino acid sequence of SEQ ID NO: 326, and the heavy chain variable region having the amino acid sequence of SEQ ID NO: 327; (b) the light chain variable region having the amino acid sequence of SEQ ID NO: 328, and the heavy chain variable region having the amino acid sequence of SEQ ID NO: 329; (c) the light chain variable region having the amino acid sequence of SEQ ID NO: 330, and the heavy chain variable region having the amino acid sequence of SEQ ID NO: 331; or (d) the light chain variable region having the amino acid sequence of SEQ ID NO: 332, and the heavy chain variable region having the amino acid sequence of SEQ ID NO: 333. In certain embodiments, the TREM2 agonist antigen binding proteins of the invention comprise a light chain and a heavy chain, wherein: (a) the light chain having the amino acid sequence of SEQ ID NO: 334, and the heavy chain having the amino acid sequence of SEQ ID NO: 335; (b) the light chain having the amino acid sequence of SEQ ID NO: 334, and the heavy chain having the amino acid sequence of SEQ ID NO: 336; (c) the light chain having the amino acid sequence of SEQ ID NO: 337, and the heavy chain having the amino acid sequence of SEQ ID NO: 338; (d) the light chain having the amino acid sequence of SEQ ID NO: 339, and the heavy chain having the amino acid sequence of SEQ ID NO: 340; or (e) the light chain having the amino acid sequence of SEQ ID NO: 341, and the heavy chain having the amino acid sequence of SEQ ID NO: 342.

The present invention also provides polynucleotides and expression vectors encoding the TREM2 agonist antigen binding proteins described herein as well as host cells, such as CHO cells, comprising the encoding polynucleotides and expression vectors. In certain embodiments, the present invention includes methods for producing the TREM2 agonist antigen binding proteins, including anti-TREM2 agonist monoclonal antibodies and binding fragments thereof. In one embodiment, the method comprises culturing a host cell comprising an expression vector encoding the antigen binding protein under conditions that allow expression of the antigen binding protein, and recovering the antigen binding protein from the culture medium or host cell.

The TREM2 agonist antigen binding proteins described herein can be used in the manufacture of a pharmaceutical composition or medicament for the treatment or prevention of conditions associated with TREM2 deficiency or loss of TREM2 biological activity, such as Alzheimer's disease, Nasu-Hakola disease, frontotemporal dementia, multiple sclerosis, prion disease, or stroke. Thus, the present invention also provides a pharmaceutical composition comprising a TREM2 agonist antigen binding protein described herein and a pharmaceutically acceptable excipient.

In certain embodiments, the present invention provides methods for treating, preventing, or reducing the risk of developing conditions associated with TREM2 deficiency or loss of TREM2 biological activity in a patient in need thereof. In one embodiment, the method comprises administering to the patient an effective amount of any of the TREM2 agonist antigen binding proteins described herein. In some embodiments, the condition to be treated, prevented, or ameliorated is Alzheimer's disease. In other embodiments, the condition to be treated, prevented, or ameliorated is multiple sclerosis. The patient in need of treatment may be determined to have one or more genotypes associated with an increased risk of developing a disease or condition that can be treated according to the methods of the invention. For instance, in some embodiments, the patient has a genotype associated with an increased risk of developing Alzheimer's disease, such as the genotypes described herein. In further embodiments, the patient may be determined to carry an allele encoding a TREM2 variant associated with an increased risk of developing Alzheimer's disease. Such variants can include the R47H TREM2 variant and the R62H TREM2 variant.

The present invention also includes methods of increasing survival or proliferation of myeloid cells, such as macrophages, microglia, and dendritic cells, in a patient in need thereof. In one embodiment, the method comprises administering to the patient an effective amount of any of the TREM2 agonist antigen binding proteins described herein. In some embodiments, the patient in need of treatment is at risk for, suffers from, or has been diagnosed with a neurodegenerative disorder, such as Alzheimer's disease. In other embodiments, the patient in need of treatment is at risk for, suffers from, or has been diagnosed with an autoimmune disorder, such as multiple sclerosis.

BRIEF DESCRIPTION OF THE DRAWINGS

FIG. 1A depicts dose-response curves for agonist activity of purified monoclonal human anti-TREM2 antibodies from harvest 1. The fold-increase in phosphorylated Syk (pSyk) levels in HEK293T cells expressing human TREM2/DAP12 is plotted as a function of concentration of human anti-TREM2 antibodies. Agonist activity of a commercially available rat anti-human/mouse TREM2 antibody (mAb17291; "R&D mAb" or "Antibody 1") is included for comparison. Human IgG2 and rat IgG2b isotype antibodies were used as controls.

Figure 1A:
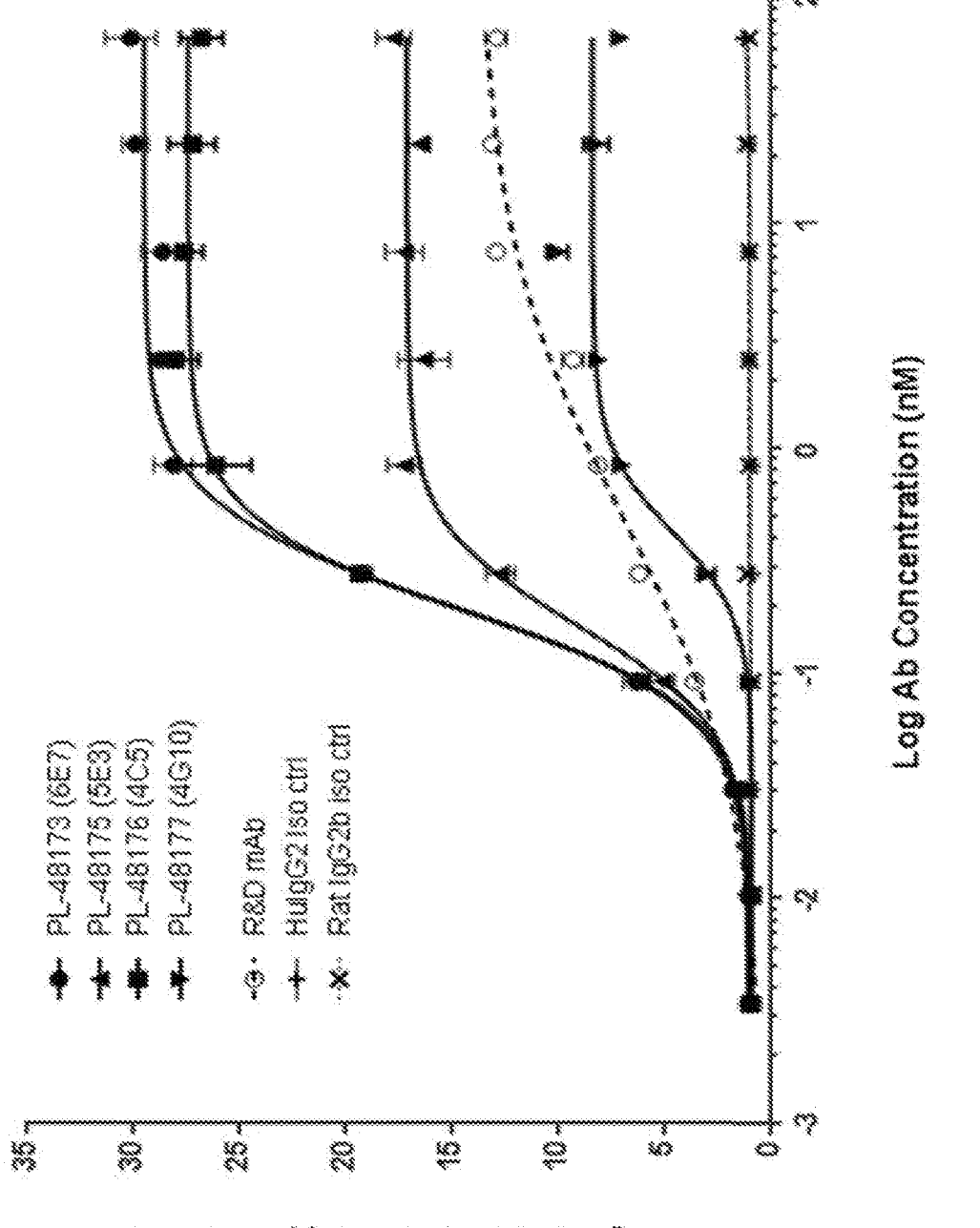
Figure 1B:
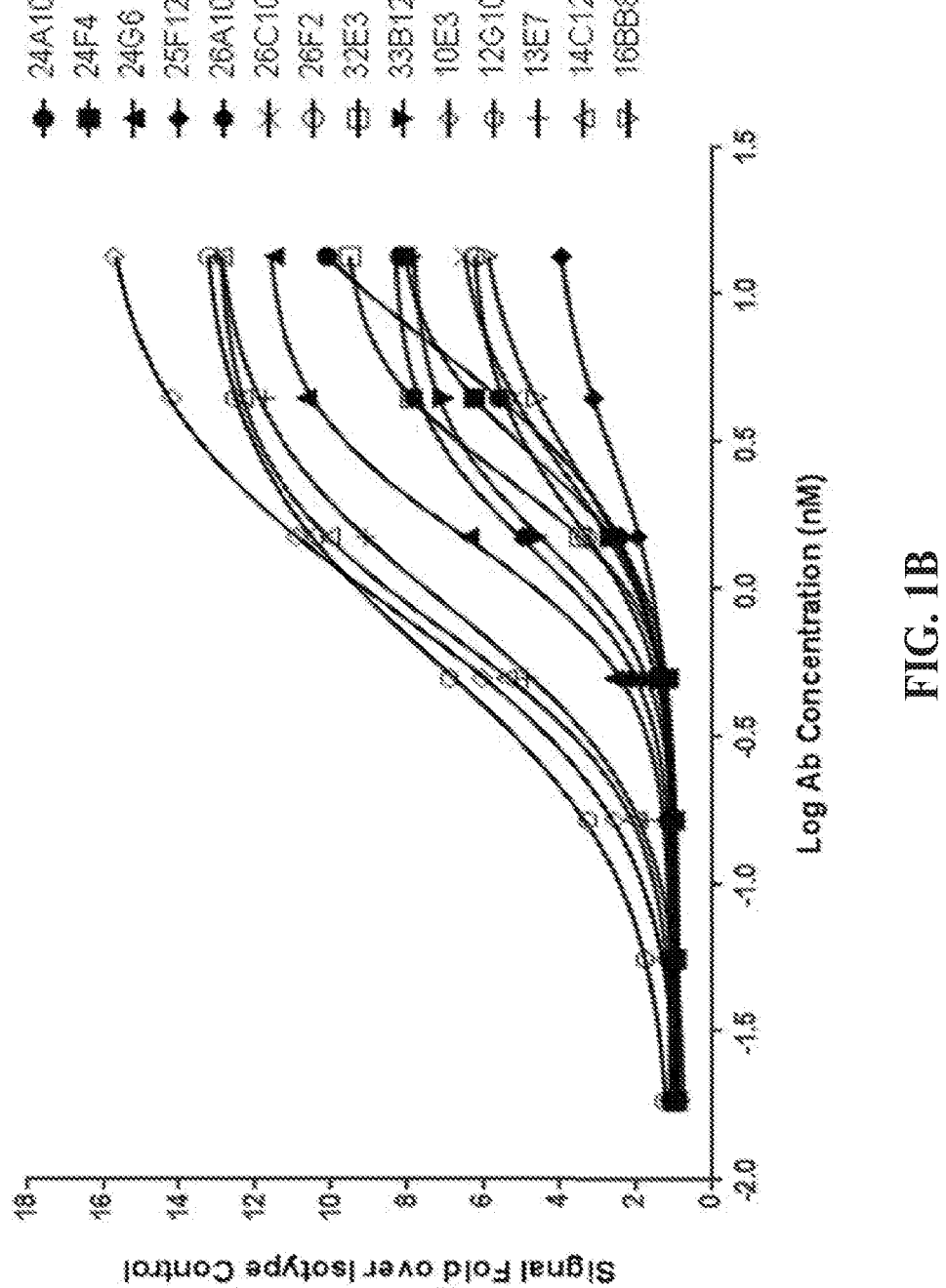

FIG. 1B depicts dose-response curves for agonist activity of unpurified monoclonal human anti-TREM2 antibodies from hybridoma supernatants from harvests 3, 4, and 5. The fold-increase in pSyk levels in HEK293T cells expressing human TREM2/DAP12 is plotted as a function of concentration of human anti-TREM2 antibodies. Human IgG2 isotype antibody was used as a control.

FIGS. 2A-2B are sequence alignments of kappa light chain variable regions of exemplary anti-TREM2 antibodies to original germline sequences. FIG. 2B is a continuation of the sequences in FIG. 2A.

FIGS. 3A-3B are sequence alignments of lambda light chain variable regions of exemplary anti-TREM2 antibodies to original germline sequences. FIG. 3B is a continuation of the sequences in FIG. 3A.

FIGS. 4A-4B are sequence alignments of heavy chain variable regions of exemplary anti-TREM2 antibodies to original germline sequences. FIG. 4B is a continuation of the sequences in FIG. 4A.

Figure 5:
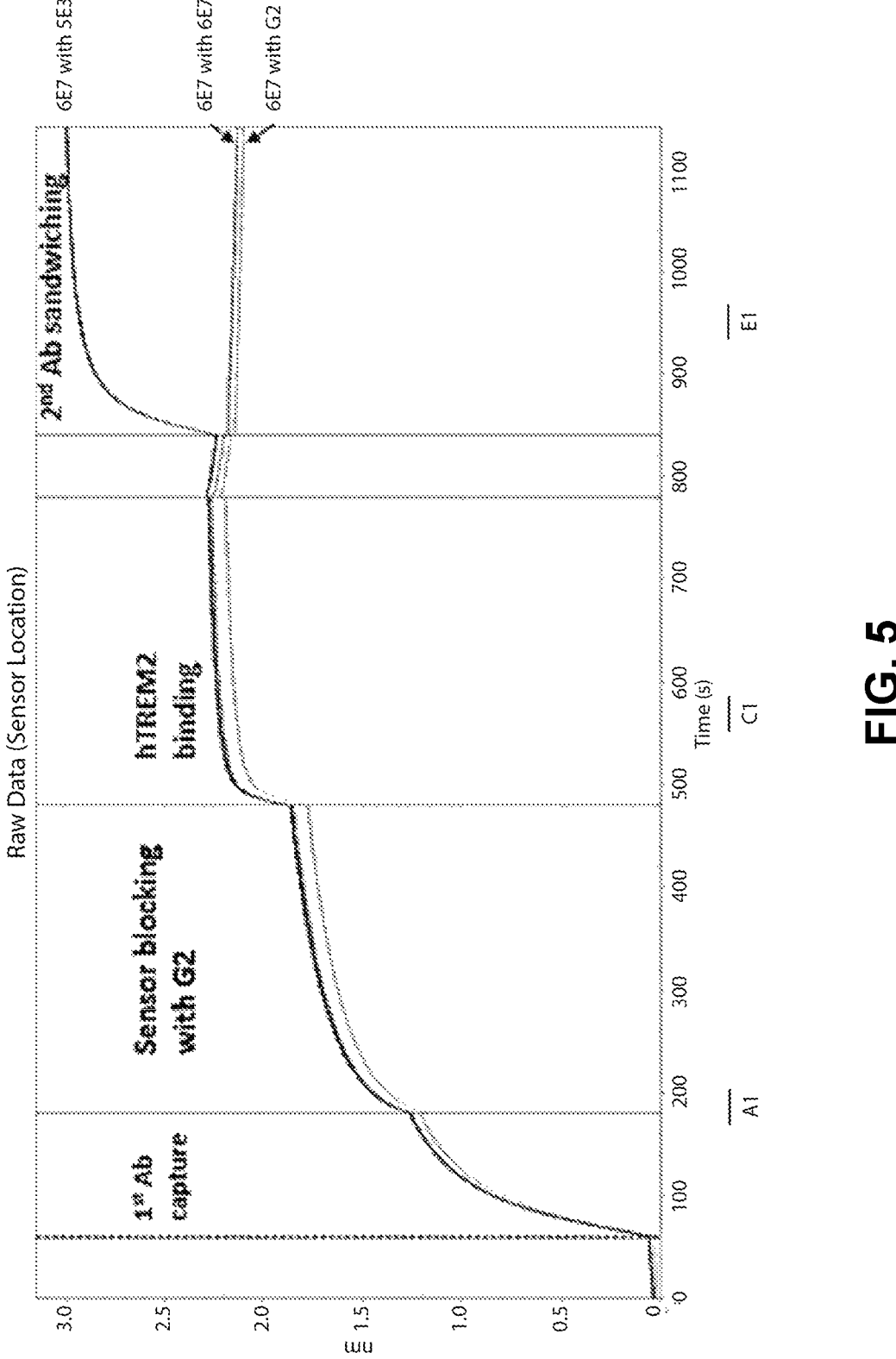

FIG. 5 is a plot of binding signal as a function of time of an anti-human Fc kinetic sensor (Octet® HTX instrument; Pall ForteBio) loaded with the 6E7 antibody at the time indicated by the dotted line ("1st Ab capture"). The first solid denotes the time at which an irrelevant human IgG2 antibody was added to the sensor to reduce non-specific binding events ("Sensor blocking with G2"). The second solid line denotes the time at which the target antigen (soluble human TREM2) was added to the sensor to interact with the captured 6E7 antibody. The final solid line indicates the time at which the sandwich antibody (5E3, 6E7, or a control IgG2 antibody) was added to the sensor. An increase in binding is observed when the 5E3 antibody is added, which suggests that the 5E3 antibody binds to a different epitope on human TREM2 from the epitope bound by the 6E7 antibody.

Figure 6:
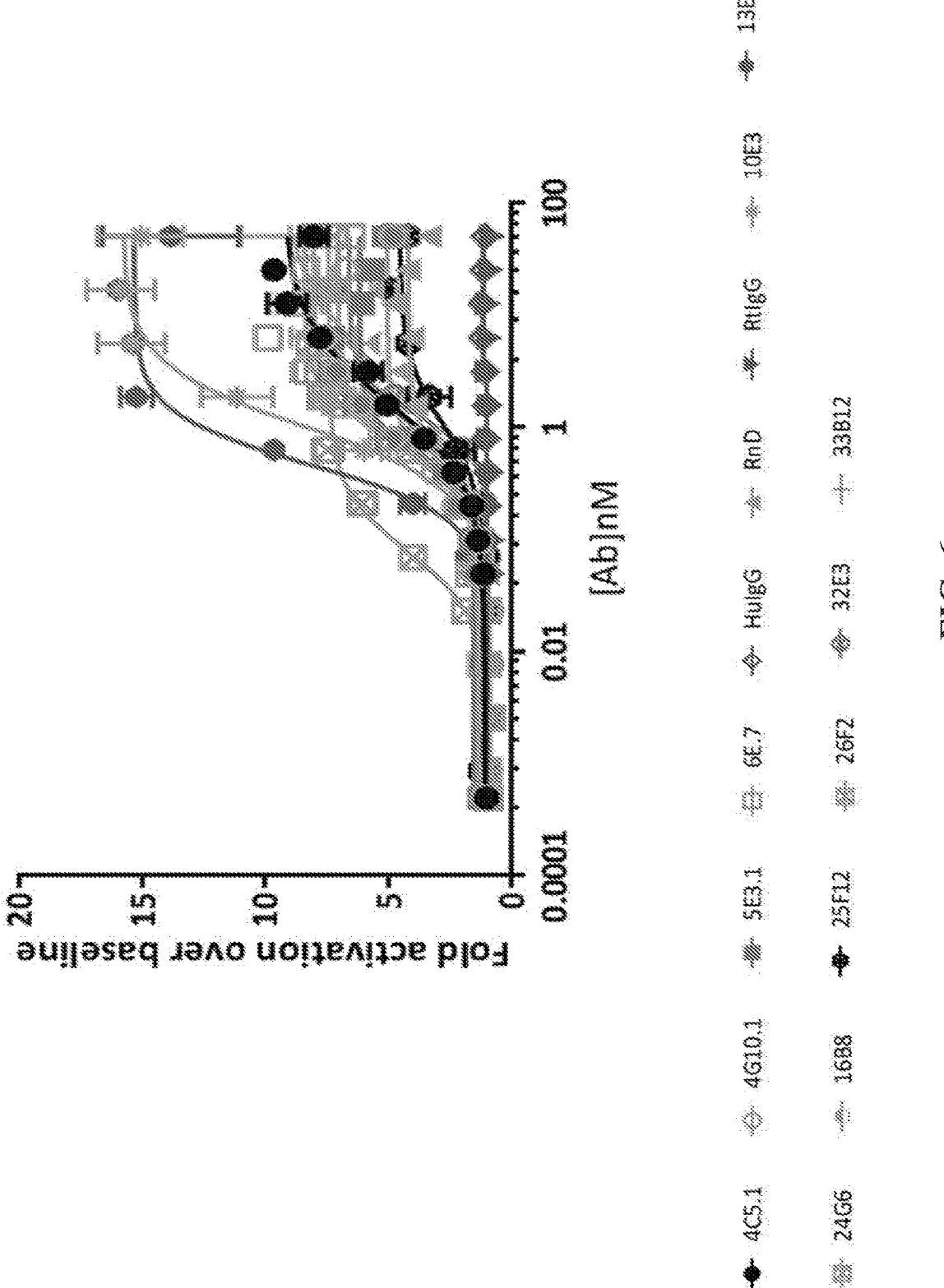

FIG. 6 depicts a dose-response curve for agonist activity of monoclonal human anti-TREM2 antibodies (4C5, 4G10, 5E3, 6E7, 10E3, 13E7, 24G6, 16B8, 25F12, 26F2, 32E3, and 33B12) in differentiated THP-1 cells. The fold-increase in phosphorylated Syk (pSyk) levels over baseline is plotted as a function of concentration of human anti-TREM2 antibodies. Human IgG2 (HuIgG) and rat IgG2b (RtIgG) isotype antibodies were used as controls. Agonist activity of a commercially available rat anti-human/mouse TREM2 antibody (mAb17291; "RnD") is included for comparison.

Figure 7:
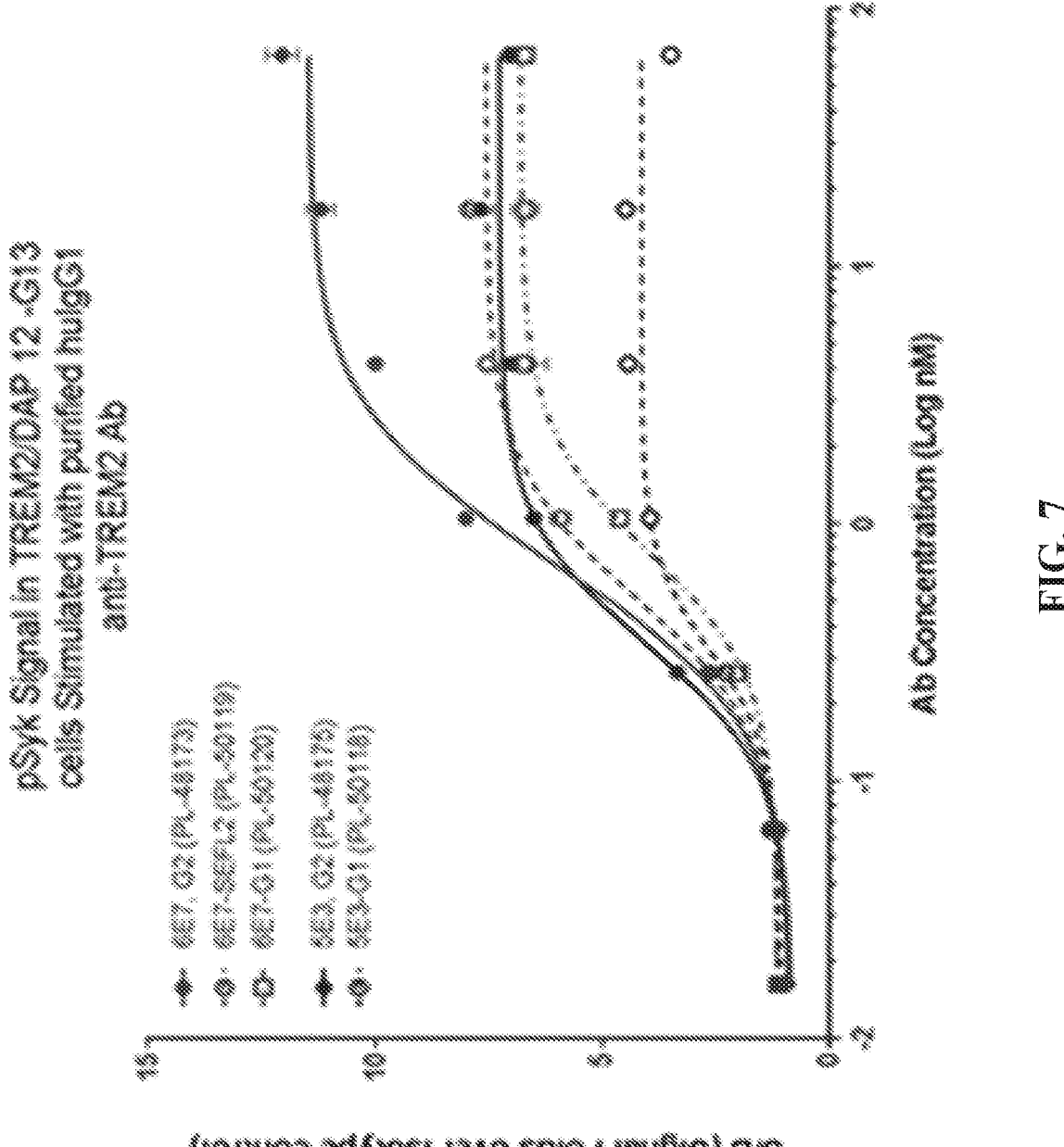

FIG. 7 depicts dose-response curves for agonist activity of purified 6E7 and 5E3 human anti-TREM2 antibodies in an IgG2 ("G2"), IgG1 ("G1") or an aglycosylated IgG1 ("SEFL2") format. The fold-increase in phosphorylated Syk (pSyk) levels over the corresponding isotype control in HEK293T cells expressing human TREM2/DAP12 is plotted as a function of concentration of the human anti-TREM2 antibodies. Conversion of the 6E7 and 5E3 antibodies from an IgG2 isotype to an IgG1 isotype results in the partial loss of agonist activity.

Figure 8A:
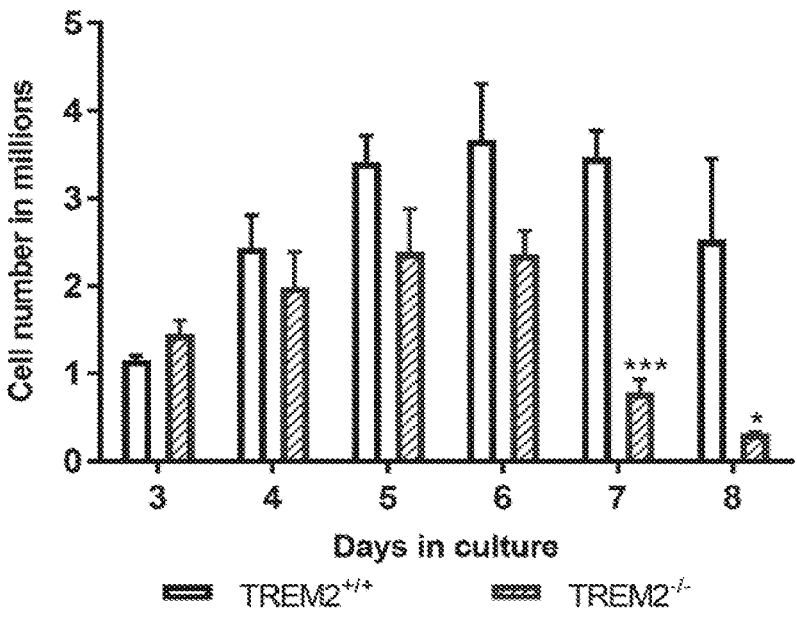

FIG. 8A is a bar graph of numbers of bone marrow derived macrophages (BMDMs) derived from wild-type (TREM+/+) and TREM2−/− mice in different days of culture under limiting conditions of CSF-1. The TREM2−/− BMDMs exhibit a survival defect in these culture conditions.

Figure 8B:
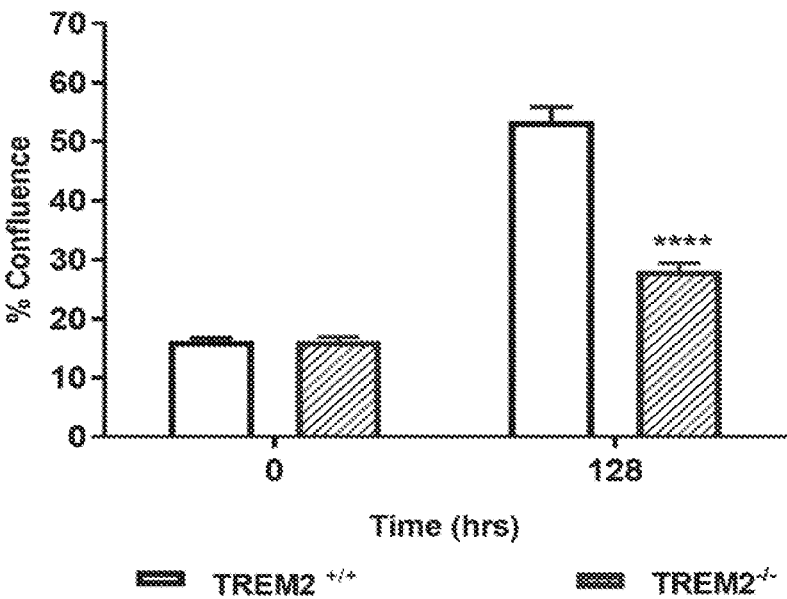

FIG. 8B is a bar graph of percent cell confluence of mouse adult microglia derived from wild-type (TREM+/+) and TREM2−/− mice at different time points in culture under limiting conditions of CSF-1. TREM2$^{-/-}$ mouse adult microglia exhibit a survival defect in these culture conditions.

Figure 8C:
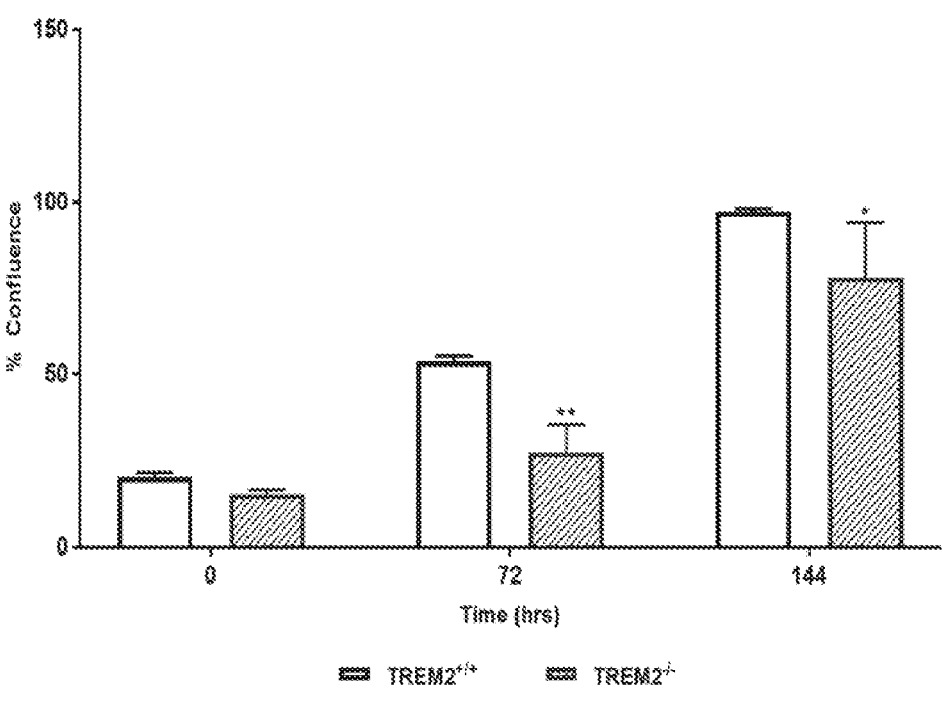

FIG. 8C is a bar graph of percent cell confluence of mouse neonatal microglia derived from wild-type (TREM$^{+/+}$) and TREM2$^{-/-}$ mice at different time points in culture under limiting conditions of CSF-1. Neonatal TREM2$^{-/-}$ microglia exhibit a survival defect over time.

Figure 8D:
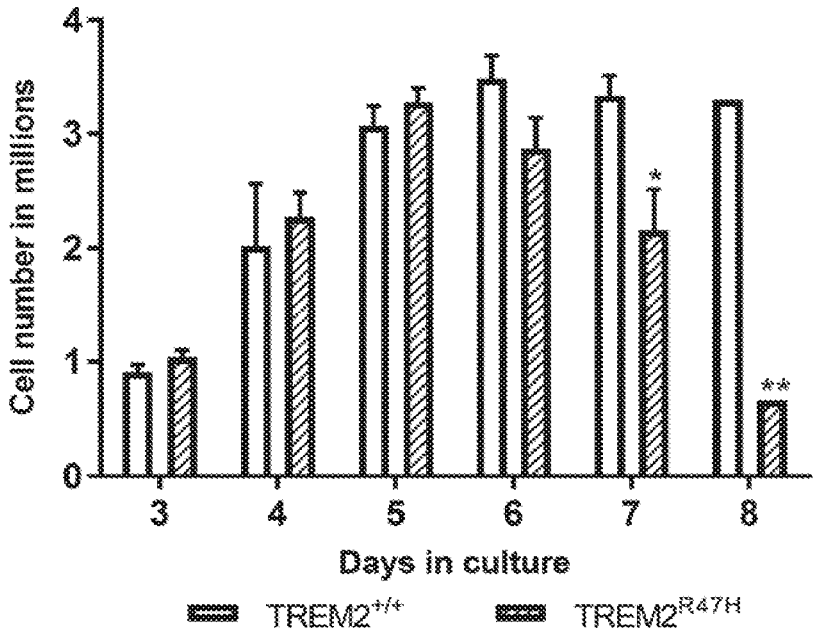

FIG. 8D is a bar graph of numbers of BMDMs derived from wild-type (TREM$^{+/+}$) and TREM2$^{R47H}$ mice in different days of culture under limiting conditions of CSF-1. TREM2$^{R47H}$ mouse BMDMs exhibit a survival defect in these culture conditions.

Figure 8E:
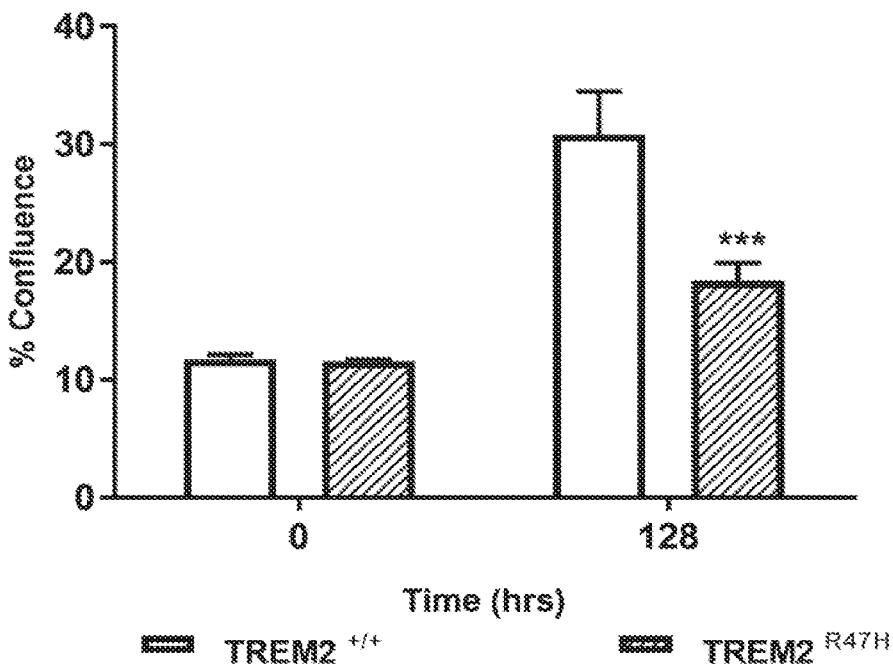

FIG. 8E is a bar graph of percent cell confluence of mouse adult microglia derived from wild-type (TREM$^{+/+}$) and TREM2$^{R47H}$ mice at different time points in culture under limiting conditions of CSF-1. TREM2$^{R47H}$ mouse adult microglia exhibit a survival defect in these culture conditions.

Figure 8F:
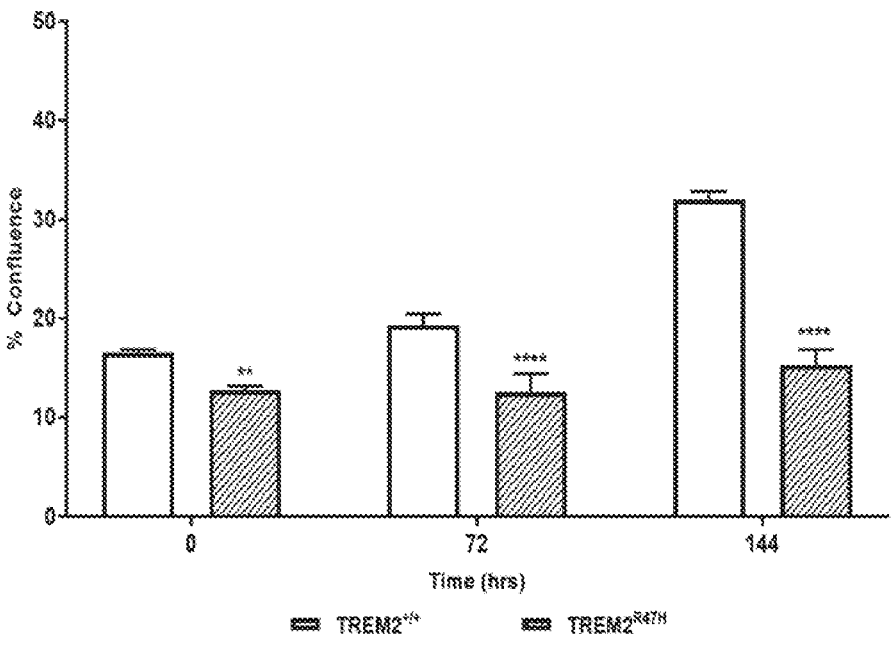

FIG. 8F is a bar graph of percent cell confluence of mouse neonatal microglia derived from wild-type (TREM$^{+/+}$) and TREM2$^{R47H}$ mice at different time points in culture under limiting conditions of CSF-1. Neonatal TREM2$^{R47H}$ microglia exhibit a survival defect that increases over time.

Figure 9A:
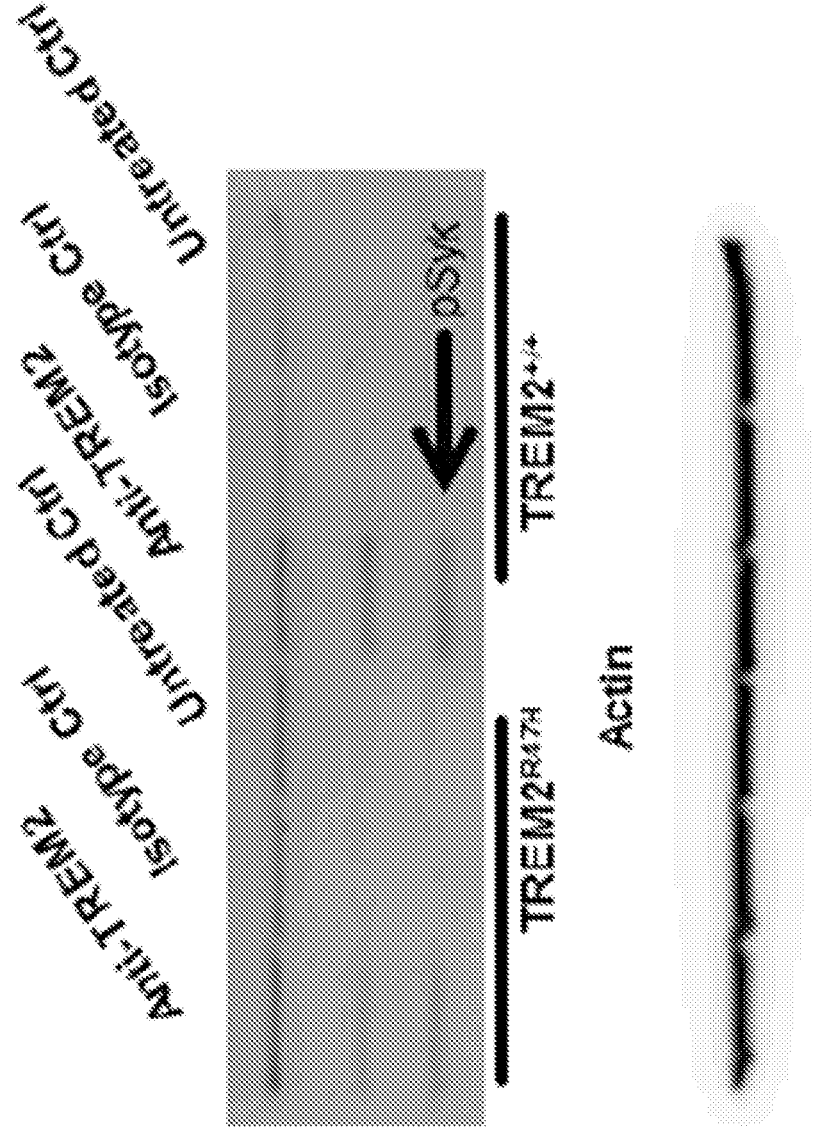

FIG. 9A is a western blot of cell lysates from TREM2$^{R47H}$ and wild-type (TREM$^{+/+}$) BMDMs treated with an anti-TREM2 antibody or an isotype control. The anti-TREM2 antibody activates TREM2/DAP12 signaling in both types of macrophage as indicated by the increase in pSyk levels.

Figure 9B:
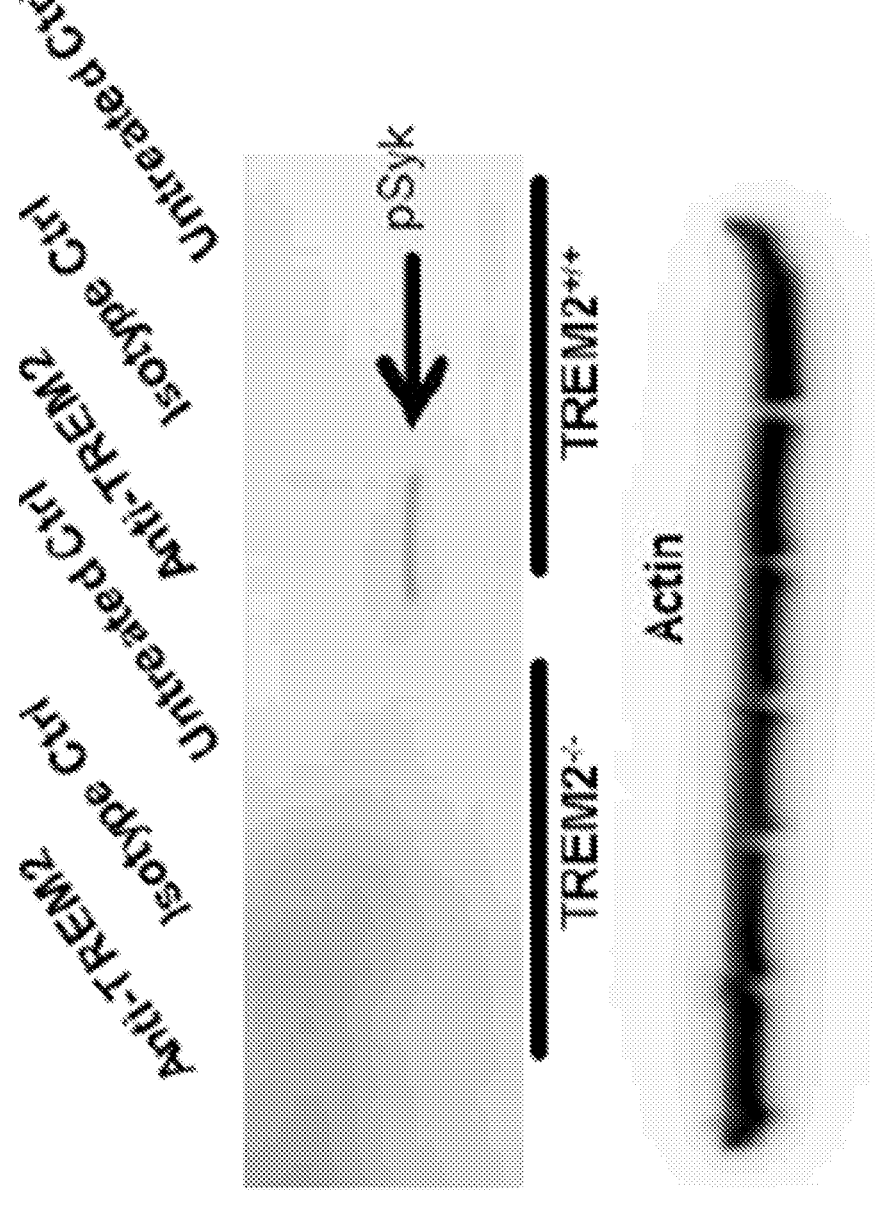

FIG. 9B is a western blot of cell lysates from TREM2$^{-/-}$ and wild-type (TREM$^{+/+}$) BMDMs treated with an anti-TREM2 antibody or an isotype control. The anti-TREM2 antibody does not increase pSyk levels in the TREM2$^{-/-}$ BMDMs confirming that the effect is specific for TREM2.

Figure 10A:
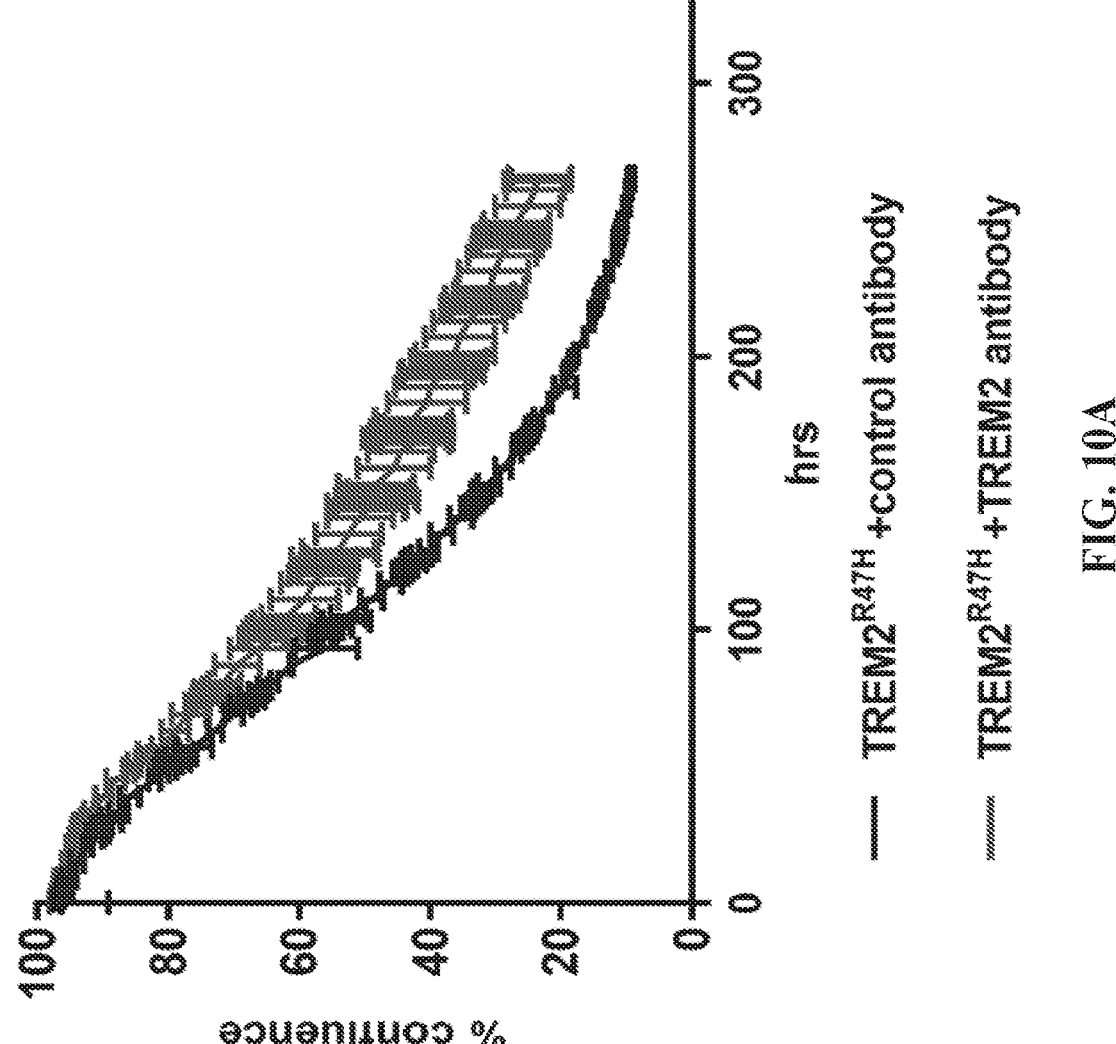

FIG. 10A is a graph depicting percent cell confluence over time for TREM2$^{R47H}$ BMDMs treated with an isotype control antibody or an anti-TREM2 agonist antibody as measured by a real-time cell confluence assay. Data are plotted as mean+/−s.d. and are from a single representative experiment. The experiment was conducted twice independently (n=2 and assayed in triplicate).

Figure 10B:
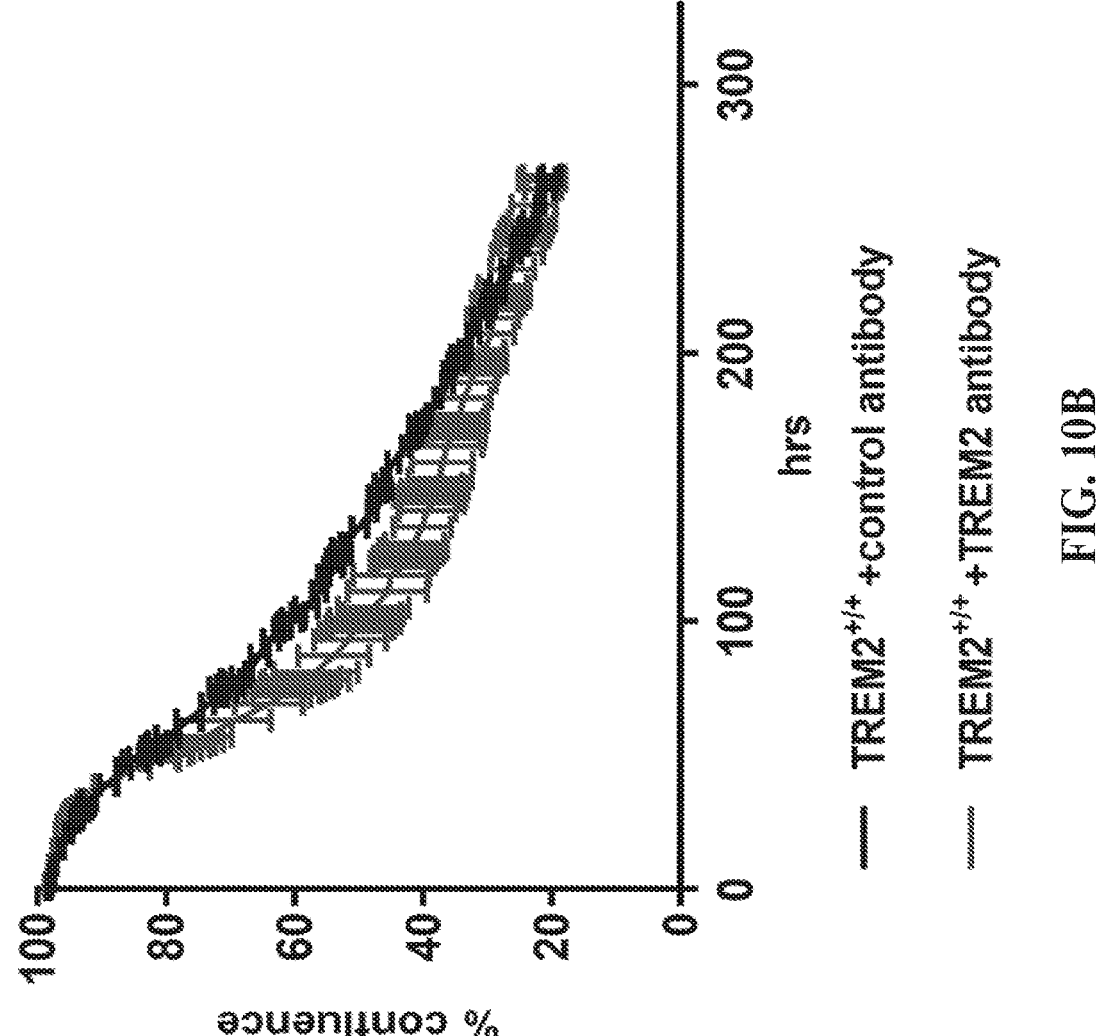

FIG. 10B is a graph depicting percent cell confluence over time for wild-type (TREM2$^{+/+}$) BMDMs treated with an isotype control antibody or an anti-TREM2 agonist antibody as measured by a real-time cell confluence assay. Data are plotted as mean+/−s.d. and are from a single representative experiment. The experiment was conducted twice independently (n=2 and assayed in triplicate).

Figure 10C:
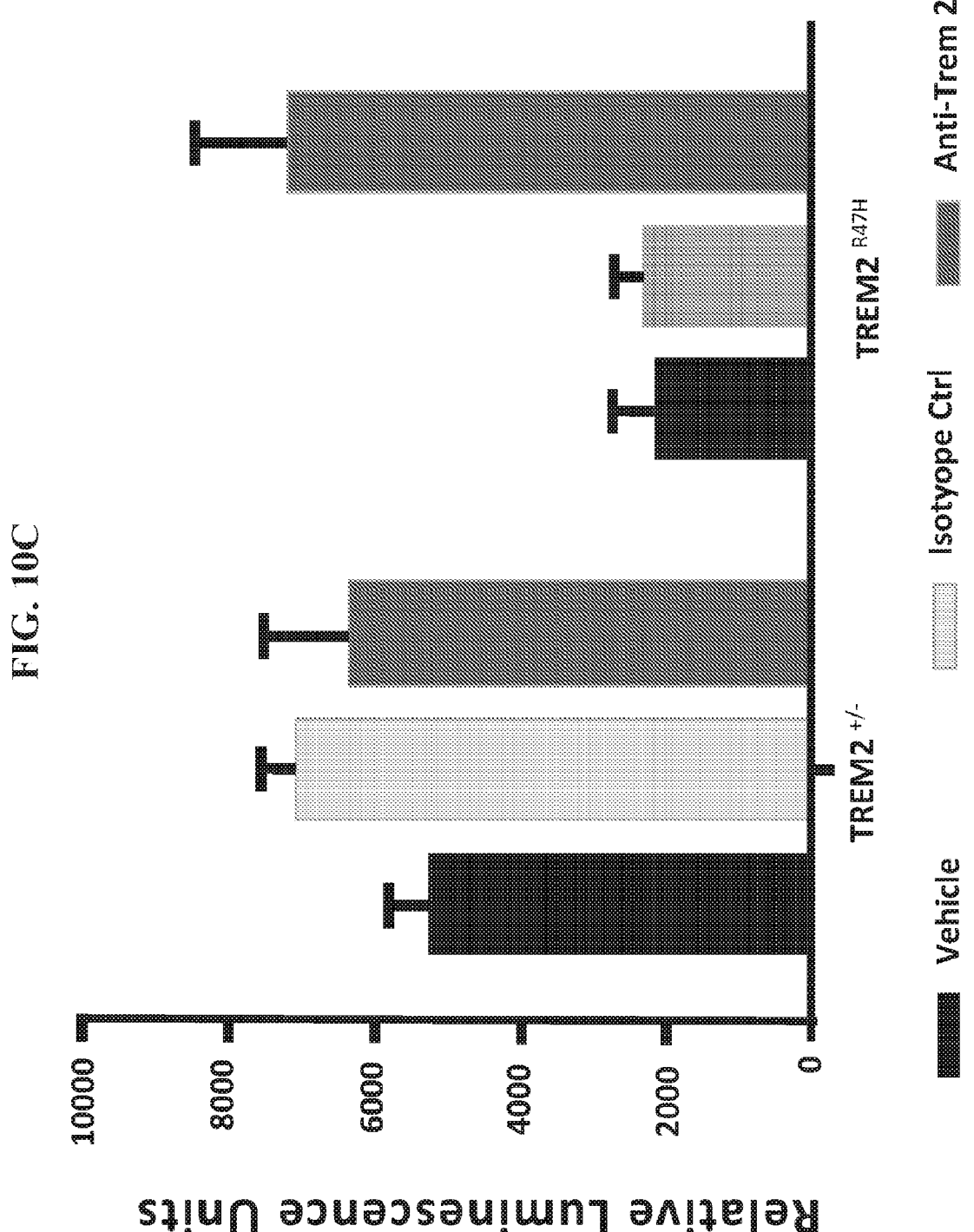

FIG. 10C is a bar graph depicting cell viability as measured by CellTiter Glo ATP detection assay for TREM2$^{R47H}$ and TREM2$^{+/-}$ BMDMs treated with vehicle, isotype control, or an anti-TREM2 agonist antibody for 14 days.

Figure 10D:
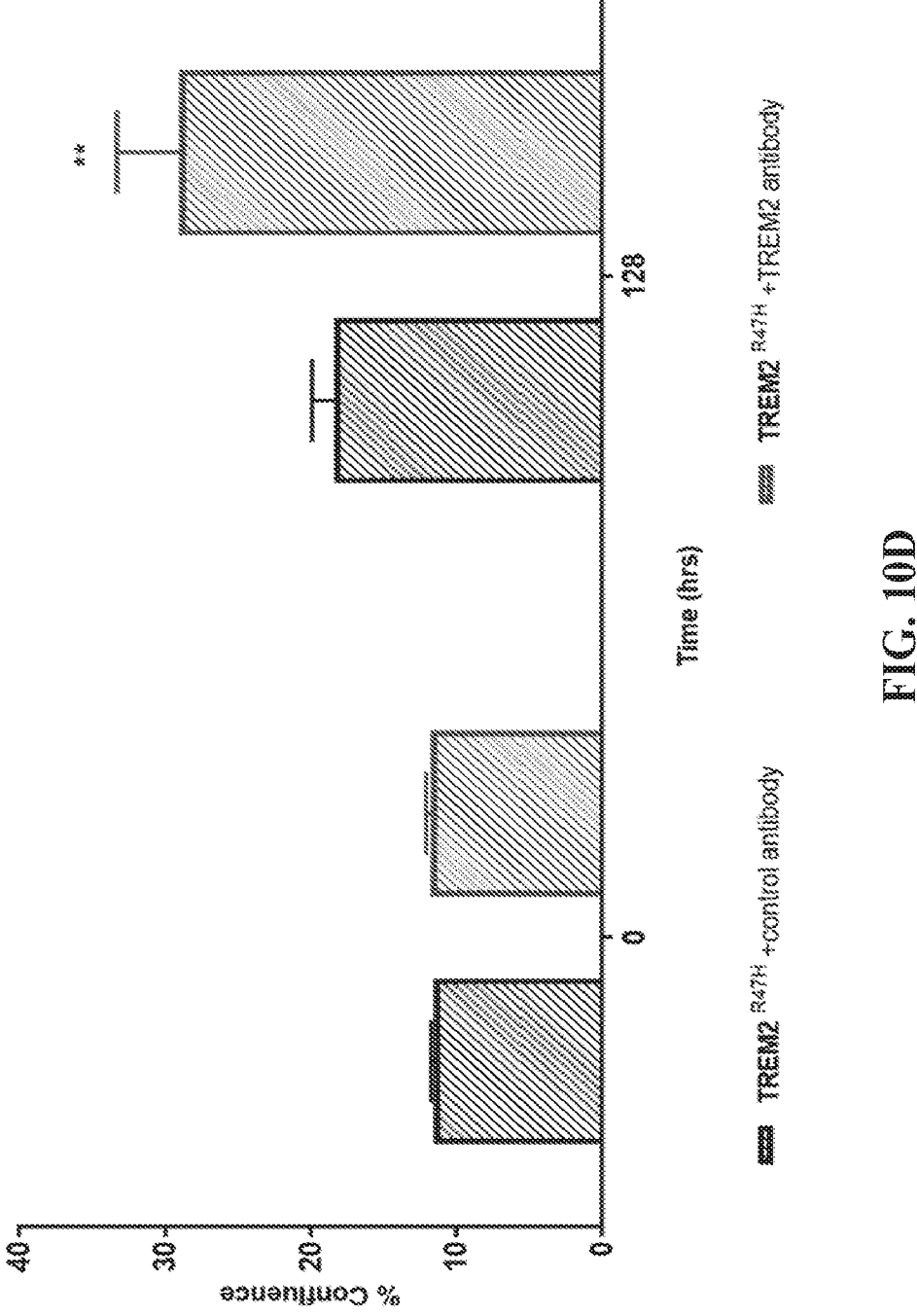

FIG. 10D is a bar graph depicting percent cell confluence at particular times in culture for TREM2$^{R47H}$ adult mouse microglia treated with an isotype control antibody or an anti-TREM2 agonist antibody. An increase in survival of TREM2$^{R47H}$ microglia is observed with anti-TREM2 agonist antibody treatment.

Figure 10E:
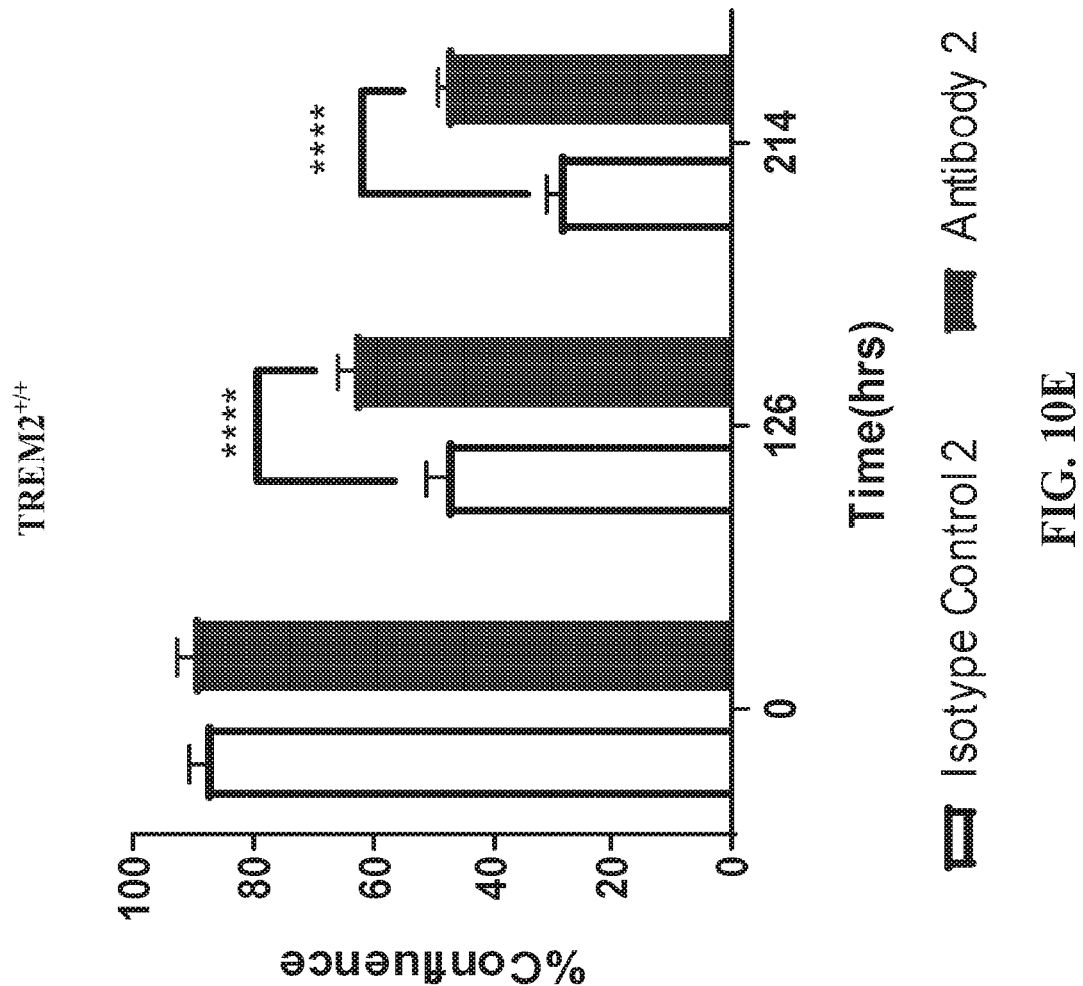

FIG. 10E is a graph depicting percent cell confluence over time for BMDMs harvested from aged (18-month old) wildtype (TREM2$^{+/+}$) mice (n=3 animals) treated with an isotype control antibody or an anti-TREM2 agonist antibody of the present invention (henceforth referred to as "Antibody 2") as measured by a real-time cell confluence assay. Data are plotted as mean+/−s.d. and are from a single representative experiment. ****p<0.0001, 2-way ANOVA with Sidak's correction for multiple comparisons.

Figure 10F:
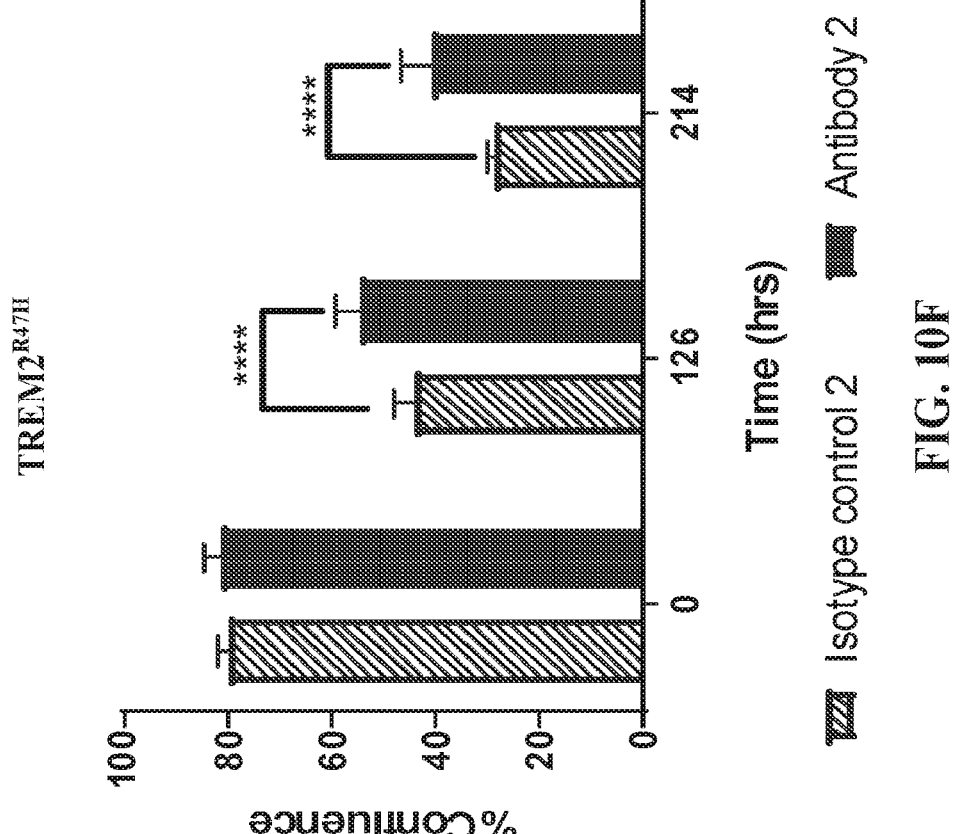

FIG. 10F is a graph depicting percent cell confluence over time for BMDMs harvested from aged (18-month old) TREM2$^{R47H}$ mice (n=3 animals, exception—wild-type age-matched littermate controls for day 6 samples in the knockout experiment) treated with an isotype control antibody or an anti-TREM2 agonist antibody (Antibody 2) as measured by a real-time cell confluence assay. Data are plotted as mean+/−s.d. and are from a single representative experiment. ****p<0.0001, 2-way ANOVA with Sidak's correction for multiple comparisons. An increase in survival of wildtype and TREM2$^{R47H}$ macrophages is observed with anti-TREM2 agonist antibody treatment.

Figures 11A, 11B:
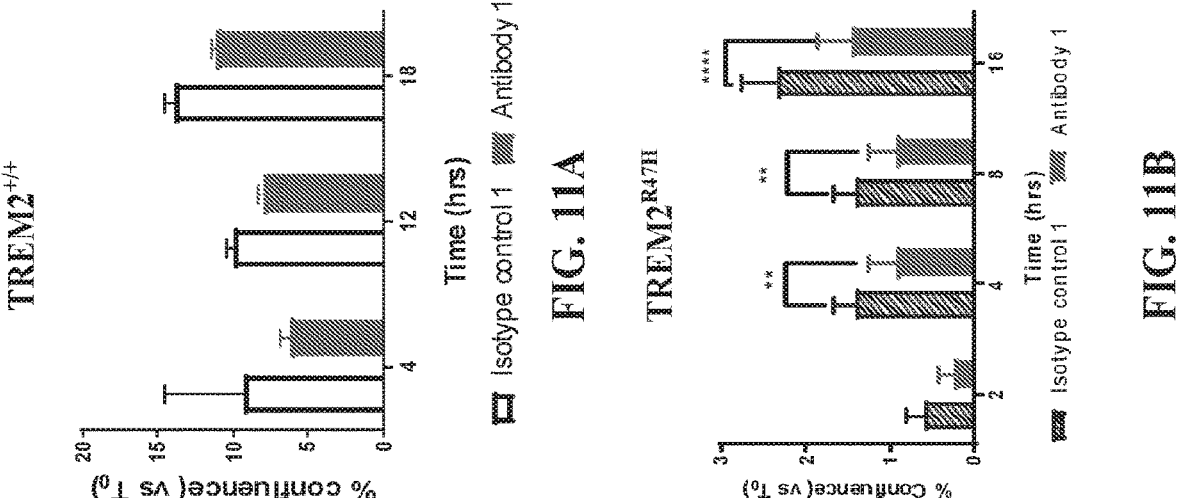

FIG. 11A is a graph depicting percent cell confluence over time in a culture compartment in a migration assay for wild-type (TREM2$^{+/+}$) BMDMs treated with an isotype control antibody or an anti-TREM2 agonist antibody (Antibody 1) as measured by a real-time cell confluence assay. The anti-TREM2 agonist antibody had minimal effects on migration of the wild-type BMDMs in this assay.

FIG. 11B is a graph depicting percent cell confluence over time in a culture compartment in a migration assay for TREM2$^{R47H}$ BMDMs treated with an isotype control antibody or an anti-TREM2 agonist antibody (Antibody 1) as measured by a real-time cell confluence assay. The anti-TREM2 agonist antibody resulted in a small but statistically significant reduction of migration of the TREM2$^{R47H}$ BMDMs in this assay.

Figure 11C:
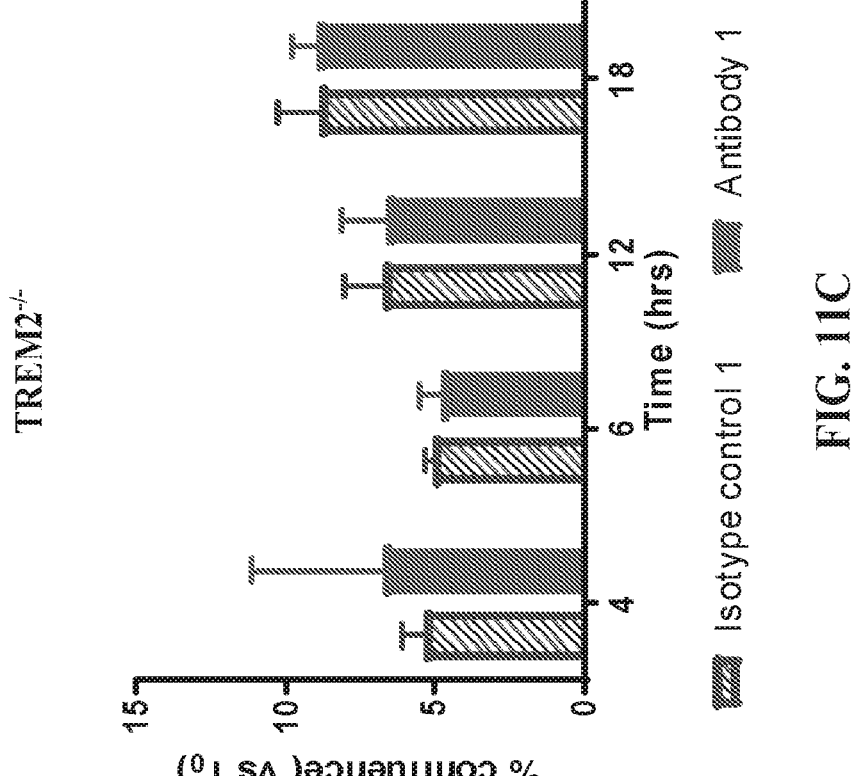

FIG. 11C is a graph depicting percent cell confluence over time in a culture compartment in a migration assay for TREM2$^{-/-}$ BMDMs treated with an isotype control antibody or an anti-TREM2 agonist antibody (Antibody 1) as measured by a real-time cell confluence assay. The anti-TREM2 agonist antibody has no effect on the migration of the TREM2$^{-/-}$ BMDMs in this assay.

FIGS. 11D-11E are graphs depicting percent cell confluence over time in a culture compartment in a migration assay for wildtype (TREM2$^{+/+}$) and TREM2$^{R47H}$ BMDMs, respectively, treated with an isotype control antibody or an anti-TREM2 agonist antibody (Antibody 2) as measured by a real-time cell confluence assay. The anti-TREM2 agonist antibody treatment has no effect on the migration of the wildtype and TREM2$^{R47H}$ BMDMs in this assay.

Figure 12A:
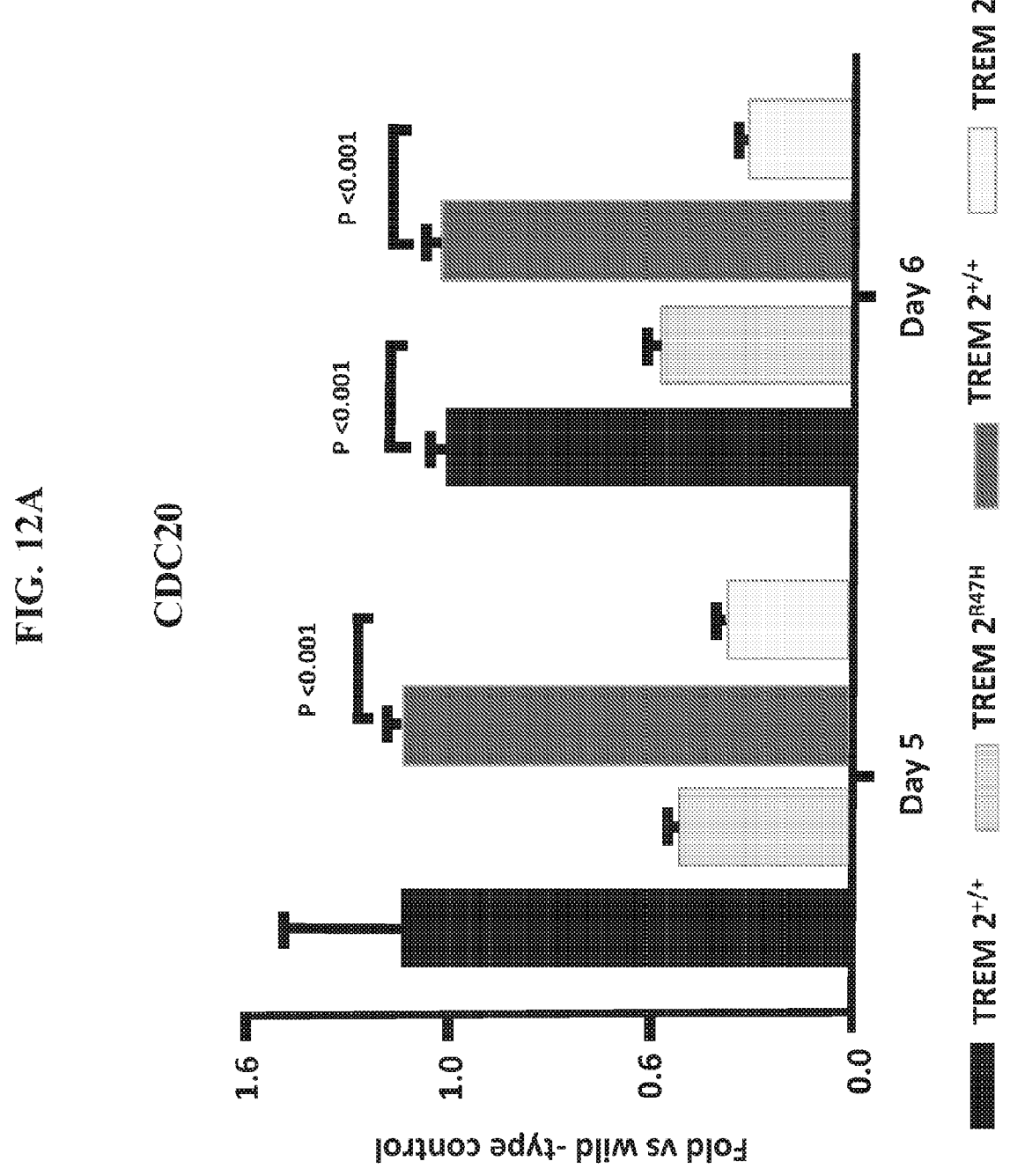

FIG. 12A shows the differential regulation of CDC20 transcripts as measured by qPCR in wild-type (TREM2$^{+/+}$), TREM2$^{R47H}$, and TREM2$^{-/-}$ macrophages at day 5 and day 6.

Figure 12B:
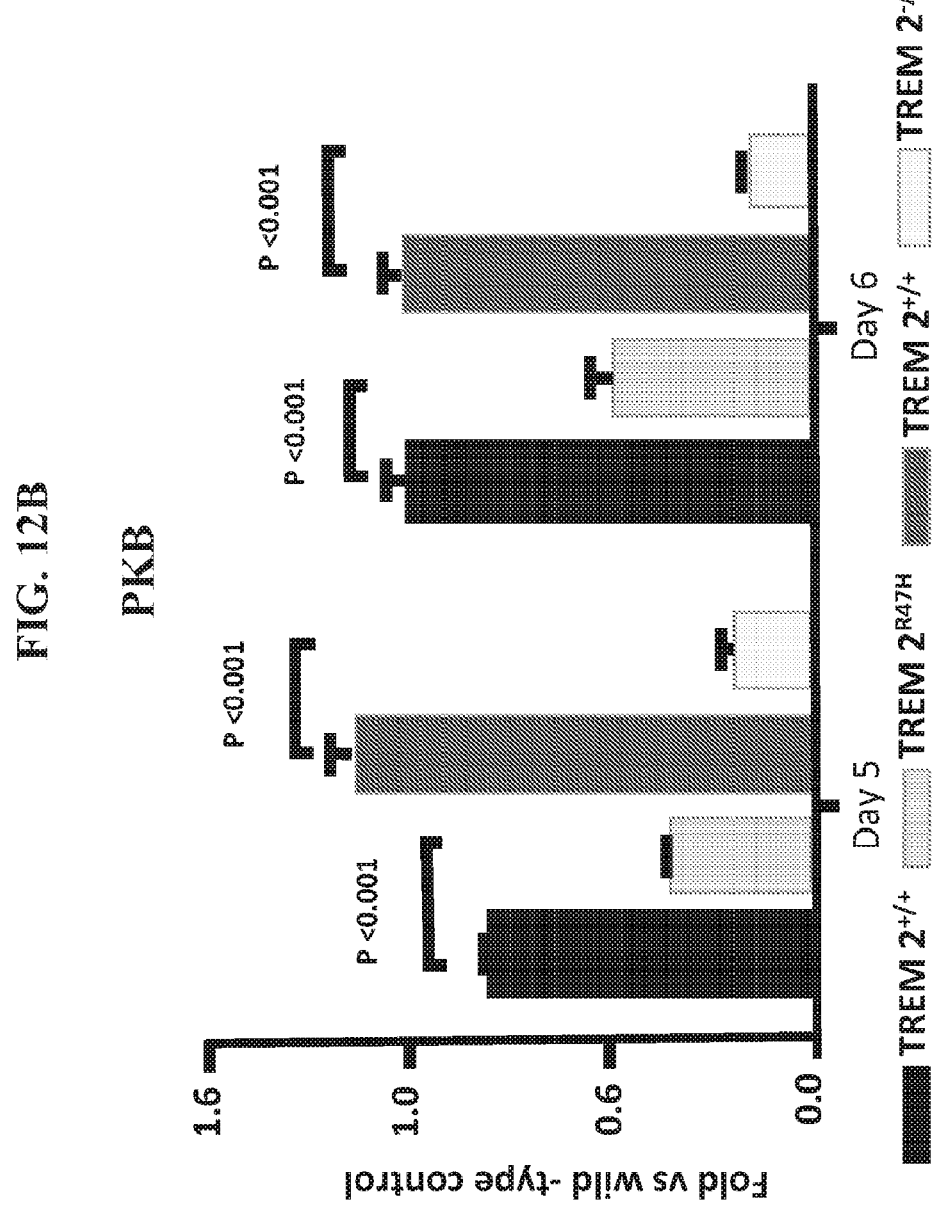

FIG. 12B shows the differential regulation of PKB transcripts as measured by qPCR in wild-type (TREM2$^{+/+}$), TREM2$^{R47H}$, and TREM2$^{-/-}$ macrophages at day 5 and day 6.

Figure 12C:
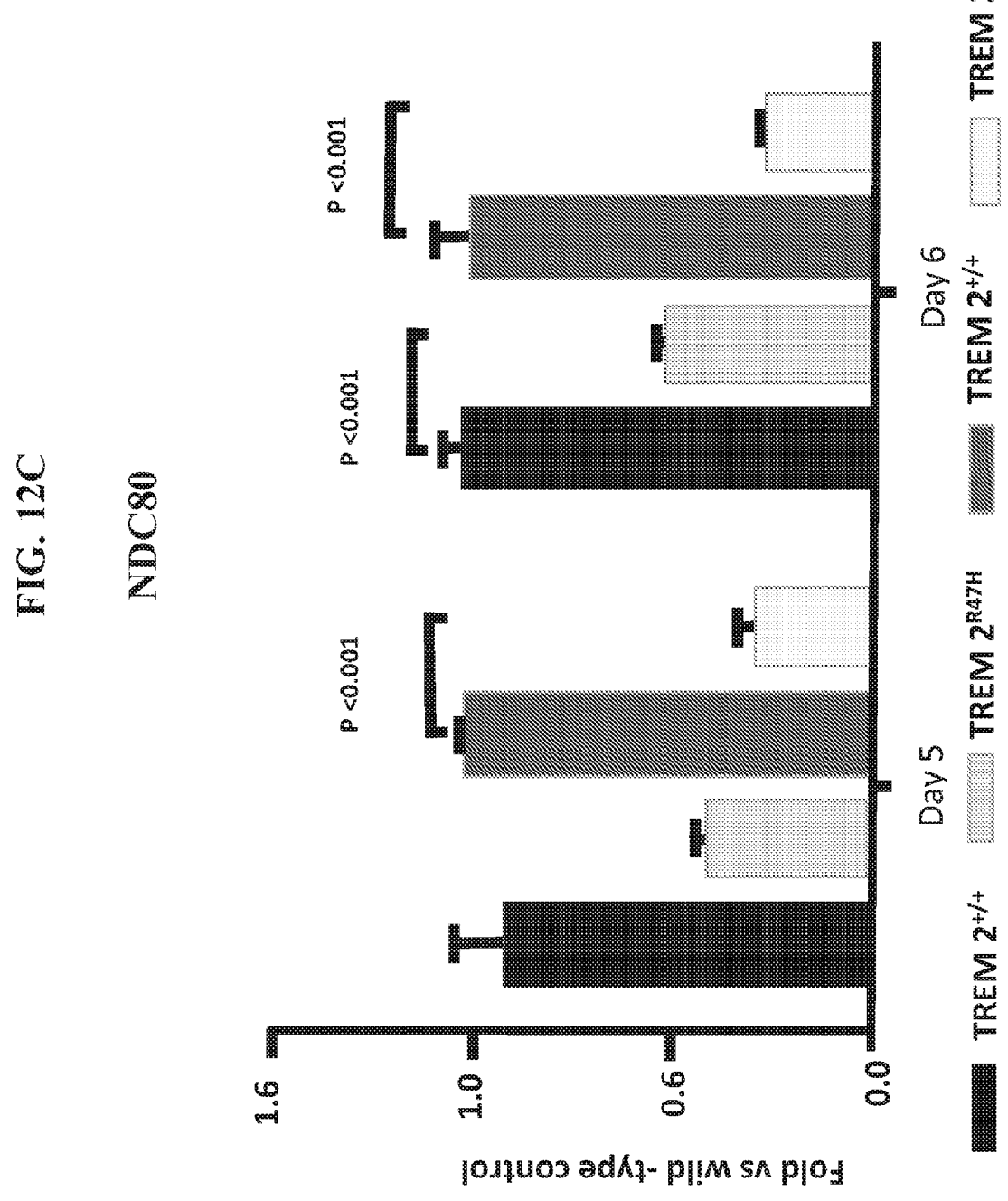

FIG. 12C shows the differential regulation of NDC80 transcripts as measured by qPCR in wild-type (TREM2$^{+/+}$), TREM2$^{R47H}$, and TREM2$^{-/-}$ macrophages at day 5 and day 6.

Figure 12D:
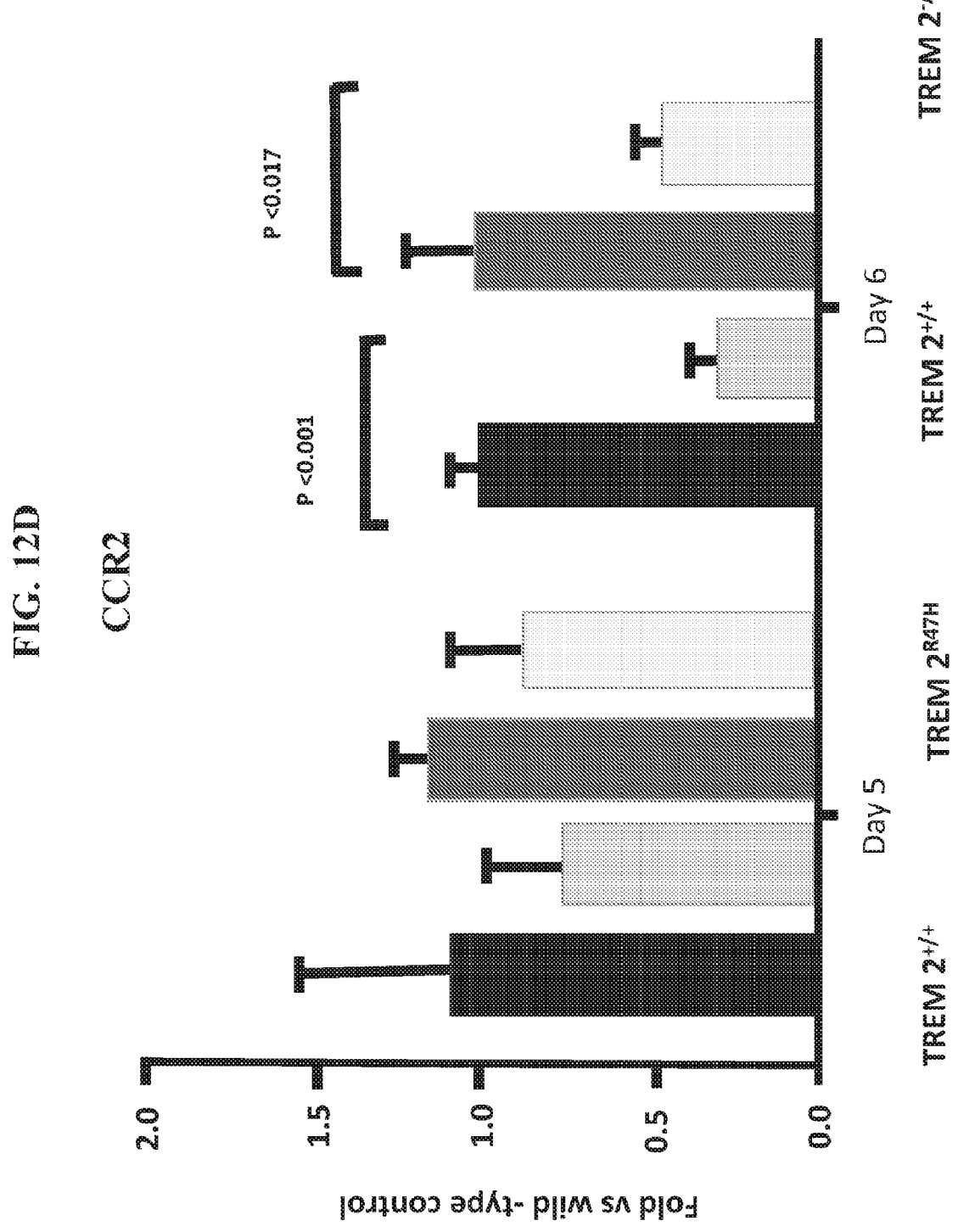

FIG. 12D shows the differential regulation of CCR2 transcripts as measured by qPCR in wild-type (TREM2$^{+/+}$), TREM2$^{R47H}$, and TREM2$^{-/-}$ macrophages at day 5 and day 6.

Figure 13A:
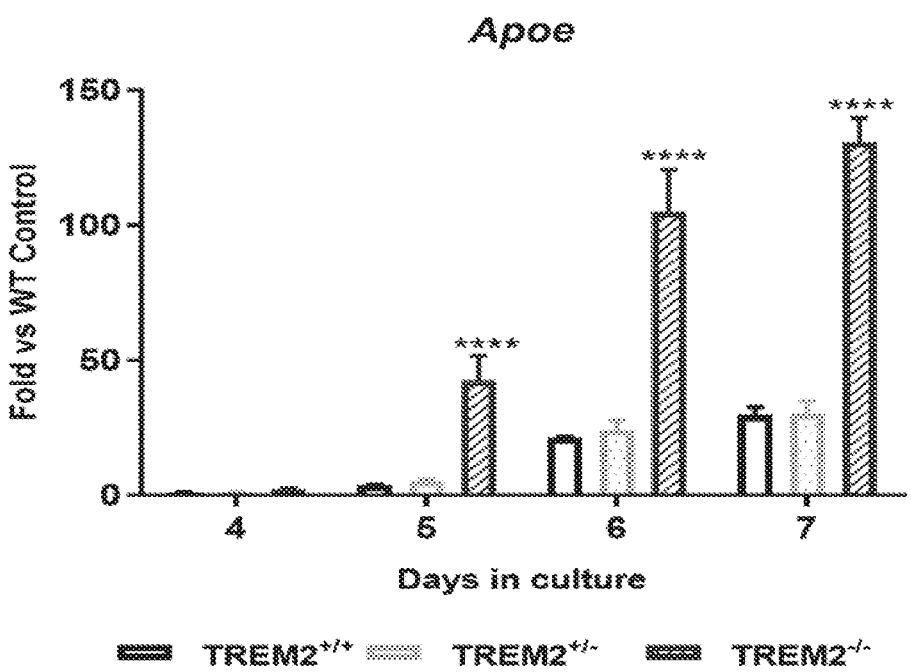

FIG. 13A depicts the differential regulation of ApoE transcripts as measured by qPCR in wild-type (TREM2$^{+/+}$), heterozygous (TREM2$^{+/-}$), and knockout (TREM2$^{-/-}$) macrophages at different time points in culture. All gene expression levels are normalized to wild-type control macrophages at Day 4 of culture.

Figure 13B:
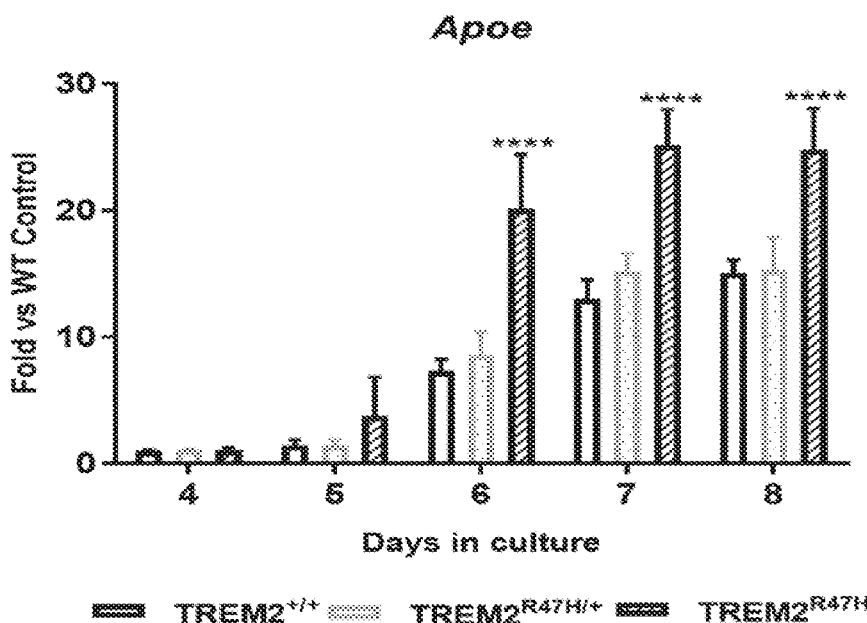

FIG. 13B depicts the differential regulation of ApoE transcripts as measured by qPCR in wild-type (TREM2$^{+/+}$), R47H heterozygous (TREM2$^{R47H/+}$), and R47H homozygous (TREM2$^{R47H}$) macrophages at different time points in culture. All gene expression levels are normalized to wild-type control macrophages at Day 4 of culture.

Figure 13C:
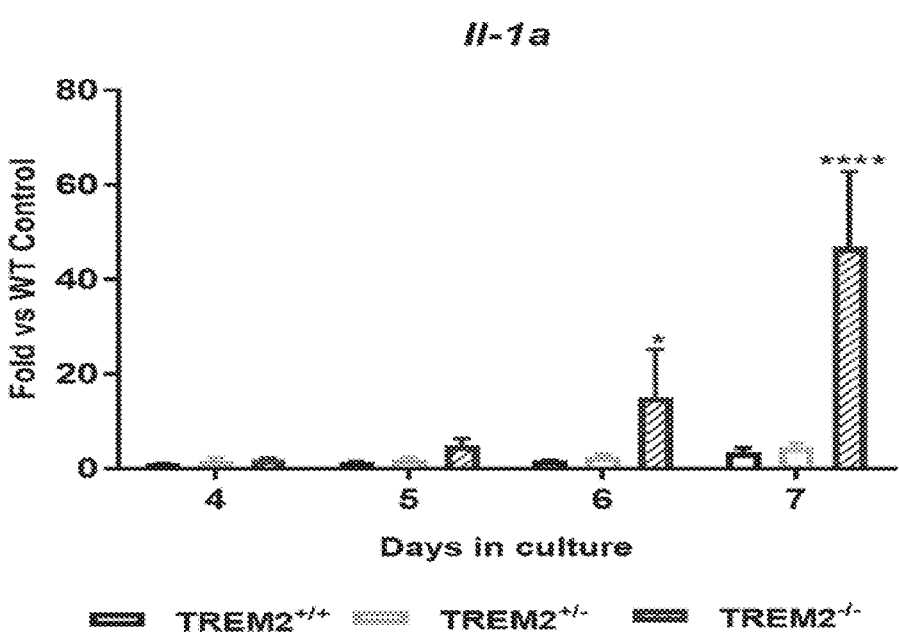

FIG. 13C depicts the differential regulation of IL-1a transcripts as measured by qPCR in wild-type (TREM2$^{+/+}$), heterozygous (TREM2$^{+/-}$), and knockout (TREM2$^{-/-}$) macrophages at different time points in culture. All gene expression levels are normalized to wild-type control macrophages at Day 4 of culture.

Figure 13D:
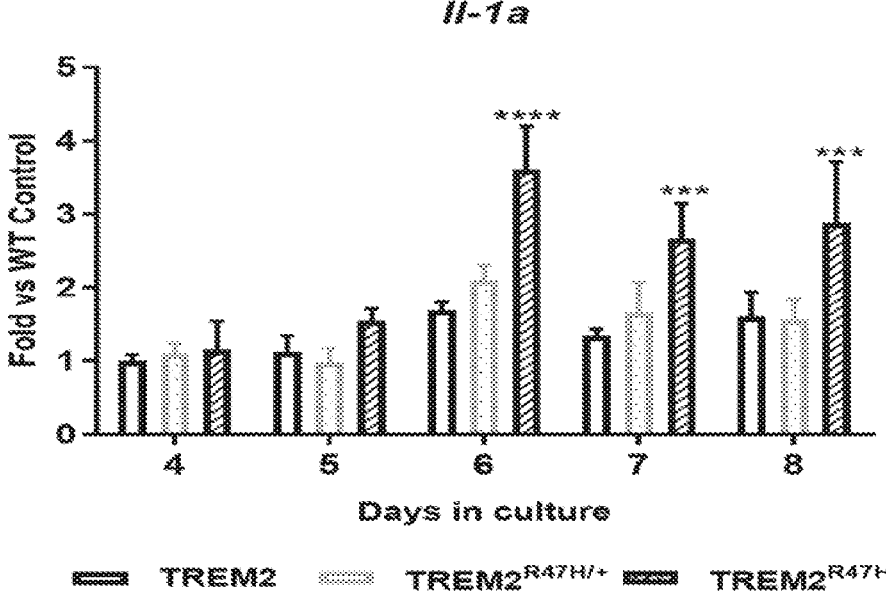

FIG. 13D depicts the differential regulation of IL-1a transcripts as measured by qPCR in wild-type (TREM2$^{+/+}$), R47H heterozygous (TREM2$^{R47H/+}$), and R47H homozygous (TREM2$^{R47H}$) macrophages at different time points in culture. All gene expression levels are normalized to wild-type control macrophages at Day 4 of culture.

Figure 13E:
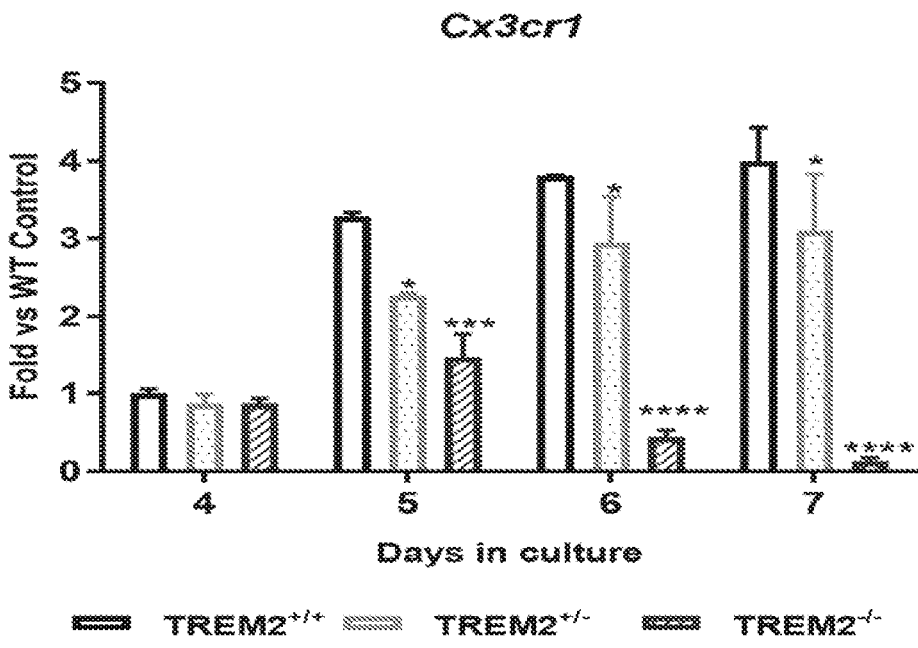

FIG. 13E depicts the differential regulation of CX3CR1 transcripts as measured by qPCR in wild-type (TREM2$^{+/+}$), heterozygous (TREM2$^{+/−}$), and knockout (TREM2$^{−/−}$) macrophages at different time points in culture. All gene expression levels are normalized to wild-type control macrophages at Day 4 of culture.

Figure 13F:
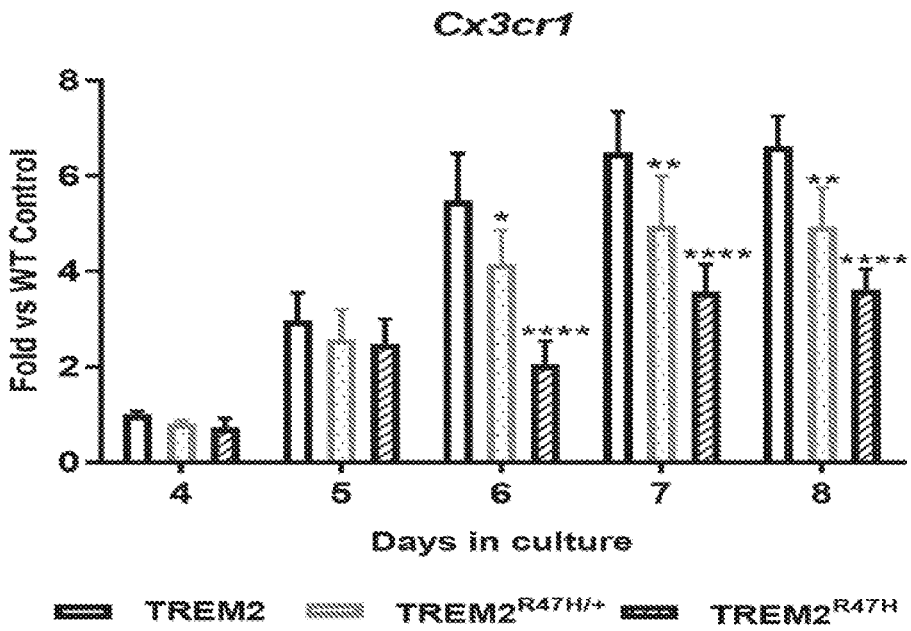

FIG. 13F depicts the differential regulation of CX3CR1 transcripts as measured by qPCR in wild-type (TREM2$^{+/+}$), R47H heterozygous (TREM2$^{R47H/+}$), and R47H homozygous (TREM2$^{R47H}$) macrophages at different time points in culture. All gene expression levels are normalized to wild-type control macrophages at Day 4 of culture.

Figure 13G:
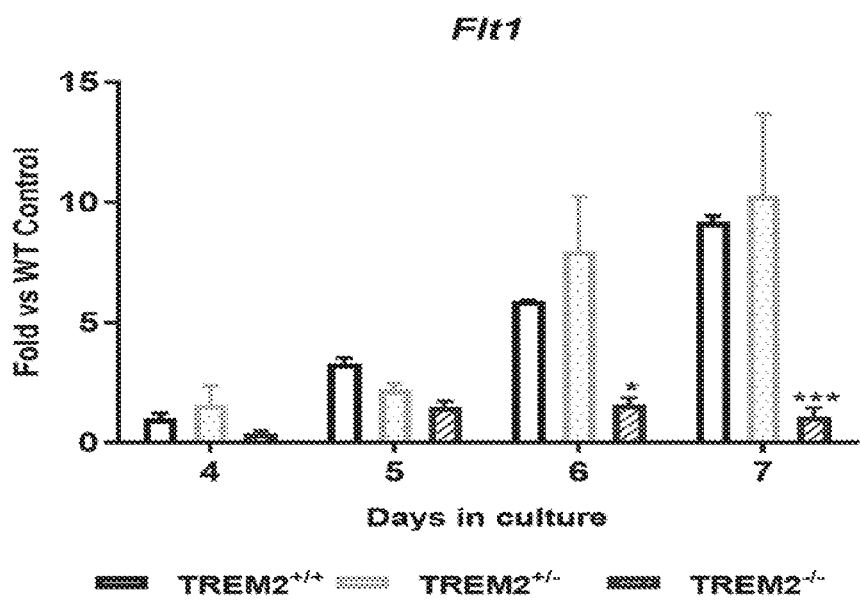

FIG. 13G depicts the differential regulation of FLT1 transcripts as measured by qPCR in wild-type (TREM2$^{+/+}$), heterozygous (TREM2$^{+/−}$), and knockout (TREM2$^{−/−}$) macrophages at different time points in culture. All gene expression levels are normalized to wild-type control macrophages at Day 4 of culture.

Figure 13H:
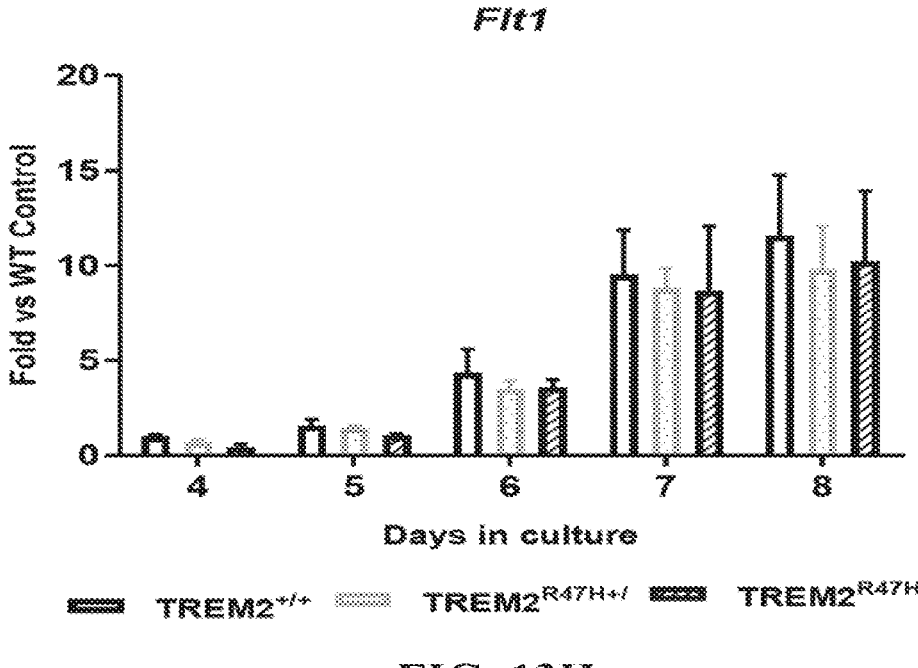

FIG. 13H depicts the differential regulation of FLT1 transcripts as measured by qPCR in wild-type (TREM2$^{+/+}$), R47H heterozygous (TREM2$^{R47H/+}$), and R47H homozygous (TREM2$^{R47H}$) macrophages at different time points in culture. All gene expression levels are normalized to wild-type control macrophages at Day 4 of culture.

Figure 13I:
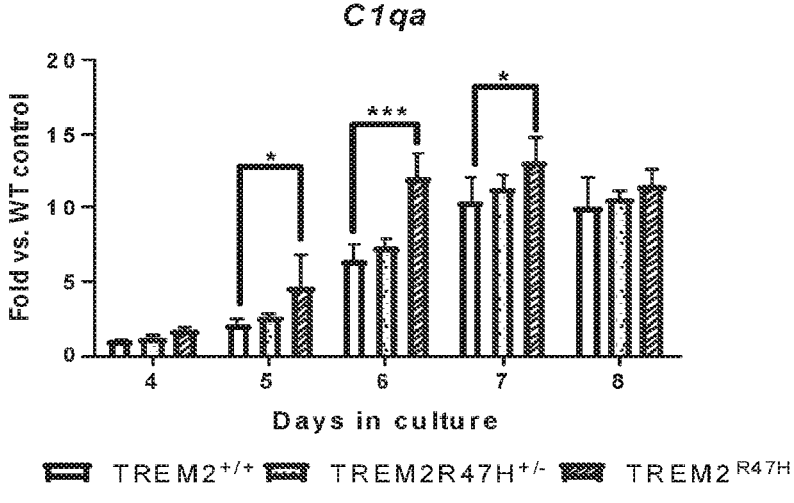
Figure 13J:
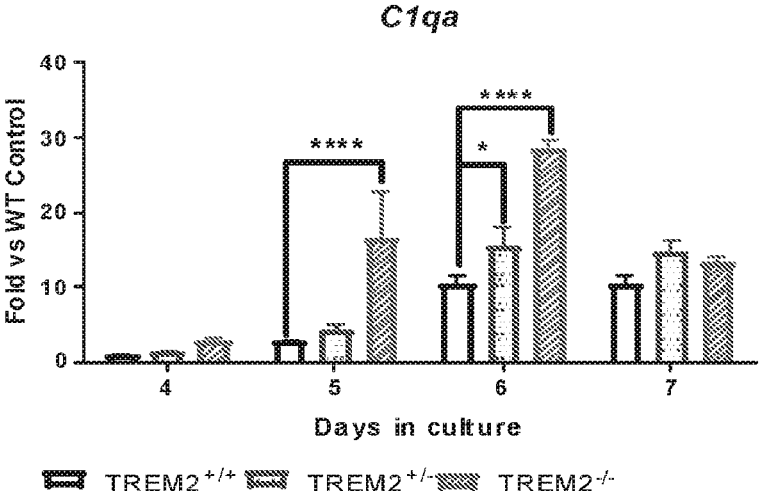

FIGS. 13I-13J depict the differential regulation of C1qa transcripts as measured by qPCR in wild-type (TREM2$^{+/+}$), R47H heterozygous (TREM2R47H$^{+/−}$), and R47H homozygous (TREM2$^{R47H}$) macrophages at different time points in culture. All gene expression levels are normalized to wild-type control macrophages at Day 4 of culture.

Figure 13K:
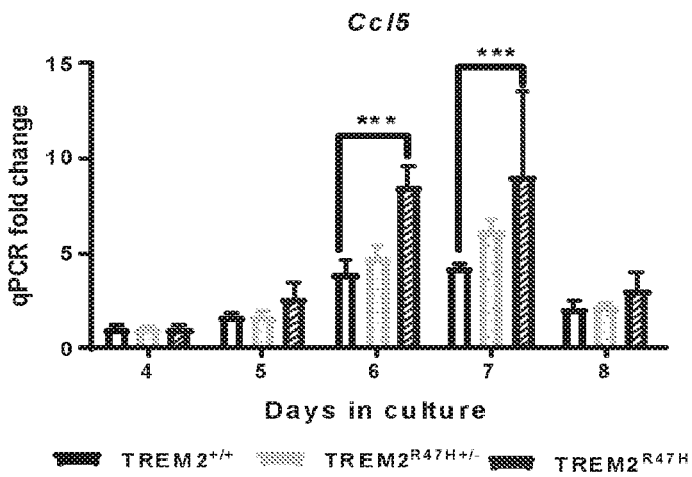
Figure 13L:
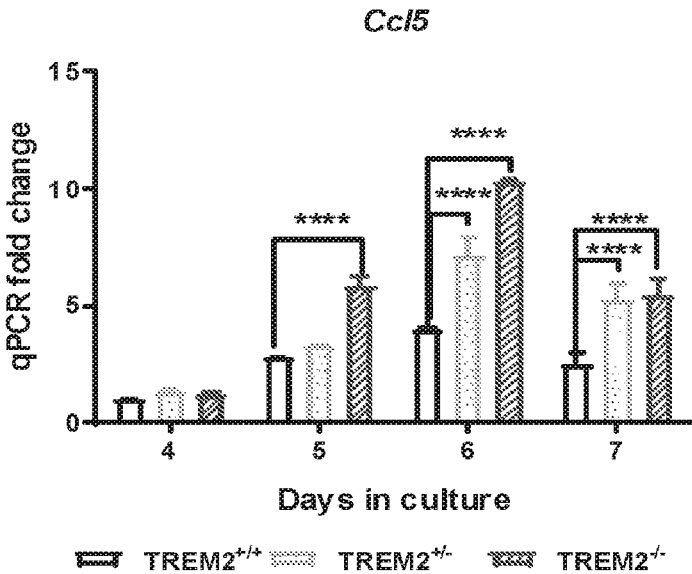

FIGS. 13K-13L depict the differential regulation of Ccl5 transcripts as measured by qPCR in wild-type (TREM2$^{+/+}$), R47H heterozygous (TREM2R47H$^{+/−}$ and TREM2$^{+/−}$), and R47H homozygous (TREM2$^{R47H}$ and TREM2$^{−/−}$) macrophages at different time points in culture. All gene expression levels are normalized to wild-type control macrophages at Day 4 of culture.

Figure 13M:
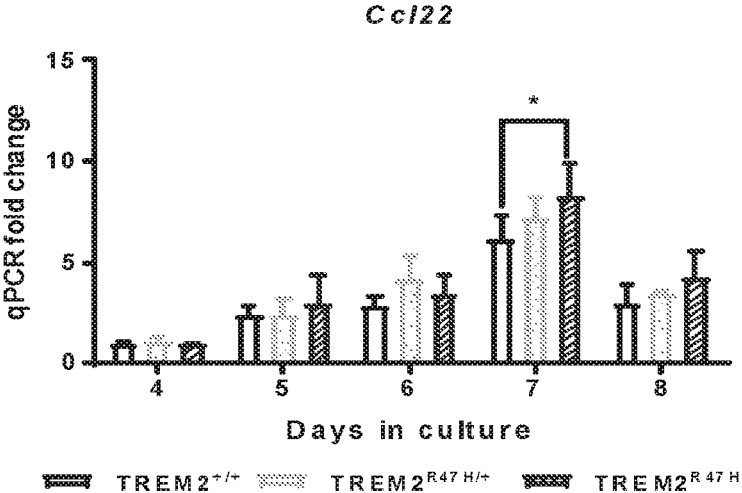
Figure 13N:
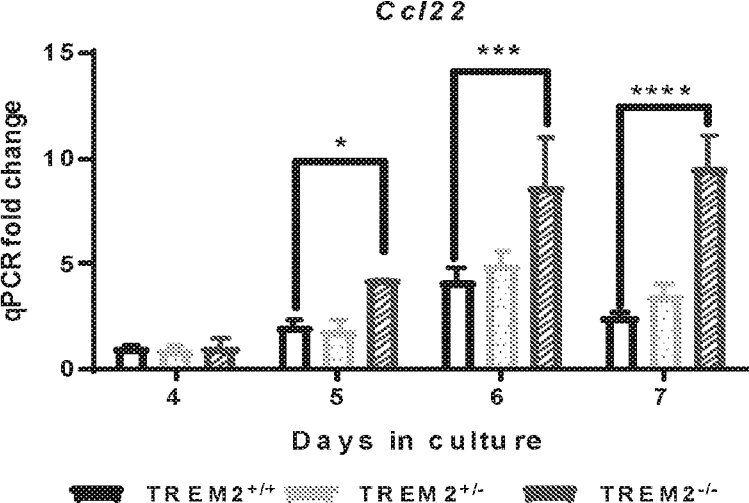

FIGS. 13M-13N depict the differential regulation of Ccl22 transcripts as measured by qPCR in wild-type (TREM2$^{+/+}$), R47H heterozygous (TREM2R47H$^{+/−}$ and TREM2$^{+/−}$), and R47H homozygous (TREM2$^{R47H}$ and TREM2$^{−/−}$) macrophages at different time points in culture. All gene expression levels are normalized to wild-type control macrophages at Day 4 of culture.

Figure 13O:
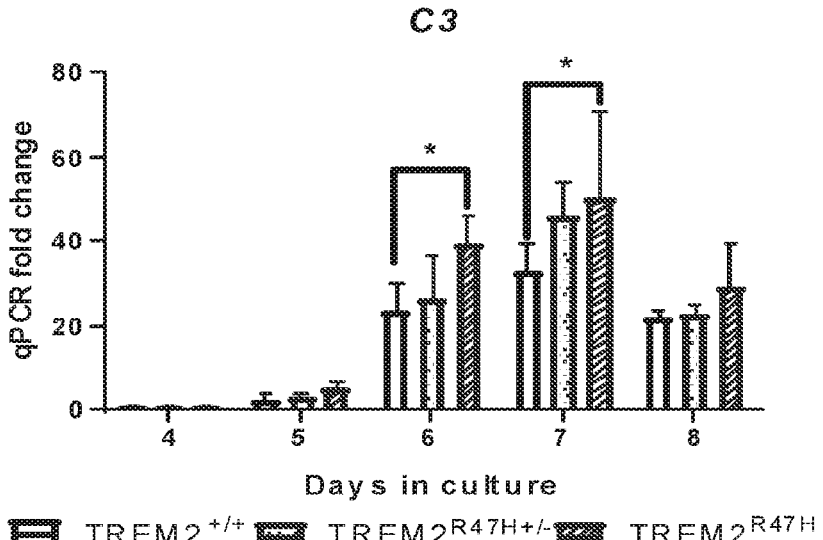
Figure 13P:
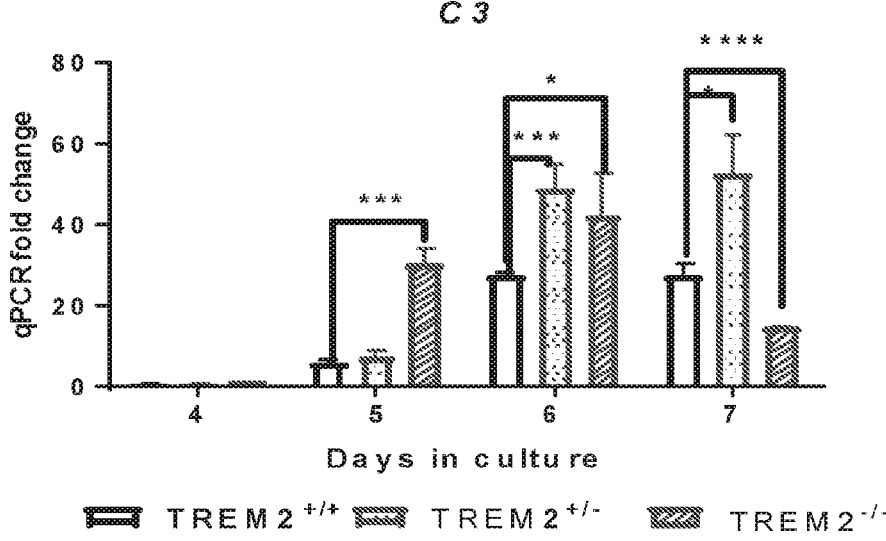

FIGS. 13O-13P depict the differential regulation of C3 transcripts as measured by qPCR in wild-type (TREM2$^{+/+}$), R47H heterozygous (TREM2R47H$^{+/−}$ and TREM2$^{+/−}$), and R47H homozygous (TREM2$^{R47H}$ and TREM2$^{−/−}$) macrophages at different time points in culture. All gene expression levels are normalized to wild-type control macrophages at Day 4 of culture.

Figure 14A:
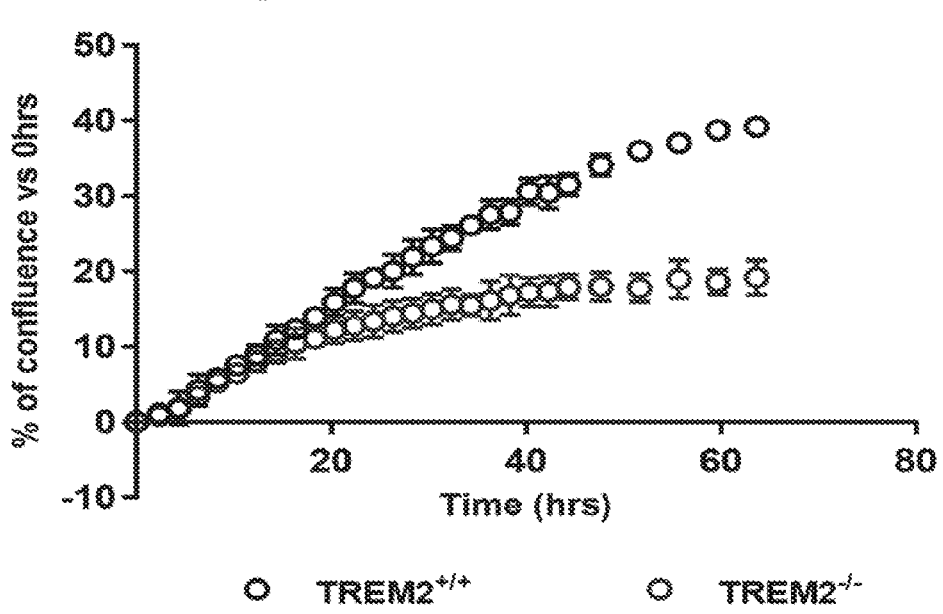

FIG. 14A is a graph depicting percent cell confluence over time in a culture compartment in a migration assay for wild-type (TREM2$^{+/+}$) and knockout (TREM2$^{−/−}$) BMDMs as measured by a real-time cell confluence assay. The TREM2 knockout macrophages exhibit a migration defect as compared to wild-type macrophages in this in vitro assay.

Figure 14B:
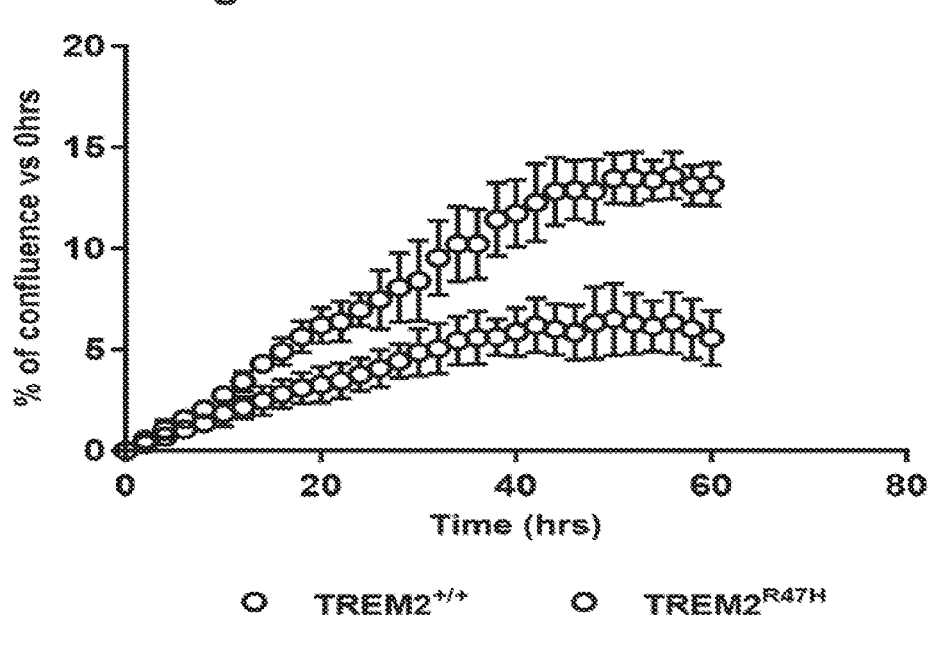

FIG. 14B is a graph depicting percent cell confluence over time in a culture compartment in a migration assay for wild-type (TREM2$^{+/+}$) and TREM2$^{R47H}$ BMDMs as measured by a real-time cell confluence assay. The TREM2$^{R47H}$ macrophages exhibit a migration defect as compared to wild-type macrophages in this in vitro assay.

Figure 15A:
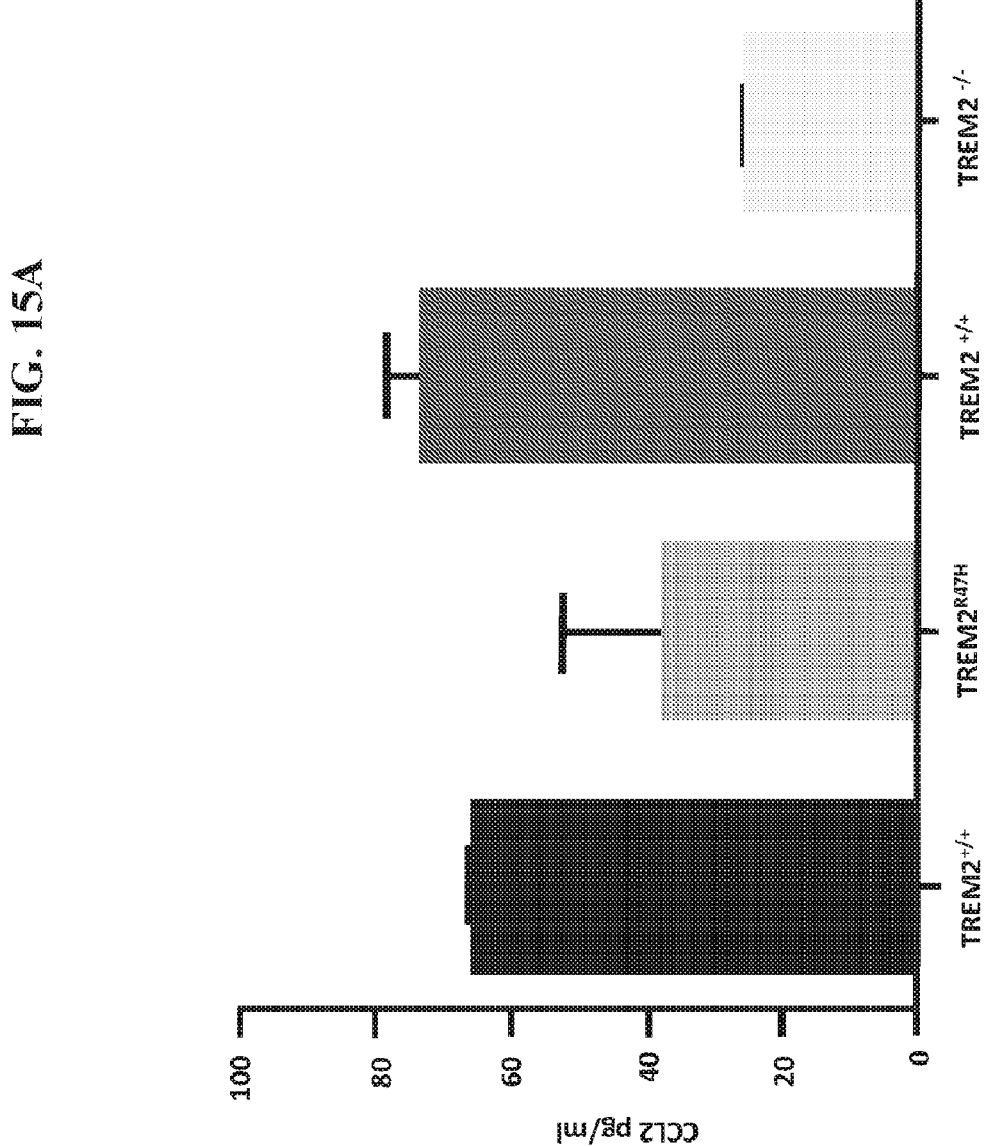

FIG. 15A shows a reduction in secreted CCL2 protein from TREM2$^{R47H}$ and TREM2$^{−/−}$ macrophages as compared with wild-type (TREM2$^{+/+}$) macrophages as measured by ELISA.

Figure 15B:
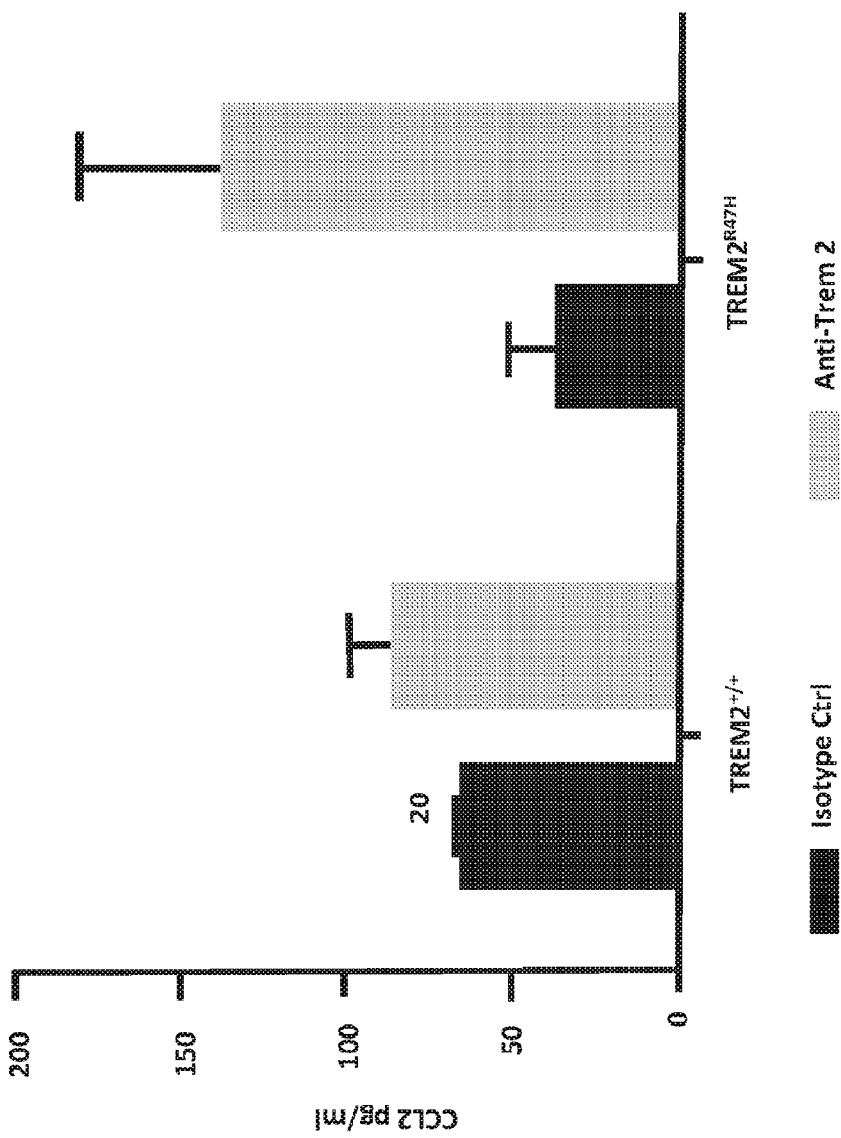

FIG. 15B depicts levels of secreted CCL2 protein as measured by ELISA from TREM2$^{R47H}$ and wild-type TREM2$^{+/+}$ macrophages treated with an anti-TREM2 agonist antibody or isotype control. Anti-TREM2 agonist antibody treatment restores levels of secreted CCL2 protein from TREM2$^{R47H}$ macrophages.

Figure 16A:
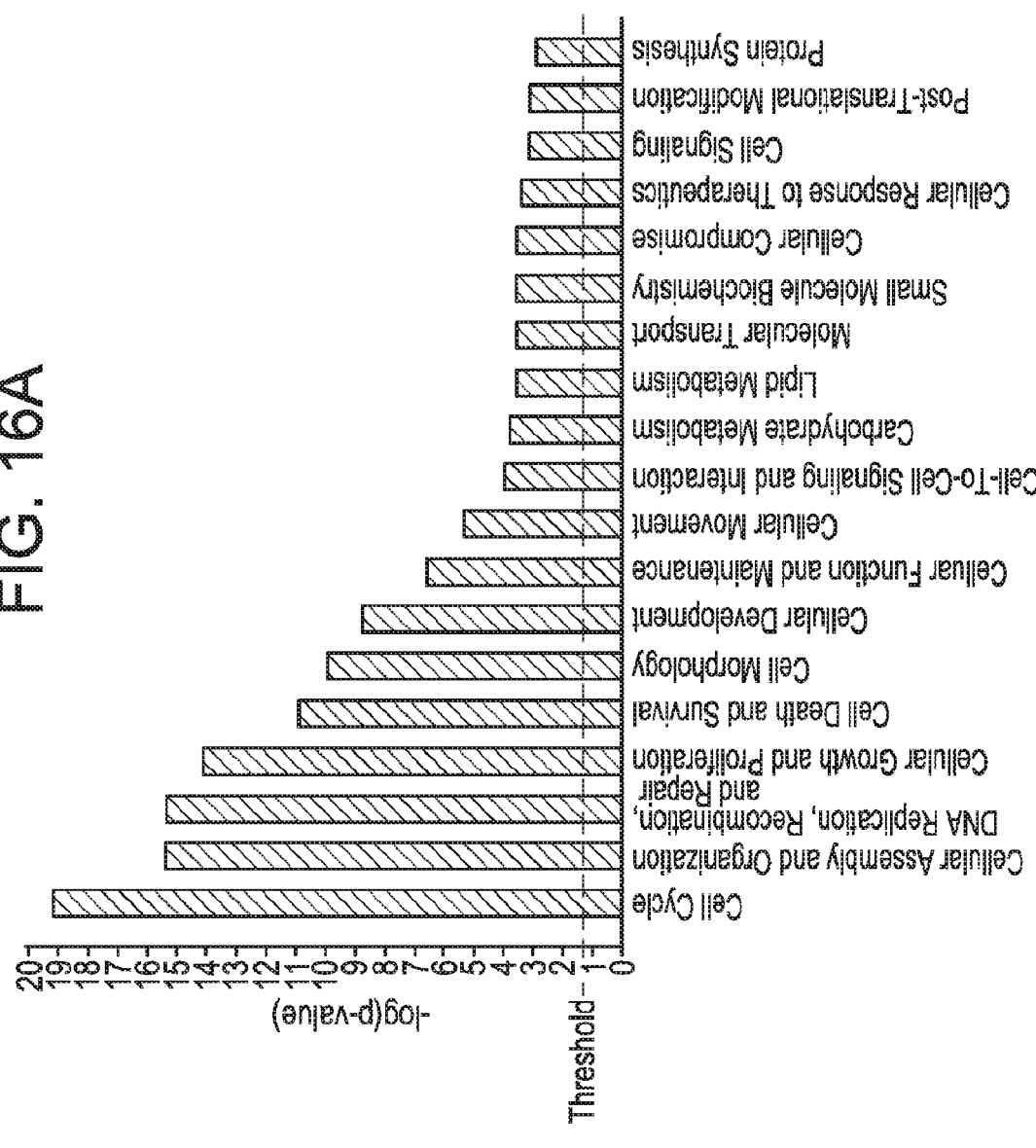

FIG. 16A shows the results of the pathway analysis of genes regulated by anti-TREM2 agonist antibody treatment in TREM2$^{R47H}$ macrophages. The modulated genes include those involved in regulation of myeloid cell migration, proliferation, cell cycle and survival.

Figure 16B:
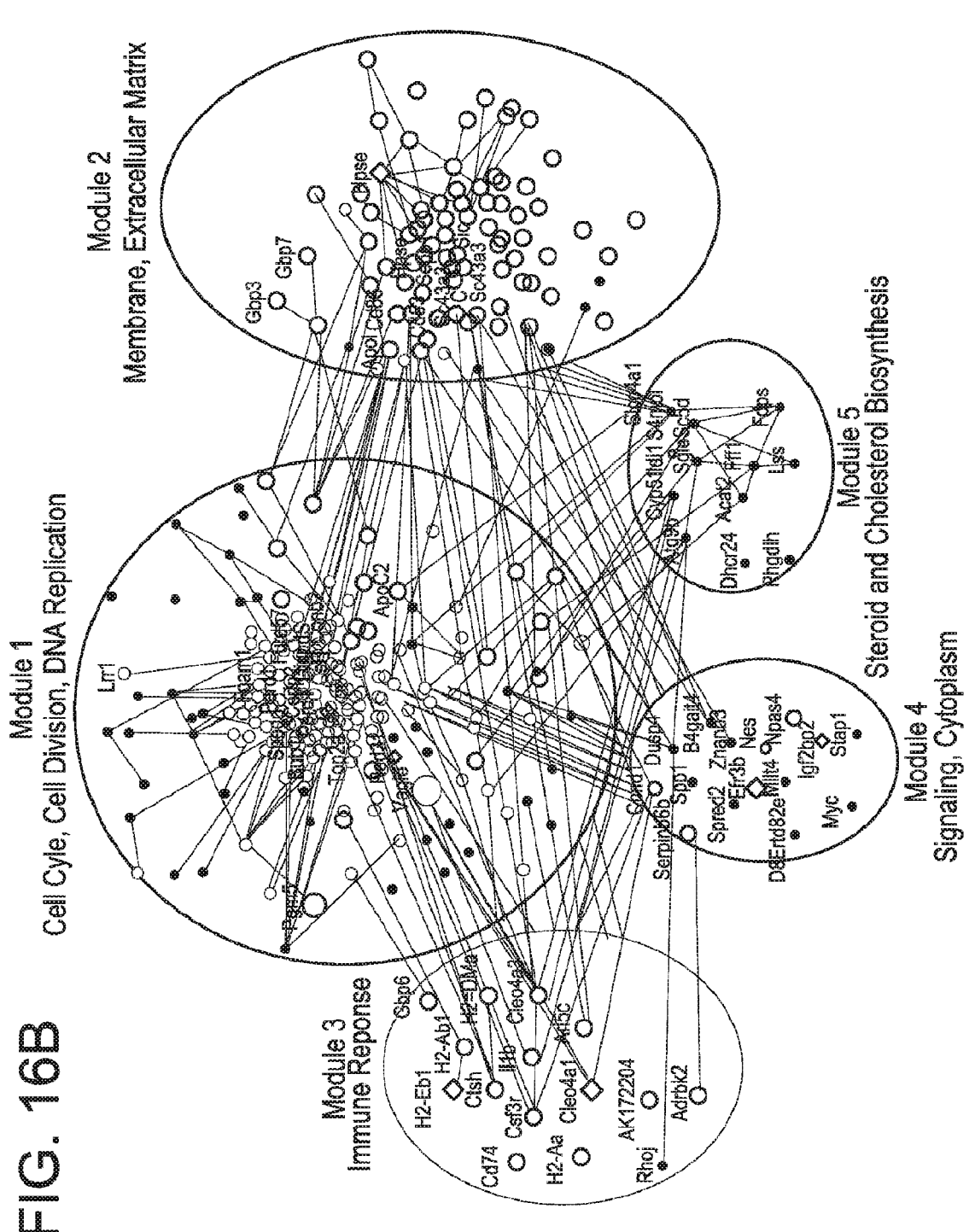

FIG. 16B shows the RNA-Seq analysis comparing wild-type (TREM2$^{+/+}$), knockout (TREM2$^{−/−}$) and TREM2$^{R47H}$ macrophages at day 7 under limiting conditions of CSF-1. Pathway analyses (WGCNA) identified 5 modules/gene networks that are differentially regulated in the knockout and TREM2$^{R47H}$ macrophages compared to wild-type. The results indicate a role for TREM2 in cell cycle/proliferation and survival, immune response and migration and lipid and cholesterol homeostasis.

FIG. 16C shows the differential regulation of UBE2C, MELK and MMP14 transcripts as measured by qPCR in wild-type (TREM2$^{+/+}$) and TREM2$^{R47H}$ macrophages treated with an anti-TREM2 agonist antibody (Antibody 1) or isotype control. The data show that expression of the expression of the MMP14 enzyme is unregulated while the expression of the UBE2C and MELK enzymes is down-regulated in the R47H macrophages, but the changes can be restored with treatment with the anti-TREM2 agonist antibody.

Figure 17:
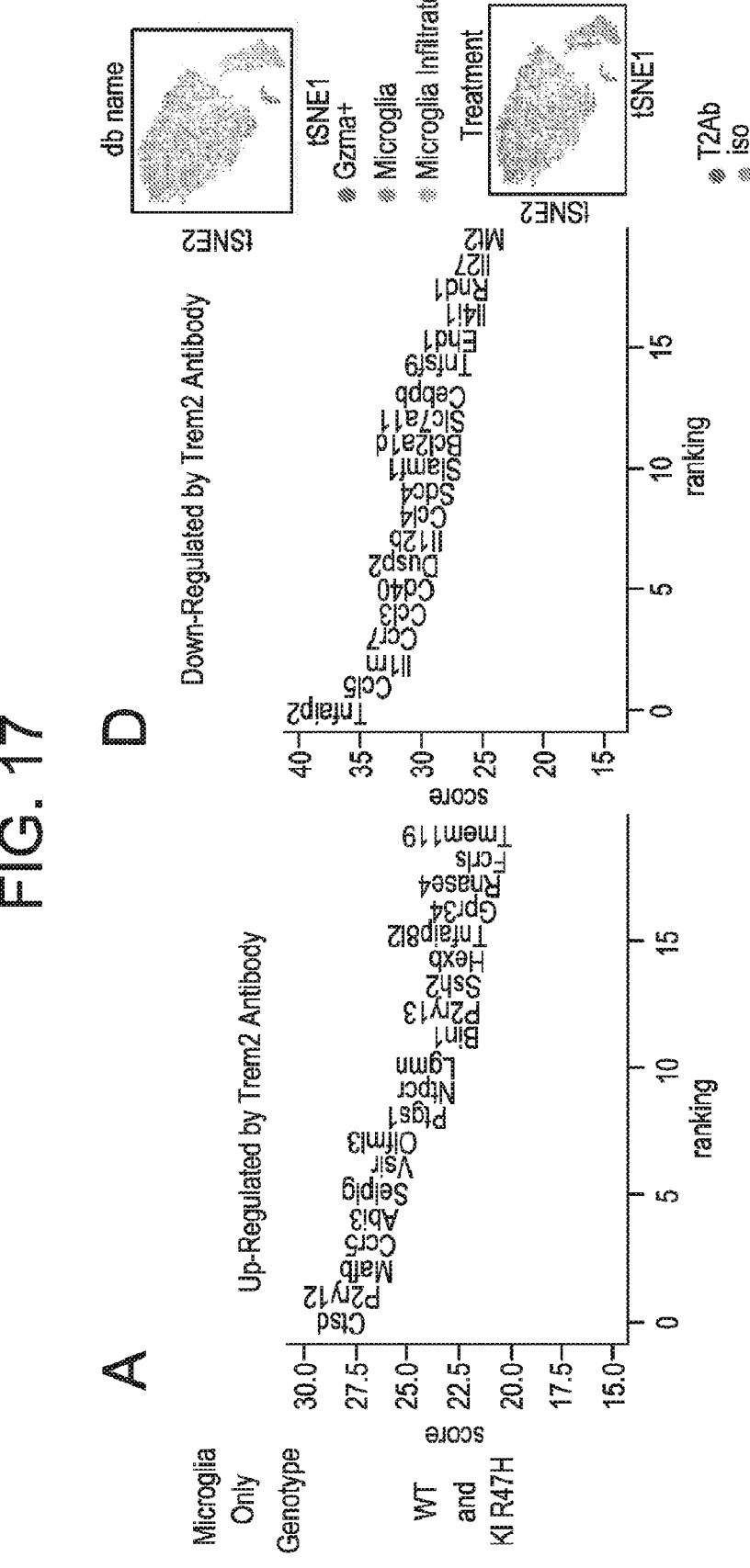
Figure 17:
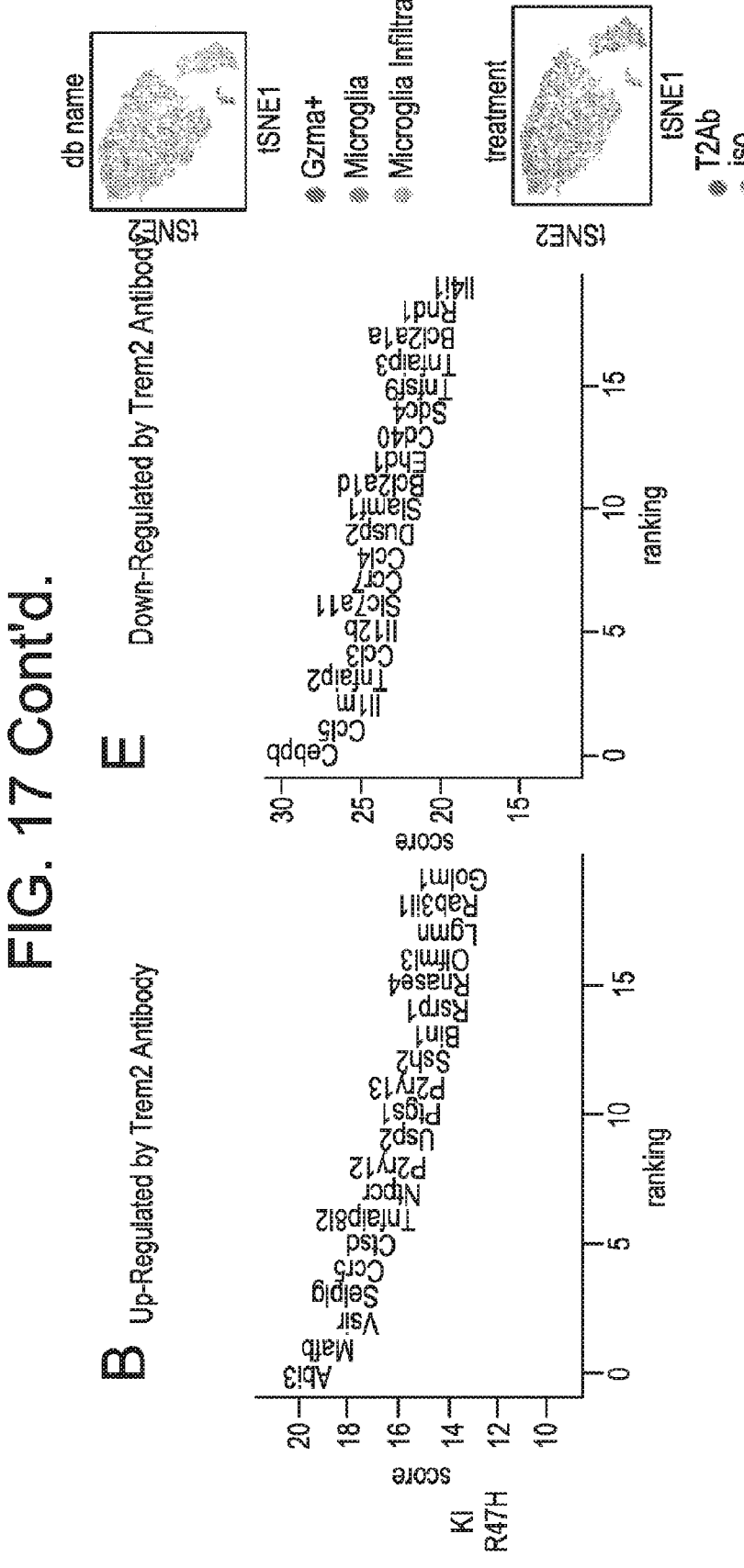
Figure 17:
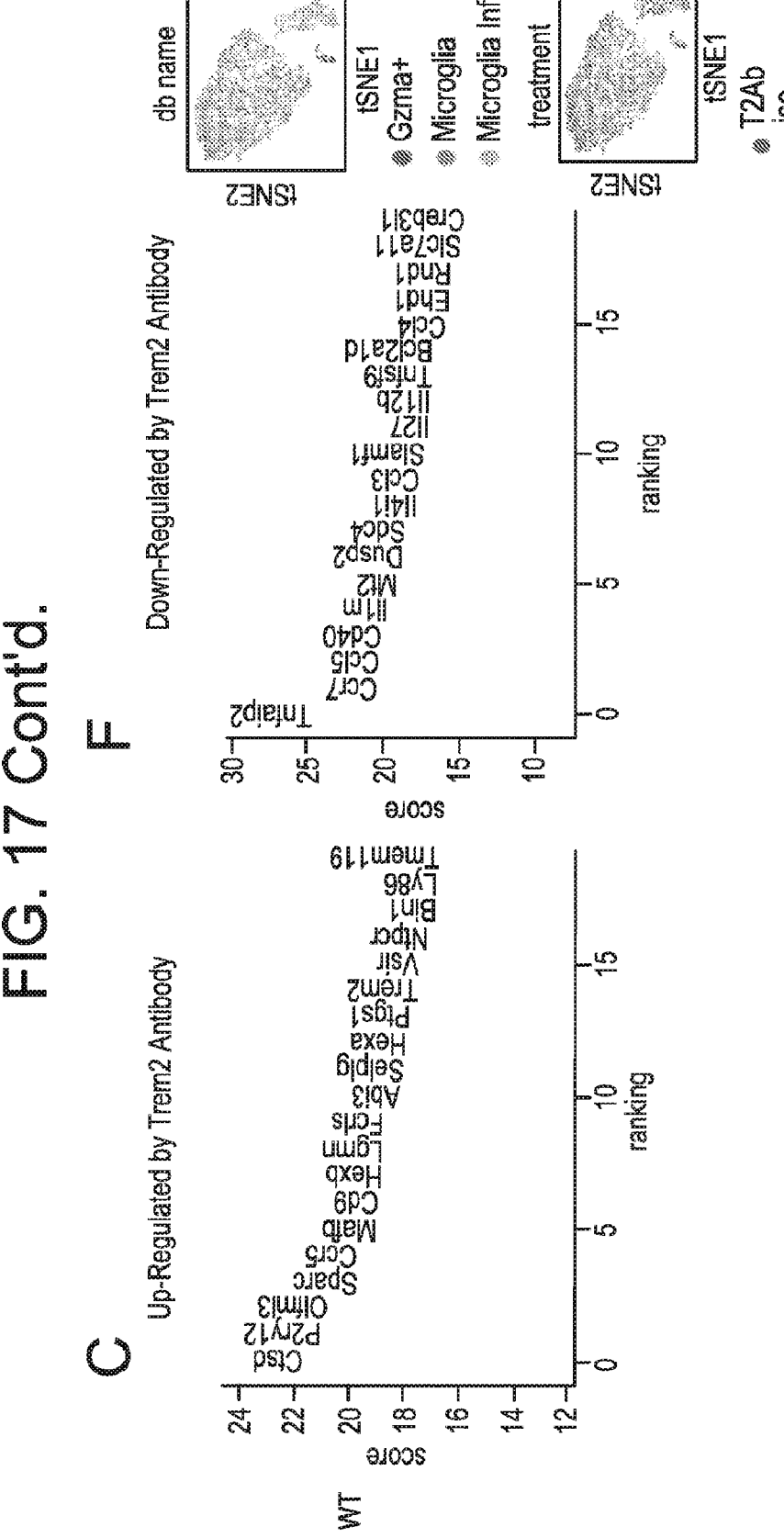

FIGS. 17A-F shows that antibody treatment increases the expression of homeostatic microglial genes (P2ry12, Tmem119) in WT and R47H KI microglia, WT microglia alone and R47H KI microglia alone (FIGS. 17A-17C). Also antibody treatment reduces the expression pro-inflammatory chemokines and cytokines such as Ccl3, Ccl4, Ccl5, Il12b (FIGS. 17D-17F). All statistics are Wilcoxon rank scores. Expression is ln(counts+1).

Figure 18A:
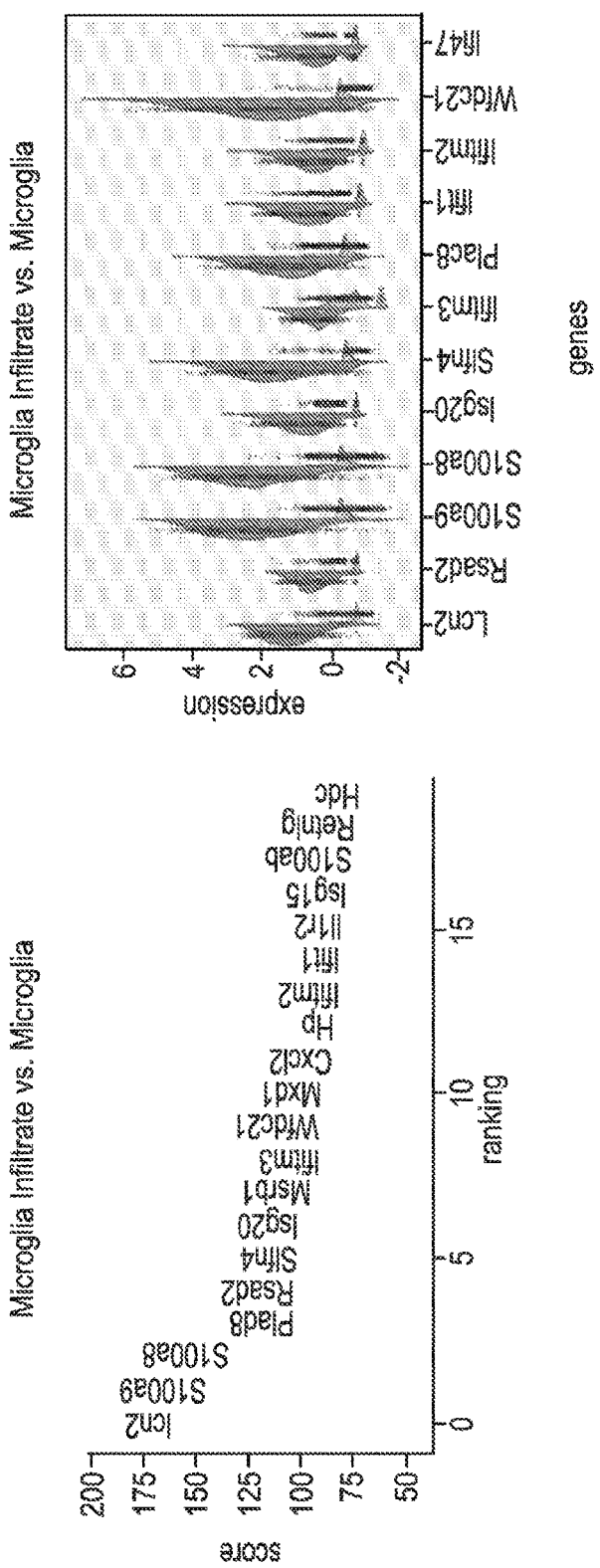
Figure 18B:
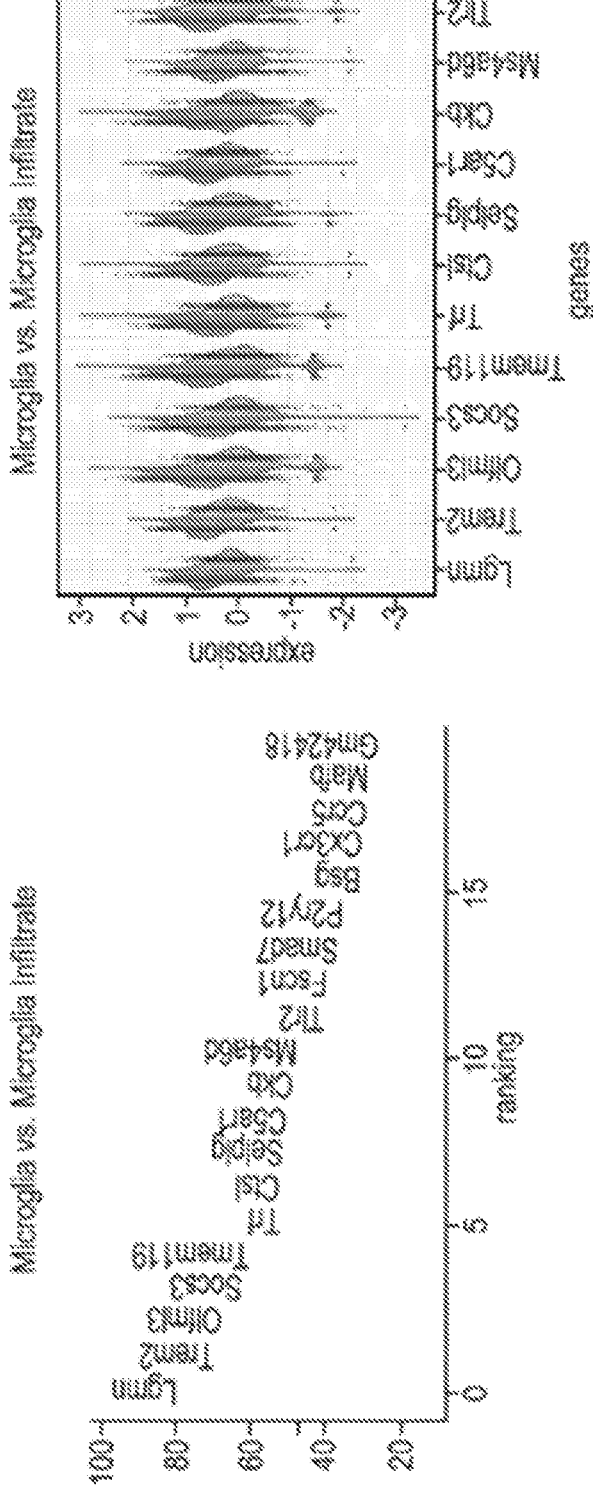
Figure 18C:
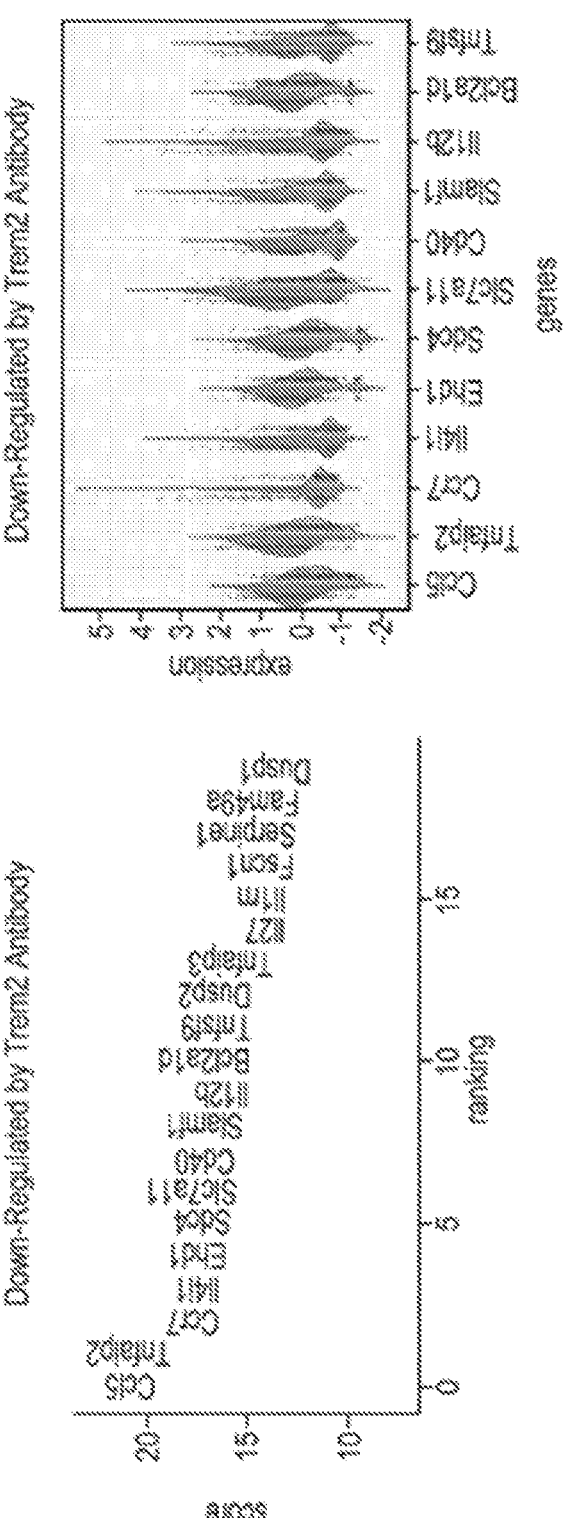
Figure 18D:
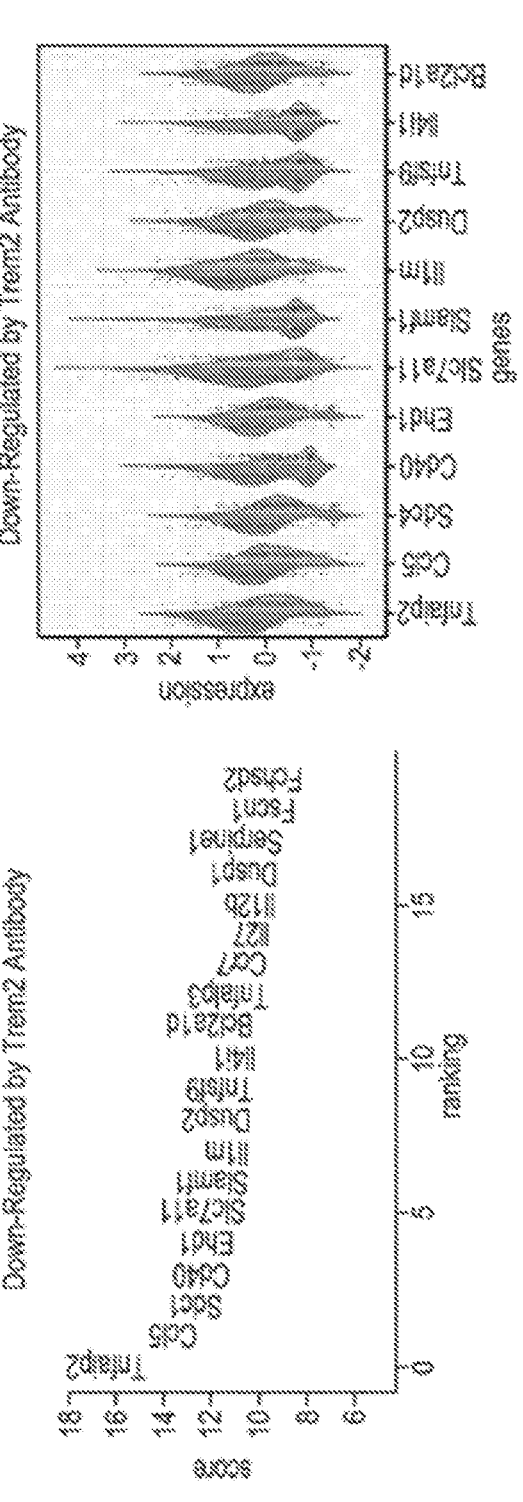

FIGS. 18A-E show that the microglia infiltrate population has increased expression of myeloid and inflammatory genes and slightly lower expression of homeostatic microglia genes (FIGS. 18A-B), and that the administration of Trem2 antibody decreased the pro-inflammatory chemokines and cytokines in the infiltrate microglia cells from WT and R47H KI mice, WT only mice and R47HKI only mice (FIGS. 18C-D). All statistics are Wilcoxon rank scores. Expression is ln(counts+1) adjusted for umi count.

DETAILED DESCRIPTION

The present invention relates to isolated antigen binding proteins that specifically bind to TREM2, particularly human TREM2. In humans, the TREM2 gene is located within a TREM gene cluster at chromosome 6p21.1. The TREM gene cluster encodes four TREM proteins (TREM1, TREM2, TREM4, and TREM5) as well as two TREM-like proteins (TLT-1 and TLT-2). The TREM2 gene encodes a 230 amino acid protein consisting of an extracellular domain, a transmembrane region, and a short cytoplasmic tail (Paradowska-Gorycka et al., Human Immunology, Vol. 74: 730-737, 2013). The extracellular domain contains a single type V Ig-super family domain, with three potential N-glycosylation sites. The wild-type human TREM2 amino acid sequence (NCBI Reference Sequence: NP_061838.1) is provided below as SEQ ID NO: 1.

```
  1  MEPLRLLILLFVTELSGAHNTTVFQGVAGQSLQVSCPYDSMKHWGRRKAWCRQLGEKGPC   60

61  QRVVSTHNLWLLSFLRRWNGSTAITDDTLGGTLTITLRNLQPHDAGLYQCQSLHGSEADT  120

121  LRKVLVEVLADPLDHRDAGDLWFPGESESFEDAHVEHSISRSLLEGEIPFPPTSILLLLA  180

181  CIFLIKILAASALWAAAWHGQKPGTHPPSELDCGHDPGYQLQTLPGLRDT            230
```

Amino acids 1 to 18 of the wild-type human TREM2 protein (SEQ ID NO: 1) is a signal peptide, which is generally removed from the mature protein. The mature human TREM2 protein comprises an extracellular domain at amino acids 19-174 of SEQ ID NO: 1, a transmembrane domain at amino acids 175-195 of SEQ ID NO: 1, and a cytoplasmic domain at amino acids 196-230 of SEQ ID NO: 1. The amino acid sequence of the extracellular domain (including the signal peptide) of human TREM2 is provided below as SEQ ID NO: 2.

```
  1  MEPLRLLILLFVTELSGAHNTTVFQGVAGQSLQVSCPYDSMKHWGRRKAWCRQLGEKGPC   60

61  QRVVSTHNLWLLSFLRRWNGSTAITDDTLGGTLTITLRNLQPHDAGLYQCQSLHGSEADT  120

121  LRKVLVEVLADPLDHRDAGDLWFPGESESFEDAHVEHSISRSLLEGEIPFPPTS        174
```

The term "human triggering receptor expressed on myeloid cells-2" or "human TREM2" can refer to a polypeptide of SEQ ID NO: 1, a polypeptide of SEQ ID NO: 2, polypeptides of SEQ ID NO: 1 or SEQ ID NO: 2 minus the signal peptide (amino acids 1-18), allelic variants of human TREM2, or splice variants of human TREM2. In some embodiments, the term "human TREM2" includes naturally occurring variants of TREM2, such as mutations R47H, Q33X (X is a stop codon), Y38C, T66M, D87N, H157Y, R98W, and S116C.

Because the cytoplasmic domain of TREM2 lacks signaling capability, it must interact with other proteins to transduce TREM2-activating signals. One such protein is DNAX-activating protein of 12 kDa (DAP12). DAP12 is also known as killer cell activating receptor-associated protein (KARAP) and tyrosine kinases binding protein (TYROBP). DAP12 is a type I transmembrane adaptor protein that comprises an ITAM motif in its cytoplasmic domain. The ITAM motif mediates signal propagation by activation of the ZAP70 and Syk tyrosine kinases, which in turn activate several downstream signaling cascades, including PI3K, PKC, ERK, and elevation of intracellular calcium (Colonna, Nature Reviews Immunology, Vol. 3: 445-453, 2003; Ulrich and Holtzman, ACS Chem. Neurosci., Vol. 7: 420-427, 2016). DAP12 and TREM2 associate through their transmembrane domains; a charged lysine residue within the transmembrane domain of TREM2 interacts with a charged aspartic acid residue within the transmembrane domain of DAP12.

Human DAP12 is encoded by the TYROBP gene located on chromosome 19q13.1. The human protein is 113 amino acids in length and comprises a leader sequence (amino acids 1-27 of SEQ ID NO: 3), a short extracellular domain (amino acids 28-41 of SEQ ID NO: 3), a transmembrane domain (amino acids 42-65 of SEQ ID NO: 3) and a cytoplasmic domain (amino acids 66-113 of SEQ ID NO: 3)

(Paradowska-Gorycka et al., Human Immunology, Vol. 74: 730-737, 2013). DAP12 forms a homodimer through two cysteine residues in the short extracellular domain. The wild-type human DAP12 amino acid sequence (NCBI Reference Sequence: NP_003323.1) is provided below as SEQ ID NO: 3.

```
  1  MGGLEPCSRLLLLPLLLAVSGLRPVQAQAQSDCSCSTVSPGVLAGIVMGDLVLTVLIALA   60

61  VYFLGRLVPRGRGAAEAATRKQRITETESPYQELQGQRSDVYSDLNTQRPYYK        113
```

The term "human DAP12" can refer to a polypeptide of SEQ ID NO: 3, a polypeptide of SEQ ID NO: 3 minus the leader peptide (amino acids 1-27), allelic variants of human DAP12, or splice variants of human DAP12.

In some embodiments, the present invention provides isolated antigen binding proteins that specifically bind to human TREM2. As used herein, the term "antigen binding protein" refers to a protein that specifically binds to one or more target antigens. An antigen binding protein typically comprises an antigen-binding fragment that specifically binds to an antigen and, optionally, a scaffold or framework portion that allows the antigen-binding fragment to adopt a conformation that promotes binding of the antigen binding protein to the antigen. An "antigen binding fragment," used interchangeably herein with "binding fragment" or "fragment," is a portion of an antibody that lacks at least some of the amino acids present in a full-length heavy chain and/or light chain, but which is still capable of specifically binding to an antigen. An antigen-binding fragment includes, but is not limited to, a single-chain variable fragment (scFv), a nanobody (e.g. VH domain of camelid heavy chain antibodies; VHH fragment, see Cortez-Retamozo et al., Cancer Research, Vol. 64:2853-57, 2004), a Fab fragment, a Fab' fragment, a F(ab')₂ fragment, a Fv fragment, a Fd fragment, and a complementarity determining region (CDR) fragment, and can be derived from any mammalian source, such as human, mouse, rat, rabbit, or camelid. Antigen-binding fragments may compete for binding of a target antigen with an intact antibody and the fragments may be produced by the modification of intact antibodies (e.g. enzymatic or chemical

US 12,649,788 B2

17                                                          18

2cleavage) or synthesized de novo using recombinant DNA technologies or peptide synthesis. In some embodiments, the antigen-binding fragment comprises at least one CDR from an antibody that binds to the antigen, for example, the heavy chain CDR3 from an antibody that binds to the antigen. In other embodiments, the antigen-binding fragment comprises all three CDRs from the heavy chain of an antibody that binds to the antigen or all three CDRs from the light chain of an antibody that binds to the antigen. In still other embodiments, the antigen-binding fragment comprises all six CDRs from an antibody that binds to the antigen (three from the heavy chain and three from the light chain). In certain embodiments, an antigen binding protein is an antibody or binding fragment thereof.

An antigen binding protein can also include a protein comprising one or more antigen-binding fragments incorporated into a single polypeptide chain or into multiple polypeptide chains. For instance, antigen binding proteins can include, but are not limited to, a diabody (see, e.g., EP 404,097; WO 93/11161; and Hollinger et al., Proc. Natl. Acad. Sci. USA, Vol. 90:6444-6448, 1993); an intrabody; a domain antibody (single VL or VH domain or two or more VH domains joined by a peptide linker; see Ward et al., Nature, Vol. 341:544-546, 1989); a maxibody (2 scFvs fused to Fc region, see Fredericks et al., Protein Engineering, Design & Selection, Vol. 17:95-106, 2004 and Powers et al., Journal of Immunological Methods, Vol. 251:123-135, 2001); a triabody; a tetrabody; a minibody (scFv fused to CH3 domain; see Olafsen et al., Protein Eng Des Sel., Vol. 17:315-23, 2004); a peptibody (one or more peptides attached to an Fc region, see WO 00/24782); a linear antibody (a pair of tandem Fd segments (VH-CH1-VH-CH1) which, together with complementary light chain polypeptides, form a pair of antigen binding regions, see Zapata et al., Protein Eng., Vol. 8:1057-1062, 1995); a small modular immunopharmaceutical (see U.S. Patent Publication No. 20030133939); and immunoglobulin fusion proteins (e.g. IgG-scFv, IgG-Fab, 2scFv-IgG, 4scFv-IgG, VH-IgG, IgG-VH, and Fab-scFv-Fc; see, e.g., Spiess et al., Mol. Immunol., Vol. 67(2 Pt A):95-106, 2015).

The term "isolated molecule" (where the molecule is, for example, a polypeptide, a polynucleotide, antigen binding protein or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

In certain embodiments of the invention, the antigen binding proteins specifically bind to human TREM2. An antigen binding protein "specifically binds" to a target antigen when it has a significantly higher binding affinity for, and consequently is capable of distinguishing, that antigen compared to its affinity for other unrelated proteins, under similar binding assay conditions. Antigen binding proteins that specifically bind an antigen may have an equilibrium dissociation constant ($K_D$)$\leq 1 \times 10^{-6}$ M. The antigen binding protein specifically binds antigen with "high affinity" when the $K_D$ is $\leq 1 \times 10^{-8}$M. In one embodiment, the antigen binding proteins of the invention bind to human TREM2 with a $K_D$ of $\leq 5 \times 10^{-7}$ M. In another embodiment, the antigen binding proteins of the invention bind to human TREM2 with a $K_D$ of $\leq 1 \times 10^{-7}$ M. In yet another embodiment, the antigen binding proteins of the invention bind to human TREM2 with a $K_D$ of $\leq 5 \times 10^{-8}$ M. In another embodiment, the antigen binding proteins of the invention bind to human TREM2 with a $K_D$ of $\leq 1 \times 10^{-8}$M. In certain embodiments, the antigen binding proteins of the invention bind to human TREM2 with a $K_D$ of $\leq 5 \times 10^{-9}$ M. In other embodiments, the antigen binding proteins of the invention bind to human TREM2 with a $K_D$ of $\leq 1 \times 10^{-9}$ M. In one particular embodiment, the antigen binding proteins of the invention bind to human TREM2 with a $K_D$ of $\leq 5 \times 10^{-10}$ M. In another particular embodiment, the antigen binding proteins of the invention bind to human TREM2 with a $K_D$ of $\leq 1 \times 10^{-10}$ M.

Affinity is determined using a variety of techniques, an example of which is an affinity ELISA assay. In various embodiments, affinity is determined by a surface plasmon resonance assay (e.g., BIAcore®-based assay). Using this methodology, the association rate constant ($k_a$ in $M^{-1}s^{-1}$) and the dissociation rate constant ($k_d$ in $s^{-1}$) can be measured. The equilibrium dissociation constant ($K_D$ in M) can then be calculated from the ratio of the kinetic rate constants ($k_d/k_a$). In some embodiments, affinity is determined by a kinetic method, such as a Kinetic Exclusion Assay (KinExA) as described in Rathanaswami et al. Analytical Biochemistry, Vol. 373:52-60, 2008. Using a KinExA assay, the equilibrium dissociation constant ($K_D$ in M) and the association rate constant ($k_a$ in $M^{-1}s^{-1}$) can be measured. The dissociation rate constant ($k_d$ in $s^{-1}$) can be calculated from these values ($K_D \times k_a$). In other embodiments, affinity is determined by a bio-layer interferometry method, such as that described in Kumaraswamy et al., Methods Mol. Biol., Vol. 1278:165-82, 2015 and employed in Octet® systems (Pall ForteBio). The kinetic ($k_a$ and $k_d$) and affinity ($K_D$) constants can be calculated in real-time using the bio-layer interferometry method. In some embodiments, the antigen binding proteins described herein exhibit desirable characteristics such as binding avidity as measured by $k_d$ (dissociation rate constant) for human TREM2 of about $10^{-2}$, $10^{-3}$, $10^{-4}$, $10^{-5}$, $10^{-6}$ $s^{-1}$ or lower (lower values indicating higher binding avidity), and/or binding affinity as measured by $K_D$ (equilibrium dissociation constant) for human TREM2 of about $10^{-8}$, $10^{-9}$, $10^{-10}$, $10^{-11}$ M or lower (lower values indicating higher binding affinity).

In certain embodiments, the antigen binding proteins of the invention specifically bind to human TREM2 with a $K_D$ from about 1 pM to about 100 nM as measured by bio-layer interferometry at 25° C. For instance, in some embodiments, the antigen binding proteins of the invention specifically bind to human TREM2 with a $K_D$ less than 100 nM as measured by bio-layer interferometry at 25° C. In other embodiments, the antigen binding proteins of the invention specifically bind to human TREM2 with a $K_D$ less than 50 nM as measured by bio-layer interferometry at 25° C. In yet other embodiments, the antigen binding proteins of the invention specifically bind to human TREM2 with a $K_D$ less than 25 nM as measured by bio-layer interferometry at 25° C. In one particular embodiment, the antigen binding proteins of the invention specifically bind to human TREM2 with a $K_D$ less than 10 nM as measured by bio-layer interferometry at 25° C. In another particular embodiment, the antigen binding proteins of the invention specifically TREM2 gene at chromosome 6p21.1. The wild-type human TREM1 amino acid sequence (NCBI Reference Sequence: NP_061113.1) is provided below as SEQ ID NO: 4.

```
  1  MRKTRLWGLLWMLFVSELRAATKLTEEKYELKEGQTLDVKCDYTLEKFASSQKAWQIIRD    60

61  GEMPKTLACTERPSKNSHPVQVGRIILEDYHDHGLLRVRMVNLQVEDSGLYQCVIYQPPK   120

121  EPHMLFDRIRLVVTKGFSGTPGSNENSTQNVYKIPPTTTKALCPLYTSPRTVTQAPPKST   180

181  ADVSTPDSEINLTNVTDIIRVPVFNIVILLAGGELSKSLVFSVLFAVTLRSFVP         234
``` bind to human TREM2 with a $K_D$ less than 5 nM as measured by bio-layer interferometry at 25° C. In another particular embodiment, the antigen binding proteins of the invention specifically bind to human TREM2 with a $K_D$ less than 1 nM as measured by bio-layer interferometry at 25° C.

The antigen binding proteins of the invention may, in some embodiments, bind to a particular region or epitope of human TREM2. As used herein, an "epitope" refers to any determinant capable of being specifically bound by an antigen binding protein, such as an antibody or fragment thereof. An epitope is a region of an antigen that is bound by, or interacts with, an antigen binding protein that targets that antigen, and when the antigen is a protein, includes specific amino acids that directly contact, or interact with, the antigen binding protein. An epitope can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or 4 amino acids, and more usually, at least 5, at least 6, or at least 7 amino acids, for example, about 8 to about 10 amino acids in a unique sequence. A "conformational epitope", in contrast to a linear epitope, is a group of discontinuous amino acids (e.g., in a polypeptide, amino acid residues that are not contiguous in the polypeptide's primary sequence but that, in the context of the polypeptide's tertiary and quaternary structure, are near enough to each other to be bound by an antigen binding protein). Epitope determinants can include chemically active surface groupings of molecules such as amino acids, sugar side chains, phosphoryl or sulfonyl groups, and can have specific three dimensional structural characteristics, and/or specific charge characteristics. Generally, antigen binding proteins specific for a particular target molecule will preferentially recognize an epitope on the target molecule in a complex mixture of proteins and/or macromolecules. In some embodiments, the antigen binding proteins bind to human TREM2 at an epitope within the extracellular domain of human TREM2 (SEQ ID NO: 2). In related embodiments, the antigen binding proteins bind to human TREM2 at an epitope within amino acids 19-174 of SEQ ID NO: 1. In certain embodiments, the antigen binding proteins bind to human TREM2 at an epitope within amino acids 23-128 of SEQ ID NO: 1.

In certain embodiments, the antigen binding proteins of the invention do not specifically bind to human TREM1. Like TREM2, TREM1 is a transmembrane glycoprotein that is expressed on myeloid cells and signals through DAP12. Activation of TREM1 signaling results in inflammatory effects, such as pro-inflammatory cytokine production, degranulation of neutrophils, and phagocytosis (Arts et al., Journal of Leukocyte Biology, Vol. 93: 209-215, 2013). As discussed above, TREM1 is encoded by the TREM1 gene, which is located in the TREM gene cluster along with the The term "human TREM1" can refer to a polypeptide of SEQ ID NO: 4, a polypeptide of SEQ ID NO: 4 minus the signal peptide (amino acids 1-20), allelic variants of human TREM1, or splice variants of human TREM1. An antigen binding protein of the invention "does not specifically bind" to human TREM1 if it has an equivalent or lower binding affinity for human TREM1 as it does for an unrelated human antigen protein. Antigen binding proteins that do not specifically bind to human TREM1 may have a $K_D$ for human TREM1$\geq 1 \times 10^{-5}$M, $\geq 1 \times 10^{-4}$ M, or $\geq 1 \times 10^{-3}$ M as determined by any of the methods for measuring affinity as described herein. An antigen binding protein of the invention may be considered to not specifically bind human TREM1 if the antigen binding protein has equivalent or lower binding to human TREM1 as compared to the binding to human TREM1 of an isotype control antibody as measured by any method known in the art, such as the FACS binding method described in Example 2.

In certain embodiments, the antigen binding proteins of the invention are agonist antigen binding proteins. An "agonist antigen binding protein" or "activating antigen binding protein" is an antigen binding protein (e.g. an antibody) that binds to and induces or increases one or more TREM2-mediated functions or activities. TREM2-mediated functions or activities include, but are not limited to, DAP12 phosphorylation (e.g. tyrosine phosphorylation within the ITAM motif within the DAP12 cytoplasmic domain); Syk phosphorylation; Src phosphorylation/activation; activation/phosphorylation of extracellular regulated kinase (ERK1/2); translocation of activated phosphatidylinositol 3-kinase (PI3K) to the membrane; activation of protein kinase B (PKB, also known as Akt); activation of NF-κB and NF-κB-mediated transcription; activation of nuclear factor of activated T-cells (NFAT)-mediated transcription; activation of protein kinase C (PKC); elevation of intracellular inositol (1,4,5)-triphosphate (IP3); elevation of intracellular calcium levels; increase in survival or proliferation of myeloid cells, such as macrophages, microglia, and dendritic cells; reduction of apoptosis of myeloid cells, such as macrophages, microglia, and dendritic cells; increase in CCL2 protein expression in macrophages; reduction of inflammatory cytokine (e.g. TNF-α, IL-6, IL-10, IL-12p70, and IFN-γ) production from myeloid cells (e.g. macrophages), and increase in phagocytosis by macrophages and microglia of necrotic and/or apoptotic cells (e.g. neuronal cells), cellular debris, and misfolded peptides.

The agonist TREM2 antigen binding proteins of the invention are capable of inducing or activating TREM2-mediated functions in the absence of aggregation, clustering, and/or Fc-mediated cross-linking of the antigen binding proteins. Accordingly, in vitro, the agonist activity of the antigen binding proteins can be detected with soluble (i.e. not bound to a solid support), monomeric, bivalent forms of the antigen binding proteins or antibodies. In vivo, the agonist activity of the antigen binding proteins of the invention can occur in the absence of the antigen binding proteins binding to receptors (e.g. Fc receptors) on adjacent cells to cluster or aggregate the antigen binding protein. Thus, in some embodiments, the agonist activity of the antigen binding proteins described herein is independent of the ability of the antigen binding proteins to bind to or interact with Fc receptors. In embodiments in which the antigen binding proteins comprise an Fc region (e.g. antibodies), the antigen binding proteins retain TREM2 agonist activity without binding or interacting with an Fcγ receptor, such as the FcγRIIB receptor. The cross-linking independent nature of the agonist antigen binding proteins of the invention is advantageous for therapeutic uses of the antigen binding proteins because the agonist activity of the antigen binding proteins will not vary with the Fcγ receptor expression or accessibility at the therapeutic site of action.

The dependence of TREM2 agonist activity on cross-linking, aggregation, and/or clustering of the antigen binding proteins can be assessed by measuring activation or induction of any of the TREM2-mediated functions described herein in the absence of a cross-linking agent. A cross-linking agent can be any agent that interacts with antigen binding proteins at a site other than the antigen-binding site to cluster two or more antigen binding proteins together. In embodiments in which the antigen-binding protein comprises an Fc region (e.g. an antibody), a cross-linking agent can be a protein that binds to or interacts with the Fc region, such as protein A, protein G, an anti-Fc antibody, or Fcγ receptor.

In some embodiments, a TREM2 agonist antigen binding protein of the invention increases levels of phosphorylated Syk (pSyk) in cells expressing a TREM2 protein (e.g. a human TREM2 protein) relative to pSyk levels in the absence of the antigen binding protein or relative to pSyk levels in the presence of a control. The cells can be cells of a myeloid linage including, but not limited to, monocytes, macrophages, microglial cells, dendritic cells, osteoclasts, neutrophils, basophils, eosinophils, megakaryocytes, and platelets. In certain embodiments, the TREM2 agonist antigen binding proteins increase pSyk levels with an EC50 less than about 100 nM, less than about 80 nM, less than about 60 nM, less than about 50 nM, less than about 40 nM, less than about 30 nM, less than about 20 nM, less than about 10 nM, less than about 5 nM, less than about 1 nM, less than about 500 pM, less than about 300 pM, or less than about 100 pM. In some embodiments, the TREM2 agonist antigen binding proteins increase pSyk levels with an EC50 from about 1 pm to about 100 nM, from about 10 pM to about 50 nM, from about 50 pM to about 5 nM, from about 100 pM to about 1 nM, or from about 150 pM to about 500 pM. An "EC50" or "half maximal effective concentration" is a measure of potency of the antigen binding protein and refers to the concentration of antigen binding protein required to induce a response halfway between baseline and maximal response after a particular exposure period. The EC50 of any particular agonist can be determined by constructing a dose-response curve and examining the effect of different concentrations of the agonist in inducing activity in a particular functional assay (e.g. pSyk levels). The EC50 is the concentration of the agonist at which 50% of its maximal effect is observed. Increases in intracellular pSyk levels induced by the TREM2 agonist antigen binding proteins of the invention can be assessed by various methods, such as the cell-based assays described in Examples 2 and 6. For instance, cells expressing TREM2 (e.g. human TREM2) are contacted with one or more concentrations of an agonist antigen binding protein, the cells are lysed, and pSyk levels in the cell lysates are assessed, for example by Western blot, FRET-based assay or chemiluminescent assay (e.g. AlphaLISA-based assay). The cells in the cell-based assay may be cells, such as HEK293T cells or CHO cells, which recombinantly express TREM2 (e.g. human TREM2). Alternatively, the cells in the cell-based assay are cells that natively express TREM2 (e.g. human TREM2), such as THP-1 cells, macrophage, microglial cells, or dendritic cells.

In certain embodiments, the potency of the TREM2 agonist antigen binding proteins for inducing or increasing pSyk levels in a cell expressing TREM2 (e.g. human TREM2) is retained in the absence of a cross-linking agent. For instance, in some embodiments, the TREM2 agonist antigen binding proteins of the invention increase pSyk levels with an EC50 from about 1 pM to about 100 nM, from about 10 pM to about 50 nM, from about 50 pM to about 5 nM, from about 100 pM to about 1 nM, or from about 150 pM to about 500 pM in the absence of a cross-linking agent as measured by a cell-based pSyk assay. In one embodiment, the TREM2 agonist antigen binding protein increases pSyk levels with an EC50 less than 5 nM in the absence of a cross-linking agent as measured by a cell-based pSyk assay. In another embodiment, the TREM2 agonist antigen binding protein increases pSyk levels with an EC50 less than 1 nM in the absence of a cross-linking agent as measured by a cell-based pSyk assay. In another embodiment, the TREM2 agonist antigen binding protein increases pSyk levels with an EC50 less than 500 pM in the absence of a cross-linking agent as measured by a cell-based pSyk assay. In still another embodiment, the TREM2 agonist antigen binding protein increases pSyk levels with an EC50 less than 300 pM in the absence of a cross-linking agent as measured by a cell-based pSyk assay. In yet another embodiment, the TREM2 agonist antigen binding protein increases pSyk levels with an EC50 less than 100 pM in the absence of a cross-linking agent as measured by a cell-based pSyk assay.

The TREM2 agonist antigen binding proteins of the invention may comprise one or more complementarity determining regions (CDRs) from the light and heavy chain variable regions of antibodies that specifically bind to human TREM2 as described herein. The term "CDR" refers to the complementarity determining region (also termed "minimal recognition units" or "hypervariable region") within antibody variable sequences. There are three heavy chain variable region CDRs (CDRH1, CDRH2 and CDRH3) and three light chain variable region CDRs (CDRL1, CDRL2 and CDRL3). The term "CDR region" as used herein refers to a group of three CDRs that occur in a single variable region (i.e. the three light chain CDRs or the three heavy chain CDRs). The CDRs in each of the two chains typically are aligned by the framework regions (FRs) to form a structure that binds specifically with a specific epitope or domain on the target protein (e.g., human TREM2). From N-terminus to C-terminus, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, MD), or Chothia & Lesk, 1987, *J. Mol. Biol.* 196:901-917; Chothia et al., 1989, Nature 342:878-883. Complementarity determining regions (CDRs) and framework regions (FR) of a given antibody may be identified using this system. Other numbering systems for the amino acids in immunoglobulin chains include IMGT® (the international ImMunoGeneTics information system; Lefranc et al., Dev. Comp. Immunol. 29:185-203; 2005) and AHo (Honegger and Pluckthun, J. Mol. Biol. 309(3):657-670; 2001). One or more CDRs may be incorporated into a molecule either covalently or noncovalently to make it an antigen binding protein.

In some embodiments, an antigen binding protein of the invention may incorporate the CDR(s) as part of a larger polypeptide chain, may covalently link the CDR(s) to another polypeptide chain, or may incorporate the CDR(s) noncovalently. The antigen binding proteins may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

In certain embodiments, the TREM2 agonist antigen binding proteins of the invention comprise at least one light chain variable region comprising a CDRL1, CDRL2, and CDRL3, and at least one heavy chain variable region comprising a CDRH1, CDRH2, and CDRH3 from an anti-TREM2 agonist antibody described herein. Light chain and heavy chain variable regions and associated CDRs of exemplary human anti-TREM2 antibodies are set forth below in Tables 1A and 1B, respectively.

TABLE 1A

| Exemplary Anti-Human TREM2 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| 12G10 | LV-01 | QAVPTQPSSLSASPGV LASLTCTLRSGINVGT YRIYWYQQKPGSPPQ YLLRYKSDSDKQQGS GVPSRFSGSKDASANA GILLISGLQSEDEADYY CMIWYSSAVVFGGGT KLTVL (SEQ ID NO: 46) | TLRSGINVGTYRIY (SEQ ID NO: 5) | YKSDSDKQQGS (SEQ ID NO: 19) | MIWYSSAVV (SEQ ID NO: 31) |
| 26A10 | LV-02 | SYELTQPPSVSVSPGQ TASITCSGDKLGDKYV CWYQQKPGQSPVLVI YQDSKRPSGIPERFSGS NSGNTATLTISGTQAM DEADYYCQAWDSNTV VFGGGTKLTVL (SEQ ID NO: 47) | SGDKLGDKYVC (SEQ ID NO: 6) | QDSKRPS (SEQ ID NO: 20) | QAWDSNTVV (SEQ ID NO: 32) |
| 26C10 | LV-03 | SFELTQPPSVSVSPGQT ASITCSGDKLGDKYVC WYQQKPGQSPMLVIY QDTKRPSGIPERFSGSN SGNTATLTISGTQAMD EADYYCQAWDSSTVV FGGGTKLTVL (SEQ ID NO: 48) | SGDKLGDKYVC (SEQ ID NO: 6) | QDTKRPS (SEQ ID NO: 21) | QAWDSSTVV (SEQ ID NO: 33) |
| 26F2 | LV-04 | SYELTQPPSVSVSPGQ TASITCSGDKLGDKYV CWYQQKPGQSPVLVIF QDSKRPSGIPERFSGSN SGNTATLTISGTQAMD EADYYCQAWDSSTVV FGGGTKLTVL (SEQ ID NO: 49) | SGDKLGDKYVC (SEQ ID NO: 6) | QDSKRPS (SEQ ID NO: 20) | QAWDSSTVV (SEQ ID NO: 33) |
| 33B12 | LV-05 | SYELTQPPSVSVSPGQ TASITCSGDKLGDKYV CWYQQKPGQSPVLVI YQDSKRPSGIPERFSGS NSGNTATLTISGTQAM DEADYYCQAWDSSTV VFGGGTKLTVL (SEQ ID NO: 50) | SGDKLGDKYVC (SEQ ID NO: 6) | QDSKRPS (SEQ ID NO: 20) | QAWDSSTVV (SEQ ID NO: 33) |
| 24C12 | LV-06 | GIVMTQSPDSLAVSLG ERATINCKSSRSVLYSS NNKNYLAWYQQKPG QPPKVLIYWASTRESG VPDRFSGSGSGTDFTL | KSSRSVLYSSNNKNYLA (SEQ ID NO: 7) | WASTRES (SEQ ID NO: 22) | QQYYITPIT (SEQ ID NO: 34) |

TABLE 1A-continued

Exemplary Anti-Human TREM2 Antibody Light
Chain Variable Region Amino Acid Sequences

| Ab ID. | VL Group | VL Amino Acid Sequence | CDRL1 | CDRL2 | CDRL3 |
|---|---|---|---|---|---|
| | | TISSLQAEDVAVYNCQ QYYITPITFGQGTRLEI K (SEQ ID NO: 51) | | | |
| 24G6 | LV-07 | DIVMTQSPDSLAVSLG ERATINCKSSQSVLYSS NNKHFLAWYQQKPGQ PPKLLIYWASTRESGV PDRFSGSGSGTDFTLTI SSLQAEDVAFYYCQQ YYSTPLTFGGGTKVEI K (SEQ ID NO: 52) | KSSQSVLYSSNNKHFLA (SEQ ID NO: 8) | WASTRES (SEQ ID NO: 22) | QQYYSTPLT (SEQ ID NO: 35) |
| 24A10 | LV-08 | DIVMTQSPDSLAVSLG ERATITCKSSHNVLYS SNNKNYLAWYQQKPG QPPKLLIYWASTRESG VPDRFSGSGSGTDFTL TISSLQAEDVAVYYCH QYYSTPCSFGQGTKLE IK (SEQ ID NO: 53) | KSSHNVLYSSNNKNYLA (SEQ ID NO: 9) | WASTRES (SEQ ID NO: 22) | HQYYSTPCS (SEQ ID NO: 36) |
| 10E3 | LV-09 | EIVMTQSPATLSVSPG ERATLSCRASQSVSSN LAWFQQKPGQAPRLLI YGASTRATGIPARFSV SGSGTEFTLTISSLQSE DFAFYYCLQDNNWPP TFGPGTKVDIK (SEQ ID NO: 54) | RASQSVSSNLA (SEQ ID NO: 10) | GASTRAT (SEQ ID NO: 23) | LQDNNWPPT (SEQ ID NO: 37) |
| 13E7 14C12 | LV-10 | EIVMTQSPATLSVSPG ERATLSCRASQSVSSN LAWFQQKPGQAPRLLI YGASTRATGIPARFSV SGSGTEFTLTISSLQSE DFAVYYCLQDNNWPP TFGPGTKVDIK (SEQ ID NO: 55) | RASQSVSSNLA (SEQ ID NO: 10) | GASTRAT (SEQ ID NO: 23) | LQDNNWPPT (SEQ ID NO: 37) |
| 25F12 | LV-11 | EKVMTQSPATLSVSPG ERATLSCRASQSVNNN LAWYQQKPGQAPRLL IYGASTRATGIPARFSG SGSGTEFTLTISSLQSE DFAVYYCQQYNNWPR TFGQGTKVEIK (SEQ ID NO: 56) | RASQSVNNNLA (SEQ ID NO: 11) | GASTRAT (SEQ ID NO: 23) | QQYNNWPRT (SEQ ID NO: 38) |
| 32E3 | LV-12 | EFVLTQSPGTLSLSPGE RATLSCRASQIISSNYL AWYQQKPGQAPRLLI YSASSRATGIPDRFSGS GSGTDFTLTISRLEPED FAVYYCQQFDSSPITF GRGTRLDIK (SEQ ID NO: 57) | RASQIISSNYLA (SEQ ID NO: 12) | SASSRAT (SEQ ID NO: 24) | QQFDSSPIT (SEQ ID NO: 39) |
| 24F4 | LV-13 | EIVLTQSPGTLSLSPGE RATLSCRASQSVSSSY LAWYQQKPGQAPRLL IYGASSRATGIPDRFSG SGSGTDFTLTISRLEPE DFALYYCQQYDTSPFT FGPGTKVDIK (SEQ ID NO: 58) | RASQSVSSSYLA (SEQ ID NO: 13) | GASSRAT (SEQ ID NO: 25) | QQYDTSPFT (SEQ ID NO: 40) |
| 16B8 | LV-14 | DIQMTQSPSSVSASVG DRVTVTCRASQDINS WLAWYQQKPGKAPK LLIYAASSLQTGVPSRF SGSGSGTDFTLTISSLQ | RASQDINSWLA (SEQ ID NO: 14) | AASSLQT (SEQ ID NO: 26) | QQSNSFPIT (SEQ ID NO: 41) |

TABLE 1A-continued

Exemplary Anti-Human TREM2 Antibody Light
Chain Variable Region Amino Acid Sequences

| Ab ID. | VL Group | VL Amino Acid Sequence | CDRL1 | CDRL2 | CDRL3 |
|---|---|---|---|---|---|
| | | PEDFATYSCQQSNSFPI TFGQGTRLEIK (SEQ ID NO: 59) | | | |
| 4C5 | LV-15 | DIQMTQSPSSVSASVG DRVTITCRASQGISNW LAWYQQKPGKAPKLL IYAASSLQVGVPLRFS GSGSGTDFTLTISSLQP EDFATYYCQQADSFPR NFGQGTKLEIK (SEQ ID NO: 60) | RASQGISNWLA (SEQ ID NO: 15) | AASSLQV (SEQ ID NO: 27) | QQADSFPRN (SEQ ID NO: 42) |
| 6E7 | LV-16 | DIQMTQSPSSVSASVG DRVTITCRASQGISSW LAWYQQKPGKAPKLL IYAASSLQNGVPSRFS GSGSGTDFTLTISSLQP EDFATYFCQQADSFPR TFGQGTKLEIK (SEQ ID NO: 61) | RASQGISSWLA (SEQ ID NO: 16) | AASSLQN (SEQ ID NO: 28) | QQADSFPRT (SEQ ID NO: 43) |
| 5E3 | LV-17 | DIQMTQSPSSLSASVG DRVTITCRASQGISNY LAWFQQKPGKAPKSLI YAASSLQSGVPSKFSG SGSGTDFTLTISSLQPE DFATYYCQQYSTYPFT FGPGTKVDIK (SEQ ID NO: 62) | RASQGISNYLA (SEQ ID NO: 17) | AASSLQS (SEQ ID NO: 29) | QQYSTYPFT (SEQ ID NO: 44) |
| 4G10 | LV-18 | DIQMTQSPSSLSASVG DRVTITCRASQGIRND LGWYQQKPGNAPKRL IYAASSLPSGVPSRFSG SGSGPEFTLTISSLQPE DFATYYCLQHNSYPW TFGQGTKVEIT (SEQ ID NO: 63) | RASQGIRNDLG (SEQ ID NO: 18) | AASSLPS (SEQ ID NO: 30) | LQHNSYPWT (SEQ ID NO: 45) |

TABLE 1B

Exemplary Anti-Human TREM2 Antibody Heavy Chain Variable Region
Amino Acid Sequences

| Ab ID. | VH Group | VH Amino Acid Sequence | CDRH1 | CDRH2 | CDRH3 |
|---|---|---|---|---|---|
| 12G10 24C12 | HV-01 | EVQLLESGGGLVQ PGGSLRLSCAASG FTFSSYAMSWVRQ APGKGLEWVSAIG GGGVSTYCADSV KGRFTISRDNSKN TLYLQMNSLRAED TAVYYCAKFYIAV AGSHFDYWGQGT LVTVSS (SEQ ID NO: 110) | SYAMS (SEQ ID NO: 77) | AIGGGGVSTYCADSVKG (SEQ ID NO: 87) | FYIAVAGSHFDY (SEQ ID NO: 95) |
| 26A10 | HV-02 | EVQLVESGGALVQ RGGSLRLSCAASR FTFSSFGMSWVRQ APGKGLEWVSYIS SSSFTIYYADSVKG RFTISRDNAKNSF YLQMNSLRDEDT AVYYCAREGGLT MVRGVSSYGLDV WGQGTTVTVSS (SEQ ID NO: 111) | SFGMS (SEQ ID NO: 78) | YISSSSFTIYYADSVKG (SEQ ID NO: 88) | EGGLTMVRGVSSYGLDV (SEQ ID NO: 96) |

TABLE 1B-continued

Exemplary Anti-Human TREM2 Antibody Heavy Chain Variable Region
Amino Acid Sequences

| Ab ID. | VH Group | VH Amino Acid Sequence | CDRH1 | CDRH2 | CDRH3 |
|---|---|---|---|---|---|
| 26C10 | HV-03 | EVQLVESGGALVQ PGGSLRLSCAASG FTFSSFGMSWVRQ APGKGLEWVSYIS SSSFTIYYADSVKG RFTISRDNAKNSF YLQMNSLRDEDT AVYFCVREGGITM VRGVSSYGMDVW GQGTTVTVSS (SEQ ID NO: 112) | SFGMS (SEQ ID NO: 78) | YISSSSFTIYYADSVKG (SEQ ID NO: 88) | EGGITMVRGVSSYGMDV (SEQ ID NO: 97) |
| 26F2 | HV-04 | EVQLVESGGALVQ PGGSLRLSCAASG FTFSSFGMSWVRQ APGKGLEWISYISS SSFTIYYADSVKG RFTISRDNAKNSF YLQMNSLRDEDT AVYFCAREGGITM VRGVSSYGMDVW GQGTTVTVSS (SEQ ID NO: 113) | SFGMS (SEQ ID NO: 78) | YISSSSFTIYYADSVKG (SEQ ID NO: 88) | EGGITMVRGVSSYGMDV (SEQ ID NO: 97) |
| 33B12 | HV-05 | EVQLVESGGALVQ PGGSLRLSCAASG FTFSSFGMSWVRQ APGKGLEWVSYIS KSSFTIYYADSVK GRFTISRDNAKNS FYLQMNSLRDEDT AVYYCAREGGLT MVRGVSSYGLDV WGQGTTVTVSS (SEQ ID NO: 114) | SFGMS (SEQ ID NO: 78) | YISKSSFTIYYADSVKG (SEQ ID NO: 89) | EGGLTMVRGVSSYGLDV (SEQ ID NO: 96) |
| 24G6 | HV-06 | EVQLLESGGGLVQ PGGSLRLSCAASG FTFSSYAMSWVRQ APGKGLEWVSAIS GSGGSTYYADSVK GRFTISRDNSKNTL YLQMNSLRAEDT AVYYCAKAYTPM AFFDYWGQGTLV TVSS (SEQ ID NO: 115) | SYAMS (SEQ ID NO: 77) | AISGSGGSTYYADSVKG (SEQ ID NO: 90) | AYTPMAFFDY (SEQ ID NO: 98) |
| 24A10 | HV-07 | EVQVLESGGGLVQ PGGSLRLSCAASG FTFSNYAMSWVR QAPGKGLEWVSAI SGSGGSTYYADSV KGRFTISRDNSKN TLYLQMNSLRAED TAVYYCAKGGWE LFYWGQGTLVTV SS (SEQ ID NO: 116) | NYAMS (SEQ ID NO: 79) | AISGSGGSTYYADSVKG (SEQ ID NO: 90) | GGWELFY (SEQ ID NO: 99) |
| 10E3 | HV-08 | EVQLVQSGAEVK KPGESLMISCKGS GYSFTNYWIGWV RQMPGKGLEWMG IIYPGDSDTRYSPS FQGQVTISADKSIS TAYLQWSSLKASD TAMYFCARRRQGI WGDALDIWGQGT LVTVSS (SEQ ID NO: 117) | NYWIG (SEQ ID NO: 80) | IIYPGDSDTRYSPSFQG (SEQ ID NO: 91) | RRQGIWGDALDI (SEQ ID NO: 100) |

TABLE 1B-continued

Exemplary Anti-Human TREM2 Antibody Heavy Chain Variable Region
Amino Acid Sequences

| Ab ID. | VH Group | VH Amino Acid Sequence | CDRH1 | CDRH2 | CDRH3 |
|---|---|---|---|---|---|
| 13E7 14C12 | HV-09 | EVQLVQSGAEVK KPGESLMISCKGS GYSFTSYWIGWVR QMPGKGLEWMGII YPGDSDTRYSPSF QGQVTISADKSIST AYLQWSSLKASDT AMYFCARRRQGI WGDALDFWGQGT LVTVSS (SEQ ID NO: 118) | SYWIG (SEQ ID NO: 81) | IIYPGDSDTRYSPSFQG (SEQ ID NO: 91) | RRQGIWGDALDF (SEQ ID NO: 101) |
| 25F12 | HV-10 | QVQLQQWGAGLL KPSETLSLTCAVY GGSFSSYYWSWIR QPPGKGLEWIGEI NHSGNTNYNPSLK SRVTISVDTSKNQF SLKLSSVTAADTA VYYCAREGYYDIL TGYHDAFDIWDQ GTMVTVFS (SEQ ID NO: 119) | SYYWS (SEQ ID NO: 82) | EINHSGNTNYNPSLKS (SEQ ID NO: 92) | EGYYDILTGYHDAFDI (SEQ ID NO: 102) |
| 32E3 | HV-11 | EVQLVQSGAEVK KPGESLKISCKGSG YSFTSYWIGWVRQ MPGKGLEWMGIIY PGDSDTRYSPSFQ GQVTISADKSISTA YLQWSTLKASDT AIYYCARHDIIPAA PGAFDIWGQGTM VTVSS (SEQ ID NO: 120) | SYWIG (SEQ ID NO: 81) | IIYPGDSDTRYSPSFQG (SEQ ID NO: 91) | HDIIPAAPGAFDI (SEQ ID NO: 103) |
| 24F4 | HV-12 | EVQLVQSGAEVK KPGESLKISCKGSG YTFTSYWIGWVR QMPGKGLEWMGII YPGDSDTRYSPSF QGQVTISVDKSSS TAYLQWSSLKASD TAIYYCTRQAIAV TGLGGFDPWGQG TLVTVSS (SEQ ID NO: 121) | SYWIG (SEQ ID NO: 81) | IIYPGDSDTRYSPSFQG (SEQ ID NO: 91) | QAIAVTGLGGFDP (SEQ ID NO: 104) |
| 16B8 | HV-13 | QVQLVQSGAEVK KPGASVKVSCKAS GYTFTNYGISWVR QAPGQGLEWMG WISAYNGNTNYA QKLQGRVTMTTD TSTSTVYMELRSL RSDDTAVYYCAR RGYSYGSFDYWG QGTLVTVSS (SEQ ID NO: 122) | NYGIS (SEQ ID NO: 83) | WISAYNGNTNYAQKLQG (SEQ ID NO: 93) | RGYSYGSFDY (SEQ ID NO: 105) |
| 4C5 | HV-14 | EVQLVQSGAEVK KPGESLKISCKGSG HSFTNYWIAWVR QMPGKGLEWMGII YPGDSDTRYSPSF QGQVTISADKSIST AYLQWSSLKASDT AVYFCARQRTFYY DSSGYFDYWGQG TLVTVSS (SEQ ID NO: 123) | NYWIA (SEQ ID NO: 84) | IIYPGDSDTRYSPSFQG (SEQ ID NO: 91) | QRTFYYDSSGYFDY (SEQ ID NO: 106) |

TABLE 1B-continued

Exemplary Anti-Human TREM2 Antibody Heavy Chain Variable Region
Amino Acid Sequences

| Ab ID. | VH Group | VH Amino Acid Sequence | CDRH1 | CDRH2 | CDRH3 |
|---|---|---|---|---|---|
| 6E7 | HV-15 | EVQLVQSGAEVK KPGESLKISCKGSG YSFTSYWIAWVRQ MPGKGLEWMGIIY PGDSDTRYSPSFQ GQVTISADKSISTA YLQWSSLKASDTA MYFCARQRTFYY DSSDYFDYWGQG TLVTVSS (SEQ ID NO: 124) | SYWIA (SEQ ID NO: 85) | IIYPGDSDTRYSPSFQG (SEQ ID NO: 91) | QRTFYYDSSDYFDY (SEQ ID NO: 107) |
| 5E3 | HV-16 | QVQLVQSGAEVK KPGASVKVSCKAS GYTFTGYYIHWVR QAPGLGLEWMGW INPYSGGTTSAQK FQGRVTMTRDTSI SSAYMELSRLRSD DTAVYYCARDGG YLALYGTDVWGQ GTTVTVSS (SEQ ID NO: 125) | GYYIH (SEQ ID NO: 86) | WINPYSGGTTSAQKFQG (SEQ ID NO: 94) | DGGYLALYGTDV (SEQ ID NO: 108) |
| 4G10 | HV-17 | EVQLVQSGAEVK KPGESLKISCKGSG YSFPSYWIAWVRQ MPGKGLEWMGIIY PGDSDTRYSPSFQ GQVTISADKSISTA FLKWSSLKASDTA MYFCARQGIEVTG TGGLDVWGQGTT VTVSS (SEQ ID NO: 126) | SYWIA (SEQ ID NO: 85) | IIYPGDSDTRYSPSFQG (SEQ ID NO: 91) | QGIEVTGTGGLDV (SEQ ID NO: 109) |

The TREM2 agonist antigen binding proteins of the invention may comprise one or more of the CDRs presented in Table 1A (light chain CDRs; i.e. CDRLs) and Table 1B (heavy chain CDRs, i.e. CDRHs). For instance, in certain embodiments, the TREM2 agonist antigen binding proteins comprise one or more light chain CDRs selected from (i) a CDRL1 selected from SEQ ID NOs: 5 to 18, (ii) a CDRL2 selected from SEQ ID NOs: 19 to 30, and (iii) a CDRL3 selected from SEQ ID NOs: 31 to 45, and (iv) a CDRL of (i), (ii) and (iii) that contains one or more, e.g., one, two, three, four or more amino acid substitutions (e.g., conservative amino acid substitutions), deletions or insertions of no more than five, four, three, two, or one amino acids. In these and other embodiments, the TREM2 agonist antigen binding proteins comprise one or more heavy chain CDRs selected from (i) a CDRH1 selected from SEQ ID NOs: 77 to 86, (ii) a CDRH2 selected from SEQ ID NOs: 87 to 94, and (iii) a CDRH3 selected from SEQ ID NOs: 95 to 109, and (iv) a CDRH of (i), (ii) and (iii) that contains one or more, e.g., one, two, three, four or more amino acid substitutions (e.g., conservative amino acid substitutions), deletions or insertions of no more than five, four, three, two, or one amino acids amino acids.

In certain embodiments, the TREM2 agonist antigen binding proteins may comprise 1, 2, 3, 4, 5, or 6 variant forms of the CDRs listed in Tables 1A and 1B, each having at least 80%, 85%, 90% or 95% sequence identity to a CDR sequence listed in Tables 1A and 1B. In some embodiments, the TREM2 agonist antigen binding proteins include 1, 2, 3, 4, 5, or 6 of the CDRs listed in Tables 1A and 1B, each differing by no more than 1, 2, 3, 4 or 5 amino acids from the CDRs listed in these tables. In some embodiments, the TREM2 agonist antigen binding proteins of the invention comprise a CDRL1 comprising a sequence selected from SEQ ID NOs: 5-18 or a variant thereof having one, two, three or four amino acid substitutions; a CDRL2 comprising a sequence selected from SEQ ID NOs: 19-30 or a variant thereof having one, two, three or four amino acid substitutions; a CDRL3 comprising a sequence selected from SEQ ID NOs: 31-45 or a variant thereof having one, two, three or four amino acid substitutions; a CDRH1 comprising a sequence selected from SEQ ID NOs: 77-86 or a variant thereof having one, two, three or four amino acid substitutions; a CDRH2 comprising a sequence selected from SEQ ID NOs: 87-94 or a variant thereof having one, two, three or four amino acid substitutions; and a CDRH3 comprising a sequence selected from SEQ ID NOs: 95-109 or a variant thereof having one, two, three or four amino acid substitutions. In other embodiments, the TREM2 agonist antigen binding proteins of the invention comprise a CDRL1 comprising a sequence selected from SEQ ID NOs: 5-18; a CDRL2 comprising a sequence selected from SEQ ID NOs: 19-30; a CDRL3 comprising a sequence selected from SEQ ID NOs: 31-45; a CDRH1 comprising a sequence selected from SEQ ID NOs: 77-86; a CDRH2 comprising a sequence selected from SEQ ID NOs: 87-94; and a CDRH3 comprising a sequence selected from SEQ ID NOs: 95-109.

In particular embodiments, the TREM2 agonist antigen binding proteins of the invention comprise a light chain variable region comprising a CDRL1, a CDRL2, and a CDRL3, wherein: (a) CDRL1, CDRL2, and CDRL3 have the sequence of SEQ ID NOs: 5, 19, and 31, respectively; (b) CDRL1, CDRL2, and CDRL3 have the sequence of SEQ ID NOs: 6, 20, and 32, respectively; (c) CDRL1, CDRL2, and CDRL3 have the sequence of SEQ ID NOs: 6, 21, and 33, respectively; (d) CDRL1, CDRL2, and CDRL3 have the sequence of SEQ ID NOs: 6, 20, and 33, respectively; (e) CDRL1, CDRL2, and CDRL3 have the sequence of SEQ ID NOs: 7, 22, and 34, respectively; (f) CDRL1, CDRL2, and CDRL3 have the sequence of SEQ ID NOs: 8, 22, and 35, respectively; (g) CDRL1, CDRL2, and CDRL3 have the sequence of SEQ ID NOs: 9, 22, and 36, respectively; (h) CDRL1, CDRL2, and CDRL3 have the sequence of SEQ ID NOs: 10, 23, and 37, respectively; (i) CDRL1, CDRL2, and CDRL3 have the sequence of SEQ ID NOs: 11, 23, and 38, respectively; (j) CDRL1, CDRL2, and CDRL3 have the sequence of SEQ ID NOs: 12, 24, and 39, respectively; (k) CDRL1, CDRL2, and CDRL3 have the sequence of SEQ ID NOs: 13, 25, and 40, respectively; (l) CDRL1, CDRL2, and CDRL3 have the sequence of SEQ ID NOs: 14, 26, and 41, respectively; (m) CDRL1, CDRL2, and CDRL3 have the sequence of SEQ ID NOs: 15, 27, and 42, respectively; (n) CDRL1, CDRL2, and CDRL3 have the sequence of SEQ ID NOs: 16, 28, and 43, respectively; (o) CDRL1, CDRL2, and CDRL3 have the sequence of SEQ ID NOs: 17, 29, and 44, respectively, or (p) CDRL1, CDRL2, and CDRL3 have the sequence of SEQ ID NOs: 18, 30, and 45, respectively.

In other particular embodiments, the TREM2 agonist antigen binding proteins of the invention comprise a heavy chain variable region comprising a CDRH1, a CDRH2, and a CDRH3, wherein: (a) CDRH1, CDRH2, and CDRH3 have the sequence of SEQ ID NOs: 77, 87, and 95, respectively; (b) CDRH1, CDRH2, and CDRH3 have the sequence of SEQ ID NOs: 78, 88, and 96, respectively; (c) CDRH1, CDRH2, and CDRH3 have the sequence of SEQ ID NOs: 78, 88, and 97, respectively; (d) CDRH1, CDRH2, and CDRH3 have the sequence of SEQ ID NOs: 78, 89, and 96, respectively; (e) CDRH1, CDRH2, and CDRH3 have the sequence of SEQ ID NOs: 77, 90, and 98, respectively; (f) CDRH1, CDRH2, and CDRH3 have the sequence of SEQ ID NOs: 79, 90, and 99, respectively; (g) CDRH1, CDRH2, and CDRH3 have the sequence of SEQ ID NOs: 80, 91, and 100, respectively; (h) CDRH1, CDRH2, and CDRH3 have the sequence of SEQ ID NOs: 81, 91, and 101, respectively; (i) CDRH1, CDRH2, and CDRH3 have the sequence of SEQ ID NOs: 82, 92, and 102, respectively; (j) CDRH1, CDRH2, and CDRH3 have the sequence of SEQ ID NOs: 81, 91, and 103, respectively; (k) CDRH1, CDRH2, and CDRH3 have the sequence of SEQ ID NOs: 81, 91, and 104, respectively; (l) CDRH1, CDRH2, and CDRH3 have the sequence of SEQ ID NOs: 83, 93, and 105, respectively; (m) CDRH1, CDRH2, and CDRH3 have the sequence of SEQ ID NOs: 84, 91, and 106, respectively; (n) CDRH1, CDRH2, and CDRH3 have the sequence of SEQ ID NOs: 85, 91, and 107, respectively; (o) CDRH1, CDRH2, and CDRH3 have the sequence of SEQ ID NOs: 86, 94, and 108, respectively; or (p) CDRH1, CDRH2, and CDRH3 have the sequence of SEQ ID NOs: 85, 91, and 109, respectively.

In certain embodiments, the TREM2 agonist antigen binding proteins of the invention comprise a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 5, 19, and 31, respectively, and CDRH1, CDRH2, and CDRH3 have the sequence of SEQ ID NOs: 77, 87, and 95, respectively;

(b) CDRL1, CDRL2, and CDRL3 have the sequence of SEQ ID NOs: 6, 20, and 32, respectively, and CDRH1, CDRH2, and CDRH3 have the sequence of SEQ ID NOs: 78, 88, and 96, respectively;

(c) CDRL1, CDRL2, and CDRL3 have the sequence of SEQ ID NOs: 6, 21, and 33, respectively, and CDRH1, CDRH2, and CDRH3 have the sequence of SEQ ID NOs: 78, 88, and 97, respectively;

(d) CDRL1, CDRL2, and CDRL3 have the sequence of SEQ ID NOs: 6, 20, and 33, respectively, and CDRH1, CDRH2, and CDRH3 have the sequence of SEQ ID NOs: 78, 88, and 97, respectively;

(e) CDRL1, CDRL2, and CDRL3 have the sequence of SEQ ID NOs: 6, 20, and 33, respectively, and CDRH1, CDRH2, and CDRH3 have the sequence of SEQ ID NOs: 78, 89, and 96, respectively;

(f) CDRL1, CDRL2, and CDRL3 have the sequence of SEQ ID NOs: 7, 22, and 34, respectively, and CDRH1, CDRH2, and CDRH3 have the sequence of SEQ ID NOs: 77, 87, and 95, respectively;

(g) CDRL1, CDRL2, and CDRL3 have the sequence of SEQ ID NOs: 8, 22, and 35, respectively, and CDRH1, CDRH2, and CDRH3 have the sequence of SEQ ID NOs: 77, 90, and 98, respectively;

(h) CDRL1, CDRL2, and CDRL3 have the sequence of SEQ ID NOs: 9, 22, and 36, respectively, and CDRH1, CDRH2, and CDRH3 have the sequence of SEQ ID NOs: 79, 90, and 99, respectively;

(i) CDRL1, CDRL2, and CDRL3 have the sequence of SEQ ID NOs: 10, 23, and 37, respectively, and CDRH1, CDRH2, and CDRH3 have the sequence of SEQ ID NOs: 80, 91, and 100, respectively;

(j) CDRL1, CDRL2, and CDRL3 have the sequence of SEQ ID NOs: 10, 23, and 37, respectively, and CDRH1, CDRH2, and CDRH3 have the sequence of SEQ ID NOs: 81, 91, and 101, respectively;

(k) CDRL1, CDRL2, and CDRL3 have the sequence of SEQ ID NOs: 11, 23, and 38, respectively, and CDRH1, CDRH2, and CDRH3 have the sequence of SEQ ID NOs: 82, 92, and 102, respectively;

(l) CDRL1, CDRL2, and CDRL3 have the sequence of SEQ ID NOs: 12, 24, and 39, respectively, and CDRH1, CDRH2, and CDRH3 have the sequence of SEQ ID NOs: 81, 91, and 103, respectively;

(m) CDRL1, CDRL2, and CDRL3 have the sequence of SEQ ID NOs: 13, 25, and 40, respectively, and CDRH1, CDRH2, and CDRH3 have the sequence of SEQ ID NOs: 81, 91, and 104, respectively;

(n) CDRL1, CDRL2, and CDRL3 have the sequence of SEQ ID NOs: 14, 26, and 41, respectively, and CDRH1, CDRH2, and CDRH3 have the sequence of SEQ ID NOs: 83, 93, and 105, respectively;

(o) CDRL1, CDRL2, and CDRL3 have the sequence of SEQ ID NOs: 15, 27, and 42, respectively, and CDRH1, CDRH2, and CDRH3 have the sequence of SEQ ID NOs: 84, 91, and 106, respectively;

(p) CDRL1, CDRL2, and CDRL3 have the sequence of SEQ ID NOs: 16, 28, and 43, respectively, and CDRH1, CDRH2, and CDRH3 have the sequence of SEQ ID NOs: 85, 91, and 107, respectively;

(q) CDRL1, CDRL2, and CDRL3 have the sequence of SEQ ID NOs: 17, 29, and 44, respectively, and CDRH1, CDRH2, and CDRH3 have the sequence of SEQ ID NOs: 86, 94, and 108, respectively; or (r) CDRL1, CDRL2, and CDRL3 have the sequence of SEQ ID NOs: 18, 30, and 45, respectively, and CDRH1, CDRH2, and CDRH3 have the sequence of SEQ ID NOs: 85, 91, and 109, respectively.

In one embodiment, the TREM2 agonist antigen binding protein comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 10, 23, and 37, respectively, and CDRH1, CDRH2, and CDRH3 have the sequence of SEQ ID NOs: 80, 91, and 100, respectively. In another embodiment, the TREM2 agonist antigen binding protein comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 10, 23, and 37, respectively, and CDRH1, CDRH2, and CDRH3 have the sequence of SEQ ID NOs: 81, 91, and 101, respectively. In yet another embodiment, the TREM2 agonist antigen binding protein comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 15, 27, and 42, respectively, and CDRH1, CDRH2, and CDRH3 have the sequence of SEQ ID NOs: 84, 91, and 106, respectively. In still another embodiment, the TREM2 agonist antigen binding protein comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 16, 28, and 43, respectively, and CDRH1, CDRH2, and CDRH3 have the sequence of SEQ ID NOs: 85, 91, and 107, respectively. In one particular embodiment, the TREM2 agonist antigen binding protein comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 17, 29, and 44, respectively, and CDRH1, CDRH2, and CDRH3 have the sequence of SEQ ID NOs: 86, 94, and 108, respectively. In another particular embodiment, the TREM2 agonist antigen binding protein comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 8, 22, and 35, respectively, and CDRH1, CDRH2, and CDRH3 have the sequence of SEQ ID NOs: 77, 90, and 98, respectively.

In certain embodiments, the TREM2 agonist antigen binding proteins of the invention comprise an immunoglobulin heavy chain variable region (VH) and an immunoglobulin light chain variable region (VL) from an antibody that specifically binds to human TREM2, such as the antibodies described herein. The "variable region," used interchangeably herein with "variable domain" (variable region of a light chain (VL), variable region of a heavy chain (VH)), refers to the region in each of the light and heavy immunoglobulin chains which is involved directly in binding the antibody to the antigen. As discussed above, the regions of variable light and heavy chains have the same general structure and each region comprises four framework (FR) regions, the sequences of which are widely conserved, connected by three CDRs. The framework regions adopt a beta-sheet conformation and the CDRs may form loops connecting the beta-sheet structure. The CDRs in each chain are held in their three-dimensional structure by the framework regions and form, together with the CDRs from the other chain, the antigen binding site.

In some embodiments, the TREM2 agonist antigen binding proteins of the invention may comprise a light chain variable region selected from LV-01, LV-02, LV-03, LV-04, LV-05, LV-06, LV-07, LV-08, LV-09, LV-10, LV-11, LV-12, LV-13, LV-14, LV-15, LV-16, LV-17, and LV-18, as shown in Table 1A, and/or a heavy chain variable region selected from HV-01, HV-02, HV-03, HV-04, HV-05, HV-06, HV-07, HV-08, HV-09, HV-10, HV-11, HV-12, HV-13, HV-14, HV-15, HV-16, and HV-17, as shown in Table 1B, and functional fragments, derivatives, muteins and variants of these light chain and heavy chain variable regions.

Each of the light chain variable regions listed in Table 1A may be combined with any of the heavy chain variable regions listed in Table 1B to form an anti-TREM2 binding domain of the antigen binding proteins of the invention. Examples of such combinations include, but are not limited to: LV-01 (SEQ ID NO: 46) and HV-01 (SEQ ID NO: 110); LV-02 (SEQ ID NO: 47) and HV-02 (SEQ ID NO: 111); LV-03 (SEQ ID NO: 48) and HV-03 (SEQ ID NO: 112); LV-04 (SEQ ID NO: 49) and HV-04 (SEQ ID NO: 113); LV-05 (SEQ ID NO: 50) and HV-05 (SEQ ID NO: 114); LV-06 (SEQ ID NO: 51) and HV-01 (SEQ ID NO: 110); LV-07 (SEQ ID NO: 52) and HV-06 (SEQ ID NO: 115); LV-08 (SEQ ID NO: 53) and HV-07 (SEQ ID NO: 116); LV-09 (SEQ ID NO: 54) and HV-08 (SEQ ID NO: 117); LV-10 (SEQ ID NO: 55) and HV-09 (SEQ ID NO: 118); LV-11 (SEQ ID NO: 56) and HV-10 (SEQ ID NO: 119); LV-12 (SEQ ID NO: 57) and HV-11 (SEQ ID NO: 120); LV-13 (SEQ ID NO: 58) and HV-12 (SEQ ID NO: 121); LV-14 (SEQ ID NO: 59) and HV-13 (SEQ ID NO: 122); LV-15 (SEQ ID NO: 60) and HV-14 (SEQ ID NO: 123); LV-16 (SEQ ID NO: 61) and HV-15 (SEQ ID NO: 124); LV-17 (SEQ ID NO: 62) and HV-16 (SEQ ID NO: 125); and LV-18 (SEQ ID NO: 63) and HV-17 (SEQ ID NO: 126).

In certain embodiments, the TREM2 agonist antigen binding proteins of the invention comprise a light chain variable region comprising the sequence of LV-09 (SEQ ID NO: 54) and a heavy chain variable region comprising the sequence of HV-08 (SEQ ID NO: 117). In some embodiments, the TREM2 agonist antigen binding proteins of the invention comprise a light chain variable region comprising the sequence of LV-10 (SEQ ID NO: 55) and a heavy chain variable region comprising the sequence of HV-09 (SEQ ID NO: 118). In other embodiments, the TREM2 agonist antigen binding proteins of the invention comprise a light chain variable region comprising the sequence of LV-15 (SEQ ID NO: 60) and a heavy chain variable region comprising the sequence of HV-14 (SEQ ID NO: 123). In still other embodiments, the TREM2 agonist antigen binding proteins of the invention comprise a light chain variable region comprising the sequence of LV-16 (SEQ ID NO: 61) and a heavy chain variable region comprising the sequence of HV-15 (SEQ ID NO: 124). In some embodiments, the TREM2 agonist antigen binding proteins of the invention comprise a light chain variable region comprising the sequence of LV-17 (SEQ ID NO: 62) and a heavy chain variable region comprising the sequence of HV-16 (SEQ ID NO: 125). In certain embodiments, the TREM2 agonist antigen binding proteins of the invention comprise a light chain variable region comprising the sequence of LV-07 (SEQ ID NO: 52) and a heavy chain variable region comprising the sequence of HV-06 (SEQ ID NO: 115).

In some embodiments, the TREM2 agonist antigen binding proteins comprise a light chain variable region comprising a sequence of contiguous amino acids that differs from the sequence of a light chain variable region in Table 1A, i.e. a VL selected from LV-01, LV-02, LV-03, LV-04, LV-05, LV-06, LV-07, LV-08, LV-09, LV-10, LV-11, LV-12, LV-13, LV-14, LV-15, LV-16, LV-17, or LV-18, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some TREM2 agonist antigen binding proteins comprises a sequence of amino acids that has at least 70%, at least 75%, at least 80%, at least 85%, at least 90%, at least 95%, at least 97% or at least 99% sequence identity to the amino acid sequences of SEQ ID NOs: 46-63 (i.e. the light chain variable regions in Table 1A). In one embodiment, the TREM2 agonist antigen binding protein comprises a light chain variable region comprising a sequence that is at least 90% identical to a sequence selected from SEQ ID NOs: 46-63. In another embodiment, the TREM2 agonist antigen binding protein comprises a light chain variable region comprising a sequence that is at least 95% identical to a sequence selected from SEQ ID NOs: 46-63. In yet another embodiment, the TREM2 agonist antigen binding protein comprises a light chain variable region comprising a sequence selected from SEQ ID NOs: 46-63. In some embodiments, the TREM2 agonist antigen binding protein comprises a light chain variable region comprising a sequence of SEQ ID NO: 54. In other embodiments, the TREM2 agonist antigen binding protein comprises a light chain variable region comprising a sequence of SEQ ID NO: 55. In yet other embodiments, the TREM2 agonist antigen binding protein comprises a light chain variable region comprising a sequence of SEQ ID NO: 60. In still other embodiments, the TREM2 agonist antigen binding protein comprises a light chain variable region comprising a sequence of SEQ ID NO: 61. In certain embodiments, the TREM2 agonist antigen binding protein comprises a light chain variable region comprising a sequence of SEQ ID NO: 62. In other embodiments, the TREM2 agonist antigen binding protein comprises a light chain variable region comprising a sequence of SEQ ID NO: 52.

In these and other embodiments, the TREM2 agonist antigen binding proteins comprise a heavy chain variable region comprising a sequence of contiguous amino acids that differs from the sequence of a heavy chain variable region in Table 1B, i.e., a VH selected from HV-01, HV-02, HV-03, HV-04, HV-05, HV-06, HV-07, HV-08, HV-09, HV-10, HV-11, HV-12, HV-13, HV-14, HV-15, HV-16, or HV-17, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some TREM2 agonist antigen binding proteins comprises a sequence of amino acids that has at least 70%, at least 75%, at least 80%, at least 85%, at least 90%, at least 95%, at least 97% or at least 99% sequence identity to the amino acid sequences of SEQ ID NOs: 110-126 (i.e. the heavy chain variable regions in Table 1B). In one embodiment, the TREM2 agonist antigen binding protein comprises a heavy chain variable region comprising a sequence that is at least 90% identical to a sequence selected from SEQ ID NOs: 110-126. In another embodiment, the TREM2 agonist antigen binding protein comprises a heavy chain variable region comprising a sequence that is at least 95% identical to a sequence selected from SEQ ID NOs: 110-126. In yet another embodiment, the TREM2 agonist antigen binding protein comprises a heavy chain variable region comprising a sequence selected from SEQ ID NOs: 110-126. In some embodiments, the TREM2 agonist antigen binding protein comprises a heavy chain variable region comprising a sequence of SEQ ID NO: 117. In other embodiments, the TREM2 agonist antigen binding protein comprises a heavy chain variable region comprising a sequence of SEQ ID NO: 118. In yet other embodiments, the TREM2 agonist antigen binding protein comprises a heavy chain variable region comprising a sequence of SEQ ID NO: 123. In still other embodiments, the TREM2 agonist antigen binding protein comprises a heavy chain variable region comprising a sequence of SEQ ID NO: 124. In certain embodiments, the TREM2 agonist antigen binding protein comprises a heavy chain variable region comprising a sequence of SEQ ID NO: 125. In other embodiments, the TREM2 agonist antigen binding protein comprises a heavy chain variable region comprising a sequence of SEQ ID NO: 115.

The term "identity," as used herein, refers to a relationship between the sequences of two or more polypeptide molecules or two or more nucleic acid molecules, as determined by aligning and comparing the sequences. "Percent identity," as used herein, means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a predetermined portion of one or both sequences). The programs provide a default opening penalty and a default gap penalty, and a scoring matrix such as PAM 250 (Dayhoff et al., in Atlas of Protein Sequence and Structure, vol. 5, supp. 3, 1978) or BLOSUM62 (Henikoff et al., 1992, Proc. Natl. Acad. Sci. U.S.A. 89:10915-10919) can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res.

12:387; Genetics Computer Group, University of Wisconsin, Madison, WI). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

Variants of the anti-TREM2 antibodies described herein can be generated by substituting one or more amino acids in the light chain or heavy chain variable regions to address chemical liabilities (e.g. aspartate isomerization, asparagine deamidation, tryptophan and methionine oxidation) or correct covariance violations (see WO 2012/125495, which is hereby incorporated by reference in its entirety) as described in Example 7. Such variants can have improved biophysical, expression, and/or stability properties as compared with the parental antibody. Thus, in some embodiments, the TREM2 agonist antigen binding proteins of the invention comprise a light chain variable region and/or heavy chain variable region having one or more of the amino acid substitutions set forth in any of Tables 13-18.

Unless indicated otherwise by reference to a specific sequence, throughout the present specification and claims, the numbering of the amino acid residues in an immunoglobulin heavy chain or light chain is according to Kabat-EU numbering as described in Kabat et al., Sequences of Proteins of Immunological Interest, 5th Ed., US Department of Health and Human Services, NIH publication No. 91-3242, pp 662,680,689 (1991) and Edelman et al., Proc. Natl. Acad. USA, Vol. 63: 78-85 (1969). The Kabat numbering scheme is typically used when referring to the position of an amino acid within the variable regions, whereas the EU numbering scheme is generally used when referring to the position of an amino acid with an immunoglobulin constant region. A chart summarizing correspondence between Kabat and EU numbering schemes with other numbering schemes is available on the IMGT® website (the international ImMunoGeneTics information system).

An amino acid substitution in an amino acid sequence is typically designated herein with a one-letter abbreviation for the amino acid residue in a particular position, followed by the numerical amino acid position relative to an original sequence of interest, which is then followed by the one-letter abbreviation for the amino acid residue substituted in. For example, "T30D" symbolizes a substitution of a threonine residue by an aspartate residue at amino acid position 30, relative to the original sequence of interest. Another example, "S218G" symbolizes a substitution of a serine residue by a glycine residue at amino acid position 218, relative to the original amino acid sequence of interest.

In some embodiments, the TREM2 agonist antigen binding protein comprises a light chain variable region comprising the sequence of SEQ ID NO: 54 with a mutation at one or more amino acid positions 64, 79, 80, 85, 94, and/or 100. Such mutations can include V64G, V64A, Q79E, Q79D, S80P, S80A, F85V, F85L, F85A, F85D, F85I, F85L, F85M, F85T, W94F, W94Y, W94S, W94T, W94A, W94H, W94I, W94Q, P100R, P100Q, P100G, or combinations thereof. In these and other embodiments, the TREM2 agonist antigen binding protein comprises a heavy chain variable region comprising the sequence of SEQ ID NO: 117 with a mutation at one or more amino acid positions 19, 55, 56, 57, 58, and/or 104. In certain embodiments, the mutation is selected from M19K, M19R, M19T, M19E, M19N, M19Q, D55E, D55Q, D55N, D55T, S56A, S56Q, S56V, D57S, D57E, D57Q, T58A, T58V, W104F, W104Y, W104T, W104S, W104A, W104H, W104I, W104Q, or combinations thereof.

In other embodiments, the TREM2 agonist antigen binding protein comprises a light chain variable region comprising the sequence of SEQ ID NO: 55 with a mutation at one or more amino acid positions 64, 79, 80, 94, and/or 100. In some embodiments, the mutation is selected from V64G, V64A, Q79E, Q79D, S80P, S80A, W94F, W94Y, W94S, W94T, W94A, W94H, W94I, W94Q, P100R, P100Q, P100G, or combinations thereof. In certain embodiments, the mutation is selected from V64G, V64A, Q79E, S80P, S80A, W94Y, W94S, P100R, P100Q, or combinations thereof. For instance, in some embodiments, the TREM2 agonist antigen binding protein comprises a light chain variable region comprising the sequence of SEQ ID NO: 55 with one or more mutations selected from V64G, Q79E, 580P, W94Y, and P100Q. In these and other embodiments, the TREM2 agonist antigen binding protein comprises a heavy chain variable region comprising the sequence of SEQ ID NO: 118 with a mutation at one or more amino acid positions 19, 55, 56, 57, 58, and/or 104. Such mutations can include M19K, M19R, M19T, M19E, M19N, M19Q, D55E, D55Q, D55N, D55T, S56A, S56Q, S56V, D57S, D57E, D57Q, T58A, T58V, W104F, W104Y, W104T, W104S, W104A, W104H, W104I, W104Q, or combinations thereof. In certain embodiments, the mutation is selected from M19K, D55E, S56A, D57E, T58A, W104Y, W104T, or combinations thereof.

In certain other embodiments, the TREM2 agonist antigen binding protein comprises a light chain variable region comprising the sequence of SEQ ID NO: 60 with a mutation at one or more amino acid positions 60, 92, and/or 93. The mutation can be selected from L60S, L60P, L60D, L60A, D92E, D92Q, D92T, D92N, S93A, S93N, S93Q, S93V, or combinations thereof. In these and other embodiments, the TREM2 agonist antigen binding protein comprises a heavy chain variable region comprising the sequence of SEQ ID NO: 123 with a mutation at one or more amino acid positions 27, 55, 56, 57, 58, 105, and/or 106. In some embodiments, the mutation is selected from H27Y, H27D, H27F, H27N, D55E, D55Q, D55N, D55T, S56A, S56Q, S56V, D57S, D57E, D57Q, T58A, T58V, D105E, D105Q, D105T, D105N, D105G, S106A, S106Q, S106V, S106T, or combinations thereof.

In some embodiments, the TREM2 agonist antigen binding protein comprises a light chain variable region comprising the sequence of SEQ ID NO: 61 with a mutation at one or more amino acid positions 56, 57, 92, and/or 93. In certain embodiments, the mutation is selected from N56S, N56T, N56Q, N56E, G57A, G57V, D92E, D92Q, D92T, D92N, S93A, S93N, S93Q, S93V, or combinations thereof. In some embodiments, the mutation is selected from N56S, N56Q, G57A, D92E, D92Q, S93A, or combinations thereof. In particular embodiments, the TREM2 agonist antigen binding protein comprises a light chain variable region comprising the sequence of SEQ ID NO: 61 with one or more mutations selected from N56S, D92E, and S93A. In these and other embodiments, the TREM2 agonist antigen binding protein comprises a heavy chain variable region comprising the sequence of SEQ ID NO: 124 with a mutation at one or more amino acid positions 55, 56, 57, 58, 105, and/or 106. The mutation can be selected from D55E, D55Q, D55N, D55T, S56A, S56Q, S56V, D57S, D57E, D57Q, T58A, T58V, D105E, D105Q, D105T, D105N, D105G, S106A, S106Q, S106V, S106T, or combinations thereof. In certain embodiments, the mutation is D55E, D55Q, S56A, D57E, T58A, D105E, D105N, S106A, or combinations thereof. In some embodiments, the TREM2 agonist antigen binding protein comprises a heavy chain variable region comprising the sequence of SEQ ID NO: 124 with one or more mutations selected from D55E, S56A, D57E, D105E, and S106A.

In other embodiments, the TREM2 agonist antigen binding protein comprises a light chain variable region comprising the sequence of SEQ ID NO: 62 with a mutation at amino acid position 36, 46, 61 and/or 100. In particular embodiments, the mutation is selected from F36Y, S46L, S46R, S46V, S46F, K61R, P100Q, P100G, P100R or combinations thereof. In some embodiments, the mutation is F36Y, K61R, P100Q, or combinations thereof. In some embodiments, the mutation is S46L, P100Q, or combinations thereof. In these and other embodiments, the TREM2 agonist antigen binding protein comprises a heavy chain variable region comprising the sequence of SEQ ID NO: 125 with a mutation at one or more amino acid positions 43, 76, 85, 99, 100, and/or 116. The mutation can be selected from L43Q, L43K, L43H, I76T, R85S, R85G, R85N, R85D, D99E, D99Q, D99S, D99T, G100A, G100Y, G100V, T116L, T116M, T116P, T116R, or combinations thereof. In certain embodiments, the mutation is L43Q, I76T, R85S, D99E, G100A, G100Y, T116L, or combinations thereof.

In still other embodiments, the TREM2 agonist antigen binding protein comprises a light chain variable region comprising the sequence of SEQ ID NO: 52 with a mutation at amino acid position 91. The mutation can be selected from F91V, F91I, F91T, F91L, or F91D. In one embodiment, the mutation is F91V. In these and other embodiments, the TREM2 agonist antigen binding protein comprises a heavy chain variable region comprising the sequence of SEQ ID NO: 115 with a mutation at amino acid position 62 and/or 63. In particular embodiments, the mutation is selected from D62E, D62Q, D62T, D62N, S63A, S63Q, S63V, or combinations thereof. In some embodiments, the mutation is selected from D62E, D62Q, S63A, or combinations thereof.

In certain embodiments, the TREM2 agonist antigen binding proteins of the invention comprise a light chain variable region comprising the amino acid sequence of SEQ ID NO: 326 and a heavy chain variable region comprising the amino acid sequence of SEQ ID NO: 327. In certain embodiments, the TREM2 agonist antigen binding proteins of the invention comprise a light chain variable region comprising the amino acid sequence of SEQ ID NO: 328 and a heavy chain variable region comprising the amino acid sequence of SEQ ID NO: 329. In certain embodiments, the TREM2 agonist antigen binding proteins of the invention comprise a light chain variable region comprising the amino acid sequence of SEQ ID NO: 330 and a heavy chain variable region comprising the amino acid sequence of SEQ ID NO: 331. In certain embodiments, the TREM2 agonist antigen binding proteins of the invention comprise a light chain variable region comprising the amino acid sequence of SEQ ID NO: 332 and a heavy chain variable region comprising the amino acid sequence of SEQ ID NO: 333.

In certain embodiments, the TREM2 agonist antigen binding proteins of the invention comprise a light chain variable region consisting of or consisting essentially of the amino acid sequence of SEQ ID NO: 326, 328, 330 or 332. In certain embodiments, the TREM2 agonist antigen binding proteins of the invention comprise a heavy chain variable region consisting of or consisting essentially of the amino acid sequence of SEQ ID NO: 327, 329, 331 or 333. In a specific embodiment, the TREM2 agonist antigen binding proteins of the invention comprise a light chain variable region and a heavy chain variable region, wherein the light chain variable region consisting of or consisting essentially of the amino acid sequence of SEQ ID NO: 326 and the heavy chain variable region consisting of or consisting essentially of the amino acid sequence of SEQ ID NO: 327. In a specific embodiment, the TREM2 agonist antigen binding proteins of the invention comprise a light chain variable region and a heavy chain variable region, wherein the light chain variable region consisting of or consisting essentially of the amino acid sequence of SEQ ID NO: 328 and the heavy chain variable region consisting of or consisting essentially of the amino acid sequence of SEQ ID NO: 329. In a specific embodiment, the TREM2 agonist antigen binding proteins of the invention comprise a light chain variable region and a heavy chain variable region, wherein the light chain variable region consisting of or consisting essentially of the amino acid sequence of SEQ ID NO: 330 and the heavy chain variable region consisting of or consisting essentially of the amino acid sequence of SEQ ID NO: 331. In a specific embodiment, the TREM2 agonist antigen binding proteins of the invention comprise a light chain variable region and a heavy chain variable region, wherein the light chain variable region consisting of or consisting essentially of the amino acid sequence of SEQ ID NO: 332 and the heavy chain variable region consisting of or consisting essentially of the amino acid sequence of SEQ ID NO: 333.

Additional variants of the anti-TREM2 antibodies described herein can be generated by affinity modulating any of the anti-TREM2 antibodies described herein. An "affinity-modulated antibody" is an antibody that comprises one or more amino acid substitutions in its light chain variable region sequence and/or heavy chain variable region sequence that increases or decreases the affinity of the antibody for the target antigen as compared to the parental antibody that does not contain the amino acid substitutions. Antibody affinity modulation methods are known to those of skill in the art and can include CDR walking mutagenesis (Yang et al., J. Mol. Biol., 254, 392-403, 1995), chain shuffling (Marks et al., Bio/Technology, 10, 779-783, 1992), use of mutation strains of *E. coli* (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996), PCR techniques (Crameri, et al., Nature, 391, 288-291, 1998), and other mutagenesis strategies (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992). Methods of affinity modulation are discussed in Hoogenboom, Trends in Biotechnology, Vol. 15: 62-70, 1995 and Vaughan et al., Nature Biotechnology, 16: 535-539, 1998. One specific method for generating affinity-modulated variants of the anti-TREM2 antibodies described herein is the use of a yeast-display Fab mutagenesis library as described in Example 8.

In certain embodiments, the TREM2 agonist antigen binding proteins of the invention comprise a light chain variable region and/or heavy chain variable region from an affinity-modulated variant of the 6E7 antibody (Example 8). For instance, in some embodiments, the TREM2 agonist antigen binding proteins comprise a light chain variable region and/or a heavy chain variable region having one or more of the amino acid substitutions set forth in Table 23. In one embodiment, the TREM2 agonist antigen binding protein comprises a light chain variable region comprising the sequence of SEQ ID NO: 61 with a mutation at one or more amino acid positions 24, 31, 50, 52, 54, 56, 89, 92, 93, 94 and/or 96. In certain embodiments, the mutation is selected from R24A, S31R, A50S, A50G, S52G, L54R, N56K, N56R, N56L, N56T, Q89G, D92V, S93R, F94Y, F94L, R96H, R96L, or combinations thereof. In these and other embodiments, the TREM2 agonist antigen binding protein comprises a heavy chain variable region comprising the sequence of SEQ ID NO: 124 with a mutation at one or more amino acid positions 27, 28, 30, 32, 50, 54, 58, 60, 61, 63, 66, 99, 101, 103, 104, and/or 110. In some embodiments, the mutation is selected from Y27S, S28G, S28H, T30N, T30G, T30E, T30A, Y32E, I50T, G54S, T58V, Y60L, S61A, S63G, S63E, G66D, Q99G, Q99S, Q99M, T101G, Y103R, Y104G, F110S, or combinations thereof. Amino acid sequences for light chain and heavy chain variable regions and associated CDRs of exemplary variants of the 6E7 antibody with improved affinity are set forth below in Tables 2A and 2B, respectively. Amino acid sequences for light chain and heavy chain variable regions and associated CDRs of exemplary variants of the 6E7 antibody with reduced affinity are set forth below in Tables 3A and 3B, respectively. The corresponding sequences for the 6E7 antibody are listed for comparison.

TABLE 2A

Light Chain Variable Region Amino Acid Sequences for Improved Affinity TREM2 Antibodies

| Variant Ab ID. | VL Group | VL Amino Acid Sequence | CDRL1 | CDRL2 | CDRL3 |
|---|---|---|---|---|---|
| 6E7 | LV-16 | DIQMTQSPSSVSASVGDRVTIT CRASQGISSWLAWYQQKPGK APKLLIYAASSLQNGVPSRFSG SGSGTDFTLTISSLQPEDFATYF CQQADSFPRTFGQGTKLEIK (SEQ ID NO: 61) | RASQGISSWLA (SEQ ID NO: 16) | AASSLQN (SEQ ID NO: 28) | QQADSFPRT (SEQ ID NO: 43) |
| V3 | LV-101 | DIQMTQSPSSVSASVGDRVTIT CRASQGISSWLAWYQQKPGK APKLLIYAASSRQNGVPSRFSG SGSGTDFTLTISSLQPEDFATYF CQQADRFPRTFGQGTKLEIK (SEQ ID NO: 153) | RASQGISSWLA (SEQ ID NO: 16) | AASSRQN (SEQ ID NO: 143) | QQADRFPRT (SEQ ID NO: 148) |
| V24 | LV-102 | DIQMTQSPSSVSASVGDRVTIT CRASQGISSWLAWYQQKPGK APKLLIYAASSLQKGVPSRFSG SGSGTDFTLTISSLQPEDFATYF CQQADSFPHTFGQGTKLEIK (SEQ ID NO: 154) | RASQGISSWLA (SEQ ID NO: 16) | AASSLQK (SEQ ID NO: 144) | QQADSFPHT (SEQ ID NO: 149) |
| V27 | LV-103 | DIQMTQSPSSVSASVGDRVTIT CRASQGISSWLAWYQQKPGK APKLLIYAASSLQRGVPSRFSG SGSGTDFTLTISSLQPEDFATYF CQQADSFPRTFGQGTKLEIK (SEQ ID NO: 155) | RASQGISSWLA (SEQ ID NO: 16) | AASSLQR SEQ ID NO: 145) | QQADSFPRT (SEQ ID NO: 43) |
| V40 | LV-104 | DIQMTQSPSSVSASVGDRVTIT CRASQGISSWLAWYQQKPGK APKLLIYAASSLQLGVPSRFSG SGSGTDFTLTISSLQPEDFATYF CQQADRFPRTFGQGTKLEIK (SEQ ID NO: 156) | RASQGISSWLA (SEQ ID NO: 16) | AASSLQL (SEQ ID NO: 146) | QQADRFPRT (SEQ ID NO: 148) |
| V48 | LV-105 | DIQMTQSPSSVSASVGDRVTIT CRASQGISSWLAWYQQKPGK APKLLIYAASSLQTGVPSRFSG SGSGTDFTLTISSLQPEDFATYF CQQADSLPRTFGQGTKLEIK (SEQ ID NO: 157) | RASQGISSWLA (SEQ ID NO: 16) | AASSLQT (SEQ ID NO: 26) | QQADSLPRT (SEQ ID NO: 150) |

TABLE 2A-continued

Light Chain Variable Region Amino Acid Sequences for Improved Affinity
TREM2 Antibodies

| Variant Ab ID. | VL Group | VL Amino Acid Sequence | CDRL1 | CDRL2 | CDRL3 |
|---|---|---|---|---|---|
| V49 V73 | LV-106 | DIQMTQSPSSVSASVGDRVTIT CRASQGISSWLAWYQQKPGK APKLLIYAASSRQNGVPSRFSG SGSGTDFTLTISSLQPEDFATYF CQQADSYPRTFGQGTKLEIK (SEQ ID NO: 158) | RASQGISSWLA (SEQ ID NO: 16) | AASSRQN (SEQ ID NO: 143) | QQADSYPRT (SEQ ID NO: 151) |
| V52 | LV-107 | DIQMTQSPSSVSASVGDRVTIT CRASQGISSWLAWYQQKPGK APKLLIYAASSLQRGVPSRFSG SGSGTDFTLTISSLQPEDFATYF CQQADRFPRTFGQGTKLEIK (SEQ ID NO: 159) | RASQGISSWLA (SEQ ID NO: 16) | AASSLQR (SEQ ID NO: 145) | QQADRFPRT (SEQ ID NO: 148) |
| V60 | LV-108 | DIQMTQSPSSVSASVGDRVTIT CRASQGISSWLAWYQQKPGK APKLLIYAASSLQRGVPSRFSG SGSGTDFTLTISSLQPEDFATYF CGQADSFPRTFGQGTKLEIK (SEQ ID NO: 160) | RASQGISSWLA (SEQ ID NO: 16) | AASSLQR (SEQ ID NO: 145) | GQADSFPRT (SEQ ID NO: 152) |
| V76 | LV-109 | DIQMTQSPSSVSASVGDRVTIT CRASQGISSWLAWYQQKPGK APKLLIYAASSLQKGVPSRFSG SGSGRDFTLTISSLQPEDFATYF CQQADSFPRTFGQGTKLEIK (SEQ ID NO: 161) | RASQGISSWLA (SEQ ID NO: 16) | AASSLQK (SEQ ID NO: 144) | QQADSFPRT (SEQ ID NO: 43) |
| V84 | LV-110 | DIQMTQSPSSVSASVGDRVTIT CRASQGISSWLAWYQQKPGK APKLLIYGASSLQNGVPSRFSG SGSGTDFTLTISSLQPEDFATYF CQQADSFPRTFGQGTKLEIK (SEQ ID NO: 162) | RASQGISSWLA (SEQ ID NO: 16) | GASSLQN (SEQ ID NO: 147) | QQADSFPRT (SEQ ID NO: 43) |

TABLE 2B

Heavy Chain Variable Region Amino Acid Sequences for Improved Affinity
TREM2 Antibodies

| Variant Ab ID. | VH Group | VH Amino Acid Sequence | FR1/ CDRH1 Border | CDRH1 | CDRH2 | CDRH3 |
|---|---|---|---|---|---|---|
| 6E7 | HV-15 | EVQLVQSGAEV KKPGESLKISCK GSGYSFTSYWIA WVRQMPGKGLE WMGIIYPGDSDT RYSPSFQGQVTI SADKSISTAYLQ WSSLKASDTAM YFCARQRTFYY DSSDYFDYWGQ GTLVTVSS (SEQ ID NO: 124) | YSFT (SEQ ID NO: 163) | SYWIA (SEQ ID NO: 85) | IIYPGDSDTRYSPSFQG (SEQ ID NO: 91) | QRTFYYDSSDYFDY (SEQ ID NO: 107) |
| V3 | HV-101 | EVQLVQSGAEV KKPGESLKISCK GSGYSFASYWIA WVRQMPGKGLE WMGIIYPGDSDT RYSPSFQDQVTI SADKSISTAYLQ WSSLKASDTAM YFCARGRTFYY DSSDYFDYWGQ GTLVTVSS (SEQ ID NO: 180) | YSFA (SEQ ID NO: 164) | SYWIA (SEQ ID NO: 85) | IIYPGDSDTRYSPSFQD (SEQ ID NO: 170) | GRTFYYDSSDYFDY (SEQ ID NO: 176) |

TABLE 2B-continued

Heavy Chain Variable Region Amino Acid Sequences for Improved Affinity
TREM2 Antibodies

| Variant Ab ID. | VH Group | VH Amino Acid Sequence | FR1/ CDRH1 Border | CDRH1 | CDRH2 | CDRH3 |
|---|---|---|---|---|---|---|
| V24 | HV-102 | EVQLVQSGAEV KKPGESLKISCK GSGYSFTSYWIA WVRQMPGKGLE WMGIIYPGDSD VRYSPSFQGQVT ISADKSISTAYLQ WSSLKASDTAM YFCARSRTFYYD SSDYFDYWGQG TLVTVSS (SEQ ID NO: 181) | YSFT (SEQ ID NO: 163) | SYWIA (SEQ ID NO: 85) | IIYPGDSDVRYSPSFQG (SEQ ID NO: 171) | SRTFYYDSSDYFDY (SEQ ID NO: 177) |
| V27 | HV-103 | EVQLVQSGAEV KKPGESLKISCK GSGYSFTSYWIA WVRQMPGKGLE WMGIIYPGDSDT RYAPSFQGQVTI SADKSISTAYLQ WSSLKASDTAM YFCVRSRTFYYD SSDYFDYWGQG TLVTVSS (SEQ ID NO: 182) | YSFT (SEQ ID NO: 163) | SYWIA (SEQ ID NO: 85) | IIYPGDSDTRYAPSFQG (SEQ ID NO: 172) | SRTFYYDSSDYFDY (SEQ ID NO: 177) |
| V40 | HV-104 | EVQLVQSGAEV KKPGESLKISCK GSGYSFGSYWIA WVRQMPGKGLE WMGIIYPGDSD VRYSPSFQGQVT ISADKSISTAYLQ WSSLKASDTAM YFCARQRTFYY DSSDYSDYWGQ GTLVTVSS (SEQ ID NO: 183) | YSFG (SEQ ID NO: 165) | SYWIA (SEQ ID NO: 85) | IIYPGDSDVRYSPSFQG (SEQ ID NO: 171) | QRTFYYDSSDYSDY (SEQ ID NO: 178) |
| V48 | HV-105 | EVQLVQSGAEV KKPGESLKISCK GSGYSFGSYWIA WVRQMPGKGLE WMGIIYPGDSD VRYSPSFQGQVT ISADKSISTAYLQ WSSLKASDTAM YFCARMRTFYY DSSDYFDYWGQ GTLVTVSS (SEQ ID NO: 184) | YSFG (SEQ ID NO: 165) | SYWIA (SEQ ID NO: 85) | IIYPGDSDVRYSPSFQG (SEQ ID NO: 171) | MRTFYYDSSDYFDY (SEQ ID NO: 179) |
| V49 | HV-106 | EVQLVQSGAEV KKPGESLKISCK GSGYSFNSYWIA WVRQMPGKGLE WMGTIYPGDSD TRLSPSFQGQVT ISADKSISTAYLQ WSSLKASDTAM YFCARSRTFYYD SSDYFDYWGQG TLVTVSS (SEQ ID NO: 185) | YSFN (SEQ ID NO: 166) | SYWIA (SEQ ID NO: 85) | TIYPGDSDTRLSPSFQG (SEQ ID NO: 173) | SRTFYYDSSDYFDY (SEQ ID NO: 177) |
| V52 | HV-107 | EVQLVQSGAEV KKPGESLKISCK GSGYSFESYWIA WVRQMPGKGLE WMGIIYPGDSDT RYSPSFQGQVTI SADKSISTAYLQ | YSFE (SEQ ID NO: 167) | SYWIA (SEQ ID NO: 85) | IIYPGDSDTRYSPSFQG (SEQ ID NO: 91) | GRTFYYDSSDYFDY (SEQ ID NO: 176) |

TABLE 2B-continued

Heavy Chain Variable Region Amino Acid Sequences for Improved Affinity
TREM2 Antibodies

| Variant Ab ID. | VH Group | VH Amino Acid Sequence | FR1/ CDRH1 Border | CDRH1 | CDRH2 | CDRH3 |
|---|---|---|---|---|---|---|
| | | WSSLKASDTAM YFCARGRTFYY DSSDYFDYWGQ GTLVTVSS (SEQ ID NO: 186) | | | | |
| V60 | HV-108 | EVQLVQSGAEV KKPGESLKISCK GSGYHFTSYWIA WVRQMPGKGLE WMGIIYPGDSD VRYSPSFQGQVT ISADKSISTAYLQ WSSLKASDTAM YFCARQRTFYY DSSDYSDYWGQ GTLVTVSS (SEQ ID NO: 187) | YHFT (SEQ ID NO: 168) | SYWIA (SEQ ID NO: 85) | IIYPGDSDVRYSPSFQG (SEQ ID NO: 171) | QRTFYYDSSDYSDY (SEQ ID NO: 178) |
| V73 | HV-109 | EVQLVQSGAEV KKPGESLKISCK GSGYSFGSYWIA WVRQMPGKGLE WMGIIYPGDSDT RYSPGFQGQVTI SADKSISTAYLQ WSSLKASDTAM YFCARGRTFYY DSSDYFDYWGQ GTLVTVSS (SEQ ID NO: 188) | YSFG (SEQ ID NO: 165) | SYWIA (SEQ ID NO: 85) | IIYPGDSDTRYSPGFQG (SEQ ID NO: 174) | GRTFYYDSSDYFDY (SEQ ID NO: 176) |
| V76 | HV-110 | EVQLVQSGAEV KKPGESLKISCK GSGYSFGSYWIA WVRQMPGKGLE WMGIIYPGDSDT RYSPEFQGQVTI SADKSISTAYLQ WSSLKASDTAM YFCARQRTFYY DSSDYSDYWGQ GTLVTVSS (SEQ ID NO: 189) | YSFG (SEQ ID NO: 165) | SYWIA (SEQ ID NO: 85) | IIYPGDSDTRYSPEFQG (SEQ ID NO: 175) | QRTFYYDSSDYSDY (SEQ ID NO: 178) |
| V84 | HV-111 | EVQLVQSGAEV KKPGESLKISCK GSGYGFTSYWIA WVRQMPGKGLE WMGIIYPGDSDT RYSPSFQGQVTI SADKSISTAYLQ WSSLKASDTAM YFCARQRTFYY DSSDYSDYWGQ GTLVTVSS (SEQ ID NO: 190) | YGFT (SEQ ID NO: 169) | SYWIA (SEQ ID NO: 85) | IIYPGDSDTRYSPSFQG (SEQ ID NO: 91) | QRTFYYDSSDYSDY (SEQ ID NO: 178) |

The TREM2 agonist antigen binding proteins of the invention may comprise one or more of the CDRs from the improved affinity variants presented in Table 2A (light chain CDRs; i.e. CDRLs) and Table 2B (heavy chain CDRs, i.e. CDRHs). In some embodiments, the TREM2 agonist antigen binding proteins comprise a consensus CDR sequence derived from the improved affinity variants. For instance, in one embodiment, the TREM2 agonist antigen binding proteins comprise a CDRL2 consensus sequence of $X_1ASSX_2QX_3$ (SEQ ID NO: 139), where $X_1$ is A or G; $X_2$ is L or R; and $X_3$ is N, K, R, L, or T. In another embodiment, the TREM2 agonist antigen binding proteins comprise a CDRL3 consensus sequence of $X_1QADX_2X_3PX_4T$ (SEQ ID NO: 140), where $X_1$ is Q or G; $X_2$ is S or R; $X_3$ is F, L, or Y; and $X_4$ is R or H. In yet another embodiment, the TREM2 agonist antigen binding proteins comprise a CDRH2 consensus sequence of $X_1IYPGDSDX_2RX_3X_4PX_5FQX_6$ (SEQ ID NO: 141), where $X_1$ is I or T; $X_2$ is T or V; $X_3$ is Y or L; $X_4$ is S or A; $X_5$ is S, G, or E; and $X_6$ is G or D. In still another embodiment, the TREM2 agonist antigen binding proteins comprise a CDRH3 consensus sequence of $X_1RTFYYDSSDYX_2DY$ (SEQ ID NO: 142), where $X_1$ is Q, G, S, or M; and $X_2$ is F or S. In certain embodiments, the TREM2 agonist antigen binding proteins comprise a light chain variable region comprising complementarity determining regions CDRL1, CDRL2, and CDRL3 and a heavy chain variable region comprising complementarity determining regions CDRH1, CDRH2, and CDRH3, wherein CDRL1 comprises the sequence of SEQ ID NO: 16, CDRL2 comprises the consensus sequence of SEQ ID NO: 139, CDRL3 comprises the consensus sequence of SEQ ID NO: 140, CDRH1 comprises the sequence of SEQ ID NO: 85, CDRH2 comprises the consensus sequence of SEQ ID NO: 141, and CDRH3 comprises the consensus sequence of SEQ ID NO: 142.

In some embodiments, the TREM2 agonist antigen binding proteins of the invention comprise a CDRL1 comprising the sequence of SEQ ID NO: 16; a CDRL2 comprising a sequence selected from SEQ ID NOs: 26 and 143-147; a CDRL3 comprising a sequence selected from SEQ ID NOs: 43 and 148-152; a CDRH1 comprising the sequence of SEQ ID NO: 85; a CDRH2 comprising a sequence selected from SEQ ID NOs: 91 and 170-175; and a CDRH3 comprising a sequence selected from SEQ ID NOs: 176-179.

In particular embodiments, the TREM2 agonist antigen binding proteins of the invention comprise a light chain variable region comprising a CDRL1, a CDRL2, and a CDRL3, wherein: (a) CDRL1, CDRL2, and CDRL3 have the sequence of SEQ ID NOs: 16, 143, and 148, respectively; (b) CDRL1, CDRL2, and CDRL3 have the sequence of SEQ ID NOs: 16, 144, and 149, respectively; (c) CDRL1, CDRL2, and CDRL3 have the sequence of SEQ ID NOs: 16, 145, and 43, respectively; (d) CDRL1, CDRL2, and CDRL3 have the sequence of SEQ ID NOs: 16, 146, and 148, respectively; (e) CDRL1, CDRL2, and CDRL3 have the sequence of SEQ ID NOs: 16, 26, and 150, respectively; (f) CDRL1, CDRL2, and CDRL3 have the sequence of SEQ ID NOs: 16, 143, and 151, respectively; (g) CDRL1, CDRL2, and CDRL3 have the sequence of SEQ ID NOs: 16, 145, and 148, respectively; (h) CDRL1, CDRL2, and CDRL3 have the sequence of SEQ ID NOs: 16, 145, and 152, respectively; (i) CDRL1, CDRL2, and CDRL3 have the sequence of SEQ ID NOs: 16, 144, and 43, respectively; or (j) CDRL1, CDRL2, and CDRL3 have the sequence of SEQ ID NOs: 16, 147, and 43, respectively.

In related embodiments, the TREM2 agonist antigen binding proteins of the invention comprise a heavy chain variable region comprising a CDRH1, a CDRH2, and a CDRH3, wherein: (a) CDRH1, CDRH2, and CDRH3 have the sequence of SEQ ID NOs: 85, 170, and 176, respectively; (b) CDRH1, CDRH2, and CDRH3 have the sequence of SEQ ID NOs: 85, 171, and 177, respectively; (c) CDRH1, CDRH2, and CDRH3 have the sequence of SEQ ID NOs: 85, 172, and 177, respectively; (d) CDRH1, CDRH2, and CDRH3 have the sequence of SEQ ID NOs: 85, 171, and 178, respectively; (e) CDRH1, CDRH2, and CDRH3 have the sequence of SEQ ID NOs: 85, 171, and 179, respectively; (f) CDRH1, CDRH2, and CDRH3 have the sequence of SEQ ID NOs: 85, 173, and 177, respectively; (g) CDRH1, CDRH2, and CDRH3 have the sequence of SEQ ID NOs: 85, 91, and 176, respectively; (h) CDRH1, CDRH2, and CDRH3 have the sequence of SEQ ID NOs: 85, 174, and 176, respectively; (i) CDRH1, CDRH2, and CDRH3 have the sequence of SEQ ID NOs: 85, 175, and 178, respectively; or (j) CDRH1, CDRH2, and CDRH3 have the sequence of SEQ ID NOs: 85, 91, and 178, respectively.

In certain embodiments, the TREM2 agonist antigen binding proteins of the invention comprise a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 16, 143, and 148, respectively, and CDRH1, CDRH2, and CDRH3 have the sequence of SEQ ID NOs: 85, 170, and 176, respectively;

(b) CDRL1, CDRL2, and CDRL3 have the sequence of SEQ ID NOs: 16, 144, and 149, respectively, and CDRH1, CDRH2, and CDRH3 have the sequence of SEQ ID NOs: 85, 171, and 177, respectively;

(c) CDRL1, CDRL2, and CDRL3 have the sequence of SEQ ID NOs: 16, 145, and 43, respectively, and CDRH1, CDRH2, and CDRH3 have the sequence of SEQ ID NOs: 85, 172, and 177, respectively;

(d) CDRL1, CDRL2, and CDRL3 have the sequence of SEQ ID NOs: 16, 146, and 148, respectively, and CDRH1, CDRH2, and CDRH3 have the sequence of SEQ ID NOs: 85, 171, and 178, respectively;

(e) CDRL1, CDRL2, and CDRL3 have the sequence of SEQ ID NOs: 16, 26, and 150, respectively, and CDRH1, CDRH2, and CDRH3 have the sequence of SEQ ID NOs: 85, 171, and 179, respectively;

(f) CDRL1, CDRL2, and CDRL3 have the sequence of SEQ ID NOs: 16, 143, and 151, respectively, and CDRH1, CDRH2, and CDRH3 have the sequence of SEQ ID NOs: 85, 173, and 177, respectively;

(g) CDRL1, CDRL2, and CDRL3 have the sequence of SEQ ID NOs: 16, 145, and 148, respectively, and CDRH1, CDRH2, and CDRH3 have the sequence of SEQ ID NOs: 85, 91, and 176, respectively;

(h) CDRL1, CDRL2, and CDRL3 have the sequence of SEQ ID NOs: 16, 145, and 152, respectively, and CDRH1, CDRH2, and CDRH3 have the sequence of SEQ ID NOs: 85, 171, and 178, respectively;

(i) CDRL1, CDRL2, and CDRL3 have the sequence of SEQ ID NOs: 16, 143, and 151, respectively, and CDRH1, CDRH2, and CDRH3 have the sequence of SEQ ID NOs: 85, 174, and 176, respectively;

(j) CDRL1, CDRL2, and CDRL3 have the sequence of SEQ ID NOs: 16, 144, and 43, respectively, and CDRH1, CDRH2, and CDRH3 have the sequence of SEQ ID NOs: 85, 175, and 178, respectively; or (k) CDRL1, CDRL2, and CDRL3 have the sequence of SEQ ID NOs: 16, 147, and 43, respectively, and CDRH1, CDRH2, and CDRH3 have the sequence of SEQ ID NOs: 85, 91, and 178, respectively.

In some embodiments, the TREM2 agonist antigen binding proteins of the invention may comprise a light chain variable region selected from LV-101, LV-102, LV-103, LV-104, LV-105, LV-106, LV-107, LV-108, LV-109, and LV-110, as shown in Table 2A, and/or a heavy chain variable region selected from HV-101, HV-102, HV-103, HV-104, HV-105, HV-106, HV-107, HV-108, HV-109, HV-110, and HV-111, as shown in Table 2B, or sequences that are at least 80% identical, at least 85% identical, at least 90% identical, or at least 95% identical to any of the sequences in Tables 2A and 2B. For instance, in certain embodiments, the TREM2 agonist antigen binding proteins comprise a light chain variable region comprising (i) a sequence that is at least 90% identical to a sequence selected from SEQ ID NOs: 153-162, (ii) a sequence that is at least 95% identical to a sequence selected from SEQ ID NOs: 153-162, or (iii) a sequence selected from SEQ ID NOs: 153-162. In related embodiments, the TREM2 agonist antigen binding proteins comprise a heavy chain variable region comprising (i) a sequence that is at least 90% identical to a sequence selected from SEQ ID NOs: 180-190, (ii) a sequence that is at least 95% identical to a sequence selected from SEQ ID NOs: 180-190, or (iii) a sequence selected from SEQ ID NOs: 180-190.

Each of the light chain variable regions listed in Table 2A may be combined with any of the heavy chain variable regions listed in Table 2B to form an anti-TREM2 binding domain of the antigen binding proteins of the invention. Examples of such combinations include, but are not limited to: LV-101 (SEQ ID NO: 153) and HV-101 (SEQ ID NO: 180); LV-102 (SEQ ID NO: 154) and HV-102 (SEQ ID NO:

181); LV-103 (SEQ ID NO: 155) and HV-103 (SEQ ID NO: 182); LV-104 (SEQ ID NO: 156) and HV-104 (SEQ ID NO: 183); LV-105 (SEQ ID NO: 157) and HV-105 (SEQ ID NO: 184); LV-106 (SEQ ID NO: 158) and HV-106 (SEQ ID NO: 185); LV-107 (SEQ ID NO: 159) and HV-107 (SEQ ID NO:

186); LV-108 (SEQ ID NO: 160) and HV-108 (SEQ ID NO: 187); LV-106 (SEQ ID NO: 158) and HV-109 (SEQ ID NO: 188); LV-109 (SEQ ID NO: 161) and HV-110 (SEQ ID NO: 189); and LV-110 (SEQ ID NO: 162) and HV-111 (SEQ ID NO: 190).

TABLE 3A

Light Chain Variable Region Amino Acid Sequences for Reduced Affinity TREM2 Antibodies

| Variant Ab ID. | VL Group | VL Amino Acid Sequence | CDRL1 | CDRL2 | CDRL3 |
|---|---|---|---|---|---|
| 6E7 | LV-16 | DIQMTQSPSSVSASVGDRVT ITCRASQGISSWLAWYQQKP GKAPKLLIYAASSLQNGVPS RFSGSGSGTDFTLTISSLQPE DFATYFCQQADSFPRTFGQG TKLEIK (SEQ ID NO: 61) | RASQGISSWLA (SEQ ID NO: 16) | AASSLQN (SEQ ID NO: 28) | QQADSFPRT (SEQ ID NO: 43) |
| V9 V30 V33 V44 V68 | LV-16 | DIQMTQSPSSVSASVGDRVT ITCRASQGISSWLAWYQQKP GKAPKLLIYAASSLQNGVPS RFSGSGSGTDFTLTISSLQPE DFATYFCQQADSFPRTFGQG TKLEIK (SEQ ID NO: 61) | RASQGISSWLA (SEQ ID NO: 16) | AASSLQN (SEQ ID NO: 28) | QQADSFPRT (SEQ ID NO: 43) |
| V10 | LV-201 | DIQMTQSPSSVSASVGDRVT ITCRASQGISSWLAWYQQKP GKAPKLLIYSASSLQNGVPS RFSGSGSGTDFTLTISSLQPE DFATYFCQQADSFPRTFGQG TKLEIK (SEQ ID NO: 295) | RASQGISSWLA (SEQ ID NO: 16) | SASSLQN (SEQ ID NO: 292) | QQADSFPRT (SEQ ID NO: 43) |
| V23 | LV-202 | DIQMTQSPSSVSASVGDRVT ITCRASQGISSWLAWYQQKP GKAPKLLIYAASSLQNGVPS RFSGSGSGTDFTLTISSLQPE DFATYFCQQADSFPLTFGQG TKLEIK (SEQ ID NO: 296) | RASQGISSWLA (SEQ ID NO: 16) | AASSLQN (SEQ ID NO: 28) | QQADSFPLT (SEQ ID NO: 294) |
| V57 | LV-203 | DIQMTQSPSSVSASVGDRVT ITCAASQGISSWLAWYQQKP GKAPKLLIYAASSLQNGVPS RFSGSGSGTDFTLTISSLQPE DFATYFCQQADSFPRTFGQG TKLEIK (SEQ ID NO: 297) | AASQGISSWLA (SEQ ID NO: 290) | AASSLQN (SEQ ID NO: 28) | QQADSFPRT (SEQ ID NO: 43) |
| V70 | LV-204 | DIQMTQSPSSVSASVGDRVT ITCRASQGISSWLAWYQQKP GKAPKLLIYAAGSLQNGVPS RFSGSGSGTDFTLTISSLQPE DFATYFCQQADSFPRTFGQG TKLEIK (SEQ ID NO: 298) | RASQGISSWLA (SEQ ID NO: 16) | AAGSLQN (SEQ ID NO: 293) | QQADSFPRT (SEQ ID NO: 43) |
| V83 | LV-205 | DIQMTQSPSSVSASVGDRVT ITCRASQGISSWLAWYQQKP GKAPKLLIYAASSLQNGVPS RFSGSGSGTDFTLTISSLQPE DFATYFCQQAVSFPRTFGQG TKLEIK (SEQ ID NO: 299) | RASQGISSWLA (SEQ ID NO: 16) | AASSLQN (SEQ ID NO: 28) | QQAVSFPRT (SEQ ID NO: 271) |
| V90 | LV-206 | DIQMTQSPSSVSASVGDRVT ITCRASQGISRWLAWYQQK PGKAPKLLIYAASSLQNGVP SRFSGSGSGTDFTLTISSLQP EDFATYFCQQADSFPRTFGQ GTKLEIK (SEQ ID NO: 300) | RASQGISRWLA (SEQ ID NO: 291) | AASSLQN (SEQ ID NO: 28) | QQADSFPRT (SEQ ID NO: 43) |

TABLE 3B

| Heavy Chain Variable Region Amino Acid Sequences for Reduced Affinity TREM2 Antibodies | | | | | | |
|---|---|---|---|---|---|---|
| Variant Ab ID. | VH Group | VH Amino Acid Sequence | FR1/ CDRH1 border | CDRH1 | CDRH2 | CDRH3 |
| 6E7 | HV-15 | EVQLVQSGAEV KKPGESLKISCK GSGYSFTSYWIA WVRQMPGKGLE WMGIIYPGDSDT RYSPSFQGQVTI SADKSISTAYLQ WSSLKASDTAM YFCARQRTFYY DSSDYFDYWGQ GTLVTVSS (SEQ ID NO: 124) | YSFT (SEQ ID NO: 163) | SYWIA (SEQ ID NO: 85) | IIYPGDSDTRYSPSFQG (SEQ ID NO: 91) | QRTFYYDSSDYFDY (SEQ ID NO: 107) |
| V9 | HV-201 | EVQLVQSGAEV KKPGESLKISCK GSGYSFTSYWIA WVRQMPGKGLE WMGIIYPGDSDT RYSPSFQGQVTI SADKSISTAYLQ WSSLKASDTAM YFCARQRGFYY DSSDYFDYWGQ GTLVTVSS (SEQ ID NO: 307) | YSFT (SEQ ID NO: 163) | SYWIA (SEQ ID NO: 85) | IIYPGDSDTRYSPSFQG (SEQ ID NO: 91) | QRGFYYDSSDYFDY (SEQ ID NO: 304) |
| V10 V23 V57 V70 V83 | HV-15 | EVQLVQSGAEV KKPGESLKISCK GSGYSFTSYWIA WVRQMPGKGLE WMGIIYPGDSDT RYSPSFQGQVTI SADKSISTAYLQ WSSLKASDTAM YFCARQRTFYY DSSDYFDYWGQ GTLVTVSS (SEQ ID NO: 124) | YSFT (SEQ ID NO: 163) | SYWIA (SEQ ID NO: 85) | IIYPGDSDTRYSPSFQG (SEQ ID NO: 91) | QRTFYYDSSDYFDY (SEQ ID NO: 107) |
| V30 | HV-202 | EVQLVQSGAEV KKPGESLKISCK GSGSSFTSYWIA WVRQMPGKGLE WMGIIYPGDSDT RYSPSFQGQVTI SADKSISTAYLQ WSSLKASDTAM YFCARQRTFYY DSSDYFDYWGQ GTLVTVSS (SEQ ID NO: 308) | SSFT (SEQ ID NO: 301) | SYWIA (SEQ ID NO: 85) | IIYPGDSDTRYSPSFQG (SEQ ID NO: 91) | QRTFYYDSSDYFDY (SEQ ID NO: 107) |
| V33 | HV-203 | EVQLVQSGAEV KKPGESLKISCK GSGYSFTSYWIA WVRQMPGKGLE WMGIIYPGDSDT RYSPSFQGQVTI SADKSISTAYLQ WSSLKASDTAM YFCARQRTFYG DSSDYFDYWGQ GTLVTVSS (SEQ ID NO: 309) | YSFT (SEQ ID NO: 163) | SYWIA (SEQ ID NO: 85) | IIYPGDSDTRYSPSFQG (SEQ ID NO: 91) | QRTFYGDSSDYFDY (SEQ ID NO: 305) |
| V44 | HV-204 | EVQLVQSGAEV KKPGESLKISCK GSGYSFTSYWIA WVRQMPGKGLE WMGIIYPSDSDT RYSPSFQGQVTI SADKSISTAYLQ WSSLKASDTAM | YSFT (SEQ ID NO: 163) | SYWIA (SEQ ID NO: 85) | IIYPSDSDTRYSPSFQG (SEQ ID NO: 303) | QRTFYYDSSDYFDY (SEQ ID NO: 107) |

TABLE 3B-continued

Heavy Chain Variable Region Amino Acid Sequences for Reduced Affinity
TREM2 Antibodies

| Variant Ab ID. | VH Group | VH Amino Acid Sequence | FR1/ CDRH1 border | CDRH1 | CDRH2 | CDRH3 |
|---|---|---|---|---|---|---|
| | | YFCARQRTFYY DSSDYFDYWGQ GTLVTVSS (SEQ ID NO: 310) | | | | |
| V68 | HV-205 | EVQLVQSGAEV KKPGESLKISCK GSGYSFTSYWIA WVRQMPGKGLE WMGIIYPGDSDT RYSPSFQGQVTI SADKSISTAYLQ WSSLKASDTAM YFCARQRTFRY DSSDYFDYWGQ GTLVTVSS (SEQ ID NO: 311) | YSFT (SEQ ID NO: 163) | SYWIA (SEQ ID NO: 85) | IIYPGDSDTRYSPSFQG (SEQ ID NO: 91) | QRTFRYDSSDYFDY (SEQ ID NO: 306) |
| V90 | HV-206 | EVQLVQSGAEV KKPGESLKISCK GSGYSFTSEWIA WVRQMPGKGLE WMGIIYPGDSDT RYSPSFQGQVTI SADKSISTAYLQ WSSLKASDTAM YFCARQRTFYY DSSDYFDYWGQ GTLVTVSS (SEQ ID NO: 312) | YSFT (SEQ ID NO: 163) | SEWIA (SEQ ID NO: 302) | IIYPGDSDTRYSPSFQG (SEQ ID NO: 91) | QRTFYYDSSDYFDY (SEQ ID NO: 107) |

The TREM2 agonist antigen binding proteins of the invention may comprise one or more of the CDRs from the reduced affinity variants presented in Table 3A (light chain CDRs; i.e. CDRLs) and Table 3B (heavy chain CDRs, i.e. CDRHs). In some embodiments, the TREM2 agonist antigen binding proteins comprise a consensus CDR sequence derived from the reduced affinity variants. For instance, in one embodiment, the TREM2 agonist antigen binding proteins comprise a CDRL1 consensus sequence of $X_1ASQGISX_2WLA$ (SEQ ID NO: 284), where $X_1$ is R or A; and $X_2$ is S or R. In another embodiment, the TREM2 agonist antigen binding proteins comprise a CDRL2 consensus sequence of $X_1AX_2SLQN$ (SEQ ID NO: 285), where $X_1$ is A or S; and $X_2$ is S or G. In another embodiment, the TREM2 agonist antigen binding proteins comprise a CDRL3 consensus sequence of $QQAX_1SFPX_2T$ (SEQ ID NO: 286), where $X_1$ is D or V; and $X_2$ is R or L. In another embodiment, the TREM2 agonist antigen binding proteins comprise a CDRH1 consensus sequence of $SX_1WIA$ (SEQ ID NO: 287), where $X_1$ is Y or E. In yet another embodiment, the TREM2 agonist antigen binding proteins comprise a CDRH2 consensus sequence of $IIYPX_1DSDTRYSPSFQG$ (SEQ ID NO: 288), where $X_1$ is G or S. In still another embodiment, the TREM2 agonist antigen binding proteins comprise a CDRH3 consensus sequence of $QRX_1FX_2X_3DSSDYFDY$ (SEQ ID NO: 289), where $X_1$ is T or G; $X_2$ is Y or R; and $X_3$ is Y or G. In certain embodiments, the TREM2 agonist antigen binding proteins comprise a light chain variable region comprising complementarity determining regions CDRL1, CDRL2, and CDRL3 and a heavy chain variable region comprising complementarity determining regions CDRH1, CDRH2, and CDRH3, wherein CDRL1 comprises the sequence of SEQ ID NO: 284, CDRL2 comprises the consensus sequence of SEQ ID NO: 285, CDRL3 comprises the consensus sequence of SEQ ID NO: 286, CDRH1 comprises the sequence of SEQ ID NO: 287, CDRH2 comprises the consensus sequence of SEQ ID NO: 288, and CDRH3 comprises the consensus sequence of SEQ ID NO: 289.

In some embodiments, the TREM2 agonist antigen binding proteins of the invention comprise a CDRL1 comprising a sequence selected from SEQ ID NOs: 16, 290, and 291; a CDRL2 comprising a sequence selected from SEQ ID NOs: 28, 292, and 293; a CDRL3 comprising a sequence selected from SEQ ID NOs: 43, 294, and 271; a CDRH1 comprising the sequence of SEQ ID NO: 85 or SEQ ID NO: 302; a CDRH2 comprising the sequence of SEQ ID NO: 91 or SEQ ID NO: 303; and a CDRH3 comprising a sequence selected from SEQ ID NOs: 107 and 304-306.

In particular embodiments, the TREM2 agonist antigen binding proteins of the invention comprise a light chain variable region comprising a CDRL1, a CDRL2, and a CDRL3, wherein: (a) CDRL1, CDRL2, and CDRL3 have the sequence of SEQ ID NOs: 16, 28, and 43, respectively; (b) CDRL1, CDRL2, and CDRL3 have the sequence of SEQ ID NOs: 16, 292, and 43, respectively; (c) CDRL1, CDRL2, and CDRL3 have the sequence of SEQ ID NOs: 16, 28, and 294, respectively; (d) CDRL1, CDRL2, and CDRL3 have the sequence of SEQ ID NOs: 290, 28, and 43, respectively; (e) CDRL1, CDRL2, and CDRL3 have the sequence of SEQ ID NOs: 16, 293, and 43, respectively; (f) CDRL1, CDRL2, and CDRL3 have the sequence of SEQ ID NOs: 16, 28, and 271, respectively; or (g) CDRL1, CDRL2, and CDRL3 have the sequence of SEQ ID NOs: 291, 28, and 43, respectively.

In related embodiments, the TREM2 agonist antigen binding proteins of the invention comprise a heavy chain variable region comprising a CDRH1, a CDRH2, and a CDRH3, wherein: (a) CDRH1, CDRH2, and CDRH3 have the sequence of SEQ ID NOs: 85, 91, and 304, respectively; (b) CDRH1, CDRH2, and CDRH3 have the sequence of SEQ ID NOs: 85, 91, and 107, respectively; (c) CDRH1, CDRH2, and CDRH3 have the sequence of SEQ ID NOs: 85, 91, and 305, respectively; (d) CDRH1, CDRH2, and CDRH3 have the sequence of SEQ ID NOs: 85, 303, and 107, respectively; (e) CDRH1, CDRH2, and CDRH3 have the sequence of SEQ ID NOs: 85, 91, and 306, respectively; or (0 CDRH1, CDRH2, and CDRH3 have the sequence of SEQ ID NOs: 302, 91, and 107, respectively.

In certain embodiments, the TREM2 agonist antigen binding proteins of the invention comprise a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 16, 28, and 43, respectively, and CDRH1, CDRH2, and CDRH3 have the sequence of SEQ ID NOs: 85, 91, and 304, respectively;

(b) CDRL1, CDRL2, and CDRL3 have the sequence of SEQ ID NOs: 16, 292, and 43, respectively, and CDRH1, CDRH2, and CDRH3 have the sequence of SEQ ID NOs: 85, 91, and 107, respectively;

(c) CDRL1, CDRL2, and CDRL3 have the sequence of SEQ ID NOs: 16, 28, and 294, respectively, and CDRH1, CDRH2, and CDRH3 have the sequence of SEQ ID NOs: 85, 91, and 107, respectively;

(d) CDRL1, CDRL2, and CDRL3 have the sequence of SEQ ID NOs: 16, 28, and 43, respectively, and CDRH1, CDRH2, and CDRH3 have the sequence of SEQ ID NOs: 85, 91, and 107, respectively;

(e) CDRL1, CDRL2, and CDRL3 have the sequence of SEQ ID NOs: 16, 28, and 43, respectively, and CDRH1, CDRH2, and CDRH3 have the sequence of SEQ ID NOs: 85, 91, and 305, respectively;

(f) CDRL1, CDRL2, and CDRL3 have the sequence of SEQ ID NOs: 16, 28, and 43, respectively, and CDRH1, CDRH2, and CDRH3 have the sequence of SEQ ID NOs: 85, 303, and 107, respectively;

(g) CDRL1, CDRL2, and CDRL3 have the sequence of SEQ ID NOs: 290, 28, and 43, respectively, and CDRH1, CDRH2, and CDRH3 have the sequence of SEQ ID NOs: 85, 91, and 107, respectively;

(h) CDRL1, CDRL2, and CDRL3 have the sequence of SEQ ID NOs: 16, 28, and 43, respectively, and CDRH1, CDRH2, and CDRH3 have the sequence of SEQ ID NOs: 85, 91, and 306, respectively;

(i) CDRL1, CDRL2, and CDRL3 have the sequence of SEQ ID NOs: 16, 293, and 43, respectively, and CDRH1, CDRH2, and CDRH3 have the sequence of SEQ ID NOs: 85, 91, and 107, respectively;

(j) CDRL1, CDRL2, and CDRL3 have the sequence of SEQ ID NOs: 16, 28, and 271, respectively, and CDRH1, CDRH2, and CDRH3 have the sequence of SEQ ID NOs: 85, 91, and 107, respectively; or (k) CDRL1, CDRL2, and CDRL3 have the sequence of SEQ ID NOs: 291, 28, and 43, respectively, and CDRH1, CDRH2, and CDRH3 have the sequence of SEQ ID NOs: 302, 91, and 107, respectively.

In some embodiments, the TREM2 agonist antigen binding proteins of the invention may comprise a light chain variable region selected from LV-16, LV-201, LV-202, LV-203, LV-204, LV-205, and LV-206, as shown in Table 3A, and/or a heavy chain variable region selected from HV-15, HV-201, HV-202, HV-203, HV-204, HV-205, and HV-206, as shown in Table 3B, or sequences that are at least 80% identical, at least 85% identical, at least 90% identical, or at least 95% identical to any of the sequences in Tables 3A and 3B. For instance, in certain embodiments, the TREM2 agonist antigen binding proteins comprise a light chain variable region comprising (i) a sequence that is at least 90% identical to a sequence selected from SEQ ID NOs: 61 and 295-300, (ii) a sequence that is at least 95% identical to a sequence selected from SEQ ID NOs: 61 and 295-300, or (iii) a sequence selected from SEQ ID NOs: 61 and 295-300. In related embodiments, the TREM2 agonist antigen binding proteins comprise a heavy chain variable region comprising (i) a sequence that is at least 90% identical to a sequence selected from SEQ ID NOs: 124 and 307-312, (ii) a sequence that is at least 95% identical to a sequence selected from SEQ ID NOs: 124 and 307-312, or (iii) a sequence selected from SEQ ID NOs: 124 and 307-312.

Each of the light chain variable regions listed in Table 3A may be combined with any of the heavy chain variable regions listed in Table 3B to form an anti-TREM2 binding domain of the antigen binding proteins of the invention. Examples of such combinations include, but are not limited to: LV-16 (SEQ ID NO: 61) and HV-201 (SEQ ID NO: 307); LV-201 (SEQ ID NO: 295) and HV-15 (SEQ ID NO: 124); LV-202 (SEQ ID NO: 296) and HV-15 (SEQ ID NO: 124); LV-16 (SEQ ID NO: 61) and HV-202 (SEQ ID NO: 308); LV-16 (SEQ ID NO: 61) and HV-203 (SEQ ID NO: 309); LV-16 (SEQ ID NO: 61) and HV-204 (SEQ ID NO: 310); LV-203 (SEQ ID NO: 297) and HV-15 (SEQ ID NO: 124); LV-16 (SEQ ID NO: 61) and HV-205 (SEQ ID NO: 311); LV-204 (SEQ ID NO: 298) and HV-15 (SEQ ID NO: 124); LV-205 (SEQ ID NO: 299) and HV-15 (SEQ ID NO: 124); and LV-206 (SEQ ID NO: 300) and HV-206 (SEQ ID NO: 312).

In certain embodiments, the TREM2 agonist antigen binding proteins of the invention are anti-TREM2 agonist antibodies or binding fragments thereof. As used herein, the term "antibody" refers to a tetrameric immunoglobulin protein comprising two light chain polypeptides (about 25 kDa each) and two heavy chain polypeptides (about 50-70 kDa each). An "antibody" is a species of an antigen binding protein. The term "light chain" or "immunoglobulin light chain" refers to a polypeptide comprising, from amino terminus to carboxyl terminus, a single immunoglobulin light chain variable region (VL) and a single immunoglobulin light chain constant domain (CL). The immunoglobulin light chain constant domain (CL) can be a human kappa (κ) or human lambda (λ) constant domain. The term "heavy chain" or "immunoglobulin heavy chain" refers to a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4). Heavy chains are classified as mu (μ), delta (Δ), gamma (γ), alpha (α), and epsilon (ε), and define the antibody's isotype as IgM, IgD, IgG, IgA, and IgE, respectively. The IgG-class and IgA-class antibodies are further divided into subclasses, namely, IgG1, IgG2, IgG3, and IgG4, and IgA1 and IgA2, respectively. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (i.e. between the light and heavy chain) and between the hinge regions of the antibody heavy chains.

The anti-TREM2 antibodies of the invention can comprise any immunoglobulin constant region. The term "constant region" as used herein refers to all domains of an antibody other than the variable region. The constant region is not involved directly in binding of an antigen, but exhibits various effector functions. As described above, antibodies are divided into particular isotypes (IgA, IgD, IgE, IgG, and IgM) and subtypes (IgG1, IgG2, IgG3, IgG4, IgA1 IgA2) depending on the amino acid sequence of the constant region of their heavy chains. The light chain constant region can be, for example, a kappa- or lambda-type light chain constant region, e.g., a human kappa- or lambda-type light chain constant region, which are found in all five antibody isotypes. Examples of human immunoglobulin light chain constant region sequences are shown in the following table.

TABLE 4

Exemplary Human Immunoglobulin Light Chain Constant Regions

| Designation | SEQ ID NO: | CL Domain Amino Acid Sequence |
|---|---|---|
| Human lambda v1 | 191 | GQPKANPTVTLFPPSSEELQANKATLVCLISDFYPGAVTVAWKA DGSPVKAGVETTKPSKQSNNKYAASSYLSLTPEQWKSHRSYSC QVTHEGSTVEKTVAPTECS |
| Human lambda v2 | 192 | GQPKAAPSVTLFPPSSEELQANKATLVCLISDFYPGAVTVAWKA DSSPVKAGVETTTPSKQSNNKYAASSYLSLTPEQWKSHRSYSCQ VTHEGSTVEKTVAPTECS |
| Human lambda v3 | 193 | QPKAAPSVTLFPPSSEELQANKATLVCLISDFYPGAVTVAWKAD SSPVKAGVETTTPSKQSNNKYAASSYLSLTPEQWKSHRSYSCQV THEGSTVEKTVAPTECS |
| Human lambda v4 | 194 | GQPKAAPSVTLFPPSSEELQANKATLVCLISDFYPGAVTVAWKA DSSPVKAGVETTTPSKQSNNKYAASSYLSLTPEQWKSHKSYSCQ VTHEGSTVEKTVAPTECS |
| Human lambda v5 | 195 | GQPKAAPSVTLFPPSSEELQANKATLVCLVSDFYPGAVTVAWK ADGSPVKVGVETTKPSKQSNNKYAASSYLSLTPEQWKSHRSYS CRVTHEGSTVEKTVAPAECS |
| Human kappa v1 | 196 | TVAAPSVFIFPPSDEQLKSGTASVVCLLNNFYPREAKVQWKVDN ALQSGNSQESVTEQDSKDSTYSLSSTLTLSKADYEKHKVYACEV THQGLSSPVTKSFNRGEC |
| Human kappa v2 | 197 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |

The heavy chain constant region of the anti-TREM2 antibodies of the invention can be, for example, an alpha-, delta-, epsilon-, gamma-, or mu-type heavy chain constant region, e.g., a human alpha-, delta-, epsilon-, gamma-, or mu-type heavy chain constant region. In some embodiments, the anti-TREM2 antibodies comprise a heavy chain constant region from an IgG1, IgG2, IgG3, or IgG4 immunoglobulin. In one embodiment, the anti-TREM2 antibody comprises a heavy chain constant region from a human IgG1 immunoglobulin. In such embodiments, the human IgG1 immunoglobulin constant region may comprise one or more mutations to prevent glycosylation of the antibody as described in more detail herein. In another embodiment, the anti-TREM2 antibody comprises a heavy chain constant region from a human IgG2 immunoglobulin. In yet another embodiment, the anti-TREM2 antibody comprises a heavy chain constant region from a human IgG4 immunoglobulin. Examples of human IgG1, IgG2, and IgG4 heavy chain constant region sequences are shown below in Table 5.

TABLE 5

Exemplary Human Immunoglobulin Heavy Chain Constant Regions

| Ig isotype | SEQ ID NO: | Heavy Chain Constant Region Amino Acid Sequence |
|---|---|---|
| Human IgG1z | 198 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |
| Human IgG1za | 199 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKGF YPSDIAVEWESNGQPENNYKTTPPVLDSDGSFFLYSKLTVDKS RWQQGNVFSCSVMHEALHNHYTQKSLSLSPGK |

TABLE 5-continued

Exemplary Human Immunoglobulin Heavy Chain Constant Regions

| Ig isotype | SEQ ID NO: | Heavy Chain Constant Region Amino Acid Sequence |
|---|---|---|
| Human IgG1f | 200 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |
| Human IgG1fa | 201 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKGF YPSDIAVEWESNGQPENNYKTTPPVLDSDGSFFLYSKLTVDKS RWQQGNVFSCSVMHEALHNHYTQKSLSLSPGK |
| Human IgG1z aglycosylated v1 | 202 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYGSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |
| Human IgG1z aglycosylated v2 | 203 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPCEEQYGSTYRCVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |
| Human IgG2 | 204 | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSD IAVEWESNGQPENNYKTTPPMLDSDGSFFLYSKLTVDKSRWQ QGNVFSCSVMHEALHNHYTQKSLSLSPGK |
| Human IgG4 | 205 | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPCEEQYGSTYRCVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK |

Each of the light chain variable regions disclosed in Tables 1A, 2A, and 3A and each of the heavy chain variable regions disclosed in Tables 1B, 2B, and 3B may be attached to the above light chain constant regions (Table 4) and heavy chain constant regions (Table 5) to form complete antibody light and heavy chains, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

The TREM2 agonist antigen binding proteins of the invention can be any of the anti-TREM2 antibodies disclosed herein. For example, in certain embodiments, the anti-TREM2 agonist antigen binding protein is an anti-TREM2 antibody selected from antibodies 12G10, 26A10, 26C10, 26F2, 33B12, 24C12, 24G6, 24A10, 10E3, 13E7, 14C12, 25F12, 32E3, 24F4, 16B8, 4C5, 6E7, 5E3, and 4G10, the variable region and CDR sequences of which are set forth in Tables 1A and 1B. In some embodiments, the anti-TREM2 agonist antigen binding protein is an anti-TREM2 antibody selected from antibodies 24G6, 10E3, 13E7, 4C5, 6E7, and 5E3. In other embodiments, the anti-TREM2 agonist antigen binding protein is an anti-TREM2 antibody selected from antibodies V3, V24, V27, V40, V48, V49, V52, V60, V73, V76, and V84, the variable region and CDR sequences of which are set forth in Tables 2A and 2B. In certain other embodiments, the anti-TREM2 agonist antigen binding protein is an anti-TREM2 antibody selected from antibodies V9, V10, V23, V30, V33, V44, V57, V68, V70, V83, and V90, the variable region and CDR sequences of which are set forth in Tables 3A and 3B.

The TREM2 agonist antigen binding proteins of the invention can be monoclonal antibodies, polyclonal antibodies, recombinant antibodies, human antibodies, human-
ized antibodies, chimeric antibodies, or multispecific anti-
bodies. In certain embodiments, the TREM2 agonist antigen
binding protein is a monoclonal antibody. In such embodi-
ments, the anti-TREM2 antibody may be a chimeric anti-
body, a humanized antibody, or a fully human antibody
having a human immunoglobulin constant domain. In these
and other embodiments, the anti-TREM2 antibody is a
human IgG1, IgG2, IgG3, or IgG4 antibody. Thus, the
anti-TREM2 antibody may, in some embodiments, have a
human IgG1, IgG2, IgG3, or IgG4 constant domain. In one
embodiment, the anti-TREM2 antibody is a monoclonal
human IgG1 antibody. In another embodiment, the anti-
TREM2 antibody is a monoclonal human IgG2 antibody. In
yet another embodiment, the anti-TREM2 antibody is a
monoclonal human IgG4 antibody.

The term "monoclonal antibody" (or "mAb") as used
herein refers to an antibody obtained from a population of
substantially homogeneous antibodies, i.e., the individual
antibodies comprising the population are identical except for
possible naturally occurring mutations that may be present
in minor amounts. Monoclonal antibodies are highly spe-
cific, being directed against an individual antigenic site or
epitope, in contrast to polyclonal antibody preparations that
typically include different antibodies directed against differ-
ent epitopes. Monoclonal antibodies may be produced using
any technique known in the art, e.g., by immortalizing
spleen cells harvested from an animal after completion of
the immunization schedule. The spleen cells can be immor-
talized using any technique known in the art, e.g., by fusing
them with myeloma cells to produce hybridomas. See, for
example, Antibodies; Harlow and Lane, Cold Spring Harbor
Laboratory Press, 1$^{st}$ Edition, e.g. from 1988, or 2$^{nd}$ Edition,
e.g. from 2014. Myeloma cells for use in hybridoma-
producing fusion procedures preferably are non-antibody-
producing, have high fusion efficiency, and enzyme defi-
ciencies that render them incapable of growing in certain
selective media, which support the growth of only the
desired fused cells (hybridomas). Examples of suitable cell
lines for use in fusions with mouse cells include, but are not
limited to, Sp-20, P3-X63/Ag8, P3-X63-Ag8.653, NS1/
1.Ag 4 1, Sp210-Ag14, FO, NSO/U, MPC-11, MPC11-X45-
GTG 1.7 and S194/5XXO Bul. Example of suitable cell
lines used for fusions with rat cells include, but are not
limited to, R210.RCY3, Y3-Ag 1.2.3, IR983F and 4B210.
Other cell lines useful for cell fusions are U-266, GM1500-
GRG2, LICR-LON-HMy2 and UC729-6.

In some instances, a hybridoma cell line is produced by
immunizing an animal (e.g., a rabbit, rat, mouse, or a
transgenic animal having human immunoglobulin
sequences) with a TREM2 immunogen (such as the immu-
nogens described in Example 1); harvesting spleen cells
from the immunized animal; fusing the harvested spleen
cells to a myeloma cell line, thereby generating hybridoma
cells; establishing hybridoma cell lines from the hybridoma
cells, and identifying a hybridoma cell line that produces an
antibody that binds to human TREM2. Another useful
method for producing monoclonal antibodies is the SLAM
method described in Babcook et al., Proc. Natl. Acad. Sci.
USA, Vol. 93: 7843-7848, 1996.

Monoclonal antibodies secreted by a hybridoma cell line
can be purified using any technique known in the art, such
as protein A-Sepharose, hydroxylapatite chromatography,
gel electrophoresis, dialysis, or affinity chromatography.
Hybridoma supernatants or mAbs may be further screened
to identify mAbs with particular properties, such as the
ability to bind human TREM2, cross-reactivity to TREM2 proteins from other species (e.g., mouse TREM2, rat
TREM2, and cynomolgous monkey TREM2), cross-reac-
tivity to other TREM family members (e.g. human TREM1),
ability to induce or increase TREM2-mediated signaling,
e.g. using a pSyk assay as described herein, or ability to
induce or increase TREM2-mediated function or activities
as described herein (e.g. proliferation or survival of
TREM2-expressing myeloid cells).

In some embodiments, the TREM2 agonist antigen bind-
ing proteins of the invention are chimeric or humanized
antibodies based upon the CDR and variable region
sequences of the anti-TREM2 antibodies described herein. A
chimeric antibody is an antibody composed of protein
segments from different antibodies that are covalently joined
to produce functional immunoglobulin light or heavy chains
or binding fragments thereof. Generally, a portion of the
heavy chain and/or light chain is identical with or homolo-
gous to a corresponding sequence in antibodies derived from
a particular species or belonging to a particular antibody
class or subclass, while the remainder of the chain(s) is/are
identical with or homologous to a corresponding sequence in
antibodies derived from another species or belonging to
another antibody class or subclass. For methods relating to
chimeric antibodies, see, for example, U.S. Pat. No. 4,816,
567 and Morrison et al., 1985, Proc. Natl. Acad. Sci. USA
81:6851-6855, both of which are hereby incorporated by
reference in their entireties.

Generally, the goal of making a chimeric antibody is to
create a chimera in which the number of amino acids from
the intended species is maximized. One example is the
"CDR-grafted" antibody, in which the antibody comprises
one or more CDRs from a particular species or belonging to
a particular antibody class or subclass, while the remainder
of the antibody chain(s) is/are identical with or homologous
to a corresponding sequence in antibodies derived from
another species or belonging to another antibody class or
subclass. CDR grafting is described, for example, in U.S.
Pat. Nos. 6,180,370, 5,693,762, 5,693,761, 5,585,089, and
5,530,101. For use in humans, the variable region or selected
CDRs from a rodent or rabbit antibody often are grafted into
a human antibody, replacing the naturally-occurring variable
regions or CDRs of the human antibody.

One useful type of chimeric antibody is a "humanized"
antibody. Generally, a humanized antibody is produced from
a monoclonal antibody raised initially in a non-human
animal, such as a rodent or rabbit. Certain amino acid
residues in this monoclonal antibody, typically from non-
antigen recognizing portions of the antibody, are modified to
be homologous to corresponding residues in a human anti-
body of corresponding isotype. Humanization can be per-
formed, for example, using various methods by substituting
at least a portion of a rodent or rabbit variable region for the
corresponding regions of a human antibody (see, e.g., U.S.
Pat. Nos. 5,585,089, and 5,693,762; Jones et al., 1986,
Nature 321:522-525; Riechmann et al., 1988, Nature 332:
323-27; and Verhoeyen et al., 1988, Science 239:1534-
1536).

In one aspect, the CDRs of the light and heavy chain
variable regions of the antibodies provided herein (see,
Tables 1A, 1B, 2A, 2B, 3A and 3B) are grafted to framework
regions (FRs) from antibodies from the same, or a different,
phylogenetic species. For example, the CDRs of the heavy
and light chain variable regions listed in Tables 1A, 1B, 2A,
2B, 3A, and 3B can be grafted to consensus human FRs. To
create consensus human FRs, FRs from several human
heavy chain or light chain amino acid sequences may be
aligned to identify a consensus amino acid sequence. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, the TREM2 agonist antigen binding proteins of the invention are fully human antibodies. Fully human antibodies that specifically bind to human TREM2 can be generated using the immunogens or fragments thereof described herein, such as polypeptides consisting of the sequences of SEQ ID NOs: 1 and 2 or the immunogens described in Example 1. A "fully human antibody" is an antibody that comprises variable and constant regions derived from or indicative of human germ line immunoglobulin sequences. One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, Nature 362:255-258; and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,939,598; 5,545,807; 6,300,129; 6,255,458; 5,877,397; 5,874,299 and 5,545,806; in PCT publications WO91/10741, WO90/04036, WO 94/02602, WO 96/30498, WO 98/24893 and in EP 546073B1 and EP 546073A1.

The transgenic mice described above, referred to herein as "HuMab" mice, contain a human immunoglobulin gene minilocus that encodes unrearranged human heavy (mu and gamma) and kappa light chain immunoglobulin sequences, together with targeted mutations that inactivate the endogenous mu and kappa chain loci (Lonberg et al., 1994, Nature 368:856-859). Accordingly, the mice exhibit reduced expression of mouse IgM and kappa proteins and in response to immunization, the introduced human heavy and light chain transgenes undergo class switching and somatic mutation to generate high affinity human IgG kappa monoclonal antibodies (Lonberg and Huszar, 1995, Intern. Rev. Immunol. 13: 65-93; Harding and Lonberg, 1995, Ann. N.Y Acad. Sci. 764:536-546). The preparation of HuMab mice is described in detail in Taylor et al., 1992, Nucleic Acids Research 20:6287-6295; Chen et al., 1993, International Immunology 5:647-656; Tuaillon et al., 1994, J. Immunol. 152:2912-2920; Lonberg et al., 1994, Nature 368:856-859; Lonberg, 1994, Handbook of Exp. Pharmacology 113:49-101; Taylor et al., 1994, International Immunology 6:579-591; Lonberg and Huszar, 1995, Intern. Rev. Immunol. 13:65-93; Harding and Lonberg, 1995, Ann. N.Y Acad. Sci. 764:536-546; Fishwild et al., 1996, Nature Biotechnology 14:845-851; the foregoing references are hereby incorporated by reference in their entireties for all purposes. See, further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entireties for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate fully human anti-TREM2 antibodies. One particular transgenic mouse line suitable for generation of fully human anti-TREM antibodies is the XenoMouse® transgenic mice described in Example 1 and in U.S. Pat. Nos. 6,114,598; 6,162,963; 6,833,268; 7,049,426; 7,064,244; Green et al., 1994, *Nature Genetics* 7:13-21; Mendez et al., 1997, *Nature Genetics* 15:146-156; Green and Jakobovitis, 1998, *J. Ex. Med,* 188:483-495; Green, 1999, Journal of Immunological Methods 231:11-23; Kellerman and Green, *Current Opinion in Biotechnology* 13, 593-597, 2002, all of which are hereby incorporated by reference in their entireties.

Human-derived antibodies can also be generated using phage display techniques. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function, if desired. Typically, the Fd fragment (VH-CH1) and light chain (VL-CL) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated. Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

Once cells producing anti-TREM2 antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described herein to generate other TREM2 agonist antigen binding proteins or antibodies according to the invention.

In certain embodiments, the TREM2 agonist antigen binding proteins of the invention (e.g. monoclonal antibodies or binding fragments thereof) compete for binding to human TREM2 (SEQ ID NO: 1) or an extracellular domain of human TREM2 (SEQ ID NO: 2) with a reference antibody, such as one or more of the anti-TREM2 antibodies described herein. The term "compete" refers to the ability of an antibody or other antigen binding protein to interfere with the binding of other antibodies or binding fragments to a target (e.g. human TREM2). The extent to which an antibody or binding fragment is able to interfere with the binding of another antibody or binding fragment to a target (e.g. human TREM2), and therefore whether it can be said to compete, can be determined using competition binding assays. Numerous types of competitive binding assays can be used, including for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619); solid phase direct-labeled assay, solid phase direct-labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176: 546-552); surface plasmon resonance-based assays (e.g. using Biacore® systems); bio-layer interferometry-based assays (e.g. using Octet® systems); and direct labeled RIA (Moldenhauer et al., 1990, Scand. J. Immunol. 32:77-82). Typically, a competitive binding assay involves the use of purified antigen bound to a solid surface or cells bearing the antigen, an unlabeled test antibody or other antigen binding protein, and a labeled reference antibody or other antigen binding protein. Competitive inhibition is measured by determining the amount of label bound to the solid surface or cells in the presence of the test antibody or other antigen binding protein. Usually the test antibody or other antigen binding protein is present in excess. Antibodies or other antigen binding proteins identified by competition assay (i.e. competing antibodies and antigen binding proteins) include antibodies and antigen binding proteins binding to the same epitope as the reference antibody or antigen binding protein. Usually, when a competing antibody or other antigen binding protein is present in excess, it will inhibit specific binding of a reference antibody or other antigen binding protein to a target antigen by at least 40%, 45%, 50%, 55%, 60%, 65%, 70% or 75%. In some instances, binding of the reference antibody or other antigen binding protein is inhibited by at least 80%, 85%, 90%, 95%, or 97% or more. In some embodiments, a competing antigen binding protein (e.g. antibody or binding fragment thereof) reduces human TREM2 binding of a reference antibody between about 40% and about 100%, such as about 60% and about 100%, specifically between about 70% and about 100%, and more specifically between about 80% and about 100%.

A particularly suitable quantitative assay for detecting competitive binding uses a Biacore® machine which measures the extent of interactions using surface plasmon resonance technology. An exemplary Biacore®-based competitive binding assay involves the immobilization of a reference antibody to a sensor chip. The target antigen is then contacted with the sensor chip where the target antigen is captured by the immobilized reference antibody. Test antibodies are then injected over the captured target antigen. If the injected test antibody recognizes a distinct epitope from that recognized by the immobilized antibody, then a second binding event is observed and the test antibody would be considered not to compete for binding to the target antigen with the reference antibody.

Another particularly suitable assay for detecting competitive binding employs kinetic sensors used with Octet® systems (Pall ForteBio), which measures binding interactions using bio-layer interferometry methodology. Such an assay is described in Example 4, in which each of sixteen different anti-TREM2 antibodies described herein were evaluated against each other for the ability to compete for binding to human TREM2. The results of the analysis provided in Table 9 show that the sixteen different antibodies could be grouped into four distinct epitope bins. That is, one group of antibodies (antibodies 10E3, 13E7, 24F4, 4C5, 4G10, 32E3, and 6E7) competed with each other for binding to human TREM2, indicating that they share the same or similar epitope on human TREM2. Antibodies 16B8, 26A10, 26C10, 26F2, 33B12, and 5E3 competed with each other for TREM2 binding, but did not compete with antibodies in the first group or antibodies 24A10, 24G6, or 25F12, indicating that this second group of antibodies bind to a distinct epitope on human TREM2. Antibodies 24A10 and 24G6 share a similar epitope on human TREM2 as these two antibodies competed with each other for human TREM2 binding, but did not compete with any other antibody. Antibody 25F12 did not compete with any of the other tested antibodies for human TREM2 binding, indicating that this antibody binds to yet another epitope.

In some embodiments, a TREM2 agonist antigen binding protein of the invention competes with a reference antibody for binding to human TREM2, wherein the reference antibody comprises a light chain variable region comprising a sequence selected from SEQ ID NOs: 46-63 and a heavy chain variable region comprising a sequence selected from SEQ ID NOs: 110-126. In other embodiments, a TREM2 agonist antigen binding protein of the invention competes with a reference antibody for binding to human TREM2, wherein the reference antibody comprises a light chain variable region comprising a sequence selected from SEQ ID NOs: 153-162 and a heavy chain variable region comprising a sequence selected from SEQ ID NOs: 180-190. In still other embodiments, a TREM2 agonist antigen binding protein of the invention competes with a reference antibody for binding to human TREM2, wherein the reference antibody comprises a light chain variable region comprising a sequence selected from SEQ ID NOs: 61 and 295-300 and a heavy chain variable region comprising a sequence selected from SEQ ID NOs: 124 and 307-312. In certain embodiments, a TREM2 agonist antigen binding protein of the invention competes for binding to human TREM2 with one or more of the anti-TREM2 antibodies described herein, including 12G10, 26A10, 26C10, 26F2, 33B12, 24C12, 24G6, 24A10, 10E3, 13E7, 14C12, 25F12, 32E3, 24F4, 16B8, 4C5, 6E7, 5E3, 4G10, V3, V9, V10, V23, V24, V27, V30, V33, V40, V44, V48, V49, V52, V57, V60, V68, V70, V73, V76, V83, V84, and V90.

In one embodiment, the TREM2 agonist antigen binding protein competes with a reference antibody for binding to human TREM2, wherein the reference antibody comprises a light chain variable region comprising the sequence of SEQ ID NO: 61 and a heavy chain variable region comprising the sequence of SEQ ID NO: 124. In such embodiments, antigen binding proteins that compete with this reference antibody for binding to human TREM2 would bind the same or similar epitope as antibody 6E7 or any of the other antibodies in epitope bin A (e.g. 10E3, 13E7, 24F4, 4C5, 4G10, 32E3), as described in Example 4.

In another embodiment, the TREM2 agonist antigen binding protein competes with a reference antibody for binding to human TREM2, wherein the reference antibody comprises a light chain variable region comprising the sequence of SEQ ID NO: 62 and a heavy chain variable region comprising the sequence of SEQ ID NO: 125. In such embodiments, antigen binding proteins that compete with this reference antibody for binding to human TREM2 would bind the same or similar epitope as antibody 5E3 or any of the other antibodies in epitope bin B (e.g. 16B8, 26A10, 26C10, 26F2, 33B12), as described in Example 4.

In yet another embodiment, the TREM2 agonist antigen binding protein competes with a reference antibody for binding to human TREM2, wherein the reference antibody comprises a light chain variable region comprising the sequence of SEQ ID NO: 52 and a heavy chain variable region comprising the sequence of SEQ ID NO: 115. In such embodiments, antigen binding proteins that compete with this reference antibody for binding to human TREM2 would bind the same or similar epitope as antibody 24G6 or antibody 24A10 (epitope bin C as described in Example 4).

In still another embodiment, the TREM2 agonist antigen binding protein competes with a reference antibody for binding to human TREM2, wherein the reference antibody comprises a light chain variable region comprising the sequence of SEQ ID NO: 56 and a heavy chain variable region comprising the sequence of SEQ ID NO: 119. In such embodiments, antigen binding proteins that compete with this reference antibody for binding to human TREM2 would bind the same or similar epitope as antibody 25F12 (epitope bin D as described in Example 4).

In certain embodiments, the TREM2 agonist antigen binding proteins of the invention may comprise one or more mutations or modifications to a constant region. For example, in embodiments in which the TREM2 agonist antigen binding proteins comprise an Fc region (e.g. monoclonal antibodies), the heavy chain constant regions or the Fc regions of the antigen binding proteins (e.g. monoclonal antibodies) may comprise one or more amino acid substitutions that affect the glycosylation, effector function, and/or Fcγ receptor binding of the antigen binding protein.

The term "Fc region" refers to the C-terminal region of an immunoglobulin heavy chain which may be generated by papain digestion of an intact antibody. The Fc region of an immunoglobulin generally comprises two constant domains, a CH2 domain and a CH3 domain, and optionally comprises a CH4 domain. In certain embodiments, the Fc region is an Fc region from an IgG1, IgG2, IgG3, or IgG4 immunoglobulin. In some embodiments, the Fc region comprises CH2 and CH3 domains from a human IgG1 or human IgG2 immunoglobulin. The Fc region may retain effector function, such as C1q binding, complement-dependent cytotoxicity (CDC), Fc receptor binding, antibody-dependent cell-mediated cytotoxicity (ADCC), and phagocytosis. In other embodiments, the Fc region may be modified to reduce or eliminate effector function as described in further detail below.

One of the functions of the Fc region of an immunoglobulin is to communicate to the immune system when the immunoglobulin binds its target. This is commonly referred to as "effector function." Communication leads ADCC, antibody-dependent cellular phagocytosis (ADCP), and/or CDC. ADCC and ADCP are mediated through the binding of the Fc region to Fc receptors on the surface of cells of the immune system. CDC is mediated through the binding of the Fc with proteins of the complement system, e.g., C1q. In some embodiments, the antigen binding proteins, e.g. monoclonal antibodies, of the invention comprise one or more amino acid substitutions in the Fc region to enhance effector function, including ADCC activity, CDC activity, ADCP activity, and/or the clearance or half-life of the antigen binding protein. Exemplary amino acid substitutions (according to EU numbering scheme) that can enhance effector function include, but are not limited to, E233L, L234I, L234Y, L235S, G236A, S239D, F243L, F243V, P247I, D280H, K290S, K290E, K290N, K290Y, R292P, E294L, Y296W, S298A, S298D, S298V, S298G, S298T, T299A, Y300L, V305I, Q311M, K326A, K326E, K326W, A330S, A330L, A330M, A330F, I332E, D333A, E333S, E333A, K334A, K334V, A339D, A339Q, P396L, or combinations of any of the foregoing.

In other embodiments, the TREM2 agonist antigen binding proteins (e.g. monoclonal antibodies) of the invention comprise one or more amino acid substitutions in a heavy chain constant region to reduce effector function. Exemplary amino acid substitutions (according to EU numbering scheme) that can reduce effector function include, but are not limited to, C220S, C226S, C229S, E233P, L234A, L234V, V234A, L234F, L235A, L235E, G237A, P238S, S267E, H268Q, N297A, N297G, V309L, E318A, L328F, A330S, A331S, P331S or combinations of any of the foregoing.

Glycosylation can contribute to the effector function of antibodies, particularly IgG1 antibodies. Thus, in some embodiments, the TREM2 agonist antigen binding proteins of the invention may comprise one or more amino acid substitutions that affect the level or type of glycosylation of the binding proteins. Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

In certain embodiments, glycosylation of the TREM2 agonist antigen binding proteins described herein is increased by adding one or more glycosylation sites, e.g., to the Fc region of the binding protein. Addition of glycosylation sites to the antigen binding protein can be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at pre-selected bases such that codons are generated that will translate into the desired amino acids.

The invention also encompasses production of TREM2 antigen binding protein molecules with altered carbohydrate structure resulting in altered effector activity, including antigen binding proteins with absent or reduced fucosylation that exhibit improved ADCC activity. Various methods are known in the art to reduce or eliminate fucosylation. For example, ADCC effector activity is mediated by binding of the antibody molecule to the FcγRIII receptor, which has been shown to be dependent on the carbohydrate structure of the N-linked glycosylation at the N297 residue of the CH2 domain. Non-fucosylated antibodies bind this receptor with increased affinity and trigger FcγRIII-mediated effector functions more efficiently than native, fucosylated antibodies. For example, recombinant production of non-fucosy-lated antibody in CHO cells in which the alpha-1,6-fucosyl transferase enzyme has been knocked out results in antibody with 100-fold increased ADCC activity (see Yamane-Ohnuki et al., Biotechnol Bioeng. 87(5):614-22, 2004). Similar effects can be accomplished through decreasing the activity of alpha-1,6-fucosyl transferase enzyme or other enzymes in the fucosylation pathway, e.g., through siRNA or antisense RNA treatment, engineering cell lines to knockout the enzyme(s), or culturing with selective glycosylation inhibitors (see Rothman et al., Mol Immunol. 26(12):1113-23, 1989). Some host cell strains, e.g. Lec13 or rat hybridoma YB2/0 cell line naturally produce antibodies with lower fucosylation levels (see Shields et al., J Biol Chem. 277(30):26733-40, 2002 and Shinkawa et al., J Biol Chem. 278(5):3466-73, 2003). An increase in the level of bisected carbohydrate, e.g. through recombinantly producing anti-body in cells that overexpress GnTIII enzyme, has also been determined to increase ADCC activity (see Umana et al., Nat Biotechnol. 17(2):176-80, 1999).

In other embodiments, glycosylation of the TREM2 ago-nist antigen binding proteins described herein is decreased or eliminated by removing one or more glycosylation sites, e.g., from the Fc region of the binding protein. In some embodiments, the TREM2 agonist antigen binding protein is an aglycosylated human monoclonal antibody, e.g. an agly-cosylated human IgG1 monoclonal antibody. Amino acid substitutions that eliminate or alter N-linked glycosylation sites can reduce or eliminate N-linked glycosylation of the antigen binding protein. In certain embodiments, the TREM2 agonist antigen binding proteins described herein comprise a mutation at position N297 (according to EU numbering scheme), such as N297Q, N297A, or N297G. In some embodiments, the TREM2 agonist antigen binding proteins of the invention comprise an Fc region from a human IgG1 antibody with a mutation at position N297. In one particular embodiment, the TREM2 agonist antigen binding proteins of the invention comprise an Fc region from a human IgG1 antibody with a N297G mutation. For instance, in some embodiments, the TREM2 agonist antigen binding proteins of the invention comprise a heavy chain constant region comprising the sequence of SEQ ID NO: 202.

To improve the stability of molecules comprising a N297 mutation, the Fc region of the TREM2 agonist antigen binding proteins may be further engineered. For instance, in some embodiments, one or more amino acids in the Fc region are substituted with cysteine to promote disulfide bond formation in the dimeric state. Residues corresponding to V259, A287, R292, V302, L306, V323, or I332 (accord-ing to EU numbering scheme) of an IgG1 Fc region may thus be substituted with cysteine. Preferably, specific pairs of residues are substituted with cysteine such that they preferentially form a disulfide bond with each other, thus limiting or preventing disulfide bond scrambling. Preferred pairs include, but are not limited to, A287C and L306C, V259C and L306C, R292C and V302C, and V323C and I332C. In certain embodiments, the TREM2 agonist antigen binding proteins described herein comprise an Fc region from a human IgG1 antibody with mutations R292C and V302C. In such embodiments, the Fc region may also comprise a N297 mutation, such as a N297G mutation. In some embodiments, the TREM2 agonist antigen binding proteins of the invention comprise a heavy chain constant region comprising the sequence of SEQ ID NO: 203.

Modifications to the hinge region and/or CH1 domain of the heavy chain and/or the constant region of the light chain of the TREM2 agonist antigen binding proteins (e.g. mono-clonal antibodies) of the invention can be made to reduce or eliminate disulfide heterogeneity. Structural heterogeneity of IgG2 antibodies has been observed where the disulfide bonds in the hinge and CH1 regions of IgG2 antibodies can be shuffled to create different structural disulfide isoforms (IgG2A, IgG2B, and IgG2A-B), which can have different levels of activity. See, e.g., Dillon et al., J. Biol. Chem., Vol. 283: 16206-16215; Martinez et al., Biochemistry, Vol. 47: 7496-7508, 2008; and White et al., Cancer Cell, Vol. 27: 138-148, 2015. Amino acid substitutions can be made in the hinge region, CH1 domain, and/or light chain constant region to promote the formation of a single disulfide isoform or lock the antigen binding protein (e.g. monoclonal anti-body) into a particular disulfide isoform (e.g. IgG2A or IgG2B). Such mutations are described in WO 2009/036209 and White et al., Cancer Cell, Vol. 27: 138-148, 2015, both of which are hereby incorporated by reference in its entirety, and include C131S, C219S, and C220S (according to EU numbering scheme) mutations in the heavy chain and a C214S (according to EU numbering scheme) mutation in the light chain. In certain embodiments, the TREM2 agonist antigen binding proteins of the invention are human IgG2 anti-TREM2 agonist antibodies. In some such embodiments, the TREM2 agonist antibodies comprise a C131S mutation (according to the EU numbering scheme) in their heavy chains. In other embodiments, the TREM2 agonist antibod-ies comprise a C214S mutation (according to the EU num-bering scheme) in their light chains and a C220S mutation (according to the EU numbering scheme) in their heavy chains. In still other embodiments, the TREM2 agonist antibodies comprise a C214S mutation (according to the EU numbering scheme) in their light chains and a C219S mutation (according to the EU numbering scheme) in their heavy chains.

In other embodiments, the TREM2 agonist antigen bind-ing proteins of the invention are anti-TREM2 agonist anti-bodies comprising a CH1 region and hinge region from a human IgG2 antibody and an Fc region from a human IgG1 antibody. The unique arrangement of the disulfide bonds in the hinge region of IgG2 antibodies has been reported to impart enhanced stimulatory activity for certain anticancer antibodies (White et al., Cancer Cell, Vol. 27: 138-148, 2015). This enhanced activity could be transferred to IgG1-type antibodies by exchanging the CH1 and hinge regions of the IgG1 antibody for those in the IgG2 antibody (White et al., 2015). The IgG2 hinge region includes the amino acid sequence ERKCCVECPPCP (SEQ ID NO: 206). The amino acid sequence of the CH1 and hinge regions from a human IgG2 antibody may comprise the amino acid sequence of ASTKGPSVFP LAPCSRSTSE STAALGCLVK DYF-PEPVTVS WNSGALTSGV HTFPAVLQSS GLYS-LSSVVT VPSSNFGTQT YTCNVDHKPS NTKVDKTVER KCCVECPPCP (SEQ ID NO: 207). Thus, in some embodiments, the anti-TREM2 agonist antibodies comprise the sequence of SEQ ID NO: 207 in combination with an Fc region from a human IgG1 antibody. In such embodiments, the anti-TREM2 antibodies can comprise one or more of the mutations described above to lock the anti-TREM2 antibodies into a particular disulfide isoform. For instance, in one embodiment, the anti-TREM2 antibody comprises a CH1 region and hinge region from a human IgG2 antibody and an Fc region from a human IgG1 antibody and comprises a C131S mutation (according to the EU numbering scheme) in its heavy chain. In another embodiment, the anti-TREM2 antibody comprises a CH1 region and hinge region from a human IgG2 antibody and an Fc region from a human IgG1 antibody and comprises a C214S mutation (according to the EU numbering scheme) in its light chain and a C220S mutation (according to the EU numbering scheme) in its heavy chain. In yet another embodiment, the anti-TREM2 antibody comprises a CH1 region and hinge region from a human IgG2 antibody and an Fc region from a human IgG1 antibody and comprises a C214S mutation (according to the EU numbering scheme) in its light chain and a C219S mutation (according to the EU numbering scheme) in its heavy chain.

In embodiments in which the anti-TREM2 antibodies comprise a CH1 region and hinge region from a human IgG2 antibody and an Fc region from a human IgG1 antibody, the anti-TREM2 antibodies may comprise any of the mutations in the Fc region described above to modulate the glycosylation of the antibodies. For instance, the human IgG1 Fc region of such anti-TREM2 antibodies may comprise a mutation at amino acid position N297 (according to the EU numbering scheme) in its heavy chain. In one particular embodiment, the N297 mutation is a N297G mutation. In certain embodiments, the Fc region may further comprise R292C and V302C mutations (according to the EU numbering scheme) in its heavy chain.

In certain embodiments, the anti-TREM2 antibodies of the invention comprise a CH1 region and hinge region from a human IgG2 antibody and an Fc region from a human IgG1 antibody, wherein the Fc region comprises the amino acid sequence of:

```
                              (SEQ ID NO: 281)
APELLGGPSVFLFPPKPKDTLMISRTPEVTCVVVDVSHEDPEVKFNWYVD

GVEVHNAKTKPREEQYGSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK.
```

In other embodiments, the anti-TREM2 antibodies of the invention comprise a CH1 region and hinge region from a human IgG2 antibody and an Fc region from a human IgG1 antibody, wherein the Fc region comprises the amino acid sequence of:

```
                              (SEQ ID NO: 282)
APELLGGPSVFLFPPKPKDTLMISRTPEVTCVVVDVSHEDPEVKFNWYVD

GVEVHNAKTKPCEEQYGSTYRCVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK.
```

Modifications of the TREM2 agonist antigen binding proteins of the invention to increase serum half-life also may desirable, for example, by incorporation of or addition of a salvage receptor binding epitope (e.g., by mutation of the appropriate region or by incorporating the epitope into a peptide tag that is then fused to the antigen binding protein at either end or in the middle, e.g., by DNA or peptide synthesis; see, e.g., WO96/32478) or adding molecules such as PEG or other water soluble polymers, including polysaccharide polymers. The salvage receptor binding epitope preferably constitutes a region wherein any one or more amino acid residues from one or two loops of an Fc region are transferred to an analogous position in the antigen binding protein. Even more preferably, three or more residues from one or two loops of the Fc region are transferred. Still more preferred, the epitope is taken from the CH2 domain of the Fc region (e.g., an IgG Fc region) and transferred to the CH1, CH3, or VH region, or more than one such region, of the antigen binding protein. Alternatively, the epitope is taken from the CH2 domain of the Fc region and transferred to the CL region or VL region, or both, of the antigen binding protein. See International applications WO 97/34631 and WO 96/32478 for a description of Fc variants and their interaction with the salvage receptor.

In some embodiments, the TREM2 agonist antigen binding proteins of the invention comprise a light chain comprising the sequence of SEQ ID NO: 334 and a heavy chain comprising the sequence of SEQ ID NO: 335. In some embodiments, the TREM2 agonist antigen binding proteins of the invention comprise a light chain comprising the sequence of SEQ ID NO: 334 and a heavy chain comprising the sequence of SEQ ID NO: 336. In some embodiments, the TREM2 agonist antigen binding proteins of the invention comprise a light chain comprising the sequence of SEQ ID NO: 337 and a heavy chain comprising the sequence of SEQ ID NO: 338. In some embodiments, the TREM2 agonist antigen binding proteins of the invention comprise a light chain comprising the sequence of SEQ ID NO: 339 and a heavy chain comprising the sequence of SEQ ID NO: 340. In some embodiments, the TREM2 agonist antigen binding proteins of the invention comprise a light chain comprising the sequence of SEQ ID NO: 341 and a heavy chain comprising the sequence of SEQ ID NO: 342.

In some embodiments, the TREM2 agonist antigen binding proteins of the invention comprise a light chain consisting of or consisting essentially of the amino acid sequence of SEQ ID NO: 334, 337, 339 or 341. In some embodiments, the TREM2 agonist antigen binding proteins of the invention comprise a heavy chain consisting of or consisting essentially of the amino acid sequence of SEQ ID NO: 335, 336, 338, 340, or 342. In a specific embodiment, the TREM2 agonist antigen binding proteins of the invention comprise a light chain and a heavy chain, wherein (a) the light chain consisting of or consisting essentially of the amino acid sequence of SEQ ID NO: 334 and the heavy chain consisting of or consisting essentially of the amino acid sequence of SEQ ID NO: 335; (b) the light chain consisting of or consisting essentially of the amino acid sequence of SEQ ID NO: 334 and the heavy chain consisting of or consisting essentially of the amino acid sequence of SEQ ID NO: 336; (c) the light chain consisting of or consisting essentially of the amino acid sequence of SEQ ID NO: 337 and the heavy chain consisting of or consisting essentially of the amino acid sequence of SEQ ID NO: 338; (d) the light chain consisting of or consisting of essentially of the amino acid sequence of SEQ ID NO: 339 and the heavy chain consisting of or consisting essentially of the amino acid sequence of SEQ ID NO: 340; or (e) the light chain consisting of or consisting essentially of the amino acid sequence of SEQ ID NO: 341 and the heavy chain consisting of or consisting essentially of the amino acid sequence of SEQ ID NO: 342.

In some embodiments, the TREM2 agonist antigen binding proteins of the invention are "bispecific" meaning that they are capable of specifically binding to two different antigens, human TREM2 and a second antigen. In certain embodiments, the second antigen is a protein that facilitates transport across the blood-brain barrier, such as a receptor that mediates blood-brain barrier transport. Such receptors include, but are not limited to, the insulin receptor, the transferrin receptor, the leptin receptor, the insulin-like growth factor (IGF) receptor, low density lipoprotein receptors (e.g. low density lipoprotein receptor-related protein 8 (LRP8), low density lipoprotein receptor-related protein 1 (LRP1), low density lipoprotein receptor-related protein 2(LRP2)), heparin-binding epidermal growth factor-like growth factor, CD98 heavy chain (CD98hc), basigin, the human transmembrane protein 30A (TMEM30A), and Glu-cose Transporter Type 1 (Glut1. In one embodiment, the second antigen is the human insulin receptor. In one embodiment, the second antigen is the human insulin-like growth receptor. In another embodiment, the second antigen is the human transferrin receptor. In one embodiment, the second antigen is TMEM30A. In any of these instances, the human TREM2 binding domain could be at the N-terminal end or the C-terminal end of the multivalent bispecific (IgG-Fab, IgG-scFv), or expressed in the multi-specific binding formats described in Spiess, C. et al., *Molecular Immunology* 67, 95-106 (2015) and Brinkman, U. et al., *MABS* 9(2)182-212 (2017).

In certain embodiments, the TREM2 agonist antigen binding proteins are multivalent. The valency of the binding protein denotes the number of individual antigen binding domains within the binding protein. For example, the terms "monovalent," "bivalent," and "tetravalent" with reference to the antigen binding proteins of the invention refer to binding proteins with one, two, and four antigen binding domains, respectively. Thus, a multivalent antigen binding protein comprises two or more antigen binding domains. In some embodiments, the bispecific antigen binding proteins of the invention are bivalent. Thus, such bispecific, bivalent antigen binding proteins contain two antigen binding domains: one antigen-binding domain binding to human TREM2 and one antigen-binding domain binding to a second antigen, such as an antigen that facilitates transport across the blood-brain barrier. In other embodiments, the bispecific antigen binding proteins are multivalent. For instance, in certain embodiments, the bispecific antigen binding proteins are trivalent or tetravalent comprising three or four antigen-binding domains: one or two antigen-binding domains binding to human TREM2 and one or two antigen-binding domains binding to a second antigen, such as an antigen that facilitates transport across the blood-brain barrier.

The term "antigen binding domain," which is used interchangeably with "binding domain," refers to the region of the antigen binding protein that contains the amino acid residues that interact with the antigen and confer on the antigen binding protein its specificity and affinity for the antigen. The binding domain may be derived from an antibody or functional fragment thereof that specifically binds to the antigen. In certain embodiments, the bispecific antigen binding proteins of the invention comprise one antigen-binding domain binding to human TREM2 and one antigen-binding domain binding to the human insulin receptor. In other embodiments, the bispecific antigen binding proteins of the invention comprise one antigen-binding domain binding to human TREM2 and one antigen-binding domain binding to the human transferrin receptor. In some embodiments, the bispecific antigen binding proteins of the invention comprise two antigen-binding domains binding to human TREM2 and two antigen-binding domains binding to the human insulin receptor. In other embodiments, the bispecific antigen binding proteins of the invention comprise two antigen-binding domains binding to human TREM2 and two antigen-binding domains binding to the human transferrin receptor. In one embodiment, the bispecific antigen binding proteins of the invention comprise one or two antigen-binding domains binding to human TREM2 and one or two antigen-binding domains binding to the human insulin-like growth receptor. In one embodiment, the bispecific antigen binding proteins of the invention comprise one or two antigen-binding domains binding to human TREM2 and one or two antigen-binding domains binding to TMEM30A. The antigen binding domains binding to human TREM2 of the bispecific TREM2 agonist antigen binding proteins can be derived from any of the anti-TREM2 agonist antibodies described herein. The antigen binding domains binding to the human insulin receptor, the human insulin like growth receptor, TMEM30A, or the human transferrin receptor can be derived from monoclonal antibodies to these receptors known in the art, such as those described in U.S. Pat. Nos. 7,388,079; 8,663,598; and US Patent Publication No. 2015/0110791, Abulrob, A. et al., *J. Neurochem.* 95, 1201-1214 (2005), and Muruganandam, A. et al., *FASEB J.* 16, 240-242 (2002). In certain embodiments, the antigen binding domains binding to the human insulin receptor, the human insulin like growth receptor, TMEM30A, or the human transferrin receptor is a single domain antibody. In certain embodiments, the human TREM2 binding domain is at the N-terminal end or the C-terminal end of the multivalent bispecific (IgG-Fab, IgG-scFv), or expressed in the multi-specific binding formats known in the art, such as those described in Spiess, C. et al., *Molecular Immunology* 67, 95-106 (2015) and Brinkman, U. et al., *MABS* 9(2)182-212 (2017).

Methods of making bispecific antibodies are known in the art. One such method of making a "bispecific" antigen binding protein or antibody involves the fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. Another method involves engineering the Fc portion of the heavy chains such as to create "knobs" and "holes" which facilitate heterodimer formation of the heavy chains when co-expressed in a cell. See, e.g., WO 96/027011. Still another method also involves engineering the Fc portion of the heavy chain but uses electrostatic steering to encourage heterodimer formation while discouraging homodimer formation of the heavy chains when co-expressed in a cell. See, e.g., WO2009089004 and WO2014081955.

The present invention includes one or more isolated polynucleotides or isolated nucleic acids encoding the TREM2 agonist antigen binding proteins, such as the anti-TREM2 agonist monoclonal antibodies, described herein. In addition, the present invention encompasses vectors comprising the nucleic acids, host cells or cell lines comprising the nucleic acids, and methods of making the antigen binding proteins of the invention. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense oligonucleotides for inhibiting expression of a polynucleotide, and complementary sequences of the foregoing. The nucleic acids can be any length as appropriate for the desired use or function, and can comprise one or more additional sequences, for example, regulatory sequences, and/or be part of a larger nucleic acid, for example, a vector. Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention can be derived from human sources as well as non-human species.

Relevant amino acid sequences from an immunoglobulin or region thereof (e.g. variable region, Fc region, etc.) or polypeptide of interest may be determined by direct protein sequencing, and suitable encoding nucleotide sequences can be designed according to a universal codon table. Alternatively, genomic or cDNA encoding monoclonal antibodies or binding fragments thereof of the invention can be isolated and sequenced from cells producing such antibodies (e.g. hybridomas) using conventional procedures, such as the methods described in Example 3.

An "isolated nucleic acid," which is used interchangeably herein with "isolated polynucleotide," is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' production of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The present invention also includes nucleic acids that hybridize under moderately stringent conditions, and more preferably highly stringent conditions, to nucleic acids encoding polypeptides as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989).

When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids above 18 base pairs in length, Tm (° C.)=81.5+16.6(log 10 [Na+])+0.41(% G+C)−(600/N), where N is the number of bases in the hybrid, and [Na+] is the concentration of sodium ions in the hybridization buffer ([Na+] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

Variants of the antigen binding proteins, including the variants described herein, can be prepared by site-specific mutagenesis of nucleotides in the DNA encoding the polypeptide, using cassette or PCR mutagenesis or other techniques well known in the art, to produce DNA encoding the variant, and thereafter expressing the recombinant DNA in cell culture as outlined herein. However, antigen binding proteins comprising variant CDRs having up to about 100-150 residues may be prepared by in vitro synthesis using established techniques. The variants typically exhibit the same qualitative biological activity as the naturally occurring analogue, e.g., binding to antigen. Such variants include, for example, deletions and/or insertions and/or substitutions of residues within the amino acid sequences of the antigen binding proteins. Any combination of deletion, insertion, and substitution is made to arrive at the final construct, provided that the final construct possesses the desired characteristics. The amino acid changes also may alter post-translational processes of the antigen binding protein, such as changing the number or position of glycosylation sites. In certain embodiments, antigen binding protein variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions, framework regions, and/or constant regions is contemplated. Covariance analysis techniques can be employed by the skilled artisan to design useful modifications in the amino acid sequence of the antigen binding protein. See, e.g., Choulier, et al., Proteins 41:475-484, 2000; Demarest et al., J. Mol. Biol. 335:41-48, 2004; Hugo et al., Protein Engineering 16(5):381-86, 2003; Aurora et al., US Patent Publication No. 2008/0318207 A1; Glaser et al., US Patent Publication No. 2009/0048122 A1; Urech et al., WO 2008/110348 A1; Borras et al., WO 2009/000099 A2. Such modifications determined by covariance analysis can improve potency, pharmacokinetic, pharmacodynamic, and/or manufacturability characteristics of an antigen binding protein.

Table 6 shows exemplary nucleic acid sequences encoding the light and heavy chain variable regions of anti-TREM2 antibodies described herein. Polynucleotides encoding the anti-TREM2 antibody variable regions can be used to construct the antigen binding proteins described herein.

TABLE 6

| | Exemplary Anti-TREM2 Antibody Variable Region Nucleic Acid Sequences | | |
|---|---|---|---|
| Ab ID. | VL or VH Group Designation | Nucleic Acid Sequence | SEQ ID NO: |
| | | Light chain variable regions | |
| 12G10 | LV-01 | CAGGCTGTGCCGACTCAGCCGTCTTCCCTCTCTGCATCTCCTGGAGTATT AGCCAGTCTCACCTGCACCTTACGCAGTGGCATCAATGTTGGTACCTAC AGGATATACTGGTACCAGCAGAAGCCAGGGAGTCCTCCCCAGTATCTCC TGAGGTACAAATCAGACTCAGATAAGCAGCAGGGCTCTGGAGTCCCCA GCCGCTTCTCTGGATCCAAGGATGCTTCGGCCAATGCAGGGATTTTACT CATCTCTGGGCTCCAGTCTGAGGATGAGGCTGACTATTACTGTATGATT TGGTACAGCAGTGCTGTGGTATTCGGCGGAGGGACCAAACTGACCGTC CTA | 208 |
| 26A10 | LV-02 | TCCTATGAGCTGACTCAGCCACCCTCAGTGTCCGTGTCCCCAGGACAGA CAGCCAGCATCACCTGCTCTGGAGATAAATTGGGAGATAAGTATGTTTG CTGGTATCAGCAGAAGCCAGGCCAGTCCCCTGTGCTGGTCATCTATCAA GATAGCAAGCGGCCCTCAGGGATCCCTGAGCGATTCTCTGGCTCCAACT CTGGGAACACAGCCACTCTGACCATCAGCGGGACCCAGGCTATGGATG AGGCTGACTATTACTGTCAGGCGTGGGACAGTAACACTGTGGTATTCGG CGGAGGGACCAAGCTGACCGTCCTA | 209 |
| 26C10 | LV-03 | TCCTTTGAGCTGACTCAGCCACCCTCAGTGTCCGTGTCCCCAGGACAGA CAGCCAGCATCACCTGCTCTGGAGATAAATTGGGGGATAAGTATGTTTG CTGGTATCAGCAGAAGCCAGGCCAGTCCCCTATGTTGGTCATCTATCAA GATACCAAGCGGCCCTCAGGGATCCCTGAACGATTCTCTGGCTCCAACT CTGGGAACACAGCCACTCTGACCATCAGCGGGACCCAGGCTATGGATG AGGCTGACTATTACTGTCAGGCGTGGGACAGCAGCACTGTGGTCTTCGG CGGAGGGACCAAGCTGACCGTCCTA | 210 |
| 26F2 | LV-04 | TCCTATGAGCTGACTCAGCCACCCTCAGTGTCCGTGTCCCCAGGACAGA CAGCCAGCATCACCTGCTCTGGAGATAAATTGGGGGATAAGTATGTTTG CTGGTATCAGCAGAAGCCAGGCCAGTCCCCTGTGTTGGTCATCTTTCAA GATAGCAAGCGGCCCTCAGGGATCCCTGAGCGATTCTCTGGCTCCAACT | 211 |

TABLE 6-continued

<u>Exemplary Anti-TREM2 Antibody Variable Region Nucleic Acid Sequences</u>

| Ab ID. | VL or VH Group Designation | Nucleic Acid Sequence | SEQ ID NO: |
|---|---|---|---|
| | | CTGGGAACACAGCCACTCTGACCATCAGCGGGACCCAGGCTATGGATG AGGCTGACTATTACTGTCAGGCGTGGGACAGCAGCACTGTGGTATTCGG CGGAGGGACCAAGCTGACCGTCCTA | |
| 33B12 | LV-05 | TCCTATGAGCTGACTCAGCCACCCTCAGTGTCCGTGTCCCCAGGACAGA CAGCCAGCATCACCTGCTCTGGAGATAAATTGGGGGATAAGTATGTTTG CTGGTATCAGCAGAAGCCAGGCCAGTCCCCTGTGTTGGTCATCTATCAA GATAGCAAGCGGCCCTCAGGGATCCCTGAGCGATTCTCTGGCTCCAACT CTGGGAACACAGCCACTCTGACCATCAGCGGGACCCAGGCTATGGATG AGGCTGACTATTACTGTCAGGCGTGGGACAGTAGCACTGTGGTATTCGG CGGAGGGACCAAGCTGACCGTCCTA | 212 |
| 24C12 | LV-06 | GGCATCGTGATGACCCAGTCTCCAGACTCCCTGGCTGTGTCTCTGGGCG AGAGGGCCACCATCAACTGCAAGTCCAGCCGGAGTGTTTTGTACAGCTC CAACAATAAGAACTACTTAGCTTGGTACCAGCAGAAACCAGGACAGCC TCCTAAGGTGCTCATTTACTGGGCATCTACCCGGGAATCCGGGGTCCCT GACCGATTCAGTGGCAGCGGGTCTGGGACAGATTTCACTCTCACCATCA GCAGCCTGCAGGCTGAAGATGTGGCAGTTTATAACTGTCAGCAATATTA TATTACTCCGATCACCTTCGGCCAAGGGACACGACTGGAGATTAAA | 213 |
| 24G6 | LV-07 | GACATCGTGATGACCCAGTCTCCAGACTCCCTGGCTGTGTCTCTGGGCG AGAGGGCCACCATCAACTGCAAGTCCAGCCAGAGTGTTTTATACAGCTC CAACAATAAGCACTTCTTAGCTTGGTACCAGCAGAAACCAGGACAGCC TCCTAAGCTGCTCATTTACTGGGCATCTACCCGGGAGTCCGGGGTCCCT GACCGATTCAGTGGCAGCGGGTCTGGGACAGATTTCACTCTCACCATCA GCAGCCTGCAGGCTGAAGATGTGGCATTTTATTACTGTCAGCAATATTA TAGTACTCCGCTCACTTTCGGCGGAGGGACCAAGGTGGAGATCAAA | 214 |
| 24A10 | LV-08 | GACATCGTGATGACCCAGTCTCCAGACTCCCTGGCTGTGTCTCTGGGCG AGAGGGCCACCATCACCTGCAAGTCCAGCCACAATGTTTTATACAGCTC CAACAATAAGAACTACTTAGCTTGGTATCAGCAGAAACCAGGACAGCC TCCTAAACTGCTCATTTACTGGGCATCTACCCGGGAATCCGGGGTCCCT GACCGATTCAGTGGCAGCGGGTCTGGGACAGATTTCACTCTCACCATCA GCAGCCTGCAGGCTGAAGATGTGGCAGTTTATTACTGTCACCAATATTA TAGTACTCCGTGCAGTTTTGGCCAGGGGACCAAGCTGGAGATCAAA | 215 |
| 10E3 | LV-09 | GAAATAGTGATGACGCAGTCTCCAGCCACCCTGTCTGTGTCTCCAGGGG AAAGAGCCACCCTCTCCTGCAGGGCCAGTCAGAGTGTTAGCAGCAACTT AGCCTGGTTCCAGCAGAAACCTGGCCAGGCTCCCAGGCTCCTCATCTAT GGTGCTTCCACCAGGGCCACTGGTATTCCAGCCAGGTTCAGTGTCAGTG GGTCTGGGACAGAGTTCACTCTCACCATCAGCAGCCTGCAGTCTGAAGA TTTTGCATTTTATTACTGTCTGCAGGATAATAATTGGCCTCCCACTTTCG GCCCTGGGACCAAAGTGGATATCAAA | 216 |
| 13E7 | LV-10 | GAAATAGTGATGACGCAGTCTCCAGCCACCCTGTCTGTGTCTCCAGGGG AAAGAGCCACCCTCTCCTGCAGGGCCAGTCAGAGTGTTAGCAGCAACTT AGCCTGGTTCCAGCAGAAACCTGGCCAGGCTCCCAGGCTCCTCATCTAT GGTGCTTCCACCAGGGCCACTGGTATTCCAGCCAGGTTCAGTGTCAGTG GGTCTGGGACAGAGTTCACTCTCACCATCAGCAGCCTGCAGTCTGAAGA TTTTGCAGTTTATTACTGTCTGCAGGATAATAATTGGCCTCCCACTTTCG GCCCTGGGACCAAAGTGGATATCAAA | 217 |
| 25F12 | LV-11 | GAAAAAGTGATGACGCAGTCTCCAGCCACCCTGTCTGTGTCTCCAGGGG AAAGAGCCACCCTCTCCTGCAGGGCCAGTCAGAGTGTTAACAACAACTT AGCCTGGTACCAGCAGAAACCTGGCCAGGCTCCCAGGCTCCTCATCTAT GGTGCATCCACCAGGGCCACTGGTATCCCAGCCAGGTTCAGTGGCAGTG GGTCTGGGACAGAGTTCACTCTCACCATCAGCAGCCTGCAGTCTGAAGA TTTTGCAGTTTATTACTGTCAGCAGTATAATAACTGGCCTCGGACGTTCG GCCAAGGGACCAAGGTGGAAATCAAA | 218 |
| 32E3 | LV-12 | GAATTTGTGTTGACGCAGTCTCCAGGCACCCTGTCTTTGTCTCCGGGGG AAAGAGCCACCCTCTCCTGCAGGGCCAGTCAGATTATTAGCAGCAACTA CTTAGCCTGGTACCAGCAGAAACCTGGCCAGGCTCCCAGGCTCCTCATC TATAGTGCATCCAGCAGGGCCACTGGCATCCCAGACAGGTTCAGTGGC AGTGGGTCTGGGACAGACTTCACTCTCACCATCAGCAGACTGGAGCCTG AAGATTTTGCAGTGTATTACTGTCAGCAGTTTGATAGCTCACCGATCAC CTTCGGCCGAGGGACACGACTGGACATTAAA | 219 |
| 24F4 | LV-13 | GAAATTGTGTTGACGCAGTCTCCAGGCACCCTGTCTTTGTCTCCAGGGG AAAGAGCCACCCTCTCCTGCAGGGCCAGTCAGAGTGTTAGCAGCAGCT ACTTAGCCTGGTACCAGCAGAAACCTGGCCAGGCTCCCAGGCTCCTCAT CTATGGTGCATCCAGCAGGGCCACTGGCATCCCAGACAGGTTCAGTGGC | 220 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| | | AGTGGGTCTGGGACAGACTTCACTCTCACCATCAGCAGACTGGAGCCTG AAGATTTTGCACTGTATTACTGTCAGCAGTATGATACCTCACCATTCACT TTCGGCCCTGGGACCAAAGTGGATATCAAA | |
| 16B8 | LV-14 | GACATCCAGATGACCCAGTCTCCATCTTCCGTGTCTGCATCTGTAGGAG ACAGAGTCACCGTCACTTGTCGGGCGAGTCAGGATATTAACAGCTGGTT AGCCTGGTATCAGCAGAAACCAGGGAAAGCCCCTAAGCTCCTGATCTA TGCTGCATCCTCTTTGCAAACTGGGGTCCCTTCAAGGTTCAGCGGCAGT GGATCTGGGACAGATTTCACTCTCACCATCAGCAGCCTGCAGCCTGAAG ATTTTGCAACTTACTCTTGTCAACAGTCTAACAGTTTCCCGATCACCTTC GGCCAAGGGACACGACTGGAGATTAAA | 221 |
| 4C5 | LV-15 | GACATCCAGATGACCCAGTCTCCATCTTCCGTGTCTGCATCTGTAGGAG ACAGAGTCACCATCACTTGTCGGGCGAGTCAGGGTATTAGCAACTGGTT AGCCTGGTATCAGCAGAAACCAGGGAAAGCCCCTAAGCTCCTGATCTA TGCTGCATCCAGTTTGCAAGTTGGGGTCCCATTAAGGTTCAGCGGCAGT GGATCTGGGACAGATTTCACTCTCACCATCAGCAGCCTGCAGCCTGAAG ATTTTGCAACTTACTATTGTCAACAGGCTGACAGTTTCCCTCGCAATTTT GGCCAGGGGACCAAGCTGGAGATCAAA | 222 |
| 6E7 V9 V30 V33 V44 V68 | LV-16 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCTCGCACTTTT GGCCAGGGGACCAAGCTGGAGATCAAA | 223 |
| 5E3 | LV-17 | GACATCCAGATGACCCAGTCTCCATCCTCACTGTCTGCATCTGTAGGAG ACAGAGTCACCATCACTTGTCGGGCGAGTCAGGGCATTAGCAATTATTT AGCCTGGTTTCAGCAGAAACCAGGGAAAGCCCCTAAATCCCTGATCTAT GCTGCATCCAGTTTGCAAAGTGGGGTCCCATCAAAGTTCAGCGGCAGTG GATCTGGGACAGATTTCACTCTCACCATCAGCAGCCTGCAGCCTGAAGA TTTTGCAACTTATTACTGCCAACAGTATAGTACTTACCCATTCACTTTCG GCCCTGGGACCAAAGTGGATATCAAA | 224 |
| 4G10 | LV-18 | GACATCCAGATGACCCAGTCTCCATCCTCCCTGTCTGCATCTGTAGGAG ACAGAGTCACCATCACTTGCCGGGCAAGTCAGGGCATAAGAAATGATT TAGGCTGGTATCAGCAGAAACCAGGGAATGCCCCTAAGCGCCTGATCT ATGCTGCATCCAGTTTGCCAAGTGGGGTCCCATCAAGGTTCAGCGGCAG TGGATCTGGGCCAGAATTCACTCTCACAATCAGCAGTCTGCAGCCTGAA GATTTTGCAACTTATTACTGTCTACAGCATAATAGTTACCCGTGGACGTT CGGCCAAGGGACCAAGGTGGAAATCACA | 225 |
| V3 | LV-101 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTAGGCAAAATGGGGTCCCATCAAGGTTCAGCGGCAG TGGATCTGGGACAGATTTCACTCTCACCATCAGCAGCCTGCAGCCTGAA GATTTTGCAACTTACTTTTGTCAACAGGCTGACAGGTTCCCTCGCACTTT TGGCCAGGGGACCAAGCTGGAGATCAAA | 226 |
| V24 | LV-102 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAAGGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCTCATACTTTT GGCCAGGGGACCAAGCTGGAGATCAAA | 227 |
| V27 | LV-103 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAACGTGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCTCGCACTTTT GGCCAGGGGACCAAGCTGGAGATCAAA | 228 |
| V40 | LV-104 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA | 229 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| | | TGCTGCATCCAGTTTGCAACTTGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACCGTTTCCCTCGCACTTTT GGCCAGGGGACCAAGCTGGAGATCAAA | |
| V48 | LV-105 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAACGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTGCCTCGCACTTTT GGCCAGGGGACCAAGCTGGAGATCAAA | 230 |
| V49 | LV-106 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTCGGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTATCCTCGCACTTTT GGCCAGGGGACCAAGCTGGAGATCAAA | 231 |
| V52 | LV-107 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAGGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACCGTTTCCCTCGCACTTTT GGCCAGGGGACCAAGCTGGAGATCAAA | 232 |
| V60 | LV-108 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAGGGGGTCCCATCAAGGTTCAGCGGCAGT GGATCTGGGACAGATTTCACTCTCACCATCAGCAGCCTGCAGCCTGAAG ATTTTGCAACTTACTTTTGTGGGCAGGCTGACAGTTTCCCTCGCACTTTT GGCCAGGGGACCAAGCTGGAGATCAAA | 233 |
| V73 | LV-106 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTCGTCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTATCCTCGCACTTTT GGCCAGGGGACCAAGCTGGAGATCAAA | 234 |
| V76 | LV-109 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAAGGGGGTCCCATCAAGGTTCAGCGGCAGT GGATCTGGGAGAGATTTCACTCTCACCATCAGCAGCCTGCAGCCTGAAG ATTTTGCAACTTACTTTTGTCAACAGGCTGACAGTTTCCCTCGCACTTTT GGCCAGGGGACCAAGCTGGAGATCAAA | 235 |
| V84 | LV-110 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGGTGCATCCAGTTTGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCGCGCACTTTT GGCCAGGGGACCAAGCTGGAGATCAAA | 236 |
| V10 | LV-201 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TTCTGCATCCAGTTTGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCTCGCACTTTT GGCCAGGGGACCAAGCTGGAGATCAAA | 313 |
| V23 | LV-202 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAATGGGGTCCCATCAAGGTTCAGCGGCAGT | 314 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| | | GGATCTGGGACAGATTTCACTCTCACCATCAGCAGCCTGCAGCCTGAAG ATTTTGCAACTTACTTTTGTCAACAGGCTGACAGTTTCCCTCTTACTTTT GGCCAGGGGACCAAGCTGGAGATCAAA | |
| V57 | LV-203 | GACATCCAGATGACCCAGTCTCCATCTTCCGTGTCTGCATCTGTAGGAG ACAGAGTCACCATCACTTGTGCGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCTCGCACTTTT GGCCAGGGGACCAAGCTGGAGATCAAA | 315 |
| V70 | LV-204 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCAGGGAGTTTGCAAAATGGGGTCCCATCAAGGTTCAGCGGCAG TGGATCTGGGACAGATTTCACTCTCACCATCAGCAGCCTGCAGCCTGAA GATTTTGCAACTTACTTTTGTCAACAGGCTGACAGTTTCCCTCGCACTTT TGGCCAGGGGACCAAGCTGGAGATCAAA | 316 |
| V83 | LV-205 | GACATCCAGATGACCCAGTCTCCATCTTCCGTGTCTGCATCTGTAGGAG ACAGAGTCACCATCACTTGTCGGGCGAGTCAGGGTATTAGCAGCTGGTT AGCCTGGTATCAGCAGAAACCAGGGAAAGCCCCTAAGCTCCTGATCTA TGCTGCATCCAGTTTGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGTGAGTTTCCCTCGCACTTTT GGCCAGGGGACCAAGCTGGAGATCAAA | 317 |
| V90 | LV-206 | GACATCCAGATGACCCAGTCTCCATCTTCCGTGTCTGCATCTGTAGGAG ACAGAGTCACCATCACTTGTCGGGCGAGTCAGGGTATTAGCAGATGGTT AGCCTGGTATCAGCAGAAACCAGGGAAAGCCCCTAAGCTCCTGATCTA TGCTGCATCCAGTTTGCAAAATGGGGTCCCATCAAGGTTCAGCGGCAGT GGATCTGGGACAGATTTCACTCTCACCATCAGCAGCCTGCAGCCTGAAG ATTTTGCAACTTACTTTTGTCAACAGGCTGACAGTTTCCCTCGCACTTTT GGCCAGGGGACCAAGCTGGAGATCAAA | 318 |

Heavy chain variable regions

| 12G10 24C12 | HV-01 | GAGGTGCAGCTGTTGGAGTCTGGGGGAGGCTTGGTACAGCCTGGGGGG TCCCTGAGACTCTCCTGTGCAGCCTCTGGATTCACCTTTAGCAGCTATGC CATGAGCTGGGTCCGCCAGGCTCCAGGGAAGGGGCTGGAGTGGGTCTC AGCTATTGGTGGTGGTGGTGTTAGCACATACTGCGCAGACTCCGTGAAG GGCCGGTTCACCATCTCCAGAGACAATTCCAAGAATACGCTGTATCTGC AAATGAACAGCCTGAGAGCCGAGGACACGGCCGTATATTACTGTGCGA AATTTTATATAGCAGTGGCTGGTTCTCACTTTGACTACTGGGGCCAGGG AACCCTGGTCACCGTCTCCTCA | 237 |
| 26A10 | HV-02 | GAGGTGCAACTGGTGGAGTCTGGGGGAGCCTTGGTACAGCGGGGGGGG TCCCTGAGACTCTCCTGTGCAGCCTCTAGATTCACCTTCAGTAGCTTTGG CATGAGCTGGGTCCGCCAGGCTCCAGGGAAGGGGCTGGAGTGGGTTTC ATACATTAGTAGTAGTAGTTTTACCATATATTACGCAGACTCTGTGAAG GGCCGATTCACCATCTCCAGAGACAATGCCAAGAATTCATTCTATCTGC AAATGAACAGCCTGAGAGACGAGGACACGGCTGTGTATTACTGTGCGA GAGAGGGGGGTCTTACTATGGTTCGGGGAGTCTCTTCCTACGGTTTGGA CGTCTGGGGCCAAGGGACCACGGTCACCGTCTCCTCA | 238 |
| 26C10 | HV-03 | GAGGTGCAACTGGTGGAGTCTGGGGGAGCCTTGGTACAGCCTGGGGGG TCCCTGAGACTCTCCTGTGCAGCCTCTGGATTCACCTTCAGTAGCTTTGG CATGAGCTGGGTCCGCCAGGCTCCAGGGAAGGGGCTGGAGTGGGTTTC ATACATTAGTAGTAGTAGTTTTACCATATACTACGCAGACTCTGTGAAG GGCCGATTCACCATCTCCAGAGACAATGCCAAGAATTCGTTCTATCTGC AAATGAACAGCCTGAGAGACGAGGACACGGCTGTGTATTTCTGTGTGA GAGAGGGGGGTATAACTATGGTTCGGGGAGTCTCTTCCTACGGTATGGA CGTCTGGGGCCAAGGGACCACGGTCACCGTCTCCTCA | 239 |
| 26F2 | HV-04 | GAGGTGCAACTGGTGGAGTCTGGGGGAGCCTTGGTACAGCCTGGGGGG TCCCTGAGACTCTCCTGTGCAGCCTCTGGATTCACCTTCAGTAGCTTTGG CATGAGCTGGGTCCGCCAGGCTCCAGGGAAGGGGCTGGAGTGGATTTC ATACATTAGTAGTAGTAGTTTTACCATATACTACGCAGACTCTGTGAAG GGCCGATTCACCATCTCCAGAGACAATGCCAAGAATTCATTCTATCTGC AAATGAACAGCCTGAGAGACGAGGACACGGCTGTGTATTTCTGTGCGA GAGAGGGGGGTATTACTATGGTTCGGGGAGTCTCTTCCTACGGTATGGA CGTCTGGGGCCAAGGGACCACGGTCACCGTCTCCTCA | 240 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| 33B12 | HV-05 | GAGGTGCAACTGGTGGAGTCTGGGGGAGCCTTGGTACAGCCTGGGGGG TCCCTGAGACTCTCCTGTGCAGCCTCTGGATTCACCTTCAGTAGCTTTGG CATGAGCTGGGTCCGCCAGGCTCCAGGGAAGGGCCTGGAGTGGGTTTC ATACATTAGTAAAAGTAGTTTTACCATATACTACGCAGACTCTGTGAAG GGCCGATTCACCATCTCCAGAGACAATGCCAAGAATTCATTCTATCTGC AAATGAACAGCCTGAGAGACGAGGACACGGCTGTGTATTACTGTGCGA GAGAGGGGGGTCTTACTATGGTTCGGGGAGTCTCTTCCTACGGTTTGGA CGTCTGGGGCCAAGGGACCACGGTCACCGTCTCCTCA | 241 |
| 24G6 | HV-06 | GAGGTGCAGCTGTTGGAGTCTGGGGGAGGCTTGGTACAGCCTGGGGGG TCCCTGAGACTCTCCTGTGCAGCCTCTGGATTCACCTTTAGCAGCTATGC CATGAGCTGGGTCCGCCAGGCTCCAGGGAAGGGACTGGAGTGGGTCTC AGCTATTAGTGGTAGTGGTGGTAGCACATACTACGCAGACTCCGTGAAG GGCCGGTTCACCATCTCCAGAGACAATTCCAAGAACACGCTGTATCTGC AAATGAACAGCCTGAGAGCCGAGGACACGGCCGTATATTACTGTGCGA AGGCGTATACACCTATGGCATTCTTTGACTACTGGGGCCAGGGAACCCT GGTCACCGTCTCCTCA | 242 |
| 24A10 | HV-07 | GAGGTGCAGGTGTTGGAGTCTGGGGGAGGCTTGGTACAGCCTGGGGGG TCCCTGAGACTCTCCTGTGCAGCCTCTGGATTCACCTTTAGCAACTATGC CATGAGCTGGGTCCGCCAGGCTCCAGGGAAGGGGCTGGAGTGGGTCTC AGCTATTAGTGGTAGTGGTGGTAGCACATACTACGCAGACTCCGTGAAG GGCCGGTTCACCATCTCCAGAGACAATTCCAAGAACACGCTGTATCTGC AAATGAACAGCCTGAGAGCCGAGGACACGGCCGTATATTACTGTGCGA AAGGAGGGTGGGAGCTATTTTACTGGGGCCAGGGAACCCTGGTCACCG TCTCCTCA | 243 |
| 10E3 | HV-08 | GAGGTGCAGCTGGTGCAGTCTGGAGCAGAGGTGAAAAAGCCCGGGGAG TCTCTGATGATCTCCTGTAAGGGTTCTGGATACAGCTTTACCAACTACTG GATCGGCTGGGTGCGCCAGATGCCCGGGAAAGGCCTGGAGTGGATGGG GATCATCTATCCTGGAGACTCTGATACCAGATACAGCCCGTCCTTCCAA GGCCAGGTCACCATCTCAGCCGACAAGTCCATCAGCACCGCCTACCTGC AGTGGAGCAGCCTGAAGGCCTCGGACACCGCCATGTATTTCTGTGCGAG ACGGAGACAGGGGATCTGGGGTGATGCTCTTGATATCTGGGGCCAAGG GACATTGGTCACCGTCTCTTCA | 244 |
| 13E7 | HV-09 | GAGGTGCAGCTGGTGCAGTCTGGAGCAGAGGTGAAAAAGCCCGGGGAG TCTCTGATGATCTCCTGTAAGGGTTCTGGATACAGCTTTACCAGCTACTG GATCGGCTGGGTGCGCCAGATGCCCGGGAAAGGCCTGGAGTGGATGGG GATCATCTATCCTGGAGACTCTGATACCAGATACAGCCCGTCCTTCCAA GGCCAGGTCACCATCTCAGCCGACAAGTCCATCAGCACCGCCTACCTGC AGTGGAGCAGCCTGAAGGCCTCGGACACCGCCATGTATTTCTGTGCGAG ACGGAGACAGGGGATCTGGGGTGATGCTCTTGATTTCTGGGGCCAAGG GACATTGGTCACCGTCTCTTCA | 245 |
| 25F12 | HV-10 | CAGGTGCAGCTACAGCAGTGGGGCGCAGGACTGTTGAAGCCTTCGGAG ACCCTGTCCCTCACCTGCGCTGTCTATGGTGGGTCCTTCAGTAGTTACTA CTGGAGCTGGATCCGCCAGCCCCCAGGGAAGGGGCTGGAGTGGATTGG GGAAATCAATCATAGTGGAAACACCAACTACAACCCGTCCCTCAAGAG TCGAGTCACCATATCAGTAGACACGTCCAAGAACCAGTTCTCCCTGAAG CTGAGCTCTGTGACCGCCGCGGACACGGCTGTGTATTACTGTGCGAGAG AGGGGTATTACGATATCTTGACTGGTTATCATGATGCTTTTGATATTTGG GACCAAGGGACAATGGTCACCGTNTTTTCA | 246 |
| 32E3 | HV-11 | GAGGTGCAGCTGGTGCAGTCTGGAGCAGAGGTGAAAAAGCCCGGGGAG TCTCTGAAGATCTCCTGTAAGGGTTCTGGATACAGCTTTACCAGCTACT GGATCGGCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTG CAGTGGAGCACCCTGAAGGCCTCGGACACCGCCATATATTACTGTGCGC GACATGACATTTATACCAGCAGCCCCTGGTGCTTTTGATATCTGGGGCCA AGGGACAATGGTCACCGTCTCTTCA | 247 |
| 24F4 | HV-12 | GAGGTGCAGCTGGTGCAGTCTGGAGCAGAGGTGAAAAAGCCCGGGGAG TCTCTGAAGATCTCCTGTAAGGGTTCTGGATACACCTTTACCAGCTACT GGATCGGCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGTCGACAAGTCCAGCAGCACCGCCTACCTG CAGTGGAGCAGCCTGAAGGCCTCGGACACCGCCATATATTACTGTACGC AGACAGGCCATAGCAGTGACTGGTTTGGGGGGGTTTCGACCCCTGGGGC CAGGGAACCCTGGTCACCGTCTCCTCA | 248 |
| 16B8 | HV-13 | CAGGTTCAGCTGGTGCAGTCTGGAGCTGAGGTGAAGAAGCCTGGGGCC TCAGTGAAGGTCTCCTGCAAGGCTTCTGGTTACACCTTTACCAACTATG | 249 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| | | GTATCAGCTGGGTGCGACAGGCCCCTGGACAAGGGCTTGAGTGGATGG GATGGATCAGCGCTTACAATGGTAACACAAACTATGCACAGAAGCTCC AGGGCAGAGTCACCATGACCACAGACACATCCACGAGTACAGTCTACA TGGAGCTGAGGAGCCTGAGATCTGACGACACGGCCGTGTATTACTGTGC GAGACGGGGATACAGCTATGGTTCCTTTGACTACTGGGGCCAGGGAAC CCTGGTCACCGTCTCCTCA | |
| 4C5 | HV-14 | GAGGTGCAGCTGGTGCAGTCTGGAGCAGAAGTGAAAAAGCCCGGGGAG TCTCTGAAGATCTCCTGTAAGGGGTTCTGGACACAGTTTTACCAACTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTG CAGTGGAGCAGCCTGAAGGCCTCGGACACCGCCGTGTATTTCTGTGCGA GACAAAGGACGTTTTACTATGATAGTAGTGGTTATTTTGACTACTGGGG CCAGGGAACCCTGGTCACCGTCTCCTCA | 250 |
| 6E7 | HV-15 | GAGGTGCAGCTGGTGCAGTCTGGAGCAGAGGTGAAAAAGCCCGGGGAG TCTCTGAAGATCTCCTGTAAGGGGTTCTGGATACAGTTTTACCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTTTGACTACTGGGG CCAGGGAACCCTGGTCACCGTCTCCTCA | 251 |
| 5E3 | HV-16 | CAGGTGCAGCTGGTGCAGTCTGGGGCTGAGGTGAAGAAGCCTGGGGCC TCAGTGAAGGTCTCCTGCAAGGCTTCTGGATACACCTTCACCGGCTACT ATATACACTGGGTGCGACAGGCCCCTGGACTAGGGCTTGAGTGGATGG GATGGATCAACCCTTACAGTGGTGGCACAACCTCTGCACAGAAGTTTCA GGGCAGGGTCACCATGACCAGGGACACGTCCATCAGCTCAGCCTACAT GGAACTGAGCAGGCTGAGATCTGACGACACGGCCGTGTATTACTGTGC GAGAGATGGAGGCTACCTGGCCCTCTACGGTACGGACGTCTGGGGCCA AGGGACCACGGTCACCGTCTCCTCA | 252 |
| 4G10 | HV-17 | GAGGTGCAGCTGGTGCAGTCTGGAGCAGAGGTGAAAAAGCCCGGGGAG TCTCTGAAGATCTCCTGTAAGGGGTTCTGGATACAGCTTTCCCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTTTTTG AAGTGGAGTAGCCTGAAGGCCTCGGACACCGCCATGTATTTCTGTGCGC GACAGGGTATAGAAGTGACTGGTACGGGAGGTTTGGACGTCTGGGGCC AAGGGACCACGGTCACCGTCTCCTCA | 253 |
| V3 | HV-101 | GAGGTGCAGCTGGTGCAGTCTGGAGCAGAGGTGAAAAAGCCCGGGGAG TCTCTGAAGATCTCCTGTAAGGGGTTCTGGATACAGTTTTGCGAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGATCAGGTCACCATCTCAGCCGACAAGTCCATCAGCACCGCCTACCTA CAGTGGAGCAGCCTGAAGGCCTCGGACACCGCCATGTATTTCTGTGCGA GAGGGAGGACGTTTTATTATGATAGTAGTGATTATTTTGACTACTGGGG CCAGGGAACCCTGGTCACCGTCTCCTCA | 254 |
| V24 | HV-102 | GAGGTGCAGCTGGTGCAGTCTGGAGCAGAGGTGAAAAAGCCCGGGGAG TCTCTGAAGATCTCCTGTAAGGGGTTCTGGATACAGTTTTACCAGCTACT GGATTGCCTGGGTGCGCCAGATGCCCGGGAAAGGCCTGGAGTGGATGG GGATCATCTATCCTGGTGACTCTGATGTGAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GATCTAGGACGTTTTATTATGATAGTAGTGATTATTTTGACTACTGGGG CCAGGGAACCCTGGTCACCGTCTCCTCA | 255 |
| V27 | HV-103 | GAGGTGCAGCTGGTGCAGTCTGGAGCAGAGGTGAAAAAGCCCGGGGAG TCTCTGAAGATCTCCTGTAAGGGGTTCTGGATACAGTTTTACCAGCTACT GGATCGCCTGGGTGCGCCAGATGCCCGGGAAAGGCCTGGAGTGGATGG GGATCATCTATCCTGGTGACTCTGATACCAGATACGCTCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGTGA GAAGTAGGACGTTTTATTATGATAGTAGTGATTATTTTGACTACTGGGG CCAGGGAACCCTGGTCACCGTGTCCTCA | 256 |
| V40 | HV-104 | GAGGTGCAGCTGGTGCAGTCTGGAGCAGAGGTGAAAAAGCCCGGGGAG TCTCTGAAGATCTCCTGTAAGGGGTTCTGGATACAGTTTTGGGAGCTACT GGATCGCCTGGGTGCGCCAGATGCCCGGGAAAGGCCTGGAGTGGATGG GGATCATCTATCCTGGTGACTCTGATGTTAGATACAGCCCGTCCTTCCA | 257 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| | | AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTCGGACTACTGGGG CCAGGGAACCCTGGTCACCGTGTCCTCA | |
| V48 | HV-105 | GAGGTGCAGCTGGTGCAGTCTGGAGCAGAGGTGAAAAAGCCCGGGGAG TCTCTGAAGATCTCCTGTAAGGGTTCTGGATACAGTTTTGGTAGCTACT GGATCGCCTGGGTGCGCCAGATGCCCGGGAAAGGCCTGGAGTGGATGG GGATCATCTATCCTGGTGACTCTGATGTGAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GAATGAGGACGTTTTATTATGATAGTAGTGATTATTTTGACTACTGGGG CCAGGGAACCCTGGTCACCGTGTCCTCA | 258 |
| V49 | HV-106 | GAGGTGCAGCTGGTGCAGTCTGGAGCAGAGGTGAAAAAGCCCGGGGAG TCTCTGAAGATCTCCTGTAAGGGTTCTGGATACAGTTTTAATAGCTACT GGATCGCCTGGGTGCGCCAGATGCCCGGGAAAGGCCTGGAGTGGATGG GGACGATCTATCCTGGTGACTCTGATACCAGACTGAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GAAGTAGGACGTTTTATTATGATAGTAGTGATTATTTTGACTACTGGGG CCAGGGAACCCTGGTCACCGTGTCCTCA | 259 |
| V52 | HV-107 | GAGGTGCAGCTGGTGCAGTCTGGAGCAGAGGTGAAAAAGCCCGGGGAG TCTCTGAAGATCTCCTGTAAGGGTTCTGGATACAGTTTTGAGAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GAGGGAGGACGTTTTATTATGATAGTAGTGATTATTTTGACTACTGGGG CCAGGGAACCCTGGTCACCGTGTCCTCA | 260 |
| V60 | HV-108 | GAGGTGCAGCTGGTGCAGTCTGGAGCAGAGGTGAAAAAGCCCGGGGAG TCTCTGAAGATCTCCTGTAAGGGTTCTGGATACCATTTTACCAGCTACTG GATCGCCTGGGTGCGCCAGATGCCCGGGAAAGGCCTGGAGTGGATGGG GATCATCTATCCTGGTGACTCTGATGTGAGATACAGCCCGTCCTTCCAA GGCCAGGTCACCATCTCAGCCGACAAGTCCATCAGCACCGCCTACCTAC AGTGGAGCAGCCTGAAGGCCTCGGACACCGCCATGTATTTCTGTGCGAG ACAAAGGACGTTTTATTATGATAGTAGTGATTATAGTGACTACTGGGGC CAGGGAACCCTGGTCACCGTGTCCTCA | 261 |
| V73 | HV-109 | GAGGTGCAGCTGGTGCAGTCTGGAGCAGAGGTGAAAAAGCCCGGGGAG TCTCTGAAGATCTCCTGTAAGGGTTCTGGATACAGTTTTGGTAGCTACT GGATCGCCTGGGTGCGCCAGATGCCCGGGAAAGGCCTGGAGTGGATGG GGATCATCTATCCTGGTGACTCTGATACCAGATACAGCCCGGGGGTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GAGGGAGGACGTTTTATTATGATAGTAGTGATTATTTTGACTACTGGGG CCAGGGAACCCTGGTCACCGTGTCCTCA | 262 |
| V76 | HV-110 | GAGGTGCAGCTGGTGCAGTCTGGAGCAGAGGTGAAAAAGCCCGGGGAG TCTCTGAAGATCTCCTGTAAGGGTTCTGGATACAGTTTTGGGAGCTACT GGATCGCCTGGGTGCGCCAGATGCCCGGGAAAGGCCTGGAGTGGATGG GGATCATCTATCCTGGTGACTCTGATACCAGATACAGCCCGGAGTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATAGTGACTACTGGGG CCAGGGAACCCTGGTCACCGTGTCCTCA | 263 |
| V84 | HV-111 | GAGGTGCAGCTGGTGCAGTCTGGAGCAGAGGTGAAAAAGCCCGGGGAG TCTCTGAAGATCTCCTGTAAGGGTTCTGGATACGGGTTTACCAGCTACT GGATCGCCTGGGTGCGCCAGATGCCCGGGAAAGGCCTGGAGTGGATGG GGATCATCTATCCTGGTGACAGTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTCGGACTACTGGGG CCAGGGAACCCTGGTCACCGTGTCCTCA | 264 |
| V9 | HV-201 | GAGGTGCAGCTGGTGCAGTCTGGAGCAGAGGTGAAAAAGCCCGGGGAG TCTCTGAAGATCTCCTGTAAGGGTTCTGGATACAGTTTTTACCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA | 319 |

TABLE 6-continued

Exemplary Anti-TREM2 Antibody Variable Region Nucleic Acid Sequences

| Ab ID. | VL or VH Group Designation | Nucleic Acid Sequence | SEQ ID NO: |
|---|---|---|---|
| | | GACAAAGGGGGTTTTATTATGATAGTAGTGATTATTTTGACTACTGGGG CCAGGGAACCCTGGTCACCGTGTCCTCA | |
| V10 V23 V57 V70 V83 | HV-15 | GAGGTGCAGCTGGTGCAGTCTGGAGCAGAGGTGAAAAAGCCCGGGGAG TCTCTGAAGATCTCCTGTAAGGGTTCTGGATACAGTTTTACCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTTTGACTACTGGGG CCAGGGAACCCTGGTCACCGTGTCCTCA | 320 |
| V30 | HV-202 | GAGGTGCAGCTGGTGCAGTCTGGAGCAGAGGTGAAAAAGCCCGGGGAG TCTCTGAAGATCTCCTGTAAGGGTTCTGGATCGAGTTTTACCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTTTGACTACTGGGG CCAGGGAACCCTGGTCACCGTGTCCTCA | 321 |
| V33 | HV-203 | GAGGTGCAGCTGGTGCAGTCTGGAGCAGAGGTGAAAAAGCCCGGGGAG TCTCTGAAGATCTCCTGTAAGGGTTCTGGATACAGTTTTACCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATGGGGATAGTAGTGATTATTTTGACTACTGGGG CCAGGGAACCCTGGTCACCGTGTCCTCA | 322 |
| V44 | HV-204 | GAGGTGCAGCTGGTGCAGTCTGGAGCAGAGGTGAAAAAGCCCGGGGAG TCTCTGAAGATCTCCTGTAAGGGTTCTGGATACAGTTTTACCAGCTACT GGATCGCCTGGGTGCGCCAGATGCCCGGGAAAGGCCTGGAGTGGATGG GGATCATCTATCCTAGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTTTGACTACTGGGG CCAGGGAACCCTGGTCACCGTGTCCTCA | 323 |
| V68 | HV-205 | GAGGTGCAGCTGGTGCAGTCTGGAGCAGAGGTGAAAAAGCCCGGGGAG TCTCTGAAGATCTCCTGTAAGGGTTCTGGATACAGTTTTACCAGCTACT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTAGGTATGATAGTAGTGATTATTTTGACTACTGGGG CCAGGGAACCCTGGTCACCGTGTCCTCA | 324 |
| V90 | HV-206 | GAGGTGCAGCTGGTGCAGTCTGGAGCAGAGGTGAAAAAGCCCGGGGAG TCTCTGAAGATCTCCTGTAAGGGTTCTGGATACAGTTTTACCAGCGAGT GGATCGCCTGGGTGCGCCAGATGCCCGGGAAAGGCCTGGAGTGGATGG GGATCATCTATCCTGGTGACTCTGATACCAGATACAGCCCGTCCTTCCA AGGCCAGGTCACCATCTCAGCCGACAAGTCCATCAGCACCGCCTACCTA CAGTGGAGCAGCCTGAAGGCCTCGGACACCGCCATGTATTTCTGTGCGA GACAAAGGACGTTTTATTATGATAGTAGTGATTATTTTGACTACTGGGG CCAGGGAACCCTGGTCACCGTGTCCTCA | 325 |

Isolated nucleic acids encoding the anti-TREM2 binding domain of the antigen binding proteins of the invention may comprise a nucleotide sequence that is at least 80% identical, at least 90% identical, at least 95% identical, or at least 98% identical to any of the nucleotide sequences listed in Table 6. In some embodiments, an isolated nucleic acid encoding an anti-TREM2 antibody light chain variable region comprises a sequence that is at least 80% identical, at least 90% identical, at least 95% identical, or at least 98% identical to a sequence selected from SEQ ID NOs: 208-236 and 313-318. In certain embodiments, an isolated nucleic acid encoding an anti-TREM2 antibody light chain variable region comprises a sequence selected from SEQ ID NOs: 208-236 and 313-318. In related embodiments, an isolated nucleic acid encoding an anti-TREM2 antibody heavy chain variable region comprises a sequence that is at least 80% identical, at least 90% identical, at least 95% identical, or at least 98% identical to a sequence selected from SEQ ID NOs: 237-264 and 319-325. In other related embodiments, an isolated nucleic acid encoding an anti-TREM2 antibody heavy chain variable region comprises a sequence selected from SEQ ID NOs: 237-264 and 319-325.

The nucleic acid sequences provided in Table 6 are exemplary only. As will be appreciated by those in the art, due to the degeneracy of the genetic code, an extremely large number of nucleic acids may be made, all of which encode the CDRs, variable regions, and heavy and light chains or other components of the antigen binding proteins described herein. Thus, having identified a particular amino acid sequence, those skilled in the art could make any number of different nucleic acids, by simply modifying the sequence of one or more codons in a way which does not change the amino acid sequence of the encoded protein.

The present invention also includes vectors comprising one or more nucleic acids encoding one or more components of the antigen binding proteins of the invention (e.g. variable regions, light chains, and heavy chains). The term "vector" refers to any molecule or entity (e.g., nucleic acid, plasmid, bacteriophage or virus) used to transfer protein coding information into a host cell. Examples of vectors include, but are not limited to, plasmids, viral vectors, non-episomal mammalian vectors and expression vectors, for example, recombinant expression vectors. The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. For instance, in some embodiments, signal peptide sequences may be appended/fused to the amino terminus of any of the variable region polypeptide sequences listed in Tables 1A, 1B, 2A, 2B, 3A, and 3B. In certain embodiments, a signal peptide having the amino acid sequence of MDMRVPAQLLGLLLLWLRGARC (SEQ ID NO: 265) is fused to the amino terminus of any of the variable region polypeptide sequences in Tables 1A, 1B, 2A, 2B, 3A, and 3B. In other embodiments, a signal peptide having the amino acid sequence of MAWALLLLTLLTQGTGSWA (SEQ ID NO: 266) is fused to the amino terminus of any of the variable region polypeptide sequences in Tables 1A, 1B, 2A, 2B, 3A, and 3B. In still other embodiments, a signal peptide having the amino acid sequence of MTCSPLLLTL-LIHCTGSWA (SEQ ID NO: 267) is fused to the amino terminus of any of the variable region polypeptide sequences in Tables 1A, 1B, 2A, 2B, 3A, and 3B. Other suitable signal peptide sequences that can be fused to the amino terminus of the variable region polypeptide sequences described herein include: MEAPAQLLFLLLLWLPDTTG (SEQ ID NO: 268), MEWTWRVLFLVAAATGAHS (SEQ ID NO: 269), METPAQLLFLLLLWLPDTTG (SEQ ID NO: 270), MKHLWFFLLLVAAPRWVLS (SEQ ID NO: 272), MEWSWVFLFFLSVTTGVHS (SEQ ID NO: 273), MDI-RAPTQLLGLLLLWLPGAKC (SEQ ID NO: 274), MDI-RAPTQLLGLLLLWLPGARC (SEQ ID NO: 275), MDTRAPTQLLGLLLLWLPGATF (SEQ ID NO: 276), MDTRAPTQLLGLLLLWLPGARC (SEQ ID NO: 277), METGLRWLLLVAVLKGVQC (SEQ ID NO: 278), METGLRWLLLVAVLKGVQCQE (SEQ ID NO: 279), and MDMRAPTQLLGLLLLWLPGARC (SEQ ID NO: 280). Other signal or secretory peptides are known to those of skill in the art and may be fused to any of the variable region polypeptide chains listed in Tables 1A, 1B, 2A, 2B, 3A, and 3B, for example, to facilitate or optimize expression in particular host cells.

Typically, expression vectors used in the host cells to produce the TREM2 agonist antigen binding proteins of the invention will contain sequences for plasmid maintenance and for cloning and expression of exogenous nucleotide sequences encoding the components of the antigen binding proteins. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the polypeptide coding sequence; the oligonucleotide tag sequence encodes polyHis (such as hexaHis), FLAG, HA (hemaglutinin influenza virus), myc, or another "tag" molecule for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using routine methods for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, MA) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using known methods for nucleic acid synthesis.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as one or more components of the antigen binding proteins described herein. As a result, increased quantities of a polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the polypeptide. The term "operably linked" as used herein refers to the linkage of two or more nucleic acid sequences in such a manner that a nucleic acid molecule capable of directing the transcription of a given gene and/or the synthesis of a desired protein molecule is produced. For example, a control sequence in a vector that is "operably linked" to a protein coding sequence is ligated thereto so that expression of the protein coding sequence is achieved under conditions compatible with the transcriptional activity of the control sequences. More specifically, a promoter and/or enhancer sequence, including any combination of cis-acting transcriptional control elements is operably linked to a coding sequence if it stimulates or modulates the transcription of the coding sequence in an appropriate host cell or other expression system.

Promoters are non-transcribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding e.g., heavy chain, light chain, or other component of the antigen binding proteins of the invention, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus serotypes 2, 8 or 9), bovine papilloma virus, avian sarcoma virus, cytomegalovirus, retroviruses, hepatitis-B virus and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thomsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78: 1444-1445); promoter and regulatory sequences from the metallothionine gene Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315: 115-122); the immunoglobulin gene control region that is active in lymphoid cells (Grosschedl et al., 1984, Cell 38:647-658; Adames et al., 1985, Nature 318:533-538; Alexander et al., 1987, Mol. Cell. Biol. 7: 1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-fetoprotein gene control region that is active in liver (Krumlauf et al., 1985, Mol. Cell. Biol. 5: 1639-1648; Hammer et al., 1987, Science 253:53-58); the alpha 1-antitrypsin gene control region that is active in liver (Kelsey et al., 1987, Genes and Devel. 1: 161-171); the beta-globin gene control region that is active in myeloid cells (Mogram et al, 1985, Nature 315:338-340; Kollias et al, 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234: 1372-1378).

An enhancer sequence may be inserted into the vector to increase transcription of DNA encoding a component of the antigen binding proteins (e.g., light chain, heavy chain, or variable regions) by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-fetoprotein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antigen binding protein. The choice of signal peptide or leader depends on the type of host cells in which the antigen binding protein is to be produced, and a heterologous signal sequence can replace the native signal sequence. Examples of signal peptides are described above. Other signal peptides that are functional in mammalian host cells include the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art. The expression vectors can be introduced into host cells to thereby produce proteins, including fusion proteins, encoded by nucleic acids as described herein.

In certain embodiments, nucleic acids encoding the different components of the TREM2 agonist antigen binding proteins of the invention may be inserted into the same expression vector. For instance, the nucleic acid encoding an anti-TREM2 antibody light chain or variable region can be cloned into the same vector as the nucleic acid encoding an anti-TREM2 antibody heavy chain or variable region. In such embodiments, the two nucleic acids may be separated by an internal ribosome entry site (IRES) and under the control of a single promoter such that the light chain and heavy chain are expressed from the same mRNA transcript. Alternatively, the two nucleic acids may be under the control of two separate promoters such that the light chain and heavy chain are expressed from two separate mRNA transcripts. In some embodiments, the nucleic acid encoding the anti-TREM2 antibody light chain or variable region is cloned into one expression vector and the nucleic acid encoding the anti-TREM2 antibody heavy chain or variable region is cloned into a second expression vector. In such embodiments, a host cell may be co-transfected with both expression vectors to produce complete antigen binding proteins of the invention.

After the vector has been constructed and the one or more nucleic acid molecules encoding the components of the antigen binding proteins described herein has been inserted into the proper site(s) of the vector or vectors, the completed vector(s) may be inserted into a suitable host cell for amplification and/or polypeptide expression. Thus, the present invention encompasses an isolated host cell or cell line comprising one or more expression vectors encoding the components of the TREM2 agonist antigen binding proteins described herein. The term "host cell" as used herein refers to a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. A host cell that comprises an isolated nucleic acid of the invention, preferably operably linked to at least one expression control sequence (e.g. promoter or enhancer), is a "recombinant host cell."

The transformation of an expression vector for an antigen binding protein into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Exemplary host cells include prokaryote, yeast, or higher eukaryote cells. Prokaryotic host cells include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacillus, such as B. subtilis and B. licheniformis, Pseudomonas, and Streptomyces. Eukaryotic microbes such as filamentous fungi or yeast are suitable cloning or expression hosts for recombinant polypeptides. Saccharomyces cerevisiae, or common baker's yeast, is the most commonly used among lower eukaryotic host microorganisms. However, a number of other genera, species, and strains are commonly available and useful herein, such as Pichia, e.g. P. pastoris, Schizosaccharomyces pombe; Kluyveromyces, Yarrowia; Candida; Trichoderma reesia; Neurospora crassa; Schwanniomyces, such as Schwanniomyces occidentalis; and filamentous fungi, such as, e.g., Neurospora, Penicillium, Tolypocladium, and Aspergillus hosts such as A. nidulans and A. niger.

Host cells for the expression of glycosylated antigen binding proteins can be derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection of such cells are publicly available, e.g., the L-1 variant of Autographa californica NPV and the Bm-5 strain of Bombyx mori NPV.

Vertebrate host cells are also suitable hosts, and recombinant production of antigen binding proteins from such cells has become routine procedure. Mammalian cell lines available as hosts for expression are well known in the art and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51);

TRI cells (Mather et al., Annals N.Y Acad. Sci. 383: 44-68, 1982); MRC 5 cells or FS4 cells; mammalian myeloma cells, and a number of other cell lines. In certain embodiments, cell lines may be selected through determining which cell lines have high expression levels and constitutively produce antigen binding proteins with human TREM2 binding properties. In another embodiment, a cell line from the B cell lineage that does not make its own antibody but has a capacity to make and secrete a heterologous antibody can be selected. CHO cells are preferred host cells in some embodiments for expressing the TREM2 agonist antigen binding proteins of the invention.

Host cells are transformed or transfected with the above-described nucleic acids or vectors for production of TREM2 agonist antigen binding proteins and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antigen binding proteins. Thus, the present invention also provides a method for producing a TREM2 agonist antigen binding protein described herein, such as an anti-TREM2 agonist monoclonal antibody or binding fragment thereof, comprising culturing a host cell comprising one or more expression vectors described herein in a culture medium under conditions permitting expression of the antigen binding protein encoded by the one or more expression vectors; and recovering the antigen binding protein from the culture medium or host cell.

The host cells used to produce the antigen binding proteins of the invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham et al., Meth. Enz. 58: 44, 1979; Barnes et al., Anal. Biochem. 102: 255, 1980; U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinary skilled artisan.

Upon culturing the host cells, the antigen binding protein can be produced intracellularly, in the periplasmic space, or directly secreted into the medium. If the antigen binding protein is produced intracellularly, as a first step, the particulate debris, either host cells or lysed fragments, is removed, for example, by centrifugation or ultrafiltration. The antigen binding protein can be purified using, for example, hydroxyapatite chromatography, cation or anion exchange chromatography, size-exclusion chromatography, or preferably affinity chromatography, using the antigen(s) of interest or protein A or protein Gas an affinity ligand.

Protein A can be used to purify proteins that include polypeptides that are based on human immunoglobulin γ1, γ2, or γ4 heavy chains (Lindmark et al., J. Immunol. Meth. 62: 1-13, 1983). Protein G is recommended for all mouse isotypes and for human immunoglobulin γ3 (Guss et al., EMBO J. 5: 15671575, 1986). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a CH3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the particular antigen binding protein to be recovered.

In certain embodiments, the invention provides a composition (e.g. a pharmaceutical composition) comprising one or a plurality of the TREM2 agonist antigen binding proteins of the invention (e.g. anti-TREM2 agonist monoclonal antibodies or binding fragments thereof) together with pharmaceutically acceptable diluents, carriers, excipients, solubilizers, emulsifiers, preservatives, and/or adjuvants. Pharmaceutical compositions of the invention include, but are not limited to, liquid, frozen, and lyophilized compositions. "Pharmaceutically-acceptable" refers to molecules, compounds, and compositions that are non-toxic to human recipients at the dosages and concentrations employed and/or do not produce allergic or adverse reactions when administered to humans. In some embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Methods and suitable materials for formulating molecules for therapeutic use are known in the pharmaceutical arts, and are described, for example, in REMINGTON'S PHARMACEUTICAL SCIENCES, 18th Edition, (A. R. Genrmo, ed.), 1990, Mack Publishing Company.

In some embodiments, the pharmaceutical composition of the invention comprises a standard pharmaceutical carrier, such as a sterile phosphate buffered saline solution, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary concentrations of the antigen binding proteins in the formulation may range from about 0.1 mg/ml to about 200 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antigen binding protein may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antigen binding protein, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antigen binding protein formulation to reduce aggregation of the formulated antigen binding protein and/or minimize the formation of particulates in the formulation and/or reduce adsorption. Exemplary surfactants include nonionic surfactants such as polysorbates (e.g. polysorbate 20 or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antigen binding protein, buffer, polyol and surfactant) and is essentially free of one or more preservatives, such as benzyl alcohol, phenol, m-cresol, chlorobutanol and benzethonium chloride. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in REMINGTON'S PHARMACEUTICAL SCIENCES, 18th Edition, (A. R. Genrmo, ed.), 1990, Mack Publishing Company, may be included in the formulation provided that they do not adversely affect the desired characteristics of the formulation.

Therapeutic formulations of the antigen binding protein are prepared for storage by mixing the antigen binding protein having the desired degree of purity with optional physiologically acceptable carriers, excipients or stabilizers (REMINGTON'S PHARMACEUTICAL SCIENCES, 18th Edition, (A. R. Genrmo, ed.), 1990, Mack Publishing Company), in the form of lyophilized formulations or aqueous solutions. Acceptable carriers, excipients, or stabilizers are nontoxic to recipients at the dosages and concentrations employed, and include buffers (e.g. phosphate, citrate, and other organic acids); antioxidants (e.g. ascorbic acid and methionine); preservatives (such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol; resorcinol, cyclohexanol, 3-pentanol, and m-cresol); low molecular weight (e.g. less than about 10 residues) polypeptides; proteins (such as serum albumin, gelatin, or immunoglobulins); hydrophilic polymers (e.g. polyvinylpyrrolidone); amino acids (e.g. glycine, glutamine, asparagine, histidine, arginine, or lysine); monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants, such as polysorbates (e.g. polysorbate 20 or polysorbate 80) or poloxamers (e.g. poloxamer 188); or polyethylene glycol (PEG).

In one embodiment, a suitable formulation of the claimed invention contains an isotonic buffer such as a phosphate, acetate, or TRIS buffer in combination with a tonicity agent, such as a polyol, sorbitol, sucrose or sodium chloride, which tonicifies and stabilizes. One example of such a tonicity agent is 5% sorbitol or sucrose. In addition, the formulation could optionally include a surfactant at 0.01% to 0.02% wt/vol, for example, to prevent aggregation or improve stability. The pH of the formulation may range from 4.5 to 6.5 or 4.5 to 5.5. Other exemplary descriptions of pharmaceutical formulations for antigen binding proteins may be found in US Patent Publication No. 2003/0113316 and U.S. Pat. No. 6,171,586, each of which is hereby incorporated by reference in its entirety.

Suspensions and crystal forms of antigen binding proteins are also contemplated. Methods to make suspensions and crystal forms are known to one of skill in the art.

The formulations to be used for in vivo administration must be sterile. The compositions of the invention may be sterilized by conventional, well-known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying (see Williams and Polli, Journal of Parenteral Science and Technology, Volume 38, Number 2, pages 48-59, 1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration (see Chen, Drug Development and Industrial Pharmacy, Volume 18: 1311-1354, 1992).

Excipients have been noted in some cases to act as stabilizers for freeze-dried products (see Carpenter et al., Volume 74: 225-239, 1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antigen binding protein, which matrices are in the form of shaped articles, e.g., films, or microcapsule. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing. Thus, the pharmaceutical formulations may also be formulated for controlled release or for slow release.

Specific dosages may be adjusted depending on the disease, disorder, or condition to be treated (e.g. Alzheimer's disease, multiple sclerosis, frontotemporal dementia, or Nasu-Hakola disease), the age, body weight, general health conditions, sex, and diet of the subject, dose intervals, administration routes, excretion rate, and combinations of drugs.

The TREM2 agonist antigen binding proteins of the invention can be administered by any suitable means, including parenteral, subcutaneous, intraperitoneal, intrapulmonary, intrathecal, intracerebral, intracerebroventricular, and intranasal, and, if desired for local treatment, intralesional administration. Parenteral administration includes intravenous, intraarterial, intraperitoneal, intramuscular, intradermal or subcutaneous administration. In addition, the antigen binding protein is suitably administered by pulse infusion, particularly with declining doses of the antigen binding protein. Preferably, the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. In certain embodiments, the TREM2 agonist antigen binding protein of the invention is administered intravenously or subcutaneously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of once per week, once every two weeks, or once a month.

The TREM2 agonist antigen binding proteins described herein (e.g. anti-TREM2 agonist monoclonal antibodies and binding fragments thereof) are useful for preventing, treating, or ameliorating a condition associated with TREM2 deficiency or loss of biological function of TREM2 in a patient in need thereof. As used herein, the term "treating" or "treatment" is an intervention performed with the intention of preventing the development or altering the pathology of a disorder. Accordingly, "treatment" refers to both therapeutic treatment and prophylactic or preventative measures. Patients in need of treatment include those already diagnosed with or suffering from the disorder or condition as well as those in which the disorder or condition is to be prevented, such as patients who are at risk of developing the disorder or condition based on, for example, genetic markers. "Treatment" includes any indicia of success in the amelioration of an injury, pathology or condition, including any objective or subjective parameter such as abatement, remission, diminishing of symptoms, or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, self-reporting by a patient, cognitive tests, motor function tests, neuropsychiatric exams, and/or a psychiatric evaluation.

TREM2 biological activity has been implicated in various physiological processes, including myeloid cell processes, such as phagocytosis, proliferation, survival, and regulation of inflammatory cytokine production; osteoclastogenesis; osteoclast differentiation; negative regulation of autoimmunity; inflammatory responses; bone remodeling and repair; bone resorption; tissue repair, microgliosis, and brain homeostasis. See, e.g., Colonna, Nature Reviews Immunology, Vol. 3: 445-453, 2003; Paradowska-Gorycka et al., Human Immunology, Vol. 74: 730-737, 2013; and Ulrich and Holtzman, ACS Chem. Neurosci., Vol. 7: 420-427, 2016. Loss of TREM2 function or TREM2 deficiency has been linked to several disorders and diseases including polycystic lipomembranous osteodysplasia with sclerosing leukoencephalopathy (PLOSL; also known as Nasu-Hakola disease), Alzheimer's disease, frontotemporal dementia, multiple sclerosis, prion disease, stroke, osteoporosis, and osteopetrosis. See, e.g., Jonsson et al., New England Journal of Medicine, Vol. 368: 107-116, 2013; Guerreiro et al., New England Journal of Medicine, Vol. 368: 117-127, 2013; Paradowska-Gorycka et al., Human Immunology, Vol. 74: 730-737, 2013; and Ulrich and Holtzman, ACS Chem. Neurosci., Vol. 7: 420-427, 2016. Thus, the TREM2 agonist antigen binding proteins of the invention can be administered to patients to prevent, ameliorate, or treat any of these diseases or disorders or other conditions associated with TREM2 deficiency or loss of TREM2 biological function or activity. In certain embodiments, the present invention provides methods for preventing, treating, or ameliorating a condition associated with TREM2 deficiency or loss of TREM2 function in a patient in need thereof comprising administering to the patient an effective amount of a TREM2 agonist antigen binding protein described herein. In certain embodiments, the TREM2 agonist antigen binding protein is an anti-TREM2 agonist monoclonal antibody or binding fragment thereof. The term "patient" includes human patients and is used interchangeably with the term "subject."

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a particular condition. In some embodiments, the effective amount is a therapeutically effective amount or a prophylactically effective amount. A "therapeutically effective amount" is an amount sufficient to remedy a disease state or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of antigen binding protein, when administered to a subject, will have the intended prophylactic effect, e.g., preventing or delaying the onset (or reoccurrence) of the condition, or reducing the likelihood of the onset (or reoccurrence) of the condition. The full therapeutic or prophylactic effect does not necessarily occur by administration of one dose, and may occur only after administration of a series of doses. Thus, a therapeutically or prophylactically effective amount may be administered in one or more administrations.

Conditions or disorders associated with TREM2 deficiency or loss of TREM2 function that may be prevented, treated, or ameliorated according to the methods of the invention include, but are not limited to, Nasu-Hakola disease, Alzheimer's disease, frontotemporal dementia, multiple sclerosis, Guillain-Barre syndrome, amyotrophic lateral sclerosis, Parkinson's disease, traumatic brain injury, spinal cord injury, systemic lupus erythematosus, rheumatoid arthritis, prion disease, stroke, osteoporosis, osteopetrosis, and osteosclerosis. In certain embodiments, the condition or disorder to be prevented, treated, or ameliorated according to the methods of the invention is Alzheimer's disease, Nasu-Hakola disease, frontotemporal dementia, multiple sclerosis, prion disease, or stroke.

In one embodiment, the present invention provides a method for preventing, treating, or ameliorating Alzheimer's disease in a patient in need thereof comprising administering to the patient an effective amount of a TREM2 agonist antigen binding protein described herein. In certain embodiments, the TREM2 agonist antigen binding protein administered to the patient is an anti-TREM2 agonist monoclonal antibody, such as the antibodies whose variable and CDR sequences are set forth in Tables 1A, 1B, 2A, 2B, 3A, and 3B. In some embodiments, the patient to be administered a TREM2 agonist antigen binding protein is a patient at risk of developing Alzheimer's disease. For instance, in one embodiment, the patient has been determined to have at least one allele containing the rs75932628-T mutation in the TREM2 gene, e.g. the patient has a genotype of CT at rs75932628. In related embodiments, the patient at risk of developing Alzheimer's disease is a patient who has been determined to carry a TREM2 variant allele that encodes a histidine in place of arginine at position 47 in SEQ ID NO: 1. In other embodiments, the patient has been determined to have at least one allele containing the rs143332484-T mutation in the TREM2 gene, e.g. the patient has a genotype of CT at rs143332484. In related embodiments, the patient at risk of developing Alzheimer's disease is a patient who has been determined to carry a TREM2 variant allele that encodes a histidine in place of arginine at position 62 in SEQ ID NO: 1. In some embodiments, a patient at risk of developing Alzheimer's disease has been determined to have at least one allele containing the rs6910730-G mutation in the TREM1 gene, at least one allele containing the rs7759295-C mutation upstream of the TREM2 gene, and/or at least one ε4 allele of the APOE gene.

In another embodiment, the present invention provides a method for preventing, treating, or ameliorating frontotemporal dementia or Nasu-Hakola disease in a patient in need thereof comprising administering to the patient an effective amount of a TREM2 agonist antigen binding protein described herein. In certain embodiments, the TREM2 agonist antigen binding protein administered to the patient is an anti-TREM2 agonist monoclonal antibody, such as the antibodies whose variable and CDR sequences are set forth in Tables 1A, 1B, 2A, 2B, 3A, and 3B. In some embodiments, the patient to be administered a TREM2 agonist antigen binding protein is a patient at risk of developing frontotemporal dementia or Nasu-Hakola disease. For example, in one such embodiment, the patient has been determined to have at least one allele containing the rs104894002-A mutation in the TREM2 gene, e.g. the patient has a genotype of GA or AA at rs104894002. In related embodiments, the patient at risk of developing frontotemporal dementia or Nasu-Hakola disease is a patient who has been determined to carry a TREM2 variant allele that encodes a truncated TREM2 protein as a result of the substitution of a stop codon in place of glutamine at position 33 in SEQ ID NO: 1. In another embodiment, the patient has been determined to have at least one allele containing the rs201258663-A mutation in the TREM2 gene, e.g. the patient has a genotype of GA or AA at rs201258663. In related embodiments, the patient at risk of developing frontotemporal dementia or Nasu-Hakola disease is a patient who has been determined to carry a TREM2 variant allele that encodes a methionine in place of threonine at position 66 in SEQ ID NO: 1. In some embodiments, the patient at risk of developing frontotemporal dementia or Nasu-Hakola disease is a patient who has been determined to carry a TREM2 variant allele that encodes a cysteine in place of tyrosine at position 38 in SEQ ID NO: 1.

In yet another embodiment, the present invention provides a method for preventing, treating, or ameliorating multiple sclerosis in a patient in need thereof comprising administering to the patient an effective amount of a TREM2 agonist antigen binding protein described herein. In certain embodiments, the TREM2 agonist antigen binding protein administered to the patient is an anti-TREM2 agonist monoclonal antibody, such as the antibodies whose variable and CDR sequences are set forth in Tables 1A, 1B, 2A, 2B, 3A, and 3B. In some embodiments, the patient to be administered a TREM2 agonist antigen binding protein is a patient at risk of developing multiple sclerosis.

As described in Examples 9 and 10, an agonist anti-TREM2 antibody capable of activating TREM2/DAP12 signaling as measured by increases in pSyk levels rescued the viability defect from macrophages and microglia resulting from a loss of function mutation in TREM2 and restored CCL2 secretion from TREM2-deficient macrophages. These results indicate that activation of TREM2/DAP12 signaling with an agonist anti-TREM2 antibody can enhance macrophage/microglia function, which in turn could be therapeutic in conditions associated with insufficient macrophage/microglia function. Thus, in certain embodiments, the present invention includes a method of increasing survival or proliferation of myeloid cells, such as microglia, macrophages, or dendritic cells, in a patient in need thereof comprising administering to the patient an effective amount of a TREM2 agonist antigen binding protein described herein. In certain embodiments, the TREM2 agonist antigen binding protein administered to the patient is an anti-TREM2 agonist monoclonal antibody, such as the antibodies whose variable and CDR sequences are set forth in Tables 1A, 1B, 2A, 2B, 3A, and 3B. In some embodiments, the patient in need of treatment is at risk for, suffers from, or has been diagnosed with a neurodegenerative disorder. In one embodiment, the neurodegenerative disorder is Alzheimer's disease. In some embodiments, the patient in need of treatment is at risk for, suffers from, or has been diagnosed with an autoimmune disorder. In one embodiment, the autoimmune disorder is multiple sclerosis.

The TREM2 agonist antigen binding proteins of the invention are also useful for detecting human TREM2 in biological samples and identification of cells or tissues that express human TREM2. For instance, the antigen binding proteins can be used in diagnostic assays, e.g., immunoassays to detect and/or quantify TREM2 expressed in a tissue or cell (macrophages or microglia) or presence of soluble forms of TREM2 in a bodily fluid, such as cerebrospinal fluid, blood, serum, or plasma. In addition, the TREM2 agonist antigen binding proteins described herein can be used to activate TREM2/DAP12 signaling in myeloid cells, thereby modulating the biological activity of these cells. Such biological activities include cytokine release, phagocytosis, and microgliosis.

The TREM2 agonist antigen binding proteins described herein can be used for diagnostic purposes to detect, diagnose, or monitor conditions associated with TREM2 dysfunction, such as neurodegenerative diseases (e.g. Alzheimer's disease, Parkinson's disease), central nervous system injury (traumatic brain injury, spinal cord injury, stroke), autoimmune diseases (multiple sclerosis, rheumatoid arthritis, systemic lupus erythematosus), frontotemporal dementia, Nasu-Hakola disease, and bone disorders (e.g. osteoporosis, osteopetrosis, osteosclerosis). For instance, elevation in the level of a soluble form of TREM2 in cerebrospinal fluid has been observed in patients with multiple sclerosis (Piccio et al., Brain, Vol. 131: 3081-3091, 2008). Also provided are methods for the detection of the presence of TREM2 in a sample using classical immunohistological methods known to those of skill in the art (e.g., Tijssen, 1993, Practice and Theory of Enzyme Immunoassays, Vol 15 (Eds R. H. Burdon and P. H. van Knippenberg, Elsevier, Amsterdam); Zola, 1987, Monoclonal Antibodies: A Manual of Techniques, pp. 147-158 (CRC Press, Inc.); Jalkanen et al., 1985, J. Cell. Biol. 101:976-985; Jalkanen et al., 1987, J. Cell Biol. 105:3087-3096). Examples of methods useful in the detection of the presence of TREM2 include immunoassays, such as the enzyme linked immunosorbent assay (ELISA) and the radioimmunoassay (RIA), using the antigen binding proteins described herein. The detection of TREM2 can be performed in vivo or in vitro.

For diagnostic applications, the antigen binding protein can be labeled with a detectable labeling group. Suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used.

In another embodiment, the antigen binding proteins described herein can be used to identify a cell or cells that express TREM2. In a specific embodiment, the antigen binding protein is labeled with a labeling group and the binding of the labeled antigen binding protein to TREM2 is detected. The antigen binding proteins can also be used in immunoprecipitation assays in biological samples. In a further specific embodiment, the binding of the antigen binding protein to TREM2 is detected in vivo. In a further specific embodiment, the antigen binding protein is isolated and measured using techniques known in the art. See, for example, Harlow and Lane, 1988, Antibodies: A Laboratory Manual, New York: Cold Spring Harbor (ed. 1991 and periodic supplements); John E. Coligan, ed., 1993, Current Protocols In Immunology New York: John Wiley & Sons.

The following examples, including the experiments conducted and the results achieved, are provided for illustrative purposes only and are not to be construed as limiting the scope of the appended claims.

EXAMPLES

Example 1. Generation of Human Anti-TREM2 Antibodies

Immunizations

Fully human antibodies to human TREM2 were generated by immunizing XenoMouse® transgenic mice. These transgenic mice carry human immunoglobulin transgenes that allow for production of antigen-specific fully human antibodies upon immunization. See, e.g., U.S. Pat. Nos. 6,114,598; 6,162,963; 6,833,268; 7,049,426; 7,064,244; Green et al., 1994, Nature Genetics 7:13-21; Mendez et al., 1997, Nature Genetics 15:146-156; Green and Jakobovits, 1998, J. Ex. Med, 188:483-495; Green, 1999, Journal of Immunological Methods 231:11-23; Kellerman and Green, Current Opinion in Biotechnology 13, 593-597, 2002, all of which are hereby incorporated by reference in their entireties. Animals from the XMG2-K, XMG2-KL, XMG4-K and XMG4-KL XenoMouse® strains were used for immunizations. Mice of the XenoMouse® strains XMG2-K and XMG2-KL produce fully human IgG2 antibodies with kappa light chains (XMG2-K) or both kappa and lambda light chains (XMG2-KL). Mice of the XenoMouse® strains XMG4-K and XMG4-KL produce fully human IgG4 antibodies with kappa light chains (XMG4-K) or both kappa and lambda light chains (XMG4-KL).

Multiple immunogens and routes of immunization were used to produce an immune response to human TREM2 in the XenoMouse® strains. For soluble recombinant protein immunizations, mice were immunized with a soluble TREM2 protein, which was a fusion protein comprising the extracellular domain (ECD) of human TREM2 (amino acids 1-174; SEQ ID NO: 2) fused to the N-terminus of a human IgG1 Fc region through a Gly-Ser-Ser linker. Animals were immunized with the soluble TREM2 protein mixed with CpG oligodeoxynucleotides (CpG-ODN) or CpG-ODN and polyinosinic:polycytidylic acid (Poly I:C) and QS-21 adjuvant, 8-12 times over 4-8 weeks using subcutaneous injections. The initial boost contained 10 μg of protein while subsequent boosts contained 5 μg of protein.

The immunogen for genetic immunization was created by coating gold beads (BioRad, Hercules, California) with mouse GM-CSF, CpG-ODN, and expression vectors encoding wild-type human TREM2 (SEQ ID NO: 1) and wild-type human DAP12 (SEQ ID NO: 3). The genetic immunogen was delivered to the epidermis of a shaved mouse abdomen using the Helios Gene Gun system according to the manufacturer's instructions (BioRad, Hercules, California). Mice were immunized with the genetic immunogen 12-16 times over 6-8 weeks.

Human TREM2-specific serum titers were monitored by live-cell FACS analysis on an Accuri or FacsCalibur (BD Biosciences) flow cytometer or by TREM2-specific ELISA. Animals with the highest serum native titers directed against human TREM2 from four separate harvests were sacrificed and used for hybridoma generation. Table 7 below provides a description of each harvest group.

TABLE 7

| | TREM2 Immunization Groups | | | |
| --- | --- | --- | --- | --- |
| Group | Immunogen | Adjuvant | XenoMouse ® Strain | Harvest |
| Harvest 1 | Human TREM2 soluble protein | CpG | G2K G2KL | 3 mice 3 mice |
| Harvest 3 | Human TREM2 soluble protein | CpG + Poly I:C + QS-21 | G2K G2KL | 6 mice 4 mice |
| Harvest 4 | pTT5 vector/human TREM2 + pTT5 vector/human DAP12 | CpG + mGM-CSF | G2K G2KL | 10 mice 4 mice |
| Harvest 5 | pTT5 vector/human TREM2 + pTT5 vector/human DAP12 | CpG + mGM-CSF | G4K G4KL | 4 mice 4 mice |

Preparation of Monoclonal Antibodies

Animals exhibiting suitable antigen-specific serum titers were identified and lymphocytes were obtained from spleen and/or draining lymph nodes. Pooled lymphocytes (from each harvest) were dissociated from lymphoid tissue by grinding in a suitable medium (for example, Dulbecco's Modified Eagle Medium (DMEM); Invitrogen, Carlsbad, CA). B cells were selected and/or expanded using standard methods, and fused with a suitable fusion partner (e.g. non-secretory myeloma P3X63Ag8.653 cells) using conventional techniques.

For harvest 1, fused hybridoma pools from select immune tissue harvest were plated as polyclonal wells, exhausted to generate conditioned media, and then screened for binding to the soluble human TREM2 protein (fusion protein described above). The hits from this plating were pooled and then clonally FACS-sorted to obtain one live cell per well.

For harvest 3, 4 and 5, fused hybridoma pools from select immune tissue were used as a source of material for FACS-based enrichments. Specifically, hybridoma cells were thawed and cultured in DMEM selection media for 3-4 days. Media was changed to BDQY hybridoma media a day before bulk sort. Cells were washed in 10 mL sterile FACS buffer and then incubated with biotinylated soluble TREM2 protein at 2 to 5 μg/mL concentration at 1 mL reaction volume for 1 hour at 4° C. For the harvest 3 group, which was immunized with soluble TREM2 protein, this step was performed in the presence of 100 μg/mL polyclonal human IgG (Jackson ImmunoResearch) to block any binders to the Fc region. The polyclonal human IgG blocking step was omitted for harvest 4 and 5 as these harvests were from genetically-immunized animals.

After one dilution wash in 10 mL FACS buffer, 1 mL antibody cocktail containing 5 μg/mL each of Alexa Fluor 488 conjugated goat anti-human IgG (Jackson Immunoresearch) and Alexa Fluor 647 conjugated streptavidin (Jackson Immunoresearch) was added to the cells. The cells were then incubated at 4° C. for 30 minutes. After the incubation, the cells were washed in 10 mL FACS buffer, resuspended in 2 mL of BDQY hybridoma media containing 5 μL of 7-AAD (BD Pharmingen, Cat: 559925), then put through a 40 micron cell strainer to remove any clumps. Cells were bulk sorted on BD FACSAria by gating on live cell population dual positive for Alexa Fluor 488 and Alexa Fluor 647 fluorescence signals.

Sorted cells were transferred into 24-well tissue culture plates and cultured for a few days before they were counted and stained again using the method described above to check for enrichment of antigen specific cells. The cells were then single cell sorted into 384-well microtiter plates containing BDQY hybridoma media and cultured for up to 2 weeks before the supernatants were collected for screening.

Example 2. Selection of TREM2-Specific Binding Antibodies

Antibodies produced from the hybridomas described in Example 1 were screened for binding to human TREM2, agonist activity of human TREM2, and cross-reactivity to other TREM proteins. The methods and results of these screens are described below.

Primary TREM2 Binding Screen

Exhausted hybridoma supernatants were tested for binding to human TREM2 by ELISA. Briefly, neutravidin plates were generated by incubating a 384 well Corning Assay Plate 3702 with neutravidin (Thermo 3100B) at 10 μg/mL (40 μL/well) in 1×PBS at 4° C. overnight. The plates were washed with 1×PBS using a Biotek plate washer and then blocked with 1% milk/1×PBS (90 μL/well) at room temperature (RT) for 30 minutes. The plates were then washed again with 1×PBS using the plate washer. The capture sample was biotinylated soluble human TREM2 protein (TREM2 ECD-huIgG1 Fc fusion protein) and was added at 0.5 μg/mL in 1% milk/1×PBS at a volume of 40 μL/well. The plates were then incubated at RT for 1 hour to immobilize the TREM2 protein to the wells of the plates. Following the incubation, the plates were again washed with 1×PBS using the plate washer. 10 μL of each hybridoma supernatant to be tested and 40 μL of 1% milk/1×PBS (1:5 dilution) were added to each well of the plates and incubated at RT for 1 hour. Again, the plates were washed with 1×PBS using the plate washer. Goat anti-human kappa-HRP (Southern Biotech, 2060-05) and goat anti-human lambda-HRP (Southern Biotech, 2070-05) diluted together 1:2000 in 1% milk/1×PBS or goat anti-human IgG Fc POD diluted 1:4000 in 1% milk/1×PBS was added to the plates (40 μl/well) and the plates were incubated at RT for 1 hour. After the plates were washed with 1×PBS using the plate washer, 40 μL/well of TMB substrate (Neogen, lot #150114) was added to the plates and the plates were incubated at RT for 30 minutes. The reaction was quenched with 1N hydrochloric acid (40 uL/well) following the incubation period. OD readings at 450 nm were obtained with a plate reader.

The primary ELISA screen identified 2,523 antibodies that were positive for TREM2 binding from the four separate harvests groups. These identified antibodies were advanced to the functional assay screens.

TREM2 Functional Assay Screens

The antibodies that tested positive for TREM2 binding in the ELISA assay were evaluated for agonist activity of human TREM2 in a cell-based phospho-Syk (pSyk) signaling assay. Human TREM2, which is a transmembrane glycoprotein, couples with the adaptor protein, DAP12, for signaling and function through the recruitment of tyrosine kinases ζ-chain associate protein 70 (ZAP70) and spleen tyrosine kinase (Syk) (Colonna, Nature Reviews Immunology, Vol. 3: 445-453, 2003). The phosphorylated form of Syk is indicative of activation of TREM2/DAP12 signaling. Thus, a cell-based AlphaLISA (Perkins Elmer) assay to detect phosphorylated forms of Syk in response to TREM2/DAP12 modulation was developed. The assay employs a rabbit-anti-pSyk antibody, a biotinylated mouse anti-total Syk antibody, acceptor beads conjugated to anti-rabbit IgG antibodies, and donor beads coated with streptavidin. Phosphorylated forms of Syk present in cell lysates are bound by both the rabbit-anti-pSyk antibody and the mouse anti-total Syk antibody. The acceptor beads, which are conjugated to an anti-rabbit IgG antibody, bind to the rabbit anti-pSyk antibody, and the streptavidin-coated donor beads bind to the biotinylated mouse anti-total Syk antibody. Excitation of the donor beads at a wavelength of 680 nm results in the release of singlet oxygen, which in turn produces an amplified fluorescent signal in the acceptor beads, thereby producing an emission at 615 nm. The emission at 615 nm is not detected if the donor and acceptor beads are not located within close proximity to each other (i.e. acceptor bead is not recruited to the complex because Syk is not phosphorylated and thus, not bound by the rabbit anti-pSyk antibody). Thus, the amount of light emitted at 615 nm is proportional to the amount of phosphorylated Syk present in the cell lysate, which in turn is indicative of activation of TREM2/DAP12 signaling by the anti-TREM2 antibody.

HEK293T cells stably expressing human TREM2 and human DAP12 (G13 cell line) were plated in growth media at 40,000 cells per well (in 90 or 80 μL) in tissue culture treated 96-half area well plates or 50,000 cells per well (in 200 μL) in poly-D-lysine-coated plates. The cells were incubated overnight at 37° C. and 5% $CO_2$. Anti-human TREM2 antibodies were added either at a single concentration (for initial single point screening) or a range of concentrations (for potency testing). After incubation of cells and antibody at room temperature for 30 to 40 minutes, culture media was completely removed. The cells were lysed with 20 μL (for 40,000 cells) or 25 μL (for 50,000 cells) of lysis buffer containing protease/phosphatases inhibitors on ice for 45 to 60 minutes. The cell lysate (5 μL) was transferred to appropriate wells of a 384-well white assay plate containing a 15 μL mixture of rabbit anti-pSyk antibody (final concentration: 1 nM), biotinylated mouse anti-Syk antibodies (final concentration: 1 nM) and acceptor beads conjugated to anti-rabbit IgG antibodies (final concentration: 10 μg/mL). The assay plates were then incubated on ice for 2 hours. Donor beads coated with streptavidin (5 μL) were subsequently added to the wells (final concentration: 40 μg/mL) and the assay plates were incubated at room temperature for 1 hour in the dark. The AlphaLISA signal (counts) was measured by EnVision Multilabel Reader. The antibody agonist activity was reported as fold over control (S/B): S/B=Sample pSyk signal (counts)/Basal pSyk signal (isotype control pSyk signal counts).

Antibodies from the hybridoma supernatants that tested positive for TREM2 binding were initially tested at a single concentration in the pSyk assay. For this single point screening, exhausted hybridoma supernatant (ESN) containing anti-huTREM2 antibody was added to the cells either based on volume (10 μL for harvest 1, 1:10 dilution) or concentration (20 μL of ESN that was previously normalized to 10 μg/mL for harvest 3, 4 and 5, 1:5 dilution). Of the 2,523 antibodies positive for TREM2 binding from the four separate harvests, 140 antibodies exhibited activity in the pSyk assay at a single concentration. These antibodies were advanced for potency screening.

Potency screening was initially performed on unpurified, quantitated clonal hybridoma-derived anti-TREM2 antibodies and later on purified hybridoma-derived and/or recombinant monoclonal antibodies. For harvest 1, the anti-TREM2 antibodies were serially titrated at 3-fold from 100 μg/mL to 0.005 μg/mL and 10 μL of each dilution was added to the cells (final antibody concentrations from 10 μg/mL to 0.0005 μg/mL, 66.67 nM to 0.003 nM). For potency screening of harvest 3, 4, and 5, the culture medium was completely removed from the cells. The anti-TREM2 antibodies were serially titrated at 3 fold from 2 μg/mL to 0.003 μg/mL in growth media and 50 μL of each dilution was added to the cells (final antibody concentration from 13.33 nM to 0.02 nM). The EC50 values for each anti-TREM2 antibody was determined by a four-parameter logistic fit model of Graph-Pad Prism Version 6.07 from the 10-point dose response curves.

Of the 140 antibodies screened for potency, 93 antibodies were selected for further screening and characterization. FIG. 1A shows the dose-response curves for the top agonist anti-TREM2 antibodies from harvest 1, whereas FIG. 1B shows the dose-response curves for the top agonist anti-TREM2 antibodies from harvests 3, 4, and 5. EC50 values for the top 18 antibodies from all four harvests are provided in Table 8 below. As evident from the low nanomolar or subnanomolar EC50 values, the majority of the anti-TREM2 antibodies are potent agonists of TREM2/DAP12 signaling. Several of the antibodies are more potent and produce a greater level of maximum activation of TREM2/DAP12 signaling than a commercially available rat anti-human/mouse TREM2 antibody (mAb17291; Rat IgG2b Clone

237920, R&D Systems), which had an EC50 value of 0.50 nM and an Emax of 13.8 in this assay. Importantly, the agonist activity of the anti-TREM2 antibodies was observed in the absence of a cross-linking agent (e.g. protein G, protein A, or anti-human secondary antibody) or immobilization of the antibodies (e.g. plate-bound antibodies), suggesting the antibodies can effectively engage and activate human TREM2 in a soluble, monomeric form. For many agonist antibodies, cross-linking of their Fc regions is required to cluster the antibodies to activate effectively the target receptor. See, e.g., Natoni et al., British Journal of Haematology, Vol. 139: 568-577, 2007; Vonderheide and Glennie, Clin. Cancer Res., Vol. 19: 1035-1043, 2013. Such a cross-linking requirement to achieve agonist activity for other TREM2 antibodies has been observed. See, e.g., U.S. Pat. No. 8,981,061 and WO 2016/023019. The TREM2 antibodies described herein have an advantage over these other TREM2 antibodies in that they are cross-linking independent agonists of human TREM2 (e.g. they do not require cross-linking or oligomerization via their Fc domains for agonistic activity).

Selectivity and Cross-Reactivity of TREM2 Antibodies

The anti-TREM2 antibodies demonstrating agonist activity in the potency screen were further evaluated for cross-reactivity to mouse and cynomolgous TREM2 as well as cross-reactivity to human TREM1 protein. For the species cross-reactivity screen, HEK293 cells were transfected with expression vectors comprising either mouse TREM2 and mouse DAP12 cDNA or cynomolgus TREM2 and cynomolgus DAP12 cDNA, Gibco™ Opti-MEM® media (Gibco, Cat. No. 31985088) and 293Fectin™ reagent (Invitrogen, Cat. No. 12347019) following the protocol set out by the manufacturer. TREM1 cross-reactivity was assessed using a cell line stably expressing human TREM1/DAP12. Hybridoma supernatants were screened for the presence of monoclonal antibodies binding to human TREM1, mouse TREM2 or cynomolgus TREM2 by incubating the supernatants on each of the transfected cells for 1 hour, followed by wash steps. The cells were then incubated with a goat anti-human Fc antibody conjugated to Alexa Fluor 647 (Jackson Immunochemicals 109-605-098) for 15 minutes. The binding was detected by FACS using the Accuri FACS machine with Intellicyt autosampler. Irrelevant isotype control antibodies were included in the FACS analysis. The data was reported as geomean (GM) fold over irrelevant control antibody binding. Of the 93 antibodies from the four harvests screened for cross-reactivity, 50 antibodies were cross-reactive with cynomolgus TREM2 and 9 antibodies were cross-reactive with mouse TREM2. None of the tested antibodies were cross-reactive with human TREM1. The data from all screens for the top 18 anti-TREM2 monoclonal antibodies from all four harvests are summarized in Table 8 below.

TABLE 8

| Antibody ID | OD 450 human TREM2 (ELISA) | Isotype | pSyk fold over control | pSyk EC50 (nM) | Cyno TREM2 GM Fold | Mouse TREM2 GM Fold | Human TREM1 GM Fold |
|---|---|---|---|---|---|---|---|
| | Summary Data for Top Anti-TREM2 Monoclonal Antibodies from Hybridoma Screen | | | | | | |
| 4C5 | 3.62 | G2 | 9.26 | 0.18 | 42.3 | 0.4 | 0.8 |
| 4G10 | 3.17 | G2 | 11.72 | 0.47 | 96.3 | 4.1 | 1.2 |
| 5E3 | 3.88 | G2 | 8.02 | 0.24 | 89.6 | 2.6 | 1.1 |
| 6E7 | 3.17 | G2 | 13.69 | 0.29 | 82.7 | 1.2 | 1.2 |
| 24A10 | 2.75 | G2 | 6.8 | 32.9 | 1.4 | 1.1 | 1.1 |

TABLE 8-continued

| | | | | | | | |
|---|---|---|---|---|---|---|---|
| Summary Data for Top Anti-TREM2 Monoclonal Antibodies from Hybridoma Screen | | | | | | | |
| Antibody ID | OD 450 human TREM2 (ELISA) | Isotype | pSyk fold over control | pSyk EC50 (nM) | Cyno TREM2 GM Fold | Mouse TREM2 GM Fold | Human TREM1 GM Fold |
| 24F4 | 1.20 | G2 | 5.8 | 2.4 | 34.0 | 10.1 | 1.2 |
| 24G6 | 2.76 | G2 | 11.8 | 1.0 | 12.2 | 0.9 | 1.3 |
| 25F12 | 1.29 | G2 | 4.2 | 2.6 | 2.2 | 0.8 | 1.2 |
| 26A10 | 1.16 | G2 | 6.0 | 1.3 | 37.5 | 0.8 | 1.5 |
| 26C10 | 1.59 | G2 | 4.8 | 2.2 | 46.0 | 0.9 | 1.7 |
| 26F2 | 1.48 | G2 | 5.4 | 1.4 | 72.8 | 1.1 | 1.6 |
| 32E3 | 1.41 | G2 | 8.2 | 1.2 | 31.0 | 1.0 | 1.1 |
| 33B12 | 1.34 | G2 | 6.0 | 1.0 | 21.7 | 1.0 | 1.4 |
| 10E3 | 0.55 | G2 | 12.1 | 0.4 | 82.8 | 1.1 | 1.6 |
| 12G10 | 3.49 | G2 | 11.1 | 0.4 | 2.1 | 1.1 | 1.1 |
| 13E7 | 0.73 | G2 | 11.4 | 0.4 | 67.5 | 1.1 | 1.4 |
| 14C12 | 0.71 | G2 | 11.1 | 0.4 | 63.2 | 1.1 | 1.4 |
| 16B8 | 0.59 | G4 | ND | ND | 23.3 | 1.1 | 1.1 |

Example 3. Sequencing of Human Anti-TREM2 Agonist Antibodies

RNA (total or mRNA) was purified from wells containing the TREM2 agonist antibody-producing hybridoma cells using a Qiagen RNeasy mini or the Invitrogen mRNA catcher plus kit. Purified RNA was used to amplify the antibody heavy and light chain variable region (V) genes using cDNA synthesis via reverse transcription, followed by a polymerase chain reaction (RT-PCR). The fully human antibody gamma heavy chain was obtained using the Qiagen One Step Reverse Transcriptase PCR kit (Qiagen). This kit was used to generate the first strand cDNA from the RNA template and then to amplify the variable region of the gamma heavy chain using multiplex PCR. The 5' gamma chain-specific primer annealed to the signal sequence of the antibody heavy chain, while the 3' primer annealed to a region of the gamma constant domain. The fully human kappa light chain was obtained using the Qiagen One Step Reverse Transcriptase PCR kit (Qiagen). This kit was used to generate the first strand cDNA from the RNA template and then to amplify the variable region of the kappa light chain using multiplex PCR. The 5' kappa light chain-specific primer annealed to the signal sequence of the antibody light chain while the 3' primer annealed to a region of the kappa constant domain. The fully human lambda light chain was obtained using the Qiagen One Step Reverse Transcriptase PCR kit (Qiagen). This kit was used to generate the first strand cDNA from the RNA template and then to amplify the variable region of the lambda light chain using multiplex PCR. The 5' lambda light chain-specific primer annealed to the signal sequence of light chain while the 3' primer annealed to a region of the lambda constant domain.

The amplified cDNA was purified enzymatically using exonuclease I and alkaline phosphatase and the purified PCR product was sequenced directly. Amino acid sequences were deduced from the corresponding nucleic acid sequences bioinformatically. Two additional, independent RT-PCR amplification and sequencing cycles were completed for each hybridoma sample in order to confirm that any mutations observed were not a consequence of the PCR. Amino acid sequences for the light chain variable regions and associated CDRs for exemplary antibodies are provided in Table 1A, whereas amino acid sequences for the heavy chain variable regions and associated CDRs for the antibodies are provided in Table 1B. Table 6 provides nucleic acid sequences encoding the light and heavy chain variable regions of the exemplary antibodies.

The derived amino acid sequences for each light and heavy chain variable region were then analyzed to determine the germline sequence origin of the antibodies and to identify deviations from the germline sequence. A comparison of each of the light chain and heavy chain variable region sequences to their original germline sequences are shown in FIGS. 2A-4B. The identity of the germline genes is indicated next to each antibody clone number. The amino acid sequences corresponding to CDRs of the sequenced antibodies were aligned and these alignments were used to group the clones by similarity.

Example 4. Epitope Binning Analysis of Agonist Anti-TREM2 Antibodies

Epitope bins of a subset of agonist anti-human TREM2 antibodies were determined using anti-human Fc (Kinetic) sensors (18-5090) on an Octet® HTX instrument (Pall ForteBio). Each of sixteen different anti-TREM2 antibodies produced from hybridomas were quantitated and loaded onto one of the anti-human Fc sensors at 5 µg/mL for 2 minutes ("Load Antibody"). The sensor was then blocked with 100 µg/mL of an irrelevant human IgG2 antibody for 5 minutes. A recombinant soluble human TREM2 protein (human TREM2 extracellular domain (amino acids 1-174) coupled to a Flag/His tag (human TREM2 ECD-FlagHis)) was added to the sensor at 4 µg/mL for 5 minutes to allow binding of the soluble TREM2 protein to the load antibody. Next, each of the sixteen different anti-TREM2 antibodies ("Sandwich Antibody") was added to the sensor at 5 µg/mL and allowed to bind for 5 minutes. All assay buffers contained 10 mM Tris (pH 7.6), 0.1% Triton X-100, 150 mM NaCl, 1 mM CaCl$_2$, and 1 mg/mL BSA. The assay was conducted at 25° C. Experimental kinetic results were fit to a 1:1 binding model.

If the load antibody and the sandwich antibody bind to a similar epitope on human TREM2, then the addition of the sandwich antibody to the sensor will not produce a binding event. However, if addition of the sandwich antibody produces a binding event, then the sandwich antibody binds to a different epitope on human TREM2 than the load antibody and the two antibodies are categorized into different epitope bins. FIG. 5 depicts binding data from a sensor loaded with the 6E7 antibody and exposed to either the 5E3 antibody or the 6E7 antibody as the sandwich antibody. As expected, an increase in binding was observed with the addition of the soluble human TREM2 protein indicating that the 6E7 antibody specifically bound to an epitope on human TREM2. No further binding was observed when 6E7 was added as the sandwich antibody as the sensor-immobilized 6E7 antibody was already bound to this particular epitope on human TREM2. However, when the 5E3 antibody was added as the sandwich antibody, an increase in binding was observed, indicating that the 5E3 antibody binds to a different epitope on human TREM2 than the 6E7 antibody.

A summary of the epitope binning data for sixteen different anti-TREM2 antibodies is shown below in Table 9. Based on the binding data, the antibodies could be grouped into four distinct epitope bins. Antibodies 10E3, 13E7, 24F4, 4C5, 4G10, 32E3, and 6E7 appear to share a similar epitope (bin A), which is different than the epitope bound by antibodies 16B8, 26A10, 26C10, 26F2, 33B12, and 5E3 (bin B). Antibodies 24A10 and 24G6 share a similar epitope on human TREM2 (bin C), whereas antibody 25F12 has a distinct binding epitope (bin D) from any of the other tested antibodies.

mined using anti-human Fc (Kinetic) sensors on an Octet® HTX instrument (Pall ForteBio). Agonist anti-TREM2 antibodies were made up in DMEM null media, 250 μL at 10 μg/mL. The, 250 uL of assay buffer (10 mM Tris (pH 7.6), 0.1% Triton X-100, 150 mM NaCl, 1 mM $CaCl_2$, and 1 mg/mL BSA) was added to the antibody solutions to a final volume of 500 μL and final antibody concentration of 5 μg/mL. The anti-human Fc sensor was pre-incubated in 200 μL of the assay buffer for a minimum of 10 minutes. The sensor was then regenerated for 5 seconds in 10 mM glycine pH 1.5. Test agonist anti-TREM2 antibodies were loaded onto the sensor for 2 minutes, and baseline measurements were taken for 2 minutes. The antibody-loaded sensor was bound to recombinant soluble human TREM2 protein (human TREM2 extracellular domain (amino acids 1-174) coupled to a Flag/His tag (human TREM2 ECD-FlagHis)) or recombinant soluble cynomolgus TREM2 protein (cynomolgus TREM2 extracellular domain coupled to a Flag/His tag) in a 2-fold serial dilution series starting at 100 nM with a 6-point dilution series. The recombinant TREM2 proteins were allowed to associate with the antibody-loaded sensor

TABLE 9

Summary of Epitope Binning Analysis

| Load Ab | Sandwich Antibody | | | | | | | | |
|---|---|---|---|---|---|---|---|---|---|
| | 10E3 | 13E7 | 24F4 | 4C5 | 4G10 | 32E3 | 6E7 | 16B8 | 26A10 |
| 10E3 | −0.024 | −0.019 | −0.032 | −0.005 | −0.019 | −0.023 | 0.051 | 0.280 | 0.259 |
| 13E7 | −0.019 | −0.017 | −0.015 | ND | ND | −0.027 | 0.051 | 0.312 | 0.272 |
| 24F4 | −0.002 | −0.002 | 0.038 | ND | ND | −0.021 | 0.054 | 0.454 | 0.449 |
| 4C5 | 0.000 | ND | ND | −0.014 | −0.018 | −0.016 | ND | ND | ND |
| 4G10 | −0.008 | ND | ND | −0.011 | −0.026 | −0.020 | ND | ND | ND |
| 32E3 | 0.007 | 0.010 | −0.001 | −0.010 | −0.029 | −0.010 | 0.079 | 0.400 | 0.362 |
| 6E7 | −0.012 | −0.010 | −0.039 | ND | ND | −0.024 | 0.009 | 0.504 | 0.491 |
| 16B8 | 0.330 | 0.329 | 0.270 | ND | ND | 0.120 | 0.429 | −0.009 | −0.018 |
| 26A10 | 0.367 | 0.371 | 0.319 | ND | ND | 0.157 | 0.475 | 0.028 | −0.001 |
| 26C10 | 0.348 | 0.369 | 0.346 | ND | ND | 0.141 | 0.472 | 0.006 | −0.033 |
| 26F2 | 0.354 | 0.363 | 0.282 | 0.310 | 0.180 | 0.143 | 0.506 | 0.031 | −0.016 |
| 33B12 | 0.303 | 0.303 | 0.250 | ND | ND | 0.132 | 0.434 | 0.007 | −0.020 |
| 5E3 | 0.415 | 0.428 | 0.311 | ND | ND | 0.176 | 0.565 | −0.004 | −0.027 |
| 24A10 | 0.380 | 0.383 | 0.335 | ND | ND | 0.162 | 0.499 | 0.423 | 0.454 |
| 24G6 | 0.317 | 0.338 | 0.251 | 0.268 | 0.184 | 0.126 | 0.412 | 0.369 | 0.354 |
| 25F12 | 0.273 | 0.278 | 0.244 | 0.265 | 0.199 | 0.154 | 0.371 | 0.399 | 0.343 |

| Load Ab | Sandwich Antibody | | | | | | | Bin |
|---|---|---|---|---|---|---|---|---|
| | 26C10 | 26F2 | 33B12 | 5E3 | 24A10 | 24G6 | 25F12 | |
| 10E3 | 0.285 | 0.275 | 0.271 | 0.222 | 0.347 | 0.331 | 0.089 | A |
| 13E7 | 0.323 | 0.294 | 0.287 | 0.259 | 0.375 | 0.356 | 0.104 | A |
| 24F4 | 0.552 | 0.477 | 0.454 | 0.434 | 0.585 | 0.523 | 0.180 | A |
| 4C5 | ND | 0.368 | ND | ND | ND | 0A38 | 0.154 | A |
| 4G10 | ND | 0.334 | ND | ND | ND | 0.376 | 0.142 | A |
| 32E3 | 0.419 | 0.411 | 0.384 | 0.338 | 0.461 | 0.444 | 0.236 | A |
| 6E7 | 0.594 | 0.523 | 0.520 | 0.514 | 0.616 | 0.583 | 0.213 | A |
| 16B8 | −0.031 | −0.003 | −0.017 | −0.047 | 0.481 | 0.481 | 0.252 | B |
| 26A10 | −0.017 | 0.009 | 0.023 | −0.052 | 0.596 | 0.557 | 0.347 | B |
| 26C10 | −0.032 | −0.003 | −0.009 | −0.073 | 0.605 | 0.554 | 0.327 | B |
| 26F2 | −0.015 | −0.008 | 0.002 | −0.045 | 0.544 | 0.529 | 0.330 | B |
| 33B12 | −0.033 | −0.009 | −0.014 | −0.055 | 0.439 | 0.446 | 0.275 | B |
| 5E3 | −0.042 | −0.014 | −0.015 | −0.165 | 0.530 | 0.552 | 0.335 | B |
| 24A10 | 0.541 | 0.490 | 0.470 | 0.441 | 0.023 | 0.000 | 0.340 | C |
| 24G6 | 0.384 | 0.399 | 0.388 | 0.328 | −0.031 | −0.019 | 0.284 | C |
| 25F12 | 0.418 | 0.366 | 0.345 | 0.380 | 0.509 | 0.488 | 0.011 | D |

Example 5. Binding Affinity Determination of Agonist Anti-TREM2 Antibodies

To quantitate the binding affinity of agonist antibodies for human TREM2, association and dissociation rate constants as well as the equilibrium dissociation constant were determined for 10 minutes, and then dissociation was measured for 10 minutes. The assay was conducted at 25° C. Experimental kinetic results were globally fit to a 1:1 binding model in order to determine the association and dissociation rate constants as well as the equilibrium dissociation constant. Table 10 provides the results of the assay for human TREM2 for select antibodies and Table 11 provides the results of the assay for cynomolgus TREM2 for select antibodies.

TABLE 10

| Binding Affinity for Human TREM2 | | | |
|---|---|---|---|
| Antibody ID | $K_D$ (M) | $k_a$ ($M^{-1}s^{-1}$) | $k_d$ ($s^{-1}$) |
| 4C5 | 3.1E−09 | 1.6E+05 | 4.9E−04 |
| 4G10 | 3.3E−09 | 3.0E+05 | 9.8E−04 |
| 5E3 | 2.1E−09 | 2.5E+05 | 5.3E−04 |
| 6E7 | 2.6E−09 | 2.7E+05 | 6.9E−04 |
| 10E3 | 1.03E−08 | 1.77E+05 | 1.82E−03 |
| 13E7 | 1.10E−08 | 1.44E+05 | 1.58E−03 |
| 24G6 | 3.13E−09 | 2.20E+05 | 6.88E−04 |

TABLE 11

| Binding Affinity for Cyno TREM2 | | | |
|---|---|---|---|
| Antibody ID | $K_D$ (M) | $k_a$ ($M^{-1}s^{-1}$) | $k_d$ ($s^{-1}$) |
| 4C5 | 3.6E−09 | 3.3E+05 | 1.2E−03 |
| 4G10 | 1.7E−09 | 5.6E+05 | 9.6E−04 |
| 5E3 | 1.6E−09 | 7.0E+05 | 1.1E−03 |
| 6E7 | 2.5E−09 | 4.6E+05 | 1.1E−03 |
| 10E3 | 1.13E−08 | 3.24E+05 | 3.66E−03 |
| 13E7 | 8.71E−09 | 2.72E+05 | 2.37E−03 |
| 24G6 | 1.99E−08 | 4.86E+05 | 9.65E−03 |

Example 6. Agonist Activity of Anti-TREM2 Antibodies in THP-1 Cells

Select anti-TREM2 antibodies were evaluated for their ability to activate human TREM2/DAP12 signaling in THP-1 cells. The THP-1 cell line is a human leukemia monocytic cell line, which is commonly used as an in vitro model of human monocyte and macrophage function (Chanput et al., International Immunopharmacology, Vol. 23: 37-45, 2014).

Suspension THP-1 cells ($1\times10^6$ cells/mL) were differentiated by incubation in growth media (RPMI, 10% FBS (heat inactivated, 1% Glutamax, 1% Hepes, 1% Pen/Strep) containing 20 nM Phorbol 12-myristate 13-acetate (PMA) at 37° C./5% $CO_2$ for 72 hours. After 72 hours stimulation, the cells attached to the surface of tissue culture-treated dishes. PMA was gently washed off with PBS, and replenished in fresh growth media containing 10 ng/mL IL-4. The cells were continually incubated at 37° C./5% $CO_2$ for another 72 hours. On day 6 (end of cell differentiation), the cells were harvested with non-enzymatic cell dissociation buffer or cell stripper and were plated in growth media at 100,000 cells per well into tissue culture-treated 96-well plates. The cells were incubated overnight at 37° C./5% $CO_2$.

On the following day, the cells were treated with anti-human TREM2 antibodies for 10 minutes at room temperature, and the media was subsequently removed. The cells were lysed with 30 μl lysis buffer for 45 to 60 minutes on ice. The cell lysate (5 μL) was transferred into 384 well plates for determination of phosphorylated Syk (pSyk) levels using the AlphaLISA assay described in Example 2. The EC50 for each anti-TREM2 antibody was determined from a dose-response curve by a four-parameter logistic fit model of GraphPad Prism Version 6.07.

The results of the experiment are shown in FIG. 6 and Table 12. All of the tested anti-TREM2 antibodies induced pSyk levels in a dose-dependent manner in the differentiated THP-1 cells. All of the anti-TREM2 antibodies produced greater activation of Syk than mAB17291 ("RnD"), a commercial rat anti-human/mouse antibody (Rat IgG2b Clone #237920, R&D Systems), with ten of the antibodies producing a 2-fold or greater maximum activation than the commercial antibody. Antibodies 10E3 and 13E7 exhibited the highest Emax values, which were about 4.5-fold greater than that that for the commercial antibody.

TABLE 12

| Activation of TREM2/DAP12 Signaling in THP-1 Cells by Anti-TREM2 Antibodies | | |
|---|---|---|
| Antibody ID | EC50 (nM) | Emax* |
| 4C5 | 1.715 | 265.4 |
| 4G10 | 0.5791 | 235.7 |
| 5E3 | 0.5935 | 194.8 |
| 6E7 | 0.8989 | 273.4 |
| 10E3 | 1.004 | 456.5 |
| 13E7 | 0.4617 | 459.6 |
| 16B8 | 0.4176 | 139.8 |
| 24G6 | 0.6622 | 221.1 |
| 25F12 | 1.048 | 121.5 |
| 26F2 | 0.07778 | 207.4 |
| 32E3 | 1.246 | 196.6 |
| 33B12 | 2.845 | 245.7 |
| RnD | 0.3834 | 100* |

*Emax = % maximum activation of antibody compared to RnD antibody (fixed as 100%)

Example 7. Engineering of Agonist Anti-TREM2 Antibodies

A subset of the anti-TREM2 antibodies were selected for subsequent engineering to improve the biophysical, expression, and/or stability properties of the antibodies. Light and heavy chain variable region sequences of antibodies 10E3, 13E7, 4C5, 6E7, 5E3, and 24G6 were analyzed for potential chemical hotspots (e.g. aspartate isomerization, asparagine deamidation, and tryptophan oxidation) and covariance violations. Correction of covariance violations can improve thermal stability, expression, and biophysical properties of antibodies (see, e.g., WO 2012/125495). Tables 13-18 below summarize the results of the sequence analysis for each of the six antibodies and identify specific mutations at particular positions within the heavy and light chain variable region sequences that can be made to improve the stability, expression, and/or biophysical properties of the antibodies. The particular region (e.g. framework regions 1, 2, 3, or 4 (FR1, FR2, FR3, or FR4) or complementarity determining regions 1, 2, or 3 (CDR1, CDR2, or CDR3) within the sequence are also indicated.

TABLE 13

| Engineered Variants of 10E3 Antibody | | | | |
|---|---|---|---|---|
| Position in 10E3 VL Sequence or VH sequence | Region | Hot Spot | Parent Amino Acid | Amino Acid Substitutions |
| Light chain variable sequence (SEQ ID NO: 54) | | | | |
| 64 | FR3 | Covariance violator | V | G, A |
| 79 | FR3 | Covariance violator | Q | E, D |
| 80 | FR3 | Covariance violator | S | P, A |
| 85 | FR3 | Covariance violator | F | V, L, A, D, I, L, M, T |

TABLE 13-continued

Engineered Variants of 10E3 Antibody

| Position in 10E3 VL Sequence or VH sequence | Region | Hot Spot | Parent Amino Acid | Amino Acid Substitutions |
|---|---|---|---|---|
| 94 | CDR3 | Potential Tryptophan Oxidation Site | W | F, Y, S, T, A, H, I, Q |
| 100 | FR4 | Covariance violator | P | R, Q, G |
| Heavy chain variable sequence (SEQ ID NO: 117) | | | | |
| 19 | FR1 | Covariance violator | M | K, R, T, E, N, Q |
| 55-56 | CDR2 | Potential Isomerization Site | DS | ES, QS, DA, NS, DQ, TS, DV |
| 57-58 | CDR2 | Potential Isomerization Site | DT | ST, ET, DA, DV, QT |
| 104 | CDR3 | Potential Tryptophan Oxidation Site | W | F, Y, T, S, A, H, I, Q |

TABLE 14

Engineered Variants of 13E7 Antibody

| Position in 13E7 VL Sequence or VH sequence | Region | Hot Spot | Parent Amino Acid | Amino Acid Substitutions |
|---|---|---|---|---|
| Light chain variable sequence (SEQ ID NO: 55) | | | | |
| 64 | FR3 | Covariance violator | V | G, A |
| 79 | FR3 | Covariance violator | Q | E, D |
| 80 | FR3 | Covariance violator | S | P, A |
| 94 | CDR3 | Potential Tryptophan Oxidation Site | W | F, Y, S, T, A, H, I, Q |
| 100 | FR4 | Covariance violator | P | R, Q, G |
| Heavy chain variable sequence (SEQ ID NO: 118) | | | | |
| 19 | FR1 | Covariance violator | M | K, R, T, E, N, Q |
| 55-56 | CDR2 | Potential Isomerization Site | DS | ES, QS, DA, DQ, NS, TS, DV |
| 57-58 | CDR2 | Potential Isomerization Site | DT | ST, ET, DA, DV, QT |
| 104 | CDR3 | Potential Tryptophan Oxidation Site | W | F, Y, T, S, A, H, I, Q |

TABLE 15

Engineered Variants of 4C5 Antibody

| Position in 4C5 VL Sequence or VH sequence | Region | Hot Spot | Parent Amino Acid | Amino Acid Substitutions |
|---|---|---|---|---|
| Light chain variable sequence (SEQ ID NO: 60) | | | | |
| 60 | FR3 | Covariance violator | L | S, P, D, A |
| 92-93 | CDR3 | Potential Isomerization Site | DS | ES, QS, DA, DN, DQ, TS, NS, DV |
| Heavy chain variable sequence (SEQ ID NO: 123) | | | | |
| 27 | FR1 | Covariance violator | H | Y, D, F, N |
| 55-56 | CDR2 | Potential Isomerization Site | DS | ES, QS, DA, DQ, DV, TS, NS |

TABLE 15-continued

Engineered Variants of 4C5 Antibody

| Position in 4C5 VL Sequence or VH sequence | Region | Hot Spot | Parent Amino Acid | Amino Acid Substitutions |
|---|---|---|---|---|
| 57-58 | CDR2 | Potential Isomerization Site | DT | ST, ET, DA, DV, QT |
| 105-106 | CDR3 | Potential Isomerization Site | DS | ES, QS, DA, DQ, DV, TS, NS, GT |

TABLE 16

Engineered Variants of 6E7 Antibody

| Position in 6E7 VL Sequence or VH sequence | Region | Hot Spot | Parent Amino Acid | Amino Acid Substitutions |
|---|---|---|---|---|
| Light chain variable sequence (SEQ ID NO: 61) | | | | |
| 56-57 | CDR2/ FR3 boundary | Potential Deamidation Site | NG | SG, TG, QG, NA, EG, NV |
| 92-93 | CDR3 | Potential Isomerization Site | DS | ES, QS, DA, DN, DQ, DV, TS, NS |
| Heavy chain variable sequence (SEQ ID NO: 124) | | | | |
| 55-56 | CDR2 | Potential Isomerization Site | DS | ES, QS, DA, DQ, DV, TS, NS |
| 57-58 | CDR2 | Potential Isomerization Site | DT | ST, ET, DA, DV, QT |
| 105-106 | CDR3 | Potential Isomerization Site | DS | ES, QS, DA, DQ, DV, TS, NS, GT |

TABLE 17

Engineered Variants of 5E3 Antibody

| Position in 5E3 VL Sequence or VH sequence | Region | Hot Spot | Parent Amino Acid | Amino Acid Substitutions |
|---|---|---|---|---|
| Light chain variable sequence (SEQ ID NO: 62) | | | | |
| 36 | FR2 | Consensus violator | F | Y |
| 46 | FR2 | Covariance violator | S | L, R,V, F |
| 61 | FR3 | Consensus violator | K | R |
| 100 | FR4 | Covariance violator | P | Q, G, R |
| Heavy chain variable sequence (SEQ ID NO: 125) | | | | |
| 43 | FR2 | Covariance violator | L | Q, K, H |
| 76 | FR3 | Covariance violator | I | T |
| 85 | FR3 | Covariance violator | R | S, G, N, D |
| 99-100 | CDR3 | Potential Isomerization Site | DG | EG, DA, DY, DV, QG, SG, TG |
| 116 | FR4 | Covariance violator | T | L, M, P, R |

TABLE 18

Engineered Variants of 24G6 Antibody

| Position in 24G6 VL Sequence or VH sequence | Region | Hot Spot | Parent Amino Acid | Amino Acid Substitutions |
|---|---|---|---|---|
| Light chain variable sequence (SEQ ID NO: 52) | | | | |
| 91 | FR3 | Covariance violator | F | V, I, T, L, D |
| Heavy chain variable sequence (SEQ ID NO: 115) | | | | |
| 62-63 | CDR2 | Potential Isomerization Site | DS | ES, QS, DA, DQ, TS, DV, NS |

5

10

TABLE 19

Exemplary Variable Region Amino Acid
Sequences of Engineered Antibodies

| Ab ID. | LC variable region sequence | HC variable region sequence |
|---|---|---|
| 24G6 (SST28347 and SST204812) | DIVMTQSPDSLAVSLGERATINCKSS QSVLYSSNNKHFLAWYQQKPGQPP KLLIYWASTRESGVPDRFSGSGSGT DFTLTISSLQAEDVAVYYCQQYYST PLTFGGGTKVEIK (SEQ ID NO: 326) | EVQLLESGGGLVQPGGSLRLSC AASGFTFSSYAMSWVRQAPGK GLEWVSAISGSGGSTYYAESVK GRFTISRDNSKNTLYLQMNSLR AEDTAVYYCAKAYTPMAFFDY WGQGTLVTVSS (SEQ ID NO: 327) |
| 6E7 (SST29857) | DIQMTQSPSSVSASVGDRVTITCRAS QGISSWLAWYQQKPGKAPKLLIYAA SSLQSGVPSRFSGSGSGTDFTLTISSL QPEDFATYFCQQADAFPRTFGQGTK LEIK (SEQ ID NO: 328) | EVQLVQSGAEVKKPGESLKISC KGSGYSFTSYWIAWVRQMPGK GLEWMGIIYPGDADARYSPSFQ GQVTISADKSISTAYLQWSSLKA SDTAMYFCARQRTFYYDSSDYF DYWGQGTLVTVSS (SEQ ID NO: 329) |
| 13E7 (SST202443) | EIVMTQSPATLSVSPGERATLSCRAS QSVSSNLAWFQQKPGQAPRLLIYGA STRATGIPARFSGSGSGTEFTLTISSL QPEDFAVYYCLQDNNFPPTFGQGTK VDIK (SEQ ID NO: 330) | EVQLVQSGAEVKKPGESLKISC KGSGYSFTSYWIGWVRQMPGK GLEWMGIIYPGDADARYSPSFQ GQVTISADKSISTAYLQWSSLKA SDTAMYFCARRRQGIFGDALDF WGQGTLVTVSS (SEQ ID NO: 331) |
| 5E3 (SST29825) | DIQMTQSPSSLSASVGDRVTITCRAS QGISNYLAWYQQKPGKAPKSLIYAA SSLQSGVPSRFSGSGSGTDFTLTISSL QPEDFATYYCQQYSTYPFTFGQGTK VDIK (SEQ ID NO: 332) | QVQLVQSGAEVKKPGASVKVS CKASGYTFTGYYIHWVRQAPGQ GLEWMGWINPYSGGTTSAQKF QGRVTMTRDTSTSSAYMELSRL RSDDTAVYYCARDAGYLALYG TDVWGQGTLVTVSS (SEQ ID NO: 333) |

TABLE 20

Exemplary Variable Nucleotide Sequences of Engineered Antibodies

| Ab ID. | LC variable region | HC variable region |
|---|---|---|
| 24G6 (SST28347 and SST204812) | GACATCGTGATGACCCAGTCTCCAG ACTCCCTGGCTGTGTCTCTGGGCGA GAGGGCCACCATCAACTGCAAGTCC AGCCAGAGTGTTTTATACAGCTCCA ACAATAAGCACTTCTTAGCTTGGTA CCAGCAGAAACCAGGACAGCCTCCT AAGCTGCTCATTTACTGGGCATCTA CCCGGGAGTCCGGGGTCCCTGACCG ATTCAGTGGCAGCGGGTCTGGGACA GATTTCACTCTCACCATCAGCAGCCT GCAGGCTGAAGATGTGGCAGTTTAT TACTGTCAGCAATATTATAGTACTCC | GAGGTGCAGCTGTTGGAGTCT GGGGGAGGCTTGGTACAGCCT GGGGGGTCCCTGAGACTCTCC TGTGCAGCCTCTGGATTCACCT TTAGCAGCTATGCCATGAGCT GGGTCCGCCAGGCTCCAGGGA AGGGACTGGAGTGGGTCTCAG CTATTAGTGGTAGTGGTGGTA GCACATACTACGCAGAATCCG TGAAGGGCCGGTTCACCATCT CCAGAGACAATTCCAAGAACA CGCTGTATCTGCAAATGAACA |

TABLE 20 -continued

Exemplary Variable Nucleotide Sequences of Engineered Antibodies

| Ab ID. | LC variable region | HC variable region |
|---|---|---|
| | GCTCACTTTCGGCGGAGGGACCAAG GTGGAGATCAAA (SEQ ID NO: 343) | GCCTGAGAGCCGAGGACACGG CCGTATATTACTGTGCGAAGG CGTATACACCTATGGCATTCTT TGACTACTGGGGCCAGGGAAC CCTGGTCACCGTCTCCTCA (SEQ ID NO: 344) |
| 6E7 (SST29857) | GACATCCAGATGACCCAGTCTCCAT CTTCCGTGTCTGCATCTGTAGGAGA CAGAGTCACCATCACTTGTCGGGCG AGTCAGGGTATTAGCAGCTGGTTAG CCTGGTATCAGCAGAAACCAGGGAA AGCCCCTAAGCTCCTGATCTATGCT GCATCCAGTTTGCAAAGTGGGGTCC CATCAAGGTTCAGCGGCAGTGGATC TGGGACAGATTTCACTCTCACCATC AGCAGCCTGCAGCCTGAAGATTTTG CAACTTACTTTTGTCAACAGGCTGA CGCTTTCCCTCGCACTTTTGGCCAGG GGACCAAGCTGGAGATCAAA (SEQ ID NO: 345) | GAGGTGCAGCTGGTGCAGTCT GGAGCAGAGGTGAAAAAGCCC GGGGAGTCTCTGAAGATCTCC TGTAAGGGTTCTGGATACAGTT TTACCAGCTACTGGATCGCCTG GGTGCGCCAGATGCCCGGGAA AGGCCTGGAGTGGATGGGGAT CATCTATCCTGGTGACGCTGAT GCCAGATACAGCCCGTCCTTCC AAGGCCAGGTCACCATCTCAG CCGACAAGTCCATCAGCACCG CCTACCTACAGTGGAGCAGCC TGAAGGCCTCGGACACCGCCA TGTATTTCTGTGCGAGACAAA GGACGTTTTATTATGATAGTAG TGATTATTTTGACTACTGGGGC CAGGGAACCCTGGTCACCGTG TCCTCA (SEQ ID NO: 346) |
| 13E7 (SST202443) | GAAATAGTGATGACGCAGTCTCCAG CCACCCTGTCTGTGTGTCTCCAGGGGA AAGAGCCACCCTCTCCTGCAGGGCC AGTCAGAGTGTTAGCAGCAACTTAG CCTGGTTCCAGCAGAAACCTGGCCA GGCTCCCAGGCTCCTCATCTATGGT GCTTCCACCAGGGCCACTGGTATTC CAGCCAGGTTCAGTGGCAGTGGGTC TGGGACAGAGTTCACTCTCACCATC AGCAGCCTGCAGCCTGAAGATTTTG CAGTTTATTACTGTCTGCAGGATAAT AATTTCCCTCCCACTTTCGGCCAGG GACCAAAGTGGATATCAAA (SEQ ID NO: 347) | GAGGTGCAGCTGGTGCAGTCT GGAGCAGAGGTGAAAAAGCCC GGGGAGTCTCTGAAGATCTCC TGTAAGGGTTCTGGATACAGC TTTACCAGCTACTGGATCGGCT GGGTGCGCCAGATGCCCGGGA AAGGCCTGGAGTGGATGGGGA TCATCTATCCTGGAGATGCTGA TGCCAGATACAGCCCGTCCTTC CAAGGCCAGGTCACCATCTCA GCCGACAAGTCCATCAGCACC GCCTACCTGCAGTGGAGCAGC CTGAAGGCCTCGGACACCGCC ATGTATTTCTGTGCGAGGCGG AGACAGGGGATCTTCGGTGAT GCTCTTGATTTCTGGGGCCAAG GGACATTGGTCACCGTGTCTTC A (SEQ ID NO: 348) |
| 5E3 (SST29825) | GACATCCAGATGACCCAGTCTCCAT CCTCACTGTCTGCATCTGTAGGAGA CAGAGTCACCATCACTTGTCGGGCG AGTCAGGGCATTAGCAATTATTTAG CCTGGTATCAGCAGAAACCAGGGAA AGCCCCTAAATCCCTGATCTATGCT GCATCCAGTTTGCAAAGTGGGGTCC CATCAAGGTTCAGCGGCAGTGGATC TGGGACAGATTTCACTCTCACCATC AGCAGCCTGCAGCCTGAAGATTTTG CAACTTATTACTGCCAACAGTATAG TACTTACCCATTCACTTTCGGCCAAG GGACCAAAGTGGATATCAAA (SEQ ID NO: 349) | CAGGTGCAGCTGGTGCAGTCT GGGGCTGAGGTGAAGAAGCCT GGGGCCTCAGTGAAGGTGTCC TGCAAGGCTTCTGGATACACCT TCACCGGCTACTATATCCACTG GGTGCGACAGGCCCCTGGACA AGGGCTTGAGTGGATGGGATG GATCAACCCTTACAGTGGTGG CACAACCTCTGCACAGAAGTT TCAGGGCAGGGTCACCATGAC CAGGGACACGTCCACCAGCTC AGCCTACATGGAACTGAGCAG GCTGAGATCTGACGACACGGC CGTGTATTACTGTGCGAGAGA TGCAGGCTACCTGGCCCTCTAC GGTACGGACGTCTGGGGCCAA GGGACCTTGGTCACCGTGTCCT CA (SEQ ID NO: 350) |

Select anti-TREM2 antibodies, which were isolated from hybridomas as human IgG2 antibodies, were converted to human IgG1 antibodies or aglycosylated variants of human IgG1 antibodies (mutations N297G, R292C, V302C according to EU numbering) by transferring the variable regions of the antibodies onto human IgG1 constant regions. The IgG1-type antibodies were evaluated for agonist activity using the AlphaLISA pSyk activation assay described in Example 2. Surprisingly, conversion of these select antibodies from an IgG2 isotype to an IgG1 isotype resulted in a partial loss of agonist activity (FIG. 7).

The unique arrangement of the disulfide bonds in the hinge region of IgG2 antibodies has been reported to impart enhanced stimulatory activity for certain anticancer antibodies (White et al., Cancer Cell, Vol. 27: 138-148, 2015). This enhanced activity could be transferred to IgG1-type antibodies by exchanging the CH1 and hinge regions of the IgG1 antibody for those in the IgG2 antibody (White et al., 2015).

To evaluate whether the agonist activity of the 24G6, 6E7 and 5E3 anti-TREM2 IgG2 antibodies could be enhanced or retained when converted to IgG1 isotypes, constructs were made in which the heavy chain variable region sequences from each of the 24G6, 6E7 and 5E3 antibodies were inserted in frame to sequences encoding the CH1 and hinge regions from a human IgG2 antibody and sequences encoding the Fc region (CH2 and CH3 regions) from an aglycosylated human IgG1 antibody. The aglycosylated human IgG1 antibody Fc region comprised the sequence of a human IgG1z Fc region with N297G, R292C, and V302C mutations according to EU numbering (SEQ ID NO: 282).

In addition to replacing the CH1 and hinge regions of the IgG1 antibodies with those from the IgG2 antibodies, point mutations were made at specific residues within the hinge and CH1 regions to lock the antibodies into a particular disulfide bond configuration. It has been reported that the disulfide bonds in the hinge and CH1 regions of IgG2 antibodies can be shuffled to create different structural disulfide isoforms (IgG2A, IgG2B, and IgG2A-B) and these different disulfide isoforms can have different levels of activity. See, e.g., Dillon et al., J. Biol. Chem., Vol. 283: 16206-16215; Martinez et al., Biochemistry, Vol. 47: 7496-7508, 2008; and White et al., Cancer Cell, Vol. 27: 138-148, 2015. To lock the hinge-modified IgG1 antibodies into a IgG2B disulfide configuration, two sets of point mutations were made: (1) a C127S mutation according to Kabat numbering (C131S according to EU numbering) in the heavy chain and (2) a C214S mutation in the light chain combined with a C233S mutation in the heavy chain, both according to Kabat numbering (C214S and C220S according to EU numbering). See, e.g., WO 2009/036209, which is hereby incorporated by reference in its entirety. The IgG2-hinge modified IgG1 versions of the 6E7 and 5E3 antibodies containing the additional point mutations are expected to show equivalent or superior agonist activity in the AlphaLISA pSyk activation assay as the parental IgG2 molecules.

TABLE 21

| Light Chain and Heavy Chain Amino Acid Sequences of Exemplary Antibodies | | |
| --- | --- | --- |
| Ab ID. | | Sequence |
| 24G6 (SST28347) | LC | MDMRVPAQLLGLLLLWLRGARCDIVMTQSPDSLAVSLGERA TINCKSSQSVLYSSNNKHFLAWYQQKPGQPPKLLIYVVASTRE SGVPDRFSGSGSGTDFTLTISSLQAEDVAVYYCQQYYSTPLTF GGGTKVEIKRTVAAPSVFIFPPSDEQLKSGTASVVCLLNNFYP REAKVQWKVDNALQSGNSQESVTEQDSKDSTYSLSSTLTLS KADYEKHKVYACEVTHQGLSSPVTKSFNRGEC (SEQ ID NO: 334) |
| | HC | MDMRVPAQLLGLLLLWLRGARCEVQLLESGGGLVQPGGSL RLSCAASGFTFSSYAMSWVRQAPGKGLEWVSAISGSGGSTY YAESVKGRFTISRDNSKNTLYLQMNSLRAEDTAVYYCAKAY TPMAFFDYVVGQGTLVTVSSASTKGPSVFPLAPSSKSTSGGTA ALGCLVKDYFPEPVTVSWNSGALTSGVHTFPAVLQSSGLYSL SSVVTVPSSSLGTQTYICNVNHKPSNTKVDKKVEPKSCDKTH TCPPCPAPELLGGPSVFLFPPKPKDTLMISRTPEVTCVVVDVS HEDPEVKFNWYVDGVEVHNAKTKPCEEQYGSTYRCVSVLT VLHQDWLNGKEYKCKVSNKALPAPIEKTISKAKGQPREPQV YTLPPSREEMTKNQVSLTCLVKGFYPSDIAVEWESNGQPENN YKTTPPVLDSDGSFFLYSKLTVDKSRWQQGNVFSCSVMHEA LHNHYTQKSLSLSPGK (SEQ ID NO: 335) |
| 24G6 (SST20812) | LC | MDMRVPAQLLGLLLLWLRGARCDIVMTQSPDSLAVSLGERA TINCKSSQSVLYSSNNKHFLAWYQQKPGQPPKLLIYVVASTRE SGVPDRFSGSGSGTDFTLTISSLQAEDVAVYYCQQYYSTPLTF GGGTKVEIKRTVAAPSVFIFPPSDEQLKSGTASVVCLLNNFYP REAKVQWKVDNALQSGNSQESVTEQDSKDSTYSLSSTLTLS KADYEKHKVYACEVTHQGLSSPVTKSFNRGEC (SEQ ID NO: 334) |
| | HC | MDMRVPAQLLGLLLLWLRGARCEVQLLESGGGLVQPGGSL RLSCAASGFTFSSYAMSWVRQAPGKGLEWVSAISGSGGSTY YAESVKGRFTISRDNSKNTLYLQMNSLRAEDTAVYYCAKAY TPMAFFDYWGQGTLVTVSSASTKGPSVFPLAPSSRSTSESTA ALGCLVKDYFPEPVTVSWNSGALTSGVHTFPAVLQSSGLYSL SSVVTVPSSNFGTQTYTCNVDHKPSNTKVDKTVERKCCVECP PCPAPELLGGPSVFLFPPKPKDTLMISRTPEVTCVVVDVSHED PEVKFNWYVDGVEVHNAKTKPCEEQYGSTYRCVSVLTVLH QDWLNGKEYKCKVSNKALPAPIEKTISKAKGQPREPQVYTLP PSREEMTKNQVSLTCLVKGFYPSDIAVEWESNGQPENNYKTT PPVLDSDGSFFLYSKLTVDKSRWQQGNVFSCSVMHEALHNH YTQKSLSLSPGK (SEQ ID NO: 336) |
| 6E7 (SST29857) | LC | MDMRVPAQLLGLLLLWLRGARCDIQMTQSPSSVSASVGDRV TITCRASQGISSWLAWYQQKPGKAPKLLIYAASSLQSGVPSRF SGSGSGTDFTLTISSLQPEDFATYFCQQADAFPRTFGQGTKLEI KRTVAAPSVFIFPPSDEQLKSGTASVVCLLNNFYPREAKVQW KVDNALQSGNSQESVTEQDSKDSTYSLSSTLTLSKADYEKHK VYACEVTHQGLSSPVTKSFNRGEC (SEQ ID NO: 337) |
| | HC | MDMRVPAQLLGLLLLWLRGARCEVQLVQSGAEVKKPGESL KISCKGSGYSFTSYWIAWVRQMPGKGLEWMGIIYPGDADAR |

TABLE 21 -continued

Light Chain and Heavy Chain Amino Acid Sequences of
Exemplary Antibodies

| Ab ID. | | Sequence |
|---|---|---|

|  |  | YSPSFQGQVTISADKSISTAYLQWSSLKASDTAMYFCARQRT |
|  |  | FYYDSSDYFDYWGQGTLVTVSSASTKGPSVFPLAPSSRSTSES |
|  |  | TAALGCLVKDYFPEPVTVSWNSGALTSGVHTFPAVLQSSGL |
|  |  | YSLSSVVTVPSSNFGTQTYTCNVDHKPSNTKVDKTVERKCC |
|  |  | VECPPCPAPELLGGPSVFLFPPKPKDTLMISRTPEVTCVVVDV |
|  |  | SHEDPEVKFNWYVDGVEVHNAKTKPCEEQYGSTYRCVSVLT |
|  |  | VLHQDWLNGKEYKCKVSNKALPAPIEKTISKAKGQPREPQV |
|  |  | YTLPPSREEMTKNQVSLTCLVKGFYPSDIAVEWESNGQPENN |
|  |  | YKTTPPVLDSDGSFFLYSKLTVDKSRWQQGNVFSCSVMHEA |
|  |  | LHNHYTQKSLSLSPGK (SEQ ID NO: 338) |
| 13E7 | LC | MDMRVPAQLLGLLLLWLRGARCEIVMTQSPATLSVSPGERA |
| (SST202443) |  | TLSCRASQSVSSNLAWFQQKPGQAPRLLIYGASTRATGIPARF |
|  |  | SGSGSGTEFTLTISSLQPEDFAVYYCLQDNNFPPTFGQGTKVD |
|  |  | IKRTVAAPSVFIFPPSDEQLKSGTASVVCLLNNFYPREAKVQ |
|  |  | WKVDNALQSGNSQESVTEQDSKDSTYSLSSTLTLSKADYEK |
|  |  | HKVYACEVTHQGLSSPVTKSFNRGEC (SEQ ID NO: 339) |
|  | HC | MDMRVPAQLLGLLLLWLRGARCEVQLVQSGAEVKKPGESL |
|  |  | KISCKGSGYSFTSYWIGWVRQMPGKGLEWMGIIYPGDADAR |
|  |  | YSPSFQGQVTISADKSISTAYLQWSSLKASDTAMYFCARRRQ |
|  |  | GIFGDALDFWGQGTLVTVSSASTKGPSVFPLAPSSKSTSGGTA |
|  |  | ALGCLVKDYFPEPVTVSWNSGALTSGVHTFPAVLQSSGLYSL |
|  |  | SSVVTVPSSSLGTQTYICNVNHKPSNTKVDKKVEPKSCDKTH |
|  |  | TCPPCPAPELLGGPSVFLFPPKPKDTLMISRTPEVTCVVVDVS |
|  |  | HEDPEVKFNWYVDGVEVHNAKTKPCEEQYGSTYRCVSVLT |
|  |  | VLHQDWLNGKEYKCKVSNKALPAPIEKTISKAKGQPREPQV |
|  |  | YTLPPSREEMTKNQVSLTCLVKGFYPSDIAVEWESNGQPENN |
|  |  | YKTTPPVLDSDGSFFLYSKLTVDKSRWQQGNVFSCSVMHEA |
|  |  | LHNHYTQKSLSLSPGK (SEQ ID NO: 340) |
| 5E3 | LC | MDMRVPAQLLGLLLLWLRGARCDIQMTQSPSSLSASVGDRV |
| (SST29825) |  | TITCRASQGISNYLAWYQQKPGKAPKSLIYAASSLQSGVPSRF |
|  |  | SGSGSGTDFTLTISSLQPEDFATYYCQQYSTYPFTFGQGTKVD |
|  |  | IKRTVAAPSVFIFPPSDEQLKSGTASVVCLLNNFYPREAKVQ |
|  |  | WKVDNALQSGNSQESVTEQDSKDSTYSLSSTLTLSKADYEK |
|  |  | HKVYACEVTHQGLSSPVTKSFNRGEC (SEQ ID NO: 341) |
|  | HC | MDMRVPAQLLGLLLLWLRGARCQVQLVQSGAEVKKPGASV |
|  |  | KVSCKASGYTFTGYYIHWVRQAPGQGLEWMGWINPYSGGT |
|  |  | TSAQKFQGRVTMTRDTSTSSAYMELSRLRSDDTAVYYCARD |
|  |  | AGYLALYGTDVWGQGTLVTVSSASTKGPSVFPLAPSSRSTSE |
|  |  | STAALGCLVKDYFPEPVTVSWNSGALTSGVHTFPAVLQSSGL |
|  |  | YSLSSVVTVPSSNFGTQTYTCNVDHKPSNTKVDKTVERKCC |
|  |  | VECPPCPAPELLGGPSVFLFPPKPKDTLMISRTPEVTCVVVDV |
|  |  | SHEDPEVKFNWYVDGVEVHNAKTKPCEEQYGSTYRCVSVLT |
|  |  | VLHQDWLNGKEYKCKVSNKALPAPIEKTISKAKGQPREPQV |
|  |  | YTLPPSREEMTKNQVSLTCLVKGFYPSDIAVEWESNGQPENN |
|  |  | YKTTPPVLDSDGSFFLYSKLTVDKSRWQQGNVFSCSVMHEA |
|  |  | LHNHYTQKSLSLSPGK (SEQ ID NO: 342) |

TABLE 22

Light Chain and Heavy Chain Nucleotide
Sequences of Exemplary Antibodies

| Ab ID. | | Sequence |
|---|---|---|
| 24G6 | LC | ATGGACATGAGGGTGCCCGCTCAGCTCCTGGGGCTCCTGC |
| (SST28347) |  | TGCTGTGGCTGAGAGGTGCGCGCTGTGACATCGTGATGAC |
|  |  | CCAGTCTCCAGACTCCCTGGCTGTGTCTCTGGGCGAGAGG |
|  |  | GCCACCATCAACTGCAAGTCCAGCCAGAGTGTTTTATACA |
|  |  | GCTCCAACAATAAGCACTTCTTAGCTTGGTACCAGCAGAA |
|  |  | ACCAGGACAGCCTCCTAAGCTGCTCATTTACTGGGCATCT |
|  |  | ACCCGGGAGTCCGGGGTCCCTGACCGATTCAGTGGCAGCG |
|  |  | GGTCTGGGACAGATTTCACTCTCACCATCAGCAGCCTGCA |
|  |  | GGCTGAAGATGTGGCAGTTTATTACTGTCAGCAATATTAT |
|  |  | AGTACTCCGCTCACTTTCGGCGGAGGGACCAAGGTGGAGA |
|  |  | TCAAACGAACGGTGGCTGCACCATCTGTCTTCATCTTCCCG |
|  |  | CCATCTGATGAGCAGTTGAAATCTGGAACTGCCTCTGTTGT |
|  |  | GTGCCTGCTGAATAACTTCTATCCCAGAGAGGCCAAAGTA |
|  |  | CAGTGGAAGGTGGATAACGCCCTCCAATCGGGTAACTCCC |
|  |  | AGGAGAGTGTCACAGAGCAGGACAGCAAGGACAGCACCT |
|  |  | ACAGCCTCAGCAGCACCCTGACGCTGAGCAAAGCAGACTA |

TABLE 22 -continued

Light Chain and Heavy Chain Nucleotide
Sequences of Exemplary Antibodies

| Ab ID. | | Sequence |
|---|---|---|
| | | CGAGAAACACAAAGTCTACGCCTGCGAAGTCACCCATCAG |
| | | GGCCTGAGCTCGCCCGTCACAAAGAGCTTCAACAGGGGAG |
| | | AGTGT (SEQ ID NO: 351) |
| | HC | ATGGACATGAGGGTGCCCGCTCAGCTCCTGGGGCTCCTGC |
| | | TGCTGTGGCTGAGAGGTGCGCGCTGTGAGGTGCAGCTGTT |
| | | GGAGTCTGGGGGAGGCTTGGTACAGCCTGGGGGGTCCCTG |
| | | AGACTCTCCTGTGCAGCCTCTGGATTCACCTTTAGCAGCTA |
| | | TGCCATGAGCTGGGTCCGCCAGGCTCCAGGGAAGGGACTG |
| | | GAGTGGGTCTCAGCTATTAGTGGTAGTGGTGGTAGCACAT |
| | | ACTACGCAGAATCCGTGAAGGGCCGGTTCACCATCTCCAG |
| | | AGACAATTCCAAGAACACGCTGTATCTGCAAATGAACAGC |
| | | CTGAGAGCCGAGGACACGGCCGTATATTACTGTGCGAAGG |
| | | CGTATACACCTATGGCATTCTTTGACTACTGGGGCCAGGG |
| | | AACCCTGGTCACCGTCTCCTCAGCCTCCACCAAGGGCCCA |
| | | TCGGTCTTCCCCCTGGCACCCTCCTCCAAGAGCACCTCTGG |
| | | GGGCACAGCGGCCCTGGGCTGCCTGGTCAAGGACTACTTC |
| | | CCCGAACCGGTGACGGTGTCGTGGAACTCAGGCGCCCTGA |
| | | CCAGCGGCGTGCACACCTTCCCGGCTGTCCTACAGTCCTC |
| | | AGGACTCTACTCCCTCAGCAGCGTGGTGACCGTGCCCTCC |
| | | AGCAGCTTGGGCACCCAGACCTACATCTGCAACGTGAATC |
| | | ACAAGCCCAGCAACACCAAGGTGGACAAGAAAGTTGAGC |
| | | CCAAATCTTGTGACAAAACTCACACATGCCCACCGTGCCC |
| | | AGCACCTGAACTCCTGGGGGGACCGTCAGTCTTCCTCTTCC |
| | | CCCCAAAACCCAAGGACACCCTCATGATCTCCCGGACCCC |
| | | TGAGGTCACATGCGTGGTGGTGGACGTGAGCCACGAAGAC |
| | | CCTGAGGTCAAGTTCAACTGGTACGTGGACGGCGTGGAGG |
| | | TGCATAATGCCAAGACAAAGCCGTGCGAGGAGCAGTACG |
| | | GCAGCACGTACCGTTGCGTCAGCGTCCTCACCGTCCTGCA |
| | | CCAGGACTGGCTGAATGGCAAGGAGTACAAGTGCAAGGT |
| | | GTCCAACAAAGCCCTCCCAGCCCCCATCGAGAAAACCATC |
| | | TCCAAAGCCAAAGGGCAGCCCCGAGAACCACAGGTGTAC |
| | | ACCCTGCCCCCATCCCGGGAGGAGATGACCAAGAACCAG |
| | | GTCAGCCTGACCTGCCTGGTCAAAGGCTTCTATCCCAGCG |
| | | ACATCGCCGTGGAGTGGGAGAGCAATGGGCAGCCGGAGA |
| | | ACAACTACAAGACCACGCCTCCCGTGCTGGACTCCGACGG |
| | | CTCCTTCTTCCTCTATAGCAAGCTCACCGTGGACAAGAGC |
| | | AGGTGGCAGCAGGGGAACGTCTTCTCATGCTCCGTGATGC |
| | | ATGAGGCTCTGCACAACCACTACACGCAGAAGAGCCTCTC |
| | | CCTGTCTCCGGGCAAA (SEQ ID NO: 352) |
| 24G6 | LC | ATGGACATGAGGGTGCCCGCTCAGCTCCTGGGGCTCCTGC |
| (SST204812) | | TGCTGTGGCTGAGAGGTGCGCGCTGTGACATCGTGATGAC |
| | | CCAGTCTCCAGACTCCCTGGCTGTGTCTCTGGGCGAGAGG |
| | | GCCACCATCAACTGCAAGTCCAGCCAGAGTGTTTTATACA |
| | | GCTCCAACAATAAGCACTTCTTAGCTTGGTACCAGCAGAA |
| | | ACCAGGACAGCCTCCTAAGCTGCTCATTTACTGGGCATCT |
| | | ACCCGGGAGTCCGGGGTCCCTGACCGATTCAGTGGCAGCG |
| | | GGTCTGGGACAGATTTCACTCTCACCATCAGCAGCCTGCA |
| | | GGCTGAAGATGTGGCAGTTTATTACTGTCAGCAATATTAT |
| | | AGTACTCCGCTCACTTTCGGCGGAGGGACCAAGGTGGAGA |
| | | TCAAACGAACGGTGGCTGCACCATCTGTCTTCATCTTCCCG |
| | | CCATCTGATGAGCAGTTGAAATCTGGAACTGCCTCTGTTGT |
| | | GTGCCTGCTGAATAACTTCTATCCCAGAGAGGCCAAAGTA |
| | | CAGTGGAAGGTGGATAACGCCCTCCAATCGGGTAACTCCC |
| | | AGGAGAGTGTCACAGAGCAGGACAGCAAGGACAGCACCT |
| | | ACAGCCTCAGCAGCACCCTGACGCTGAGCAAAGCAGACTA |
| | | CGAGAAACACAAAGTCTACGCCTGCGAAGTCACCCATCAG |
| | | GGCCTGAGCTCGCCCGTCACAAAGAGCTTCAACAGGGGAG |
| | | AGTGT (SEQ ID NO: 351) |
| | HC | ATGGACATGAGGGTGCCCGCTCAGCTCCTGGGGCTCCTGC |
| | | TGCTGTGGCTGAGAGGTGCGCGCTGTGAGGTGCAGCTGTT |
| | | GGAGTCTGGGGGAGGCTTGGTACAGCCTGGGGGGTCCCTG |
| | | AGACTCTCCTGTGCAGCCTCTGGATTCACCTTTAGCAGCTA |
| | | TGCCATGAGCTGGGTCCGCCAGGCTCCAGGGAAGGGACTG |
| | | GAGTGGGTGTCAGCTATTAGTGGTAGTGGTGGTAGCACAT |
| | | ACTACGCAGAATCCGTGAAGGGCCGGTTCACCATCTCCAG |
| | | AGACAATTCCAAGAACACGCTGTATCTGCAAATGAACAGC |
| | | CTGAGAGCCGAGGACACGGCCGTATATTACTGTGCGAAGG |
| | | CGTATACACCTATGGCATTCTTTGACTACTGGGGCCAGGG |
| | | AACCCTGGTCACCGTGTCCTCAGCCTCCACCAAGGGCCCA |
| | | TCGGTCTTCCCCCTGGCGCCCAGCTCCAGGAGCACCTCCG |
| | | AGAGCACAGCGGCCCTGGGCTGCCTGGTCAAGGACTACTT |
| | | CCCCGAACCGGTGACGGTGTCGTGGAACTCAGGCGCTCTG |
| | | ACCAGCGGCGTGCACACCTTCCCAGCTGTCCTACAGTCCT |
| | | CAGGACTCTACTCCCTCAGCAGCGTGGTGACCGTGCCCTC |

TABLE 22 -continued

| Light Chain and Heavy Chain Nucleotide Sequences of Exemplary Antibodies | |
| --- | --- |
| Ab ID. | Sequence |

|  |  |
| --- | --- |
|  | CAGCAACTTCGGCACCCAGACCTACACCTGCAACGTAGAT<br>CACAAGCCCAGCAACACCAAGGTGGACAAGACAGTTGAG<br>CGCAAATGTTGTGTCGAGTGCCCACCGTGCCCAGCACCTG<br>AACTCCTGGGGGGACCGTCAGTCTTCCTCTTCCCCCCAAA<br>ACCCAAGGACACCCTCATGATCTCCCGGACCCCTGAGGTC<br>ACATGCGTGGTGGTGGACGTGAGCCACGAAGACCCTGAG<br>GTCAAGTTCAACTGGTACGTGGACGGCGTGGAGGTGCATA<br>ATGCCAAGACAAAGCCGTGCGAGGAGCAGTACGGCAGCA<br>CGTACCGTTGCGTCAGCGTCCTCACCGTCCTGCACCAGGA<br>CTGGCTGAATGGCAAGGAGTACAAGTGCAAGGTGTCCAAC<br>AAAGCCCTCCCAGCCCCCATCGAGAAAACCATCTCCAAAG<br>CCAAAGGGCAGCCCCGAGAACCACAGGTGTACACCCTGCC<br>CCCATCCCGGGAGGAGATGACCAAGAACCAGGTCAGCCT<br>GACCTGCCTGGTCAAAGGCTTCTATCCCAGCGACATCGCC<br>GTGGAGTGGGAGAGCAATGGGCAGCCGGAGAACAACTAC<br>AAGACCACGCCTCCCGTGCTGGACTCCGACGGCTCCTTCTT<br>CCTCTATAGCAAGCTCACCGTGGACAAGAGCAGGTGGCAG<br>CAGGGGAACGTCTTCTCATGCTCCGTGATGCATGAGGCTC<br>TGCACAACCACTACACGCAGAAGAGCCTCTCCCTGTCTCC<br>GGGCAAA (SEQ ID NO: 353) |
| 6E7<br>(SST29857) | LC ATGGACATGAGGGTGCCCGCTCAGCTCCTGGGGCTCCTGC<br>TGCTGTGGCTGAGAGGTGCGCGCTGTGACATCCAGATGAC<br>CCAGTCTCCATCTTCCGTGTCTGCATCTGTAGGAGACAGA<br>GTCACCATCACTTGTCGGGCGAGTCAGGGTATTAGCAGCT<br>GGTTAGCCTGGTATCAGCAGAAACCAGGGAAAGCCCCTAA<br>GCTCCTGATCTATGCTGCATCCAGTTTGCAAAGTGGGGTCC<br>CATCAAGGTTCAGCGGCAGTGGATCTGGGACAGATTTCAC<br>TCTCACCATCAGCAGCCTGCAGCCTGAAGATTTTGCAACTT<br>ACTTTTGTCAACAGGCTGACGCTTTCCCTCGCACTTTTGGC<br>CAGGGGACCAAGCTGGAGATCAAACGAACGGTGGCTGCA<br>CCATCTGTCTTCATCTTCCCGCCATCTGATGAGCAGTTGAA<br>ATCTGGAACTGCCTCTGTTGTGTGCCTGCTGAATAACTTCT<br>ATCCCAGAGAGGCCAAAGTACAGTGGAAGGTGGATAACG<br>CCCTCCAATCGGGTAACTCCCAGGAGAGTGTCACAGAGCA<br>GGACAGCAAGGACAGCACCTACAGCCTCAGCAGCACCCT<br>GACGCTGAGCAAAGCAGACTACGAGAAACACAAAGTCTA<br>CGCCTGCGAAGTCACCCATCAGGGCCTGAGCTCGCCCGTC<br>ACAAAGAGCTTCAACAGGGGAGAGTGT (SEQ ID NO: 354)<br>HC ATGGACATGAGGGTGCCCGCTCAGCTCCTGGGGCTCCTGC<br>TGCTGTGGCTGAGAGGTGCGCGCTGTGAGGTGCAGCTGGT<br>GCAGTCTGGAGCAGAGGTGAAAAAGCCCGGGGAGTCTCT<br>GAAGATCTCCTGTAAGGGTTCTGGATACAGTTTTACCAGC<br>TACTGGATCGCCTGGGTGCGCCAGATGCCCGGGAAAGGC<br>TGGAGTGGATGGGGATCATCTATCCTGGTGACGCTGATGC<br>CAGATACAGCCCGTCCTTCCAAGGCCAGGTCACCATCTCA<br>GCCGACAAGTCCATCAGCACCGCCTACCTACAGTGGAGCA<br>GCCTGAAGGCCTCGGACACCGCCATGTATTTCTGTGCGAG<br>ACAAAGGACGTTTTATTATGATAGTAGTGATTATTTTGACT<br>ACTGGGGCCAGGGAACCCTGGTCACCGTGTCCTCAGCCTC<br>CACCAAGGGCCCATCGGTCTTCCCCCTGGCGCCCAGCTCC<br>AGGAGCACCTCCGAGAGCACAGCGGCCCTGGGCTGCCTGG<br>TCAAGGACTACTTCCCCGAACCGGTGACGGTGTCGTGGAA<br>CTCAGGCGCTCTGACCAGCGGCGTGCACACCTTCCCAGCT<br>GTCCTACAGTCCTCAGGACTCTACTCCCTCAGCAGCGTGGT<br>GACCGTGCCCTCCAGCAACTTCGGCACCCAGACCTACACC<br>TGCAACGTAGATCACAAGCCCAGCAACACCAAGGTGGAC<br>AAGACAGTTGAGCGCAAATGTTGTGTCGAGTGCCCACCGT<br>GCCCAGCACCTGAACTCCTGGGGGGACCGTCAGTCTTCCT<br>CTTCCCCCCAAAACCCAAGGACACCCTCATGATCTCCCGG<br>ACCCCTGAGGTCACATGCGTGGTGGTGGACGTGAGCCACG<br>AAGACCCTGAGGTCAAGTTCAACTGGTACGTGGACGGCGT<br>GGAGGTGCATAATGCCAAGACAAAGCCGTGCGAGGAGCA<br>GTACGGCAGCACGTACCGTTGCGTCAGCGTCCTCACCGTC<br>CTGCACCAGGACTGGCTGAATGGCAAGGAGTACAAGTGC<br>AAGGTGTCCAACAAAGCCCTCCCAGCCCCCATCGAGAAAA<br>CCATCTCCAAAGCCAAAGGGCAGCCCCGAGAACCACAGG<br>TGTACACCCTGCCCCCATCCCGGGAGGAGATGACCAAGAA<br>CCAGGTCAGCCTGACCTGCCTGGTCAAAGGCTTCTATCCC<br>AGCGACATCGCCGTGGAGTGGGAGAGCAATGGGCAGCCG<br>GAGAACAACTACAAGACCACGCCTCCCGTGCTGGACTCCG<br>ACGGCTCCTTCTTCCTCTATAGCAAGCTCACCGTGGACAA<br>GAGCAGGTGGCAGCAGGGGAACGTCTTCTCATGCTCCGTG<br>ATGCATGAGGCTCTGCACAACCACTACACGCAGAAGAGCC<br>TCTCCCTGTCTCCGGGCAAA (SEQ ID NO: 355) |

TABLE 22 -continued

Light Chain and Heavy Chain Nucleotide
Sequences of Exemplary Antibodies

| Ab ID. | | Sequence |
|---|---|---|
| 13E7 (SST202443) | LC | ATGGACATGAGGGTGCCCGCTCAGCTCCTGGGGCTCCTGC TGCTGTGGCTGAGAGGTGCGCGCTGTGAAATAGTGATGAC GCAGTCTCCAGCCACCCTGTCTGTGTCTCCAGGGGAAAGA GCCACCCTCTCCTGCAGGGCCAGTCAGAGTGTTAGCAGCA ACTTAGCCTGGTTCCAGCAGAAACCTGGCCAGGCTCCCAG GCTCCTCATCTATGGTGCTTCCACCAGGGCCACTGGTATTC CAGCCAGGTTCAGTGGCAGTGGGTCTGGGACAGAGTTCAC TCTCACCATCAGCAGCCTGCAGCCTGAAGATTTTGCAGTTT ATTACTGTCTGCAGGATAATAATTTCCCTCCCACTTTCGGC CAAGGGACCAAAGTGGATATCAAACGAACGGTGGCTGCA CCATCTGTCTTCATCTTCCCGCCATCTGATGAGCAGTTGAA ATCTGGAACTGCCTCTGTTGTGTGCCTGCTGAATAACTTCT ATCCCAGAGAGGCCAAAGTACAGTGGAAGGTGGATAACG CCCTCCAATCGGGTAACTCCCAGGAGAGTGTCACAGAGCA GGACAGCAAGGACAGCACCTACAGCCTCAGCAGCACCCT GACGCTGAGCAAAGCAGACTACGAGAAACACAAAGTCTA CGCCTGCGAAGTCACCCATCAGGGCCTGAGCTCGCCCGTC ACAAAGAGCTTCAACAGGGGAGAGTGT (SEQ ID NO: 356) |
| | HC | ATGGACATGAGGGTGCCCGCTCAGCTCCTGGGGCTCCTGC TGCTGTGGCTGAGAGGTGCGCGCTGTGAGGTGCAGCTGGT GCAGTCTGGAGCAGAGGTGAAAAAGCCCGGGGAGTCTCT GAAGATCTCCTGTAAGGGTTCTGGATACAGCTTTACCAGC TACTGGATCGGCTGGGTGCGCCAGATGCCCGGGAAAGGCC TGGAGTGGATGGGGATCATCTATCCTGGAGATGCTGATGC CAGATACAGCCCGTCCTTCCAAGGCCAGGTCACCATCTCA GCCGACAAGTCCATCAGCACCGCCTACCTGCAGTGGAGCA GCCTGAAGGCCTCGGACACCGCCATGTATTTCTGTGCGAG GCGGAGACAGGGGATCTTCGGTGATGCTCTTGATTTCTGG GGCCAAGGGACATTGGTCACCGTGTCTTCAGCCTCCACCA AGGGCCCATCGGTCTTCCCCCTGGCACCCTCCTCCAAGAG CACCTCTGGGGGCACAGCGGCCCTGGGCTGCCTGGTCAAG GACTACTTCCCCGAACCGGTGACGGTGTCGTGGAACTCAG GCGCCCTGACCAGCGGCGTGCACACCTTCCCGGCTGTCCT ACAGTCCTCAGGACTCTACTCCCTCAGCAGCGTGGTGACC GTGCCCTCCAGCAGCTTGGGCACCCAGACCTACATCTGCA ACGTGAATCACAAGCCCAGCAACACCAAGGTGGACAAGA AAGTTGAGCCCAAATCTTGTGACAAAACTCACACATGCCC ACCGTGCCCAGCACCTGAACTCCTGGGGGGACCGTCAGTC TTCCTCTTCCCCCCAAAACCCAAGGACACCCTCATGATCTC CCGGACCCCTGAGGTCACATGCGTGGTGGTGGACGTGAGC CACGAAGACCCTGAGGTCAAGTTCAACTGGTACGTGGACG GCGTGGAGGTGCATAATGCCAAGACAAAGCCGTGCGAGG AGCAGTACGGCAGCACGTACCGTTGCGTCAGCGTCCTCAC CGTCCTGCACCAGGACTGGCTGAATGGCAAGGAGTACAAG TGCAAGGTGTCCAACAAAGCCCTCCCAGCCCCCATCGAGA AAACCATCTCCAAAGCCAAAGGGCAGCCCCGAGAACCAC AGGTGTACACCCTGCCCCCATCCCGGGAGGAGATGACCAA GAACCAGGTCAGCCTGACCTGCCTGGTCAAAGGCTTCTAT CCCAGCGACATCGCCGTGGAGTGGGAGAGCAATGGGCAG CCGGAGAACAACTACAAGACCACGCCTCCCGTGCTGGACT CCGACGGCTCCTTCTTCCTCTATAGCAAGCTCACCGTGGAC AAGAGCAGGTGGCAGCAGGGGAACGTCTTCTCATGCTCCG TGATGCATGAGGCTCTGCACAACCACTACACGCAGAAGAG CCTCTCCCTGTCTCCGGGCAAA (SEQ ID NO: 357) |
| 5E3 (SST29825) | LC | ATGGACATGAGGGTGCCCGCTCAGCTCCTGGGGCTCCTGC TGCTGTGGCTGAGAGGTGCGCGCTGTGACATCCAGATGAC CCAGTCTCCATCCTCACTGTCTGCATCTGTAGGAGACAGA GTCACCATCACTTGTCGGGCGAGTCAGGGCATTAGCAATT ATTTAGCCTGGTATCAGCAGAAACCAGGGAAAGCCCCTAA ATCCCTGATCTATGCTGCATCCAGTTTGCAAAGTGGGGTCC CATCAAGGTTCAGCGGCAGTGGATCTGGGACAGATTTCAC TCTCACCATCAGCAGCCTGCAGCCTGAAGATTTTGCAACTT ATTACTGCCAACAGTATAGTACTTACCCATTCACTTTCGGC CAAGGGACCAAAGTGGATATCAAACGAACGGTGGCTGCA CCATCTGTCTTCATCTTCCCGCCATCTGATGAGCAGTTGAA ATCTGGAACTGCCTCTGTTGTGTGCCTGCTGAATAACTTCT |

TABLE 22 -continued

Light Chain and Heavy Chain Nucleotide
Sequences of Exemplary Antibodies

| Ab ID. | Sequence |
|---|---|
| | ATCCCAGAGAGGCCAAAGTACAGTGGAAGGTGGATAACG |
| | CCCTCCAATCGGGTAACTCCCAGGAGAGTGTCACAGAGCA |
| | GGACAGCAAGGACAGCACCTACAGCCTCAGCAGCACCCT |
| | GACGCTGAGCAAAGCAGACTACGAGAAACACAAAGTCTA |
| | CGCCTGCGAAGTCACCCATCAGGGCCTGAGCTCGCCCGTC |
| | ACAAAGAGCTTCAACAGGGGAGAGTGT (SEQ ID NO: 358) |
| HC | ATGGACATGAGGGTGCCCGCTCAGCTCCTGGGGCTCCTGC |
| | TGCTGTGGCTGAGAGGTGCGCGCTGTCAGGTGCAGCTGGT |
| | GCAGTCTGGGGCTGAGGTGAAGAAGCCTGGGGCCTCAGTG |
| | AAGGTGTCCTGCAAGGCTTCTGGATACACCTTCACCGGCT |
| | ACTATATCCACTGGGTGCGACAGGCCCCTGGACAAGGGCT |
| | TGAGTGGATGGGATGGATCAACCCTTACAGTGGTGGCACA |
| | ACCTCTGCACAGAAGTTTCAGGGCAGGGTCACCATGACCA |
| | GGGACACGTCCACCAGCTCAGCCTACATGGAACTGAGCAG |
| | GCTGAGATCTGACGACACGGCCGTGTATTACTGTGCGAGA |
| | GATGCAGGCTACCTGGCCCTCTACGGTACGGACGTCTGGG |
| | GCCAAGGGACCTTGGTCACCGTGTCCTCAGCCTCCACCAA |
| | GGGCCCATCGGTCTTCCCCCTGGCGCCCAGCTCCAGGAGC |
| | ACCTCCGAGAGCACAGCGGCCCTGGGCTGCCTGGTCAAGG |
| | ACTACTTCCCCGAACCGGTGACGGTGTCGTGGAACTCAGG |
| | CGCTCTGACCAGCGGCGTGCACACCTTCCCAGCTGTCCTA |
| | CAGTCCTCAGGACTCTACTCCCTCAGCAGCGTGGTGACCG |
| | TGCCCTCCAGCAACTTCGGCACCCAGACCTACACCTGCAA |
| | CGTAGATCACAAGCCCAGCAACACCAAGGTGGACAAGAC |
| | AGTTGAGCGCAAATGTTGTGTCGAGTGCCCACCGTGCCCA |
| | GCACCTGAACTCCTGGGGGGACCGTCAGTCTTCCTCTTCCC |
| | CCCAAAACCCAAGGACACCCTCATGATCTCCCGGACCCCT |
| | GAGGTCACATGCGTGGTGGTGGACGTGAGCCACGAAGAC |
| | CCTGAGGTCAAGTTCAACTGGTACGTGGACGGCGTGGAGG |
| | TGCATAATGCCAAGACAAAGCCGTGCGAGGAGCAGTACG |
| | GCAGCACGTACCGTTGCGTCAGCGTCCTCACCGTCCTGCA |
| | CCAGGACTGGCTGAATGGCAAGGAGTACAAGTGCAAGGT |
| | GTCCAACAAAGCCCTCCCAGCCCCCATCGAGAAAACCATC |
| | TCCAAAGCCAAAGGGCAGCCCCGAGAACCACAGGTGTAC |
| | ACCCTGCCCCCATCCCGGGAGGAGATGACCAAGAACCAG |
| | GTCAGCCTGACCTGCCTGGTCAAAGGCTTCTATCCCAGCG |
| | ACATCGCCGTGGAGTGGGAGAGCAATGGGCAGCCGGAGA |
| | ACAACTACAAGACCACGCCTCCCGTGCTGGACTCCGACGG |
| | CTCCTTCTTCCTCTATAGCAAGCTCACCGTGGACAAGAGC |
| | AGGTGGCAGCAGGGGAACGTCTTCTCATGCTCCGTGATGC |
| | ATGAGGCTCTGCACAACCACTACACGCAGAAGAGCCTCTC |
| | CCTGTCTCCGGGCAAA (SEQ ID NO: 359) |

Example 8. Affinity Modulation of Agonist Anti-TREM2 Antibodies

To generate antibody variants with increased or decreased affinity for human TREM2, affinity modulation of the 6E7 agonist anti-TREM2 monoclonal antibody was performed using fluorescence-activated cell sorting (FACS) of yeast-displayed Fab libraries. An unbiased library construction strategy was used, where NNK saturation mutagenesis was completed for every amino acid residue of each light-chain and heavy-chain CDR to generate point mutations. A separate Fab library was generated for each CDR. The six yeast-displayed Fab libraries were separately sorted and screened for variants with improved and reduced binding to human TREM2 using FACS. Secondary libraries that combined binding-enriched mutations through CDR and chain shuffling were also constructed, sorted, and screened. Flow cytometry screening data for the 6E7 variants is shown in Table 19 below. The amino acid positions of the point mutations in the indicated regions of the 6E7 heavy and light chain variable regions are numbered with respect to the 6E7 heavy chain variable region sequence (SEQ ID NO: 124) and the 6E7 light chain variable region sequence (SEQ ID NO: 61). Twenty-two variants were selected for further evaluation and characterization. The full heavy and light chain variable region sequences and associated CDRs for select variants having improved binding affinity relative to the 6E7 antibody are provided in Tables 2A and 2B, whereas the full heavy and light chain variable region sequences and associated CDRs for select variants having reduced binding affinity relative to the 6E7 antibody are provided in Tables 3A and 3B.

TABLE 23

| | Substitutions with respect to 6E7 VH sequence (SEQ ID NO: 124) | | | Substitutions with respect to 6E7 VL sequence (SEQ ID NO: 61) | | | Binding Signal (fold over 6E7 parental antibody) | | | |
|---|---|---|---|---|---|---|---|---|---|---|
| | HC | | | | | | $1^{st}$ screen 110 | $2^{nd}$ | | $2^{nd}$ screen |
| Variant Ab ID | FR1-CDR1 | HC CDR2 | HC CDR3 | LC CDR1 | LC CDR2 | LC CDR3 | nM or 10nM$^a$ | screen 2 nM | screen 10 nM | 100 nM |
| V1 | Y32S | | Q99S | | Q55T | F94Y | 1.68 | 1.29 | 1.92 | |
| V2 | Y27S | S56G | Q99S | | L54R | S93R | 2.55 | 2.23 | 2.90 | |
| V3 | T30A | G66D | Q99G | | L54R | S93R | 1.97 | 1.95 | 2.24 | |
| V4 | T30G | Y60V | Q99S | | S53R | F94Y | 6.00 | 5.88 | 5.51 | |
| V5 | | I50T | | | | F94H | 2.73 | 1.25 | 2.84 | |
| V6 | Y32M | | | | | | 0.20* | | | 0.56 |
| V7 | Y32E | | | | | | 0.11* | | | 0.32 |
| V8 | | R59K | | | | | 0.28* | | | 0.77 |
| V9 | | | T101G | | | | 0.67* | | | 0.54 |
| V10 | | | | | A50S | | 0.76* | | | 0.70 |
| V11 | | | | | | D92A | 0.79* | | | 0.42 |
| V12 | S28E | T58V | Q99G | | N56R | | 2.29 | 1.04 | 2.58 | |
| V13 | T30G | P62A | Q99G | | N56G | F94M | 1.31 | 1.15 | 1.35 | |
| V14 | T30G | S56Q | Q99G | | S53R | | 4.71 | 2.57 | 4.64 | |
| V15 | T30A | I50T | Q99S | | S53W | F94Y | 5.23 | 4.72 | 4.78 | |
| V16 | F29M | S56G | Q99S | | S53N | | 4.01 | 3.57 | 4.04 | |
| V17 | T30G | | Q99S | | L54R | F94S | 5.37 | 4.22 | 5.51 | |
| V18 | W33H | | | | | | 0.17* | | | 0.42 |
| V19 | Y32S | | | | | | 0.59* | | | 0.48 |
| V20 | | I50R | | | | | 0.18* | | | 0.52 |
| V21 | | | Y109F | | | | 0.76* | | | 0.68 |
| V22 | | | | | A50R | | 0.30* | | | 0.71 |
| V23 | | | | | | R96L | 0.40* | | | 0.40 |
| V24 | | T58V | Q99S | | N56K | R96H | 2.64 | 1.42 | 2.90 | |
| V25 | T30G | I50L | Q99S | | Q55A | F94M | 4.23 | 3.15 | 4.70 | |
| V26 | A35G | I50T | F102M, Y112A | | N56R | F94Y | 3.57 | 2.83 | 3.47 | |
| V27 | | S61A | Q99S | | N56R | | 5.50 | 5.67 | 5.69 | |
| V28 | T30Q | I50T | Y103F | | N56S | F94L | 3.08 | 2.63 | 3.61 | |
| V29 | T30K | | | | | | 1.53 | 0.84 | 1.67 | |
| V30 | Y27S | | | | | | 0.79* | | | 0.72 |
| V31 | | D57E | | | | | 0.61* | | | 0.73 |
| V32 | | P62N | | | | | 0.82* | | | 0.89 |
| V33 | | | Y104G | | | | 0.23* | | | 0.34 |
| V34 | | | | | N56D | | 0.34* | | | 1.02 |
| V35 | | | | | | D92Y | 0.21* | | | 0.29 |
| V36 | I34L | | Q99S | | L54R | F94Y | 3.38 | 4.00 | 3.44 | |
| V37 | F29H | Q65A | Q99S | | N56W | F94Y | 3.46 | 3.69 | 3.49 | |
| V38 | T30Q | T58V | | | L54R | F94H | 4.34 | 3.44 | 4.36 | |
| V39 | T30Q | S61N | Q99G | | Q55V | F94S | 6.15 | 5.11 | 5.81 | |
| V40 | T30Q | T58V | F110S | | N56L | S93R | 4.48 | 3.41 | 4.16 | |
| V41 | | I50T | | | | | 1.74 | 0.58 | 1.72 | |
| V42 | Y32A | | | | | | 0.45* | | | 0.41 |
| V43 | | D57G | | | | | 0.20* | | | 0.33 |
| V44 | | G54S | | | | | 0.65* | | | 0.52 |
| V45 | | | | W32F | | | 0.43* | | | 0.53 |
| V46 | | | | | S53T | | 0.83* | | | 0.96 |
| V47 | | | | | | R96M | 0.42* | | | 0.47 |
| V48 | T30Q | T58V | Q99M | | N56T | F94L | 2.42 | 2.30 | 2.54 | |
| V49 | T30N | I50T, Y60L | Q99S | | L54R | F94Y | 6.51 | 5.02 | 6.58 | |
| V50 | T30Q | I50V | F110L | | L54R | F94L | 4.10 | 3.39 | 4.16 | |
| V51 | | T58V | Q99G, Y112N | | L54R | | 2.81 | 1.83 | 3.18 | |
| V52 | T30E | | Q99G | | N56R | S93R | 3.00 | 1.78 | 3.09 | |
| V53 | | S63H | | | | | 1.25 | 0.66 | 1.17 | |
| V54 | Y32Q | | | | | | 0.55* | | | 0.54 |
| V55 | | R59I, F64H | | | | | 0.24* | | | 0.66 |
| V56 | | S61Q | | | | | 0.23* | | | 0.59 |
| V57 | | | | R24A | | | 0.84* | | | 0.85 |
| V58 | | | | | A50K | | 0.28* | | | 0.68 |
| V59 | | | | | | Q89M | 0.19* | | | 0.60 |
| V60 | S28H | T58V | F110S | | N56R | Q89G | 3.26 | 3.35 | 3.63 | |
| V61 | T30S | S61N | Q99G | | Q55V | F94L | 5.08 | 3.63 | 5.22 | |
| V62 | T30G | S61A | D108G | | N56R | Q89G | 2.49 | 1.87 | 2.89 | |
| V63 | T30R | | Q99S | | N56R | S93R | 3.76 | 4.91 | 3.71 | |

TABLE 23-continued

6E7 Antibody Affinity Modulation Variants

| | Substitutions with respect to 6E7 VH sequence (SEQ ID NO: 124) | | | Substitutions with respect to 6E7 VL sequence (SEQ ID NO: 61) | | | Binding Signal (fold over 6E7 parental antibody) | | | |
|---|---|---|---|---|---|---|---|---|---|---|
| | HC | | | | | | $1^{st}$ screen 110 | $2^{nd}$ | $2^{nd}$ | $2^{nd}$ screen |
| Variant Ab ID | FR1-CDR1 | HC CDR2 | HC CDR3 | LC CDR1 | LC CDR2 | LC CDR3 | nM or 10nM$^a$ | screen 2 nM | screen 10 nM | 100 nM |
| V64 | T30Q | | Q99G | | Q55A | F94Y | 5.41 | 4.88 | 5.48 | |
| V65 | | | Q99S | | | | 2.05 | 1.29 | 2.75 | |
| V66 | Y27T | | | | | | 0.25* | | | 0.74 |
| V67 | | I50M | | | | | 0.80* | | | 0.84 |
| V68 | | | Y103R | | | | 0.44* | | | 0.43 |
| V69 | | | | W32Y | | | 0.41* | | | 0.40 |
| V70 | | | | | S52G | | 0.79* | | | 0.84 |
| V71 | | | | | | F94E | 0.37* | | | 0.48 |
| V72 | A35G | | Q99G | | Q55V | F94Y | 3.64 | 2.50 | 4.01 | |
| V73 | T30G | S63G | Q99G | | L54R | F94Y | 5.12 | 4.17 | 5.44 | |
| V74 | T30A | T58V | Q99G | | N56L | | 3.94 | 2.54 | 4.01 | |
| V75 | | | Q99G | | N56A | F94Y | 4.64 | 3.74 | 4.52 | |
| V76 | T30G | S63E | F110S | | N56K | | 4.57 | 4.34 | 4.93 | |
| V77 | | | | | L54R | | 1.43 | 0.83 | 1.38 | |
| V78 | S28R | | | | | | 0.86* | | | 1.11 |
| V79 | | R59N | | | | | 0.70* | | | 0.52 |
| V80 | | | T101N | | | | 0.59* | | | 0.50 |
| V81 | | | | W32L | | | 0.17* | | | 0.23 |
| V82 | | | | | A51G | | 0.30* | | | 0.79 |
| V83 | | | | | | D92V | 0.20* | | | 0.29 |
| V84 | S28G | | F110S | | A50G | | 1.44 | 1.45 | 1.62 | |
| V85 | T30R | I50T | Q99S | | L54R | | 5.41 | 5.41 | 5.37 | |
| V86 | T30G, I34L | Q65E | Q99S | | L54R | | 4.80 | 5.17 | 5.02 | |
| V87 | T30R | T58V, S63D | Q99S | | N56W | | 3.84 | 4.86 | 3.93 | |
| V88 | T30G | | | | S53R, N56R | F94S | 4.92 | 5.57 | 5.30 | |
| V89 | | | | | | F94H | 1.33 | 0.94 | 1.46 | |
| V90 | Y32E | | | S31R | | | 0.33* | | | 0.36 |
| V91 | | G54D | | | | | 0.25* | | | 0.61 |
| V92 | | | Y103H | | | | 0.22* | | | 0.65 |
| V93 | | | | S31G | | | 0.35* | | | 1.05 |
| V94 | | | | | S52A | | 0.31* | | | 0.87 |

$^a$Binding signal values marked with an * were obtained with the 110 nM Ab concentration, whereas the remaining values in the column were obtained with the 10 nM Ab concentration Example 9. Rescue of Macrophage and Microglia Survival Defect by Agonist Anti-TREM2 Antibody The R47H variant of human TREM2 has been associated with increased risk for late-onset Alzheimer's disease (Jonsson et al., New England Journal of Medicine, Vol. 368: 107-116, 2013). To specifically target the Trem2 gene without perturbing additional regulatory elements, a gene-editing based approach was used to generate Trem2$^{-/-}$ or Trem2$^{R47H}$ mice. The Trem2$^{-/-}$ strain was generated by engineering a 5 bp or 11 bp deletion in exon 1 of the Trem2 gene and Trem2$^{R47H}$ strain was generated by engineering a point mutation at residue 47 in the mouse Trem2 gene analogous to the human variant. Detailed qPCR analyses of brain homogenates from Trem2$^{-/-}$ and Trem2$^{R47H}$ mice confirmed a loss of the gene in the knockouts and Trem2 expression comparable to wild-type age-matched controls for the Trem$^{R47H}$ mice (data not shown). No significant differences were observed in other TREM genes in the locus (Trem1, TremL1, and TremL2) under basal or LPS stimulated conditions in wild-type, Trem2$^{-/-}$ or Trem2$^{R47H}$ mice (data not shown).

To understand the effect of TREM2 changes on myeloid cells, the properties of TREM2$^{-/-}$ bone marrow derived macrophages (BMDMs) and adult and neonatal microglia were compared with wild-type macrophages and microglia in limiting conditions of CSF-1. Consistent with recent studies on TREM2$^{-/-}$ microglia and macrophages that suffer from a survival deficiency at low levels of CSF-1 (Wang et al., Cell, Vol. 160; 1061-1071, 2015; Wu et al., Journal of Experimental Medicine, Vol. 212: 681-697, 2015), reduced survival of BMDMs and microglia isolated from our TREM2$^{-/-}$ mice was also observed confirming that they display TREM2-dependent behavior reported in other TREM2$^{-/-}$ models (FIGS. 8A-8C). To determine if the R47H mutation also impacts the ability of myeloid cells to survive in challenge conditions, similar studies were performed on TREM2$^{R47H}$ BMDMs and microglia. Interestingly, the TREM2$^{R47H}$ BMDMs and microglia also exhibited poorer survival under similar culture conditions much like the TREM2$^{-/-}$ BMDMs and microglia (FIGS. 8D-8F). However, the survival defects of TREM2$^{R47H}$ BMDMs and microglia were less pronounced than the survival defects of TREM2$^{-/-}$ BMDMs and microglia. Gene dosage-dependent effects on survival of both TREM2$^{R47H}$ and TREM2$^{-/-}$ myeloid cells were also observed, with the effects being far more pronounced in the knockout cells compared to the variant cells (data not shown). While the TREM2$^{R47H}$ macrophages phenotype follow the same trend as TREM2$^{-/-}$ macrophages, the phenotypes cannot be explained simply by a reduction in cell surface expression of R47H TREM2 since wild-type and TREM2$^{R47H}$ BMDMs appeared to have comparable levels of surface TREM2 expression (data not shown). Overall, the results of these experiments support a loss-of-function for the R47H variant that mimics a loss of the TREM2 protein albeit with a phenotype that is less pronounced compared to the gene knockout.

Next, TREM2 activation was assessed in TREM2$^{R47H}$ BMDMs. A commercially available rat anti-human/mouse TREM2 antibody (mAb17291; Rat IgG2b Clone #237920, R&D Systems) increased pSyk levels in both R47H and wild-type BMDMs as measured by Western Blot with the effect being more pronounced in the wild-type BMDMs (FIG. 9A). The antibodies had no effect on the TREM2$^{-/-}$ macrophages supportive of specific activation of TREM2 (FIG. 9B). To determine if activation of TREM2/DAP12-mediated Syk signaling in macrophages can ameliorate the more downstream biological phenotypes, including reduced survival, TREM2$^{R47H}$ BMDMs were treated with the anti-TREM2 agonist antibody (mAb17291 antibody) or isotype control and the cell confluence was monitored using Incucyte Xoom Imaging System. Strikingly, a rescue in cell survival of TREM2$^{R47H}$ BMDMs was observed when the macrophages were treated with the anti-TREM2 agonist antibody with almost a complete restoration to wild-type levels (FIGS. 10A-10C). The significant boost in cell survival was observed both in live time-lapse imaging (FIGS. 10A and 10B) and endpoint cell viability (ATP accumulation) assays (FIG. 10C). An equivalent rescue in cell survival was not observed when the BMDMs were treated with isotype controls antibodies (FIGS. 10A-10C). No increase in survival of homozygous TREM2 knockout macrophages was observed confirming that the effect is specific for TREM2 activation by the antibody (data not shown). A similar rescue of cell survival was observed for adult TREM2$^{R47H}$ microglia when treated with the same anti-TREM2 agonist antibody, whereas an equivalent rescue in cell survival was not observed when the microglia were treated with an isotype control antibody (FIG. 10D).

In addition, an anti-TREM2 agonist antibody (Antibody 2) that activated Syk signaling but did not compete with the commercial antibody boosted survival of macrophages harvested from aged (18-month old) wildtype and R47H animals (FIGS. 10E and 10F), whereas an equivalent rescue in cell survival was not observed when the microglia were treated with an isotype control antibody (FIGS. 10E and 10F).

To evaluate the effect of anti-TREM2 agonist antibody treatment on migration of wild-type, TREM2 knockout and TREM2$^{R47H}$ myeloid cells, bone marrow derived macrophages isolated from mice of each of the different genotypes were assessed in a migration assay. Day 5 BMDMs from TREM2$^{+/+}$, TREM2$^{R47H}$ and TREM2$^{-/-}$ mice were harvested and seeded into Radius™ 96-well Migration Assay plates (Cell Biolabs) in complete RPMI media supplemented with 50 ng/ml M-CSF. The cells were treated with anti-TREM2 agonist antibody (Antibody 1 or Antibody 2), isotype control antibody, or vehicle for 24 hours. The cells were washed the next day following manufacturer's protocol to remove the Biocompatible Gel layer and expose the cell-free area for migration. The media was replaced with fresh growth media supplemented with 50 ng/ml M-CSF and anti-TREM2 agonist antibody, isotype control antibody, or vehicle control as above. The cell confluence was monitored using Incucyte Zoom Imaging System and data was plotted as percent confluence. Interestingly, treatment with Antibody 1 resulted in a small but statistically significant reduction in proliferation/migration of TREM2$^{R47H}$ macrophages (FIG. 11B) with minimal effects on wildtype macrophages (TREM2$^{+/+}$) (FIG. 11A) and no effect on macrophages from the knockout mice (TREM2$^{-/-}$) (FIG. 11C). Treatment with Antibody 2 had no effect on migration on either wildtype (TREM2$^{+/+}$) or TREM2$^{R47H}$ macrophages (FIGS. 11D and 11E).

At the molecular level, this reduction in macrophage migration was reflected by a reduction in cell surface FLT1 in TREM2$^{R47H}$ and wild-type macrophages upon anti-TREM2 agonist antibody treatment (both with and without treatment with lipopolysaccharide), whereas no significant differences in other chemokine/chemokine receptors (e.g. CCR5) were noted at the time points selected for the study (data not shown). The consistent correlation between migration and FLT1 both across different genotypes as well as with pharmacologic manipulation with an antibody speaks to an exciting novel link between TREM2 and FLT1 that will need further investigation. Equally interesting though is the observation that an antibody that activates TREM2/DAP12 signaling proximally can have opposing effects on survival and migration; different antibodies (depending on where they bind and how they interact with endogenous ligands) likely will have different proximal and distal activity profiles.

The results of these experiments demonstrate that an antibody that can activate TREM2/DAP12 signaling can rescue the viability defect of macrophages and microglia resulting from a loss of function mutation in TREM2. The results suggest that an agonist antibody that can activate TREM2 and boost macrophage/microglia activity may be therapeutic in Alzheimer's disease and other conditions associated with TREM2 loss of function.

Example 10. Gene Regulation by Agonist
Anti-TREM2 Antibody in Macrophages

In order to understand the basis of the phenotypic changes of the macrophages derived from TREM2$^{-/-}$ and TREM2$^{R47H}$ mice described in Example 9 at the level of the transcriptome, RNA-Seq analyses were performed comparing wild-type, TREM2$^{-/-}$ and TREM2$^{R47H}$ macrophages at day 7 under limiting conditions of CSF-1. Day 7 BMDMs were harvested and total RNA was isolated using Rneasy Mini Kit (Qiagen) according to the manufacturer's protocol.

1-2 µg of total RNA purified from bone marrow-derived ex vivo macrophages was used for cDNA library preparation by using a modified protocol based on the Illumina Truseq RNA Sample Preparation Kit (Illumina, San Diego, CA) and the published methods for strand-specific RNA-Seq (Perkins, T. T. et al., PLoS genetics, Vol. 5: e1000569, 2009; Parkhomchuk, D. et al. Nucleic acids research, Vol. 37: e123, 2009). After poly-A selection, fragmentation, and priming, reverse transcription was carried out for first strand cDNA synthesis in the presence of RNaseOut (Life Technologies, Carlsbad, CA) and actinomycin-D (MP Biomedicals, Santa Ana, CA). The synthesized cDNA was further purified by using AMPure RNAClean beads (Beckman Coulter, Pasadena, CA) following the commercial instruction. A modified method by incorporation of dUTP instead of dTTP was prepared and used for the second strand synthesis (Perkins et al., PLoS genetics, Vol. 5, e1000569, 2009; Parkhomchuk et al., Nucleic Acids Research, Vol. 37, e123, 2009). After AMPure XP bead purification (Beckman Coulter), following the standard protocol recommended by Illumina, end repairing, A-tailing, and ligation of index adaptors were sequentially performed for generation of cDNA libraries. After size selection of libraries using Pippen Prep (SAGE Biosciences, Beverly, MA), the dUTP-containing cDNA strands were destroyed by digestion of USER enzymes (New England Biolabs, Ipswich, MA) followed by a step of PCR enrichment for introduction of strand specificity. After cleaning up, the enriched cDNA libraries were analyzed in Agilent Bioanalyser and quantified by Quant-iT™ Pico-Green assays (Life Technologies) before being sequenced onto Illumina HiSeq platform. Each library generated at least 35 million of 75 bp pair-end reads for downstream analysis.

RNA-seq sequencing reads were aligned using OSA aligner (Hu et al., Bioinformatics, Vol. 28: 1933-1934, 2012) embedded in the Omicsoft ArrayStudio pipeline (Omicsoft Inc., USA). Mouse genome version GRCm38 and UCSC gene annotation were used in the alignment and quantification. Quantification was performed to the gene and transcript level based on RSEM (Li et al., BMC Bioinformatics, Vol. 12: 323, 2011). Normalized gene expression level was calculated by fragments per kilobase per million reads (FPKM) then quantile normalized at 70 percentile to 10 (FPKQ). Only genes with at least one sample expressed at FPKQ≥1 were used in the following statistical analysis. Raw reads counts from the selected genes were compared using R Bioconductor package DESeq2 following Negative Binomial distribution (Love et al., Genome Biology, Vol. 15: 550, 2014). Genes with BH corrected p value <0.05 and Fold Change ≥1.5 or ≤⅔ were selected as significantly differentially expressed genes. Pathway analysis was performed using Ingenuity Pathway Analysis (IPA, QIAGEN Redwood City, USA).

Consistent with the gradation in severity of phenotypes observed across TREM2$^{-/-}$, TREM2$^{R47H}$, and wild-type macrophages, similar trends were observed in differentially regulated transcripts with the magnitude of effect being highest in the TREM2$^{-/-}$ macrophages and TREM2$^{R47H}$ macrophages falling in between wild-type and TREM2$^{-/-}$ macrophages. This differential regulation was confirmed for a subset of the genes in an independent experiment by qPCR (FIGS. 12A-12D). Pathway analyses point to a role for TREM2 in cell cycle, cell survival, cell proliferation and migration with cross-talk putatively between the complement pathway, lipid homeostasis and chemokines/receptors and migratory factors (data not shown).

Differences in transcript regulation over time were confirmed by qPCR for several genes, including some known genetic factors linked to Alzheimer's Disease, such as ApoE (FIGS. 13A and 13B), pro-inflammatory cytokines like Il-1a (FIGS. 13C and 13D), and a host of chemokines/chemokine receptors including Cx3cr1 (FIGS. 13E and 13F), Ccl5 (FIGS. 13K and 13L), Ccl22 (FIGS. 13M and 13N), Ccr5, Ccr2, and Ccl3 as well as complement genes including C1qa (FIGS. 13I and 13J) and C3 (FIGS. 13O and 13P). In each instance, the effect was significantly more pronounced in TREM2$^{-/-}$ macrophages compared to the TREM2$^{R47H}$ macrophages. For the first time, a link between TREM2 and the pro-angiogenic receptor, Vegfr1 (Flt1) was noted with a reduction of Flt1 in TREM2$^{-/-}$ and TREM2$^{R47H}$ macrophages (FIGS. 13G and 13H). Additionally, an increase in VEGF-a in both TREM2$^{-/-}$ and TREM2$^{R47H}$ macrophages was observed consistent with a lack of receptor available for binding (data not shown). The reduction in multiple migratory factors results in a reduced migration/motility of TREM2$^{-/-}$ and TREM2$^{R47H}$ macrophages (FIGS. 14A and 14B). Recent studies have reported reduced numbers/migration of microglia in regions surrounding plaques and apoptotic cells in TREM2 knockouts (Mazaheri et al., EMBO reports, e201743922, 2017; Wang et al., Cell, Vol. 160: 1061-1071, 2015).

Consistent with the RNA seq. data, a reduction in the chemokine MCP-1/CCL2 secreted from TREM2$^{-/-}$ and TREM2$^{R47H}$ macrophages was also observed (FIG. 15A). The reduced secretion of MCP-1/CCL2 by TREM2$^{R47H}$ macrophages in challenge conditions could be restored with treatment with an agonist anti-TREM2 antibody (mAb17291 antibody) (FIG. 15B). The ability of the agonist anti-TREM2 antibody to boost MCP-1/CCL2 along with improving myeloid survival (Example 9) is noteworthy and points to an overall improvement in different aspects of myeloid cell functioning with agonist antibody treatment. Further, when TREM2$^{R47H}$ macrophages were treated with Abeta oligomers, an increase in MCP-1/CCL2 was observed that was further enhanced upon agonist anti-TREM2 antibody treatment (data not shown).

Agonist anti-TREM2 antibody treatment of TREM2$^{R47H}$ macrophages also modulated gene expression in a direction opposite to the effect of the genotype and included genes involved in regulation of myeloid cell migration, proliferation, cell cycle and survival (FIGS. 16A and 16B). Pathway analyses of the differentially regulated genes reveal a putative role for TREM2 in modulating different aspects of myeloid cell biology in challenge conditions including DNA replication, cell cycle regulation, proliferation, cell death and chemokine/cytokine modulation. In the context of Alzheimer's disease etiology, these transgenic data are supportive of the hypothesis that a deficit in TREM2, either in the form of a loss-of-function variant or reduced expression on the cell surface, contributes to a fundamental proliferation/survival deficit resulting in the subsequent inability to function efficiently with respect to phagocytosis of plaques/ apoptotic cells, cytokine modulation or potentially novel barrier function. Additionally, the direct effect on reduced secretion of migratory chemokines like CCL2 and CCR2 also likely reduce the ability of macrophages/microglia to migrate efficiently towards apoptotic cells and plaques and can further contribute to increased plaque burden early on in disease course. The ability of an antibody that boosts proximal signaling to also rescue the viability defect and restore chemokine levels elegantly demonstrates the correlation between proximal functioning and more distal biology and is strongly supportive of a therapeutic antibody strategy that can potentially boost macrophage/microglia activity and be ameliorative in disease.

Example 11. Efficacy of Agonist Anti-TREM2 Antibody in EAE Model of Multiple Sclerosis The efficacy of the agonist anti-TREM2 antibodies described herein in ameliorating symptoms and/or disease progression of multiple sclerosis is evaluated in the experimental autoimmune encephalitis (EAE) model of multiple sclerosis. EAE is induced in animals by myelin oligodendrocyte glycoprotein (MOG) and pertussis toxin as previously described in Feinstein et al., Ann. Neurol., Vol. 51: 694-702, 2002. Briefly, groups of 7-9 week-old female TREM2 wild-type (C57BL/6 strain), TREM2$^{-/-}$ and TREM2$^{R47H}$ mice are injected subcutaneously with 100 μg of MOG peptide 35-55 (MEVGWYRSPFSRVVHLYRNGK (SEQ ID NO: 283)) emulsified in complete Freund's adjuvant containing 4 mg/mL of Mycobacterium tuberculosis H37RA. Pertussis toxin is injected intraperitoneally at 200 ng/mouse in 200 μL of saline on day 0 and day 2. Anti- TREM2 antibodies (30 mg/kg and 100 mg/kg) are dosed at days 0, 7 and 14 to determine the effect of antibody treatment at different points of time in disease progression. Multiple cytokines and inflammation endpoints including soluble TREM2, MCP-1/2, MIP1a and b, CCL2, CCR2 and additional chemokines/cytokines are measured in the periphery, CNS and CSF to assess the effect of the anti-TREM2 antibodies. In addition, neurological impairment of the animals is evaluated by clinical score as follows: 0, no clinical signs of EAE; 1, limp tail; 2, flaccid tail and abnormal gait (ataxia and/or paresis of hind limbs); 3, severe hind limb paresis; 4, complete paralysis with hind body; and 5, moribund or death.

Example 12. Efficacy of Agonist Anti-TREM2 Antibody in Animal Models of Peritonitis and Sepsis The effect of the agonist anti-TREM2 antibodies described herein in modulating the acute inflammatory response is evaluated in animal models of peritonitis and sepsis. Zymosan, a polysaccharide cell wall component derived from *Saccharomyces cerevisiae*, can be injected into the peritoneal cavity of animals to reproduce the inflammatory response associated with peritonitis (see Cash et al., Methods in Enzymology, Vol. 461: 379-396, 2009). Zymosan (1 mg/kg) is administered intraperitoneally concurrently or 24 hours following administration of anti-TREM2 antibodies (20 mg/kg), isotype control antibody, or vehicle. Plasma, CSF, CNS and peritoneal lavage fluid and macrophages are collected 4 and 24 hours post treatment. Multiple cytokines and inflammation endpoints, including a quantitative assessment of different myeloid cell types, as well as soluble TREM2, MCP-1/2, MIP1a and b, CCL2, CCR2 and additional chemokines/cytokines are measured in the periphery, CNS and CSF to assess the effect of the anti-TREM2 antibodies on the inflammatory response.

In a separate series of experiments, the effect of the agonist anti-TREM2 antibodies are evaluated in a lipopolysaccharide (LPS) model of gram negative bacterial sepsis. LPS (1 mg/kg) is administered intraperitoneally 24 hours after administration of anti-TREM2 antibodies (20 mg/kg), isotype control antibody, or vehicle. Plasma, CSF and CNS samples are collected 4 and 24 hours post treatment. Multiple cytokines and inflammation endpoints, including a quantitative assessment of different myeloid cell types, as well as soluble TREM2, MCP-1/2, MIP1a and b, CCL2, CCR2 and additional chemokines/cytokines are measured in the periphery, CNS and CSF to assess the effect of the anti-TREM2 antibodies on the inflammatory response.

Example 13. Epitope Mapping of Anti-TREM2 Antibodies

Immunoblot Method for Epitope Mapping of Anti-TREM2 Antibodies

PepSpot peptides (JPT Peptide Technologies) to human soluble Trem2 were designed to cover the entire extracellular domain (beginning at histidine 21), generating 74×10 meric linear peptides, including an additional 6 control peptides, for a total of 80 pepspots per cellulose membrane. The 10 mer peptide sequences were selected by walking along the protein by 2 amino acids, resulting in an overlap of 8 amino acids. Membranes were washed with 40 ml of 100% methanol at room temperature for 10 minutes with gentle shaking, followed immediately with 3 washes of 40 ml TBST (TBS +0.05% Tween 20) for 10 minutes each.

Membranes were blocked with undiluted LICOR blocking buffer (Odyssey® Blocking Buffer 927-40000) overnight at room temperature with gentle shaking and incubated with 1 μg/ml 24G6 (PL-52705, Lot date Feb. 24, 2017, [hu anti-<huTrem2>21-191_24G6 VK4 (1-242) VL]::huKLC-CL+ [hu anti-<huTrem2>21-191_24G6 VH3 (1-471) VH]:: huIgG1zSEFL2-2 (monoclonal antibody), iPS:536553, SS-28346) overnight at 4° C. with gentle shaking in Licor blocking buffer containing 1% Tween 20. The following day, blots were washed 4× with TBST Buffer (Tris Buffered Saline+0.05% Tween 20) for 15 minutes each and probed with a secondary antibody (Licor cat #925-32232 IRDye® 800CW Goat anti-human Lot #C70419-05) at a 1:20,000 dilution in Licor blocking buffer with 1% Tween 20 and 0.1% SDS. The blots were incubated for 1 hour at room temperature with gentle shaking, protected from light, followed by another 4 washes in TBST and dried for 1 hour at room temperature. Western blot was scanned on the 800 channel using the Licor Odyssey infrared fluorescence imager.

MSD Method for Epitope Mapping of Anti-TREM2 Antibodies

Peptides (sequences designed as previously described) were synthesized with biotin on the N-terminus (Sigma) to human soluble Trem2 and normalized to 20 mg/ml in 100% DMSO. MSD GOLD 96-Well Small Spot Streptavidin SECTOR plates (MSD #L45SA) were coated with the biotinylated peptides at 5 μg/ml in 2×PBS (−ca/−mg) pH 7.8-7.9 in 50 μl total volume per well and allowed to incubate at room temperature for 2 hours with gentle shaking. Plates were washed 3× with TBST buffer (Tris buffered saline+ 0.05% Tween-20, pH 7.2), 150 μl per well, using an automated plate washer. Monoclonal antibody 24G6.1 (PL-51585 Lot date Dec. 9, 2016, hu anti-<huTrem2> IgG2, was labeled with MSD sulfo-tag as per manufacturer's SOP to serve as detection reagent and added at 1 μg/ml in MSD Diluent 100 (#R50AA-3), in a total volume of 25 μl per well. Plates were allowed to incubate for 1 hour at room temperature, with gentle shaking, then washed 3× with TBST buffer (Tris buffered saline+0.05% Tween-20, pH 7.2), 150 μl per well, using an automated plate washer, flipped and washed for an additional 3 times. MSD Read Buffer T+surfactant 4× stock (#R92TC-3) was prepared by diluting to 1× with H2O and adding 150 μl total volume per well. Plates were read immediately on MSD Sector 6000 reader.

Results

The 24G6 antibody was found to bind to the following peptides (HRDAGDLWFP (SEQ ID NO: 360), AGDLWFPGE (SEQ ID NO: 361) and GDLWFPGESE (SEQ ID NO: 362)). This provided data that 24G6 recognized the following peptide (HRDAGDLWFPGESE (SEQ ID NO: 363)) in TREM2. Alanine scanning of a slightly longer peptide PLDHRDAGDLWFPGESE (SEQ ID NO: 364) was also performed to identify key contact sites. 24G6 was found to show little to no binding to two alanine scanning peptides (PLDHRDAGDAWFPGESE (SEQ ID NO: 365); PLDHRDAGDLWAPGESE (SEQ ID NO: 366) (underlined amino acids)), suggesting those contacts were key for its recognition of this peptide. This work helped define the minimal peptide for recognition of human TREM2 by this antibody as GDLWFP (SEQ ID NO: 367). This antibody also demonstrated lower affinity to cynomolgus TREM2. Similar data was observed for peptides containing the corresponding cyno TREM2 sequence. For the other anti-TREM2 antibodies (6E7, 5E3 and 13E7), no specific peptides were identified that helped elucidate a peptide epitope using the described method.

157 158

Example 14. Peripheral Modulation of Agonist
Anti-TREM2 Antibodies on Microglia Cells In order to understand the effects of pharmacologic treatment on the global transcriptome, sc RNA-Seq studies were carried out on CNS resident Cd11b+ cells isolated from WT and R47H TREM2 mice dosed with the effectorless version of one of our agonist TREM2 antibodies. TREM2$^{+/+}$, TREM2$^{-/-}$, and TREM2$^{R47H}$ male B6 mice (60-67 days old) were used for single-cell RNA-seq studies. Antibody treatment with either anti-murine TREM2 stable effector functionless (SEFL) antibody or anti-humanHer isotype control was administered intravenously at a dose of 30 mg/kg at 5 ml/kg. In the acute inflammation model, antibody-treated animals were given LPS (<source>) intraperitoneally 16 hours after antibody treatment at 5 mg/kg at 5 ml/kg and stimulated with LPS for 4 hours. The isotype control antibody in genotype-matched, age-matched and sex-matched littermate controls were simultaneously dosed.

Brains were harvested from treated mice following $CO_2$ asphyxiation and tissues were dissociated using the Miltenyi adult brain dissociation kit for mouse and rats (Miltenyi Biotec 130-107-677) according to standard manufacturer's protocols. CD11b$^+$ cells were positively enriched using microbeads (Miltenyi Biotec 130-049-601), washed twice in freshly prepared ice cold PBS+0.04% BSA and resuspended in freshly PBS+0.04% BSA at 500-1000 cells/ul at >70% viability. The brains were collected and microglia isolated using previously published Miltenyi's Cd11b isolation kit. NGS libraries were prepared as described per the 10× Chromium manufacturers' guidelines. Reverse transcription, total cDNA amplification, and library construction was performed according to manufacturer's protocol. Single-cell RNA sequencing was performed using the Chromium Single Cell 3' Kit with V2 Chemistry (10× Genomics). Enriched CD11b+ cells were loaded and encapsulated on the Chromium Single Cell Chip A (10× Genomics) to achieve a cell recovery of 5,000 cells per sample. A sequencing read depth of >2× of the Keren-Shaul et al. study, with roughly 2095 genes identified per cell and xUMIs per cell was achieved. T-distributed stochastic neighbor embedding (t-SNE) was applied to visualize single cell gene expression profiles and cells were grouped into cell types using dbscan clustering.

Eleven distinct populations were identified in total. The most dominant cluster of cells were as expected microglia as defined by a Trem2+, Tmem119+, P2ry12+, Hexb+, Lyz2-gene signature, with microglial cells accounting for 60% of the total number of cells analyzed across all treatment groups and genotypes. Minor residual populations of endothelial cells, astrocytes, NK cells and oligodendrocytes that persisted after magnetic enrichment were also identified. The dominant microglial clusters distinctly separated out into two groups based on LPS treatment—a more homeostatic microglia cluster and an activated microglia cluster. Within the LPS activated state, the more subtle effects of the genotype differences (WT vs. R47H) and antibody treatment in both WT and R47H groups were observed. These patterns persisted even upon inspection of the microglia clusters alone. Additional smaller myeloid cell clusters that bore the hallmarks of microglial genes as well as classic infiltrate markers were also noted.

A careful analysis of the antibody treatment on the microglial clusters revealed that the antibody treatment had a few distinct biological effects. First, antibody treatment raised the level of homeostatic genes including Cx3cr1, Tmem119, Ctsd and P2ry12 in both WT and R47H microglia, WT microglia alone and R47H microglia alone (FIGS. 17A, B and C). Second, antibody treatment decreased the transcript levels of pro-inflammatory chemokines and cytokines including Il1a, Il1b, Il27, Il2b, Ccr7, Ccl2, Ccl3, Ccl4 and Ccl5 (FIGS. 17D, E and F). Thirdly, antibody treatment modulated several genes involved in Syk signaling including several DUSPs (phosphatases that regulate Src kinases) and genes in the MAPK signaling pathway. Very few differences between WT and R47H microglia isolated from normal, unchallenged, 7-week old mice were observed.

Figure 18E:
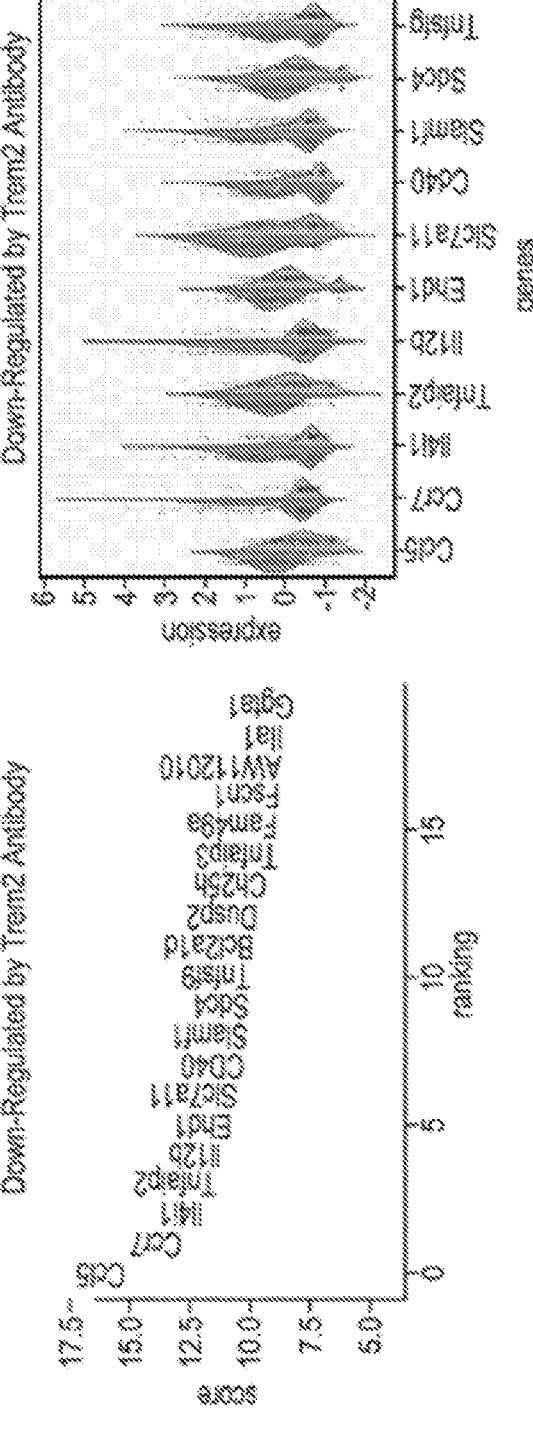

In examining the differences between WT and R47H microglia in an unperturbed state as well as determining the effects of antibody treatment, we noted that in the LPS/antibody treated animals, about 15% of the cells that were clustered with the more traditional microglia groups bore a distinct gene signature with a higher representation from the R47H genotype. A careful analysis revealed that these cells first got clustered with the larger microglia group since they were Trem2+,Tmem119+, Cx3cr1+ and Hexb+, classic markers used to define homeostatic microglia. Yet, these cells were also enriched for genes like S100a8, Lcn2, S100a9, Camp, Hp, Cxcr2, and Il1r2 in both the WT and R47H populations compared to the larger, more classic microglial cluster. When we performed pathway analysis of the top genes that were preferentially expressed in this cluster, we found that these hits were associated with monocyte and neutrophil function (FIGS. 18A and 18B). This group of infiltrate/microglia cells also responded to antibody treatment with a downregulation of the pro-inflammatory chemokines and cytokines from both WT and R47H KI, WT only and R47HKi only mice (FIGS. 18C, 18D, and 18E).

The data show that an acute dosing of the agonist antibody of the present invention in an LPS challenge model is adequate to positively regulate microglial function in the same way that constitutive gene over-expression does in a chronic indication like AD. In addition, specific activation of TREM2 by the agonist antibody of the invention impacts multiple homeostatic genes in an LPS treatment mode and restores a more homeostatic state overall.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A method of treating a condition associated with a loss of function of human TREM2 in a subject in need thereof, comprising administering to the subject an anti-human TREM2 (hTREM2) antibody comprising a light chain variable region having complementarity determining regions CDRL1, CDRL2, and CDRL3, and a heavy chain variable region having complementarity determining regions CDRH1, CDRH2, and CDRH3, wherein:

```
CDRL1 comprises the amino acid sequence of:
                              (SEQ ID NO: 10)
RASQSVSSNLA;

CDRL2 comprises the amino acid sequence of:
                              (SEQ ID NO: 23)
GASTRAT;

CDRL3 comprises the amino acid sequence of:
                             (SEQ ID NO: 368)
LQDNNFPPT;

CDRH1 comprises the amino acid sequence of:
                              (SEQ ID NO: 81)
SYWIG;

CDRH2 comprises the amino acid sequence of:
                             (SEQ ID NO: 369)
IIYPGDADARYSPSFQG;
and CDRH3 comprises the amino acid sequence of:
                             (SEQ ID NO: 370)
RRQGIFGDALDF;
``` wherein the condition associated with a loss of function of human TREM2 is a neurodegenerative disorder.

2. The method of claim 1, wherein the antibody is a chimeric antibody, a humanized antibody, or a fully human antibody.

3. The method of claim 1, wherein the antibody is an IgG1, IgG2, IgG3, or IgG4 antibody.

4. The method of claim 3, wherein the antibody is a human IgG1 antibody.

5. The method of claim 4, wherein the antibody comprises a mutation at amino acid position N297 according to EU numbering in its heavy chain.

6. The method of claim 5, wherein the mutation is N297G.

7. The method of claim 4, wherein the antibody comprises R292C and V302C mutations according to EU numbering in its heavy chain.

8. The method of claim 1, wherein the neurodegenerative disorder is Alzheimer's disease, Nasu-Hakola disease, frontotemporal dementia, multiple sclerosis, or prion disease.

9. The method of claim 8, wherein the condition associated with a loss of function of human TREM2 is Alzheimer's disease.

10. The method of claim 8, wherein the condition associated with a loss of function of human TREM2 is frontotemporal dementia.

11. The method of claim 8, wherein the condition associated with a loss of function of human TREM2 is multiple sclerosis.

12. A method of treating a condition associated with a loss of function of human TREM2 in a subject in need thereof, comprising administering to the subject an anti-human TREM2 (hTREM2) antibody comprising a light chain variable region having the amino acid sequence of SEQ ID NO:330, and a heavy chain variable region having the amino acid sequence of SEQ ID NO:331; wherein the condition associated with a loss of function of human TREM2 is a neurodegenerative disorder.

13. The method of claim 12, wherein the antibody is a human IgG1 antibody comprising a kappa light chain constant region.

14. The method of claim 13, wherein the antibody comprises a mutation at amino acid position N297 according to EU numbering in its heavy chain.

15. The method of claim 13, wherein the antibody comprises mutations R292C, N297G, and V302C according to EU numbering in its heavy chain.

16. The method of claim 12, wherein the neurodegenerative disorder is Alzheimer's disease, Nasu-Hakola disease, frontotemporal dementia, multiple sclerosis, or prion disease.

17. A method of treating a condition associated with a loss of function of human TREM2 in a subject in need thereof, comprising administering to the subject an anti-human TREM2 (hTREM2) antibody, comprising a light chain having the amino acid sequence of:

(SEQ ID NO: 371)
EIVMTQSPATLSVSPGERATLSCRASQSVSSNLAWFQQKPGQAPRLLIYGA

STRATGIPARFSGSGSGTEFTLTISSLQPEDFAVYYCLQDNNFPPTFGQGT

KVDIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;
and a heavy chain having the amino acid sequence of:

(SEQ ID NO: 372)
EVQLVQSGAEVKKPGESLKISCKGSGYSFTSYWIGWVRQMPGKGLEWMGII

YPGDADARYSPSFQGQVTISADKSISTAYLQWSSLKASDTAMYFCARRRQG

IFGDALDFWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTL

MISRTPEVTCVVVDVSHEDPEVKFNWYVDGVEVHNAKTKPCEEQYGSTYRC

VSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK;

wherein the condition associated with a loss of function of human TREM2 is a neurodegenerative disorder.

18. The method of claim 17, wherein the neurodegenerative disorder is Alzheimer's disease, Nasu-Hakola disease, frontotemporal dementia, multiple sclerosis, or prion disease.

\* \* \* \* \*